US011155795B2

(12) United States Patent
Zhang et al.

(10) Patent No.: US 11,155,795 B2
(45) Date of Patent: Oct. 26, 2021

(54) CRISPR-CAS SYSTEMS, CRYSTAL STRUCTURE AND USES THEREOF

(71) Applicants: The Broad Institute, Inc., Cambridge, MA (US); Massachusetts Institute of Technology, Cambridge, MA (US); University of Tokyo, Tokyo (JP)

(72) Inventors: Feng Zhang, Cambridge, MA (US); Osamu Nureki, Kanagawa (JP); Hiroshi Nishimasu, Tokyo (JP); Ryuichiro Ishitani, Tokyo (JP)

(73) Assignees: THE BROAD INSTITUTE, INC., Cambridge, MA (US); MASSACHUSETTS INSTITUTE OF TECHNOLOGY, Cambridge, MA (US); UNIVERSITY OF TOKYO, Tokyo (JP)

( * ) Notice: Subject to any disclaimer, the term of this patent is extended or adjusted under 35 U.S.C. 154(b) by 131 days.

(21) Appl. No.: 15/171,141

(22) Filed: Jun. 2, 2016

(65) Prior Publication Data
US 2016/0340660 A1 Nov. 24, 2016

Related U.S. Application Data

(63) Continuation-in-part of application No. PCT/US2014/069925, filed on Dec. 12, 2014.

(60) Provisional application No. 61/930,214, filed on Jan. 22, 2014, provisional application No. 61/915,251, filed on Dec. 12, 2013.

(51) Int. Cl.
*C12N 9/22* (2006.01)
*G16B 15/00* (2019.01)
*G16B 15/20* (2019.01)
*G16B 15/30* (2019.01)

(52) U.S. Cl.
CPC .............. *C12N 9/22* (2013.01); *G16B 15/00* (2019.02); *G16B 15/20* (2019.02); *G16B 15/30* (2019.02); *C07K 2299/00* (2013.01)

(58) Field of Classification Search
CPC combination set(s) only.
See application file for complete search history.

(56) References Cited

U.S. PATENT DOCUMENTS

| | | | |
|---|---|---|---|
| 5,622,856 A | 4/1997 | Natsoulis | |
| 6,251,677 B1 | 6/2001 | Wilson et al. | |
| 7,601,492 B2 | 10/2009 | Fu et al. | |
| 7,691,995 B2 | 4/2010 | Zamore et al. | |
| 8,697,359 B1 | 4/2014 | Zhang | |
| 8,771,945 B1 | 7/2014 | Zhang | |
| 8,865,406 B2 | 10/2014 | Zhang et al. | |
| 8,871,445 B2 | 10/2014 | Cong et al. | |
| 8,889,418 B2 | 11/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 9,512,446 B1 | 12/2016 | Joung et al. | |
| 9,549,901 B2 | 1/2017 | Shi et al. | |
| 9,597,357 B2 | 3/2017 | Gregory et al. | |
| 9,623,071 B2 | 4/2017 | Guo et al. | |
| 9,637,739 B2 | 5/2017 | Siksnys et al. | |
| 9,701,964 B2 | 7/2017 | Clube et al. | |
| 9,834,791 B2 | 12/2017 | Zhang et al. | |
| 9,873,894 B2 | 1/2018 | Conway et al. | |
| 10,301,651 B2 | 5/2019 | Doudna et al. | |
| 10,660,943 B2 | 5/2020 | Bikard et al. | |
| 2003/0186238 A1 | 10/2003 | Allawi et al. | |
| 2004/0111221 A1 | 10/2004 | Kenneth | |
| 2005/0196851 A1* | 9/2005 | Uckun ................. | C12N 9/1205 435/194 |
| 2005/0220796 A1 | 10/2005 | Dynan et al. | |
| 2006/0178297 A1 | 8/2006 | Troy et al. | |
| 2006/0234247 A1 | 10/2006 | Puttaraju et al. | |
| 2007/0016012 A1 | 1/2007 | Hartlep | |
| 2007/0244031 A1 | 10/2007 | Lu et al. | |
| 2008/0293655 A1 | 11/2008 | Aygun et al. | |
| 2010/0055798 A1 | 3/2010 | Battersby | |
| 2010/0076057 A1 | 3/2010 | Sontheimer et al. | |
| 2010/0081707 A1 | 4/2010 | Ali et al. | |

(Continued)

FOREIGN PATENT DOCUMENTS

BR 112015013784 7/2017
CN 101228176 7/2008

(Continued)

OTHER PUBLICATIONS

Böhm et al., "The computer program LUDI: A new method for the de novo design of enzyme inhibitors", Journal of Computer-Aided Molecular Design, 1992, vol. 6, pp. 61-78.*
Morris et al., J. of Computer-Aided Molecular Design. 1996. vol. 10, pp. 293-304.*
Dean et al., "Recent Advances in Drug Design Methods : Where Will They Lead ?", BioEssays, 1994, 16(9):683-687.*
International Preliminary Report and Written Opinion of the International Searching Authority dated Jun. 14, 2016, which issued during prosecution of International Application No. PCT/US2014/069925.
Platt, et al. "CRISPR-Cas9 Knockin Mice for Genome Editing and Cancer Modeling" Cell, 2014, 159(2):440-455.

(Continued)

*Primary Examiner* — Suzanne M Noakes
(74) *Attorney, Agent, or Firm* — Foley & Lardner LLP

(57) ABSTRACT

The invention provides for systems, methods, and compositions for altering expression of target gene sequences and related gene products. Provided are structural information on the Cas protein of the CRISPR-Cas system, use of this information in generating modified components of the CRISPR complex, vectors and vector systems which encode one or more components or modified components of a CRISPR complex, as well as methods for the design and use of such vectors and components. Also provided are methods of directing CRISPR complex formation in eukaryotic cells and methods for utilizing the CRISPR-Cas system.

6 Claims, 43 Drawing Sheets

Specification includes a Sequence Listing.

(56) References Cited

U.S. PATENT DOCUMENTS

| | | |
|---|---|---|
| 2010/0093617 A1 | 4/2010 | Barrangou et al. |
| 2010/0233084 A1 | 9/2010 | Narasimhaswamy et al. |
| 2011/0016540 A1 | 1/2011 | Weinstein |
| 2011/0059502 A1 | 3/2011 | Chalasani |
| 2011/0189776 A1 | 8/2011 | Terns et al. |
| 2011/0223638 A1 | 9/2011 | Widenheft et al. |
| 2011/0239315 A1 | 9/2011 | Bonas et al. |
| 2012/0029891 A1 | 2/2012 | Behlke et al. |
| 2013/0096182 A1 | 4/2013 | Chatterjee et al. |
| 2013/0130248 A1 | 5/2013 | Haurwitz et al. |
| 2013/0315831 A1 | 11/2013 | Shi et al. |
| 2014/0068797 A1 | 3/2014 | Doudna et al. |
| 2014/0294771 A1 | 10/2014 | Schaffer et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0356956 A1 | 12/2014 | Church et al. |
| 2014/0357530 A1 | 12/2014 | Zhang et al. |
| 2015/0045546 A1 | 2/2015 | Siksnys et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0232881 A1 | 8/2015 | Glucksmann et al. |
| 2015/0247150 A1 | 9/2015 | Zhang et al. |
| 2015/0291965 A1 | 10/2015 | Zhang et al. |
| 2015/0322457 A1 | 11/2015 | Kim et al. |
| 2015/0353905 A1 | 12/2015 | Weiss et al. |
| 2016/0017366 A1 | 1/2016 | Chen et al. |
| 2016/0024510 A1 | 1/2016 | Bikard et al. |
| 2016/0024524 A1 | 1/2016 | Joung et al. |
| 2016/0130609 A1 | 5/2016 | Doudna et al. |
| 2016/0237456 A1 | 8/2016 | Church et al. |
| 2016/0251648 A1 | 9/2016 | Wang et al. |
| 2016/0281072 A1 | 9/2016 | Zhang |
| 2016/0298135 A1 | 10/2016 | Chen et al. |
| 2016/0298137 A1 | 10/2016 | Chen et al. |
| 2016/0324938 A1 | 11/2016 | Bikard et al. |
| 2016/0340662 A1 | 11/2016 | Zhang et al. |
| 2017/0175144 A1 | 6/2017 | Zhang et al. |
| 2018/0127783 A1 | 5/2018 | Zhang et al. |
| 2018/0230495 A1 | 8/2018 | Doudna et al. |
| 2019/0010471 A1 | 1/2019 | Zhang et al. |
| 2020/0282026 A1 | 9/2020 | Bikard et al. |
| 2020/0282027 A1 | 9/2020 | Bikard et al. |
| 2021/0060140 A1 | 3/2021 | Bikard et al. |
| 2021/0060141 A1 | 3/2021 | Bikard et al. |

FOREIGN PATENT DOCUMENTS

| | | |
|---|---|---|
| CN | 103388006 | 11/2013 |
| CN | 103668472 | 3/2014 |
| CN | 104520429 A | 4/2015 |
| CN | 104854241 A | 8/2015 |
| CN | 107532161 A | 1/2018 |
| EP | 2591770 | 5/2013 |
| EP | 2 784 162 | 1/2014 |
| EP | 2764103 | 8/2014 |
| EP | 2771468 | 9/2014 |
| EP | 2 828 386 A1 | 1/2015 |
| FR | 2872170 A1 | 12/2005 |
| IN | 49/2015 | 12/2015 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009-502170 A | 1/2009 |
| JP | 2009-536827 A | 10/2009 |
| JP | 2010-522547 A | 7/2010 |
| JP | 2012-508235 | 4/2012 |
| JP | 2012-510812 A | 5/2012 |
| JP | 2012-511332 A | 5/2012 |
| JP | 2012-529287 A | 11/2012 |
| JP | 2013-500045 A | 1/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500003 A | 1/2016 |
| JP | 2016-500262 | 1/2016 |
| JP | 2016-501532 A | 1/2016 |
| JP | 2016-025710 A | 2/2016 |
| JP | 2016-502840 A | 2/2016 |
| JP | 2016-504026 A | 2/2016 |
| JP | 2016-505256 A | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-523082 A | 8/2016 |
| JP | 2016-524472 | 8/2016 |
| JP | 2016-182140 A | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | WO-2004/029219 A2 | 4/2004 |
| WO | WO-2004/046321 A2 | 6/2004 |
| WO | WO-2004/062618 A2 | 7/2004 |
| WO | WO-2005/014791 | 2/2005 |
| WO | WO-2005/049642 A2 | 6/2005 |
| WO | WO-2007/014275 A2 | 2/2007 |
| WO | WO-2007/134161 A2 | 11/2007 |
| WO | WO-2008/093152 A1 | 8/2008 |
| WO | 2008108989 | 9/2008 |
| WO | WO-2008/116860 A2 | 10/2008 |
| WO | 2010054108 | 5/2010 |
| WO | WO-2010/065123 A1 | 6/2010 |
| WO | WO-2010/068816 A1 | 6/2010 |
| WO | WO-2010/075424 A2 | 7/2010 |
| WO | WO-2010/079430 A1 | 7/2010 |
| WO | WO-2010/143917 | 12/2010 |
| WO | WO-2011/011767 A1 | 1/2011 |
| WO | WO-2011/016840 A2 | 2/2011 |
| WO | WO-2011/036510 A1 | 3/2011 |
| WO | WO-2011/064736 A1 | 6/2011 |
| WO | WO-2011/076873 A1 | 6/2011 |
| WO | WO-2011/100058 | 8/2011 |
| WO | 2011146121 | 11/2011 |
| WO | WO-2012/012738 A2 | 1/2012 |
| WO | WO-2012/031205 | 3/2012 |
| WO | WO-2012/051343 A1 | 4/2012 |
| WO | WO-2012/149470 A1 | 11/2012 |
| WO | 2012164565 | 12/2012 |
| WO | WO-2013/044008 A2 | 3/2013 |
| WO | WO-2013/052681 | 4/2013 |
| WO | WO-2013/155572 | 4/2013 |
| WO | WO-2013/071440 A1 | 5/2013 |
| WO | WO-2013/078400 A1 | 5/2013 |
| WO | 2013082519 | 6/2013 |
| WO | 2013098244 | 7/2013 |
| WO | 2013130824 | 9/2013 |
| WO | 2013141680 | 9/2013 |
| WO | 2013142578 | 9/2013 |
| WO | 2013176772 | 11/2013 |
| WO | WO-2014/165349 A1 | 3/2014 |
| WO | 2014065596 | 5/2014 |
| WO | 2014089290 | 6/2014 |
| WO | 2014093479 | 6/2014 |
| WO | 2014093622 | 6/2014 |
| WO | 2014093635 | 6/2014 |
| WO | 2014093661 | 6/2014 |
| WO | 2014093694 | 6/2014 |
| WO | 2014093712 | 6/2014 |
| WO | 2014099744 | 6/2014 |
| WO | 2014099750 | 6/2014 |

(56) References Cited

FOREIGN PATENT DOCUMENTS

| WO | WO-2014/093595 | | 6/2014 |
|---|---|---|---|
| WO | WO-2014/093655 | | 6/2014 |
| WO | WO-2014/093701 | A1 | 6/2014 |
| WO | WO-2014/093709 | | 6/2014 |
| WO | WO-2014/093718 | | 6/2014 |
| WO | WO-2015/031775 | | 8/2014 |
| WO | WO-2014/144761 | | 9/2014 |
| WO | WO-2014/186585 | A2 | 11/2014 |
| WO | 2014204724 | | 12/2014 |
| WO | 2014204725 | | 12/2014 |
| WO | 2014204729 | | 12/2014 |
| WO | WO-2014/191518 | A1 | 12/2014 |
| WO | WO-2014/197568 | A2 | 12/2014 |
| WO | WO-2014/197748 | | 12/2014 |
| WO | WO-2014/204726 | | 12/2014 |
| WO | WO-2014/204727 | A1 | 12/2014 |
| WO | WO-2014/204728 | | 12/2014 |
| WO | WO-2015/006747 | A2 | 1/2015 |
| WO | WO-2015/035136 | A2 | 3/2015 |
| WO | WO-2015/048577 | | 4/2015 |
| WO | WO-2015/065964 | A1 | 5/2015 |
| WO | WO-2015/070083 | A1 | 5/2015 |
| WO | WO-2015/071474 | | 5/2015 |
| WO | 2015089419 | | 6/2015 |
| WO | WO-2015/089351 | A1 | 6/2015 |
| WO | WO-2015/089364 | | 6/2015 |
| WO | WO-2015/089427 | A1 | 6/2015 |
| WO | WO-2015/113063 | A1 | 7/2015 |
| WO | WO-2016/022866 | A1 | 2/2016 |
| WO | WO-2016/141224 | A1 | 9/2016 |

OTHER PUBLICATIONS

Porteus, et al. "Gene targeting using zinc finger nucleases" Nature Biotechnology, 2005, 23(8):967-973.
Pougach, et al. "Transcription, Processing and Function of CRISPR Cassettes in *Escherichia coli*" Mol. Microbiol, 2010, 77(6):1367-1379.
Qi, et al. "Repurposing CRISPR as an RNA-Guided Platform for Sequence-Specific Control of Gene Expression" Cell, 2013, 152(5):1173-1183.
Ran, et al., "In vivo genome editing using *Staphylococcus aureus* Cas9," Nature, 2015, doi:10.1038/nature14299.
Ran et al. "Double Nicking by RNA-Guided CRISPR Cas9 for Enhanced Genome Editing Specificity," Cell 154, 1-10, Sep. 12, 2013.
Ran, et al. "Genome engineering using the CRISPR-Cas9 system" Nature Protocols, 2013, 8(11):2281-2308.
Rand, et al. "Argonaute2 Cleaves the Anti-Guide Strand of siRNA during RISC Activation" Cell, 2005, 123:621-629.
Raymond, et al. "High-Efficiency FLP and φC31 Site-Specific Recombination in Mammalian Cells" PLoS ONE, 2007, 2(1):e162. Doi. 10.1371/journal.pone.0000162.
Rebar, et al. "Induction of angiogenesis in a mouse model using engineered transcription factors" Nature Medicine, Dec. 2002, 8(12):1427-1432.
Reiss, et al. "RecA protein stimulates homologous recombination in plants" Proc. Natl. Acad. Sci. USA, 1996, 93:3094-3098.
Sanders, et al. "Use of a macromolecular crowding agent to dissect interactions and define functions in transcriptional activation by a DNA-tracking protein: Bacteriophage T4 gene 45 protein and late transcription" PNAS, 1994, 9:7703-7707.
Sapranauskas, et al. "The *Streptococcus thermophilus* CRISPR-Cas system provides immunity in *Escherichia coli*" Nucleic Acids Research, 2011, 39(21): 9275-9282.
Sauer, "Functional Expression of the cre-lox Site-Specific Recombination System in the Yeast *Saccharomyces cerevisiae*" Mol. Cell. Biol., 1987, 7(6):2087-2096.
Sauer, et al. "Site-specific DNA recombination in mammalian cells by the Cre recombinase of bacteriophage P1" Proc. Natl. Acad. Sci. U.S.A., 1988, 85:5166-5170.

Schiffer, et al. "Predictors of Hepatitis B Cure Using Gene Therapy to Deliver DNA Cleavage Enzymes: A Mathematical Modeling Approach" PLOS Computational Biology,, 2013, 9(7):e1003131. www.ploscompbiol.org.
Scholze, et al. "TAL effector-DNA specificity" Virulence, 2010, 1(5):428-432, DOI:10.4161/viru.1.5.12863.
Schunder, et al. "First indication for a functional CRISPR/Cas system in Francisella tularensis" International Journal of Medical Microbiology, 2013, 303:1438-4221.
Schramm et al. "Recruitment of RNA polymerase III to its target promoters" Genes & Development, 2002, 16:2593-2620.
Seung Woo Cho, et al., "Targeted genome engineering in human cells with the Cas9 RNA-guided endonuclease" Nature Biotechnology, Mar. 2013, 31(3):230-232.
Seung Woo Cho, et al. "Supplementary Information: Targeted genome engineering in human cells with RNA-guided endonuclease" Nature Biotechnology, Mar. 2013, 31(3):1-10.
Seung Woo Cho, et al. "Analysis off-target effects of CRISPR/Cas-derived RNA-guided endonucleases and nickases" Genome Research, Nov. 2014, 24:132-141.
Shalem et al., "Genome-Scale CRISPR-Cas9 Knockout Screening in Human Cells", Science, 2014, 343;84-87. DOI:10.1126/science. 1247005.
Shen, et al. "Efficient genome modification by CRISPR-Cas9 nickase with minimal off-target effects" 2014, Nature Methods, 11(4):399-404.
Shen, et al. "Generation of gene-modified mice via Cas9/RNA-mediated gene targeting" Cell Research, 2013, 23:720-723.
Sims, et al., "High-throughput RNA interference screening using pooled shRNA libraries and next generation sequencing", Genome Biology 12(10):R104, Oct. 2011.
Sontheimer, "Project 7: Establishing RNA-Directed DNA Targeting in Eukaryotic Cells" Physical Sciences-Onc., Nov. 16, 2011-Dec. 31, 2012, htt://groups.molbiosci.northwestern.edu/sontheimer/Sontheimer_cv.php) Molecular Biosciences.
Sosa, ET A. "Animal transgenesis: an overiew" Brain Struct Funct, 2010, 214:91-109.
Stolfi, et al., "Tissue-specific genome editing in Ciona embryos by CRISPR/Cas9," Development, 2014, 141:4115-4120 doi: 10.1242/dev.114488.
Swiech et al., "In vivo interrogation of gene function in the mammalian brain using CRISPR-Cas9," Nature Biotechnology, 2015, doi:10.1038/nbt.3055.
Terns, et al. "Crispr-based adaptive immune systems" Current Opinion in Microbiology, 2011, 14:321-327.
Tolia, et al. "Slicer and the Argonautes" Nature Chemical Biology, 2007, 3(1):36-43.
Trevino, et al. "Genome Editing Using Cas9 Nickases" Methods in Enxymology, 2014, 546:161-174.
Urnov, et al. "Highly efficient endogenous human gene correction using designed zinc-finger nucleases" Nature, 2005, 435:646-651.
Vestergaard, et al. "CRISPR adaptive immune systems of Archaea" RNA Biology, 2014, 11(2):156-167.
Wang, et al. One-Step Generation Of Mice Carrying Mutations In Multiple Genes By CRISPR/Cas-Mediated Genome Engineering, Cell, 2013, 153:910-918.
Wiedenheft, et al. "RNA-guided genetic silencing systems in bacteria and archaea" Nature, 2012, 482:331-338.
Wu, et al. "Genome-wide binding of the CRISPR endonuclease Cas9 in mammalian cells" Nature Biotechnology, 2014, doi:10. 1038/nbt.2889.
Xiao, et al. "Chromosomal deletions and inversions mediated by TALENs and CRIPPR/Cas in zebrafish" Nucleic Acids Research, 2013, 41(14):E141. doi:10.1093/nar/gkt464.
Xiao, et al. Production of High-Titer Recombinant Adeno-Associated Virus Vectors in the Absence of Helper Adenovirus.
Zetsche et al. "A split-Cas9 architecture for inducible genome editing and transcription modulation," Nature biotechnology, 2015, 33(2): 139-142.
Zetsche, et al. "CPF1 is a Single RNA-Guided Endonuclease of a Class 2 CRISPR-Cas System" Cell, 2015, 163:759-771.

(56) References Cited

OTHER PUBLICATIONS

Zhang, X. D., et al., "cSSMD: assessing collective activity for addressing off-target effects in genome-scale RNA interference screens", Bioinformatics (Oxford), 27(20);2775-2781, Oct. 2011.
Zhang, et al. "Efficient construction of sequence-specific TAL effectors for modulating mammalian transcription" nature biotechnology, 2011, 29(2):149-154.
Zhu, et al. "Crystal structure of Cmr2 suggests a nucleotide cyclase-related enzyme in type III CRISPR-Cas sytems" FEBS Letters, 2012, 939-945. Doi: 10.1016/j.febslet2012.02.036.
International Search Report dated May 4, 2015, which issued during prosecution of International Application No. PCT/US2014/069925.
Jinek, et al. "A Programmable Dual-RNA-Guided DNA Endonuclease in Adaptive Bacterial Immunity" Science 337:816-821, Aug. 2012.
Jinek, et al. "Supplementary Material-A Programmable Dual-RNA-Guided DNA Endonuclease in Adaptive Bacterial Immunity" Science, 2012, DOI: 10.1126/science. 1225829.
Mali, et al. "CAS9 Transcriptional activators for target specificity screening and paired nickases for cooperative genome engineering" Nature Biotechnology, 2013, 31(9):833-838.
Xing Yu, et al. "Crystal structure of Cmr2 suggests a nucleotide cyclase-related enzyme in type III CRISPR-Cas systems" Febs Letters, 2012, 586:939-945.
Nishimasu, et al. "Crystal Structure of Cas9 in Complex with Guide RNA and Target DNA" Cell, 2014, 156:935-949.
Hale, et al. "Prokaryotic siliencing (psi) RNAs in Pyrococcus furiosus", RNA, 2008, 14:2572-2579.
Handel, et al. "Versatile and Efficient Genome Editing in Human Cells by Combining Zinc-Finger Nucleases With Adeno-Associated Viral-Vectors" Human Gene Therapy, Mar. 2012, 23:321-329.
Hibbitt, et al. "RNAi-mediated knockdown of HMG CoA reductase enhances gene expression from physiologically regulated low-density lipoprotein receptor therapeutic vectors in vivo" Gene Therapy, 2012, 19:463-467.
Hou, et al., "Efficient genome engineering in human pluripotent stem cells using Cas9 from Neisseria meningitides," PNAS.2013, 110(39):15644-15649.
Horvath et al. "RNA-guidded genome editing a la carte" Cell Research, 2013, 23:733-734, doi:10.1038/cr.2013.39.
Hsu, et al. "Development and Applications of CRISPR-Cas9 for Genome Engineering" Cell, Jun. 2014, 157:1262-1278.
Hsu et al., "DNA targeting specificity of RNA-guided Cas9 nucleases," Nature Biotechnology, 2013, 31(9):827-834.
Hsu et al., "Supplementary Information-DNA targeting specificity of RNA-guided Cas9 nucleases," Nature Biotechnology, 2013, doi:10.1038/nbt.2647.
Hwang Woong, et al. "Efficient genome editing in zebrafish using a CRISPR-Cas System" Nature Biotechnology, Mar. 2013, 31(3):227-229.
Hwang Woong, et al. "Efficient In Vivo Genome Editing Usng RNA-Guided Nucleases" Nat. Biotechnol., 2013, 31(3):227.229. doi. 1.1038/mbt.2501.
Janssen, et al., "Mouse Models of K-ras-Initiated Carcinogenesis" Biochimicia et Biophysica Acta, 2005, 1756:145-154.
Jiang, et al. "RNA-guided editing of bacterial genomes using CRISPR-Cas systems" Nature Biotechnology, 2013, 31(3):233-239.
Jinek, et al., "RNA-programmed genome editing in human cells;" 2013, eLife 2013:e00471, DOI:10.7554/eLife.00471.
Kanasty, et al. "Delivery materials for siRNA therapeutics" Nature Materials, 2013, 12:967-977.
Karvelis, et al. "crRNA and tracrRNA guide Cas9-mediated DNA interference in Streptococcus thermophiles" RNA Biology, 2013, 10(5):841-851.
Karvelis, et al. "Supplemental Material to: crRNA and tracrRNA guide Cas9-mediated DNA interference in *Streptococcus thermophiles*" Landes Bioscience, 2013, 10(5), http://dx.doi.org/10.4161/rna.24203.
Kim, et al. "Crystal structure of Cas1 from Archaeoglobus fulgidus and characterization of its nucleolytic activity" Biochemical and Biophysical Research Communications, 2013, 441:720-725.
Konermann, et al., "Genome-scale transcriptional activation by an engineered CRISPR-Cas9 complex" Nature, 2015, 517:583-588.
Koornneef, et al. "Apoliprotein B Knockdown By AAV-Delivered shRNA Lowers Plasma Cholesterol In Mice" Molecular Therapy, Apr. 2011, 19( 4)731-740.
Lambowitz, et al. "Group II Introns: Mobile Ribozymes that Invade DNA" Cold Spring Harb Perspect Biol., 2011,3:a003616.
Larson, et al. "CRISPR interference (CRISPRi) for sequence-specific control of gene expression" Nature Protocols, 2013, 8(11):2180-2196.
Lewis, et al., "The c-myc and PyMT oncogenes induce different tumor types in a somatic mouse model for pancreatic cancer" Genes & Development, 2003, 17:3127-3138.
Li, et al. "In vivo genome editing restores hemostasis in a mouse model of hemophilia" Nature, 2011, 475(7355):217-221. doi: 10.1038/nature10177.
Li, et al. "Multiplex and homologous recombination-mediated genome editing in *Arabidopsis* and Nicotaina benthamiana using guide RNA and Cas9" Nature Biotechnology, 2013, 31(9):688-691.
Lombardo, et al., "Gene editing in human stem cells using zinc finger nucleases and integrase-defective lentiviral vector delivery" Nature Biotechnology, 2007, 25(11):1298-1306.
Luo, et al., "Highly parallel identification of essential genes in cancer cells", Proceeding of the National Academy of Sciences, 2008, 105(51);20380-20385.
Ma, et al. "A Guide RNA Sequence Design Platform for the CRISPR/Cas9 System for Model Organism Genomes", BioMed Research International, 2014, 2013:270805-4. http://dx.doi.org/10.1155/2014/270805.
Maeder, et al. "CRISPR RNA-guided activation of endogenous human genes" Nature Methods, 2013, 10(10):977-979. doi.10.1038/nmeth.2556.
Makarova, et al, "Evolution and classification of the CRISPR-CAS Systems" Nature Reviews Microbiology, 2011, 9(6):467-477.
Makarova et al. "Unification of Cas protein families and a simple scenario for the origin and evolution of CRISPR-Cas systms" Biology Direct, 2011, 6:38. http:///www.biology-direct.com/content/6/1/38.
Mali, et al. "Supplementary Materials for—RNA-Guided Human Genome Engineering Via Cas9" Science, 2013, 339:823-826.
Mali, et al. "RNA-Guided Human Genome engineering Via Cas9" Science, 2013, DOI: 10.1126/SCIENCE.1232033.
Mali, et al. "Supplementary Information: Use of adjacent sgRNA:Cas9 complexes for transcriptional activation and genome engineering" Nature Biotechnoly, doi:10.1037/nbt.2675.
Malina, et al. "Repurposing CRISPR/Cas9 for in situ functional assays" Genes & Development, 2013, 27:2602-2614.
Marraffini, et al. "Self vs. non-self discrimination during CRISPR RNA-directed immunity" Nature, 2010, 463 (7280):568-571.
Mastroianni, et al. "Group II Intron-Based Gene Targeting Reactions in Eukaryotes" Plos One, 2008, 3(9):e3121. Doi:10.1371/journal.pone.0003121.
Meshorer, et al. "Chromatin in pluripotent embryonic stem cells and differentiation" Nature Reviews Molecular Cell Biology, 2006, 7:540-546.
Miller, et al. "A TALE nuclease architecture for efficient genome editing" Nature Biotechnology, 2011, 29(2): 143-150.
Minton, "How can biochemical reactions within cells differ from those in test tubes?" Journal Of Cell Science, 2006, 119:2863-2869.
Mojica, et al. "Short motif sequences determine the targets of the prokaryotic CRISPR defence system", Microbiology, 2009, 155:733-740.
Morgan, et al. "Inducible Expression and Cytogenetic Effects of the EcoRI Restriction Endonuclease in Chinese Hamster Ovary Cells" Molecular and Cellular Biology, 1988, 8(10):4204-4211.
Mukhopadyay, "On the Same Wavelength," ASBMBTODAY, Aug. 2014, http://www.asbmb.org/asbmbtoday/201408/Features/Doudna/.
Nakamura, et al. "Codon usage tabulated from international DNA sequence databases: status for the year 2000" Nucleic Acids Research, 2000, 28(1): 292.
Nomura, et al., "Low-density lipoprotein receptor gene therapy using helper-dependent adenovirus produces long-term protection

(56) References Cited

OTHER PUBLICATIONS against atherosclerosis in a mouse model of familial hypercholesterolemia" Gene Therapy, 2004, 11:1540-1548.
Nishimasu et al. "Crystal Structure of *Staphylococcus aureus* Cas9," Cell 162, 1113-1126, Aug. 27, 2015.
Oost, "New Tool For Genome Surgery" Science, Feb. 15, 2013, 399:768-770.
Panyam, et al. "Biodegradable nanoparticles for drug and gene delivery to cells and tissue" Advanced Drug Delivery Reviews, 2003, 55:329-347.
Patterson, et al. "Codon optimization of bacterial luciferase (lux) for expression in mammalian cells" J. Ind. Microbio. Biotechnology, 2005, 32:115-123.
Pinera, et al. "RNA-guided gene activation by CRISPR-Cas9-based transcription factors" Nature Methods, 2013, 10(10):973-978.
Andreas, et al. "Enhanced efficiency through nuclear localization signal fusion on phage C31-integrase: activity comparison with Cre and FLPe recombinase in mammalian cells" Nucleic Acids Research, 2002, 30(11):2299-2306.
Asuri, et al. "Directed Evolution of Adeno-Associated Virus for Enhanced Gene Delivery and Gene Targeting in Human Pluripotent Stem Cells" Molecular Therapy, Feb. 2012, 30(2):329-338.
Al-Attar, et al., "Clustered regularly interspaced short palindromic repeats (CRISPRs): the hallmark of an ingenious antiviral defense mechanism in prokaryotes" Biol Chem., 2011, 392(4):277-289.
Baker, "Gene editing at CRISPR Speed" Nature Biotechnology, 2014, 32(4):309-312.
Banaszewska, et al. "Proprotein Convertase Subtilisin/Kexin Type 9: A New Target Molecule For Gene Therapy" Cellular & Molecular Biology Letters, Feb. 2012, 17(2):228-239.
Barrangou, "RNA-mediated programmable DNA cleavage" Nature Biotechnology, Sep. 2012, 30(9):836-388.
Bergemann, et al. "Excision of specific DNA-sequences from integrated retroviral vectors via site-specific recombination" Nucleic Acids Res., 1995, 23(21):4451-4456.
Bikard, et al. "CRISPR Interference Can Prevent Natural Transformation And Virulence Acquisition During In Vivo Bacterial Infection" Cell Host & Microbe, Aug. 2012, vol. 12:177-186.
Boch, et al. "Breaking the Code of DNA Binding Specificity of TAL-Type III Effecors" Science, 2009, 326:1509-1512.
Boch, et al. "Xanthomonas AvrBs3 Family-Type III Effectors: Discovery And Function" Annu. Rev. Phytopathol, 2010, Vo. 48:419-436.
Bogdanove, et al. "TAL Effectors:Customizable Proteins for DNA Targeting" Science, 2011, 333:1843-1846.
Briner, et al. "Guide RNA Functional Modules Direct Cas9 Activity and Orthogonality" Molecular Cell, Oct. 2014, 56:333-339.
Carroll, "A CRISPR Approach To Gene Targeting" Molecular Therapy, 2012, 20(9): 1658-1660.
Cermak, et al. Efficient design and assembly of custom TALEN and other TAL Effector-Based Constructs For DNA Targeting, Nucleic Acids Research (2011) vol. 39, No. 12, e82, p. 1-11.
Chen, et al. "Dynamic Imaging of Genomic Loci in Living Human Cells by an Optimized CRISPR/Cas System" Cell, Dec. 2013, vol. 155:1479-1491.
Jieliang Chen, et al. "An Efficient Antiviral Strategy for Targeting Hepatitis B Virus Genome Using Transcription Activator-Like Effector Nucleases" Molecular Therapy, 2014, 22(2):303-311.
Sidi Chen, et al., "Genome-wide CRISPR Screen in a Mouse Model of Tumor Growth and Metastasis," Cell, 2015, 160:1-15, http://dx.doi.org/10.1016/j.cell.2015.02.038.
Cho, et al. "Generation of Transgenic Mice" Curr Protoc Cell Biol., 2011, 19.11.doi:10.1002/0471143030. cb1911s42.
Choulika, et al., "Transfer of Single Gene-Containing Long Terminal Repeats into the Genome of Mammalian Cells by a Retroviral Vector Carrying the cre Gene and the IoxP site" Journal of Virology, 1996, 70(3):1792-1798.
Christian, et al. "Targeting DNA Double-Strand Breaks With TAL Effector Nucleases" Genetics, Oct. 2010, vol. 186:757-761.
Christian, et al. "Supporting Information-Targeting DNA Double-Strand Breaks With TAL Effector Nucleases" Genetics, 2010, DOI:10.1534/110.120717:1SI-8SI.
Chylinski, et al. "The tractRNA and Cas9 Families of Type II CRISPR-Cas Immunity Systems" RNA Biology, May 2013, 10(5):726-737.
Cong, et al. "Comprehensive interrogation of natural TALE DNA-binding modules and transcriptional repressor domains" Nature Communications, 2012, 3:968, DOI:10/2038/ncomms1962.
Cong, et al., "Multiplex Genome Engineering Using CRISPR-Cas Systems" Science, 2013, 339:819-823.
Cong, et al., "Supplementary Material: Multiplex Genome Engineering Using CRISPR-Cas Systems" Science Express, Jan. 3, 2013. http://www.sciencemag.org/content/339/6121/819/suppl/DC1.
Connor, "Scientific split—the human genome breakthrough dividing former colleagues," Science, The Independent, Apr. 25, 2014, http://www.independent.co.uk/news/science/scientific-split--the-human-genome-breakthrough-dividing-former-colleagues-9300456.html.
CRISPR-associated endonuclease Cas9; Oct. 21, 2012, XP002738511M, http://ibis/exam/dbfetch.jsp?id=uniprot:J7RUA5.
Dahlman, et al. "In vivo endothelial siRNA delivery using polymeric nanoparticles with low molecular weight" Nat. Nanotechnol., 2014, 9(8)648-655. doi:10.1038/nnano.2014.84.
Datensenko, et al. "Molecular memory of prior infections activates the CRISPR/Cas adaptive bacterial immunity system" Nature Communications, Jul. 10, 2012, 3:935, DOI:10.1038/ncomms1937.
Dingwall, et al. "Abstract: A Polypeptide Domain That Specifies Migration Of Nucleoplasmin into The Nucleus" Cell, 1982, 30(2):449-58.
Deltcheva, et al. "CRISPR RNA maturation by trans-encoded small RNA and host Factor RNase III" Nature, Mar. 2011, vol. 471:602-609.
Deltcheva, et al. "Supplementary Information: CRISPR RNA Maturation By Trans-Encoded Small RNA and Host Factor RNase III" www.Nature.com/doi:10.1038/nature09886:1-35.
Drittanti, et al. "High throughput production, screening and anyalysis of adeno-associated viral vectors" Gene Therapy, 2000, 7:924-929.
Ebina, et al. "Harnessing the CRISPR/Cas9 system to disrupt latent HIV-1 provirus" Scientific Reports, 2013, 2:2510, doi:10.1038/srep02510.
Ellis, et al. Macromolecular Crowding: Obvious But Underappreciated, TRENDS in Biochemical Sciences, Oct. 2001, 26(10):597-604.
Ellis, et al. "Zinc-finger nuclease-mediated gene correction using single AAV vector transduction and enhanced by Food and Drug Administration-Approved Drugs" Gene Therapy, 2013, vol. 20:35-42.
Enyeart, et al., "Biotechnological applications of mobile group II introns and their reverse transcriptases: gene targeting, RNA-seq, and non-coding RNA analysis" Mobile DNA, 2014, 5:2, http://www.mobilednajournal.com/contents5/1/2.
Gabriel, et al. "An unbiased genome-wide analysis of zinc-finger nuclease specificity" Nature Biotechnology, Aug. 2011, 29(9):816-823.
Gaj, et al. "ZFN, TALEN, and CRISPR/Cas-Based Methods for Genome Engineering" Trends in Biotechnology, Jul. 2013, 31(7):397-405.
Garneau, et al. "The CRISPR-Cas bacterial immune systems cleaves bacteriophage and plasmid DNA" Nature, Nov. 2010, 468:67-71.
Gasiunas, et al. "Cas9-crRNA ribonucleoprotein complex mediates specific DNA cleavage For adaptive immunity in bacteria" PNAS, Sep. 2012, 109(39): E2579-E2586.
Geißler, et al. "Trancscriptional Activators of Human Genes with Programmable DNA-Specificity" PLone, 2011, 6(5):e19509. Doi: 10.1371/hournal.pone.0019509.
Gilbert, et al. "CRISPR-Mediated Modular RNA-Guided Regulation of Transcription in Eukaryotes" Cell, Jul. 2013, 154:442-451.
Goldfarb, et al. "Synthetic peptides as nuclear localization signals" Nature, Aug. 1986, 322(14):641-644.

(56) References Cited

OTHER PUBLICATIONS

Grens, Enzyme Improves CRISPR A smaller Cas9 protein enables in vivo genome engineering via viral vectors, The Scientist, Apr. 1, 2015.
Gustafsson, et al. "Codon Bias and heterologous protein expression" TRENDS in Biotechnology, Jul. 2004, 22(7): 346-353.
Haft, et al. "A Guild of 45 CRISPR-Associated (Cas) Protein Families and Multiple CRISPR/Cas Subtypes Exist in Prokaryotic Genomes" PLoS Computational Biology, 2005, 1(6):0474-0483.
Haft, D.H., "HMM Summary Page: TIGR04330" 2012, XP-002757584, http://jcvi.org/cgi-bin/tigrfams/HmmReportPage.cgi?acc=TIGR04330.
Hale, et al. "Essential Features and Rational Design Of CRISPR RNAs that Function With The Cas RAMP Module Complex To Cleave RNAs" Molecular Cell, 2012, 45(3):292-302.
Hale, et al. "RNA-Guided RNA Cleavage by a CRISPR RNA-Cas Protein Complex" Cell, 2009, 139:945-956.
U.S. Appl. No. 14/054414, filed Oct. 15, 2013, Leith, Nancy J.
U.S. Appl. No. 14/104,837, filed Dec. 12, 2013, Poliakova-Georgan, Ekaterina.
U.S. Appl. No. 14/104,900, filed Dec. 12, 2013, Leith, Nancy J.
U.S. Appl. No. 14/104,977, filed Dec. 12, 2013, Holland, Paul J.
U.S. Appl. No. 14/104,990, filed Dec. 12, 2013, Leith, Nancy J.
U.S. Appl. No. 14/105,017, filed Dec. 12, 2013, Leith, Nancy J.
U.S. Appl. No. 14/105,031, filed Dec. 12, 2013, Leith, Nancy J.
U.S. Appl. No. 14/105,035, filed Dec. 12, 2013, Leith, Nancy J.
U.S. Appl. No. 14/183,429, filed Feb. 18, 2014, Leith, Nancy J.
U.S. Appl. No. 14/183,471, filed Feb. 18, 2014, Leith, Nancy J.
U.S. Appl. No. 14/183,486, filed Feb. 18, 2014, Leith, Nancy J.
U.S. Appl. No. 14/183,512, filed Feb. 18, 2014, Poliakova-Georgan, Ekaterina.
U.S. Appl. No. 14/222,930, filed Mar. 24, 2014, Leith, Nancy J.
U.S. Appl. No. 14/226,274, filed Mar. 26, 2014, Leith, Nancy J.
U.S. Appl. No. 14/256,912, filed Apr. 18, 2014 Leith, Nancy J.
U.S. Appl. No. 14/258,458, filed Apr. 22, 2014 Leith, Nancy J.
U.S. Appl. No. 14/259,420, filed Apr. 23, 2014, Leith, Nancy J.
U.S. Appl. No. 14/293,498, filed Jun. 2, 2014, Holland, Paul J.
U.S. Appl. No. 14/293,674, filed Jun. 2, 2014, Holland, Paul J.
U.S. Appl. No. 14/324,960, filed Jul. 7, 2014, Brown, Mindy G.
U.S. Appl. No. 14/463,253, filed Aug. 19, 2014, Zhang, Kaijiang.
U.S. Appl. No. 14/481,339, filed Sep. 9, 2014, Marvich, Maria.
U.S. Appl. No. 14/497,627, filed Sep. 26, 2014, Leith, Nancy J.
U.S. Appl. No. 14/523,799, filed Oct. 24, 2014, Leith, Nancy J.
U.S. Appl. No. 14/681,382, filed Apr. 8, 2015, Leith, Nancy J.
U.S. Appl. No. 14/705,719, filed May 6, 2015, Leith, Nancy J.
U.S. Appl. No. 14/738,398, filed Jun. 12, 2015, Ramirez, Delia M.
U.S. Appl. No. 14/738,483, filed Jun. 12, 2015, Woitach, Joseph T.
U.S. Appl. No. 14/970,967, filed Dec. 16, 2015, Leith, Nancy J.
U.S. Appl. No. 14/971,169, filed Dec. 16, 2015, Aron, Kimberly A.
U.S. Appl. No. 14/971,356, filed Dec. 16, 2015, Noble, Marcia Stephens.
U.S. Appl. No. 14/972,523, filed Dec. 17, 2015, Montanari, David A.
U.S. Appl. No. 14/972,927, filed Dec. 17, 2015, Leonard, Arthur S.
U.S. Appl. No. 14/973,062, filed Dec. 17, 2015, Leith, Nancy J.
U.S. Appl. No. 14/990,444, filed Jan. 7, 2016, Leith, Nancy J.
U.S. Appl. No. 14/991,083, filed Jan. 8, 2016, Leith, Nancy J.
U.S. Appl. No. 15/160,710, filed May 20, 2016, Leith, Nancy J.
U.S. Appl. No. 15/171,141, Jun. 2, 2016, Noakes, Suzanne Marie.
U.S. Appl. No. 15/179,711, filed Jun. 10, 2016, Ware, Deborah K.
U.S. Appl. No. 15/179,799, filed Jun. 10, 2016, Leonard, Arthur S.
U.S. Appl. No. 15/179,938, filed Jun. 10, 2016, Leith, Nancy J.
U.S. Appl. No. 15/179,941, filed Jun. 10, 2016, Leith, Nancy J.
U.S. Appl. No. 15/217,489, filed Jul. 22, 2016, Brown, Mindy G.
U.S. Appl. No. 15/229,702, filed Aug. 5, 2016, Leith, Nancy J.
U.S. Appl. No. 15/230,161, filed Aug. 5, 2016, Leith, Nancy J.
U.S. Appl. No. 15/330,876, filed Nov. 7, 2016, Holland, Paul J.
U.S. Appl. No. 15/349,603, filed Nov. 11, 2016, Marvich, Maria.
U.S. Appl. No. 15/430,260, filed Feb. 10, 2017, Leith, Nancy J.
U.S. Appl. No. 15/436,396, filed Feb. 17, 2017, Leonard, Arthur S.
U.S. Appl. No. 15/620,098, filed Jun. 12, 2017, Montanari, David A.
U.S. Appl. No. 15/620,391, filed Jun. 12, 2017, Hill, Kevin Kai.
U.S. Appl. No. 15/633,126, filed Jun. 26, 2017, Leith, Nancy J.
U.S. Appl. No. 15/834,736, filed Dec. 7, 2017, Not Assigned.
U.S. Appl. No. 15/838,064, filed Dec. 11, 2017, Leith, Nancy J.
U.S. Appl. No. 15/838,720, filed Dec. 12, 2017, to Be Assigned.
U.S. Appl. No. 15/844,528, filed Dec. 16, 2017, Leith, Nancy J.
U.S. Appl. No. 15/887,377, filed Feb. 2, 2018, Leith, Nancy J.
U.S. Appl. No. 15/967,464, filed Apr. 30, 2018, Leith, Nancy J.
U.S. Appl. No. 15/967,495, filed Apr. 30, 2018, Leith, Nancy J.
U.S. Appl. No. 15/967,510, filed Apr. 30, 2018, to Be Assigned.
U.S. Appl. No. 16/012,692, filed Jun. 19, 2018, Wilder, Cynthia B.
U.S. Appl. No. 16/158,295, filed Oct. 11, 2018, Leith, Nancy J.
U.S. Appl. No. 16/177,403, filed Oct. 31, 2018, to Be Assigned.
U.S. Appl. No. 16/178,551, filed Nov. 1, 2018, to Be Assigned.
U.S. Appl. No. 16/262,905, filed Jan. 30, 2019, to Be Assigned.
"Crispr genome engineering"XP055167591, Oct. 2013, https://web.archive.org/web/2013100500 [retrieved on Feb. 5, 2015].
"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].
"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).
Abudayyeh, et al., "C2c2 is a single-component programmable RNA-guided RNA-targeting CRISPR effector," Science, vol. 10, dated 2016.
Addgene Materials May 2015.
Addgene Materials Oct. 2014 including Addgene News 2013.
Addgene Reagent distribution list for Zhang Lab.
Addgene, "gRNA_Cloning vector", retrieved on Jan. 30, 2019, <https://www/addgenen.org/41824/>, 2 pages.
Alberts, et al., Molecular Biology of The Cell, fourth edition, 2002, 671-676.
*Arbitron, Inc.* v. *Kiefl*, No. 09-CV-04013 PAC, 2010 WL 3239414, at*1 (S.D.N.Y. Aug. 13, 2010).
Ausubel, et al. "Compendium of Methods from Current Protocols in Molecular Biology", Short Protocols in Molecular Biology, Fourth Edition, 1999, 9: 9-3-9-4.
Autofluorescence MIT Flow Cytometry Core Facility (2018), 6 pages.
Baena-Lopez, L., et al., "Accelerated homologous recombination and subsequent genome modification in *Drosophila*," Development, vol. 140, No. 23, pp. 4818-4825, dated Dec. 2013, 18 pages, including Supplementary Material.
Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, 78(3):1181-1194.
Balboa et al., "Conditionally Stabilized dCas9 Activator for Controlling Gene Expression in Human Cell Reprogramming and Differentiation, (plus Supplemental Information)", Stem Cell Reports, vol. 5, No. 3, Sep. 8, 2015, pp. 448-459 16PP.
Barrangou and Van Der Oost (Eds.), "CRISPR-Cas Systems," Springer Heidelberg (2013; written in 2012 before the publication of Cong et al.).
Barrangou, R et al.: "CRISPR provides acquired resistance against viruses in prokaryotes," Science, vol. 315, pp. 1709-1712, dated Mar. 23, 2007, 5 pages.
Bassett, et al. "Highly Efficient Targeted Mutagenesis of *Drosophila* with the CRISPR/Cas9 System" Cell Reports, 2013, 4:220-228.
Bassett, et al., "A Genome-Wide CRISPR Library for High-Throughput Genetic Screening in *Drosophila* Cells," Journal of Genetics and Genomics, vol. 42, pp. 301-309, dated 2015.
Bauer, et al., "An Erythroid Enhancer of BCL11A Subject to Genetic Variation Determines Fetal Hemoglobin Level," Science, vol. 342, pp. 253-257, dated 2013.
Beerli, et al. "Positive and negative regulation of endogenous genes by designed transcription factors:" PNAS, 2000, 97(4):1495-1500.
Beerli, et al. "Toward controlling gene expression at will: Specific regulation of the erbB-2/HER-2 promoter by using polydactyl zinc

(56) References Cited

OTHER PUBLICATIONS finger proteins constructed from modular building blocks", Proc. Natl. Acad. Sci., 1998, 95:14628-14633.

Beerli, R., et al., "Engineering polydactyl zinc-finger transcription factors," Nature Biotechnology, vol. 20, pp. 135-141, dated Feb. 2002, 7 pages.

Bennett et al., "Stable transgene expression in rod photoreceptors after recombinant adeno-associated virus-mediated gene transfer to monkey retina", Proc. Natl. Acad. Sci., USA, vol. 96, Aug. 1999, pp. 9920-9925.

Berns, K., et al. "A Large-Scale RNAi Screen in Human Cells Identifies New Components of the p53 Pathway," Nature 2004, vol. 428, pp. 431-437, dated Mar. 25, 2004, 7 pages Bhaya, D., et al., "CRISPR-Cas Systems in Bacteria and Archaea: Versatile Small RNAs for Adaptive Defense and Regulation," Annual Review of Genetics, vol. 45, No. 1, pp. 273-297, dated Dec. 15, 2011, 27 pages.

Bikard, et al. Supplementary Information for: "CRISPR Interference Can Prevent Natural Transformation And Virulence Acquisition During In Vivo Bacterial Infection," Cell Host & Microbe, vol. 12, No. 2, pp. 177-186, dated Aug. 16, 2012, 10 pages.

Birch, et al. "Plant Transformation: Problems and Strategies for Practical Application", Annu. Rev. Plant Physiol. Plant Mol. Biol., 1997, 48:297-326.

Bloom et al., "Inactivation of hepatitis B virus replication in cultured cells and in vivo with engineered transcription activator-like effector nucleases", Molecular Therapy, Aug. 20, 2013, vol. 21, No. 10, pp. 1889-1897.

Bobis-Wozowicz, S., et al., "Targeted genome editing in pluripotent stem cells using zinc-finger nucleases," Methods, vol. 53, pp. 339-346, dated 2011, 8 pages.

Boden, et al. "Efficient Gene Transfer of HIV-1-Specific Short Hairpin RNA into Human Lymphocytic Cells Using Recombinant Adeno-associated Virus Vectors", Molecular Therapy, 2004, 9(3):396-402.

Bouard, et al. "Themed Section: Vector Design and Drug Delivery Review, Viral vectors: from virology to transgene expression", British Journal of Pharmacology, 2009, 157:153-165.

Boutros et al.: "Genome-wide RNAi analysis of growth and viability in Drosophila cells," Science, American Association for the Advancement of Science, vol. 303, No. 5659, pp. 832-835, dated Feb. 6, 2004, 4 pages.

Branden, C., and Tooze, J., "Prediction, Engineering, and Design of Protein Structures," Introduction to Protein Structure, Chapter 16, p. 247, Garland Publishing, Inc., New York, dated 1991, 3 pages.

Brouns, S, "A Swiss Army Knife of Immunity," Science, vol. 337, No. 6096, pp. 808-809, dated Aug. 17, 2012, 3 pages.

Brouns, S., et al., "Small CRISPR RNAs Guide Antiviral Defense in Prokaryotes," Science, vol. 321, pp. 960-964, dated Aug. 15, 2008, 6 pages.

Campeau, et al. "A Versatile Viral System for Expression and Depletion of Proteins in Mammalian Cells", PLoS One, 2009, 4(8):e6529.

Canver, et al., "BCL11A enhancer dissection by Cas9-mediated in situ saturating mutagenesis," Nature, vol. 527, pp. 192-197, including Supplementary Material, dated 2015.

Carr, et al., "Genome engineering", Nature Biotechnology, 2009, 27(12):1151-1162.

Carroll, "Genome Engineering With Zing-Finger Nucleases", Genetics, 2011, 188:773.782.

Carroll, "Progress and prospects: Zinc-finger nucleases as gene therapy agents", Gene Therapy, 2008, 15:1463-1468.

Chan, et al. "Characterization of the Kinetochore Binding Domain of CENP-E Reveals Interactions with the Kinetochore Proteins CENP-F and hBuBR1", The Journal of Cell Biology, 1998, 143:49-63.

Chan, Wai-Ting, et al. "Toxin-Antitoxin Genes of the Gram-Positive Pathogen *Streptococcus pneumoniae*: So Few and Yet So Many", Microbiology and Molecular Biology Reviews, 2012, 76(4)773-791.

Chang, N., et al. "Genome editing with RNA-guided Cas9 nuclease in Zebrafish embryos", Cell Research, vol. 23, pp. 465-472, dated Mar. 26, 2013, 8 pages.

Chen, Fuqiang et al. "High-frequency genome editing using ssDNA oligonucleotides with zinc-finger nucleases". Nature Methods, 2011, 8(9)753-755, including Supplemental Online Methods.

Chinnasamy, D., et al., "Multicistronic lentiviral vectors containing the FMCV 2A Cleavage factor demonstrate robust expression of encoded genes at limiting MOI," Virology Journal, vol. 3, No. 4, dated Mar. 15, 2006, 16 pages.

Chiu et al., "Engineered GFP as a vital reporter in plants", Current Biology, (1996), 6(3):325-330.

Chou, Jy, and Mansfield, BC, "Recombinant AAV-directed gene therapy for type I glycogen storage diseases," Expert Opinion on Biological Therapy, vol. 11, No. 8, pp. 1011-1024, dated Apr. 20, 2011, 21 pages.

Chylinski, et al. "Classification and evolution of type II CRISPR-Cas systems", Nucleic Acids Research, 2014, 42(10):6091-6105,doi:10.1093Inarlgku241.

Clark, K., et al., "A Tale of Two Nucleases: Gene Targeting for the Masses?" Zebrafish, vol. 8, No. 3, pp. 147-149, dated 2011, 3 pages.

Cockrell, "Berkeley's Wikipedian-in-residence is a first," NewsCenter, Feb. 25, 2014.

Community Corner, "CRISPR technology for gene therapy," Nature Medicine, vol. 20, No. 5, pp. 476-477, dated May 2014, 3 pages.

Cong, et al., Oct. 2012 Manuscript including Supplementary Materials, "CRISPR-Assisted Mammalian Genome Engineering," published as "Multiplex Genome Engineering Using CRISPR-Cas Systems," Science, vol. 339, pp. 819-823, dated Feb. 15, 2013, 36 pages.

Cong, L., et al., "In Vivo Genome Engineering With AAV Vector Carrying CRISPR-Cas9 System," Molecular Therapy, vol. 22, Supplement 1, p. S214, dated May 23, 2014, 1 page.

Cong, L., et al., Supplementary Material for: "Multiplex Genome Engineering Using CRISPR-Cas Systems," Science Express, dated Jul. 5, 2012.

Costantino, et al., "Enhanced levels of alpha Red-mediated recombinants in mismatch repair mutants", PNAS, 100(26):15748-15753.

Cotropia, et al., "Copying in Patent Law," N.C.L. Rev., Stanford Public Law Working Paper No. 1270160 (2009), 87:1421.

Cummings et al., "Fourteen and counting: unraveling trinucleotide repeat diseases", Human Molecular Genetics, 2000, vol. 9, No. 6, pp. 909-916.

Daboussi, F., et al., "Chromosomal context and epigenetic mechanisms control the efficacy of genome editing by rare-cutting designer endonucleases," Nucleic Acids Research, vol. 40, No. 13, pp. 6367-6379, dated Jul. 13, 2012, 13 pages.

Dai, et al. "Genes:Structures and Regulation: The Transcription Factors GATA4 and dHAND Physically Interact to Synergistically Activate Cardiac Gene Expression through a p300-dependent Mechanism", J. Biol. Chern., 2002, 277:24390-24398.

Daley, J., and Wilson, T., "Rejoining of DNA Double-Strand Breaks as a Function of Overhang Length," Molecular and Cellular Biology, vol. 25, No. 3, pp. 896-906, dated Feb. 2005, 11 pages.

Damian, M., and Porteus, M., "A Crisper Look at Genome Editing: RNA-guided Genome Modification," Molecular Therapy, vol. 21, No. 4, pp. 720-722, dated Apr. 2013, 3 pages.

Database GenBank, "*Staphylococcus aureus* subsp.aureus ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.

Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.

Database UniProtKB/TrEMBL [online], Accession No. Q0P897, "The genome sequence of the food-borne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.

(56) References Cited

OTHER PUBLICATIONS

Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.
Database UniProtKB/TrEMBL, Accession No. Q0P897, http://www.uniprot.org/uniprot/Q0P897.txt?version=28, dated Oct. 3, 2012, 1 page.
Database UniProtKB/TrEMBL, Accession No. Q6NK13, http://www.uniprot.org/uniprot/Q6NKI3.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; AN 2014-J79552, XP-002737563, 2 pages.
Declaration of Feng Zhang for U.S. Appl. No. 14/054,414 dated Jan. 30, 2014, 10 pages.
Declaration of Paul Simons dated Dec. 22, 2015.
Deltcheva, et al. "Supplementary Information: CRISPR RNA Maturation by Trans-Encoded Small RNA and Host Factor RNase III" www.Nature.com/doi:10.1038/nature09886:1-35, 2011.
DiCarlo, et al. "Genome engineering in Saccharomyces cerevisiae using CRISPTR-Cas systems", Nucleic Acids Research, 2013, 41(7):4336-4343, doi:10.1093/nar/gkt135.
Dingwall, et al. "The Nucleoplasmin Nuclear Location Sequence Is Larger and More Complex than That of SV-40 Large T Antigen", The Journal of Cell Biology, 1988, 107:841-849.
Do, et al. "Identitication of multiple nuclear localization signals in murine Elf3, an ETS transcription factor" FEBS Letters, 2006, 580:1865-1871.
Doench, et al., "Rational design of highly active sgRNAs for CRISPR-Cas9-mediated gene inactivation," Nature Biotechnology, vol. 32, No. 12, pp. 1262-1267, including Supplementary Material, dated 2014.
Dominguez, et al., "Beyond editing: repurposing CRISPR-Cas 9 for precision genome regulation and interrogation" Nat Rev Mol Cell Biol., 2016, 17(1):5-15, doi:10.1038/nrm.2015.2.
Dong, et al. "The crystal structure of Cpf1 in complex with CRISPR RNA," Nature, vol. 532, pp. 523-525, including Research Letter, dated 2016.
Dworetzky, S., et al., "The Effects of Variations in the Number and Sequence of Targeting Signals on Nuclear Uptake," The Journal of Cell Biology, vol. 107, pp. 1279-1287, dated Oct. 1988, 9 pages.
Ellis, Hilary, et al. "High efficiency mutagenesis, repair, and engineering of chromosomal DNA using single-stranded oligonucleotids" PNAS, 2001, 98(12):6742-6746.
Espinoza, et al., "Characterization of the structure, function, and mechanism of B2 RNA, an ncRNA repressor of RNA polymerase II transcription", RNA, 2007, 13(4):583-596.
Excerpt from Declaration of Feng Zhang, dated Sep. 9, 2015.
*Federal Circuit decision in Dow Chemical Co. v. Nova Chemicals Corp.*, Appeal Nos. 2014-1431, 2014-1462 (Fed. Cir. Aug. 28, 2015) (Dow v. Nova), 25 pages.
Feldgarden et al., "*Staphylococcus aureus* M0408 acrHk-supercont1.1, whole genome shotgun sequence", NCBI Reference Sequence: NK_KB821326.1, Direct Submission, Dec. 10, 2012, pp. 1-4.
Fieck, et al. "Modifications of the *E.coli* Lac repressor for expression in eukaryotic cells: effects of nuclear signal sequences on protein activity and nuclear accumulation", Nucleic Acids Research, 1992, 20(7):1785-1791.
Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, No. 12, pp. 5495-5503, dated 1988, 10 pages.

Fleming, J., et al.: "Adeno-Associated Virus and Lentivirus Vectors Mediate Efficient and Sustained Transduction of Cultured Mouse and Human Dorsal Root Ganglia Sensory Neurons," Human Gene Therapy, vol. 12, pp. 77-86, dated Jan. 1, 2001, 10 pages.
Foecking, et al. "Powerful and versatile enhance-promoter unit for mammalian expression vectors", Gene, 1986, 101-105.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.
Freitas, et al. "Mechanisms and Signals for the Nuclear Import of Proteins", Current Genomics, 2009, 10:550-557.
Fu et al, "Targeted genome editing in human cells using CRISPR/Cas nucleases and truncated guide RNAsc", Jan. 1, 2014, The Use of CRISPR/Cas9 ZFNs and Talens in Generating Site-Specific Genome Alterations; Methods in Enzymology; ISSN 1557-7988, vol. 546, Elsevier, NL, pp. 21-45.
Fu, et al. "High-frequency off-target mutagenesis induced by CRISPR-Cas nucleases in human cells", Nature Biotechnology, 2013, 31(9):822-826.
Gaj, T., et al., "Targeted Gene knockout by direct delivery of zinc-finger nuclease proteins," Nature Methods, vol. 9, No. 8, pp. 805-807, dated Aug. 2012, 5 pages.
Gao, et al. "Engineered Cpf1 Enzymes with Altered PAM Specificities", BioRxiv Preprint, XP-002769442, 2016, doi:http://dx.doi.org/10.1101/091611, 1-13, including Figure Legends.
Gao, et al. "Engineered Cpf1 variants with altered PAM specificities", Nature Biotechnology, 2017, 1-4, doi:10.1038/nbt.3900, advanced online publication including Supplementary Information.
Garcia-Bustos, et al. "Nuclear protein localization", Biochimica et Biophysica Acta, 1991, 1071:83-101.
Gardlik, R., et al., "Vectors and delivery systems in gene therapy," Medical Science Monitor, vol. 11, No. 4, pp. RA110-RA121, dated Apr. 1, 2005, 12 pages.
Garg, et al. "Engineering synthetic TAL effectors with orthogonal target sites", Nucleic Acids Research, 2012, 40(15):7584-7595, doi:10.1093/nar/gks404.
Garriga-Canut, M., et al., "Synthetic zinc finger repressors reduce mutant huntingtin expression in the brain of R6/2 mice," Proceedings of the National Academy of Sciences, vol. 109, No. 45, pp. E3136-E3145, dated Nov. 6, 2012, 10 pages.
Geisinger et al., "In vivo blunt-end cloning through CRISPR/CAS9-facilitated non-homologous end-joining", Nucleic Acid Research Advance Access, Jan. 13, 2016, pp. 1-15.
Gomaa et al. "Programmable removal of bacterial strains by use of genome-targeting CRISPR-Cas systems", MBio., 2014, 5(1):e00928-13.
Goncalves, M., et al., "Concerted nicking of donor and chromosomal acceptor DNA promotes homology-directed gene targeting in Human Cells," Nucleic Acids Research, vol. 40, No. 8, pp. 3443-3455, dated Dec. 20, 2011, 13 pages.
Gratz, et al. "Genome Engineering of *Drosophila* with the CRISPR RNA-Guided Cas9 Nuclease", Genetics, 2013, 194:1029-1035.
Greenspan, et al. "Two Nuclear Location Signals in the Influenza Virus NS1 Nonstructural Protein", Journal of Virology, 1988, 62(8):3020-3026.
Grieger, J., and Samulski, R., "Packaging Capacity of Adeno-Associated Virus Serotypes: Impact of Larger Genomes on Infectivity and Postentry Steps," Journal of Virology, vol. 79, No. 15, pp. 9933-9944, dated Aug. 2005, 12 pages.
Grissa, I., et al., "CRISPRFinder: a web tool to identify clustered regularly interspaced short palindromic repeats," Nucleic Acids Research, vol. 35, pp. W52-W57, dated 2007, 6 pages.
Guan, et al. "Heritable endogenous gene regulation in plants with designed polydactyl zinc finger transcription factors", PNAS, 2002, 99(20):13296-13301.
Habib, N., Assignment to Broad Institute, dated Jun. 9, 2014, 4 pages.
Hall, B., et al., "Overview: Generation of Gene Knockout Mice," Current Protocols in Cell Biology, unit 19.12, suppl. 44, pp. 1-17, dated 2009, 17 pages.
Harrison et al., "A CRISPR view of development", Genes & Development, vol. 28, No. 17, Sep. 1, 2014, pp. 1859-1872.

(56) References Cited

OTHER PUBLICATIONS

Heintze, et al. "A CRISPR CASe for high-throughput silencing", Frontiers in Genetics, Oct. 2013, 4(193): DOI:10.3389/gfene.2013.00193.

Hicks, et al. "Protein Import Into the Nucleus: An Integrated View", Annu. Rev. Cell Dev. Biol., 1995, 11:155-188.

Ho, et al., "Targeting non-coding RNAs with the CRISPR/Cas9 system in human cell lines," Nucleic Acids Research, vol. 43, No. 3, p. e17, dated 2015.

Hockemeyer, et al. "Highly efficient gene targeting of expressed and silent genes in human ESCs and iPSCs using zinc finger nucleases", Nat Biotechnol., 2009, 27(9):851-857, doi:10.1038/nbt.1562.

Holkers, M., et al., "Adenoviral vector DNA for accurate genome editing with engineered nucleases," Nature Methods, vol. 11, No. 10, pp. 1051-1057, Aug. 24, 2014, 8 pages. (Only Abstract Available).

Holmes, "CRISPR Genome Engineering Resources" XP055167586, Oct. 2, 2013, https://groups.google/forum/#!top1c/crispr/5BpJj_Y3yIG [retrieved on Feb. 5, 2015].

Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-l/rziHxKT76pYJ [retrieved on Feb. 6, 2015].

Houdebine, L., "The methods to generate transgenic animals and to control transgene expression," Journal of Biotechnology, vol. 98, pp. 145-160, dated 2002, 16 pages.

*Huang v. California Institute of Technology*, 2004 WL 2296330 (C.D. Cal. Feb. 18, 2004).

Hung, S., et al., "AAV-Mediated CRISPR/Cas Gene Editing of Retinal Cells in Vivo," Investigative Ophthalmology & Visual Science, vol. 57, No. 7, pp. 3470-3476, dated Jun. 2016, 7 pages.

Hwang Woong, et al. "Efficient In Vivo Genome Editing Using RNA-Guided Nucleases", Nat. Biotechnol., 2013, 31 (3):227.229. doi. 1.1038/mbt.2501.

Imagawa, et al. "Two nuclear localization signals are required for nuclear translocation of nuclear factor 1-A", FEBS Letters, 2000, 484118-124.

Incontro, S., et al., "Efficient, Complete Deletion of Synaptic Proteins using CRISPR," Neuron, vol. 83, No. 5, pp. 1051-1057, dated Sep. 3, 2014, 13 pages.

Iwamoto et al., "A General Chemical Method to Regulate Protein Stability in the Mammalian Central Nervous System", Chemistry and Biology, Current Biology, London, GB, vol. 17, No. 9, Sep. 24, 2010, pp. 981-988.

Jackson, A., et al. "Widespread siRNA "off-target"transcript silencing mediated by seed region sequence complementarity," RNA 2006, vol. 12, No. 7, dated Mar. 16, 2006, 10 pages.

Jao, et al. "Efficient multiplex biallelic zebrafish genome editing using a CRISPR nuclease system", Proceeding of the National Academy of Sciences, 2013, www.pnas.org/cgi/doi/10.1073/pnas.1308335110.

Jinek, M., et al., Figures and figure supplements for: "RNA-programmed genome editing in human cells," eLIFE, vol. 2, No. e00471, dated Jan. 29, 2013, 5 pages.

Joseph, T., and Osman, R., "Thermodynamic basis of selectivity in guide-target-mismatched RNA interference," Proteins, vol. 80, No. 5, pp. 1283-1298, dated May 2012, 26 pages.

Joshi, et al., "Evolution of I-Scel homing endonucleases with increased DNA recognition site specificity", Journal of Molecular Biology, 2011, 405(1):185-200; ePub: Oct. 26, 2010.

Joung, et al. "TALENs: a widely applicable technology for targeted genome editing", Nat Ref. Mol. Cell Biol., 2013, 14(1):49-55. doi:10.1038/nrm3586.

Kalderon, et al. "A Short Amino Acid Sequence Able to Specify Nuclear Location", Cell, 1984, 39:499-509.

Kiani, et al. "CAS9 gRNA engineering for genome editing, activation and repression", Nature Methods, Advanced Online Publication, 2015, DOI:10.1038/NMETH.3580.

Kim et al., "High Cleavage Efficiency of a 2A Peptide Derived from Porcine Teschovirus-1 in Human Cell Lines, Zebrafish and Mice," PLoS One, 6(4):el 8556, (2011).

Kim, E., et al., "Precision genome engineering with programmable DNA-nicking enzymes," Genome Research, vol. 22, pp. 1327-1333, dated 2012, 8 pages.

Kim, S., et al., "CRISPER RNAs trigger innate immune responses in human cells," Genome Research, pp. 1-7, dated Feb. 22, 2018, 8 pages.

Kinnevery, P., et al., "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, No. 1, pp. 524-531, dated Jan. 2013, 8 pages.

Kleinstiver et al., "High-fidelity CRISP-Cas9 nucleases with no detectable genome-wide off-target effects", Nature, vol. 529, No. 7587, Jan. 28, 2016, pp. 490-495.

Kleinstiver, et al. "Engineered CRISPR-Cas9 nucleases with altered PAM specificities," Nature, vol. 523, pp. 481-485, including Research Letter, dated 2015.

Kondo, et al. "Highly Improved Gene Targeting by Germline-Specific Cas9 Expression in *Drosphila*", Genetics, 2013, 195:715-721.

Kosugi, et al. "Six Classes of Nuclear Localization Signals Specific to Different Binding Grooves of Importin a . . . " The Journal of Biological Chemistry, 2009, 284(1):478-485.

Kowalski, Thomas J., PowerPoint Presentation, "Interview Sep. 9, 2015."

Krauer, et al. "Identification of the nuclear localization signals within the Epstein-Barr virus EBNA-6 protein", Journal of General Virology, 2004, 85:165-172.

Kuhlman, et al. "A place for everything$201 D Chromosomal intergration of large constructs", Bioengineered Bugs, Jul./Aug. 2010, 1(4)296-299.

Kuhlman, et al. "Site-specific chromosomal integration of large synthetic constructs", Nucleic Acids Research, 2010, 38(6):1-10, doi:10.1093/nar/gkp1193.

Kumar, M., et al., "Systematic Determination of the Packaging Limit of Lentiviral Vectors," Human Gene Therapy, vol. 12, pp. 1893-1905, dated Oct. 10, 2001, 21 pages.

Kuwayama, H., "Enhancement of Homologous Recombination Efficiency by Homologous Oligonucleotides," Cell Interaction Sivakumar Gowder, IntechOpen, DOI: 10.5772/47779, dated Oct. 10, 2012, 12 pages.

Lanford, et al. "Induction of Nuclear Transport with a Synthetic Peptide Homologous to the SV40 T Antigen Transport Signal", Cell, 1986, 46:575-582.

Lange, et al. "Classical Nuclear Localization Signals: Definition, Function, and Interaction with Importin$2026" J. Biol. Chem., 2007, 282(8):5101-5105.

Lebherz, C., et al., "Gene therapy with novel adeno-associated virus vectors substantially diminished atherosclerosis in a murine model of familial hypercholesterolemia," The Journal of Gene Medicine, vol. 6, pp. 663-672, dated Mar. 2, 2004, 10 pages.

Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.

Leenay, et al. "Identifying and Visualizing Functional PAM Diversity across CRISPR-Cas Systems", Molecular Cell, 2016, 62:137-147.

Lemay, et al. "Folding of the Adenine Riboswitch", Chemistry & Biology, 2006, 13:857-868.

Levitt, J., et al., "Intrinsic fluorescence and redox changes associated with apoptosis of primary human epithelial cells," Journal of Biomedical Optics, vol. 11, No. 6, pp. 064012 1-10, dated Nov./Dec. 2006, 10 pages.

Lewin, et al. "Nuclear localization sequences target proteins to the nucleus" Cells, 2006, 5:224.

Li et al., "Coevolution of CRISPR-Cas system with bacteria and phages", Hereditas, vol. 33, No. 3, Mar. 31, 2011, pp. 213-218.

(56) References Cited

OTHER PUBLICATIONS

Li, P., et al., "Biallelic knockout of alpha-1,3 galactosyltransferase gene in porcine liver-derived cells using zing finger nucleases," Journal of Surgical Research, vol. 181, No. 1, pp. E39-E45, dated Jul. 3, 2012, 7 pages.

Li, Ting, et al. "Modularly assembled designer TAL effector nucleases for targeted gene knockout and gene replacement in eukaryotes" Nucleic Acids Research, 2011, 39(14):6315-6325.

Liu, et al. "Epstein-Barr Virus DNase Contains Two Nuclear Localization Signals Which Are Different in Sensitivity to the Hydrophobic Regions" Virology, 1998, 247:62-73.

Los, et al. "Halotag Technology: Cell Imaging and Protein Analysis" Cell Notes, 2006, 14:10-14.

Luo, Ming, et al. "Multiple Nuclear Localization Sequences Allow Modulation of 5-Lipoxygenase Nuclear Import" Traffic, 2004, 5:847-854.

Lyssenko, et al. "Cognate putative nuclear localization signal effects strong nuclear localization of a GFP reporter and facilitates gene expression studies in Caenorhabditis elegans" BioTechniques, 2007, 43:596-600.

Maczuga, P., et al., "Embedding siRNA sequences targeting Apolipoprotein B100 in shRNA and miRNA scaffolds results in differential processing and in vivo efficacy," Molecular Therapy, vol. 21, No. 1, pp. 217-227, dated Jan. 2013, 11 pages.

Madisen et al., "A robust and high-throughput Cre reporting and characterization system for the whole mouse brain," Nat. Neurosci., 13(1): 133-140, (2010) (author manuscript; available in PMC Jul. 1, 2010).

Maeder, M., and Gersbach, C., "Genome-editing Technologies for Gene and Cell Therapy," Molecular Therapy, vol. 24, No. 3, pp. 430-446, dated Mar. 2016, 17 pages.

Maeder, M., et al., "Robust, synergistic regulation of human gene expression using TALE activators," Nature Methods, vol. 10, No. 3, pp. 243-245, dated Mar. 2013, 9 pages.

Mahfouz, et al. "Targeted transcriptional repression using a chimeric TALE-SRDX repressor protein" Plant Mol Biol, 2012, 78:311-321.

Mahfouz, M., et al. "De novo-engineered transcription activator-like effector (TALE) hybrid nuclease with novel DNA binding specificity creates double-strand breaks," Proceedings of the National Academy of Science, vol. 108, No. 6, pp. 2623-2628, dated Feb. 8, 2011, 6 pages.

Makarova, et al. "An updated evolutionary classification of CRISPR-Cas systems" Nature Reviews-Microbiology, 2015, 13:722-736.

Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages. (Includes Supplemental Information).

Manjunath, N et al., "Newer Gene Editing Technologies toward HIV Gene Therapy," VIRUSES, vol. 5, No. 11, pp. 2748-2766, dated Nov. 14, 2013, 19 pages.

*Manning v. Paradis*, 296 F.3d 1098 (Fed. Cir. 2012).

Marraffini, L., "CRISPR-Cas Immunity against Phages: Its Effects on the Evolution and Survival of Bacterial Pathogens," PLOS, Pathogens, dated Dec. 12, 2013, 6 pages.

Marraffini, L, Assignment to Rockefeller University, dated Dec. 12, 2013, 3 pages.

*Maxwell v. The Stanley Works*, 2006 WL 1967012, *5 (M.D. Tenn. Jul. 11, 2006).

Mincer, J., and Simon, S., "Simulations of nuclear pore transport yield mechanistic insights and quantitative predictions," Proceedings of the National Academy of Science, vol. 108, No. 31, pp. E351-E358, dated Aug. 2, 2011, 8 pages.

Mojica, F. J., et al., Supplementary Material for: "Short motif sequences determine the targets of the prokaryotic CRISPR defence system," Microbiology, vol. 155, No. 3, pp. 733-740, dated Mar. 1, 2009, 8 pages.

Morbitzer, et al. "Assembly of custom TALE-type DNA binding domains by modular cloning" 2011, 39(13):5790-5799.

Morbitzer, et al. "Regulation of selected genome loci using de novo-engineered transcription activator-like effector (TALE)-type transcription factors" PNAS, 2010, 108(50):21617-21622.

Morin, et al. "Nuclear Localization of the Adenovirus DNA-Binding Protein: Requirement for Two Signals and Complementation during Viral Infection" Molecular and Cellular Biology, 1989, 9(10):4372-4380.

Moscou, et al. "A Simple Cipher Governs DNA Regognition by TAL Effectors" Science, 2009, 326:1501.

Mussolino, et al. "TALE nucleases: tailored genome engineering made easy" Current Opinion in Biotechnology, 2012, 23(5):644-650.

Musunuru, "Abstract 18593: Use of a CRISPR/Cas System for Cardiovascular Disease Modeling and Therapeutic Applications", Circulation, vol. 128, No. 22, Suppl. 1, Nov. 26, 2013, 4 pages (Meeting info: American Heart Association, 2013 Scientific Sessions and Resuscitation Science Symposium, Dallas, TX, US, Nov. 16-20, 2013).

Muther, N., et al.: "Viral Hybrid Vectors for Somatic Integration— Are They the Better Solution?" Viruses, vol. 1, pp. 1295-1324, dated Dec. 15, 2009, 30 pages.

Nagarajan, et al. "A Hierarchy of Nuclear Localization Signals Governs the Import of the Regulatory Factor X Complex Subunits and MHC Class II Expression" The Journal of Immunology, 2004, 173:410.419.

Nakai, et al. "PSORT: a program for detecting sorting signals in proteins and predicting their subcellular localization" Trends in Biochem Sciences, 1999 24:34-35.

Noguchi, et al. "PDX-1 Protein Containing Its Own Antennapedia-Like Protein Transduction Domain Can Transduce Pancreatic Duct and Islet Cells" Diabetes, 2003, 52:1732-1737.

Notice of Opposition filed Aug. 11, 2017 by Schlich against EP Patent No. 2840140.

Notice of Opposition filed Aug. 14, 2017 by Grund against EP Patent No. 2840140.

Notice of Opposition filed Aug. 16, 2017 by Mathys & Squire LLP against EP Patent No. 2840140.

Notice of Opposition filed by Aug. 16, 2017 by Vossius against EP Patent No. 2840140.

O'Hare, et al. "Transformation of mouse fibroblasts to methotrexate resistance by a recombinant plasmid expressing a prokaryotic dihydrofolate reductase" Proc. Natl. Acad. Sci., 1981, 78(3):1527-1531.

Opposition Against Appl. Ser. No. EP13818570.7 submitted by Schlich dated Oct. 26, 2015, 8 pages.

Opposition Against EP Appl. Ser. No. 2771468-B1 dated Oct. 26, 2015.

Ozawa, K., "Gene therapy using AAV," Uirusu, vol. 57, No. 1, pp. 47-55, dated Nov. 27, 2007, 13 pages. (with English Abstract; No English Translation).

Pandika, et al., www.ozy.com/rising-stars-and-provocateurs/jennifer-doudna-crispr-code-killer/4690; 2014 (Jul. 1, 2014).

Park, et al. "Regulation of Ribosomal S6 Kinase 2 by Mammalian Target of Rapamycin", The Journal of Biological Chemistry, 2002, 277(35):31423-31429.

Pattanayak, et al., "High-throughput profiling of off-target DNA cleavage reveals RNA-programmed Cas9 nuclease specificity," Nature Biotechnology, vol. 31, No. 9, pp. 839-843, dated 2013, including Supplementary Materials.

Perez-Pinera, et al. "Advances in Targeted Genome Editiong" Curr Opin Chern Biol., 2012, 16(3-4):268.277, doi:10.1016/j.cbpa.2012. 06.007.

Phillips, A., "The challenge of gene therapy and DNA delivery," The Journal of Pharmacy and Pharmacology, vol. 53, pp. 1169-1174, dated 2001, 6 pages.

Planey, et al. "Mechanisms of Signal Transduction: Inhibition of Glucocorticoid-induced Apoptosis in 697 Pre-B Lymphocytes by the Mineralocorticoid Receptor N-terminal Domain", J. Biol. Chem., 2002, 277:42188-42196.

Porteus, M., and Balitmore, D., "Chimeric Nucleases Stimulate Gene Targeting in Human Cells," Science, vol. 300, p. 763, dated May 2, 2003, 2 pages.

(56) References Cited

OTHER PUBLICATIONS

Posfai, et al. "Markerless gene replacement in *Escherichia coli* stimulated by a double-strand break in the chromosome" Nucleic Acids Resarch, 1999, 27(22):4409-4415.

Pougach, K.S., et al.: "CRISPR Adaptive Immunity Systems of Prokaryotes," Molecular Biology, vol. 46, No. 2, Apr. 2012, pp. 195-203, 1 page (English Abstract).

PowerPoint slide entitled "Development and Applications of CRISPR-Cas9 for Genome Editing" dated Sep. 9, 2015.

Pride, D., et al., "Analysis of Streptococcal CRISPRs from Human Saliva Reveals Substantial Sequence Diversity Within and Between Subjects Over Time," Genome Research, vol. 21, No. 1, pp. 126-136, dated Jan. 2011, 11 pages.

Primo, et al. "Lentiviral vectors for cutaneous RNA managing" Experimental Dermatology, 2012, 21:162-170.

Qi, J., et al., "microRNAs regulate human embryonic stem cell division," Cell Cycle, vol. 8, No. 22, pp. 3729-3741, dated Nov. 15, 2009, 13 pages.

Radecke, S., et al., "Zinc-finger Nuclease-induced Gene Repair With Oligodeoxynucleotides: Wanted and Unwanted Target Locus Modifications," Molecular Therapy, vol. 18, No. 4, pp. 743-753, dated Apr. 2010, 11 pages.

Radulovich, et al. "Modified gateway system for double shRNA expression and Cre/lox based gene expression" BMC Biotechnology, 2011, 11(24):1-9.

Redeclaration—37 C.F.R. 41.203(c); filed Mar. 17, 2016.

Request for Ex Parte Reexamination of U.S. Pat. No. 8,771,945 filed Feb. 16, 2016.

Response to Third Party Observations in EP No. 13824232.6 filed Oct. 2, 2014, with Redlined and Clean Amended Claims.

Rho, M., et al., "Diverse CRISPRs Evolving in Human Microbiomes," PLOS Genetics, vol. 8, No. 6, pp. e1002441, dated Jun. 2012, 12 pages.

Rhun, A., and Charpentier, E., "Small RNAs in streptococci," RNA Biology, vol. 9, No. 4, pp. 414-426, dated Apr. 2012, 13 pages.

Roberts, et al. "Nuclear location signal-mediated protein transport" Biochimica et Biophysica Acta, 1989, 1008:263-280.

Roberts, et al. "The Effect of Protein Content on Nuclear Location Signal Function" Cell, 1987, 50:465-475.

Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-inst-itute-mit-and-harvard-announce-update-crispr-cas9, 3 pages.

Rodrigues, et al. "Red Fluorescent Protein (DsRed) as a Reporter in Saccharomyces cerevisiae" Journal of Bacteriology, 2001, 183(12):3791-3794.

Rodriguez et al., "AAV-CRISPR: A New Therapeutic Approach To Nucleotide Repeat Diseases", Molecular Therapy, vol. 22, Supplement 1, Abstract 247, May 2014, p. S94.

Rolling, "Recombinant AAV-mediated gene transfer to the retina: gene therapy perspectives", Gene Therapy, Vo. 11,2004, pp. S26-S32.

*Rubin v. The General Hospital Corp.*, 2011-1439 (Fed. Cir. Mar. 28, 2013).

Sadowski, M., and Jones, D., "The sequence-structure relationship and protein function prediction," Current Opinion in Structural Biology, vol. 19, pp. 357-362, dated May 4, 2009, 6 pages.

Sambrook, et al., Molecular Cloning, A Laboratory Manual on the Web, 2001, Chapter 16.

Sander, et al., "CRISPR-Cas systems for editing, regulating and targeting genomes," Nature Biotechnology, vol. 32, pp. 347-355, dated 2014.

Sanders, UC Berkeley Jan. 7, 2013 Press Release, available at http://newscenter.berkeley.edu/2013/01/07/cheap-and-easy-technique-to-snip-dna-could-revolutionize-gene-therapy/.

Sanjana, et al., "Improved vectors and genome-wide libraries for CRISPR screening," HHS Public Access Author Manuscript, 2014, 11(8):2145-2148.

Sanjana, N., et al., "A Transcription Activator-Like Effector (TALE) Toolbox for Genome Engineering," Nature Protocols, vol. 7, No. 1, pp. 171-192, dated Jan. 1, 2012, 39 pages.

Sato, et al. "Generation of Adeno-Associated Virus Vector Enabling Functional Expression of Oxytocin Receptor and Fluorescence Marker Genes Using the Human elF4G Internal Ribosome Entry Site Elemet" Biosci. Biotechno. Biochem, 2009, 73(9):2145-2148.

Sebastiani, et al., "BCL11A enhancer haplotypes and fetal hemoglobin in sickle cell anemia," Blood Cells, vol. 54, No. 3, pp. 1079-9796, dated 2015.

Sebo, et al. "A simplified and efficient germline-specific CRISPR/Cas9 system for Drosophila genomic engineering" Fly, 2014, 8(1):52-57.

Seffernick, J., et al., "Melamine Deaminase and Atrazine Chlorohydrolase: 98 Percent Identical but Functionally Different," Journal of Bacteriology, vol. 183, No. 8, pp. 2405-2410, dated Apr. 2001, 6 pages.

Senis, E., et al., "CRISPR/Cas9-mediated genome engineering: An adeno-associated viral (AAV) vector toolbox," Biotechnology Journal, vol. 9, No. 11, Sp. Iss. SI, pp. 1402-1412, dated Sep. 4, 2014, 12 pages.

Senturk et al., "A rapid and tunable method to temporally control cas9 expression enables the identification of essential genes and the interrogation of functional gene interactions in vitro and in vivo", Jul. 28, 2015, pp. 1-27, XP002756303, doi:10.1101/023366, Retrieved from the Internet: URL:http://biorxiv.org/content/early/2015/07/28/023366 [retrieved on Apr. 11, 2016).

Shalem, et al., "High-throughput functional genomics using CRISP-Cas9," Nature Reviews Genetics, vol. 16, No. 5, pp. 1471-0056, dated 2015.

Sharan, et al. "Recombineering: A Homologous Recombination-Based Method of Genetic Engineering" Nat. Protoc., 2009, 4(2):206-223, doi:10.1038/nprot.2008.227.

Shengdar Tsai et al., "Dimeric CRISPR RNS-guided FokI nucleases for highly specific genome editing", Nature Biotechnology, vol. 32, No. 6, Apr. 25, 2014, pp. 569-576.

Shieh, et al. "Nuclear Targeting of the Maize R. Protein Requires Two Nuclear Localization Sequences" Plant Physiol, 1993, 101:353-361.

Siegl, et al. "I-SceI endonuclease: a new tool for DNA repair studies and genetic manipulations in streptomycetes" Appl Microbiol Bitotechnol, 2010, 87:1525-1532.

Singer, et al. "Applications of Lentiviral Vectors for shRNA Delivery and Transgenesis" Curr Gene Ther., 2008, 8(6):483-488.

Slaymaker et al., Rationally engineered Cas9 nucleases with improved specificity, Science, American Association for the Advancement of Science, US, vol. 351, No. 6268, Jan. 1, 2016, pp. 84-88.

Stoller, J. and Aboussouan, L., "Alphal-antitrypsin deficiency," The Lancet, Seminar, vol. 365, No. 9478, pp. 2225-2236, dated Jun. 25, 2005, 12 pages.

Stratikopoulos, E., et al., "The hormonal action of IGF1 in postnatal mouse growth," Proceedings of the National Academy of Sciences, vol. 105, No. 49, pp. 19378-19383, dated Dec. 9, 2008, 6 pages.

Straub, C., et al., "CRISPR/Cas9-Mediated Gene Knock-Down in Post-Mitotic Neurons," PLOS One, vol. 9, No. 8, art. E105584, pp. 1-5, dated Aug. 2014, 6 pages.

Sung, et al. "An rpsL Cassette, Janus, for Gene Replacement through Negative Selectionin *Streptococcus pneumoniae*" Applied and Environmental Microbiology, 2001, 67(11):5190-5196.

Sung, M., et al., "The importance of valency in enhancing the import and cell routing potential of protein transduction domain-containing molecules," Biochimica et Biophysica Aeta, vol. 1758, pp. 355-363, dated 2006, 9 pages.

Sung, Young Hoon, et al. "Mouse genetics: Catalogue and scissors" BMB Reports, 2012, 45(12):686-692.

Suzuki, K., et al., "In vivo genome editing via CRISPR/Cas9 mediated homology-independent targeted integration," Nature, vol. 540, art. 7631, pp. 144-149, dated Dec. 1, 2016, 44 pages.

Swarthout, J., et al., "Zinc Finger Nucleases: A new era for transgenic animals," Annals of Neurosciences, vol. 18, No. 1, pp. 25-28, dated Jan. 2011, 4 pages.

Swiech et al., "CRISPR-Mediated Genome Editing in the Mammalian Brain", Molecular Therapy, vol. 22, 749, May 2012, p. S289.

(56) References Cited

OTHER PUBLICATIONS

Tang, T., et al., "A mouse knockout library for secreted and transmembrane proteins," Nature Biotechnology, vol. 28, No. 7, pp. 749-755, dated Jul. 2010, 9 pages.
*The Broad Inst. v. The Regents of University of UCA*—Decision on Motions for Patent Interference No. 106,048 filed Feb. 15, 2017.
Third Party Observation for Application No. EP20130824232 filed Sep. 22, 2014.
Third Party Observations Concerning App. No. GB1420270.9 dated Jun. 30, 2015.
Third Party Observations Concerning Appl. No. EP2800811, dated Jul. 24, 2015.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, dated Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, Feb. 16, 2015.
Third-Party Observation for Application No. EP20130824232 Aug. 9, 2014.
Tinland, et al. "The T-DNA-linked VirD2 protein contains two distinct functional nuclear localization signals" Proc. Natl. Acad. Sci, 1992, 89:7442-7446.
Tiscornia, et al. "Development of Lentiviral Vectors Expressing siRNA" Gene Transferdelivery and Expression of DNA and RNA-A Laboratory Manual, 2007, Chapter 3:23-34.
Trafton, A., "CRISPR-carrying nanoparticles edit the genome," MIT News, dated Nov. 13, 2017, 3 pages.
Tulpan, D., et al., "Free energy estimation of short DNA duplex hybridizations," BMC Bioinformatics, vol. 11, pp. 105-127, dated 2012, 22 pages.
Type V CRISPR-associated protein Cpfi [*Acidaminococcus* sp. Bv3L6], 2017, NCBI Reference Sequence: WP_02173622.1, Non-redundant Protein Sequence.
*Ultra-Precision Mfg. Ltd. v. Ford Motor Co.*, 2004 WL 3507671, *7, *11-12 (E.D. Mich. Mar. 30, 2004).
Urnov, F., et al., "Genome editing with engineered zinc finger nucleases," Nature Reviews, Genetics, vol. 11, pp. 637-646, dated Sep. 2010, 11 pages.
Urrutia, et al. "KRAB-containing zing finger repressor proteins" Genome Biology, 2003, 4(10):231-231.8.
Van Den Ackerveken, et al. "Recognition of the Bacterial Avirulence Protein AvrBs3 Occurs inside the Host Plant Cell" Cell, 1996, 87:1307-1316.
Van Der Oost, "New tool for genome surgery", Science, Feb. 2013, vol. 339, pp. 768-770.
Van Nierop, G., et al., "Stimulation of homology-directed gene targeting at an endogenous human locus by a nicking endonuclease," Nucleic Acids Research, vol. 37, No. 17, pp. 5725-5736, dated Aug. 3, 2009, 12 pages.
Villion, et al. "The double-edged sword of CRISPR-Cas systems" Cell Research, 2013, 23:15-17.
Wang, et al. "Genetic Screens in Human Cells Using the CRISPR-Cas9 System", Science, 2014, 343:80-84.
Weber et al., "TALENs Targeting HBV: Designer Endonuclease Therapies for Viral Infections", Molecular Therapy, vol. 21, No. 10, Oct. 2013, pp. 1819-1821.
Welch, et al. "Designing Genes for Successful Protein Expression" Methods in Enzymology, 2011, 498:43-66, DOI: 10.1016/6978-0-12-385120-8.00003-6.
Wienert, B., et al., "In vitro transcribed guide RNAs trigger an innate immune response via the RIG-I pathway," BioRxiv Preprint, dated Mar. 3, 2018, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, pp. 11643-11650, dated Aug. 18, 1999, 8 pages.
Wittmann et al., "Engineered riboswitches: Expanding researchers' toolbox with synthetic RNA regulators", FEBS Letters, vol. 586, No. 15, Feb. 28, 2012, pp. 2076-2083.
Wolff, et al. "Nuclear security breached" Nature Biotechnology, 2001, 19:1118-1120.
Wu, Y., et al., "Correction of a Genetic Disease in Mouse via Use of CRISPR-Cas9," Cell Stem Cell, vol. 13, No. 6, pp. 659-662, dated Dec. 5, 2013, 4 pages.
Wu, Z., et al., "Effect of Genome Size on AAV Vector Packaging," The American Society of Gene & Cell Therapy, vol. 18, No. 1, pp. 80-86, dated Jan. 2010, 7 pages.
Xie, et al. "RNA-Guided Genome Editing in Plants Using a CRISPR-Cas System" Molecular Plant, 2013, 6(6):1975-1983.
Yaghmai, et al. "Optimized Regulation of Gene Expression Using Artificial Transcription Factors", Molecular Therapy, 2002, 5(6):685-694.
Yamano, et al. "Crystal Structure of Cpf1 in Complex with Guide RNA and Target DNA" Cell, 2016, 165:949-962.
Yanfang Fu et al., "Improving CRISPR-Cas nuclease specificity using truncated guide RNAs" (with Supplement Table), Nature Biotechnology, vol. 32, No. 3, Jan. 26, 2014, pp. 279-284.
Yang et al., "HIV-1 TAT-mediated protein transduction and subcellular localization using novel expression vectors," FEBS Letters 532:36-44, (2002).
Yang, H., et al., "One-Step Generation of Mice Carrying Reporter and Conditional Alleles by CRISPR/Cas-Mediated Genome Engineering," Cell, vol. 154, No. 6, pp. 1370-1379, dated Sep. 12, 2013, 14 pages.
Yi, et al. "Current Advances in Retroviral Gene Therapy" Current Gene Therapy, 2011, 11:218:228.
Yin, H., et al., "Structure-guided chemical modification of guide RNA enables potent non-viral in vivo genome editing," Nature Biotechnology, vol. 35, pp. 1179-1187, dated Nov. 13, 2017, 22 pages.
Yu, et al. "An efficient recombination system for chromosome engineering in *Escherichia coli*" PNAS, 2000, 97(11):5978-5983.
Yu, W., et al., "Nrl knockdown by AAV-delivered CRISPR/Cas9 prevents retinal degeneration in mice," Nature Communications, vol. 8, art. 14716, dated Mar. 14, 2017, 15 pages.
Yu, Zhongsen, et al. "Highly Efficient Genome Modifications Mediated by Crispr/Cas9 in *Drosophila*" Genetics, 2013, 195:289-291.
Yusuke Miyazaki et al., Destabilizing Domains Derived from the Human Estrogen Receptor:, Journal of the American Chemical Society, vol. 134, No. 9, Mar. 7, 2012, pp. 3942-3945.
Zhang, "Processing-Independent CRISPR RNAs Limit Natural Transformation in Neisseria meningitidis", Molecular Cell, vol. 50, May 23, 2013. pp. 488-503.
Zhang, et al. "Optogenetic interrogation of neural circuits: technology for probing mammalian brain structures" Nat Protoc., 2010, 5(3):439-456, doi:10.1038/nprot.2009.226.
Zhang, et al., "Optimized CRISPR Design", MIT, XP055167487, Oct. 23, 2013, URL:http//crispr.mit.edu/about[retrieved on Feb. 5, 2015].
Zhang, F., PowerPoint Presentation: "Development and Applications of CRISPR-Cas9 for Genome Editing," Broad Institute/MIT, dated Sep. 9, 2015, 50 pages.
Zhang, L., et al., "Efficient Expression of CFTR Function with Adeno-Associated Virus Vectors that Carry Shortened CFTR Genes," Proceedings of the National Academy of Science USA, vol. 95, pp. 10158-10163, dated Aug. 1998, 6 pages.

(56) References Cited

OTHER PUBLICATIONS

Zhou, et al., "High-throughput screening of a CRISPR/Cas9 library for functional genomics in human cells," Nature, vol. 509, pp. 487-491, dated 2014.
Zolkiewska, et al. "ADAM Proteases:Ligand Processing and Modulation of the Notch Pathway" Cell Mol Life Sci, 2008, 65(13):2056-2068.
Zuris, et al., "Cationic lipid-mediated delivery of proteins enables efficient protein-based genome editing in vitro and in vivo" Nature Biotechnology, 2014, Advanced Online publication, doi:10.1038/nbt.3081.
Zuris, et al., Supplementary Information—"Cationic lipid-mediated delivery proteins enables efficient protein-based genome editing in vitro and in vivo" Nature Biotechnology, 2014, Advanced Online publication, doi:10.1038/nbt.3081.
U.S. Appl. No. 15/838,720, filed Dec. 12, 2017, Calamita, Heather.
Allen, et al., "Liposomal drug delivery systems: From concept to clinical applications" Advanced Drug Delivery Reviews 65, Oct. 1, 2012, pp. 36-48.
Cho, Minseon, et al., "Quantitative selection and parallel characterization of aptamers," PNAS, Nov. 12, 2013, vol. 110, No. 46, p. 18460-18465 (6 pages).
Gaj, T., et al., "Targeted Gene knockout by direct delivery of zinc-finger nuclease proteins," Nature Methods, vol. 9, No. 8, pp. 805-809, dated Aug. 2012, 5 pages.
Gao, et al., "A Sustained, Cytoplasmic Transgene Expression System delivered by Cationic Liposomes", Biochemical and Biophysical Research Communications, vol. 200, No. 3, May 16, 1994, pp. 1201-1206.
Goncalves, Manuel A. F. V., et al. "Concerted Nicking of Donor and Chromosomal Acceptor DNA Promotes Homology-directed gene targeting in human cells," Nucleic Acids Research, vol. 40, No. 8, pp. 3443-3455, dated Dec. 20, 2011, 13 pages.
Koo et al., "Measuring and Reducing Off-Target Activities of Programmable Nucleases Including CRISPR-Cas9", Molecules and Cells, vol. 38, No. 6, May 19, 2015, pp. 475-481.
Swarthout, John T., et al. "Zin Finger Nucleases: A new Era for Transgenic Animals," Animals of Neurosciences, vol. 18, No. 1 pp. 25-28, dated Jan. 2011, 4 pages.
Symington et al., "Double-Strand Break End Resection and Repair Pathway Choice", Annual Review of Genetics 2011, vol. 45, Sep. 12, 2011, pp. 247-271.
Takara Bio USA, Inc., "Lenti-X™ Tet-On© 3G CRISPR/Cas9 System User Manual", 2016, pp. 1-35.
Third Party Observation in Application No. PCT/US2013/074819 dated Apr. 10, 2015, 10 pages.
Third Party Observation Under Article 115 EPC in Application No. 13818570.7 dated Oct. 1, 2014, 15 pages.
Venken et al., "P[acman]: A Bac Transgenic Platform for Targeted Insertion of Large DNA Fragments in D. melanogaster", Science, vol. 314, No. 5806, Nov. 30, 2006, pp. 1747-1751.
Xu, Zhi-Li et al., "Regulated gene expression from adenovirus vectors: a systematic comparison of various inducible systems," Gene, 2003, vol. 309, pp. 145-151 (7 pages).
A. Amsterdam et al., "Identification of 315 genes essential for early zebrafish development," proc Natl Acad Sci., vol. 101, Aug. 31, 2004, pp. 12792-12797, 6 pages.
A. Fire et al., "Potent and specific genetic interference by double-stranded RNA in Caenorhabditis elegans," Nature, vol. 391, Feb. 19, 1998, pp. 806-811, 6 pages.
A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.
A.C. Spradling et al., "The Berkeley Drosophila Genome Project Gene Disruption Project: Single P-Element Insertions Mutating 25% of Vital *Drosophila* Genes," Genetics, vol. 153, Sep. 1999, pp. 135-177, 43 pages.
A.H. Tong et al., "Global mapping of the yeast genetic interaction network," Science, vol. 303, Feb. 6, 2004, pp. 808-813, 6 pages.
A.L. Lin and D.H Gutmann, "Advances in the treatment of neurofibromatosis-associated tumours," Nature, vol. 10, Nov. 2013, pp. 616-624, 9 pages.
A.P. Blanchard and L. Hood, "Sequence to array: probing the genome's secrets," Nat Biotechnol, vol. 14, Dec. 14, 1996, p. 1649.
Au, et al., "Characterization of a baculovirus nuclear localization signal domain in the late express factor 3 protein", Virology, vol. 385, 2009, pp. 209-217.
B. Langmead et al., "Ultrafast and memory-efficient alignment of short DNA sequences to the human genome," Genome biology, vol. 10, Mar. 4, 2009, 10 pages.
B.Langmead and S.L. Salzberg, "Fast gapped-read alignment with Bowtie 2," Nat Meth, vol. 9, 2012, pp. 357-359, 3 pages.
B.Scappini et al., "Changes associated with the development of resistance to imatinib (STI571) in two leukemia cell lines expressing p210 Bcr/Abl protein," Cancer, vol. 10 0, Apr. 1, 2004, pp. 1459-1471, 13 pages.
B.Sonnichsen et al., "Full-genome RNAi profiling of early embryogenesis in Caenorhabditis elegans," Nature, vol. 434, Mar. 24, 2005, pp. 462-469, 8 pages.
Bae, T. and Schneewind, O. "Allelic replacement in *Staphylococcus aureus* with inducible counterselection," Plasmid, vol. 55, 2006, pp. 58-63, 6 pages.
Botta, S. et al., "Transcriptional Repression with Zinc-Finger and Tale Protein Scaffold", Molecular Therapy, 2013, Supplement 1, p. S208, Abstract No. 539.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M Johannessen et al., "COT drives resistance to RAF inhibition through MAP kinase pathway reactivation," Nature, vol. 468, Dec. 16, 2010, p. 968.
C.M. Johnston et al., "Large-scale population study of human cell lines indicate that dosage compensation is virtually complete," PLoS Genet., vol. 4, Jan. 2008, pp. 88-98, 11 pages.
Carte, J., et al., "Cas6 is an endoribonuclease that generates guide RNAs for invader defense in prokaryotes," Genes Dev., vol. 22, 2008, pp. 3489-3496.
Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chevalier et al., "Homing endonuclease: structural and functional insight into the catalysts of intron/intein mobility," Oxford University Press., vol. 29, 2001, pp. 3757-3774.
D.J.Burgess et al., "Topoisomerase levels determine chemotherapy response in vitro and in vivo," Proceedings of the National Academy of Sciences, vol. 105, Jul. 1, 2008, pp. 9053-9058.
Deveau, H. et al., "Phage response to CRISPR-encoded resistance in *Streptococcus thermophilus*," Journal of Bacteriology, vol. 190, Feb. 2008, pp. 1390-1400.
Deveau, H., et al., "CRISPR/Cas system and its role in phage-bacteria interactions," Annu. Rev. Microbiol., vol. 64, 2010, pp. 475-493.
E.S. Lander, "Initial impact of the sequencing of the human genome," Nature, vol. 470, Feb. 10, 2011, p. 187-197.
Edgar, R. and Qimron, U., "The *Escherichia coli* CRISPR system protects from A lysogenization, lysogens, and prophage induction," Journal of Bacteriology, vol. 192, Dec. 2010, pp. 6291-6294.
Esvelt et al., "Orthogonal Cas9 proteins for RNA-guided gene regulation and editing", Nature Methods, vol. 10, No. 11, Nov. 2013 (available online Sep. 29, 2013), pp. 1116-1123.

(56) References Cited

OTHER PUBLICATIONS

Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Flannery, J. G., "Ribozyme-Mediated Gene Therapy for Autosomal Dominant Retinal Degeneration", Retinal Degenerative Diseases and Experimental Therapy, 1999, pp. 277-291.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.
GenBank: "CRISPR-associated protein Cas9/Csn1 [*Staphylococcus aureus* subsp. *aureus*]", GenBank: CCK74173.1, Year: 2012, http://www.ncbi.nlm.nih.gov/protein/403411236?sat=16&satkey=13804560, dated Dec. 14, 2016, 2 pages.
Gibson, D.G. et al., "Enzymatic assembly of DNA molecules up to several hundred kilobases," Nat methods, vol. 6, 2009, pp. 343-345.
Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Grosse, et al. "Meganuclease-medicated Inhibition of HSV1 Infection in Cultured Cells", Molecular Therapy, vol. 19, No. 4, Apr. 1, 2011, pp. 694-702.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
H. Davies et al., "Mutations of the BRAF gene in human cancer," Nature, vol. 417, Jun. 27, 2002, p. 949-954.
H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.
Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*," Proc. Natl. Acad. Sci., vol. 92, Nov. 1995, pp. 11140-11144.
Hemann et al., "An epi-allelic series of p53 hypomorphs created by stable RNAi produces distinct tumor phenotypes in vivo," Nat Genetics, vol. 33, Mar. 2003, pp. 396-400.
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.
Husmann, L.K., et al., "Expression of the Arp protein, a member of the M protein family, is not sufficient to inhibit phagocytosis of *Streptococcus pyogenes*," Infection and immunity, vol. 63, Jan. 1995, pp. 345-348.

Hwang, W.Y., et al., "Efficient Genome Editing in Zebrafish Using a CRISPR-Cas System", Nature Biotechnology, vol. 31, No. 3, Jan. 29, 2013, pp. 227-229.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.
J.E. Carette et al., "Haploid genetic screens in human cells identify host factors used by pathogens," Science, vol. 326, Nov. 27, 2009, p. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist lncRNA exploits three-dimensional genome architecture to spread across the X chromosome," Science, vol. 341, Aug. 16, 2013, pp. 1-8, 8 pages.
Jansen R. et al., "Identification of genes that are associated with DNA repeats in prokaryotes," Molecular Microbiology, vol. 43, 2002, pp. 1565-1575, 11 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt.2800.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Marraffini, L.A., et al., "Sortases and the art of anchoring proteins to the envelopes of gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Moffat J et al., "A lentiviral RNAi library for human and mouse genes applied to an arrayed viral high-content screen," Cell, vol. 124, Mar. 24, 2006, pp. 1283-1298, 16 pages.
Mojica F. J. M et al., "Biological significance of a family of regularly spaced repeats in the genomes of Archaea, Bacteria and mitochondria," Molecular Microbiology, vol. 36, 2000, pp. 244-246, 3 pages.
Motamedi, M.R., et al., "Double-strand-break repair recombination in Escherichia coli: physical evidence for a DNA replication mechanism in vivo," Genes Dev., vol. 13, 1999, pp. 2889-2903.
Paddison et al., "A resource for large-scale RNA-interference-based screens in mammals," Nature, vol. 428, Mar. 25, 2004, pp. 427-431, 5 pages.
Podbielski, A., et al., "R. Novel series of plasmid vectors for gene inactivation and expression analysis in group A streptococci (GAS)," Gene, vol. 177, 1996, pp. 137-147, 11 pages.
R. Rad et al., "PiggyBac transposon mutagenesis: a tool for cancer gene discovery in mice," Science, vol. 330, Nov. 19, 2010, p. 1104-1107, 4 pages.

(56) References Cited

OTHER PUBLICATIONS

R.D Kolodner and G.T. Marsischky, "Eukaryotic DNA mismatch repair," Current Opinion in Genetics and Development, vol. 9, 1999, p. 89-96, 8 pages.
R.Renella et al., "Codanin-1 mutations in congenital dyserthropoietic anemia type 1 affect HP1.alpha. localization in erythroblasts," Blood, vol. 117, Jun. 2011, pp. 6928-6938, 11 pages.
S. Huang et al., "MED12 Controls the Response to Multiple Cancer Drugs through Regulation of TGF-β; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.
S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.
S.R. Whittaker et al., "A Genome-Scale RNA Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, clorf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. pp. 355-369, 15 pages.
Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.
Schiffer, et al. "Targeted DNA Mutagenesis for the Cure of Chronic Viral Infections" Journal of Virology, vol. 86, No. 17, Jun. 20, 2012, pp. 8920-8936.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Spencer, J.M., et al., "Development of a Nuclease Screen to Improve Cas9 Targeting Specificity", Molecular Therapy, May 2015, vol. 23, Suppl. 1, S136(340).
Stewart SA et al., "Lentivirus-delivered stable gene silencing by RNAi in primary cells," RNA, vol. 9, 2003, pp. 493-501, 9 pages.
T. Horii et al., "Generation of an ICF Syndrome Model by Efficient Genome Editing of Human Induced Pluripotent Stem Cells Using the CRISPR System," International Journal of Molecular Sciences, vol. 14, 2013, p. 19774-19781, 9 pages.
T.J. Cradick et al., "CRISPR/Cas9 systems targeting β-globin and CCR5 genes have substantial off-target activity," Nucleic Acids Research, vol. 41, 2013, 9584-9592, 9 pages.
T.Yan et al., "DNA mismatch repair (MMR) mediates 6-thioguanine genotoxicity by introducing single-strand breaks to signal a G2-M arrest in MMR-proficient RKO cells," Clinical Cancer Research, vol. 9, Jun. 2003, p. 2327-2334, 9 pages.
V.N. Ngo et al., "A loss-of-function RNA interference screen for molecular targets in cancer," Nature, vol. 441, May 4, 2006, pp. 106-110, 5 pages.
Van Der Oost, J., et al., "CRISPR-based adaptive and heritable immunity in prokaryotes," Trends. Biochem. Sci., vol. 34, 2009, pp. 401-407, 7 pages.
W.G. Kaelin., "Use and Abuse of RNAi to Study Mammalian Gene Function," Science, vol. 337, Jul. 27, 2012, p. 421-422, 2 pages.
Wang, H.H et al., "Genome-scale promoter engineering by coselection MAGE," Nat methods, vol. 9, Jun. 2012, pp. 591-593, 3 pages.
Wayengera, M., "Identity of zinc finger nucleases with specificity to herpes simplex virus type II genomic DNA; novel HSV-2 vaccine/ therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.
Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.
Xiao, W., et al., "Gene Therapy Vectors Based on Adeno-Associated Virus Type 1", Journal of Virology, May 1999, vol. 73, No. 5, p. 3994-4003.
Zahner, D. and Hakenbeck, R. "The *Streptococcus pneumoniae* beta-galactosidase is a surface protein," J. Bacteriology, vol. 182, Oct. 2000, pp. 5919-5921, 3 pages.
Zeng Y et al., "Both natural and designed micro RNAs can inhibit the expression of cognate mRNAs when expressed in human cells," Mol Cell., vol. 9, Jun. 2002, pp. 1327-1333, 7 pages.
Zuris, et al., "Efficient Delivery of Genome-Editing Proteins In Vitro and In Vivo" Nature Biotechnology, vol. 33, No. 1, Jan. 2015, pp. 1-26.
Anders et al., "Structural basis of PAM-dependent target DNA recognition by the Cas9 endonuclease," Nature, vol. 513, Sep. 25, 2014 pp. 569-573.
Decision on Motions—PTAB, *The Regents of the University of California v. The Broad Institute, Inc.*, filed Sep. 10, 2020, in Patent Interference No. 106,115 (DK), 113 pages.
Declaration of Interference—PTAB, The Broad Institute, Inc., *Massachusetts Institute of Technology, and President and Fellows of Harvard College v. Toolgen, Inc.*, filed Dec. 14, 2020, in Patent Interference No. 106,126 (DK), 19 pages.
Hemphill et al., "Optical Control of CRISPR/Cas9 Gene Editing," Journal of the American Chemical Society, vol. 137, May 6, 2015 (9 pages).
Hirano et al., "Structure and Engineering of Francisella novicida Cas9," Cell, vol. 164, Feb. 25, 2016, pp. 950-961.
Ran, F.A., "CRISPR-Cas: Development and Applications for Mammalian Genome Editing", Ph.D. Dissertation, Harvard University, Apr. 2014.
Redeclaration—PTAB, *The Regents of the University of California v. The Broad Institute, Inc.*, filed Aug. 26, 2019, in Patent Interference No. 106,115 (DK), 20 pages.
Redeclaration—PTAB, *The Regents of the University of California v. The Broad Institute, Inc.*, filed Sep. 10, 2020, in Patent Interference No. 106,115 (DK), 3 pages.
Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.
U.S. Appl. No. 14/290,575, filed May 29, 2014, Whisenant, Ethan C.
U.S. Appl. No. 14/703,511, filed May 4, 2015, Leith, Nancy J.
U.S. Appl. No. 14/704,551, filed May 5, 2015, Leonard, Arthur S.
U.S. Appl. No. 15/172,636, filed Jun. 3, 2016, Leonard, Arthur S.
U.S. Appl. No. 15/179,912, filed Jun. 10, 2016, Visone, Thomas J.
U.S. Appl. No. 15/230,025, filed Aug. 5, 2016, Leith, Nancy J.
U.S. Appl. No. 15/838,720, filed Dec. 12, 2017, Hasan, Khaleda B.
U.S. Appl. No. 16/517,534, filed Jul. 19, 2019, Noakes, Suzanne Marie.
U.S. Appl. No. 16/592,744, filed Oct. 3, 2019, to Be Assigned.
U.S. Appl. No. 17/123,918, filed Dec. 16, 2020, to Be Assigned.
Adhin et al., "Complete nucleotide sequence of the group I RN A bacteriophage fr," Biochimica et Biophysica Acta, Elsevier, vol. 1050, 1990 pp. 104-109.
Anguela et al., "Robust ZFN-mediated geno1 ne editing in adult hemophilic mice", Blood, vol. 122, No. 19, Nov. 7, 2013, (pp. 3283-3287).
Bikard et al., "Exploiting CRISPR-Cas nucleases to produce sequence-specific antimicrobials", Nature Biotechnology, vol. 32, No. 11, Nov. 2014 (pp. 1146-1151).
Chapdelaine et al., "Meganucleases can restore the reading frame of a mutated dystrophin", Gene Therapy, vol. 17, 2010 (pp. 846-858).

(56) References Cited

OTHER PUBLICATIONS

Database UniPro Accession No. J7RUA5, 2012, [online] downloaded from https:/lwww.uniprot.org/uniprol/J7RUA5 on Mar. 23, 2021 (10 pages).

He et al., "Pollen fertility restoration by nuclear gene Fr in CMS common bean: an Fr linkage map and the mode of Fraction," Theor. Appl. Genet. Vol.90, 1995, pp. 1056-1062.

Huang and Honkanen, "Molecular Cloning, Expression, and Characterization of a Novel Human Serine/Threonine Protein Phosphatase, PP7, That Is Homologous to '*Drosophila*' Retinal Degeneration C Gene Product (rdgC)*," The Journal of Biological Chemistry, vol. 273, No. 3, Iss. 16, 1998, pp. 1462-1468.

Koonin et al., "Diversity, classification and evolution of CRISPR-Cas systems", Current Opinion in Microbiology vol. 37, 2017 (pp. 67-78).

Sorek et al., "CRISPR-Mediated Adaptive Immune Systems in Bacteria and Archea", Annual Review of Biochemistry, vol. 82, 2013, (pp. 237-266).

\* cited by examiner

HEL (L169)-linker-Effector-linker-HEL (K314)

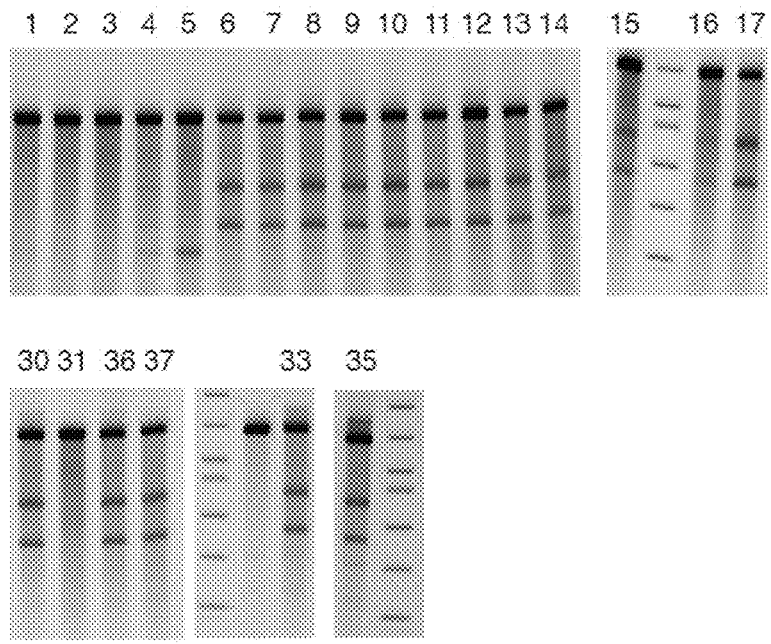

sgRNA mutations

| Region of mutation | Activity (indel %) | Specific description of mutation | Complete Sequence | Length |
|---|---|---|---|---|
| Stem1 | 14.33 | Proximal poly U tract switch to C | gCCCCagagctaGAAAtagcaagttGGGGtaaggctagtccgttatcaacttGAAAaagttgcaccgAGTcggttgcTTTTT | 81 |
| Stem1 | 14.74 | Distal CUA to CCC | gtttagagcCCCgAAAGcgaagttaaaataaggctagtccgttatcaacttGAAAaagttgcaccgAGTcggttgcTTTTT | 81 |
| Stem1 | 15.16 | Truncate distal UA | gtttagagcGAAAgcaagttaaaataaggctagtccgttatcaacttGAAAaagttgcaccgAGTcggttgc | 77 |
| Stem1 | 16.05 | Truncate distal CUA | gtttagagCgAAAcaagttaaaataaggctagtccgttatcaacttGAAAaagttgcaccgAGTcggttgcTTTTT | 75 |
| Stem1 | 18.19 | Truncate distal CUA and Loop 1 | gtttagagAcaagttaaaataaggctagtccgttatcaacttGAAAaagttgcaccgAGTcggttgcTTTTT | 72 |
| Bulge | NONE | Replace Bulge with A-U pair | gtttagagctaGAAAtagcTTtaaaataaggctagtccgttatcaacttGAAAaagttgcaccgAGTcggttgcTTTTT | 79 |
| Bulge | 1.30 | Replace Bulge with C-G pair (keep G43) | gtttagCgctaGAAAtagcGtaaaataaggctagtccgttatcaacttGAAAaagttgcaccgAGTcggttgcTTTTT | 79 |
| Bulge | 21.55 | Replace Bulge with C-AAG pair | gtttagCgctaGAAAtagcAAGtaaaataaggctagtccgttatcaacttGAAAaagttgcaccgAGTcggttgcTTTTT | 81 |
| Bulge | 17.56 | Replace Bulge with T-AAG pair | gtttagTgctaGAAAtagcAAGtaaaataaggctagtccgttatcaacttGAAAaagttgcaccgAGTcggttgcTTTTT | 81 |
| Bulge | 19.64 | Replace Bulge with G-AAG pair | gtttagGgctaGAAAtagcAAGtaaaataaggctagtccgttatcaacttGAAAaagttgcaccgAGTcggttgcTTTTT | 81 |
| Bulge | 12.11 | Replace Bulge with A-TTG pair (keep G43) | gtttagagctaGAAAtagcTTGtaaaataaggctagtccgttatcaacttGAAAaagttgcaccgAGTcggttgcTTTTT | 81 |
| Bulge | 5.44 | Replace Bulge with A-AAC pair (remove G43) | gtttagagctaGAAAtagcAACtaaaataaggctagtccgttatcaacttGAAAaagttgcaccgAGTcggttgcTTTTT | 81 |
| Bulge | 14.74 | Replace Bulge with A-AAA pair (remove G43) | gtttagagctaGAAAtagcAAAtaaaataaggctagtccgttatcaacttGAAAaagttgcaccgAGTcggttgcTTTTT | 81 |
| Bulge | 10.63 | Replace Bulge with A-AAT pair (remove G43) | gtttagagctaGAAAtagcAATtaaaataaggctagtccgttatcaacttGAAAaagttgcaccgAGTcggttgcTTTTT | 81 |
| Linker 1 | 14.56 | Shorten Linker 1 (del UAUC) | gtttagagctaGAAAtagcaagttGAAAaagttgcaccgAGTcggttgcTTTTT | 77 |
| Linker 1 | 14.99 | Change Linker 1 (UAUC to AUAG) | gtttagagctaGAAAtagcaagttATACaacttGAAAaagttgcaccgAGTcggttgcTTTTT | 81 |
| Stem 2 | 20.35 | Replace Stem 2 with G-C track | gtttagagctaGAAAtagcaagttaaaataaggCGCCGAAAGGCGggtccgttatcaacttGAAAaagttgcaccgAGTcggttgcTTTTT | 82 |
| Stem 2 | 16.87 | Replace and lengthen Stem 2 with G-C track | gtttagagctaGAAAtagcaagttaaaataaggccCGCCggccGAAAggccGGcgggtccgttatcaacttGAAAaagttgcaccgAGTcggttgcTTTTT | 82 |
| Loop 2 | 17.57 | Change Loop 2 sequence | gtttagagctaGAAAtagcaagttaaaataaggctagtcCgCccGCgcggGgcTTTTT | 81 |
| Stem 3 | 13.07 | Replace Stem 3 with G-C track | gtttagagctaGAAAtagcaagttaaaataaggctagtccgttatcaacttGAAAaagttgcaccgCGgcggGgcTTTTT | 81 |
| Stem3 | 20.05 | Add 1 bp to Stem 3 | gtttagagctaGAAAtagcaagttaaaataaggctagtccgttatcaacttGAAAaagttgcaccgAAGTcggttgcTTTTT | 83 |
| Stem3 | 12.86 | Add 2 bp to Stem 3 | gtttagagctaGAAAtagcaagttaaaataaggctagtccgttatcaacttGAAAaagttgcaccgAAAGTTcggttgcTTTTT | 85 |
| Stem3 Cas9 contact (S1) | 16.35 | mutate G-U44 to C44 (basepairing) | gtttagagctaGAAAtagcaagCtaaaataaggctagtccgttatcaacttGAAAaagttgcaccgAGTcggttgcTTTTT | 81 |
| Cas9 contact | | mutate G-U44 to U-G44 | gtttagaTctaGAAAtagcaagCtaaaataaggctagtccgttatcaacttGAAAaagttgcaccgAGTcggttgcTTTTT | 81 |

FIG. 5A
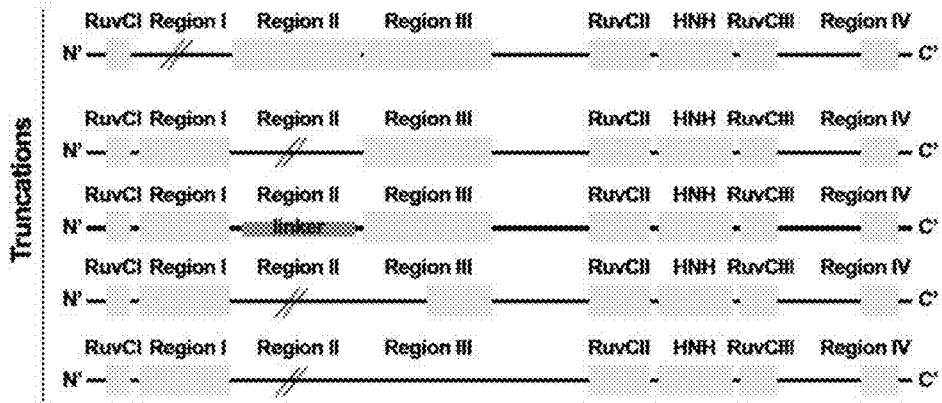
FIG. 5B
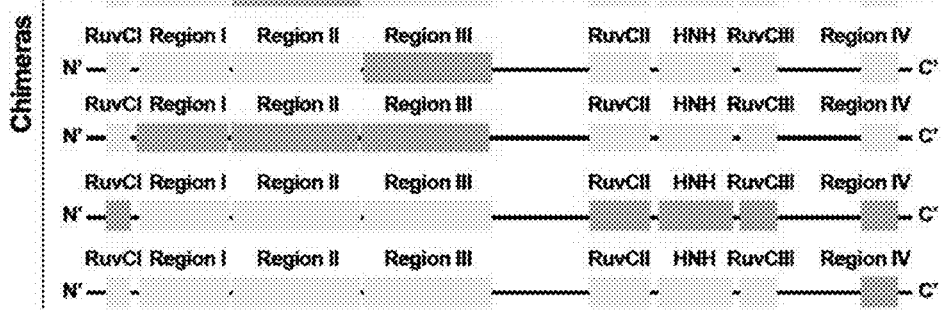
FIG. 5C
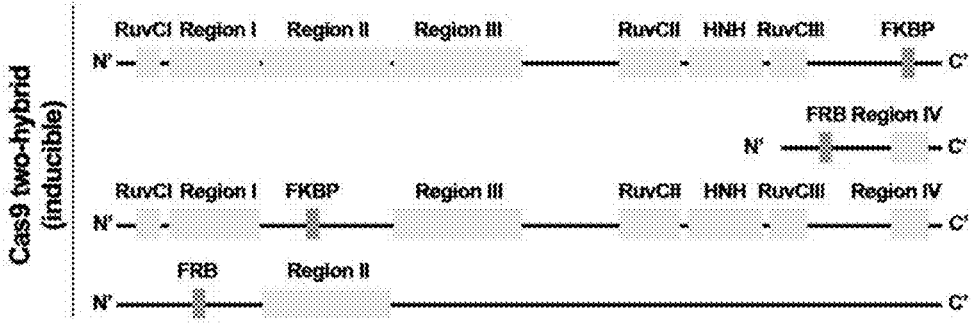

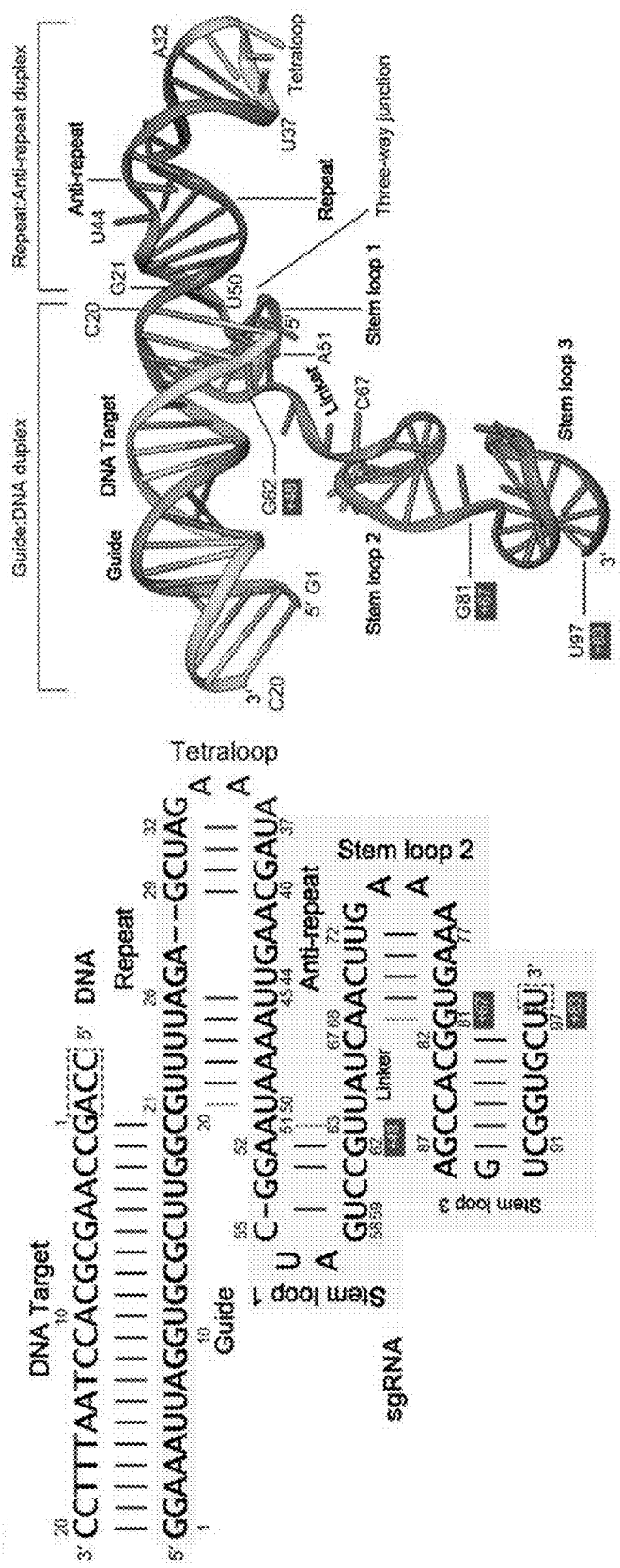

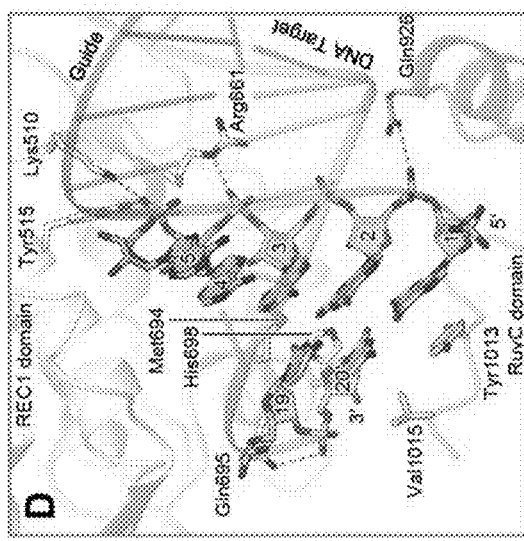
FIG. 12B  FIG. 12C  FIG. 12D
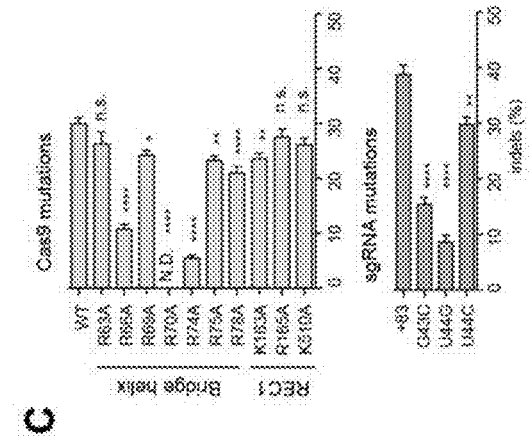
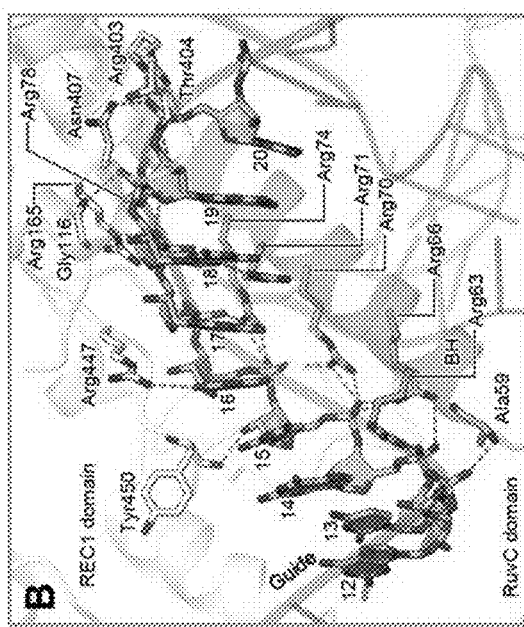
FIG. 12E
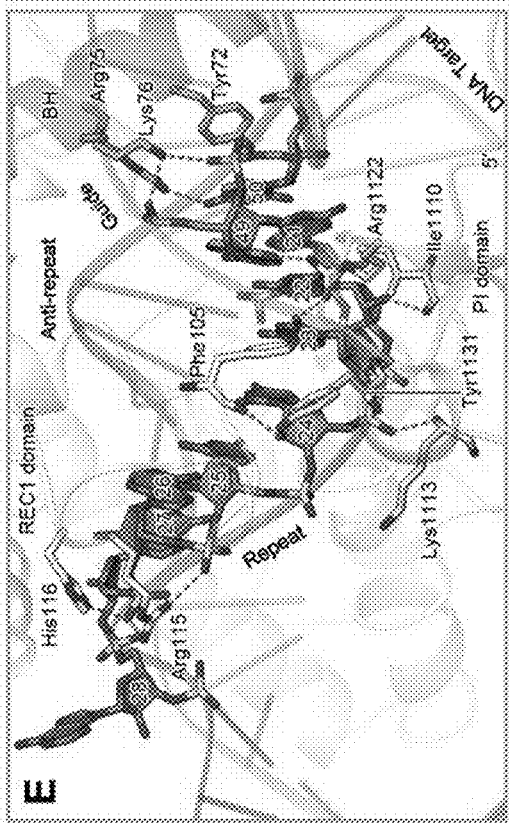
FIG. 12F

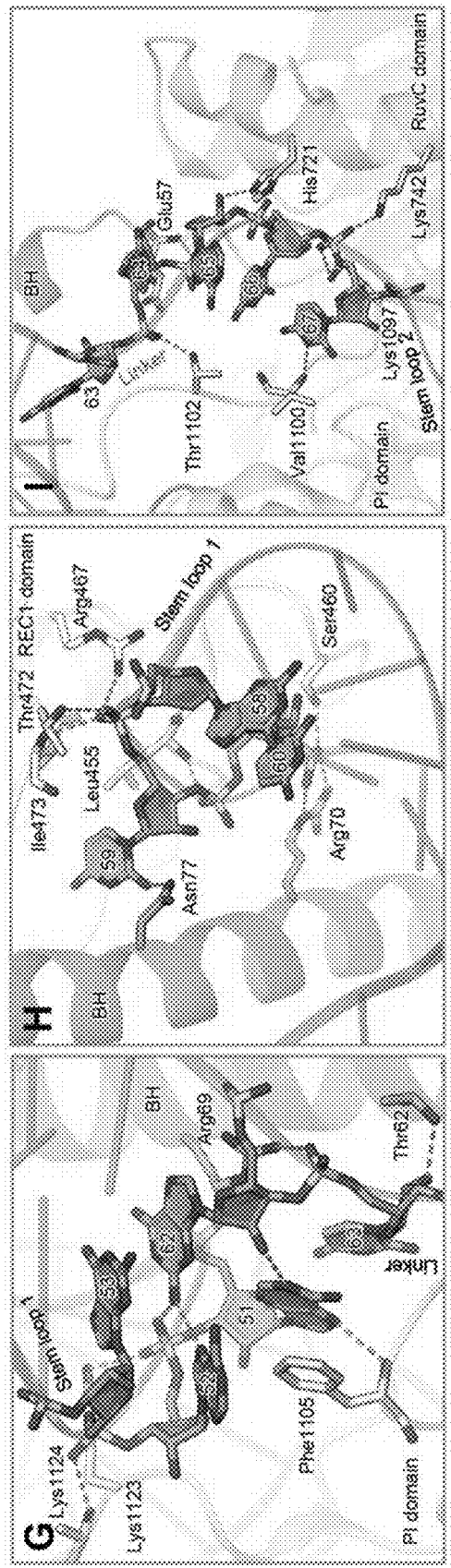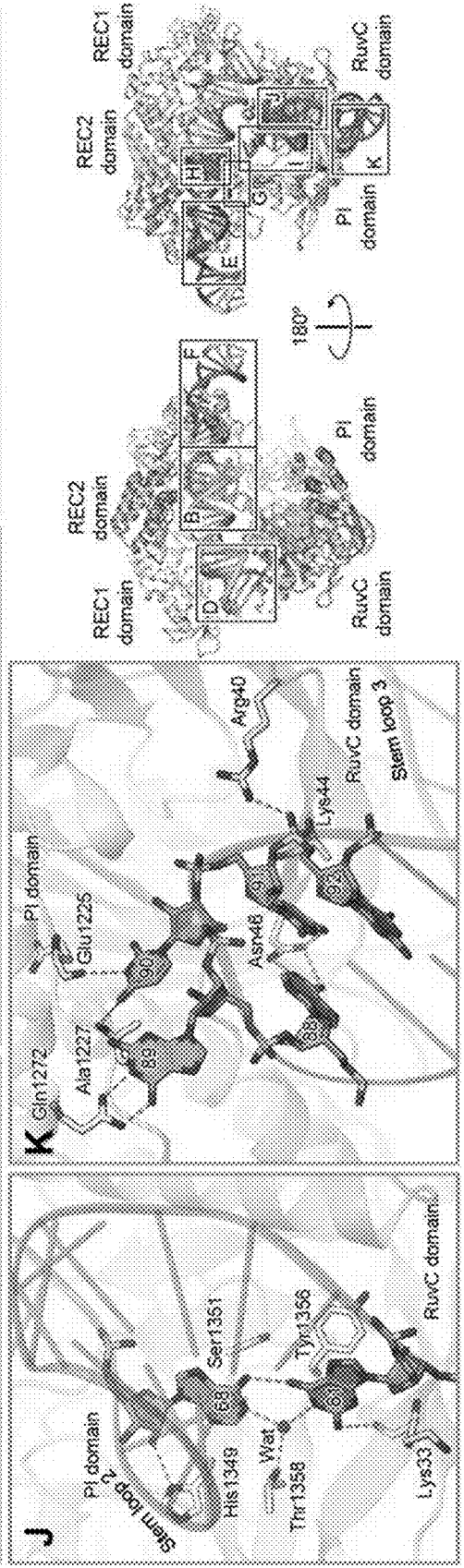
FIG. 12G FIG. 12H FIG. 12I FIG. 12J FIG. 12K

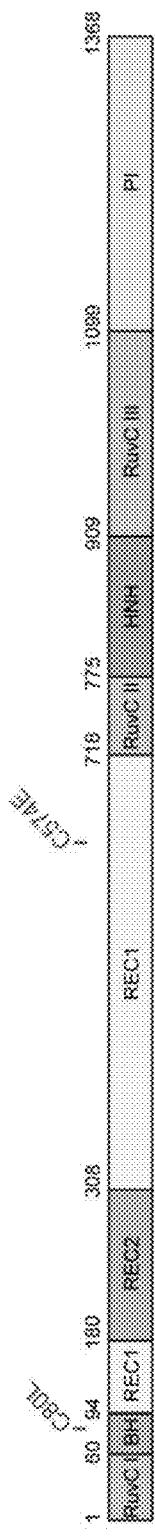
FIG. 16A
FIG. 16B
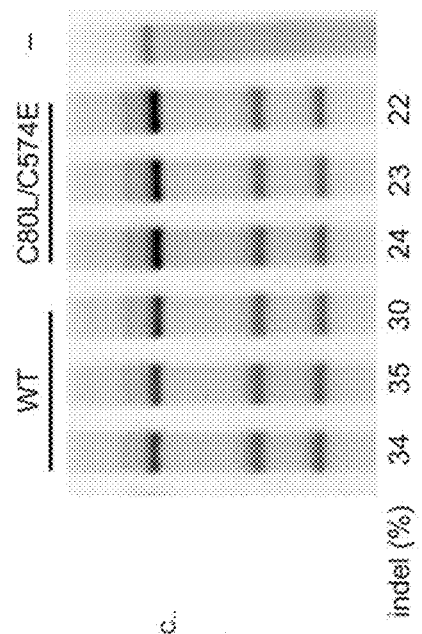
FIG. 16C

```
                β15    β16       α46           β17       P1                              β17-β18 loop
         1050      1060      1070      1080      1090      1100      1110      1120      1130
    Sp   ITLANGEIRKRPLIETNGETGEIVWDKGRDFATVRKVLSMPQVRIVKKTEVQTGGFSKE..........SILPKRNSDKLIARKKD...WDPKKYGGFDS
    Sm   DVRTD...........KNGEIIWKKDEHISNIKKVLSYPQVRIVKKVEEQTGGFSKE..........SILPKGNSDKLIPRKTAKFYWDTKKYGGFDS
    St3  ISLADGRVIERPLIEVNEETGESVWNKESDLATVRRVLSYPQVRVVKKVEEQNHGLDRGKPKGLFNANLSSKPKPNSNENLVGAKEY..LDPKKYGGYAG
    St1  LKSKE........FEDSILFSYQVDSKFNRKISDATIYATRQAKVGKDKADETYVLGKIK.........DIYTQDGYDAFMKIYKK....DKSKFLMYRH
    Cj   ..................FSGFRQKVLDKIDEIFVSKPERK..................KPSGALHEETFRK....EEEFYQSYGG
    Mm   EKNNIKFKEKASFDNFLLINALDELNEKLNQMRFSRMVITKKNTQLFNETLYSGKYDKGK.........NTIKKVEKLNLLDNRTDKIKKIEEFFDEDKL β18               β19              α47           α48      η8  β20    β21  η9  β22       β23
         1140      1150      1160      1170      1180      1190      1200      1210      1220
    Sp   PTVAYSVLVVAKVEKGKSKKLKSVKELLGITIMERSSFEKNPIDFLEAKGVKEVKKDLIIKLPKYS....LFELENGRKRMLASAG.......ELQKGNE
    Sm   PIVAYSILVIADIEKGKSKKLFTVKALVGVTIMEKMTFERDPVAFLERKGYRNYQEENIIKLPKYS....LPKLENGRKRLLASAR.......ELQKGNE
    St3  ISNSFTVLVKGTIEKGAKAKITNVLEFQGISILDRINYRKDKLNFLLEAGYKDI..ELIIELPKYS....LFELSDGSRKMLASILSTNNKRGELHKGNQ
    St1  DPQTFEKVIEPILENYPNKQINEKGKEVPCNPFLKYKEEHGYIRKYSKKGNGPEIKSLKYYDSKLGNHIDITPKDSNNKVLQSVSPWR....ADVYFNK
    Cj   KEGVLKALELGKIRFVNGKIVKNGDMFRVDIFKHRKTNKFYAVPIYTMDFALKVLPNKAVARSKKG..............................EIKDWIL
    Mm   KENELTKLHIFNHDKNLYETLKIIWNEVKIEIKNKNLNEKNYFKYFVNKKLQEGKISFNEWVPILDN..........DFKIIRKIR.......YIKFSSE α49            α50             α51            α52            α53          η10
         1230      1240      1250      1260      1270      1280      1290      1300      1310
    Sp   LALPSKYVNFLYLASHYEFLKGSPEDNEQKQLFVEQHKHYLDEIIEQISEFSKRVILADANLDKVLSAYNKHRDKPIREQAENIIH........LFTLTN
    Sm   IVLPNHLGTLLYHAKNIHKV.....DEPKHLDYVDKHKDEFKELLDVVSNFSKKYTLAEGNLEKIKELYAQNNGEDLKELASSFIN........LLTFTA
    St3  IFLSQKFVKLLYHAKRISNT.....INENHRKYYENHKKEFEELFYYILEFNENYVGAKKNGKLLNSAFQSWQNHSIDELCSSFIGPTGSERKGLFELTS
    St1  TTGKYEILGLKYADLQFEKGTGTYKISQEKYNDIKKKEGVDSDSEFKFTLYKNDLLLVKDTETKEQQLFRFLSRTMPKQKHYVELKP.......YDKQKF
    Cj   MDENYEFCFSLYKDS..........LILIQTKDMQEPEFVYYNAFTSSTVSLIVSKHDNKFETLSKNQKILFKN.....................
    Mm   EKETDEIIFSQSNFLKYDQRQNFSFHNTLYWVQLWVYKNQKDQYCFISIDARNSKFEKDEIKINYEKLKTQKEKLQTINEEPILKIN.......KGDLFE β24  β25         η11  β26       β27  η12
         1320      1330      1340      1350      1360
    Sp   LGAPAAFKYFDTTIDRKR.YYSTKEVLDATLIHQSITGLYETRIDLSQLGGD........
    Sm   IGAPATFKFFDKNIDRKR.YYSTTEILNATLIHQSTTGLYETRIDLNKLGGD........
    St3  RGSAADFEFLGVKIPRYRDYTPSSLLKDATLIHQSVTGLYETRIDLAKLGEG........
    St1  EGGEALIKVLGNVANSGQ..CKKGLGKSNISIYKVRTDVLGNQHIIKNEGDKPKLDF...
    Cj   ...ANEKEVIAKSIGIQN..LKVFEKYIVSALGEVTKAEFRQREDFKK............
    Mm   NEEKELFYIVGRDEKPQKLEIKYILGKKIKDQKOIQKPVKKYFPNWKFVNLTYMGEIFKK
```

FIG. 18B

CRISPR-CAS SYSTEMS, CRYSTAL STRUCTURE AND USES THEREOF

RELATED APPLICATIONS AND INCORPORATION BY REFERENCE

This application is a Continuation-In-Part of International Application Number PCT/US2014/069925 filed Dec. 12, 2014 which published as PCT Publication Number WO2015/089364 on Jun. 18, 2015. This application claims priority from US provisional patent applications: 61/915,251, filed Dec. 12, 2013; and 61/930,214 filed Jan. 22, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy created on Jun. 2, 2016, is named 47627992049SL.TXT and is 331,779 bytes in size.

STATEMENT AS TO FEDERALLY SPONSORED RESEARCH

This invention was made with government support under Grant No. MH100706, awarded by the National Institutes of Health. The government has certain rights in the invention.

FIELD OF THE INVENTION

The present invention generally relates to systems, methods and compositions used for the control of gene expression involving sequence targeting, such as genome perturbation or gene-editing, that may use vector systems related to Clustered Regularly Interspaced Short Palindromic Repeats (CRISPR) and components thereof.

This invention was made with government support under PRESTO (Precursory Research for Embryonic Science and Technology, Sakigake) in the field of "Structural life science and advanced core technologies for innovative life science research", awarded by JST (Japan Science and Technology Agency) in 2012. JST has certain rights in the invention.

This invention was made with government support under CREST in the field of "Creation of Basic Medical Technologies to Clarify and Control the Mechanisms Underlying Chronic Inflammation", awarded by JST (Japan Science and Technology Agency) in 2013. JST has certain rights in the invention.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

There exists a pressing need for alternative and robust systems and techniques for sequence targeting with a wide array of applications. This invention addresses this need and provides related advantages. The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

In one aspect, the invention provides a method for altering or modifying expression of a gene product. The said method may comprise introducing into a cell containing and expressing a DNA molecule encoding the gene product an engineered, non-naturally occurring CRISPR-Cas system comprising a Cas protein and guide RNA that targets the DNA molecule, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides an engineered, non-naturally occurring CRISPR-Cas system comprising a Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and a second regulatory element operably linked to a Cas protein. Components (a) and (b) may be located on same or different vectors of the system. The guide RNA targets the DNA molecule encoding the gene product in a cell and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and (b) a second regulatory element operably linked to an enzyme-coding sequence encoding said CRISPR enzyme comprising a nuclear localization sequence; wherein components (a) and (b) are located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is *S. pneumoniae*, *S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is S. pneumoniae, S. pyogenes or S. thermophilus Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cell(s) in which one or more mutations have been introduced to be selected. In a preferred embodiment, the CRISPR enzyme is Cas9. In another preferred embodiment of the invention the cell to be selected may be a eukaryotic cell. Aspects of the invention allow for selection of specific cells without requiring a selection marker or a two-step process that may include a counter-selection system.

In another aspect the invention comprehends a CRISPR-cas9 (*S. pyogenes*) system having an X-ray diffraction pattern corresponding to or resulting from any or all of the foregoing and/or a crystal having the structure defined by the co-ordinates of the Crystal Structure Table in Example 1 (the CRISPR-cas9 crystal structure).

In a further aspect, the invention involves a computer-assisted method for identifying or designing potential compounds to fit within or bind to CRISPR-cas9 system or a functional portion thereof or vice versa (a computer-assisted method for identifying or designing potential CRISPR-cas9 systems or a functional portion thereof for binding to desired compounds) or a computer-assisted method for identifying or designing potential CRISPR-cas9 systems (e.g., with regard to predicting areas of the CRISPR-cas9 system to be able to be manipulated—for instance, based on crystal structure data or based on data of cas9 orthologs, or with respect to where a functional group such as an activator or repressor can be attached to the CRISPR-cas9 system, or as to cas9 truncations or as to designing nickases), said method comprising:

(a) inputting into the programmed computer through said input device data comprising the three-dimensional co-ordinates of a subset of the atoms from or pertaining to the CRISPR-cas9 crystal structure, e.g., in the CRISPR-cas9 system binding domain or alternatively or additionally in domains that vary based on variance among cas9 orthologs or as to cas9s or as to nickases or as to functional groups, optionally with structural information from CRISPR-cas9 system complex(es), thereby generating a data set;

(b) comparing, using said processor, said data set to a computer database of structures stored in said computer data storage system, e.g., structures of compounds that bind or putatively bind or that are desired to bind to a CRISPR-cas9 system or as to cas9 orthologs (e.g., as cas9s or as to domains or regions that vary amongst cas9 orthologs) or as to the CRISPR-cas9 crystal structure or as to nickases or as to functional groups;

(c) selecting from said database, using computer methods, structure(s)—e.g., CRISPR-cas9 structures that may bind to desired structures, desired structures that may bind to certain CRISPR-cas9 structures, portions of the CRISPR-cas9 system that may be manipulated, e.g., based on data from other portions of the CRISPR-cas9 crystal structure and/or from cas9 orthologs, truncated cas9s, novel nickases or particular functional groups, or positions for attaching functional groups or functional-group-CRISPR-cas9 systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-cas9 system;

or, said method comprising: providing the co-ordinates of at least two atoms of the CRISPR-cas9 crystal structure, e.g., at least two atoms of the herein Crystal Structure Table of the CRISPR-cas9 crystal structure or co-ordinates of at least a sub-domain of the CRISPR-cas9 crystal structure ("selected co-ordinates"), providing the structure of a candidate comprising a binding molecule or of portions of the CRISPR-cas9 system that may be manipulated, e.g., based on data from other portions of the CRISPR-cas9 crystal structure and/or from cas9 orthologs, or the structure of functional groups, and fitting the structure of the candidate to the selected co-ordinates, to thereby obtain product data comprising CRISPR-cas9 structures that may bind to desired structures, desired structures that may bind to certain CRISPR-cas9 structures, portions of the CRISPR-cas9 system that may be manipulated, truncated cas9s, novel nickases, or particular functional groups, or positions for attaching functional groups or functional-group-CRISPR-cas9 systems, with output thereof; and optionally synthesizing compound(s) from said product data and further optionally comprising testing said synthesized compound(s) as or in a CRISPR-cas9 system.

The testing can comprise analyzing the CRISPR-cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (eg POWERPOINT), internet, email, documentary communication such as a computer program (eg WORD) document and the like. Accordingly, the invention also comprehends computer readable media containing: atomic co-ordinate data according to the herein Crystal Structure Table and/or the Figures, said data defining the three dimensional structure of CRISPR-cas9 or at least one sub-domain thereof, or structure factor data for CRISPR-cas9, said structure factor data being derivable from the atomic co-ordinate data of herein Crystal Structure Table and/or the Figures. The computer readable media can also contain any data of the foregoing methods. The invention further comprehends methods a computer system for generating or performing rational design as in the foregoing methods containing either: atomic co-ordinate data according to herein Crystal Structure Table and/or the Figures, said data defining the three dimensional structure of CRISPR-cas9 or at least one sub-domain thereof, or structure factor data for CRISPR-cas9, said structure factor data being derivable from the atomic co-ordinate data of herein Crystal Structure Table and/or the Figures. The invention further comprehends a method of doing business comprising providing to a user the computer system or the media or the three dimensional structure of CRISPR-cas9 or at least one sub-domain thereof, or structure factor data for CRISPR-cas9, said structure set forth in and said structure factor data being derivable from the atomic co-ordinate data of herein Crystal Structure Table and/or the Figures, or the herein computer media or a herein data transmission.

A "binding site" or an "active site" comprises or consists essentially of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further By "root mean square (or rms) deviation", we mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g. so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is to be construed as a promise.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1J discloses SEQ ID NO: 108. FIG. 1L discloses SEQ ID NOS 109 and 110.

FIGS. 3A-B show Surveyor gel test results of SpCas9 truncation mutants from the crystal structure that retain cleavage activity (A) and a table showing the amino acid truncations and flexible (GGGS) (SEQ ID NO: 1) or rigid (A(EAAAK)) (SEQ ID NO: 2) linker substitutions of the lanes of the gels of FIG. 25A (B). FIG. 3B discloses linker sequences as SEQ ID NOS 45, 47, 49, 53, 111, 112, 113, 53, 111, 47, and 51, respectively, top to bottom, left to right, in order of appearance.

FIGS. 4A-B show SpCas9 sgRNAs from the crystal structure including those mutated to investigate contribution to activity of specific bases or groups to basses. FIG. 4A discloses SEQ ID NOS 114-137, and FIG. 4B discloses SEQ ID NOS 138-152, all respectively, in order of appearance.

FIGS. 5A-C show truncation and creation of chimeric (S. pyogenes) Cas9s based on the herein crystal structure, including mutants for mapping essential functional domains (A), chimeras that contain regions from S. thermophilus Cas9 (B), and designs for chemically inducible dimerization of SpCas9 (C).

FIG. 9E discloses SEQ ID NOS 153 and 107, respectively, in order of appearance.

FIG. 11A-D shows sgRNA and its target DNA. (A) Schematic of the sgRNA:DNA complex. The guide and repeat regions of the crRNA sequence are colored skyblue and blue, respectively. The tracrRNA sequence is colored red, with the linker region colored violet. The target DNA and tetraloop are colored yellow and black, respectively. The numbering of the 3' tails of tracrRNA is shown on red background. Watson-Crick and non-Watson-Crick base pairs are indicated by black and gray lines, respectively. Disordered nucleotides are boxed by dashed lines. (B) Structure of the sgRNA:DNA complex. (C) Structure of the repeat:anti-repeat duplex and three-way junction. Key interactions are shown as gray dashed lines. (D) Effect of sgRNA mutations on ability to induce indels. Base changes from the +83 sgRNA scaffold are shown at respective positions, with dashes indicating unaltered bases (n=3, error bars show mean±S.E.M., p values based on unpaired Student's t-test, N.D., not detectable). See also FIG. 42. FIG. 11A discloses SEQ ID NOS 155 and 156, and FIG. 11D discloses SEQ ID NOS 157-170, all respectively, in order of appearance.

FIG. 12A-K shows Recognition of the sgRNA:DNA. (A) Schematic of sgRNA:DNA recognition by Cas9. Residues that interact with the sgRNA:DNA via their main chain are shown in parentheses. (B and C-K) Recognition of the guide (B), guide:DNA duplex (D), repeat (E), anti-repeat (F), three-way junction (G), stem loop 1 (H), linker (I), stem loop 2 (J) and stem loop 3 (K). Hydrogen bonds and salt bridges are shown as dashed lines. (C) Effect of Cas9 (top) and sgRNA (bottom) mutations on ability to induce indels (n=3, error bars show mean±S.E.M., p values based on unpaired Student's t-test. N.D., not detectable). FIG. 12A discloses SEQ ID NOS 171 and 172.

FIG. 16A-C shows Di-cysteine mutant (C80L/C574E) is functional in HEK 293FT cells. (A) Schematic illustrating positions of cysteine mutations (C80L and C574E) in Cas9. (B) Sequence of the target site (SEQ ID NO: 173) used to test the function of the C80L/C574E mutant of Cas9. (C) SURVEYOR nuclease assay showing indels generated by either the wild-type or C80L/C574E mutant (n=3).

FIG. 18A-B shows the sequence alignment of Cas9 orthologs in families II-A and II-C(SEQ ID NOS 174-179, respectively, in order of appearance). The catalytic residues are shown in red triangles. Critical arginine residues on Bridge helix are shown in green triangles. The secondary structure of *S. pyogenes* Cas9 is shown above the sequences. The figure was prepared using TCoffee (Notredame et al., 2000) and ESPript (Gouet et al., 1999). Sp, *S. pyogenes*; Sm, *Streptococcus mutans*; St3, *Streptococcus thermophilus* CRISPR-3; St1, *Streptococcus thermophilus* CRISPR-1; Cj, *Campylobacter jejuni*; Mm; *Neisseria meningiditis*.

DETAILED DESCRIPTION OF THE INVENTION

Figure 1A:
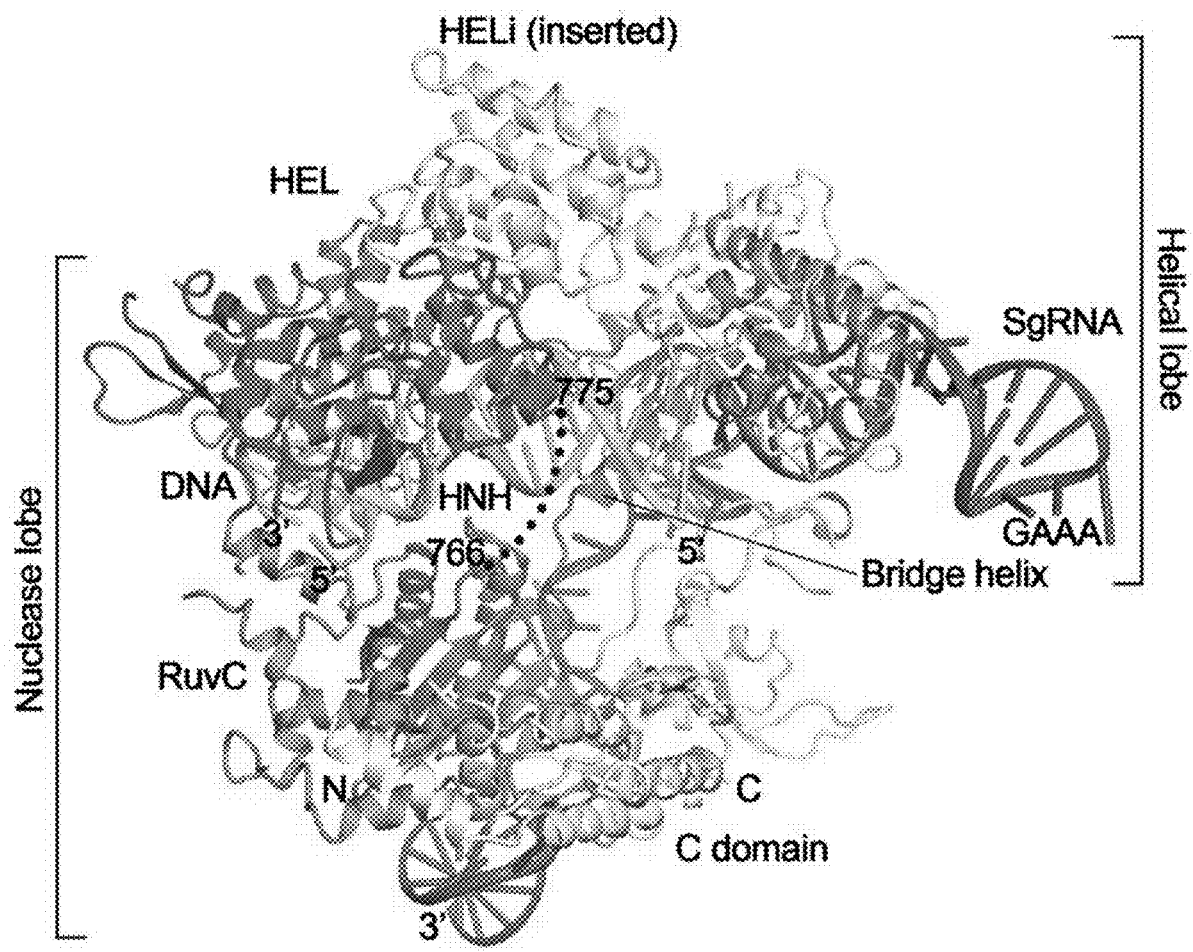
FIGS. 1A-M provide: a diagram showing the topology of the Cas9 protein. Helices are shown as tubes and beta sheets are shown as arrows and various views of the CRISPR-cas complex crystal structure (A-I), chimeric RNA architecture from the crystal structure (J-K), an interaction schematic from the crystal structure (L) and a topology schematic from the crystal structure (M).
Figure 1B:
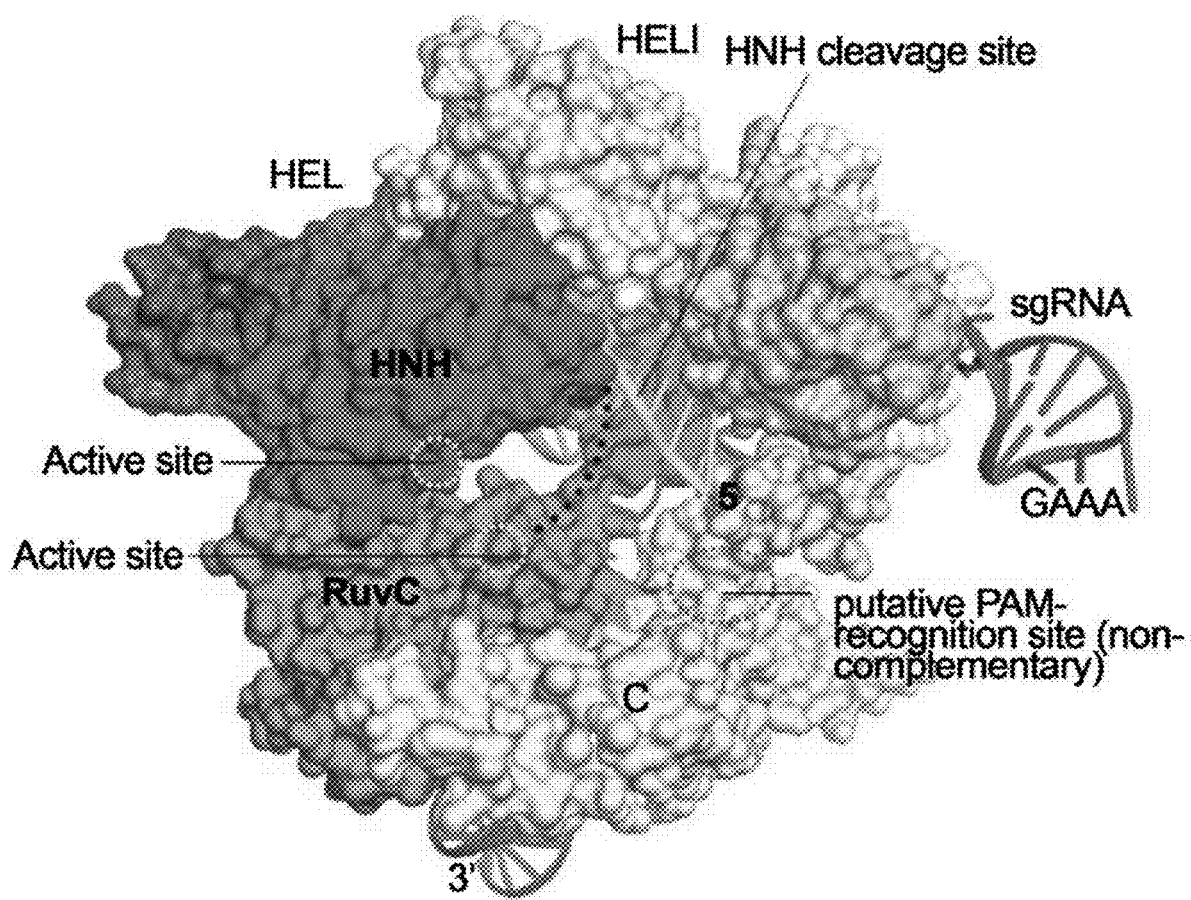
Figure 1C:
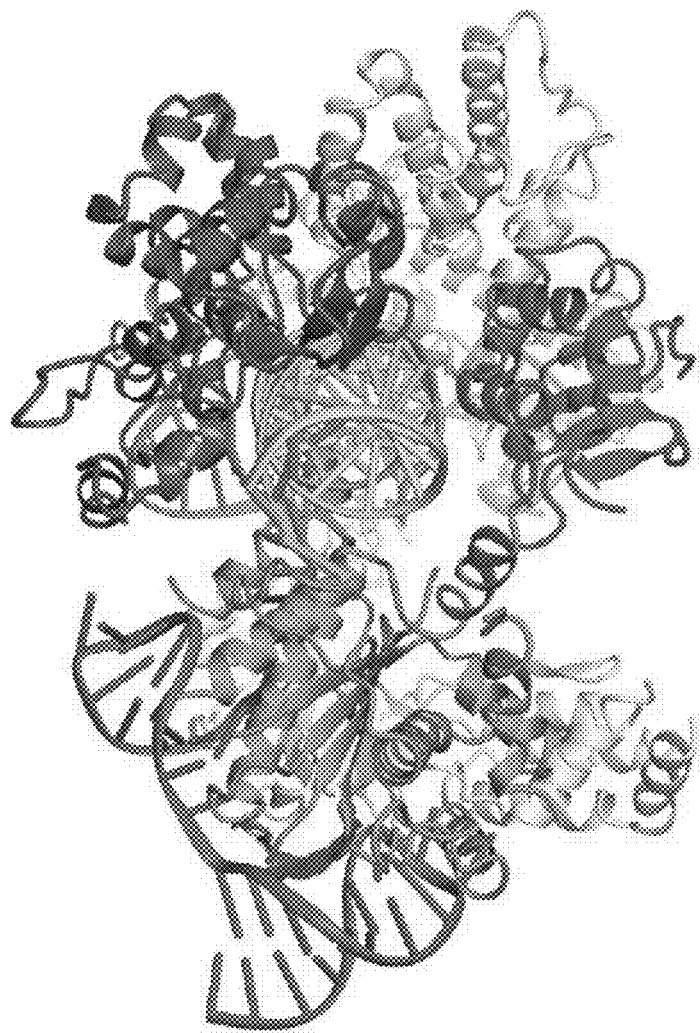
Figure 1D:
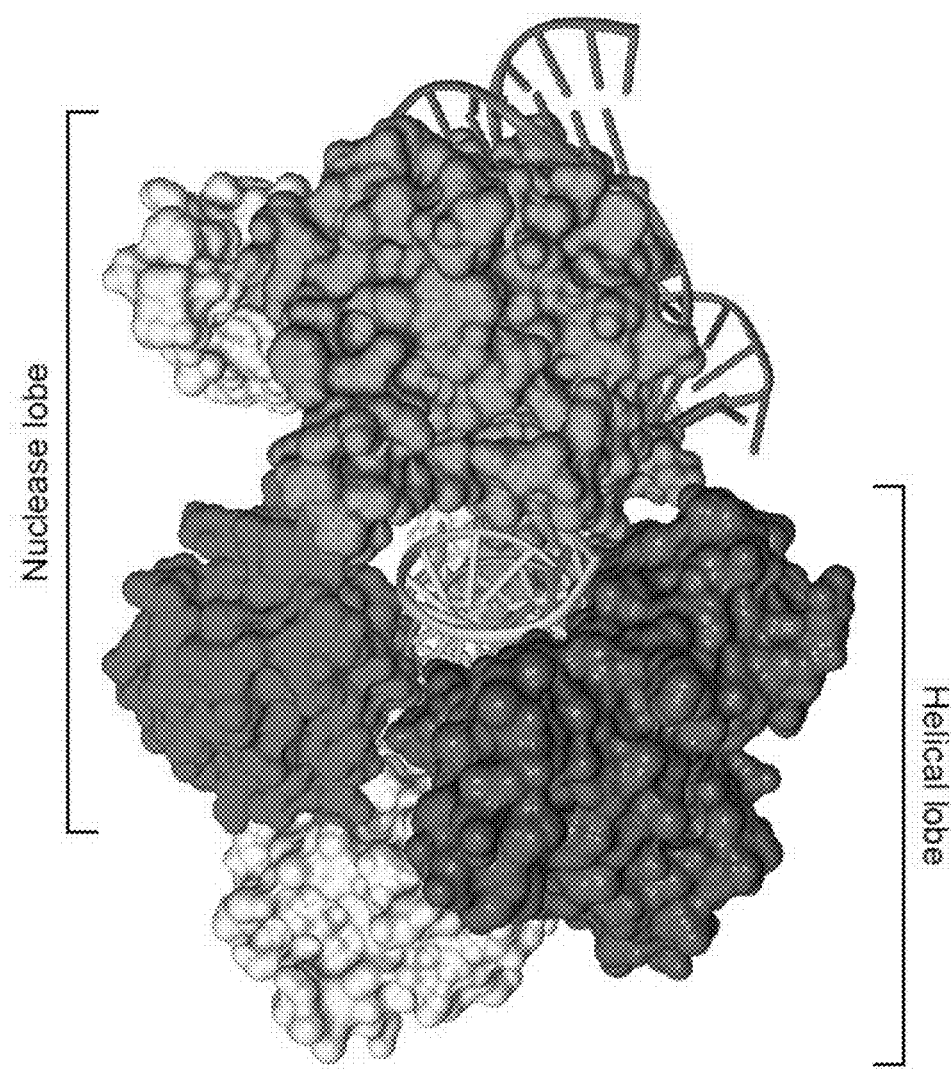
Figure 1E:
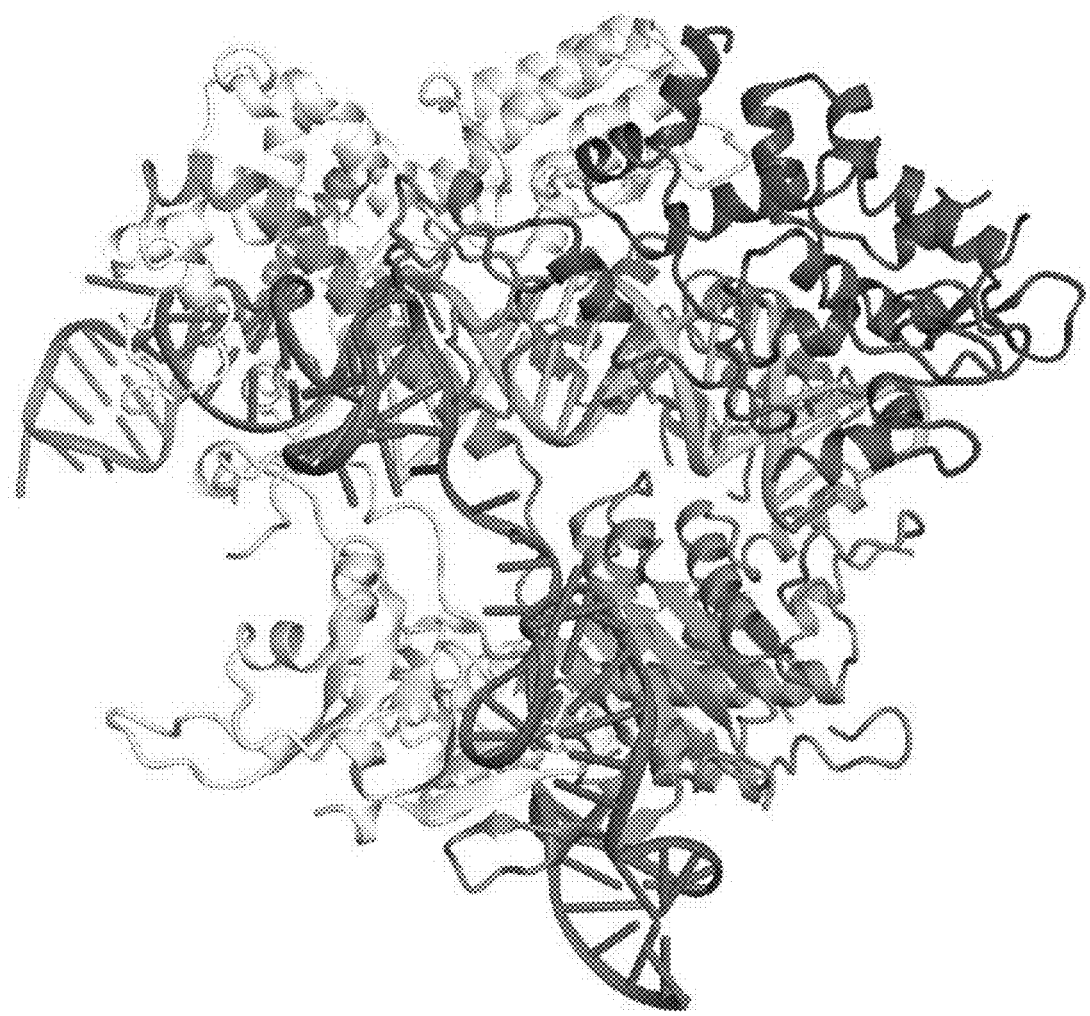
Figure 1F:
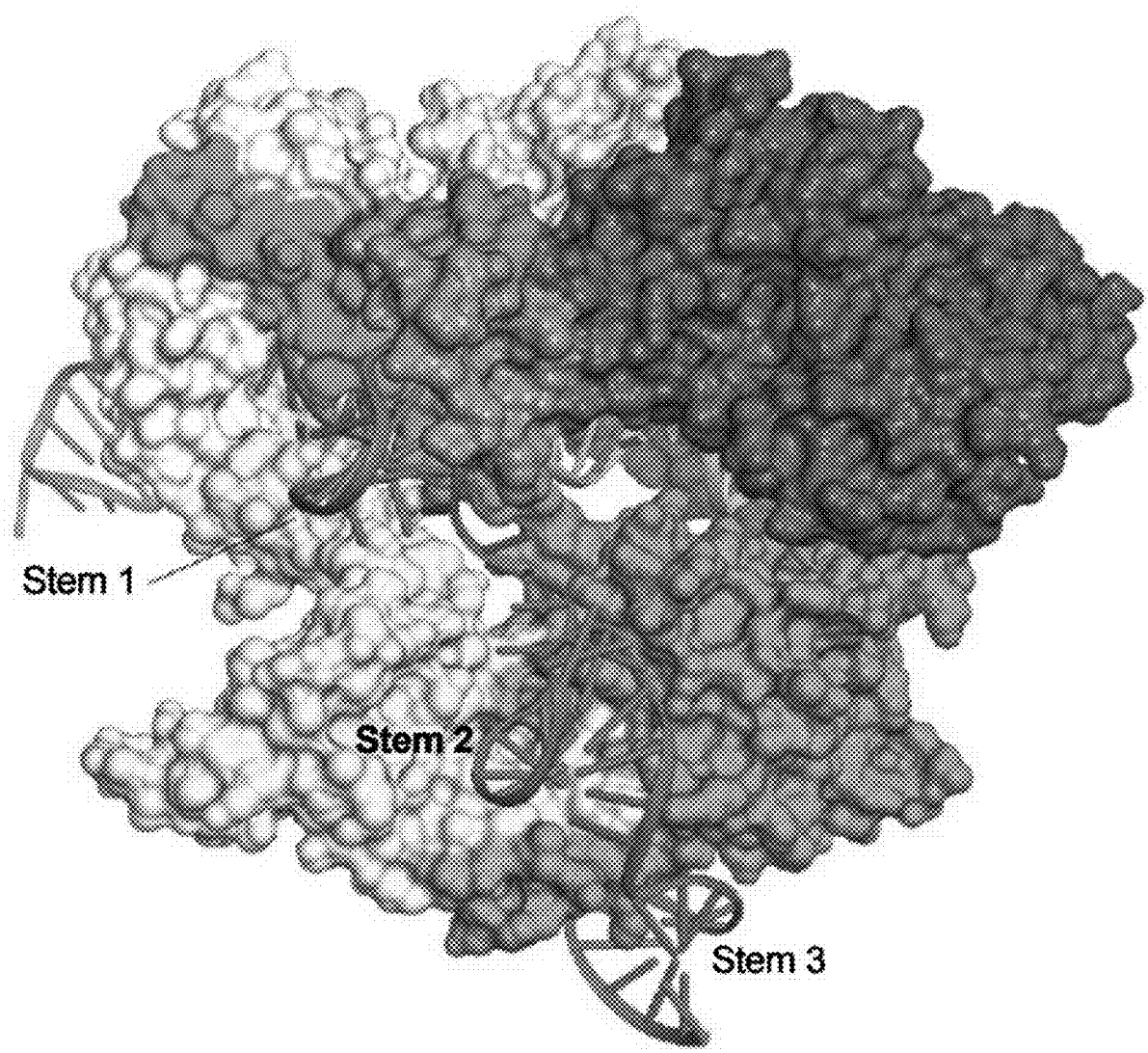
Figure 1G:
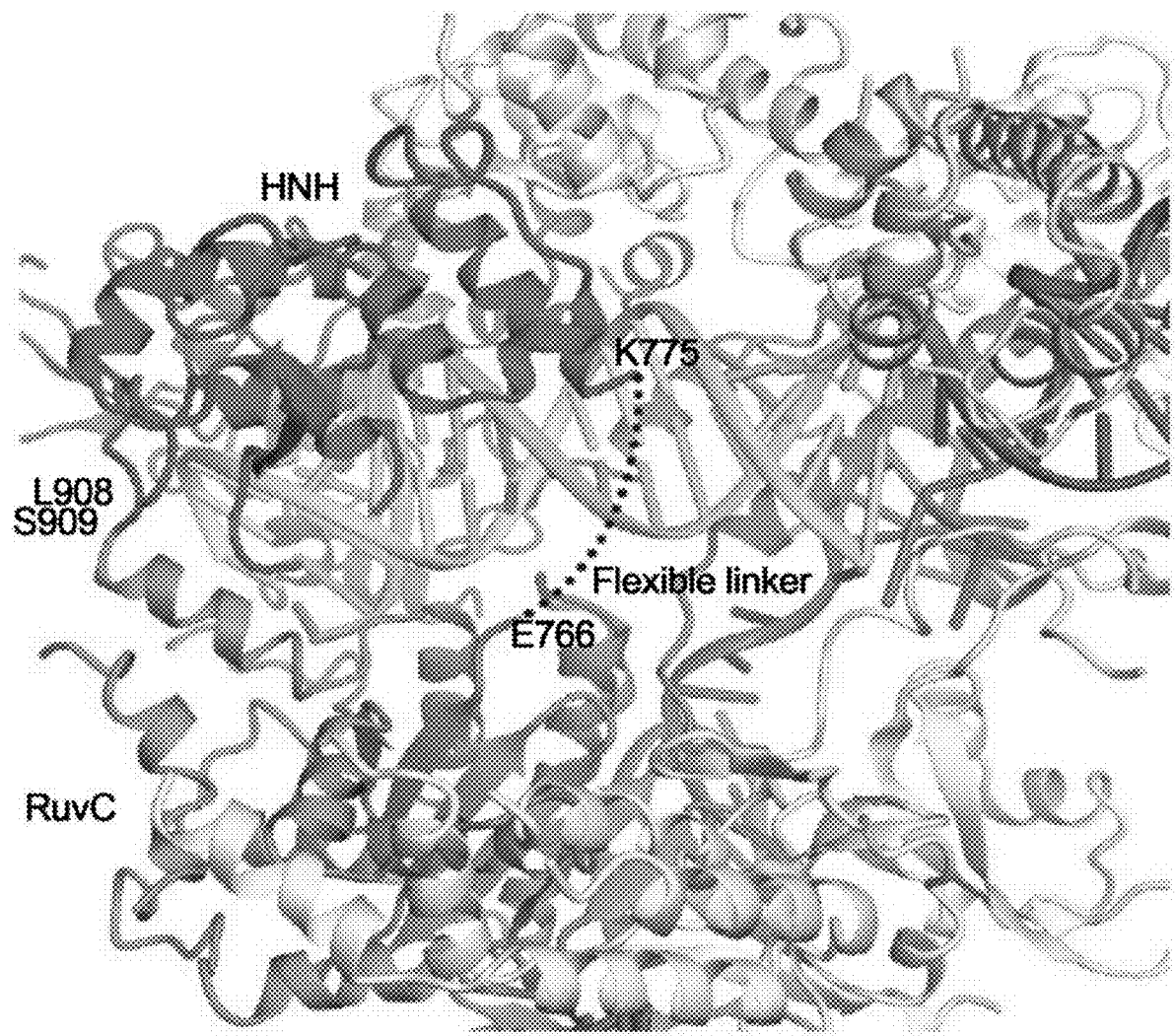
Figure 1H:
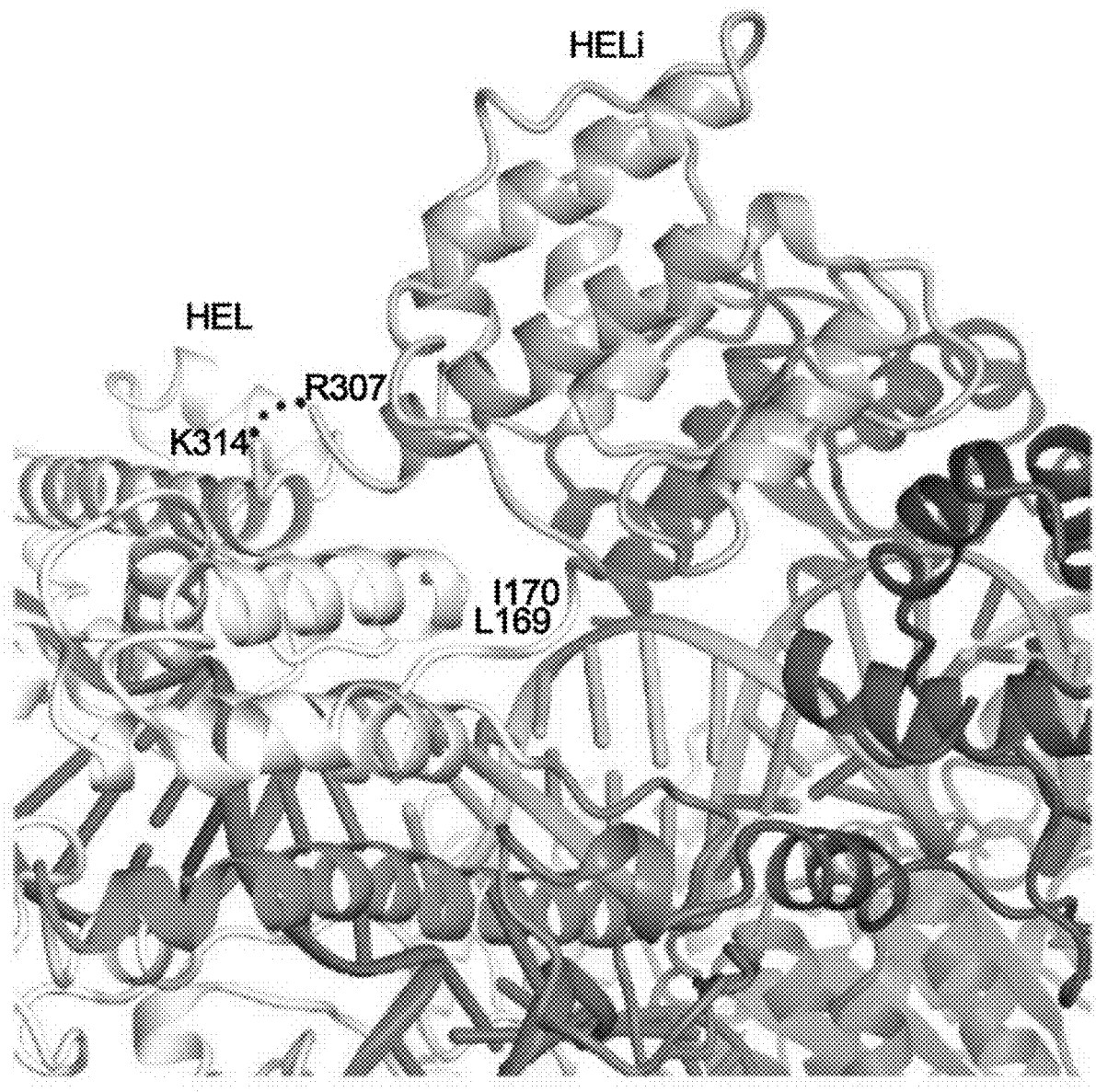
Figure 1I:
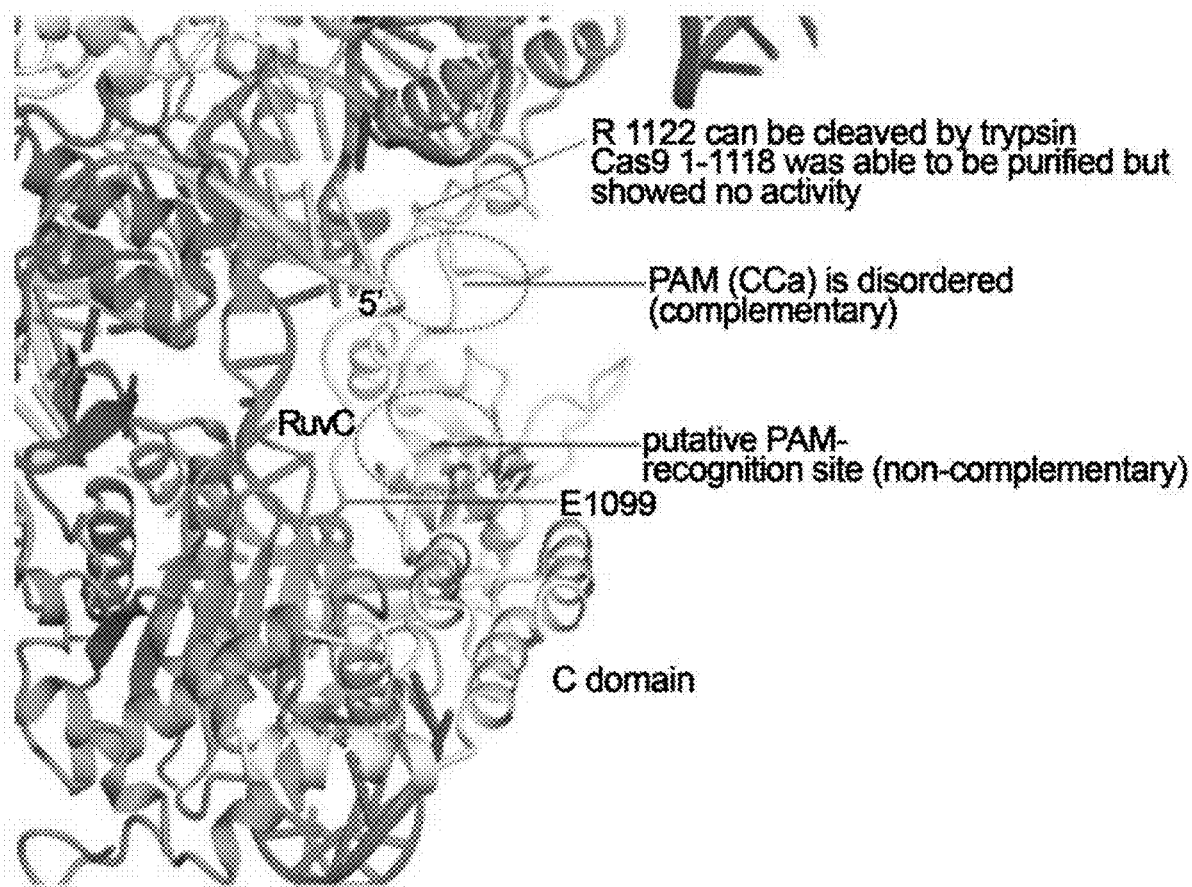

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418 and 8,895,308; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/U52013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), and WO2014/018423 (PCT/US2013/051418). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent application Nos: PCT/US2014/041803, PCT/U52014/041800, PCT/U52014/041809, PCT/U52014/041804 and PCT/U52014/041806, each filed Jun. 10, 2014 Jun. 10, 2014; PCT/US2014/041808 filed Jun. 11, 2014; and PCT/US2014/62558 filed Oct. 28, 2014, and U.S. Provisional Patent Application Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of:

*Multiplex genome engineering using CRISPR/Cas systems.* Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121):819-23 (2013);

*RNA-guided editing of bacterial genomes using CRISPR-Cas systems.* Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering.* Wang H., Yang H., Shivalila C S., Dawlaty M M., Cheng A W., Zhang F., Jaenisch R. Cell May 9; 153(4): 910-8 (2013);

*Optical control of mammalian endogenous transcription and epigenetic states.* Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature 12466. Epub 2013 Aug. 23;

*Double Nicking by RNA-Guided CRISPR Cas9 for Enhanced Genome Editing Specificity.* Ran, F A., Hsu, P D., Lin, C Y., Gootenberg, J S., Konermann, S., Trevino, A E., Scott, D A., Inoue, A., Matoba, S., Zhang, Y., & Zhang, F. *Cell* August 28. pii: S0092-8674(13)01015-5. (2013);

*DNA targeting specificity of RNA guided Cas9 nucleases.* Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

*Genome engineering using the CRISPR-Cas9 system.* Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells.* Shalem, O., Sanjana, N E., Hartenian, E., Shi, X., Scott, D A., Mikkelson, T., Heckl, D., Ebert, B L., Root, D E., Doench, J G., Zhang, F. *Science* December 12. (2013). [Epub ahead of print];

*Crystal structure of cas9 in complex with guide RNA and target DNA.* Nishimasu, H., Ran, F A., Hsu, P D., Konermann, S., Shehata, S I., Dohmae, N., Ishitani, R., Zhang, F., Nureki, O. *Cell* February 27. (2014). 156(5):935-49;

*Genome-wide binding of the CRISPR endonuclease Cas9 in mammalian cells.* Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889,

*CRISPR-Cas9 Knockin Mice for Genome Editing and Cancer Modeling*, Platt et al., Cell 159(2): 440-455 (2014) DOI: 10.1016/j.cell.2014.09.014,

*Development and Applications of CRISPR-Cas9 for Genome Engineering*, Hsu et al, Cell 157, 1262-1278 (Jun. 5, 2014) (Hsu 2014),

*Genetic screens in human cells using the CRISPR/Cas9 system*, Wang et al., Science. 2014 Jan. 3; 343(6166): 80-84. doi:10.1126/science.1246981,

*Rational design of highly active sgRNAs for CRISPR-Cas9-mediated gene inactivation*, Doench et al., Nature Biotechnology published online 3 Sep. 2014; doi:10.1038/nbt.3026, and

*In vivo interrogation of gene function in the mammalian brain using CRISPR-Cas9*, Swiech et al, Nature Biotechnology; published online 19 Oct. 2014; doi:10.1038/nbt.3055.

each of which is incorporated herein by reference, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors As discussed in the present specification, the Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used. In some embodiments it may be preferred in a CRISPR complex that the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II Cas9 enzyme.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and PA Carr and GM Church, 2009, *Nature Biotechnology* 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNN-NNNNNgttttgtactctcaagatttaGAAAtaaatcttgcagaagctaca-aagataaggcttcatgccgaaatcaacaccctgtcattttatggcagggtgttttcg-ttatttaaTTTTTT (SEQ ID NO: 3); (2) NNNNNNNNNNN-NNNNNNNNNgttttgtactctcaGAAAtgcagaagctacaaaga-taaggcttcatgccg aaatcaacaccctgtcattttatggcagggtgttttcgttatt-taaTTTTTT (SEQ ID NO: 4); (3) NNNNNNNNNNNNNN-NNNNNNNNgttttgtactctcaGAAAtgcagaagctacaaagataa-ggcttcatgccg aaatcaacaccctgtcattttatggcagggtgtTTTTTT (SEQ ID NO: 5); (4) NNNNNNNNNNNNNNNNNN-NNNgttttagagctaGAAAtagcaagttaaaataaggctagtccgttatca-actt gaaaaagtggcaccgagtcggtgcTTTTTT (SEQ ID NO: 6); (5) NNNNNNNNNNNNNNNNNNNNNgttttagagctaGA-AATAGcaagttaaaataaggctagtccgttatcaac ttgaaaaagtgTTTT-TTT (SEQ ID NO: 7); and (6) NNNNNNNNNNNNN-NNNNNNNNgttttagagctagAAATAGcaagttaaaataaggctagt-ccgttatcaTT TTTTTT (SEQ ID NO: 8). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 9) in the EMX1 gene of the human genome, deep sequencing can be used to assess the level of modification at the following two off-target loci, 1: 5'-GAGTCCTAGCAGGAGAAGAA-3' (SEQ ID NO: 10) and 2: 5'-GAGTCTAAGCAGAAGAAGAA-3' (SEQ ID NO: 11). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to mimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (S. pyogenes Cas9) or saCas9 (S. aureus Cas9). StCas9" refers to wild type Cas9 from S. thermophilus, the protein sequence of which is given in the SwissProt database under accession number G3ECR1. Similarly, S pyogenes Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in Streptococcus pyogenes. However, it will be appreciated that this invention includes many more Cas9s from other species of microbes, such as SpCas9, SaCa9, St1Cas9 and so forth. Enzymatic action by Cas9 derived from Streptococcus pyogenes or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, January 15; 37(1): 7. The type II CRISPR locus from Streptococcus pyogenes SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

With respect to mutations of the CRISPR enzyme, when the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa, or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 12); the NLS from nucleoplasmin (e.g. the nucleoplasmin bipartite NLS with the sequence KRPAATKKAGQAKKKK (SEQ ID NO: 13)); the c-myc NLS having the amino acid sequence PAAKRVKLD (SEQ ID NO: 14) or RQRRNELKRSP (SEQ ID NO: 15); the hRNPA1 M9 NLS having the sequence NQSSNFGPMKGGNFGGRSSGPYGGGG-QYFAKPRNQGGY (SEQ ID NO: 16); the sequence RMRIZFKNKGKDTAELRRRRVEVSVELRKAKKDEQI-LKRRNV (SEQ ID NO: 17) of the IBB domain from importin-alpha; the sequences VSRKRPRP (SEQ ID NO: 18) and PPKKARED (SEQ ID NO: 19) of the myoma T protein; the sequence PQPKKKPL (SEQ ID NO: 20) of human p53; the sequence SALIKKKKKMAP (SEQ ID NO: 21) of mouse c-abl IV; the sequences DRLRR (SEQ ID NO: 22) and PKQKKRK (SEQ ID NO: 23) of the influenza virus NS1; the sequence RKLKKKIKKL (SEQ ID NO: 24) of the Hepatitis virus delta antigen; the sequence REKKKFLKRR (SEQ ID NO: 25) of the mouse Mx1 protein; the sequence KRKGDEVDGVDEVAKKKSKK (SEQ ID NO: 26) of the human poly(ADP-ribose) polymerase; and the sequence RKCLQAGMNLEARKTKK (SEQ ID NO: 27) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9. An advantage of the present methods is that the CRISPR system minimizes or avoids off-target binding and its resulting side effects. This is achieved using systems arranged to have a high degree of sequence specificity for the target DNA.

Crystallization of CRISPR-Cas9 and Crystal Structure

Crystallization of CRISPR-cas9 and Characterization of Crystal Structure: The crystals of the invention can be obtained by techniques of protein crystallography, including batch, liquid bridge, dialysis, vapor diffusion and hanging drop methods. Generally, the crystals of the invention are grown by dissolving substantially pure CRISPR-cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases.

Uses of the Crystals, Crystal Structure and Atomic Structure Co-Ordinates: The crystals of the invention, and particularly the atomic structure co-ordinates obtained therefrom, have a wide variety of uses. The crystals and structure co-ordinates are particularly useful for identifying compounds (nucleic acid molecules) that bind to CRISPR-cas9, and CRISPR-cas9s that can bind to particular compounds (nucleic acid molecules). Thus, the structure co-ordinates described herein can be used as phasing models in determining the crystal structures of additional synthetic or mutated CRISPR-cas9s, cas9s, nickases, binding domains. The provision of the crystal structure of CRISPR-cas9 complexed with a nucleic acid molecule as in the herein Crystal Structure Table and the Figures provide the skilled artisan with a detailed insight into the mechanisms of action of CRISPR-cas9. This insight provides a means to design modified CRISPR-cas9s, such as by attaching thereto a functional group, such as a repressor or activator. While one can attach a functional group such as a repressor or activator to the N or C terminal of CRISPR-cas9, the crystal structure demonstrates that the N terminal seems obscured or hidden, whereas the C terminal is more available for a functional group such as repressor or activator. Moreover, the crystal structure demonstrates that there is a flexible loop between approximately CRISPR-cas9 (*S. pyogenes*) residues 534-676 which is suitable for attachment of a functional group such as an activator or repressor. Attachment can be via a linker, e.g., a flexible glycine-serine (GlyGlyGlySer) (SEQ ID NO: 1) or (GGGS)$_3$ (SEQ ID NO: 28) or a rigid alpha-helical linker such as (Ala(GluAlaAlaAlaLys)Ala) (SEQ ID NO: 29). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn.

The provision of the crystal structure of CRISPR-cas9 complexed with a nucleic acid molecule allows a novel approach for drug or compound discovery, identification, and design for compounds that can bind to CRISPR-cas9 and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans. Accordingly, the invention provides a computer-based method of rational design of CRISPR-cas9 complexes. This rational design can comprise: providing the structure of the CRISPR-cas9 complex as defined by some or all (e.g., at least 2 or more, e.g., at least 5, advantageously at least 10, more advantageously at least 50 and even more advantageously at least 100 atoms of the structure) co-ordinates in the herein Crystal Structure Table and/or in Figure(s); providing a structure of a desired nucleic acid molecule as to which a CRISPR-cas9 complex is desired; and fitting the structure of the CRISPR-cas9 complex as defined by some or all co-ordinates in the herein Crystal Structure Table and/or in Figures to the desired nucleic acid molecule, including in said fitting obtaining putative modification(s) of the CRISPR-cas9 complex as defined by some or all co-ordinates in the herein Crystal Structure Table and/or in Figures for said desired nucleic acid molecule to bind for CRISPR-cas9 complex(es) involving the desired nucleic acid molecule. The method or fitting of the method may use the co-ordinates of atoms of interest of the CRISPR-cas9 complex as defined by some or all co-ordinates in the herein Crystal Structure Table and/or in Figures which are in the vicinity of the active site or binding region (e.g., at least 2 or more, e.g., at least 5, advantageously at least 10, more advantageously at least 50 and even more advantageously at least 100 atoms of the structure) in order to model the vicinity of the active site or binding region. These co-ordinates may be used to define a space which is then screened "in silico" against a desired or candidate nucleic acid molecule. Thus, the invention provides a computer-based method of rational design of CRISPR-cas9 complexes. This method may include: providing the co-ordinates of at least two atoms of the herein Crystal Structure Table ("selected co-ordinates"); providing the structure of a candidate or desired nucleic acid molecule; and fitting the structure of the candidate to the selected co-ordinates. In this fashion, the skilled person may also fit a functional group and a candidate or desired nucleic acid molecule. For example, providing the structure of the CRISPR-cas9 complex as defined by some or all (e.g., at least 2 or more, e.g., at least 5, advantageously at least 10, more advantageously at least 50 and even more advantageously at least 100 atoms of the structure) co-ordinates in the herein Crystal Structure Table and/or in Figure(s); providing a structure of a desired nucleic acid molecule as to which a CRISPR-cas9 complex is desired; fitting the structure of the CRISPR-cas9 complex as defined by some or all co-ordinates in the herein Crystal Structure Table and/or in Figures to the desired nucleic acid molecule, including in said fitting obtaining putative modification(s) of the CRISPR-cas9 complex as defined by some or all co-ordinates in the herein Crystal Structure Table and/or in Figures for said desired nucleic acid molecule to bind for CRISPR-cas9 complex(es) involving the desired nucleic acid molecule; selecting putative fit CRISPR-cas9-desired nucleic acid molecule complex(es), fitting such putative fit CRISPR-cas9-desired nucleic acid molecule complex(es) to the functional group (e.g., activator, repressor), e.g., as to locations for situating the functional group (e.g., positions within the flexible loop) and/or putative modifications of the putative fit CRISPR-cas9-desired nucleic acid molecule complex(es) for creating locations for situating the functional group. As alluded to, the invention can be practiced using co-ordinates in the herein Crystal Structure Table and/or in Figures which are in the vicinity of the active site or binding region; and therefore, the methods of the invention can employ a sub-domain of interest of the CRISPR-cas9 complex. Methods of the invention can be practiced using coordinates of a domain or sub-domain. The methods can optionally include synthesizing the candidate or desired nucleic acid molecule and/or the CRISPR-cas9 systems from the "in silico" output and testing binding and/or activity of "wet" or actual a functional group linked to a "wet" or actual CRISPR-cas9 system bound to a "wet" or actual candidate or desired nucleic acid molecule. The methods can include synthesizing the CRISPR-cas9 systems (including a functional group) from the "in silico" output and testing binding and/or activity of "wet" or actual a functional group linked to a "wet" or actual CRISPR-cas9 system bound to an in vivo "wet" or actual candidate or desired nucleic acid molecule, e.g., contacting "wet" or actual CRISPR-cas9 system including a functional group from the "in silico" output with a cell containing the desired or candidate nucleic acid molecule. These methods can include observing the cell or an organism containing the cell for a desired reaction, e.g., reduction of symptoms or condition or disease. The step of providing the structure of a candidate nucleic acid molecule may involve selecting the compound by computationally screening a database containing nucleic acid molecule data, e.g., such data as to conditions or diseases. A 3-D descriptor for binding of the candidate nucleic acid molecule may be derived from geometric and functional constraints derived from the architecture and chemical nature of the CRISPR-cas9 complex or domains or regions thereof from the herein crystal structure. In effect, the descriptor can be a type of virtual modification(s) of the CRISPR-cas9 complex crystal structure herein for binding CRISPR-cas9 to the candidate or desired nucleic acid molecule. The descriptor may then be used to interrogate the nucleic acid molecule database to ascertain those nucleic acid molecules of the database that have putatively good binding to the descriptor. The herein "wet" steps can then be performed using the descriptor and nucleic acid molecules that have putatively good binding.

"Fitting" can mean determining, by automatic or semi-automatic means, interactions between at least one atom of the candidate and at least one atom of the CRISPR-cas9 complex and calculating the extent to which such an interaction is stable. Interactions can include attraction, repulsion, brought about by charge, steric considerations, and the like. A "sub-domain" can mean at least one, e.g., one, two, three, or four, complete element(s) of secondary structure. Particular regions or domains of the CRISPR-cas9 include those identified in the herein Crystal Structure Table and the Figures.

In any event, the determination of the three-dimensional structure of CRISPR-cas 9 (*S. pyogenes* cas9) complex provides a basis for the design of new and specific nucleic acid molecules that bind to CRISPR-cas 9 (e.g., *S. pyogenes* cas9), as well as the design of new CRISPR-cas9 systems, such as by way of modification of the CRISPR-cas9 system to bind to various nucleic acid molecules, by way of modification of the CRISPR-cas9 system to have linked thereto to any one or more of various functional groups that may interact with each other, with the CRISPR-cas9 (e.g., an inducible system that provides for self-activation and/or self-termination of function), with the nucleic acid molecule nucleic acid molecules (e.g., the functional group may be a regulatory or functional domain which may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator; see, e.g., Zhang et al., U.S. Pat. No. 8,507,272, and it is again mentioned that it and all documents cited herein and all appln cited documents are hereby incorporated herein by reference), by way of modification of cas9, by way of novel nickases). Indeed, the herewith CRISPR-cas9 (*S. pyogenes* cas9) crystal structure has a multitude of uses. For example, from knowing the three-dimensional structure of CRISPR-cas9 (*S. pyogenes* cas9) crystal structure, computer modelling programs may be used to design or identify different molecules expected to interact with possible or confirmed sites such as binding sites or other structural or functional features of the CRISPR-cas9 system (e.g., *S. pyogenes* cas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders ascertain how well the shape and the chemical structure of the potential binder will bind to a CRISPR-cas9 system (e.g., *S. pyogenes* cas9). Computer-assisted, manual examination of the active site or binding site of a CRISPR-cas9 system (e.g., *S. pyogenes* cas9) may be performed. Programs such as GRID (P. Goodford, J. Med. Chem, 1985, 28, 849-57)—a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., CRISPR-cas9 system (e.g., *S. pyogenes* cas9) and a candidate nucleic acid molecule or a nucleic acid molecule and a candidate CRISPR-cas9 system (e.g., *S. pyogenes* cas9); and the CRISPR-cas9 crystal structure (*S. pyogenes* cas9) herewith enables such methods. Generally, the tighter the fit, the fewer the steric hindrances, and the greater the attractive forces, the more potent the potential binder, since these properties are consistent with a tighter binding constant. Furthermore, the more specificity in the design of a candidate CRISPR-cas9 system (e.g., *S. pyogenes* cas9), the more likely it is that it will not interact with off-target molecules as well. Also, "wet" methods are enabled by the instant invention. For example, in an aspect, the invention provides for a method for determining the structure of a binder (e.g., target nucleic acid molecule) of a candidate CRISPR-cas9 system (e.g., *S. pyogenes* cas9) bound to the candidate CRISPR-cas9 system (e.g., *S. pyogenes* cas9), said method comprising, (a) providing a first crystal of a candidate CRISPR-cas9 system (*S. pyogenes* cas9) according to the invention or a second crystal of a candidate a candidate CRISPR-cas9 system (e.g., *S. pyogenes* cas9), (b) contacting the first crystal or second crystal with said binder under conditions whereby a complex may form; and (c) determining the structure of said a candidate (e.g., CRISPR-cas9 system (e.g., *S. pyogenes* cas9) or CRISPR-cas9 system (*S. pyogenes* cas9) complex. The second crystal may have essentially the same coordinates discussed herein, however due to minor alterations in CRISPR-cas9 system (e.g., from the cas9 of such a system being e.g., *S. pyogenes* cas9 versus being *S. pyogenes* cas9), wherein "e.g., *S. pyogenes* cas9" indicates that the cas9 is a cas9 and can be of or derived from *S. pyogenes* or an ortholog thereof), the crystal may form in a different space group.

The invention further involves, in place of or in addition to "in silico" methods, other "wet" methods, including high throughput screening of a binder (e.g., target nucleic acid molecule) and a candidate CRISPR-cas9 system (e.g., *S. pyogenes* cas9), or a candidate binder (e.g., target nucleic acid molecule) and a CRISPR-cas9 system (e.g., *S. pyogenes* cas9), or a candidate binder (e.g., target nucleic acid molecule) and a candidate CRISPR-cas9 system (e.g., *S. pyogenes* cas9) (the foregoing CRISPR-cas9 system(s) with or without one or more functional group(s)), to select compounds with binding activity. Those pairs of binder and CRISPR-cas9 system which show binding activity may be selected and further crystallized with the CRISPR-cas9 crystal having a structure herein, e.g., by co-crystallization or by soaking, for X-ray analysis. The resulting X-ray structure may be compared with that of the herein Crystal Structure Table and the information in the Figures for a variety of purposes, e.g., for areas of overlap. Having designed, identified, or selected possible pairs of binder and CRISPR-cas9 system by determining those which have favorable fitting properties, e.g., predicted strong attraction based on the pairs of binder and CRISPR-cas9 crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate CRISPR-cas9 system (e.g., *S. pyogenes* cas9), or a candidate binder (e.g., target nucleic acid molecule) and a CRISPR-cas9 system (e.g., *S. pyogenes* cas9), or a candidate binder (e.g., target nucleic acid molecule) and a candidate CRISPR-cas9 system (e.g., *S. pyogenes* cas9) (the foregoing CRISPR-cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex(es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-cas9 system or components thereof. These steps may be repeated and re-repeated as necessary. Alternatively or additionally, potential CRISPR-cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of CRISPR-cas systems or complex(es) of unknown structure by using the structural co-ordinates of the herein Crystal Structure Table and the information in the Figures. For example, if X-ray crystallographic or NMR spectroscopic data are provided for a CRISPR-cas system or complex of unknown crystal structure, the structure of a CRISPR-cas9 complex as defined in the herein Crystal Structure Table and the Figures may be used to interpret that data to provide a likely structure for the unknown system or complex by such techniques as by phase modeling in the case of X-ray crystallography. Thus, an inventive method can comprise: aligning a representation of the CRISPR-cas system or complex having an unknown crystal structure with an analogous representation of the CRISPR-cas(9) system and complex of the crystal structure herein to match homologous or analogous regions (e.g., homologous or analogous sequences); modeling the structure of the matched homologous or analogous regions (e.g., sequences) of the CRISPR-cas system or complex of unknown crystal structure based on the structure as defined in the herein Crystal Structure Table and/or in the Figures of the corresponding regions (e.g., sequences); and, determining a conformation (e.g. taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as of nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Advantageously, the first and third steps are performed by computer modeling. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-cas9 crystal structure herein and those of a CRISPR-cas system of unknown crystal structure aid in the prediction and determination of the crystal structure of the CRISPR-cas system of unknown crystal structure. Further still, the aspects of the invention which employ the CRISPR-cas9 crystal structure in silico may be equally applied to new CRISPR-cas crystal structures divined by using the herein CRISPR-cas9 crystal structure. In this fashion, a library of CRISPR-cas crystal structures can be obtained. Rational CRISPR-cas system design is thus provided by the instant invention. For instance, having determined a conformation or crystal structure of a CRISPR-cas system or complex, by the methods described herein, such a conformation may be used in a computer-based methods herein for determining the conformation or crystal structure of other CRISPR-cas systems or complexes whose crystal structures are yet unknown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of a CRISPR-cas system or complex. The system can contain: atomic co-ordinate data according to the herein Crystal Structure Table and the Figures or be derived therefrom e.g., by modeling, said data defining the three-dimensional structure of a CRISPR-cas system or complex or at least one domain or sub-domain thereof, or structure factor data therefor, said structure factor data being derivable from the atomic co-ordinate data of the herein Crystal Structure Table and the Figures. The invention also involves computer readable media with: atomic co-ordinate data according to the herein Crystal Structure Table and/or the Figures or derived therefrom e.g., by homology modeling, said data defining the three-dimensional structure of a CRISPR-cas system or complex or at least one domain or sub-domain thereof, or structure factor data therefor, said structure factor data being derivable from the atomic co-ordinate data of the herein Crystal Structure Table and/or the Figures. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-cas systems or complexes; advantageously, the three-dimensional structure being as defined by the atomic co-ordinate data according to the herein Crystal Structure Table and/or the Figures. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein Crystal Structure Table (see Example 1) gives atomic co-ordinate data for a CRISPR-cas9 (S. pyogenes), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number. See also the text herein and the Figures.

Nucleic Acids, Amino Acids and Proteins, Regulatory Sequences, Vectors, Etc

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4$^{th}$ Ed. —Chapter 18), FASTA (Altschul et al., 1990 *J Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| | Set | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 30). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome), In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Crystal Structure

FIGS. 1A-M provide: various views of the CRISPR-cas complex crystal structure (A-I), chimeric RNA architecture from the crystal structure (J-K), an interaction schematic from the crystal structure (L) and a topology schematic from the crystal structure (M).

Figure 1J:
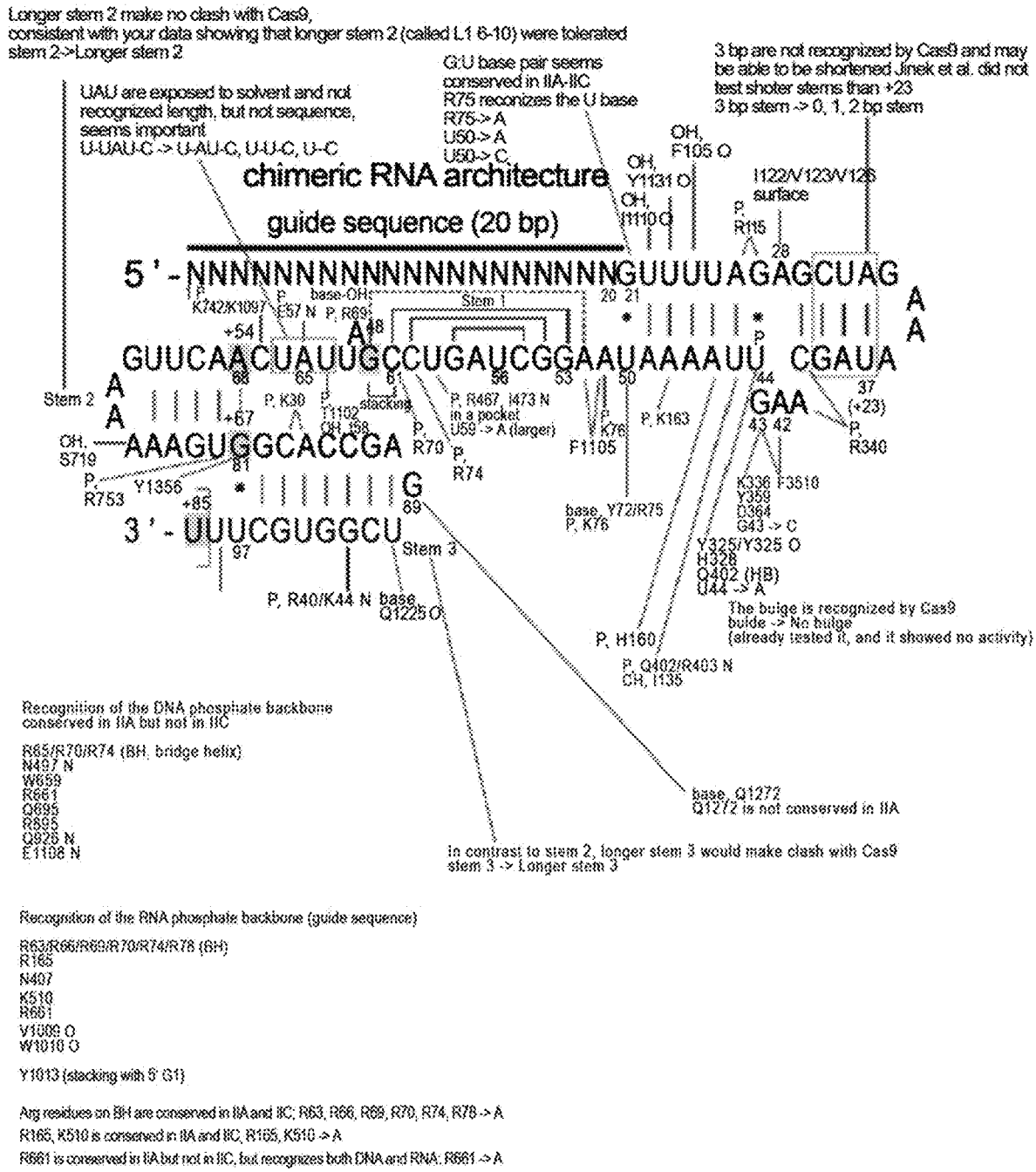
Figure 1K:
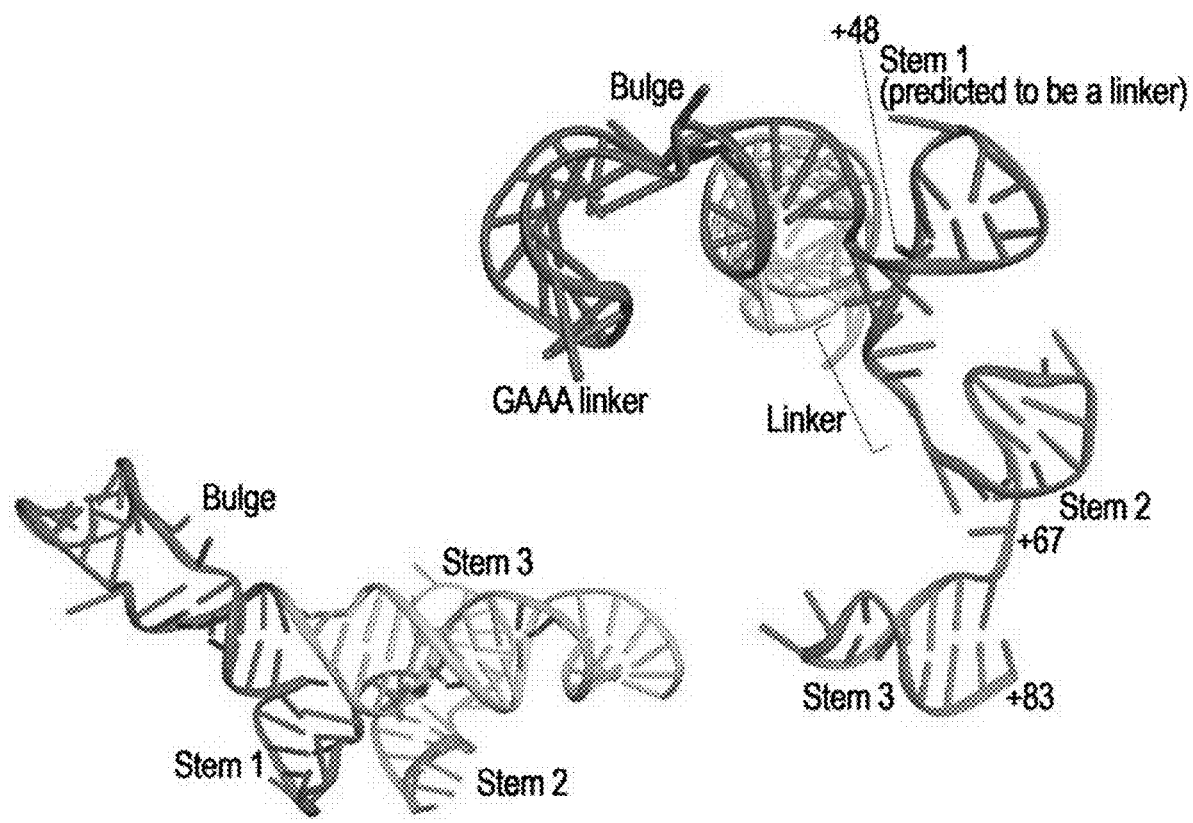
Figure 1L:
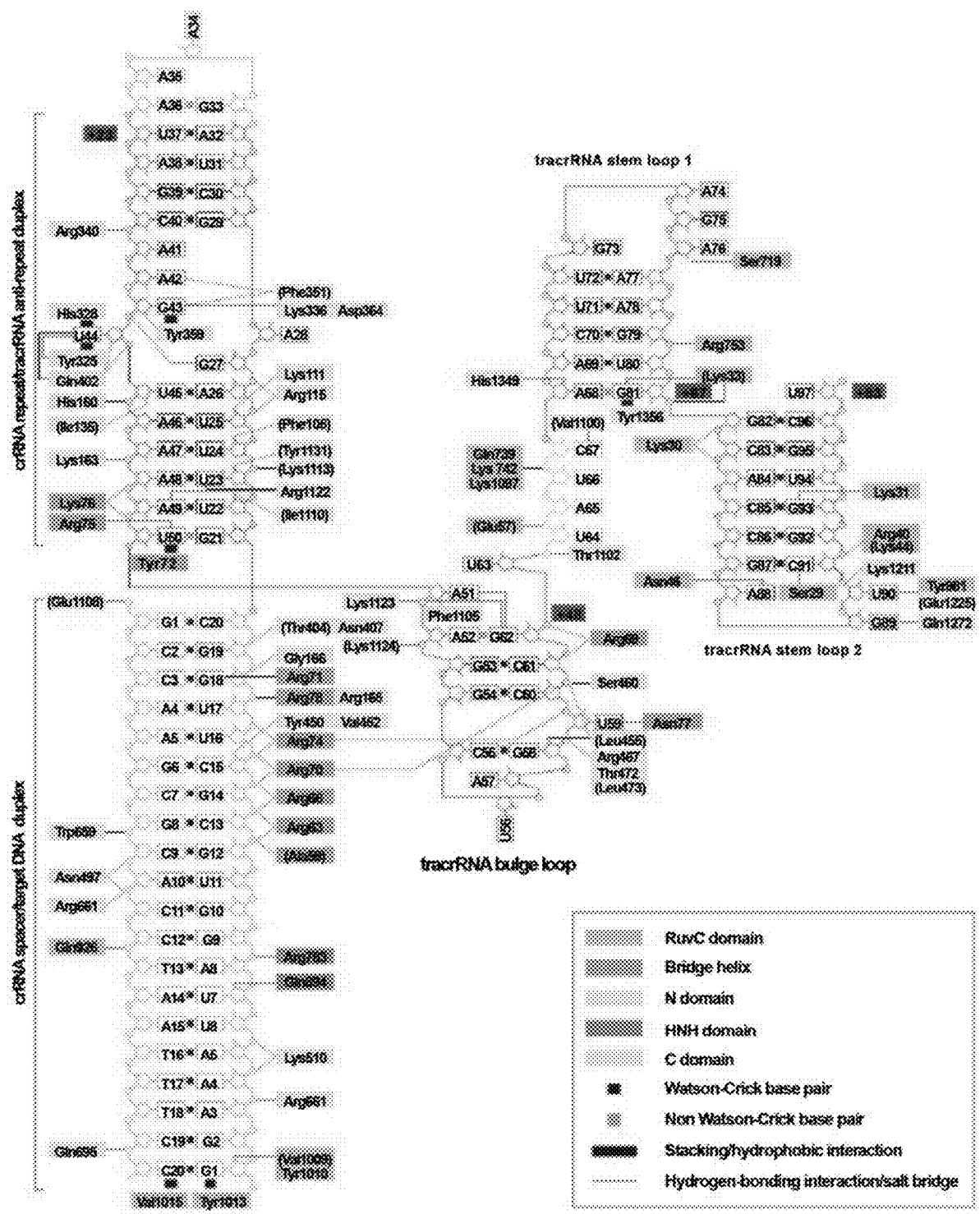
Figure 1M:
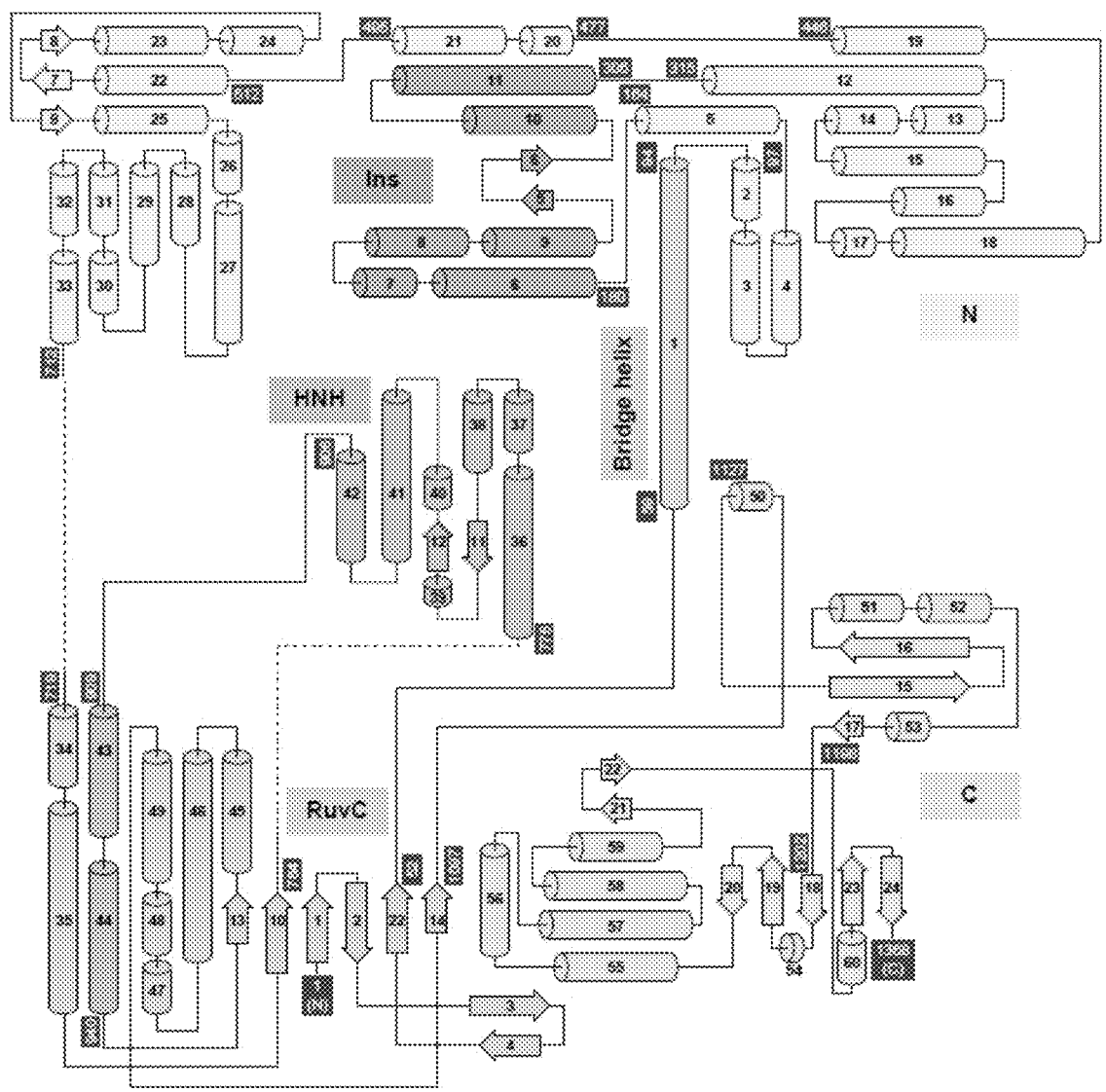
Figure 4B:
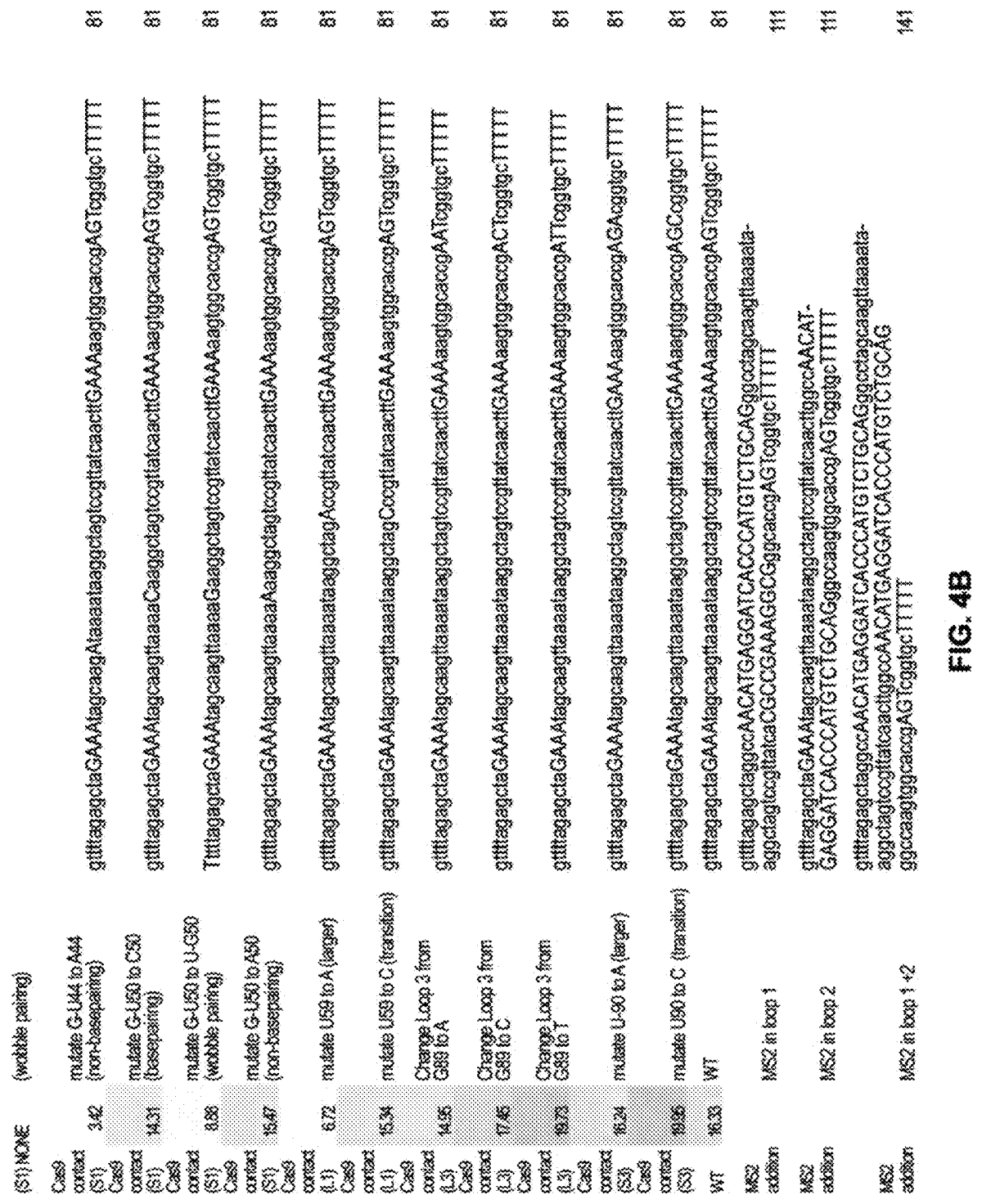

FIGS. 1J-K concern a SpCas9 sgRNA structural study, and FIGS. 4A-B also pertain to sgRNA mutations. SpCas9 sgRNAs were mutated to investigate contribution of specific bases or groups of bases to activity. These include mutations in the direct repeat (DR) and tracrRNA regions of the sgRNA, divided into: stem 1 (base-pairing region between DR and tracrRNA), bulge (un-paired bases between DR and tracrRNA), loop 1 (artificial GAAA connector between DR and tracrRNA), linker 1 (between stem 1 and stem 2), stem 2 (first hairpin formed by tracrRNA tail), loop 2 (loop in between stem 2), stem 3 (second, or last hairpin formed by tracrRNA tail), and loop 3 (loop in between stem 3). Mutations were chosen based on predicted secondary structure as well as secondary structure as illustrated in FIGS. 1A-M, especially FIG. 1J. In addition, three (3) sgRNA scaffolds were designed to incorporate MS2 loops in loop regions for interaction/binding to recruit functional domains fused to MBP. sgRNAs were synthesized as U6:PCR amplicon and tested in co-transfection with wildtype SpCas9.

400 ng of Cas9 plasmid, 100 ng of sgRNA into 200,000 HEK 293FT cells with Lipofectamine 2000; DNA was harvested 3 days post-transfection for SURVEYOR analysis.

The invention thus comprehends the invention comprehends a CRISPR-cas9 (*S. pyogenes*) system having a crystal having the structure defined by the co-ordinates of following Table A (the CRISPR-cas9 crystal structure). Table A discloses SEQ ID NOS 180-202, respectively, in order of appearance.

TABLE A

Lengthy table referenced here

US11155795-20211026-T00001

Please refer to the end of the specification for access instructions.

Example 2

*S. pyogenes* (Sp) SpCas9 Truncations from Crystal Structure

FIGS. 3A-B pertain to SpCas9 truncations from full length SpCas9. These figures show Surveyor gel test results of SpCas9 truncation mutants from the crystal structure that retain cleavage activity (A) and a table showing the amino acid truncations and flexible (GGGS) (SEQ ID NO: 1) or rigid (A(EAAAK)) (SEQ ID NO: 2) linker substitutions of the lanes of the gels of FIG. 3A (B)

In this Example, SpCas9 sequences were analyzed by 1. Comparing against orthologs (*S. aureus, S. thermophilus* CRISPR1, *S. thermophilus* CRISPR3, and *N. meningiditis*), including smaller Cas9s (*S. aureus, S. thermophilus* CRISPR1, and *N. meningiditis*) for regions that are conserved or variable, and 2. Boundaries identified by crystallography as being potentially non-critical for contacting target DNA: sgRNA duplex. A region of SpCas9 (helical domain 2) was not present in many smaller Cas9 orthologs, and predicted to be dispensable for function. Two similar sets of truncations were made, one by sequence alignment with smaller Cas9s, one by crystal prediction. In addition, several sets of flexible glycine-serine (GlyGlyGlySer) (SEQ ID NO: 1) or rigid alpha-helical linkers (Ala(GluAlaAlaAla-Lys)Ala) (SEQ ID NO: 29) in groups of 3, 6, 9, or 12 repeats were also used to replace helical domain 2 for potential structural stabilization and/or aiding of retaining SpCas9:sgRNA specificity. All of the helical region 2 truncations and linker substitutions retained SpCas9 activity. SpCas9 was truncated systematically in Helical 1, 2, and 3 domains, as well as the C'-terminal putative PAM-recognizing domain. Truncation mutants were transfected into HEK 293FT cells as follows: 400 ng of truncation Cas9 plasmid and 100 ng of sgRNA co-transfected into 200,000 cells by Lipofectamine 2000. DNAs from cells were harvested for SURVEYOR analysis.

Below: full length SpCas9 DNA sequence and sequences of the subdomains; followed by helical domain 2 truncation and variants.

```
> Full length NLS-SpCas9-NLS
                                                           (SEQ ID NO: 31)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGAACCCCGACAACAGCGACGTGGACAAGCTGTTCATCCAG

CTGGTGCAGACCTACAACCAGCTGTTCGAGGAAAACCCCATCAACGCCAGCGGCGT

GGACGCCAAGGCCATCCTGTCTGCCAGACTGAGCAAGAGCAGACGGCTGGAAAATC

TGATCGCCCAGCTGCCCGGCGAGAAGAAGAATGGCCTGTTCGGAAACCTGATTGCC

CTGAGCCTGGGCCTGACCCCCAACTTCAAGAGCAACTTCGACCTGGCCGAGGATGC

CAAACTGCAGCTGAGCAAGGACACCTACGACGACGACCTGGACAACCTGCTGGCCC

AGATCGGCGACCAGTACGCCGACCTGTTTCTGGCCGCCAAGAACCTGTCCGACGCC

ATCCTGCTGAGCGACATCCTGAGAGTGAACACCGAGATCACCAAGGCCCCCCTGAG

CGCCTCTATGATCAAGAGATACGACGAGCACCACCAGGACCTGACCCTGCTGAAAG

CTCTCGTGCGGCAGCAGCTGCCTGAGAAGTACAAAGAGATTTTCTTCGACCAGAGCA

AGAACGGCTACGCCGGCTACATTGACGGCGGAGCCAGCCAGGAAGAGTTCTACAAG

TTCATCAAGCCCATCCTGGAAAAGATGGACGGCACCGAGGAACTGCTCGTGAAGCT

GAACAGAGAGGACCTGCTGCGGAAGCAGCGGACCTTCGACAACGGCAGCATCCCCC

ACCAGATCCACCTGGGAGAGCTGCACGCCATTCTGCGGCGGCAGGAAGATTTTTAC

CCATTCCTGAAGGACAACCGGGAAAAGATCGAGAAGATCCTGACCTTCCGCATCCC

CTACTACGTGGGCCCTCTGGCCAGGGGAAACAGCAGATTCGCCTGGATGACCAGAA

AGAGCGAGGAAACCATCACCCCCTGGAACTTCGAGGAAGTGGTGGACAAGGGCGCT

TCCGCCCAGAGCTTCATCGAGCGGATGACCAACTTCGATAAGAACCTGCCCAACGA

GAAGGTGCTGCCCAAGCACAGCCTGCTGTACGAGTACTTCACCGTGTATAACGAGCT

GACCAAAGTGAAATACGTGACCGAGGGAATGAGAAAGCCCGCCTTCCTGAGCGGCG

AGCAGAAAAAGGCCATCGTGGACCTGCTGTTCAAGACCAACCGGAAAGTGACCGTG

AAGCAGCTGAAAGAGGACTACTTCAAGAAAATCGAGTGCTTCGACTCCGTGGAAAT

CTCCGGCGTGGAAGATCGGTTCAACGCCTCCCTGGGCACATACCACGATCTGCTGAA

AATTATCAAGGACAAGGACTTCCTGGACAATGAGGAAAACGAGGACATTCTGGAAG
```

-continued

```
ATATCGTGCTGACCCTGACACTGTTTGAGGACAGAGAGATGATCGAGGAACGGCTG

AAAACCTATGCCCACCTGTTCGACGACAAAGTGATGAAGCAGCTGAAGCGGCGGAG

ATACACCGGCTGGGGCAGGCTGAGCCGGAAGCTGATCAACGGCATCCGGGACAAGC

AGTCCGGCAAGACAATCCTGGATTTCCTGAAGTCCGACGGCTTCGCCAACAGAAAC

TTCATGCAGCTGATCCACGACGACAGCCTGACCTTTAAAGAGGACATCCAGAAAGC

CCAGGTGTCCGGCCAGGGCGATAGCCTGCACGAGCACATTGCCAATCTGGCCGGCA

GCCCCGCCATTAAGAAGGGCATCCTGCAGACAGTGAAGGTGGTGGACGAGCTCGTG

AAAGTGATGGGCCGGCACAAGCCCGAGAACATCGTGATCGAAATGGCCAGAGAGA

ACCAGACCACCCAGAAGGGACAGAAGAACAGCCGCGAGAGAATGAAGCGGATCGA

AGAGGGCATCAAAGAGCTGGGCAGCCAGATCCTGAAAGAACACCCCGTGGAAAAC

ACCCAGCTGCAGAACGAGAAGCTGTACCTGTACTACCTGCAGAATGGGCGGGATAT

GTACGTGGACCAGGAACTGGACATCAACCGGCTGTCCGACTACGATGTGGACCATA

TCGTGCCTCAGAGCTTTCTGAAGGACGACTCCATCGACAACAAGGTGCTGACCAGA

AGCGACAAGAACCGGGGCAAGAGCGACAACGTGCCCTCCGAAGAGGTCGTGAAGA

AGATGAAGAACTACTGGCGGCAGCTGCTGAACGCCAAGCTGATTACCCAGAGAAAG

TTCGACAATCTGACCAAGGCCGAGAGAGGCGGCCTGAGCGAACTGGATAAGGCCGG

CTTCATCAAGAGACAGCTGGTGGAAACCCGGCAGATCACAAAGCACGTGGCACAGA

TCCTGGACTCCCGGATGAACACTAAGTACGACGAGAATGACAAGCTGATCCGGGAA

GTGAAAGTGATCACCCTGAAGTCCAAGCTGGTGTCCGATTTCCGGAAGGATTTCCAG

TTTTACAAAGTGCGCGAGATCAACAACTACCACCACGCCCACGACGCCTACCTGAA

CGCCGTCGTGGGAACCGCCCTGATCAAAAAGTACCCTAAGCTGGAAAGCGAGTTCG

TGTACGGCGACTACAAGGTGTACGACGTGCGGAAGATGATCGCCAAGAGCGAGCAG

GAAATCGGCAAGGCTACCGCCAAGTACTTCTTCTACAGCAACATCATGAACTTTTTC

AAGACCGAGATTACCCTGGCCAACGGCGAGATCCGGAAGCGGCCTCTGATCGAGAC

AAACGGCGAAACCGGGGAGATCGTGTGGGATAAGGGCCGGGATTTTGCCACCGTGC

GGAAAGTGCTGAGCATGCCCCAAGTGAATATCGTGAAAAAGACCGAGGTGCAGACA

GGCGGCTTCAGCAAAGAGTCTATCCTGCCCAAGAGGAACAGCGATAAGCTGATCGC

CAGAAAGAAGGACTGGGACCCTAAGAAGTACGGCGGCTTCGACAGCCCCACCGTGG

CCTATTCTGTGCTGGTGGTGGCCAAAGTGGAAAAGGGCAAGTCCAAGAAACTGAAG

AGTGTGAAAGAGCTGCTGGGGATCACCATCATGGAAAGAAGCAGCTTCGAGAAGAA

TCCCATCGACTTTCTGGAAGCCAAGGGCTACAAAGAAGTGAAAAAGGACCTGATCA

TCAAGCTGCCTAAGTACTCCCTGTTCGAGCTGGAAAACGGCCGGAAGAGAATGCTG

GCCTCTGCCGGCGAACTGCAGAAGGGAAACGAACTGGCCCTGCCCTCCAAATATGT

GAACTTCCTGTACCTGGCCAGCCACTATGAGAAGCTGAAGGGCTCCCCCGAGGATA

ATGAGCAGAAACAGCTGTTTGTGGAACAGCACAAGCACTACCTGGACGAGATCATC

GAGCAGATCAGCGAGTTCTCCAAGAGAGTGATCCTGGCCGACGCTAATCTGGACAA

AGTGCTGTCCGCCTACAACAAGCACCGGGATAAGCCCATCAGAGAGCAGGCCGAGA

ATATCATCCACCTGTTTACCCTGACCAATCTGGGAGCCCCTGCCGCCTTCAAGTACTT

TGACACCACCATCGACCGGAAGAGGTACACCAGCACCAAAGAGGTGCTGGACGCCA

CCCTGATCCACCAGAGCATCACCGGCCTGTACGAGACACGGATCGACCTGTCTCAGC
```

-continued

TGGGAGGCGACAAAAGGCCGGCGGCCACGAAAAAGGCCGGCCAGGCAAAAAGAA

AAAGtaa

>N'-terminal NLS
(SEQ ID NO: 32)
ATGGCCCCAAAGAAGAAGCGGAAGGTCGGTATCCACGGAGTCCCAGCAG

CC

>RuvCI domain
(SEQ ID NO: 33)
GACAAGAAGTACAGCATCGGCCTGGACATCGGCACCAACTCTGTGGGCTG

GGCCGTGATCACCGACGAGTACAAGGTGCCCAGCAAGAAATTCAAGGTGCTGGGCA

ACACCGACCGGCACAGCATCAAGAAGAACCTGATCGGAGCCCTGCTGTTCGACAGC

GGCGAAACA

>Bridging helix
(SEQ ID NO: 34)
GCCGAGGCCACCCGGCTGAAGAGAACCGCCAGAAGAAGATACACCAGAC

GGAAGAACCGGATCTGCTATCTGCAAGAGATCTTC

>Helical domain 1
(SEQ ID NO: 35)
AGCAACGAGATGGCCAAGGTGGACGACAGCTTCTTCCACAGACTGGAAG

AGTCCTTCCTGGTGGAAGAGGATAAGAAGCACGAGCGGCACCCCATCTTCGGCAAC

ATCGTGGACGAGGTGGCCTACCACGAGAAGTACCCCACCATCTACCACCTGAGAAA

GAAACTGGTGGACAGCACCGACAAGGCCGACCTGCGGCTGATCTATCTGGCCCTGG

CCCACATGATCAAGTTCCGGGGCCACTTCCTGATCGAGGGCGAC

>Helical domain 2 (dispensable)
(SEQ ID NO: 36)
CTGAACCCCGACAACAGCGACGTGGACAAGCTGTTCATCCAGCTGGTGCA

GACCTACAACCAGCTGTTCGAGGAAAACCCCATCAACGCCAGCGGCGTGGACGCCA

AGGCCATCCTGTCTGCCAGACTGAGCAAGAGCAGACGGCTGGAAAATCTGATCGCC

CAGCTGCCCGGCGAGAAGAAGAATGGCCTGTTCGGAAACCTGATTGCCCTGAGCCT

GGGCCTGACCCCCAACTTCAAGAGCAACTTCGACCTGGCCGAGGATGCCAAACTGC

AGCTGAGCAAGGACACCTACGACGACGACCTGGACAACCTGCTGGCCCAGATCGGC

GACCAGTACGCCGACCTGTTTCTGGCCGCCAAGAACCTGTCCGACGCCATCCTGCTG

AGCGACATCCTGAGAGTGAACACCGAG

>Helical domain 3
(SEQ ID NO: 37)
ATCACCAAGGCCCCCCTGAGCGCCTCTATGATCAAGAGATACGACGAGCA

CCACCAGGACCTGACCCTGCTGAAAGCTCTCGTGCGGCAGCAGCTGCCTGAGAAGT

ACAAAGAGATTTTCTTCGACCAGAGCAAGAACGGCTACGCCGGCTACATTGACGGC

GGAGCCAGCCAGGAAGAGTTCTACAAGTTCATCAAGCCCATCCTGGAAAAGATGGA

CGGCACCGAGGAACTGCTCGTGAAGCTGAACAGAGAGGACCTGCTGCGGAAGCAGC

GGACCTTCGACAACGGCAGCATCCCCCACCAGATCCACCTGGGAGAGCTGCACGCC

ATTCTGCGGCGGCAGGAAGATTTTTACCCATTCCTGAAGGACAACCGGGAAAAGAT

CGAGAAGATCCTGACCTTCCGCATCCCCTACTACGTGGGCCCTCTGGCCAGGGGAAA

CAGCAGATTCGCCTGGATGACCAGAAAGAGCGAGGAAACCATCACCCCCTGGAACT

TCGAGGAAGTGGTGGACAAGGGCGCTTCCGCCCAGAGCTTCATCGAGCGGATGACC

AACTTCGATAAGAACCTGCCCAACGAGAAGGTGCTGCCCAAGCACAGCCTGCTGTA

CGAGTACTTCACCGTGTATAACGAGCTGACCAAAGTGAAATACGTGACCGAGGGAA

-continued

```
TGAGAAAGCCCGCCTTCCTGAGCGGCGAGCAGAAAAAGGCCATCGTGGACCTGCTG

TTCAAGACCAACCGGAAAGTGACCGTGAAGCAGCTGAAAGAGGACTACTTCAAGAA

AATCGAGTGCTTCGACTCCGTGGAAATCTCCGGCGTGGAAGATCGGTTCAACGCCTC

CCTGGGCACATACCACGATCTGCTGAAAATTATCAAGGACAAGGACTTCCTGGACA

ATGAGGAAAACGAGGACATTCTGGAAGATATCGTGCTGACCCTGACACTGTTTGAG

GACAGAGAGATGATCGAGGAACGGCTGAAAACCTATGCCCACCTGTTCGACGACAA

AGTGATGAAGCAGCTGAAGCGGCGGAGATACACCGGCTGGGGCAGGCTGAGCCGG

AAGCTGATCAACGGCATCCGGGACAAGCAGTCCGGCAAGACAATCCTGGATTTCCT

GAAGTCCGACGGCTTCGCCAACAGAAACTTCATGCAGCTGATCCACGACGACAGCC

TGACCTTTAAAGAGGACATCCAGAAAGCC
```

>Flexible linker
(SEQ ID NO: 38)
```
CAGGTGTCCGGCCAGGGCGAT
```

>RuvCII
(SEQ ID NO: 39)
```
ATCGTGATCGAAATGGCCAGAGAG
```

>HNH
(SEQ ID NO: 40)
```
GACTACGATGTGGACCATATCGTGCCTCAGAGCTTTCTGAAGGACGACTC

CATCGACAACAAGGTGCTGACCAGAAGCGACAAGAAC
```

>RuvCIII
(SEQ ID NO: 41)
```
CACCACGCCCACGACGCCTACCTG
```

>C-terminal (PAM recognizing domain)
(SEQ ID NO: 42)
```
ACCGAGGTGCAGACAGGCGGCTTCAGCAAAGAGTCTATCCTGCCCAAGA

GGAACAGCGATAAGCTGATCGCCAGAAAGAAGGACTGGGACCCTAAGAAGTACGG

CGGCTTCGACAGCCCCACCGTGGCCTATTCTGTGCTGGTGGTGGCCAAAGTGGAAAA

GGGCAAGTCCAAGAAACTGAAGAGTGTGAAAGAGCTGCTGGGGATCACCATCATGG

AAAGAAGCAGCTTCGAGAAGAATCCCATCGACTTTCTGGAAGCCAAGGGCTACAAA

GAAGTGAAAAAGGACCTGATCATCAAGCTGCCTAAGTACTCCCTGTTCGAGCTGGA

AAACGGCCGGAAGAGAATGCTGGCCTCTGCCGGCGAACTGCAGAAGGGAAACGAA

CTGGCCCTGCCCTCCAAATATGTGAACTTCCTGTACCTGGCCAGCCACTATGAGAAG

CTGAAGGGCTCCCCCGAGGATAATGAGCAGAAACAGCTGTTTGTGGAACAGCACAA

GCACTACCTGGACGAGATCATCGAGCAGATCAGCGAGTTCTCCAAGAGAGTGATCC

TGGCCGACGCTAATCTGGACAAAGTGCTGTCCGCCTACAACAAGCACCGGGATAAG

CCCATCAGAGAGCAGGCCGAGAATATCATCCACCTGTTTACCCTGACCAATCTGGGA

GCCCCTGCCGCCTTCAAGTACTTTGACACCACCATCGACCGGAAGAGGTACACCAGC

ACCAAAGAGGTGCTGGACGCCACCCTGATCCACCAGAGCATCACCGGCCTGTACGA

GACACGGATCGACCTGTCTCAGCTGGGAGGCGAC
```

C'-NLS
(SEQ ID NO: 43)
```
AAAAGGCCGGCGGCCACGAAAAAGGCCGGCCAGGCAAAAAAGAAAAAG
```

6. Sp_A_hel 2(174-311) helical domain 2 deletion
(from ortholog alignment)
(SEQ ID NO: 44)
```
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC
```

-continued

```
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACATCACCAAGGCaCCaCTGAGCGCCTCTATGATCAAGAGATACG
ACGAGCACCACCAGGACCTGACCCTGCTGAAAGCTCTCGTGCGGCAGCAGCTGCCT
GAGAAGTACAAAGAGATTTTCTTCGACCAGAGCAAGAACGGCTACGCCGGCTACAT
TGACGGCGGAGCCAGCCAGGAAGAGTTCTACAAGTTCATCAAGCCCATCCTGGAAA
AGATGGACGGCACCGAGGAACTGCTCGTGAAGCTGAACAGAGAGGACCTGCTGCGG
AAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGG
AAAAGATCGAGAAGATCCTGACCTTCCGCATCCCCTACTACGTGGGCCCTCTGGCCA
GGGGAAACAGCAGATTCGCCTGGATGACCAGAAAGAGCGAGGAAACCATCACCCC
CTGGAACTTCGAGGAAGTGGTGGACAAGGGCGCTTCCGCCCAGAGCTTCATCGAGC
GGATGACCAACTTCGATAAGAACCTGCCCAACGAGAAGGTGCTGCCCAAGCACAGC
CTGCTGTACGAGTACTTCACCGTGTATAACGAGCTGACCAAAGTGAAATACGTGACC
GAGGGAATGAGAAAGCCCGCCTTCCTGAGCGGCGAGCAGAAAAAGGCCATCGTGG
ACCTGCTGTTCAAGACCAACCGGAAAGTGACCGTGAAGCAGCTGAAAGAGGACTAC
TTCAAGAAAATCGAGTGCTTCGACTCCGTGGAAATCTCCGGCGTGGAAGATCGGTTC
AACGCCTCCCTGGGCACATACCACGATCTGCTGAAAATTATCAAGGACAAGGACTT
CCTGGACAATGAGGAAAACGAGGACATTCTGGAAGATATCGTGCTGACCCTGACAC
TGTTTGAGGACAGAGAGATGATCGAGGAACGGCTGAAAACCTATGCCCACCTGTTC
GACGACAAAGTGATGAAGCAGCTGAAGCGGCGGAGATACACCGGCTGGGGCAGGC
TGAGCCGGAAGCTGATCAACGGCATCCGGGACAAGCAGTCCGGCAAGACAATCCTG
GATTTCCTGAAGTCCGACGGCTTCGCCAACAGAAACTTCATGCAGCTGATCCACGAC
GACAGCCTGACCTTTAAAGAGGACATCCAGAAAGCCCAGGTGTCCGGCCAGGGCGA
TAGCCTGCACGAGCACATTGCCAATCTGGCCGGCAGCCCCGCCATTAAGAAGGGCA
TCCTGCAGACAGTGAAGGTGGTGGACGAGCTCGTGAAAGTGATGGGCCGGCACAAG
CCCGAGAACATCGTGATCGAAATGGCCAGAGAGAACCAGACCACCCAGAAGGGAC
AGAAGAACAGCCGCGAGAGAATGAAGCGGATCGAAGAGGGCATCAAAGAGCTGGG
CAGCCAGATCCTGAAAGAACACCCCGTGGAAAACACCCAGCTGCAGAACGAGAAG
CTGTACCTGTACTACCTGCAGAATGGGCGGGATATGTACGTGGACCAGGAACTGGA
CATCAACCGGCTGTCCGACTACGATGTGGACCATATCGTGCCTCAGAGCTTTCTGAA
GGACGACTCCATCGACAACAAGGTGCTGACCAGAAGCGACAAGAACCGGGGCAAG
AGCGACAACGTGCCCTCCGAAGAGGTCGTGAAGAAGATGAAGAACTACTGGCGGCA
GCTGCTGAACGCCAAGCTGATTACCCAGAGAAAGTTCGACAATCTGACCAAGGCCG
```

-continued

```
AGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACAC
TAAGTACGACGAGAATGACAAGCTGATCCGGGAAGTGAAAGTGATCACCCTGAAGT
CCAAGCTGGTGTCCGATTTCCGGAAGGATTTCCAGTTTTACAAAGTGCGCGAGATCA
ACAACTACCACCACGCCCACGACGCCTACCTGAACGCCGTCGTGGGAACCGCCCTG
ATCAAAAAGTACCCTAAGCTGGAAAGCGAGTTCGTGTACGGCGACTACAAGGTGTA
CGACGTGCGGAAGATGATCGCCAAGAGCGAGCAGGAAATCGGCAAGGCTACCGCC
AAGTACTTCTTCTACAGCAACATCATGAACTTTTTCAAGACCGAGATTACCCTGGCC
AACGGCGAGATCCGGAAGCGGCCTCTGATCGAGACAAACGGCGAAACCGGGGAGA
TCGTGTGGGATAAGGGCCGGGATTTTGCCACCGTGCGGAAAGTGCTGAGCATGCCC
CAAGTGAATATCGTGAAAAAGACCGAGGTGCAGACAGGCGGCTTCAGCAAAGAGTC
TATCCTGCCCAAGAGGAACAGCGATAAGCTGATCGCCAGAAAGAAGGACTGGGACC
CTAAGAAGTACGGCGGCTTCGACAGCCCCACCGTGGCCTATTCTGTGCTGGTGGTGG
CCAAAGTGGAAAAGGGCAAGTCCAAGAAACTGAAGAGTGTGAAAGAGCTGCTGGG
GATCACCATCATGGAAAGAAGCAGCTTCGAGAAGAATCCCATCGACTTTCTGGAAG
CCAAGGGCTACAAAGAAGTGAAAAAGGACCTGATCATCAAGCTGCCTAAGTACTCC
CTGTTCGAGCTGGAAAACGGCCGGAAGAGAATGCTGGCCTCTGCCGGCGAACTGCA
GAAGGGAAACGAACTGGCCCTGCCCTCCAAATATGTGAACTTCCTGTACCTGGCCA
GCCACTATGAGAAGCTGAAGGGCTCCCCCGAGGATAATGAGCAGAAACAGCTGTTT
GTGGAACAGCACAAGCACTACCTGGACGAGATCATCGAGCAGATCAGCGAGTTCTC
CAAGAGAGTGATCCTGGCCGACGCTAATCTGGACAAAGTGCTGTCCGCCTACAACA
AGCACCGGGATAAGCCCATCAGAGAGCAGGCCGAGAATATCATCCACCTGTTTACC
CTGACCAATCTGGGAGCCCCTGCCGCCTTCAAGTACTTTGACACCACCATCGACCGG
AAGAGGTACACCAGCACCAAAGAGGTGCTGGACGCCACCCTGATCCACCAGAGCAT
CACCGGCCTGTACGAGACACGGATCGACCTGTCTCAGCTGGGAGGCGACAAAAGGC
CGGCGGCCACGAAAAAGGCCGGCCAGGCAAAAAAGAAAAAGtaa
```

7. Sp_A_hel 2-(GGGGS)3 helical domain 2 deletion (from ortholog alignment) ("(GGGGS)3" disclosed as SEQ ID NO: 45)

(SEQ ID NO: 46)
```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACGGTGGCGGTGGCtcgGGTGGCGGTGGCtcgGGTGGCGGTGGCtcg
ATCACCAAGGCCCCCCTGAGCGCCTCTATGATCAAGAGATACGACGAGCACCACCA
GGACCTGACCCTGCTGAAAGCTCTCGTGCGGCAGCAGCTGCCTGAGAAGTACAAAG
```

-continued

```
AGATTTTCTTCGACCAGAGCAAGAACGGCTACGCCGGCTACATTGACGGCGGAGCC

AGCCAGGAAGAGTTCTACAAGTTCATCAAGCCCATCCTGGAAAAGATGGACGGCAC

CGAGGAACTGCTCGTGAAGCTGAACAGAGAGGACCTGCTGCGGAAGCAGCGGACCT

TCGACAACGGCAGCATCCCCCACCAGATCCACCTGGGAGAGCTGCACGCCATTCTG

CGGCGGCAGGAAGATTTTTACCCATTCCTGAAGGACAACCGGGAAAAGATCGAGAA

GATCCTGACCTTCCGCATCCCCTACTACGTGGGCCCTCTGGCCAGGGGAAACAGCAG

ATTCGCCTGGATGACCAGAAAGAGCGAGGAAACCATCACCCCCTGGAACTTCGAGG

AAGTGGTGGACAAGGGCGCTTCCGCCCAGAGCTTCATCGAGCGGATGACCAACTTC

GATAAGAACCTGCCCAACGAGAAGGTGCTGCCCAAGCACAGCCTGCTGTACGAGTA

CTTCACCGTGTATAACGAGCTGACCAAAGTGAAATACGTGACCGAGGGAATGAGAA

AGCCCGCCTTCCTGAGCGGCGAGCAGAAAAAGGCCATCGTGGACCTGCTGTTCAAG

ACCAACCGGAAAGTGACCGTGAAGCAGCTGAAAGAGGACTACTTCAAGAAAATCGA

GTGCTTCGACTCCGTGGAAATCTCCGGCGTGGAAGATCGGTTCAACGCCTCCCTGGG

CACATACCACGATCTGCTGAAAATTATCAAGGACAAGGACTTCCTGGACAATGAGG

AAAACGAGGACATTCTGGAAGATATCGTGCTGACCCTGACACTGTTTGAGGACAGA

GAGATGATCGAGGAACGGCTGAAAACCTATGCCCACCTGTTCGACGACAAAGTGAT

GAAGCAGCTGAAGCGGCGGAGATACACCGGCTGGGGCAGGCTGAGCCGGAAGCTG

ATCAACGGCATCCGGGACAAGCAGTCCGGCAAGACAATCCTGGATTTCCTGAAGTC

CGACGGCTTCGCCAACAGAAACTTCATGCAGCTGATCCACGACGACAGCCTGACCTT

TAAAGAGGACATCCAGAAAGCCCAGGTGTCCGGCCAGGGCGATAGCCTGCACGAGC

ACATTGCCAATCTGGCCGGCAGCCCCGCCATTAAGAAGGGCATCCTGCAGACAGTG

AAGGTGGTGGACGAGCTCGTGAAAGTGATGGGCCGGCACAAGCCCGAGAACATCGT

GATCGAAATGGCCAGAGAGAACCAGACCACCCAGAAGGGACAGAAGAACAGCCGC

GAGAGAATGAAGCGGATCGAAGAGGGCATCAAAGAGCTGGGCAGCCAGATCCTGA

AAGAACACCCCGTGGAAAACACCCAGCTGCAGAACGAGAAGCTGTACCTGTACTAC

CTGCAGAATGGGCGGGATATGTACGTGGACCAGGAACTGGACATCAACCGGCTGTC

CGACTACGATGTGGACCATATCGTGCCTCAGAGCTTTCTGAAGGACGACTCCATCGA

CAACAAGGTGCTGACCAGAAGCGACAAGAACCGGGGCAAGAGCGACAACGTGCCC

TCCGAAGAGGTCGTGAAGAAGATGAAGAACTACTGGCGGCAGCTGCTGAACGCCAA

GCTGATTACCCAGAGAAAGTTCGACAATCTGACCAAGGCCGAGAGAGGCGGCCTGA

GCGAACTGGATAAGGCCGGCTTCATCAAGAGACAGCTGGTGGAAACCCGGCAGATC

ACAAAGCACGTGGCACAGATCCTGGACTCCCGGATGAACACTAAGTACGACGAGAA

TGACAAGCTGATCCGGGAAGTGAAAGTGATCACCCTGAAGTCCAAGCTGGTGTCCG

ATTTCCGGAAGGATTTCCAGTTTTACAAAGTGCGCGAGATCAACAACTACCACCACG

CCCACGACGCCTACCTGAACGCCGTCGTGGGAACCGCCCTGATCAAAAAGTACCCT

AAGCTGGAAAGCGAGTTCGTGTACGGCGACTACAAGGTGTACGACGTGCGGAAGAT

GATCGCCAAGAGCGAGCAGGAAATCGGCAAGGCTACCGCCAAGTACTTCTTCTACA

GCAACATCATGAACTTTTTCAAGACCGAGATTACCCTGGCCAACGGCGAGATCCGG

AAGCGGCCTCTGATCGAGACAAACGGCGAAACCGGGGAGATCGTGTGGGATAAGG

GCCGGGATTTTGCCACCGTGCGGAAAGTGCTGAGCATGCCCCAAGTGAATATCGTG
```

```
AAAAAGACCGAGGTGCAGACAGGCGGCTTCAGCAAAGAGTCTATCCTGCCCAAGAG

GAACAGCGATAAGCTGATCGCCAGAAAGAAGGACTGGGACCCTAAGAAGTACGGC

GGCTTCGACAGCCCCACCGTGGCCTATTCTGTGCTGGTGGTGGCCAAAGTGGAAAAG

GGCAAGTCCAAGAAACTGAAGAGTGTGAAAGAGCTGCTGGGGATCACCATCATGGA

AAGAAGCAGCTTCGAGAAGAATCCCATCGACTTTCTGGAAGCCAAGGGCTACAAAG

AAGTGAAAAAGGACCTGATCATCAAGCTGCCTAAGTACTCCCTGTTCGAGCTGGAA

AACGGCCGGAAGAGAATGCTGGCCTCTGCCGGCGAACTGCAGAAGGGAAACGAAC

TGGCCCTGCCCTCCAAATATGTGAACTTCCTGTACCTGGCCAGCCACTATGAGAAGC

TGAAGGGCTCCCCCGAGGATAATGAGCAGAAACAGCTGTTTGTGGAACAGCACAAG

CACTACCTGGACGAGATCATCGAGCAGATCAGCGAGTTCTCCAAGAGAGTGATCCT

GGCCGACGCTAATCTGGACAAAGTGCTGTCCGCCTACAACAAGCACCGGGATAAGC

CCATCAGAGAGCAGGCCGAGAATATCATCCACCTGTTTACCCTGACCAATCTGGGA

GCCCCTGCCGCCTTCAAGTACTTTGACACCACCATCGACCGGAAGAGGTACACCAGC

ACCAAAGAGGTGCTGGACGCCACCCTGATCCACCAGAGCATCACCGGCCTGTACGA

GACACGGATCGACCTGTCTCAGCTGGGAGGCGACAAAAGGCCGGCGGCCACGAAA

AAGGCCGGCCAGGCAAAAAAGAAAAAGtaa

8. Sp_Δ_hel 2-(GGGGS)6 helical domain 2 deletion
(from ortholog alignment) ("(GGGGS)6" disclosed
as SEQ ID NO: 47)
                                                    (SEQ ID NO: 48)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACGGTGGCGGTGGCtcgGGTGGCGGTGGCtcgGGTGGCGGTGGCtcg

GGTGGCGGTGGCtcgGGTGGCGGTGGCtcgGGTGGCGGTGGCtcgATCACCAAGGCCCCC

CTGAGCGCCTCTATGATCAAGAGATACGACGAGCACCACCAGGACCTGACCCTGCT

GAAAGCTCTCGTGCGGCAGCAGCTGCCTGAGAAGTACAAAGAGATTTTCTTCGACC

AGAGCAAGAACGGCTACGCCGGCTACATTGACGGCGGAGCCAGCCAGGAAGAGTTC

TACAAGTTCATCAAGCCCATCCTGGAAAAGATGGACGGCACCGAGGAACTGCTCGT

GAAGCTGAACAGAGAGGACCTGCTGCGGAAGCAGCGGACCTTCGACAACGGCAGC

ATCCCCCACCAGATCCACCTGGGAGAGCTGCACGCCATTCTGCGGCGGCAGGAAGA

TTTTTACCCATTCCTGAAGGACAACCGGGAAAAGATCGAGAAGATCCTGACCTTCCG

CATCCCCTACTACGTGGGCCCTCTGGCCAGGGGAAACAGCAGATTCGCCTGGATGA

CCAGAAAGAGCGAGGAAACCATCACCCCCTGGAACTTCGAGGAAGTGGTGGACAA

GGGCGCTTCCGCCCAGAGCTTCATCGAGCGGATGACCAACTTCGATAAGAACCTGC

CCAACGAGAAGGTGCTGCCCAAGCACAGCCTGCTGTACGAGTACTTCACCGTGTAT
```

-continued

```
AACGAGCTGACCAAAGTGAAATACGTGACCGAGGGAATGAGAAAGCCCGCCTTCCT

GAGCGGCGAGCAGAAAAAGGCCATCGTGGACCTGCTGTTCAAGACCAACCGGAAA

GTGACCGTGAAGCAGCTGAAAGAGGACTACTTCAAGAAAATCGAGTGCTTCGACTC

CGTGGAAATCTCCGGCGTGGAAGATCGGTTCAACGCCTCCCTGGGCACATACCACG

ATCTGCTGAAAATTATCAAGGACAAGGACTTCCTGGACAATGAGGAAAACGAGGAC

ATTCTGGAAGATATCGTGCTGACCCTGACACTGTTTGAGGACAGAGAGATGATCGA

GGAACGGCTGAAAACCTATGCCCACCTGTTCGACGACAAAGTGATGAAGCAGCTGA

AGCGGCGGAGATACACCGGCTGGGGCAGGCTGAGCCGGAAGCTGATCAACGGCATC

CGGGACAAGCAGTCCGGCAAGACAATCCTGGATTTCCTGAAGTCCGACGGCTTCGC

CAACAGAAACTTCATGCAGCTGATCCACGACGACAGCCTGACCTTTAAAGAGGACA

TCCAGAAAGCCCAGGTGTCCGGCCAGGGCGATAGCCTGCACGAGCACATTGCCAAT

CTGGCCGGCAGCCCCGCCATTAAGAAGGGCATCCTGCAGACAGTGAAGGTGGTGGA

CGAGCTCGTGAAAGTGATGGGCCGGCACAAGCCCGAGAACATCGTGATCGAAATGG

CCAGAGAGAACCAGACCACCCAGAAGGGACAGAAGAACAGCCGCGAGAGAATGAA

GCGGATCGAAGAGGGCATCAAAGAGCTGGGCAGCCAGATCCTGAAAGAACACCCC

GTGGAAAACACCCAGCTGCAGAACGAGAAGCTGTACCTGTACTACCTGCAGAATGG

GCGGGATATGTACGTGGACCAGGAACTGGACATCAACCGGCTGTCCGACTACGATG

TGGACCATATCGTGCCTCAGAGCTTTCTGAAGGACGACTCCATCGACAACAAGGTGC

TGACCAGAAGCGACAAGAACCGGGGCAAGAGCGACAACGTGCCCTCCGAAGAGGT

CGTGAAGAAGATGAAGAACTACTGGCGGCAGCTGCTGAACGCCAAGCTGATTACCC

AGAGAAAGTTCGACAATCTGACCAAGGCCGAGAGAGGCGGCCTGAGCGAACTGGAT

AAGGCCGGCTTCATCAAGAGACAGCTGGTGGAAACCCGGCAGATCACAAAGCACGT

GGCACAGATCCTGGACTCCCGGATGAACACTAAGTACGACGAGAATGACAAGCTGA

TCCGGGAAGTGAAAGTGATCACCCTGAAGTCCAAGCTGGTGTCCGATTTCCGGAAG

GATTTCCAGTTTTACAAAGTGCGCGAGATCAACAACTACCACCACGCCCACGACGCC

TACCTGAACGCCGTCGTGGGAACCGCCCTGATCAAAAAGTACCCTAAGCTGGAAAG

CGAGTTCGTGTACGGCGACTACAAGGTGTACGACGTGCGGAAGATGATCGCCAAGA

GCGAGCAGGAAATCGGCAAGGCTACCGCCAAGTACTTCTTCTACAGCAACATCATG

AACTTTTTCAAGACCGAGATTACCCTGGCCAACGGCGAGATCCGGAAGCGGCCTCT

GATCGAGACAAACGGCGAAACCGGGGAGATCGTGTGGGATAAGGGCCGGGATTTTG

CCACCGTGCGGAAAGTGCTGAGCATGCCCCAAGTGAATATCGTGAAAAAGACCGAG

GTGCAGACAGGCGGCTTCAGCAAAGAGTCTATCCTGCCCAAGAGGAACAGCGATAA

GCTGATCGCCAGAAAGAAGGACTGGGACCCTAAGAAGTACGGCGGCTTCGACAGCC

CCACCGTGGCCTATTCTGTGCTGGTGGTGGCCAAAGTGGAAAAGGGCAAGTCCAAG

AAACTGAAGAGTGTGAAAGAGCTGCTGGGGATCACCATCATGGAAAGAAGCAGCTT

CGAGAAGAATCCCATCGACTTTCTGGAAGCCAAGGGCTACAAAGAAGTGAAAAAGG

ACCTGATCATCAAGCTGCCTAAGTACTCCCTGTTCGAGCTGGAAAACGGCCGGAAG

AGAATGCTGGCCTCTGCCGGCGAACTGCAGAAGGGAAACGAACTGGCCCTGCCCTC

CAAATATGTGAACTTCCTGTACCTGGCCAGCCACTATGAGAAGCTGAAGGGCTCCCC

CGAGGATAATGAGCAGAAACAGCTGTTTGTGGAACAGCACAAGCACTACCTGGACG
```

-continued

AGATCATCGAGCAGATCAGCGAGTTCTCCAAGAGAGTGATCCTGGCCGACGCTAAT

CTGGACAAAGTGCTGTCCGCCTACAACAAGCACCGGGATAAGCCCATCAGAGAGCA

GGCCGAGAATATCATCCACCTGTTTACCCTGACCAATCTGGGAGCCCCTGCCGCCTT

CAAGTACTTTGACACCACCATCGACCGGAAGAGGTACACCAGCACCAAAGAGGTGC

TGGACGCCACCCTGATCCACCAGAGCATCACCGGCCTGTACGAGACACGGATCGAC

CTGTCTCAGCTGGGAGGCGACAAAAGGCCGGCGGCCACGAAAAAGGCCGGCCAGG

CAAAAAAGAAAAAGtaa

9. Sp_A_hel 2-(GGGGS)9 helical domain 2 deletion
(from ortholog alignment) ("(GGGGS)9" disclosed
as SEQ ID NO: 49)

(SEQ ID NO: 50)

ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACGGTGGCGGTGGCtcgGGTGGCGGTGGCtcgGGTGGCGGTGGCtcg

GGTGGCGGTGGCtcgGGTGGCGGTGGCtcgGGTGGCGGTGGCtcgGGTGGCGGTGGCtcgG

GTGGCGGTGGCtcgGGTGGCGGTGGCtcgATCACCAAGGCCCCCCTGAGCGCCTCTATG

ATCAAGAGATACGACGAGCACCACCAGGACCTGACCCTGCTGAAAGCTCTCGTGCG

GCAGCAGCTGCCTGAGAAGTACAAAGAGATTTTCTTCGACCAGAGCAAGAACGGCT

ACGCCGGCTACATTGACGGCGGAGCCAGCCAGGAAGAGTTCTACAAGTTCATCAAG

CCCATCCTGGAAAAGATGGACGGCACCGAGGAACTGCTCGTGAAGCTGAACAGAGA

GGACCTGCTGCGGAAGCAGCGGACCTTCGACAACGGCAGCATCCCCCACCAGATCC

ACCTGGGAGAGCTGCACGCCATTCTGCGGCGGCAGGAAGATTTTTACCCATTCCTGA

AGGACAACCGGGAAAAGATCGAGAAGATCCTGACCTTCCGCATCCCCTACTACGTG

GGCCCTCTGGCCAGGGGAAACAGCAGATTCGCCTGGATGACCAGAAAGAGCGAGG

AAACCATCACCCCCTGGAACTTCGAGGAAGTGGTGGACAAGGGCGCTTCCGCCCAG

AGCTTCATCGAGCGGATGACCAACTTCGATAAGAACCTGCCCAACGAGAAGGTGCT

GCCCAAGCACAGCCTGCTGTACGAGTACTTCACCGTGTATAACGAGCTGACCAAAG

TGAAATACGTGACCGAGGGAATGAGAAAGCCCGCCTTCCTGAGCGGCGAGCAGAAA

AAGGCCATCGTGGACCTGCTGTTCAAGACCAACCGGAAAGTGACCGTGAAGCAGCT

GAAAGAGGACTACTTCAAGAAAATCGAGTGCTTCGACTCCGTGGAAATCTCCGGCG

TGGAAGATCGGTTCAACGCCTCCCTGGGCACATACCACGATCTGCTGAAAATTATCA

AGGACAAGGACTTCCTGGACAATGAGGAAAACGAGGACATTCTGGAAGATATCGTG

CTGACCCTGACACTGTTTGAGGACAGAGAGATGATCGAGGAACGGCTGAAAACCTA

TGCCCACCTGTTCGACGACAAAGTGATGAAGCAGCTGAAGCGGCGGAGATACACCG

GCTGGGGCAGGCTGAGCCGGAAGCTGATCAACGGCATCCGGGACAAGCAGTCCGGC

-continued

```
AAGACAATCCTGGATTTCCTGAAGTCCGACGGCTTCGCCAACAGAAACTTCATGCAG
CTGATCCACGACGACAGCCTGACCTTTAAAGAGGACATCCAGAAAGCCCAGGTGTC
CGGCCAGGGCGATAGCCTGCACGAGCACATTGCCAATCTGGCCGGCAGCCCCGCCA
TTAAGAAGGGCATCCTGCAGACAGTGAAGGTGGTGGACGAGCTCGTGAAAGTGATG
GGCCGGCACAAGCCCGAGAACATCGTGATCGAAATGGCCAGAGAGAACCAGACCA
CCCAGAAGGGACAGAAGAACAGCCGCGAGAGAATGAAGCGGATCGAAGAGGGCAT
CAAAGAGCTGGGCAGCCAGATCCTGAAAGAACACCCCGTGGAAAACACCCAGCTGC
AGAACGAGAAGCTGTACCTGTACTACCTGCAGAATGGGCGGGATATGTACGTGGAC
CAGGAACTGGACATCAACCGGCTGTCCGACTACGATGTGGACCATATCGTGCCTCA
GAGCTTTCTGAAGGACGACTCCATCGACAACAAGGTGCTGACCAGAAGCGACAAGA
ACCGGGCAAGAGCGACAACGTGCCCTCCGAAGAGGTCGTGAAGAAGATGAAGAA
CTACTGGCGGCAGCTGCTGAACGCCAAGCTGATTACCCAGAGAAAGTTCGACAATC
TGACCAAGGCCGAGAGAGGCGGCCTGAGCGAACTGGATAAGGCCGGCTTCATCAAG
AGACAGCTGGTGGAAACCCGGCAGATCACAAAGCACGTGGCACAGATCCTGGACTC
CCGGATGAACACTAAGTACGACGAGAATGACAAGCTGATCCGGGAAGTGAAAGTGA
TCACCCTGAAGTCCAAGCTGGTGTCCGATTTCCGGAAGGATTTCCAGTTTTACAAAG
TGCGCGAGATCAACAACTACCACCACGCCCACGACGCCTACCTGAACGCCGTCGTG
GGAACCGCCCTGATCAAAAAGTACCCTAAGCTGGAAAGCGAGTTCGTGTACGGCGA
CTACAAGGTGTACGACGTGCGGAAGATGATCGCCAAGAGCGAGCAGGAAATCGGCA
AGGCTACCGCCAAGTACTTCTTCTACAGCAACATCATGAACTTTTTCAAGACCGAGA
TTACCCTGGCCAACGGCGAGATCCGGAAGCGGCCTCTGATCGAGACAAACGGCGAA
ACCGGGGAGATCGTGTGGGATAAGGGCCGGGATTTTGCCACCGTGCGGAAAGTGCT
GAGCATGCCCCAAGTGAATATCGTGAAAAAGACCGAGGTGCAGACAGGCGGCTTCA
GCAAAGAGTCTATCCTGCCCAAGAGGAACAGCGATAAGCTGATCGCCAGAAAGAAG
GACTGGGACCCTAAGAAGTACGGCGGCTTCGACAGCCCCACCGTGGCCTATTCTGTG
CTGGTGGTGGCCAAAGTGGAAAAGGGCAAGTCCAAGAAACTGAAGAGTGTGAAAG
AGCTGCTGGGGATCACCATCATGGAAAGAAGCAGCTTCGAGAAGAATCCCATCGAC
TTTCTGGAAGCCAAGGGCTACAAAGAAGTGAAAAAGGACCTGATCATCAAGCTGCC
TAAGTACTCCCTGTTCGAGCTGGAAAACGGCCGGAAGAGAATGCTGGCCTCTGCCG
GCGAACTGCAGAAGGGAAACGAACTGGCCCTGCCCTCCAAATATGTGAACTTCCTG
TACCTGGCCAGCCACTATGAGAAGCTGAAGGGCTCCCCCGAGGATAATGAGCAGAA
ACAGCTGTTTGTGGAACAGCACAAGCACTACCTGGACGAGATCATCGAGCAGATCA
GCGAGTTCTCCAAGAGAGTGATCCTGGCCGACGCTAATCTGGACAAAGTGCTGTCCG
CCTACAACAAGCACCGGGATAAGCCCATCAGAGAGCAGGCCGAGAATATCATCCAC
CTGTTTACCCTGACCAATCTGGGAGCCCCTGCCGCCTTCAAGTACTTTGACACCACC
ATCGACCGGAAGAGGTACACCAGCACCAAAGAGGTGCTGGACGCCACCCTGATCCA
CCAGAGCATCACCGGCCTGTACGAGACACGGATCGACCTGTCTCAGCTGGGAGGCG
ACAAAAGGCCGGCGGCCACGAAAAAGGCCGGCCAGGCAAAAAAGAAAAAGtaa
```

-continued

10. Sp_A_hel 2-(GGGGS)12 helical domain 2 deletion
(from ortholog alignment) ("(GGGGS)12" disclosed
as SEQ ID NO: 51)

(SEQ ID NO: 52)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACGGTGGCGGTGGCtcgGGTGGCGGTGGCtcgGGTGGCGGTGGCtcg

GGTGGCGGTGGCtcgGGTGGCGGTGGCtcgGGTGGCGGTGGCtcgGGTGGCGGTGGCtcgG

GTGGCGGTGGCtcgGGTGGCGGTGGCtcgGGTGGCGGTGGCtcgGGTGGCGGTGGCtcgGG

TGGCGGTGGCtcgATCACCAAGGCCCCCCTGAGCGCCTCTATGATCAAGAGATACGAC

GAGCACCACCAGGACCTGACCCTGCTGAAAGCTCTCGTGCGGCAGCAGCTGCCTGA

GAAGTACAAAGAGATTTTCTTCGACCAGAGCAAGAACGGCTACGCCGGCTACATTG

ACGGCGGAGCCAGCCAGGAAGAGTTCTACAAGTTCATCAAGCCCATCCTGGAAAAG

ATGGACGGCACCGAGGAACTGCTCGTGAAGCTGAACAGAGAGGACCTGCTGCGGAA

GCAGCGGACCTTCGACAACGGCAGCATCCCCCACCAGATCCACCTGGGAGAGCTGC

ACGCCATTCTGCGGCGGCAGGAAGATTTTTACCCATTCCTGAAGGACAACCGGGAA

AAGATCGAGAAGATCCTGACCTTCCGCATCCCCTACTACGTGGGCCCTCTGGCCAGG

GGAAACAGCAGATTCGCCTGGATGACCAGAAAGAGCGAGGAAACCATCACCCCCTG

GAACTTCGAGGAAGTGGTGGACAAGGGCGCTTCCGCCCAGAGCTTCATCGAGCGGA

TGACCAACTTCGATAAGAACCTGCCCAACGAGAAGGTGCTGCCCAAGCACAGCCTG

CTGTACGAGTACTTCACCGTGTATAACGAGCTGACCAAAGTGAAATACGTGACCGA

GGGAATGAGAAAGCCCGCCTTCCTGAGCGGCGAGCAGAAAAAGGCCATCGTGGACC

TGCTGTTCAAGACCAACCGGAAAGTGACCGTGAAGCAGCTGAAAGAGGACTACTTC

AAGAAAATCGAGTGCTTCGACTCCGTGGAAATCTCCGGCGTGGAAGATCGGTTCAA

CGCCTCCCTGGGCACATACCACGATCTGCTGAAAATTATCAAGGACAAGGACTTCCT

GGACAATGAGGAAAACGAGGACATTCTGGAAGATATCGTGCTGACCCTGACACTGT

TTGAGGACAGAGAGATGATCGAGGAACGGCTGAAAACCTATGCCCACCTGTTCGAC

GACAAAGTGATGAAGCAGCTGAAGCGGCGGAGATACACCGGCTGGGGCAGGCTGA

GCCGGAAGCTGATCAACGGCATCCGGGACAAGCAGTCCGGCAAGACAATCCTGGAT

TTCCTGAAGTCCGACGGCTTCGCCAACAGAAACTTCATGCAGCTGATCCACGACGAC

AGCCTGACCTTTAAAGAGGACATCCAGAAAGCCCAGGTGTCCGGCCAGGGCGATAG

CCTGCACGAGCACATTGCCAATCTGGCCGGCAGCCCCGCCATTAAGAAGGGCATCC

TGCAGACAGTGAAGGTGGTGGACGAGCTCGTGAAAGTGATGGGCCGGCACAAGCCC

GAGAACATCGTGATCGAAATGGCCAGAGAGAACCAGACCACCCAGAAGGGACAGA

AGAACAGCCGCGAGAGAATGAAGCGGATCGAAGAGGGCATCAAAGAGCTGGGCAG

-continued

```
CCAGATCCTGAAAGAACACCCCGTGGAAAACACCCAGCTGCAGAACGAGAAGCTGT
ACCTGTACTACCTGCAGAATGGGCGGGATATGTACGTGGACCAGGAACTGGACATC
AACCGGCTGTCCGACTACGATGTGGACCATATCGTGCCTCAGAGCTTTCTGAAGGAC
GACTCCATCGACAACAAGGTGCTGACCAGAAGCGACAAGAACCGGGGCAAGAGCG
ACAACGTGCCCTCCGAAGAGGTCGTGAAGAAGATGAAGAACTACTGGCGGCAGCTG
CTGAACGCCAAGCTGATTACCCAGAGAAAGTTCGACAATCTGACCAAGGCCGAGAG
AGGCGGCCTGAGCGAACTGGATAAGGCCGGCTTCATCAAGAGACAGCTGGTGGAAA
CCCGGCAGATCACAAAGCACGTGGCACAGATCCTGGACTCCCGGATGAACACTAAG
TACGACGAGAATGACAAGCTGATCCGGGAAGTGAAAGTGATCACCCTGAAGTCCAA
GCTGGTGTCCGATTTCCGGAAGGATTTCCAGTTTTACAAAGTGCGCGAGATCAACAA
CTACCACCACGCCCACGACGCCTACCTGAACGCCGTCGTGGGAACCGCCCTGATCA
AAAAGTACCCTAAGCTGGAAAGCGAGTTCGTGTACGGCGACTACAAGGTGTACGAC
GTGCGGAAGATGATCGCCAAGAGCGAGCAGGAAATCGGCAAGGCTACCGCCAAGT
ACTTCTTCTACAGCAACATCATGAACTTTTTCAAGACCGAGATTACCCTGGCCAACG
GCGAGATCCGGAAGCGGCCTCTGATCGAGACAAACGGCGAAACCGGGGAGATCGT
GTGGGATAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAGTCTATC
CTGCCCAAGAGGAACAGCGATAAGCTGATCGCCAGAAAGAAGGACTGGGACCCTA
AGAAGTACGGCGGCTTCGACAGCCCCACCGTGGCCTATTCTGTGCTGGTGGTGGCCA
AAGTGGAAAAGGGCAAGTCCAAGAAACTGAAGAGTGTGAAAGAGCTGCTGGGGAT
CACCATCATGGAAGAAGCAGCTTCGAGAAGAATCCCATCGACTTTCTGGAAGCCA
AGGGCTACAAAGAAGTGAAAAAGGACCTGATCATCAAGCTGCCTAAGTACTCCCTG
TTCGAGCTGGAAAACGGCCGGAAGAGAATGCTGGCCTCTGCCGGCGAACTGCAGAA
GGGAAACGAACTGGCCCTGCCCTCCAAATATGTGAACTTCCTGTACCTGGCCAGCCA
CTATGAGAAGCTGAAGGGCTCCCCCGAGGATAATGAGCAGAAACAGCTGTTTGTGG
AACAGCACAAGCACTACCTGGACGAGATCATCGAGCAGATCAGCGAGTTCTCCAAG
AGAGTGATCCTGGCCGACGCTAATCTGGACAAAGTGCTGTCCGCCTACAACAAGCA
CCGGGATAAGCCCATCAGAGAGCAGGCCGAGAATATCATCCACCTGTTTACCCTGA
CCAATCTGGGAGCCCCTGCCGCCTTCAAGTACTTTGACACCACCATCGACCGGAAGA
GGTACACCAGCACCAAAGAGGTGCTGGACGCCACCCTGATCCACCAGAGCATCACC
GGCCTGTACGAGACACGGATCGACCTGTCTCAGCTGGGAGGCGACAAAAGGCCGGC
GGCCACGAAAAGGCCGGCCAGGCAAAAAAGAAAAAGtaa
```

11. Sp_A_hel 2-A(EAAAK)3A helical domain 2 deletion
(from ortholog alignment) ("A(EAAAK)3A" disclosed
as SEQ ID NO: 53)

(SEQ ID NO: 54)
```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
```

-continued

```
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACgctGAAGCTGCTGCTAAAGAAGCTGCTGCTAAAGAAGCTGCTG
CTAAAgctATCACCAAGGCCCCCCTGAGCGCCTCTATGATCAAGAGATACGACGAGC
ACCACCAGGACCTGACCCTGCTGAAAGCTCTCGTGCGGCAGCAGCTGCCTGAGAAG
TACAAAGAGATTTTCTTCGACCAGAGCAAGAACGGCTACGCCGGCTACATTGACGG
CGGAGCCAGCCAGGAAGAGTTCTACAAGTTCATCAAGCCCATCCTGGAAAAGATGG
ACGGCACCGAGGAACTGCTCGTGAAGCTGAACAGAGAGGACCTGCTGCGGAAGCA
GCGGACCTTCGACAACGGCAGCATCCCCCACCAGATCCACCTGGGAGAGCTGCACG
CCATTCTGCGGCGGCAGGAAGATTTTTACCCATTCCTGAAGGACAACCGGGAAAAG
ATCGAGAAGATCCTGACCTTCCGCATCCCCTACTACGTGGGCCCTCTGGCCAGGGGA
AACAGCAGATTCGCCTGGATGACCAGAAAGAGCGAGGAAACCATCACCCCCTGGAA
CTTCGAGGAAGTGGTGGACAAGGGCGCTTCCGCCCAGAGCTTCATCGAGCGGATGA
CCAACTTCGATAAGAACCTGCCCAACGAGAAGGTGCTGCCCAAGCACAGCCTGCTG
TACGAGTACTTCACCGTGTATAACGAGCTGACCAAAGTGAAATACGTGACCGAGGG
AATGAGAAAGCCCGCCTTCCTGAGCGGCGAGCAGAAAAAGGCCATCGTGGACCTGC
TGTTCAAGACCAACCGGAAAGTGACCGTGAAGCAGCTGAAAGAGGACTACTTCAAG
AAAATCGAGTGCTTCGACTCCGTGGAAATCTCCGGCGTGGAAGATCGGTTCAACGCC
TCCCTGGGCACATACCACGATCTGCTGAAAATTATCAAGGACAAGGACTTCCTGGAC
AATGAGGAAAACGAGGACATTCTGGAAGATATCGTGCTGACCCTGACACTGTTTGA
GGACAGAGAGATGATCGAGGAACGGCTGAAAACCTATGCCCACCTGTTCGACGACA
AAGTGATGAAGCAGCTGAAGCGGCGGAGATACACCGGCTGGGGCAGGCTGAGCCG
GAAGCTGATCAACGGCATCCGGGACAAGCAGTCCGGCAAGACAATCCTGGATTTCC
TGAAGTCCGACGGCTTCGCCAACAGAAACTTCATGCAGCTGATCCACGACGACAGC
CTGACCTTTAAAGAGGACATCCAGAAAGCCCAGGTGTCCGGCCAGGGCGATAGCCT
GCACGAGCACATTGCCAATCTGGCCGGCAGCCCCGCCATTAAGAAGGGCATCCTGC
AGACAGTGAAGGTGGTGGACGAGCTCGTGAAAGTGATGGGCCGGCACAAGCCCGA
GAACATCGTGATCGAAATGGCCAGAGAGAACCAGACCACCCAGAAGGGACAGAAG
AACAGCCGCGAGAGAATGAAGCGGATCGAAGAGGGCATCAAAGAGCTGGGCAGCC
AGATCCTGAAAGAACACCCCGTGGAAAACACCCAGCTGCAGAACGAGAAGCTGTAC
CTGTACTACCTGCAGAATGGGCGGGATATGTACGTGGACCAGGAACTGGACATCAA
CCGGCTGTCCGACTACGATGTGGACCATATCGTGCCTCAGAGCTTTCTGAAGGACGA
CTCCATCGACAACAAGGTGCTGACCAGAAGCGACAAGAACCGGGGCAAGAGCGAC
AACGTGCCCTCCGAAGAGGTCGTGAAGAAGATGAAGAACTACTGGCGGCAGCTGCT
GAACGCCAAGCTGATTACCCAGAGAAAGTTCGACAATCTGACCAAGGCCGAGAGAG
GCGGCCTGAGCGAACTGGATAAGGCCGGCTTCATCAAGAGACAGCTGGTGGAAACC
CGGCAGATCACAAAGCACGTGGCACAGATCCTGGACTCCCGGATGAACACTAAGTA
CGACGAGAATGACAAGCTGATCCGGGAAGTGAAAGTGATCACCCTGAAGTCCAAGC
TGGTGTCCGATTTCCGGAAGGATTTCCAGTTTTACAAAGTGCGCGAGATCAACAACT
```

-continued

```
ACCACCACGCCCACGACGCCTACCTGAACGCCGTCGTGGGAACCGCCCTGATCAAA

AAGTACCCTAAGCTGGAAAGCGAGTTCGTGTACGGCGACTACAAGGTGTACGACGT

GCGGAAGATGATCGCCAAGAGCGAGCAGGAAATCGGCAAGGCTACCGCCAAGTAC

TTCTTCTACAGCAACATCATGAACTTTTTCAAGACCGAGATTACCCTGGCCAACGGC

GAGATCCGGAAGCGGCCTCTGATCGAGACAAACGGCGAAACCGGGGAGATCGTGTG

GGATAAGGGCCGGGATTTTGCCACCGTGCGGAAAGTGCTGAGCATGCCCCAAGTGA

ATATCGTGAAAAAGACCGAGGTGCAGACAGGCGGCTTCAGCAAGAGTCTATCCTG

CCCAAGAGGAACAGCGATAAGCTGATCGCCAGAAAGAAGGACTGGGACCCTAAGA

AGTACGGCGGCTTCGACAGCCCCACCGTGGCCTATTCTGTGCTGGTGGTGGCCAAAG

TGGAAAAGGGCAAGTCCAAGAAACTGAAGAGTGTGAAAGAGCTGCTGGGGATCAC

CATCATGGAAAGAAGCAGCTTCGAGAAGAATCCCATCGACTTTCTGGAAGCCAAGG

GCTACAAAGAAGTGAAAAAGGACCTGATCATCAAGCTGCCTAAGTACTCCCTGTTC

GAGCTGGAAAACGGCCGGAAGAGAATGCTGGCCTCTGCCGGCGAACTGCAGAAGG

GAAACGAACTGGCCCTGCCCTCCAAATATGTGAACTTCCTGTACCTGGCCAGCCACT

ATGAGAAGCTGAAGGGCTCCCCCGAGGATAATGAGCAGAAACAGCTGTTTGTGGAA

CAGCACAAGCACTACCTGGACGAGATCATCGAGCAGATCAGCGAGTTCTCCAAGAG

AGTGATCCTGGCCGACGCTAATCTGGACAAAGTGCTGTCCGCCTACAACAAGCACC

GGGATAAGCCCATCAGAGAGCAGGCCGAGAATATCATCCACCTGTTTACCCTGACC

AATCTGGGAGCCCCTGCCGCCTTCAAGTACTTTGACACCACCATCGACCGGAAGAG

GTACACCAGCACCAAAGAGGTGCTGGACGCCACCCTGATCCACCAGAGCATCACCG

GCCTGTACGAGACACGGATCGACCTGTCTCAGCTGGGAGGCGACAAAAGGCCGGCG

GCCACGAAAAAGGCCGGCCAGGCAAAAAAGAAAAAGtaa
```

12. Sp_Λ_hel 2-A(EAAAK)3ALEA(EAAAK)3A helical domain 2 deletion (from ortholog alignment) ("A(EAAAK)3ALEA(EAAAK)3A" disclosed as SEQ ID NO: 55)

(SEQ ID NO: 56)
```
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACgctGAAGCCGCTGCTAAAGAAGCcGCTGCTAAAGAAGCCGCTGC

TAAAGccCTGGAGgctGAAGCcGCTGCTAAAGAAGCcGCTGCTAAAGAAGCCGCTGCT

AAAgctATCACCAAGGCCCCCCTGAGCGCCTCTATGATCAAGAGATACGACGAGCAC

CACCAGGACCTGACCCTGCTGAAAGCTCTCGTGCGGCAGCAGCTGCCTGAGAAGTA

CAAAGAGATTTTCTTCGACCAGAGCAAGAACGGCTACGCCGGCTACATTGACGGCG

GAGCCAGCCAGGAAGAGTTCTACAAGTTCATCAAGCCCATCCTGGAAAAGATGGAC
```

-continued

```
GGCACCGAGGAACTGCTCGTGAAGCTGAACAGAGAGGACCTGCTGCGGAAGCAGC

GGACCTTCGACAACGGCAGCATCCCCCACCAGATCCACCTGGGAGAGCTGCACGCC

ATTCTGCGGCGGCAGGAAGATTTTTACCCATTCCTGAAGGACAACCGGGAAAAGAT

CGAGAAGATCCTGACCTTCCGCATCCCCTACTACGTGGGCCCTCTGGCCAGGGGAAA

CAGCAGATTCGCCTGGATGACCAGAAAGAGCGAGGAAACCATCACCCCCTGGAACT

TCGAGGAAGTGGTGGACAAGGGCGCTTCCGCCCAGAGCTTCATCGAGCGGATGACC

AACTTCGATAAGAACCTGCCCAACGAGAAGGTGCTGCCCAAGCACAGCCTGCTGTA

CGAGTACTTCACCGTGTATAACGAGCTGACCAAAGTGAAATACGTGACCGAGGGAA

TGAGAAAGCCCGCCTTCCTGAGCGGCGAGCAGAAAAAGGCCATCGTGGACCTGCTG

TTCAAGACCAACCGGAAAGTGACCGTGAAGCAGCTGAAAGAGGACTACTTCAAGAA

AATCGAGTGCTTCGACTCCGTGGAAATCTCCGGCGTGGAAGATCGGTTCAACGCCTC

CCTGGGCACATACCACGATCTGCTGAAAATTATCAAGGACAAGGACTTCCTGGACA

ATGAGGAAAACGAGGACATTCTGGAAGATATCGTGCTGACCCTGACACTGTTTGAG

GACAGAGAGATGATCGAGGAACGGCTGAAAACCTATGCCCACCTGTTCGACGACAA

AGTGATGAAGCAGCTGAAGCGGCGAGATACACCGGCTGGGGCAGGCTGAGCCGG

AAGCTGATCAACGGCATCCGGGACAAGCAGTCCGGCAAGACAATCCTGGATTTCCT

GAAGTCCGACGGCTTCGCCAACAGAAACTTCATGCAGCTGATCCACGACGACAGCC

TGACCTTTAAAGAGGACATCCAGAAAGCCCAGGTGTCCGGCCAGGGCGATAGCCTG

CACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAG

AACATCGTGATCGAAATGGCCAGAGAGAACCAGACCACCCAGAAGGGACAGAAGA

ACAGCCGCGAGAGAATGAAGCGGATCGAAGAGGGCATCAAAGAGCTGGGCAGCCA

GATCCTGAAAGAACACCCCGTGGAAAACACCCAGCTGCAGAACGAGAAGCTGTACC

TGTACTACCTGCAGAATGGGCGGGATATGTACGTGGACCAGGAACTGGACATCAAC

CGGCTGTCCGACTACGATGTGGACCATATCGTGCCTCAGAGCTTTCTGAAGGACGAC

TCCATCGACAACAAGGTGCTGACCAGAAGCGACAAGAACCGGGGCAAGAGCGACA

ACGTGCCCTCCGAAGAGGTCGTGAAGAAGATGAAGAACTACTGGCGGCAGCTGCTG

AACGCCAAGCTGATTACCCAGAGAAAGTTCGACAATCTGACCAAGGCCGAGAGAGG

CGGCCTGAGCGAACTGGATAAGGCCGGCTTCATCAAGAGACAGCTGGTGGAAACCC

GGCAGATCACAAAGCACGTGGCACAGATCCTGGACTCCCGGATGAACACTAAGTAC

GACGAGAATGACAAGCTGATCCGGGAAGTGAAAGTGATCACCCTGAAGTCCAAGCT

GGTGTCCGATTTCCGGAAGGATTTCCAGTTTTACAAAGTGCGCGAGATCAACAACTA

CCACCACGCCCACGACGCCTACCTGAACGCCGTCGTGGGAACCGCCCTGATCAAAA

AGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTT

CTTCTACAGCAACATCATGAACTTTTTCAAGACCGAGATTACCCTGGCCAACGGCGA

GATCCGGAAGCGGCCTCTGATCGAGACAAACGGCGAAACCGGGGAGATCGTGTGGG

ATAAGGGCCGGGATTTTGCCACCGTGCGGAAAGTGCTGAGCATGCCCCAAGTGAAT

ATCGTGAAAAAGACCGAGGTGCAGACAGGCGGCTTCAGCAAAGAGTCTATCCTGCC

CAAGAGGAACAGCGATAAGCTGATCGCCAGAAAGAAGGACTGGGACCCTAAGAAG

TACGGCGGCTTCGACAGCCCCACCGTGGCCTATTCTGTGCTGGTGGTGGCCAAAGTG
```

-continued

```
GAAAAGGGCAAGTCCAAGAAACTGAAGAGTGTGAAAGAGCTGCTGGGGATCACCA

TCATGGAAAGAAGCAGCTTCGAGAAGAATCCCATCGACTTTCTGGAAGCCAAGGGC

TACAAAGAAGTGAAAAAGGACCTGATCATCAAGCTGCCTAAGTACTCCCTGTTCGA

GCTGGAAAACGGCCGGAAGAGAATGCTGGCCTCTGCCGGCGAACTGCAGAAGGGA

AACGAACTGGCCCTGCCCTCCAAATATGTGAACTTCCTGTACCTGGCCAGCCACTAT

GAGAAGCTGAAGGGCTCCCCCGAGGATAATGAGCAGAAACAGCTGTTTGTGGAACA

GCACAAGCACTACCTGGACGAGATCATCGAGCAGATCAGCGAGTTCTCCAAGAGAG

TGATCCTGGCCGACGCTAATCTGGACAAAGTGCTGTCCGCCTACAACAAGCACCGG

GATAAGCCCATCAGAGAGCAGGCCGAGAATATCATCCACCTGTTTACCCTGACCAA

TCTGGGAGCCCCTGCCGCCTTCAAGTACTTTGACACCACCATCGACCGGAAGAGGTA

CACCAGCACCAAAGAGGTGCTGGACGCCACCCTGATCCACCAGAGCATCACCGGCC

TGTACGAGACACGGATCGACCTGTCTCAGCTGGGAGGCGACAAAAGGCCGGCGGCC

ACGAAAAAGGCCGGCCAGGCAAAAAAGAAAAAGtaa
```

13. Sp_Δ_hel 2-A(EAAAK)3ALEA(EAAAK)3ALEA(EAAAK)3A
helical domain 2 deletion (from ortholog alignment)
("A(EAAAK)3ALEA(EAAAK)3ALEA(EAAAK)3A" disclosed
as SEQ ID NO: 57)

(SEQ ID NO: 58)
```
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACgctGAAGCTGCTGCTAAAGAAGCTGCTGCTAAAGAAGCTGCTG

CTAAAGccCTGGAGgctGAAGCTGCTGCTAAAGAAGCTGCTCTAAAGAAGCTGCTGC

TAAAGccCTGGAGgctGAAGCTGCTGCTAAAGAAGCTGCTGCTAAAGAAGCTGCTGCT

AAAgctATCACCAAGGCCCCCCTGAGCGCCTCTATGATCAAGAGATACGACGAGCAC

CACCAGGACCTGACCCTGCTGAAAGCTCTCGTGCGGCAGCAGCTGCCTGAGAAGTA

CAAAGAGATTTTCTTCGACCAGAGCAAGAACGGCTACGCCGGCTACATTGACGGCG

GAGCCAGCCAGGAAGAGTTCTACAAGTTCATCAAGCCCATCCTGGAAAAGATGGAC

GGCACCGAGGAACTGCTCGTGAAGCTGAACAGAGAGGACCTGCTGCGGAAGCAGC

GGACCTTCGACAACGGCAGCATCCCCCACCAGATCCACCTGGGAGAGCTGCACGCC

ATTCTGCGGCGGCAGGAAGATTTTTACCCATTCCTGAAGGACAACCGGGAAAAGAT

CGAGAAGATCCTGACCTTCCGCATCCCCTACTACGTGGGCCCTCTGGCCAGGGGAAA

CAGCAGATTCGCCTGGATGACCAGAAAGAGCGAGGAAACCATCACCCCCTGGAACT

TCGAGGAAGTGGTGGACAAGGGCGCTTCCGCCCAGAGCTTCATCGAGCGGATGACC

AACTTCGATAAGAACCTGCCCAACGAGAAGGTGCTGCCCAAGCACAGCCTGCTGTA

CGAGTACTTCACCGTGTATAACGAGCTGACCAAAGTGAAATACGTGACCGAGGGAA
```

```
TGAGAAAGCCCGCCTTCCTGAGCGGCGAGCAGAAAAAGGCCATCGTGGACCTGCTG

TTCAAGACCAACCGGAAAGTGACCGTGAAGCAGCTGAAAGAGGACTACTTCAAGAA

AATCGAGTGCTTCGACTCCGTGGAAATCTCCGGCGTGGAAGATCGGTTCAACGCCTC

CCTGGGCACATACCACGATCTGCTGAAAATTATCAAGGACAAGGACTTCCTGGACA

ATGAGGAAAACGAGGACATTCTGGAAGATATCGTGCTGACCCTGACACTGTTTGAG

GACAGAGAGATGATCGAGGAACGGCTGAAAACCTATGCCCACCTGTTCGACGACAA

AGTGATGAAGCAGCTGAAGCGGCGGAGATACACCGGCTGGGGCAGGCTGAGCCGG

AAGCTGATCAACGGCATCCGGGACAAGCAGTCCGGCAAGACAATCCTGGATTTCCT

GAAGTCCGACGGCTTCGCCAACAGAAACTTCATGCAGCTGATCCACGACGACAGCC

TGACCTTTAAAGAGGACATCCAGAAAGCCCAGGTGTCCGGCCAGGGCGATAGCCTG

CACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAG

AACATCGTGATCGAAATGGCCAGAGAGAACCAGACCACCCAGAAGGGACAGAAGA

ACAGCCGCGAGAGAATGAAGCGGATCGAAGAGGGCATCAAAGAGCTGGGCAGCCA

GATCCTGAAAGAACACCCCGTGGAAAACACCCAGCTGCAGAACGAGAAGCTGTACC

TGTACTACCTGCAGAATGGGCGGGATATGTACGTGGACCAGGAACTGGACATCAAC

CGGCTGTCCGACTACGATGTGGACCATATCGTGCCTCAGAGCTTTCTGAAGGACGAC

TCCATCGACAACAAGGTGCTGACCAGAAGCGACAAGAACCGGGGCAAGAGCGACA

ACGTGCCCTCCGAAGAGGTCGTGAAGAAGATGAAGAACTACTGGCGGCAGCTGCTG

AACGCCAAGCTGATTACCCAGAGAAAGTTCGACAATCTGACCAAGGCCGAGAGAGG

CGGCCTGAGCGAACTGGATAAGGCCGGCTTCATCAAGAGACAGCTGGTGGAAACCC

GGCAGATCACAAAGCACGTGGCACAGATCCTGGACTCCCGGATGAACACTAAGTAC

GACGAGAATGACAAGCTGATCCGGGAAGTGAAAGTGATCACCCTGAAGTCCAAGCT

GGTGTCCGATTTCCGGAAGGATTTCCAGTTTTACAAAGTGCGCGAGATCAACAACTA

CCACCACGCCCACGACGCCTACCTGAACGCCGTCGTGGGAACCGCCCTGATCAAAA

AGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTT

CTTCTACAGCAACATCATGAACTTTTTCAAGACCGAGATTACCCTGGCCAACGGCGA

GATCCGGAAGCGGCCTCTGATCGAGACAAACGGCGAAACCGGGGAGATCGTGTGGG

ATAAGGGCCGGGATTTTGCCACCGTGCGGAAAGTGCTGAGCATGCCCCAAGTGAAT

ATCGTGAAAAAGACCGAGGTGCAGACAGGCGGCTTCAGCAAAGAGTCTATCCTGCC

CAAGAGGAACAGCGATAAGCTGATCGCCAGAAAGAAGGACTGGGACCCTAAGAAG

TACGGCGGCTTCGACAGCCCCACCGTGGCCTATTCTGTGCTGGTGGTGGCCAAAGTG

GAAAAGGGCAAGTCCAAGAAACTGAAGAGTGTGAAAGAGCTGCTGGGGATCACCA

TCATGGAAAGAAGCAGCTTCGAGAAGAATCCCATCGACTTTCTGGAAGCCAAGGGC

TACAAAGAAGTGAAAAAGGACCTGATCATCAAGCTGCCTAAGTACTCCCTGTTCGA

GCTGGAAAACGGCCGGAAGAGAATGCTGGCCTCTGCCGGCGAACTGCAGAAGGGA

AACGAACTGGCCCTGCCCTCCAAATATGTGAACTTCCTGTACCTGGCCAGCCACTAT

GAGAAGCTGAAGGGCTCCCCCGAGGATAATGAGCAGAAACAGCTGTTTGTGGAACA

GCACAAGCACTACCTGGACGAGATCATCGAGCAGATCAGCGAGTTCTCCAAGAGAG
```

-continued

TGATCCTGGCCGACGCTAATCTGGACAAAGTGCTGTCCGCCTACAACAAGCACCGG

GATAAGCCCATCAGAGAGCAGGCCGAGAATATCATCCACCTGTTTACCCTGACCAA

TCTGGGAGCCCCTGCCGCCTTCAAGTACTTTGACACCACCATCGACCGGAAGAGGTA

CACCAGCACCAAAGAGGTGCTGGACGCCACCCTGATCCACCAGAGCATCACCGGCC

TGTACGAGACACGGATCGACCTGTCTCAGCTGGGAGGCGACAAAAGGCCGGCGGCC

ACGAAAAAGGCCGGCCAGGCAAAAAAGAAAAAGtaa

14. Sp_del_hel 2-A(EAAAK)3LE(EAAAK)3LE(EAAAK)3LE
(EAAAK)3Ahelical domain 2 deletion (from ortholog
alignment) ("A(EAAAK)3LE(EAAAK)3LE(EAAAK)3LE(EAAAK)
3A" disclosed as SEQ ID NO: 59)

(SEQ ID NO: 60)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACgctGAAGCTGCTGCTAAAGAAGCTGCTGCTAAAGAAGCTGCTG

CTAAAGccCTGGAGgctGAAGCTGCTGCTAAAGAAGCTGCTGCTAAAGAAGCTGCTGC

TAAAGccCTGGAGgctGAAGCTGCTGCTAAAGAAGCTGCTGCTAAAGAAGCTGCTGCT

AAAGccCTGGAGgctGAAGCTGCTGCTAAAGAAGCTGCTGCTAAAGAAGCTGCTGCTA

AAgctATCACCAAGGCCCCCCTGAGCGCCTCTATGATCAAGAGATACGACGAGCACC

ACCAGGACCTGACCCTGCTGAAAGCTCTCGTGCGGCAGCAGCTGCCTGAGAAGTAC

AAAGAGATTTTCTTCGACCAGAGCAAGAACGGCTACGCCGGCTACATTGACGGCGG

AGCCAGCCAGGAAGAGTTCTACAAGTTCATCAAGCCCATCCTGGAAAAGATGGACG

GCACCGAGGAACTGCTCGTGAAGCTGAACAGAGAGGACCTGCTGCGGAAGCAGCG

GACCTTCGACAACGGCAGCATCCCCCACCAGATCCACCTGGGAGAGCTGCACGCCA

TTCTGCGGCGGCAGGAAGATTTTTACCCATTCCTGAAGGACAACGGGAAAAGATC

GAGAAGATCCTGACCTTCCGCATCCCCTACTACGTGGGCCCTCTGGCCAGGGGAAAC

AGCAGATTCGCCTGGATGACCAGAAAGAGCGAGGAAACCATCACCCCCTGGAACTT

CGAGGAAGTGGTGGACAAGGGCGCTTCCGCCCAGAGCTTCATCGAGCGGATGACCA

ACTTCGATAAGAACCTGCCCAACGAGAAGGTGCTGCCCAAGCACAGCCTGCTGTAC

GAGTACTTCACCGTGTATAACGAGCTGACCAAAGTGAAATACGTGACCGAGGGAAT

GAGAAAGCCCGCCTTCCTGAGCGGCGAGCAGAAAAAGGCCATCGTGGACCTGCTGT

TCAAGACCAACCGGAAAGTGACCGTGAAGCAGCTGAAAGAGGACTACTTCAAGAAA

ATCGAGTGCTTCGACTCCGTGGAAATCTCCGGCGTGGAAGATCGGTTCAACGCCTCC

CTGGGCACATACCACGATCTGCTGAAAATTATCAAGGACAAGGACTTCCTGGACAA

TGAGGAAAACGAGGACATTCTGGAAGATATCGTGCTGACCCTGACACTGTTTGAGG

ACAGAGAGATGATCGAGGAACGGCTGAAAACCTATGCCCACCTGTTCGACGACAAA

-continued

```
GTGATGAAGCAGCTGAAGCGGCGGAGATACACCGGCTGGGGCAGGCTGAGCCGGA

AGCTGATCAACGGCATCCGGGACAAGCAGTCCGGCAAGACAATCCTGGATTTCCTG

AAGTCCGACGGCTTCGCCAACAGAAACTTCATGCAGCTGATCCACGACGACAGCCT

GACCTTTAAAGAGGACATCCAGAAAGCCCAGGTGTCCGGCCAGGGCGATAGCCTGC

ACGAGCACATTGCCAATCTGGCCGGCAGCCCCGCCATTAAGAAGGGCATCCTGCAG

ACAGTGAAGGTGGTGGACGAGCTCGTGAAAGTGATGGGCCGGCACAAGCCCGAGA

ACATCGTGATCGAAATGGCCAGAGAGAACCAGACCACCCAGAAGGGACAGAAGAA

CAGCCGCGAGAGAATGAAGCGGATCGAAGAGGGCATCAAAGAGCTGGGCAGCCAG

ATCCTGAAAGAACACCCCGTGGAAAACACCCAGCTGCAGAACGAGAAGCTGTACCT

GTACTACCTGCAGAATGGGCGGGATATGTACGTGGACCAGGAACTGGACATCAACC

GGCTGTCCGACTACGATGTGGACCATATCGTGCCTCAGAGCTTTCTGAAGGACGACT

CCATCGACAACAAGGTGCTGACCAGAAGCGACAAGAACCGGGGCAAGAGCGACAA

CGTGCCCTCCGAAGAGGTCGTGAAGAAGATGAAGAACTACTGGCGGCAGCTGCTGA

ACGCCAAGCTGATTACCCAGAGAAAGTTCGACAATCTGACCAAGGCCGAGAGAGGC

GGCCTGAGCGAACTGGATAAGGCCGGCTTCATCAAGAGACAGCTGGTGGAAACCCG

GCAGATCACAAAGCACGTGGCACAGATCCTGGACTCCCGGATGAACACTAAGTACG

ACGAGAATGACAAGCTGATCCGGGAAGTGAAAGTGATCACCCTGAAGTCCAAGCTG

GTGTCCGATTTCCGGAAGGATTTCCAGTTTTACAAAGTGCGCGAGATCAACAACTAC

CACCACGCCCACGACGCCTACCTGAACGCCGTCGTGGGAACCGCCCTGATCAAAAA

GTACCCTAAGCTGGAAAGCGAGTTCGTGTACGGCGACTACAAGGTGTACGACGTGC

GGAAGATGATCGCCAAGAGCGAGCAGGAAATCGGCAAGGCTACCGCCAAGTACTTC

TTCTACAGCAACATCATGAACTTTTTCAAGACCGAGATTACCCTGGCCAACGGCGAG

ATCCGGAAGCGGCCTCTGATCGAGACAAACGGCGAAACCGGGGAGATCGTGTGGGA

TAAGGGCCGGGATTTTGCCACCGTGCGGAAAGTGCTGAGCATGCCCCAAGTGAATA

TCGTGAAAAAGACCGAGGTGCAGACAGGCGGCTTCAGCAAAGAGTCTATCCTGCCC

AAGAGGAACAGCGATAAGCTGATCGCCAGAAAGAAGGACTGGGACCCTAAGAAGT

ACGGCGGCTTCGACAGCCCCACCGTGGCCTATTCTGTGCTGGTGGTGGCCAAAGTGG

AAAAGGGCAAGTCCAAGAAACTGAAGAGTGTGAAAGAGCTGCTGGGGATCACCATC

ATGGAAAGAAGCAGCTTCGAGAAGAATCCCATCGACTTTCTGGAAGCCAAGGGCTA

CAAAGAAGTGAAAAAGGACCTGATCATCAAGCTGCCTAAGTACTCCCTGTTCGAGC

TGGAAAACGGCCGGAAGAGAATGCTGGCCTCTGCCGGCGAACTGCAGAAGGGAAA

CGAACTGGCCCTGCCCTCCAAATATGTGAACTTCCTGTACCTGGCCAGCCACTATGA

GAAGCTGAAGGGCTCCCCCGAGGATAATGAGCAGAAACAGCTGTTTGTGGAACAGC

ACAAGCACTACCTGGACGAGATCATCGAGCAGATCAGCGAGTTCTCCAAGAGAGTG

ATCCTGGCCGACGCTAATCTGGACAAAGTGCTGTCCGCCTACAACAAGCACCGGGA

TAAGCCCATCAGAGAGCAGGCCGAGAATATCATCCACCTGTTTACCCTGACCAATCT

GGGAGCCCCTGCCGCCTTCAAGTACTTTGACACCACCATCGACCGGAAGAGGTACA

CCAGCACCAAAGAGGTGCTGGACGCCACCCTGATCCACCAGAGCATCACCGGCCTG

TACGAGACACGGATCGACCTGTCTCAGCTGGGAGGCGACAAAAGGCCGGCGGCCAC

GAAAAAGGCCGGCCAGGCAAAAAAGAAAAAGtaa
```

30. Sp_del (175-307) (from crystal data)

(SEQ ID NO: 61)

ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGGTGAACACCGAGATCACCAAGGCCCCCCTGAGCGCCTCT

ATGATCAAGAGATACGACGAGCACCACCAGGACCTGACCCTGCTGAAAGCTCTCGT

GCGGCAGCAGCTGCCTGAGAAGTACAAAGAGATTTTCTTCGACCAGAGCAAGAACG

GCTACGCCGGCTACATTGACGGCGGAGCCAGCCAGGAAGAGTTCTACAAGTTCATC

AAGCCCATCCTGGAAAAGATGGACGGCACCGAGGAACTGCTCGTGAAGCTGAACAG

AGAGGACCTGCTGCGGAAGCAGCGGACCTTCGACAACGGCAGCATCCCCCACCAGA

TCCACCTGGGAGAGCTGCACGCCATTCTGCGGCGGCAGGAAGATTTTTACCCATTCC

TGAAGGACAACCGGGAAAAGATCGAGAAGATCCTGACCTTCCGCATCCCCTACTAC

GTGGGCCCTCTGGCCAGGGGAAACAGCAGATTCGCCTGGATGACCAGAAAGAGCGA

GGAAACCATCACCCCCTGGAACTTCGAGGAAGTGGTGGACAAGGGCGCTTCCGCCC

AGAGCTTCATCGAGCGGATGACCAACTTCGATAAGAACCTGCCCAACGAGAAGGTG

CTGCCCAAGCACAGCCTGCTGTACGAGTACTTCACCGTGTATAACGAGCTGACCAAA

GTGAAATACGTGACCGAGGGAATGAGAAAGCCCGCCTTCCTGAGCGGCGAGCAGAA

AAAGGCCATCGTGGACCTGCTGTTCAAGACCAACCGGAAAGTGACCGTGAAGCAGC

TGAAAGAGGACTACTTCAAGAAAATCGAGTGCTTCGACTCCGTGGAAATCTCCGGC

GTGGAAGATCGGTTCAACGCCTCCCTGGGCACATACCACGATCTGCTGAAAATTATC

AAGGACAAGGACTTCCTGGACAATGAGGAAAACGAGGACATTCTGGAAGATATCGT

GCTGACCCTGACACTGTTTGAGGACAGAGAGATGATCGAGGAACGGCTGAAAACCT

ATGCCCACCTGTTCGACGACAAAGTGATGAAGCAGCTGAAGCGGCGGAGATACACC

GGCTGGGGCAGGCTGAGCCGGAAGCTGATCAACGGCATCCGGGACAAGCAGTCCGG

CAAGACAATCCTGGATTTCCTGAAGTCCGACGGCTTCGCCAACAGAAACTTCATGCA

GCTGATCCACGACGACAGCCTGACCTTTAAAGAGGACATCCAGAAAGCCCAGGTGT

CCGGCCAGGGCGATAGCCTGCACGAGCACATTGCCAATCTGGCCGGCAGCCCCGCC

ATTAAGAAGGGCATCCTGCAGACAGTGAAGGTGGTGGACGAGCTCGTGAAAGTGAT

GGGCCGGCACAAGCCCGAGAACATCGTGATCGAAATGGCCAGAGAGAACCAGACC

ACCCAGAAGGGACAGAAGAACAGCCGCGAGAGAATGAAGCGGATCGAAGAGGGCA

TCAAAGAGCTGGGCAGCCAGATCCTGAAAGAACACCCCGTGGAAAACACCCAGCTG

CAGAACGAGAAGCTGTACCTGTACTACCTGCAGAATGGGCGGGATATGTACGTGGA

CCAGGAACTGGACATCAACCGGCTGTCCGACTACGATGTGGACCATATCGTGCCTCA

GAGCTTTCTGAAGGACGACTCCATCGACAACAAGGTGCTGACCAGAAGCGACAAGA

-continued

```
ACCGGGGCAAGAGCGACAACGTGCCCTCCGAAGAGGTCGTGAAGAAGATGAAGAA

CTACTGGCGGCAGCTGCTGAACGCCAAGCTGATTACCCAGAGAAAGTTCGACAATC

TGACCAAGGCCGAGAGAGGCGGCCTGAGCGAACTGGATAAGGCCGGCTTCATCAAG

AGACAGCTGGTGGAAACCCGGCAGATCACAAAGCACGTGGCACAGATCCTGGACTC

CCGGATGAACACTAAGTACGACGAGAATGACAAGCTGATCCGGGAAGTGAAAGTGA

TCACCCTGAAGTCCAAGCTGGTGTCCGATTTCCGGAAGGATTTCCAGTTTTACAAAG

TGCGCGAGATCAACAACTACCACCACGCCCACGACGCCTACCTGAACGCCGTCGTG

GGAACCGCCCTGATCAAAAAGTACCCTAAGCTGGAAAGCGAGTTCGTGTACGGCGA

CTACAAGGTGTACGACGTGCGGAAGATGATCGCCAAGAGCGAGCAGGAAATCGGCA

AGGCTACCGCCAAGTACTTCTTCTACAGCAACATCATGAACTTTTTCAAGACCGAGA

TTACCCTGGCCAACGGCGAGATCCGGAAGCGGCCTCTGATCGAGACAAACGGCGAA

ACCGGGGAGATCGTGTGGGATAAGGGCCGGGATTTTGCCACCGTGCGGAAAGTGCT

GAGCATGCCCCAAGTGAATATCGTGAAAAAGACCGAGGTGCAGACAGGCGGCTTCA

GCAAAGAGTCTATCCTGCCCAAGAGGAACAGCGATAAGCTGATCGCCAGAAAGAAG

GACTGGGACCCTAAGAAGTACGGCGGCTTCGACAGCCCCACCGTGGCCTATTCTGTG

CTGGTGGTGGCCAAAGTGGAAAAGGGCAAGTCCAAGAAACTGAAGAGTGTGAAAG

AGCTGCTGGGGATCACCATCATGGAAAGAAGCAGCTTCGAGAAGAATCCCATCGAC

TTTCTGGAAGCCAAGGGCTACAAAGAAGTGAAAAAGGACCTGATCATCAAGCTGCC

TAAGTACTCCCTGTTCGAGCTGGAAAACGGCCGGAAGAGAATGCTGGCCTCTGCCG

GCGAACTGCAGAAGGGAAACGAACTGGCCCTGCCCTCCAAATATGTGAACTTCCTG

TACCTGGCCAGCCACTATGAGAAGCTGAAGGGCTCCCCCGAGGATAATGAGCAGAA

ACAGCTGTTTGTGGAACAGCACAAGCACTACCTGGACGAGATCATCGAGCAGATCA

GCGAGTTCTCCAAGAGAGTGATCCTGGCCGACGCTAATCTGGACAAAGTGCTGTCCG

CCTACAACAAGCACCGGGATAAGCCCATCAGAGAGCAGGCCGAGAATATCATCCAC

CTGTTTACCCTGACCAATCTGGGAGCCCCTGCCGCCTTCAAGTACTTTGACACCACC

ATCGACCGGAAGAGGTACACCAGCACCAAAGAGGTGCTGGACGCCACCCTGATCCA

CCAGAGCATCACCGGCCTGTACGAGACACGGATCGACCTGTCTCAGCTGGGAGGCG

ACAAAAGGCCGGCGGCCACGAAAAAGGCCGGCCAGGCAAAAAAGAAAAAGtaa

31. Sp_del (1098-end)
                                                (SEQ ID NO: 62)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGAACCCCGACAACAGCGACGTGGACAAGCTGTTCATCCAG
```

-continued

```
CTGGTGCAGACCTACAACCAGCTGTTCGAGGAAAACCCCATCAACGCCAGCGGCGT

GGACGCCAAGGCCATCCTGTCTGCCAGACTGAGCAAGAGCAGACGGCTGGAAAATC

TGATCGCCCAGCTGCCCGGCGAGAAGAAGAATGGCCTGTTCGGAAACCTGATTGCC

CTGAGCCTGGGCCTGACCCCCAACTTCAAGAGCAACTTCGACCTGGCCGAGGATGC

CAAACTGCAGCTGAGCAAGGACACCTACGACGACGACCTGGACAACCTGCTGGCCC

AGATCGGCGACCAGTACGCCGACCTGTTTCTGGCCGCCAAGAACCTGTCCGACGCC

ATCCTGCTGAGCGACATCCTGAGAGTGAACACCGAGATCACCAAGGCCCCCCTGAG

CGCCTCTATGATCAAGAGATACGACGAGCACCACCAGGACCTGACCCTGCTGAAAG

CTCTCGTGCGGCAGCAGCTGCCTGAGAAGTACAAAGAGATTTTCTTCGACCAGAGCA

AGAACGGCTACGCCGGCTACATTGACGGCGGAGCCAGCCAGGAAGAGTTCTACAAG

TTCATCAAGCCCATCCTGGAAAAGATGGACGGCACCGAGGAACTGCTCGTGAAGCT

GAACAGAGAGGACCTGCTGCGGAAGCAGCGGACCTTCGACAACGGCAGCATCCCCC

ACCAGATCCACCTGGGAGAGCTGCACGCCATTCTGCGGCGGCAGGAAGATTTTTAC

CCATTCCTGAAGGACAACCGGGAAAAGATCGAGAAGATCCTGACCTTCCGCATCCC

CTACTACGTGGGCCCTCTGGCCAGGGGAAACAGCAGATTCGCCTGGATGACCAGAA

AGAGCGAGGAAACCATCACCCCCTGGAACTTCGAGGAAGTGGTGGACAAGGGCGCT

TCCGCCCAGAGCTTCATCGAGCGGATGACCAACTTCGATAAGAACCTGCCCAACGA

GAAGGTGCTGCCCAAGCACAGCCTGCTGTACGAGTACTTCACCGTGTATAACGAGCT

GACCAAAGTGAAATACGTGACCGAGGGAATGAGAAAGCCCGCCTTCCTGAGCGGCG

AGCAGAAAAAGGCCATCGTGGACCTGCTGTTCAAGACCAACCGGAAAGTGACCGTG

AAGCAGCTGAAAGAGGACTACTTCAAGAAAATCGAGTGCTTCGACTCCGTGGAAAT

CTCCGGCGTGGAAGATCGGTTCAACGCCTCCCTGGGCACATACCACGATCTGCTGAA

AATTATCAAGGACAAGGACTTCCTGGACAATGAGGAAAACGAGGACATTCTGGAAG

ATATCGTGCTGACCCTGACACTGTTTGAGGACAGAGAGATGATCGAGGAACGGCTG

AAAACCTATGCCCACCTGTTCGACGACAAAGTGATGAAGCAGCTGAAGCGGCGGAG

ATACACCGGCTGGGGCAGGCTGAGCCGGAAGCTGATCAACGGCATCCGGGACAAGC

AGTCCGGCAAGACAATCCTGGATTTCCTGAAGTCCGACGGCTTCGCCAACAGAAAC

TTCATGCAGCTGATCCACGACGACAGCCTGACCTTTAAAGAGGACATCCAGAAAGC

CCAGGTGTCCGGCCAGGGCGATAGCCTGCACGAGCACATTGCCAATCTGGCCGGCA

GCCCCGCCATTAAGAAGGGCATCCTGCAGACAGTGAAGGTGGTGGACGAGCTCGTG

AAAGTGATGGGCCGGCACAAGCCCGAGAACATCGTGATCGAAATGGCCAGAGAGA

ACCAGACCACCCAGAAGGGACAGAAGAACAGCCGCGAGAGAATGAAGCGGATCGA

AGAGGGCATCAAAGAGCTGGGCAGCCAGATCCTGAAAGAACACCCCGTGGAAAAC

ACCCAGCTGCAGAACGAGAAGCTGTACCTGTACTACCTGCAGAATGGGCGGGATAT

GTACGTGGACCAGGAACTGGACATCAACCGGCTGTCCGACTACGATGTGGACCATA

TCGTGCCTCAGAGCTTTCTGAAGGACGACTCCATCGACAACAAGGTGCTGACCAGA

AGCGACAAGAACCGGGGCAAGAGCGACAACGTGCCCTCCGAAGAGGTCGTGAAGA

AGATGAAGAACTACTGGCGGCAGCTGCTGAACGCCAAGCTGATTACCCAGAGAAAG

TTCGACAATCTGACCAAGGCCGAGAGAGGCGGCCTGAGCGAACTGGATAAGGCCGG

CTTCATCAAGAGACAGCTGGTGGAAACCCGGCAGATCACAAAGCACGTGGCACAGA

TCCTGGACTCCCGGATGAACACTAAGTACGACGAGAATGACAAGCTGATCCGGGAA
```

-continued

GTGAAAGTGATCACCCTGAAGTCCAAGCTGGTGTCCGATTTCCGGAAGGATTTCCAG

TTTTACAAAGTGCGCGAGATCAACAACTACCACCACGCCCACGACGCCTACCTGAA

CGCCGTCGTGGGAACCGCCCTGATCAAAAAGTACCCTAAGCTGGAAAGCGAGTTCG

TGTACGGCGACTACAAGGTGTACGACGTGCGGAAGATGATCGCCAAGAGCGAGCAG

GAAATCGGCAAGGCTACCGCCAAGTACTTCTTCTACAGCAACATCATGAACTTTTTC

AAGACCGAGATTACCCTGGCCAACGGCGAGATCCGGAAGCGGCCTCTGATCGAGAC

AAACGGCGAAACCGGGGAGATCGTGTGGGATAAGGGCCGGGATTTTGCCACCGTGC

GGAAAGTGCTGAGCATGCCCCAAGTGAATATCGTGAAAAAGACCAAAAGGCCGGCG

GCCACGAAAAAGGCCGGCCAGGCAAAAAGAAAAAGtaa

32. Sp_del (175-307)-(GGGGS)3 ("(GGGGS)3"
disclosed as SEQ ID NO: 45)

(SEQ ID NO: 63)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGGGTGGaGGTGGCtcgGGTGGaGGTGGCtcgGGTGGaGGTGGCt cgGTGAACACCGAGATCACCAAGGCCCCCCTGAGCGCCTCTATGATCAAGAGATACG

ACGAGCACCACCAGGACCTGACCCTGCTGAAAGCTCTCGTGCGGCAGCAGCTGCCT

GAGAAGTACAAAGAGATTTTCTTCGACCAGAGCAAGAACGGCTACGCCGGCTACAT

TGACGGCGGAGCCAGCCAGGAAGAGTTCTACAAGTTCATCAAGCCCATCCTGGAAA

AGATGGACGGCACCGAGGAACTGCTCGTGAAGCTGAACAGAGAGGACCTGCTGCGG

AAGCAGCGGACCTTCGACAACGGCAGCATCCCCCACCAGATCCACCTGGGAGAGCT

GCACGCCATTCTGCGGCGGCAGGAAGATTTTTACCCATTCCTGAAGGACAACCGGG

AAAAGATCGAGAAGATCCTGACCTTCCGCATCCCCTACTACGTGGGCCCTCTGGCCA

GGGGAAACAGCAGATTCGCCTGGATGACCAGAAAGAGCGAGGAAACCATCACCCC

CTGGAACTTCGAGGAAGTGGTGGACAAGGGCGCTTCCGCCCAGAGCTTCATCGAGC

GGATGACCAACTTCGATAAGAACCTGCCCAACGAGAAGGTGCTGCCCAAGCACAGC

CTGCTGTACGAGTACTTCACCGTGTATAACGAGCTGACCAAAGTGAAATACGTGACC

GAGGGAATGAGAAAGCCCGCCTTCCTGAGCGGCGAGCAGAAAAAGGCCATCGTGG

ACCTGCTGTTCAAGACCAACCGGAAAGTGACCGTGAAGCAGCTGAAAGAGGACTAC

TTCAAGAAAATCGAGTGCTTCGACTCCGTGGAAATCTCCGGCGTGGAAGATCGGTTC

AACGCCTCCCTGGGCACATACCACGATCTGCTGAAAATTATCAAGGACAAGGACTT

CCTGGACAATGAGGAAAACGAGGACATTCTGGAAGATATCGTGCTGACCCTGACAC

TGTTTGAGGACAGAGAGATGATCGAGGAACGGCTGAAAACCTATGCCCACCTGTTC

GACGACAAAGTGATGAAGCAGCTGAAGCGGCGGAGATACACCGGCTGGGGCAGGC

-continued

```
TGAGCCGGAAGCTGATCAACGGCATCCGGGACAAGCAGTCCGGCAAGACAATCCTG
GATTTCCTGAAGTCCGACGGCTTCGCCAACAGAAACTTCATGCAGCTGATCCACGAC
GACAGCCTGACCTTTAAAGAGGACATCCAGAAAGCCCAGGTGTCCGGCCAGGGCGA
TAGCCTGCACGAGCACATTGCCAATCTGGCCGGCAGCCCCGCCATTAAGAAGGGCA
TCCTGCAGACAGTGAAGGTGGTGGACGAGCTCGTGAAAGTGATGGGCCGGCACAAG
CCCGAGAACATCGTGATCGAAATGGCCAGAGAGAACCAGACCACCCAGAAGGGAC
AGAAGAACAGCCGCGAGAGAATGAAGCGGATCGAAGAGGGCATCAAAGAGCTGGG
CAGCCAGATCCTGAAAGAACACCCCGTGGAAAACACCCAGCTGCAGAACGAGAAG
CTGTACCTGTACTACCTGCAGAATGGGCGGGATATGTACGTGGACCAGGAACTGGA
CATCAACCGGCTGTCCGACTACGATGTGGACCATATCGTGCCTCAGAGCTTTCTGAA
GGACGACTCCATCGACAACAAGGTGCTGACCAGAAGCGACAAGAACCGGGGCAAG
AGCGACAACGTGCCCTCCGAAGAGGTCGTGAAGAAGATGAAGAACTACTGGCGGCA
GCTGCTGAACGCCAAGCTGATTACCCAGAGAAAGTTCGACAATCTGACCAAGGCCG
AGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACAC
TAAGTACGACGAGAATGACAAGCTGATCCGGGAAGTGAAAGTGATCACCCTGAAGT
CCAAGCTGGTGTCCGATTTCCGGAAGGATTTCCAGTTTTACAAAGTGCGCGAGATCA
ACAACTACCACCACGCCCACGACGCCTACCTGAACGCCGTCGTGGGAACCGCCCTG
ATCAAAAAGTACCCTAAGCTGGAAAGCGAGTTCGTGTACGGCGACTACAAGGTGTA
CGACGTGCGGAAGATGATCGCCAAGAGCGAGCAGGAAATCGGCAAGGCTACCGCC
AAGTACTTCTTCTACAGCAACATCATGAACTTTTTCAAGACCGAGATTACCCTGGCC
AACGGCGAGATCCGGAAGCGGCCTCTGATCGAGACAAACGGCGAAACCGGGGAGA
TCGTGTGGGATAAGGGCCGGGATTTTGCCACCGTGCGGAAAGTGCTGAGCATGCCC
CAAGTGAATATCGTGAAAAAGACCGAGGTGCAGACAGGCGGCTTCAGCAAAGAGTC
TATCCTGCCCAAGAGGAACAGCGATAAGCTGATCGCCAGAAAGAAGGACTGGGACC
CTAAGAAGTACGGCGGCTTCGACAGCCCCACCGTGGCCTATTCTGTGCTGGTGGTGG
CCAAAGTGGAAAAGGGCAAGTCCAAGAAACTGAAGAGTGTGAAAGAGCTGCTGGG
GATCACCATCATGGAAAGAAGCAGCTTCGAGAAGAATCCCATCGACTTTCTGGAAG
CCAAGGGCTACAAAGAAGTGAAAAAGGACCTGATCATCAAGCTGCCTAAGTACTCC
CTGTTCGAGCTGGAAAACGGCCGGAAGAGAATGCTGGCCTCTGCCGGCGAACTGCA
GAAGGGAAACGAACTGGCCCTGCCCTCCAAATATGTGAACTTCCTGTACCTGGCCA
GCCACTATGAGAAGCTGAAGGGCTCCCCCGAGGATAATGAGCAGAAACAGCTGTTT
GTGGAACAGCACAAGCACTACCTGGACGAGATCATCGAGCAGATCAGCGAGTTCTC
CAAGAGAGTGATCCTGGCCGACGCTAATCTGGACAAAGTGCTGTCCGCCTACAACA
AGCACCGGGATAAGCCCATCAGAGAGCAGGCCGAGAATATCATCCACCTGTTTACC
CTGACCAATCTGGGAGCCCCTGCCGCCTTCAAGTACTTTGACACCACCATCGACCGG
AAGAGGTACACCAGCACCAAAGAGGTGCTGGACGCCACCCTGATCCACCAGAGCAT
CACCGGCCTGTACGAGACACGGATCGACCTGTCTCAGCTGGGAGGCGACAAAAGGC
CGGCGGCCACGAAAAAGGCCGGCCAGGCAAAAAAGAAAAAGtaa
```

-continued

33. Sp_del (175-307)-(GGGGS)6 ("(GGGGS)6" disclosed as SEQ ID NO: 47)

(SEQ ID NO: 64)

ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGGGTGGaGGTGGCtcgGGTGGaGGTGGCtcgGGTGGaGGTGGCt cgGGTGGaGGTGGCtcgGGTGGaGGTGGCtcgGGTGGaGGTGGCtcgGTGAACACCGAGAT

CACCAAGGCCCCCCTGAGCGCCTCTATGATCAAGAGATACGACGAGCACCACCAGG

ACCTGACCCTGCTGAAAGCTCTCGTGCGGCAGCAGCTGCCTGAGAAGTACAAAGAG

ATTTTCTTCGACCAGAGCAAGAACGGCTACGCCGGCTACATTGACGGCGGAGCCAG

CCAGGAAGAGTTCTACAAGTTCATCAAGCCCATCCTGGAAAAGATGGACGGCACCG

AGGAACTGCTCGTGAAGCTGAACAGAGAGGACCTGCTGCGGAAGCAGCGGACCTTC

GACAACGGCAGCATCCCCCACCAGATCCACCTGGGAGAGCTGCACGCCATTCTGCG

GCGGCAGGAAGATTTTTACCCATTCCTGAAGGACAACCGGGAAAAGATCGAGAAGA

TCCTGACCTTCCGCATCCCCTACTACGTGGGCCCTCTGGCCAGGGGAAACAGCAGAT

TCGCCTGGATGACCAGAAAGAGCGAGGAAACCATCACCCCCTGGAACTTCGAGGAA

GTGGTGGACAAGGGCGCTTCCGCCCAGAGCTTCATCGAGCGGATGACCAACTTCGA

TAAGAACCTGCCCAACGAGAAGGTGCTGCCCAAGCACAGCCTGCTGTACGAGTACT

TCACCGTGTATAACGAGCTGACCAAAGTGAAATACGTGACCGAGGGAATGAGAAAG

CCCGCCTTCCTGAGCGGCGAGCAGAAAAAGGCCATCGTGGACCTGCTGTTCAAGAC

CAACCGGAAAGTGACCGTGAAGCAGCTGAAAGAGGACTACTTCAAGAAAATCGAGT

GCTTCGACTCCGTGGAAATCTCCGGCGTGGAAGATCGGTTCAACGCCTCCCTGGGCA

CATACCACGATCTGCTGAAAATTATCAAGGACAAGGACTTCCTGGACAATGAGGAA

AACGAGGACATTCTGGAAGATATCGTGCTGACCCTGACACTGTTTGAGGACAGAGA

GATGATCGAGGAACGGCTGAAAACCTATGCCCACCTGTTCGACGACAAAGTGATGA

AGCAGCTGAAGCGGCGGAGATACACCGGCTGGGGCAGGCTGAGCCGGAAGCTGAT

CAACGGCATCCGGGACAAGCAGTCCGGCAAGACAATCCTGGATTTCCTGAAGTCCG

ACGGCTTCGCCAACAGAAACTTCATGCAGCTGATCCACGACGACAGCCTGACCTTTA

AAGAGGACATCCAGAAAGCCCAGGTGTCCGGCCAGGGCGATAGCCTGCACGAGCAC

ATTGCCAATCTGGCCGGCAGCCCCGCCATTAAGAAGGGCATCCTGCAGACAGTGAA

GGTGGTGGACGAGCTCGTGAAAGTGATGGGCCGGCACAAGCCCGAGAACATCGTGA

TCGAAATGGCCAGAGAGAACCAGACCACCCAGAAGGGACAGAAGAACAGCCGCGA

GAGAATGAAGCGGATCGAAGAGGGCATCAAAGAGCTGGGCAGCCAGATCCTGAAA

GAACACCCCGTGGAAAACACCCAGCTGCAGAACGAGAAGCTGTACCTGTACTACCT

-continued

```
GCAGAATGGGCGGGATATGTACGTGGACCAGGAACTGGACATCAACCGGCTGTCCG
ACTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAGC
TGATTACCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCAGATCAC
AAAGCACGTGGCACAGATCCTGGACTCCCGGATGAACACTAAGTACGACGAGAATG
ACAAGCTGATCCGGGAAGTGAAAGTGATCACCCTGAAGTCCAAGCTGGTGTCCGAT
TTCCGGAAGGATTTCCAGTTTTACAAAGTGCGCGAGATCAACAACTACCACCACGCC
CACGACGCCTACCTGAACGCCGTCGTGGGAACCGCCCTGATCAAAAAGTACCCTAA
GCTGGAAAGCGAGTTCGTGTACGGCGACTACAAGGTGTACGACGTGCGGAAGATGA
TCGCCAAGAGCGAGCAGGAAATCGGCAAGGCTACCGCCAAGTACTTCTTCTACAGC
AACATCATGAACTTTTTCAAGACCGAGATTACCCTGGCCAACGGCGAGATCCGGAA
GCGGCCTCTGATCGAGACAAACGGCGAAACCGGGGAGATCGTGTGGGATAAGGGCC
GGGATTTTGCCACCGTGCGGAAAGTGCTGAGCATGCCCCAAGTGAATATCGTGAAA
AAGACCGAGGTGCAGACAGGCGGCTTCAGCAAAGAGTCTATCCTGCCCAAGAGGAA
CAGCGATAAGCTGATCGCCAGAAAGAAGGACTGGGACCCTAAGAAGTACGGCGGCT
TCGACAGCCCCACCGTGGCCTATTCTGTGCTGGTGGTGGCCAAAGTGGAAAAGGGC
AAGTCCAAGAAACTGAAGAGTGTGAAAGAGCTGCTGGGGATCACCATCATGGAAAG
AAGCAGCTTCGAGAAGAATCCCATCGACTTTCTGGAAGCCAAGGGCTACAAGAAG
TGAAAAAGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGAACTGG
CCCTGCCCTCCAAATATGTGAACTTCCTGTACCTGGCCAGCCACTATGAGAAGCTGA
AGGGCTCCCCCGAGGATAATGAGCAGAAACAGCTGTTTGTGGAACAGCACAAGCAC
TACCTGGACGAGATCATCGAGCAGATCAGCGAGTTCTCCAAGAGAGTGATCCTGGC
CGACGCTAATCTGGACAAAGTGCTGTCCGCCTACAACAAGCACCGGGATAAGCCCA
TCAGAGAGCAGGCCGAGAATATCATCCACCTGTTTACCCTGACCAATCTGGGAGCCC
CTGCCGCCTTCAAGTACTTTGACACCACCATCGACCGGAAGAGGTACACCAGCACC
AAAGAGGTGCTGGACGCCACCCTGATCCACCAGAGCATCACCGGCCTGTACGAGAC
ACGGATCGACCTGTCTCAGCTGGGAGGCGACAAAAGGCCGGCGGCCACGAAAAAG
GCCGGCCAGGCAAAAAAGAAAAAGtaa
```

34. Sp_del (175-307)-(GGGGS)9 ("(GGGGS)9" disclosed
as SEQ ID NO: 49)
(SEQ ID NO: 65)

```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
```

-continued

```
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGGGTGGaGGTGGCtcgGGTGGaGGTGGCtcgGGTGGaGGTGGCt
cgGGTGGaGGTGGCtcgGGTGGaGGTGGCtcgGGTGGaGGTGGCtcgGGTGGaGGTGGCtcgG
GTGGaGGTGGCtcgGGTGGaGGTGGCtcgGTGAACACCGAGATCACCAAGGCCCCCCTG
AGCGCCTCTATGATCAAGAGATACGACGAGCACCACCAGGACCTGACCCTGCTGAA
AGCTCTCGTGCGGCAGCAGCTGCCTGAGAAGTACAAAGAGATTTTCTTCGACCAGA
GCAAGAACGGCTACGCCGGCTACATTGACGGCGGAGCCAGCCAGGAAGAGTTCTAC
AAGTTCATCAAGCCCATCCTGGAAAAGATGGACGGCACCGAGGAACTGCTCGTGAA
GCTGAACAGAGAGGACCTGCTGCGGAAGCAGCGGACCTTCGACAACGGCAGCATCC
CCCACCAGATCCACCTGGGAGAGCTGCACGCCATTCTGCGGCGGCAGGAAGATTTTT
ACCCATTCCTGAAGGACAACCGGGAAAAGATCGAGAAGATCCTGACCTTCCGCATC
CCCTACTACGTGGGCCCTCTGGCCAGGGGAAACAGCAGATTCGCCTGGATGACCAG
AAAGAGCGAGGAAACCATCACCCCCTGGAACTTCGAGGAAGTGGTGGACAAGGGC
GCTTCCGCCCAGAGCTTCATCGAGCGGATGACCAACTTCGATAAGAACCTGCCCAAC
GAGAAGGTGCTGCCCAAGCACAGCCTGCTGTACGAGTACTTCACCGTGTATAACGA
GCTGACCAAAGTGAAATACGTGACCGAGGGAATGAGAAAGCCCGCCTTCCTGAGCG
GCGAGCAGAAAAAGGCCATCGTGGACCTGCTGTTCAAGACCAACCGGAAAGTGACC
GTGAAGCAGCTGAAAGAGGACTACTTCAAGAAAATCGAGTGCTTCGACTCCGTGGA
AATCTCCGGCGTGGAAGATCGGTTCAACGCCTCCCTGGGCACATACCACGATCTGCT
GAAAATTATCAAGGACAAGGACTTCCTGGACAATGAGGAAAACGAGGACATTCTGG
AAGATATCGTGCTGACCCTGACACTGTTTGAGGACAGAGAGATGATCGAGGAACGG
CTGAAAACCTATGCCCACCTGTTCGACGACAAAGTGATGAAGCAGCTGAAGCGGCG
GAGATACACCGGCTGGGGCAGGCTGAGCCGGAAGCTGATCAACGGCATCCGGGACA
AGCAGTCCGGCAAGACAATCCTGGATTTCCTGAAGTCCGACGGCTTCGCCAACAGA
AACTTCATGCAGCTGATCCACGACGACAGCCTGACCTTTAAAGAGGACATCCAGAA
AGCCCAGGTGTCCGGCCAGGGCGATAGCCTGCACGAGCACATTGCCAATCTGGCCG
GCAGCCCCGCCATTAAGAAGGGCATCCTGCAGACAGTGAAGGTGGTGGACGAGCTC
GTGAAAGTGATGGGCCGGCACAAGCCCGAGAACATCGTGATCGAAATGGCCAGAGA
GAACCAGACCACCCAGAAGGGACAGAAGAACAGCCGCGAGAGAATGAAGCGGATC
GAAGAGGGCATCAAAGAGCTGGGCAGCCAGATCCTGAAAGAACACCCCGTGGAAA
ACACCCAGCTGCAGAACGAGAAGCTGTACCTGTACTACCTGCAGAATGGGCGGGAT
ATGTACGTGGACCAGGAACTGGACATCAACCGGCTGTCCGACTACGATGTGGACCA
TATCGTGCCTCAGAGCTTTCTGAAGGACGACTCCATCGACAACAAGGTGCTGACCAG
AAGCGACAAGAACCGGGGCAAGAGCGACAACGTGCCCTCCGAAGAGGTCGTGAAG
AAGATGAAGAACTACTGGCGGCAGCTGCTGAACGCCAAGCTGATTACCCAGAGAAA
GTTCGACAATCTGACCAAGGCCGAGAGGGCGGCCTGAGCGAACTGGATAAGGCCG
GCTTCATCAAGAGACAGCTGGTGGAAACCCGGCAGATCACAAAGCACGTGGCACAG
ATCCTGGACTCCCGGATGAACACTAAGTACGACGAGAATGACAAGCTGATCCGGGA
AGTGAAAGTGATCACCCTGAAGTCCAAGCTGGTGTCCGATTTCCGGAAGGATTTCCA
GTTTTACAAAGTGCGCGAGATCAACAACTACCACCACGCCCACGACGCCTACCTGA
```

-continued

```
ACGCCGTCGTGGGAACCGCCCTGATCAAAAAGTACCCTAAGCTGGAAAGCGAGTTC
GTGTACGGCGACTACAAGGTGTACGACGTGCGGAAGATGATCGCCAAGAGCGAGCA
GGAAATCGGCAAGGCTACCGCCAAGTACTTCTTCTACAGCAACATCATGAACTTTTT
CAAGACCGAGATTACCCTGGCCAACGGCGAGATCCGGAAGCGGCCTCTGATCGAGA
CAAACGGCGAAACCGGGGAGATCGTGTGGGATAAGGGCCGGGATTTTGCCACCGTG
CGGAAAGTGCTGAGCATGCCCCAAGTGAATATCGTGAAAAAGACCGAGGTGCAGAC
AGGCGGCTTCAGCAAAGAGTCTATCCTGCCCAAGAGGAACAGCGATAAGCTGATCG
CCAGAAAGAAGGACTGGGACCCTAAGAAGTACGGCGGCTTCGACAGCCCCACCGTG
GCCTATTCTGTGCTGGTGGTGGCCAAAGTGGAAAAGGGCAAGTCCAAGAAACTGAA
GAGTGTGAAAGAGCTGCTGGGGATCACCATCATGGAAAGAAGCAGCTTCGAGAAGA
ATCCCATCGACTTTCTGGAAGCCAAGGGCTACAAAGAAGTGAAAAAGGACCTGATC
ATCAAGCTGCCTAAGTACTCCCTGTTCGAGCTGGAAAACGGCCGGAAGAGAATGCT
GGCCTCTGCCGGCGAACTGCAGAAGGGAAACGAACTGGCCCTGCCCTCCAAATATG
TGAACTTCCTGTACCTGGCCAGCCACTATGAGAAGCTGAAGGGCTCCCCCGAGGAT
AATGAGCAGAAACAGCTGTTTGTGGAACAGCACAAGCACTACCTGGACGAGATCAT
CGAGCAGATCAGCGAGTTCTCCAAGAGAGTGATCCTGGCCGACGCTAATCTGGACA
AAGTGCTGTCCGCCTACAACAAGCACCGGGATAAGCCCATCAGAGAGCAGGCCGAG
AATATCATCCACCTGTTTACCCTGACCAATCTGGGAGCCCCTGCCGCCTTCAAGTAC
TTTGACACCACCATCGACCGGAAGAGGTACACCAGCACCAAAGAGGTGCTGGACGC
CACCCTGATCCACCAGAGCATCACCGGCCTGTACGAGACACGGATCGACCTGTCTCA
GCTGGGAGGCGACAAAAGGCCGGCGGCCACGAAAAAGGCCGGCCAGGCAAAAAAG
AAAAAGtaa
```

35. Sp_del (175-307)-(GGGGS)12 ("(GGGGS)12" disclosed as SEQ ID NO: 51)

(SEQ ID NO: 66)
```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGGGTGGaGGTGGttegGGTGGCCGGTGGCtegGGTGGaGGTGGatc
gGGTGGCCGGTGGttegGGTGGaGGTGGCtegGGcGGaGGTGGatcgGGTGGCCGGTGGCtcgGG
TGGaGGTGGCtcgGGTGGaGGTGGCtcgGGTGGCCGGTGGatcgGGTGGaGGTGGatcgGGTG
GaGGTGGttegGTGAACACCGAGATCACCAAGGCCCCCCTGAGCGCCTCTATGATCAA
GAGATACGACGAGCACCACCAGGACCTGACCCTGCTGAAAGCTCTCGTGCGGCAGC
AGCTGCCTGAGAAGTACAAAGAGATTTTCTTCGACCAGAGCAAGAACGGCTACGCC
GGCTACATTGACGGCGGAGCCAGCCAGGAAGAGTTCTACAAGTTCATCAAGCCCAT
```

```
CCTGGAAAAGATGGACGGCACCGAGGAACTGCTCGTGAAGCTGAACAGAGAGGAC

CTGCTGCGGAAGCAGCGGACCTTCGACAACGGCAGCATCCCCCACCAGATCCACCT

GGGAGAGCTGCACGCCATTCTGCGGCGGCAGGAAGATTTTTACCCATTCCTGAAGG

ACAACCGGGAAAAGATCGAGAAGATCCTGACCTTCCGCATCCCCTACTACGTGGGC

CCTCTGGCCAGGGGAAACAGCAGATTCGCCTGGATGACCAGAAAGAGCGAGGAAA

CCATCACCCCCTGGAACTTCGAGGAAGTGGTGGACAAGGGCGCTTCCGCCCAGAGC

TTCATCGAGCGGATGACCAACTTCGATAAGAACCTGCCCAACGAGAAGGTGCTGCC

CAAGCACAGCCTGCTGTACGAGTACTTCACCGTGTATAACGAGCTGACCAAAGTGA

AATACGTGACCGAGGGAATGAGAAAGCCCGCCTTCCTGAGCGGCGAGCAGAAAAA

GGCCATCGTGGACCTGCTGTTCAAGACCAACCGGAAAGTGACCGTGAAGCAGCTGA

AAGAGGACTACTTCAAGAAAATCGAGTGCTTCGACTCCGTGGAAATCTCCGGCGTG

GAAGATCGGTTCAACGCCTCCCTGGGCACATACCACGATCTGCTGAAAATTATCAAG

GACAAGGACTTCCTGGACAATGAGGAAAACGAGGACATTCTGGAAGATATCGTGCT

GACCCTGACACTGTTTGAGGACAGAGAGATGATCGAGGAACGGCTGAAAACCTATG

CCCACCTGTTCGACGACAAAGTGATGAAGCAGCTGAAGCGGCGGAGATACACCGGC

TGGGGCAGGCTGAGCCGGAAGCTGATCAACGGCATCCGGGACAAGCAGTCCGGCAA

GACAATCCTGGATTTCCTGAAGTCCGACGGCTTCGCCAACAGAAACTTCATGCAGCT

GATCCACGACGACAGCCTGACCTTTAAAGAGGACATCCAGAAAGCCCAGGTGTCCG

GCCAGGGCGATAGCCTGCACGAGCACATTGCCAATCTGGCCGGCAGCCCCGCCATT

AAGAAGGGCATCCTGCAGACAGTGAAGGTGGTGGACGAGCTCGTGAAAGTGATGGG

CCGGCACAAGCCCGAGAACATCGTGATCGAAATGGCCAGAGAGAACCAGACCACCC

AGAAGGGACAGAAGAACAGCCGCGAGAGAATGAAGCGGATCGAAGAGGGCATCAA

AGAGCTGGGCAGCCAGATCCTGAAAGAACACCCCGTGGAAAACACCCAGCTGCAGA

ACGAGAAGCTGTACCTGTACTACCTGCAGAATGGGCGGGATATGTACGTGGACCAG

GAACTGGACATCAACCGGCTGTCCGACTACGATGTGGACCATATCGTGCCTCAGAG

CTTTCTGAAGGACGACTCCATCGACAACAAGGTGCTGACCAGAAGCGACAAGAACC

GGGGCAAGAGCGACAACGTGCCCTCCGAAGAGGTCGTGAAGAAGATGAAGAACTA

CTGGCGGCAGCTGCTGAACGCCAAGCTGATTACCCAGAGAAAGTTCGACAATCTGA

CCAAGGCCGAGAGAGGCGGCCTGAGCGAACTGGATAAGGCCGGCTTCATCAAGAG

ACAGCTGGTGGAAACCCGGCAGATCACAAAGCACGTGGCACAGATCCTGGACTCCC

GGATGAACACTAAGTACGACGAGAATGACAAGCTGATCCGGGAAGTGAAAGTGATC

ACCCTGAAGTCCAAGCTGGTGTCCGATTTCCGGAAGGATTTCCAGTTTTACAAAGTG

CGCGAGATCAACAACTACCACCACGCCCACGACGCCTACCTGAACGCCGTCGTGGG

AACCGCCCTGATCAAAAAGTACCCTAAGCTGGAAAGCGAGTTCGTGTACGGCGACT

ACAAGGTGTACGACGTGCGGAAGATGATCGCCAAGAGCGAGCAGGAAATCGGCAA

GGCTACCGCCAAGTACTTCTTCTACAGCAACATCATGAACTTTTTCAAGACCGAGAT

TACCCTGGCCAACGGCGAGATCCGGAAGCGGCCTCTGATCGAGACAAACGGCGAAA

CCGGGGAGATCGTGTGGGATAAGGGCCGGGATTTTGCCACCGTGCGGAAAGTGCTG

AGCATGCCCCAAGTGAATATCGTGAAAAAGACCGAGGTGCAGACAGGCGGCTTCAG

CAAAGAGTCTATCCTGCCCAAGAGGAACAGCGATAAGCTGATCGCCAGAAAGAAGG
```

-continued

ACTGGGACCCTAAGAAGTACGGCGGCTTCGACAGCCCCACCGTGGCCTATTCTGTGC

TGGTGGTGGCCAAAGTGGAAAAGGGCAAGTCCAAGAAACTGAAGAGTGTGAAAGA

GCTGCTGGGGATCACCATCATGGAAAGAAGCAGCTTCGAGAAGAATCCCATCGACT

TTCTGGAAGCCAAGGGCTACAAAGAAGTGAAAAAGGACCTGATCATCAAGCTGCCT

AAGTACTCCCTGTTCGAGCTGGAAAACGGCCGGAAGAGAATGCTGGCCTCTGCCGG

CGAACTGCAGAAGGGAAACGAACTGGCCCTGCCCTCCAAATATGTGAACTTCCTGT

ACCTGGCCAGCCACTATGAGAAGCTGAAGGGCTCCCCCGAGGATAATGAGCAGAAA

CAGCTGTTTGTGGAACAGCACAAGCACTACCTGGACGAGATCATCGAGCAGATCAG

CGAGTTCTCCAAGAGAGTGATCCTGGCCGACGCTAATCTGGACAAAGTGCTGTCCGC

CTACAACAAGCACCGGGATAAGCCCATCAGAGAGCAGGCCGAGAATATCATCCACC

TGTTTACCCTGACCAATCTGGGAGCCCCTGCCGCCTTCAAGTACTTTGACACCACCA

TCGACCGGAAGAGGTACACCAGCACCAAAGAGGTGCTGGACGCCACCCTGATCCAC

CAGAGCATCACCGGCCTGTACGAGACACGGATCGACCTGTCTCAGCTGGGAGGCGA

CAAAAGGCCGGCGCCACGAAAAAGGCCGGCCAGGCAAAAAAGAAAAAGtaa

36. Sp_del(175-307)-A(EAAAK)3A ("A(EAAAK)3A" disclosed
as SEQ ID NO: 53)

(SEQ ID NO: 67)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGgctGAAGCTGCTGCTAAAGAAGCTGCTGCTAAAGAAGCTG

CTGCTAAAgctGTGAACACCGAGATCACCAAGGCCCCCCTGAGCGCCTCTATGATCAA

GAGATACGACGAGCACCACCAGGACCTGACCCTGCTGAAAGCTCTCGTGCGGCAGC

AGCTGCCTGAGAAGTACAAAGAGATTTTCTTCGACCAGAGCAAGAACGGCTACGCC

GGCTACATTGACGGCGGAGCCAGCCAGGAAGAGTTCTACAAGTTCATCAAGCCCAT

CCTGGAAAAGATGGACGGCACCGAGGAACTGCTCGTGAAGCTGAACAGAGAGGAC

CTGCTGCGGAAGCAGCGGACCTTCGACAACGGCAGCATCCCCCACCAGATCCACCT

GGGAGAGCTGCACGCCATTCTGCGGCGGCAGGAAGATTTTTACCCATTCCTGAAGG

ACAACCGGGAAAAGATCGAGAAGATCCTGACCTTCCGCATCCCCTACTACGTGGGC

CCTCTGGCCAGGGGAAACAGCAGATTCGCCTGGATGACCAGAAAGAGCGAGGAAA

CCATCACCCCCTGGAACTTCGAGGAAGTGGTGGACAAGGGCGCTTCCGCCCAGAGC

TTCATCGAGCGGATGACCAACTTCGATAAGAACCTGCCCAACGAGAAGGTGCTGCC

CAAGCACAGCCTGCTGTACGAGTACTTCACCGTGTATAACGAGCTGACCAAAGTGA

AATACGTGACCGAGGGAATGAGAAAGCCCGCCTTCCTGAGCGGCGAGCAGAAAAA

GGCCATCGTGGACCTGCTGTTCAAGACCAACCGGAAAGTGACCGTGAAGCAGCTGA

-continued

```
AAGAGGACTACTTCAAGAAAATCGAGTGCTTCGACTCCGTGGAAATCTCCGGCGTG
GAAGATCGGTTCAACGCCTCCCTGGGCACATACCACGATCTGCTGAAAATTATCAAG
GACAAGGACTTCCTGGACAATGAGGAAAACGAGGACATTCTGGAAGATATCGTGCT
GACCCTGACACTGTTTGAGGACAGAGAGATGATCGAGGAACGGCTGAAAACCTATG
CCCACCTGTTCGACGACAAAGTGATGAAGCAGCTGAAGCGGCGGAGATACACCGGC
TGGGGCAGGCTGAGCCGGAAGCTGATCAACGGCATCCGGGACAAGCAGTCCGGCAA
GACAATCCTGGATTTCCTGAAGTCCGACGGCTTCGCCAACAGAAACTTCATGCAGCT
GATCCACGACGACAGCCTGACCTTTAAAGAGGACATCCAGAAAGCCCAGGTGTCCG
GCCAGGGCGATAGCCTGCACGAGCACATTGCCAATCTGGCCGGCAGCCCCGCCATT
AAGAAGGGCATCCTGCAGACAGTGAAGGTGGTGGACGAGCTCGTGAAAGTGATGGG
CCGGCACAAGCCCGAGAACATCGTGATCGAAATGGCCAGAGAGAACCAGACCACCC
AGAAGGGACAGAAGAACAGCCGCGAGAGAATGAAGCGGATCGAAGAGGGCATCAA
AGAGCTGGGCAGCCAGATCCTGAAAGAACACCCCGTGGAAAACACCCAGCTGCAGA
ACGAGAAGCTGTACCTGTACTACCTGCAGAATGGGCGGGATATGTACGTGGACCAG
GAACTGGACATCAACCGGCTGTCCGACTACGATGTGGACCATATCGTGCCTCAGAG
CTTTCTGAAGGACGACTCCATCGACAACAAGGTGCTGACCAGAAGCGACAAGAACC
GGGGCAAGAGCGACAACGTGCCCTCCGAAGAGGTCGTGAAGAAGATGAAGAACTA
CTGGCGGCAGCTGCTGAACGCCAAGCTGATTACCCAGAGAAAGTTCGACAATCTGA
CCAAGGCCGAGAGAGGCGGCCTGAGCGAACTGGATAAGGCCGGCTTCATCAAGAG
ACAGCTGGTGGAAACCCGGCAGATCACAAAGCACGTGGCACAGATCCTGGACTCCC
GGATGAACACTAAGTACGACGAGAATGACAAGCTGATCCGGGAAGTGAAAGTGATC
ACCCTGAAGTCCAAGCTGGTGTCCGATTTCCGGAAGGATTTCCAGTTTTACAAAGTG
CGCGAGATCAACAACTACCACCACGCCCACGACGCCTACCTGAACGCCGTCGTGGG
AACCGCCCTGATCAAAAAGTACCCTAAGCTGGAAAGCGAGTTCGTGTACGGCGACT
ACAAGGTGTACGACGTGCGCAAGATGATCGCCAAGAGCGAGCAGGAAATCGGCAA
GGCTACCGCCAAGTACTTCTTCTACAGCAACATCATGAACTTTTTCAAGACCGAGAT
TACCCTGGCCAACGGCGAGATCCGGAAGCGGCCTCTGATCGAGACAAACGGCGAAA
CCGGGGAGATCGTGTGGGATAAGGGCCGGGATTTTGCCACCGTGCGGAAAGTGCTG
AGCATGCCCCAAGTGAATATCGTGAAAAAGACCGAGGTGCAGACAGGCGGCTTCAG
CAAAGAGTCTATCCTGCCCAAGAGGAACAGCGATAAGCTGATCGCCAGAAAGAAGG
ACTGGGACCCTAAGAAGTACGGCGGCTTCGACAGCCCCACCGTGGCCTATTCTGTGC
TGGTGGTGGCCAAAGTGGAAAAGGGCAAGTCCAAGAAACTGAAGAGTGTGAAAGA
GCTGCTGGGGATCACCATCATGGAAAGAAGCAGCTTCGAGAAGAATCCCATCGACT
TTCTGGAAGCCAAGGGCTACAAAGAAGTGAAAAAGGACCTGATCATCAAGCTGCCT
AAGTACTCCCTGTTCGAGCTGGAAAACGGCCGGAAGAGAATGCTGGCCTCTGCCGG
CGAACTGCAGAAGGGAAACGAACTGGCCCTGCCCTCCAAATATGTGAACTTCCTGT
ACCTGGCCAGCCACTATGAGAAGCTGAAGGGCTCCCCCGAGGATAATGAGCAGAAA
CAGCTGTTTGTGGAACAGCACAAGCACTACCTGGACGAGATCATCGAGCAGATCAG
CGAGTTCTCCAAGAGAGTGATCCTGGCCGACGCTAATCTGGACAAAGTGCTGTCCGC
CTACAACAAGCACCGGGATAAGCCCATCAGAGAGCAGGCCGAGAATATCATCCACC
TGTTTACCCTGACCAATCTGGGAGCCCCTGCCGCCTTCAAGTACTTTGACACCACCA
```

-continued

TCGACCGGAAGAGGTACACCAGCACCAAAGAGGTGCTGGACGCCACCCTGATCCAC

CAGAGCATCACCGGCCTGTACGAGACACGGATCGACCTGTCTCAGCTGGGAGGCGA

CAAAAGGCCGGCGGCCACGAAAAAGGCCGGCCAGGCAAAAAAGAAAAAGtaa

37. Sp_del (175-307)-A(EAAAK)3ALEA(EAAAK)3A
("A(EAAAK)3ALEA(EAAAK)3A" disclosed as
SEQ ID NO: 55)

(SEQ ID NO: 68)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGgctGAAGCCGCTGCTAAAGAAGCcGCTGCTAAAGAAGCcGC

TGCTAAAGccCTGGAGgctGAAGCcGCTGCTAAAGAAGCcGCTGCTAAAGAAGCCGCT

GCTAAAgctGTGAACACCGAGATCACCAAGGCCCCCCTGAGCGCCTCTATGATCAAG

AGATACGACGAGCACCACCAGGACCTGACCCTGCTGAAAGCTCTCGTGCGGCAGCA

GCTGCCTGAGAAGTACAAAGAGATTTTCTTCGACCAGAGCAAGAACGGCTACGCCG

GCTACATTGACGGCGGAGCCAGCCAGGAAGAGTTCTACAAGTTCATCAAGCCCATC

CTGGAAAAGATGGACGGCACCGAGGAACTGCTCGTGAAGCTGAACAGAGAGGACCT

GCTGCGGAAGCAGCGGACCTTCGACAACGGCAGCATCCCCCACCAGATCCACCTGG

GAGAGCTGCACGCCATTCTGCGGCGGCAGGAAGATTTTTACCCATTCCTGAAGGACA

ACCGGGAAAAGATCGAGAAGATCCTGACCTTCCGCATCCCCTACTACGTGGGCCCTC

TGGCCAGGGGAAACAGCAGATTCGCCTGGATGACCAGAAAGAGCGAGGAAACCAT

CACCCCCTGGAACTTCGAGGAAGTGGTGGACAAGGGCGCTTCCGCCCAGAGCTTCA

TCGAGCGGATGACCAACTTCGATAAGAACCTGCCCAACGAGAAGGTGCTGCCCAAG

CACAGCCTGCTGTACGAGTACTTCACCGTGTATAACGAGCTGACCAAAGTGAAATAC

GTGACCGAGGGAATGAGAAAGCCCGCCTTCCTGAGCGGCGAGCAGAAAAAGGCCA

TCGTGGACCTGCTGTTCAAGACCAACCGGAAAGTGACCGTGAAGCAGCTGAAAGAG

GACTACTTCAAGAAAATCGAGTGCTTCGACTCCGTGGAAATCTCCGGCGTGGAAGAT

CGGTTCAACGCCTCCCTGGGCACATACCACGATCTGCTGAAAATTATCAAGGACAA

GGACTTCCTGGACAATGAGGAAAACGAGGACATTCTGGAAGATATCGTGCTGACCC

TGACACTGTTTGAGGACAGAGAGATGATCGAGGAACGGCTGAAAACCTATGCCCAC

CTGTTCGACGACAAAGTGATGAAGCAGCTGAAGCGGCGGAGATACACCGGCTGGGG

CAGGCTGAGCCGGAAGCTGATCAACGGCATCCGGGACAAGCAGTCCGGCAAGACA

ATCCTGGATTTCCTGAAGTCCGACGGCTTCGCCAACAGAAACTTCATGCAGCTGATC

CACGACGACAGCCTGACCTTTAAAGAGGACATCCAGAAAGCCCAGGTGTCCGGCCA

GGGCGATAGCCTGCACGAGCACATTGCCAATCTGGCCGGCAGCCCCGCCATTAAGA

```
AGGGCATCCTGCAGACAGTGAAGGTGGTGGACGAGCTCGTGAAAGTGATGGGCCGG

CACAAGCCCGAGAACATCGTGATCGAAATGGCCAGAGAGAACCAGACCACCCAGA

AGGGACAGAAGAACAGCCGCGAGAGAATGAAGCGGATCGAAGAGGGCATCAAAGA

GCTGGGCAGCCAGATCCTGAAAGAACACCCCGTGGAAAACACCCAGCTGCAGAACG

AGAAGCTGTACCTGTACTACCTGCAGAATGGGCGGGATATGTACGTGGACCAGGAA

CTGGACATCAACCGGCTGTCCGACTACGATGTGGACCATATCGTGCCTCAGAGCTTT

CTGAAGGACGACTCCATCGACAACAAGGTGCTGACCAGAAGCGACAAGAACCGGG

GCAAGAGCGACAACGTGCCCTCCGAAGAGGTCGTGAAGAAGATGAAGAACTACTGG

CGGCAGCTGCTGAACGCCAAGCTGATTACCCAGAGAAAGTTCGACAATCTGACCAA

GGCCGAGAGAGGCGGCCTGAGCGAACTGGATAAGGCCGGCTTCATCAAGAGACAG

CTGGTGGAAACCCGGCAGATCACAAAGCACGTGGCACAGATCCTGGACTCCCGGAT

GAACACTAAGTACGACGAGAATGACAAGCTGATCCGGGAAGTGAAAGTGATCACCC

TGAAGTCCAAGCTGGTGTCCGATTTCCGGAAGGATTTCCAGTTTTACAAAGTGCGCG

AGATCAACAACTACCACCACGCCCACGACGCCTACCTGAACGCCGTCGTGGGAACC

GCCCTGATCAAAAAGTACCCTAAGCTGGAAAGCGAGTTCGTGTACGGCGACTACAA

GGTGTACGACGTGCGGAAGATGATCGCCAAGAGCGAGCAGGAAATCGGCAAGGCT

ACCGCCAAGTACTTCTTCTACAGCAACATCATGAACTTTTTCAAGACCGAGATTACC

CTGGCCAACGGCGAGATCCGGAAGCGGCCTCTGATCGAGACAAACGGCGAAACCGG

GGAGATCGTGTGGGATAAGGGCCGGGATTTTGCCACCGTGCGGAAAGTGCTGAGCA

TGCCCCAAGTGAATATCGTGAAAAAGACCGAGGTGCAGACAGGCGGCTTCAGCAAA

GAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGT

GGTGGCCAAAGTGGAAAAGGGCAAGTCCAAGAAACTGAAGAGTGTGAAAGAGCTG

CTGGGGATCACCATCATGGAAAGAAGCAGCTTCGAGAAGAATCCCATCGACTTTCT

GGAAGCCAAGGGCTACAAAGAAGTGAAAAAGGACCTGATCATCAAGCTGCCTAAGT

ACTCCCTGTTCGAGCTGGAAAACGGCCGGAAGAGAATGCTGGCCTCTGCCGGCGAA

CTGCAGAAGGGAAACGAACTGGCCCTGCCCTCCAAATATGTGAACTTCCTGTACCTG

GCCAGCCACTATGAGAAGCTGAAGGGCTCCCCCGAGGATAATGAGCAGAAACAGCT

GTTTGTGGAACAGCACAAGCACTACCTGGACGAGATCATCGAGCAGATCAGCGAGT

TCTCCAAGAGAGTGATCCTGGCCGACGCTAATCTGGACAAAGTGCTGTCCGCCTACA

ACAAGCACCGGGATAAGCCCATCAGAGAGCAGGCCGAGAATATCATCCACCTGTTT

ACCCTGACCAATCTGGGAGCCCCTGCCGCCTTCAAGTACTTTGACACCACCATCGAC

CGGAAGAGGTACACCAGCACCAAAGAGGTGCTGGACGCCACCCTGATCCACCAGAG

CATCACCGGCCTGTACGAGACACGGATCGACCTGTCTCAGCTGGGAGGCGACAAAA

GGCCGGCGGCCACGAAAAAGGCCGGCCAGGCAAAAAAGAAAAAGtaa

38. Sp_del(175-307)-A(EAAAK)3ALEA(EAAAK)3ALEA
(EAAAK)3A("A(EAAAK)3ALEA(EAAAK)3ALEA(EAAAK)3A"
disclosed as SEQ ID NO: 57)
                                              (SEQ ID NO: 69)
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG
```

-continued

```
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGgctGAAGCTGCTGCTAAAGAAGCTGCTGCTAAAGAAGCTG
CTGCTAAAGccCTGGAGgctGAAGCTGCTGCTAAAGAAGCTGCTGCTAAAGAAGCTGC
TGCTAAAGccCTGGAGgctGAAGCTGCTGCTAAAGAAGCTGCTGCTAAAGAAGCTGCT
GCTAAAgctGTGAACACCGAGATCACCAAGGCCCCCCTGAGCGCCTCTATGATCAAG
AGATACGACGAGCACCACCAGGACCTGACCCTGCTGAAAGCTCTCGTGCGGCAGCA
GCTGCCTGAGAAGTACAAAGAGATTTTCTTCGACCAGAGCAAGAACGGCTACGCCG
GCTACATTGACGGCGGAGCCAGCCAGGAAGAGTTCTACAAGTTCATCAAGCCCATC
CTGGAAAAGATGGACGGCACCGAGGAACTGCTCGTGAAGCTGAACAGAGAGGACCT
GCTGCGGAAGCAGCGGACCTTCGACAACGGCAGCATCCCCCACCAGATCCACCTGG
GAGAGCTGCACGCCATTCTGCGGCGGCAGGAAGATTTTTACCCATTCCTGAAGGACA
ACCGGGAAAAGATCGAGAAGATCCTGACCTTCCGCATCCCCTACTACGTGGGCCCTC
TGGCCAGGGGAAACAGCAGATTCGCCTGGATGACCAGAAAGAGCGAGGAAACCAT
CACCCCCTGGAACTTCGAGGAAGTGGTGGACAAGGGCGCTTCCGCCCAGAGCTTCA
TCGAGCGGATGACCAACTTCGATAAGAACCTGCCCAACGAGAAGGTGCTGCCCAAG
CACAGCCTGCTGTACGAGTACTTCACCGTGTATAACGAGCTGACCAAAGTGAAATAC
GTGACCGAGGGAATGAGAAAGCCCGCCTTCCTGAGCGGCGAGCAGAAAAAGGCCA
TCGTGGACCTGCTGTTCAAGACCAACCGGAAAGTGACCGTGAAGCAGCTGAAAGAG
GACTACTTCAAGAAAATCGAGTGCTTCGACTCCGTGGAAATCTCCGGCGTGGAAGAT
CGGTTCAACGCCTCCCTGGGCACATACCACGATCTGCTGAAAATTATCAAGGACAA
GGACTTCCTGGACAATGAGGAAAACGAGGACATTCTGGAAGATATCGTGCTGACCC
TGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGG
CAGGCTGAGCCGGAAGCTGATCAACGGCATCCGGGACAAGCAGTCCGGCAAGACA
ATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCA
GGGCGATAGCCTGCACGAGCACATTGCCAATCTGGCCGGCAGCCCCGCCATTAAGA
AGGGCATCCTGCAGACAGTGAAGGTGGTGGACGAGCTCGTGAAAGTGATGGGCCGG
CACAAGCCCGAGAACATCGTGATCGAAATGGCCAGAGAGAACCAGACCACCCAGA
AGGGACAGAAGAACAGCCGCGAGAATGAAGCGGATCGAAGAGGGCATCAAAGA
GCTGGGCAGCCAGATCCTGAAAGAACACCCCGTGGAAAACACCCAGCTGCAGAACG
AGAAGCTGTACCTGTACTACCTGCAGAATGGGCGGGATATGTACGTGGACCAGGAA
CTGGACATCAACCGGCTGTCCGACTACGATGTGGACCATATCGTGCCTCAGAGCTTT
CTGAAGGACGACTCCATCGACAACAAGGTGCTGACCAGAAGCGACAAGAACCGGG
GCAAGAGCGACAACGTGCCCTCCGAAGAGGTCGTGAAGAAGATGAAGAACTACTGG
```

-continued

```
CGGCAGCTGCTGAACGCCAAGCTGATTACCCAGAGAAAGTTCGACAATCTGACCAA

GGCCGAGAGAGGCGGCCTGAGCGAACTGGATAAGGCCGGCTTCATCAAGAGACAG

CTGGTGGAAACCCGGCAGATCACAAAGCACGTGGCACAGATCCTGGACTCCCGGAT

GAACACTAAGTACGACGAGAATGACAAGCTGATCCGGGAAGTGAAAGTGATCACCC

TGAAGTCCAAGCTGGTGTCCGATTTCCGGAAGGATTTCCAGTTTTACAAAGTGCGCG

AGATCAACAACTACCACCACGCCCACGACGCCTACCTGAACGCCGTCGTGGGAACC

GCCCTGATCAAAAAGTACCCTAAGCTGGAAAGCGAGTTCGTGTACGGCGACTACAA

GGTGTACGACGTGCGGAAGATGATCGCCAAGAGCGAGCAGGAAATCGGCAAGGCT

ACCGCCAAGTACTTCTTCTACAGCAACATCATGAACTTTTTCAAGACCGAGATTACC

CTGGCCAACGGCGAGATCCGGAAGCGGCCTCTGATCGAGACAAACGGCGAAACCGG

GGAGATCGTGTGGGATAAGGGCCGGGATTTTGCCACCGTGCGGAAAGTGCTGAGCA

TGCCCCAAGTGAATATCGTGAAAAAGACCGAGGTGCAGACAGGCGGCTTCAGCAAA

GAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGT

GGTGGCCAAAGTGGAAAAGGGCAAGTCCAAGAAACTGAAGAGTGTGAAAGAGCTG

CTGGGGATCACCATCATGGAAAGAAGCAGCTTCGAGAAGAATCCCATCGACTTTCT

GGAAGCCAAGGGCTACAAAGAAGTGAAAAAGGACCTGATCATCAAGCTGCCTAAGT

ACTCCCTGTTCGAGCTGGAAAACGGCCGGAAGAGAATGCTGGCCTCTGCCGGCGAA

CTGCAGAAGGGAAACGAACTGGCCCTGCCCTCCAAATATGTGAACTTCCTGTACCTG

GCCAGCCACTATGAGAAGCTGAAGGGCTCCCCCGAGGATAATGAGCAGAAACAGCT

GTTTGTGGAACAGCACAAGCACTACCTGGACGAGATCATCGAGCAGATCAGCGAGT

TCTCCAAGAGAGTGATCCTGGCCGACGCTAATCTGGACAAAGTGCTGTCCGCCTACA

ACAAGCACCGGGATAAGCCCATCAGAGAGCAGGCCGAGAATATCATCCACCTGTTT

ACCCTGACCAATCTGGGAGCCCCTGCCGCCTTCAAGTACTTTGACACCACCATCGAC

CGGAAGAGGTACACCAGCACCAAAGAGGTGCTGGACGCCACCCTGATCCACCAGAG

CATCACCGGCCTGTACGAGACACGGATCGACCTGTCTCAGCTGGGAGGCGACAAAA

GGCCGGCGGCCACGAAAAAGGCCGGCCAGGCAAAAAAGAAAAAGtaa
```

39. Sp_del(175-307)-A(EAAAK)3LE(EAAAK)3LE(EAAAK)
3LE(EAAAK)3A ("A(EAAAK)3LE(EAAAK)3LE(EAAAK)3LE
(EAAAK)3A" disclosed as SEQ ID NO: 59)

(SEQ ID NO: 70)
```
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGCTGGGCC

GTGATCACCGACGAGTACAAGGTGCCCAGCAAGAAATTCAAGGTGCTGGGCAACAC

CGACCGGCACAGCATCAAGAAGAACCTGATCGGAGCCCTGCTGTTCGACAGCGGCG

AAACAGCCGAGGCCACCCGGCTGAAGAGAACCGCCAGAAGAAGATACACCAGACG

GAAGAACCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGATAAGAAG

CACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCC

TGATCGAGGGCGACCTGgctGAAGCTGCTGCTAAAGAAGCTGCTGCTAAAGAAGCTG

CTGCTAAAGccCTGGAGgctGAAGCTGCTGCTAAAGAAGCTGCTGCTAAAGAAGCTGC
```

-continued

```
TGCTAAAGccCGGAGgctGAAGCTGCTGCTAAAGAAGCTGCTGCTAAAGAAGCTGCT
GCTAAAGccCTGGAGgctGAAGCTGCTGCTAAAGAAGCTGCTGCTAAAGAAGCTGCTG
CTAAAgctGTGAACACCGAGATCACCAAGGCCCCCCTGAGCGCCTCTATGATCAAGA
GATACGACGAGCACCACCAGGACCTGACCCTGCTGAAAGCTCTCGTGCGGCAGCAG
CTGCCTGAGAAGTACAAAGAGATTTTCTTCGACCAGAGCAAGAACGGCTACGCCGG
CTACATTGACGGCGGAGCCAGCCAGGAAGAGTTCTACAAGTTCATCAAGCCCATCC
TGGAAAAGATGGACGGCACCGAGGAACTGCTCGTGAAGCTGAACAGAGAGGACCT
GCTGCGGAAGCAGCGGACCTTCGACAACGGCAGCATCCCCCACCAGATCCACCTGG
GAGAGCTGCACGCCATTCTGCGGCGGCAGGAAGATTTTTACCCATTCCTGAAGGACA
ACCGGGAAAAGATCGAGAAGATCCTGACCTTCCGCATCCCCTACTACGTGGGCCCTC
TGGCCAGGGGAAACAGCAGATTCGCCTGGATGACCAGAAAGAGCGAGGAAACCAT
CACCCCCTGGAACTTCGAGGAAGTGGTGGACAAGGGCGCTTCCGCCCAGAGCTTCA
TCGAGCGGATGACCAACTTCGATAAGAACCTGCCCAACGAGAAGGTGCTGCCCAAG
CACAGCCTGCTGTACGAGTACTTCACCGTGTATAACGAGCTGACCAAAGTGAAATAC
GTGACCGAGGGAATGAGAAAGCCCGCCTTCCTGAGCGGCGAGCAGAAAAAGGCCA
TCGTGGACCTGCTGTTCAAGACCAACCGGAAAGTGACCGTGAAGCAGCTGAAAGAG
GACTACTTCAAGAAAATCGAGTGCTTCGACTCCGTGGAAATCTCCGGCGTGGAAGAT
CGGTTCAACGCCTCCCTGGGCACATACCACGATCTGCTGAAAATTATCAAGGACAA
GGACTTCCTGGACAATGAGGAAAACGAGGACATTCTGGAAGATATCGTGCTGACCC
TGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGG
CAGGCTGAGCCGGAAGCTGATCAACGGCATCCGGGACAAGCAGTCCGGCAAGACA
ATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCA
GGGCGATAGCCTGCACGAGCACATTGCCAATCTGGCCGGCAGCCCCGCCATTAAGA
AGGGCATCCTGCAGACAGTGAAGGTGGTGGACGAGCTCGTGAAAGTGATGGGCCGG
CACAAGCCCGAGAACATCGTGATCGAAATGGCCAGAGAGAACCAGACCACCCAGA
AGGGACAGAAGAACAGCCGCGAGAGAATGAAGCGGATCGAAGAGGGCATCAAAGA
GCTGGGCAGCCAGATCCTGAAAGAACACCCCGTGGAAAACACCCAGCTGCAGAACG
AGAAGCTGTACCTGTACTACCTGCAGAATGGGCGGGATATGTACGTGGACCAGGAA
CTGGACATCAACCGGCTGTCCGACTACGATGTGGACCATATCGTGCCTCAGAGCTTT
CTGAAGGACGACTCCATCGACAACAAGGTGCTGACCAGAAGCGACAAGAACCGGG
GCAAGAGCGACAACGTGCCCTCCGAAGAGGTCGTGAAGAAGATGAAGAACTACTGG
CGGCAGCTGCTGAACGCCAAGCTGATTACCCAGAGAAAGTTCGACAATCTGACCAA
GGCCGAGAGAGGCGGCCTGAGCGAACTGGATAAGGCCGGCTTCATCAAGAGACAG
CTGGTGGAAACCCGGCAGATCACAAAGCACGTGGCACAGATCCTGGACTCCCGGAT
GAACACTAAGTACGACGAGAATGACAAGCTGATCCGGGAAGTGAAAGTGATCACCC
TGAAGTCCAAGCTGGTGTCCGATTTCCGGAAGGATTTCCAGTTTTACAAAGTGCGCG
AGATCAACAACTACCACCACGCCCACGACGCCTACCTGAACGCCGTCGTGGGAACC
GCCCTGATCAAAAAGTACCCTAAGCTGGAAAGCGAGTTCGTGTACGGCGACTACAA
```

-continued
```
GGTGTACGACGTGCGGAAGATGATCGCCAAGAGCGAGCAGGAAATCGGCAAGGCT

ACCGCCAAGTACTTCTTCTACAGCAACATCATGAACTTTTTCAAGACCGAGATTACC

CTGGCCAACGGCGAGATCCGGAAGCGGCCTCTGATCGAGACAAACGGCGAAACCGG

GGAGATCGTGTGGGATAAGGGCCGGGATTTTGCCACCGTGCGGAAAGTGCTGAGCA

TGCCCCAAGTGAATATCGTGAAAAAGACCGAGGTGCAGACAGGCGGCTTCAGCAAA

GAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGT

GGTGGCCAAAGTGGAAAAGGGCAAGTCCAAGAAACTGAAGAGTGTGAAAGAGCTG

CTGGGGATCACCATCATGGAAAGAAGCAGCTTCGAGAAGAATCCCATCGACTTTCT

GGAAGCCAAGGGCTACAAAGAAGTGAAAAAGGACCTGATCATCAAGCTGCCTAAGT

ACTCCCTGTTCGAGCTGGAAAACGGCCGGAAGAGAATGCTGGCCTCTGCCGGCGAA

CTGCAGAAGGGAAACGAACTGGCCCTGCCCTCCAAATATGTGAACTTCCTGTACCTG

GCCAGCCACTATGAGAAGCTGAAGGGCTCCCCCGAGGATAATGAGCAGAAACAGCT

GTTTGTGGAACAGCACAAGCACTACCTGGACGAGATCATCGAGCAGATCAGCGAGT

TCTCCAAGAGAGTGATCCTGGCCGACGCTAATCTGGACAAAGTGCTGTCCGCCTACA

ACAAGCACCGGGATAAGCCCATCAGAGAGCAGGCCGAGAATATCATCCACCTGTTT

ACCCTGACCAATCTGGGAGCCCCTGCCGCCTTCAAGTACTTTGACACCACCATCGAC

CGGAAGAGGTACACCAGCACCAAAGAGGTGCTGGACGCCACCCTGATCCACCAGAG

CATCACCGGCCTGTACGAGACACGGATCGACCTGTCTCAGCTGGGAGGCGACAAAA

GGCCGGCGGCCACGAAAAAGGCCGGCCAGGCAAAAAAGAAAAAGtaa
```

Example 3

New Nickases

Figure 2A:
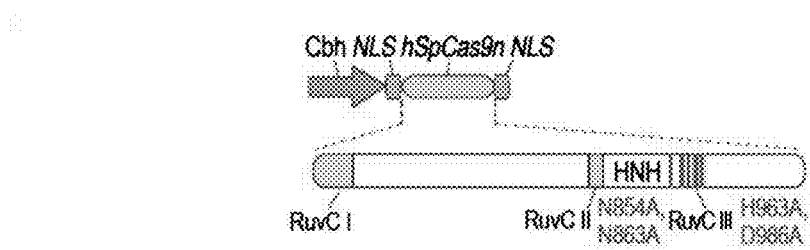
FIGS. 2A-C show, from the crystal structure, a schematic of showing catalytic domains of SpCas9, sites of mutagenesis for new nickases (A), a schematic showing locations of sgRNAs for testing double nicking (B), and results of a Surveyor gel test results showing 1 HNH mutant N854A that retains nickase activity, and 1 HNH mutant that shows nickase activity (N863A), and 2 RuvCIII mutants that show nickase activity (H983A, D986A) (C).
Figure 2B:
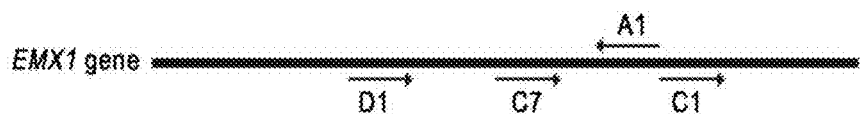
Figure 2C:
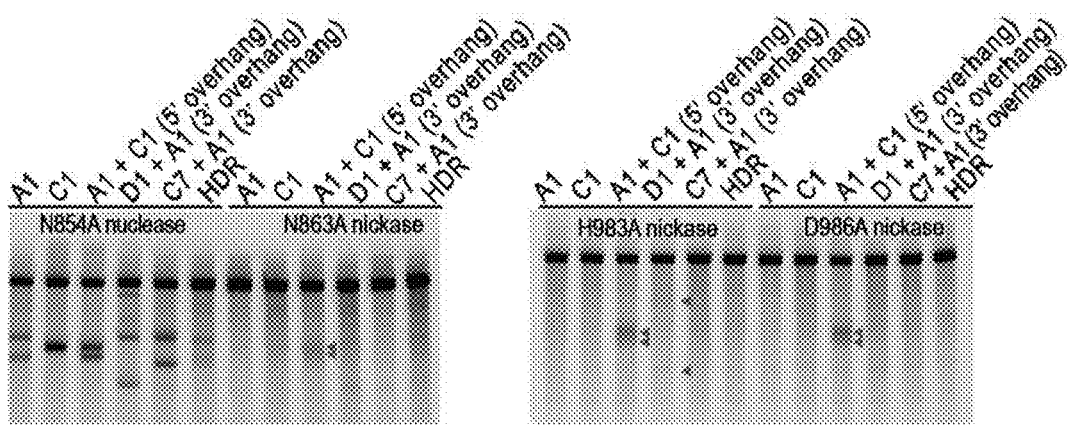
Figure 6:
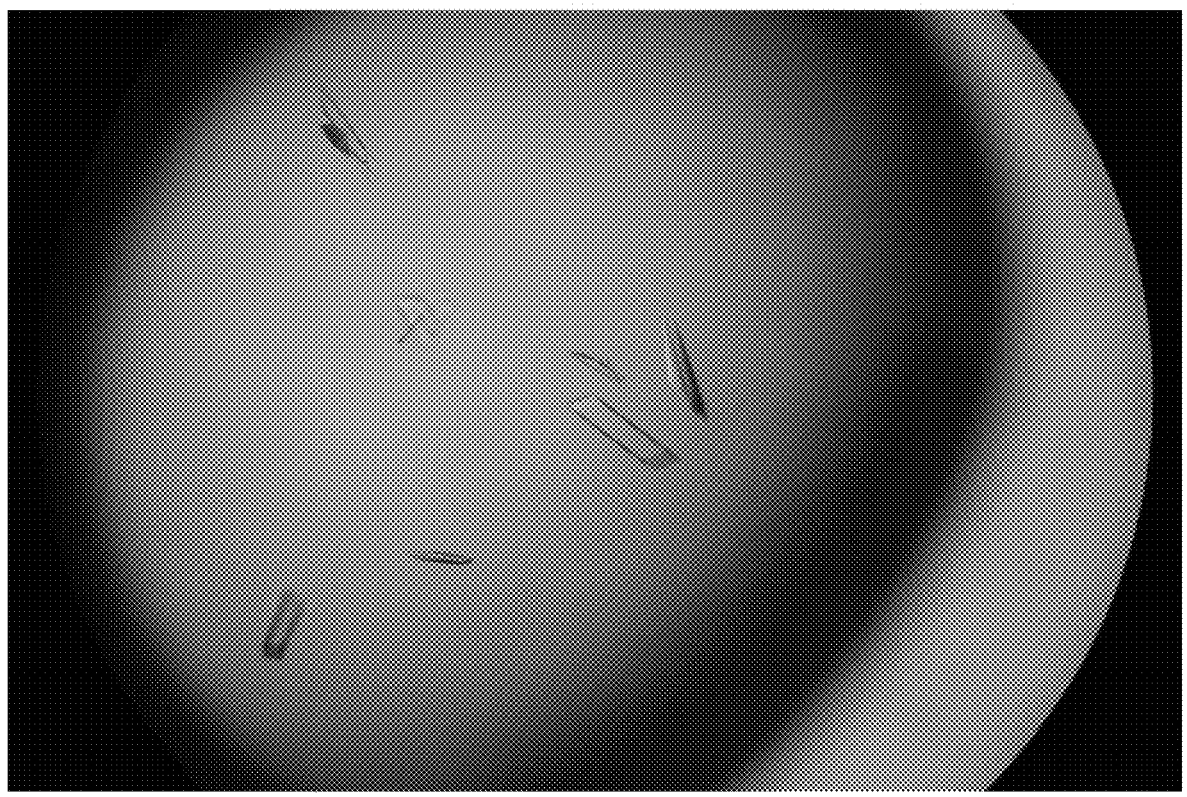
FIG. 6 shows a picture of Cas9 crystals (0.2 mm).
Figure 7:
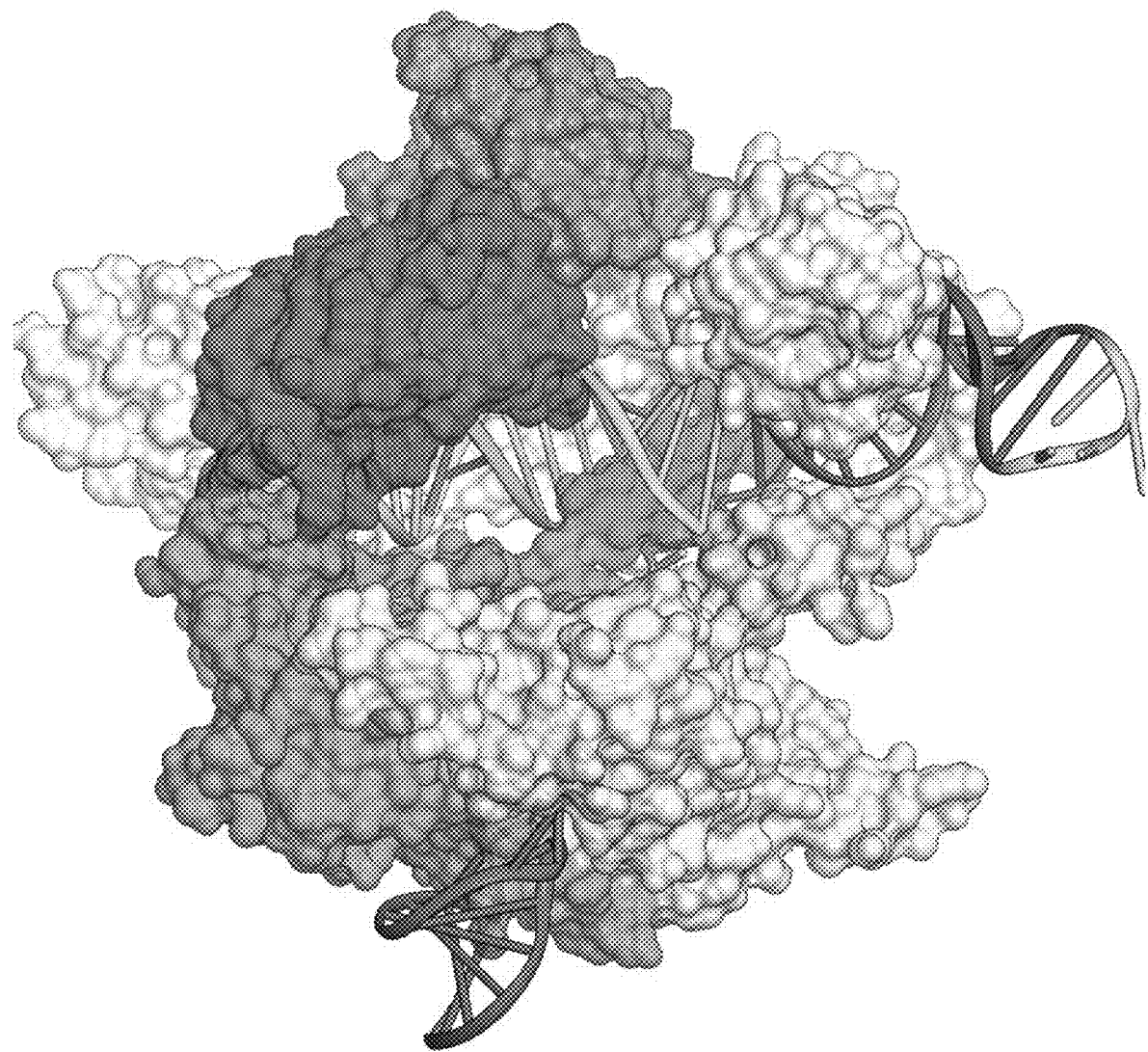
FIG. 7 shows a structural figure of showing Cas9 in a surface representation; red, sgRNA; cyan, the guide region of sgRNA; gold, target DNA.

FIGS. 2A-C pertain to new SpCas9 nickases and provide A. Schematic showing catalytic domains of SpCas9, and sites of mutagenesis for putative new nickases. RuvC domains I, II, and III are shown in orange, HNH domain in white between RuvCII and RuvCIII. Domain sizes not drawn to scale. B. Schematic showing locations of sgRNAs used for testing double nicking: when sgRNAs are transfected singly (A1 or C1 alone) with SpCas9 nickases, no indels should result. The combination of A1+C1, used in combination with RuvCIII mutation nickases result in 5'-overhang, where as D1+A1 and C7+A1 would result in 3'-overhangs. Conversely, those three combinations used with HNH mutation nickases would result in 3'-, 5'-, and 5'-overhangs, respectively. C. Surveyor test showing 1 HNH mutant that retains nuclease activity (N854A), and 1 HNH mutant that shows nickase activity (N863A), as well as 2 RuvCIII mutants that show nickase activity (H983A, D986A).

In this Example, five potential nicking mutation sites were chosen based on sequence homology between Cas9 orthologs. And three additional sites were chosen based on herein crystallography data. A subset of these sets of nickase mutant Cas9s were re-cloned to incorporate both N' and C'-NLS sequences that are identical to those of optimized SpCas9. Sequences are below.

Nickase mutants were re-cloned to incorporated designated mutations into pAAV-vector under Cbh promoter and sequence validated.

Nuclease and double-nicking activities for all potential nickases were tested in HEK 293FT cells as follows: co-transfection of 400 ng of nickase and 100 ng of U6-driven sgRNA (100 ng for one guide, or 50 ng each for a pair of sgRNAs) by Lipofectamine 2000 into 200,000 cells. DNAs from transfected cells were collected for SURVEYOR analysis. Nickases do not result in indel mutations when co-transfected with a single sgRNA, but do when co-transfected with a pair of appropriately off-set sgRNAs. Based on data from the original D10A SpCas9 nickase, the pair of sgRNA chosen (A1/C1) for RuvC domain mutants have 0-bp offset and 5'-overhang for maximal cleavage.

|  | Mutant domain | Functional? |
|---|---|---|
| Homology set: | | |
| Cbh-hSpCas9(D10A)-NLS | RuvCI | nickase activity |
| Cbh-hSpCas9(E762A)-NLS | RuvCII | |
| Cbh-hSpCas9(H840A)-NLS | HNH | no activity |

| | | |
|---|---|---|
| Cbh-hSpCas9(N854A)-NLS | HNH | wt nuclease activity |
| Cbh-hSpCas9(N863A)-NLS | HNH | nickase activity |
| Cbh-hSpCas9(D986A)-NLS | RuvCIII | |
| Crystal set set: | | |
| NLS-S15A-NLS | RuvCI | wt nuclease activity |
| NLS-E762A-NLS | RuvCII | catalytically dead |
| NLS-H982A-NLS | RuvCIII | wt nuclease activity |
| NLS-H983A-NLS | RuvCIII | nickase activity |
| NLS-D986A-NLS | RuvCIII | nickase activity |

>NLS-S15A-NLS

```
ATGGCCCCAAAGAAGAAGCGGAAGGTCGGTATCCACGGAGTCCCAGCAG
CCGACAAGAAGTACAGCATCGGCCTGGACATCGGCACCAACgccGTGGGCTGGGCCG
TGATCACCGACGAGTACAAGGTGCCCAGCAAGAAATTCAAGGTGCTGGGCAACACC
GACCGGCACAGCATCAAGAAGAACCTGATCGGAGCCCTGCTGTTCGACAGCGGCGA
AACAGCCGAGGCCACCCGGCTGAAGAGAACCGCCAGAAGAAGATACACCAGACGG
AAGAACCGGATCTGCTATCTGCAAGAGATCTTCAGCAACGAGATGGCCAAGGTGGA
CGACAGCTTCTTCCACAGACTGGAAGAGTCCTTCCTGGTGGAAGAGGATAAGAAGC
ACGAGCGGCACCCCATCTTCGGCAACATCGTGGACGAGGTGGCCTACCACGAGAAG
TACCCCACCATCTACCACCTGAGAAAGAAACTGGTGGACAGCACCGACAAGGCCGA
CCTGCGGCTGATCTATCTGGCCCTGGCCCACATGATCAAGTTCCGGGGCCACTTCCT
GATCGAGGGCGACCTGAACCCCGACAACAGCGACGTGGACAAGCTGTTCATCCAGC
TGGTGCAGACCTACAACCAGCTGTTCGAGGAAAACCCCATCAACGCCAGCGGCGTG
GACGCCAAGGCCATCCTGTCTGCCAGACTGAGCAAGAGCAGACGGCTGGAAAATCT
GATCGCCCAGCTGCCCGGCGAGAAGAAGAATGGCCTGTTCGGAAACCTGATTGCCC
TGAGCCTGGGCCTGACCCCAACTTCAAGAGCAACTTCGACCTGGCCGAGGATGCC
AAACTGCAGCTGAGCAAGGACACCTACGACGACGACCTGGACAACCTGCTGGCCCA
GATCGGCGACCAGTACGCCGACCTGTTTCTGGCCGCCAAGAACCTGTCCGACGCCAT
CCTGCTGAGCGACATCCTGAGAGTGAACACCGAGATCACCAAGGCCCCCCTGAGCG
CCTCTATGATCAAGAGATACGACGAGCACCACCAGGACCTGACCCTGCTGAAAGCT
CTCGTGCGGCAGCAGCTGCCTGAGAAGTACAAAGAGATTTTCTTCGACCAGAGCAA
GAACGGCTACGCCGGCTACATTGACGGCGGAGCCAGCCAGGAAGAGTTCTACAAGT
TCATCAAGCCCATCCTGGAAAAGATGGACGGCACCGAGGAACTGCTCGTGAAGCTG
AACAGAGAGGACCTGCTGCGGAAGCAGCGGACCTTCGACAACGGCAGCATCCCCCA
CCAGATCCACCTGGGAGAGCTGCACGCCATTCTGCGGCGGCAGGAAGATTTTTACC
ATTCCTGAAGGACAACCGGGAAAAGATCGAGAAGATCCTGACCTTCCGCATCCCCT
ACTACGTGGGCCCTCTGGCCAGGGGAAACAGCAGATTCGCCTGGATGACCAGAAAG
AGCGAGGAAACCATCACCCCCTGGAACTTCGAGGAAGTGGTGGACAAGGGCGCTTC
CGCCCAGAGCTTCATCGAGCGGATGACCAACTTCGATAAGAACCTGCCCAACGAGA
AGGTGCTGCCCAAGCACAGCCTGCTGTACGAGTACTTCACCGTGTATAACGAGCTGA
CCAAAGTGAAATACGTGACCGAGGGAATGAGAAAGCCCGCCTTCCTGAGCGGCGAG
CAGAAAAAGGCCATCGTGGACCTGCTGTTCAAGACCAACCGGAAAGTGACCGTGAA
GCAGCTGAAAGAGGACTACTTCAAGAAAATCGAGTGCTTCGACTCCGTGGAAATCT
CCGGCGTGGAAGATCGGTTCAACGCCTCCCTGGGCACATACCACGATCTGCTGAAA
ATTATCAAGGACAAGGACTTCCTGGACAATGAGGAAAACGAGGACATTCTGGAAGA
TATCGTGCTGACCCTGACACTGTTTGAGGACAGAGAGATGATCGAGGAACGGCTGA
AAACCTATGCCCACCTGTTCGACGACAAAGTGATGAAGCAGCTGAAGCGGCGGAGA
TACACCGGCTGGGGCAGGCTGAGCCGGAAGCTGATCAACGGCATCCGGGACAAGCA
GTCCGGCAAGACAATCCTGGATTTCCTGAAGTCCGACGGCTTCGCCAACAGAAACTT
CATGCAGCTGATCCACGACGACAGCCTGACCTTTAAAGAGGACATCCAGAAAGCCC
AGGTGTCCGGCCAGGGCGATAGCCTGCACGAGCACATTGCCAATCTGGCCGGCAGC
CCCGCCATTAAGAAGGGCATCCTGCAGACAGTGAAGGTGGTGGACGAGCTCGTGAA
AGTGATGGGCCGGCACAAGCCCGAGAACATCGTGATCGAAATGGCCAGAGAGAAC
CAGACCACCCAGAAGGGACAGAAGAACAGCCGCGAGAGAATGAAGCGGATCGAAG
AGGGCATCAAAGAGCTGGGCAGCCAGATCCTGAAAGAACACCCCGTGGAAAACAC
CCAGCTGCAGAACGAGAAGCTGTACCTGTACTACCTGCAGAATGGGCGGGATATGT
ACGTGGACCAGGAACTGGACATCAACCGGCTGTCCGACTACGATGTGGACCATATC
GTGCCTCAGAGCTTTCTGAAGGACGACTCCATCGACAACAAGGTGCTGACCAGAAG
CGACAAGAACCGGGGCAAGAGCGACAACGTGCCCTCCGAAGAGGTCGTGAAGAAG
ATGAAGAACTACTGGCGGCAGCTGCTGAACGCCAAGCTGATTACCCAGAGAAAGTT
CGACAATCTGACCAAGGCCGAGAGAGGCGGCCTGAGCGAACTGGATAAGGCCGGCT
TCATCAAGAGACAGCTGGTGGAAACCCGGCAGATCACAAAGCACGTGGCACAGATC
CTGGACTCCCGGATGAACACTAAGTACGACGAGAATGACAAGCTGATCCGGGAAGT
GAAAGTGATCACCCTGAAGTCCAAGCTGGTGTCCGATTTCCGGAAGGATTTCCAGTT
TTACAAAGTGCGCGAGATCAACAACTACCACCACGCCCACGACGCCTACCTGAACG
CCGTCGTGGGAACCGCCCTGATCAAAAAGTACCCTAAGCTGGAAAGCGAGTTCGTG
TACGGCGACTACAAGGTGTACGACGTGCGGAAGATGATCGCCAAGAGCGAGCAGGA
AATCGGCAAGGCTACCGCCAAGTACTTCTTCTACAGCAACATCATGAACTTTTTCAA
GACCGAGATTACCCTGGCCAACGGCGAGATCCGGAAGCGGCCTCTGATCGAGACAA
```

-continued

```
ACGGCGAAACCGGGGAGATCGTGTGGGATAAGGGCCGGGATTTTGCCACCGTGCGG
AAAGTGCTGAGCATGCCCCAAGTGAATATCGTGAAAAAGACCGAGGTGCAGACAGG
CGGCTTCAGCAAAGAGTCTATCCTGCCCAAGAGGAACAGCGATAAGCTGATCGCCA
GAAAGAAGGACTGGGACCCTAAGAAGTACGGCGGCTTCGACAGCCCCACCGTGGCC
TATTCTGTGCTGGTGGTGGCCAAAGTGGAAAAGGGCAAGTCCAAGAAACTGAAGAG
TGTGAAAGAGCTGCTGGGGATCACCATCATGGAAAGAAGCAGCTTCGAGAAGAATC
CCATCGACTTTCTGGAAGCCAAGGGCTACAAAGAAGTGAAAAAGGACCTGATCATC
AAGCTGCCTAAGTACTCCCTGTTCGAGCTGGAAAACGGCCGGAAGAGAATGCTGGC
CTCTGCCGGCGAACTGCAGAAGGGAAACGAACTGGCCCTGCCCTCCAAATATGTGA
ACTTCCTGTACCTGGCCAGCCACTATGAGAAGCTGAAGGGCTCCCCCGAGGATAAT
GAGCAGAAACAGCTGTTTGTGGAACAGCACAAGCACTACCTGGACGAGATCATCGA
GCAGATCAGCGAGTTCTCCAAGAGAGTGATCCTGGCCGACGCTAATCTGGACAAAG
TGCTGTCCGCCTACAACAAGCACCGGGATAAGCCCATCAGAGAGCAGGCCGAGAAT
ATCATCCACCTGTTTACCCTGACCAATCTGGGAGCCCCTGCCGCCTTCAAGTACTTTG
ACACCACCATCGACCGGAAGAGGTACACCAGCACCAAAGAGGTGCTGGACGCCACC
CTGATCCACCAGAGCATCACCGGCCTGTACGAGACACGGATCGACCTGTCTCAGCTG
GGAGGCGACAAAAGGCCGGCGGCCACGAAAAAGGCCGGCCAGGCAAAAAGAAA
AAGtaa (SEQ ID NO: 71)
```

>NLS-E762A-NLS

```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGAACCCCGACAACAGCGACGTGGACAAGCTGTTCATCCAG
CTGGTGCAGACCTACAACCAGCTGTTCGAGGAAAACCCCATCAACGCCAGCGGCGT
GGACGCCAAGGCCATCCTGTCTGCCGACACTGAGCAAGAGCAGACGGCTGGAAAATC
TGATCGCCCAGCTGCCCGGCGAGAAGAAGAATGGCCTGTTCGGAAACCTGATTGCC
CTGAGCCTGGGCCTGACCCCCAACTTCAAGAGCAACTTCGACCTGGCCGAGGATGC
CAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCC
ATCCTGCTGAGCGACATCCTGAGAGTGAACACCGAGATCACCAAGGCCCCCCTGAG
CGCCTCTATGATCAAGAGATACGACGAGCACCACCAGGACCTGACCCTGCTGAAAG
CTCTCGTGCGGCAGCAGCTGCCTGAGAAGTACAAAGAGATTTTCTTCGACCAGAGCA
AGAACGGCTACGCCGGCTACATTGACGGCGGAGCCAGCCAGGAAGAGTTCTACAAG
TTCATCAAGCCCATCCTGGAAAAGATGGACGGCACCGAGGAACTGCTCGTGAAGCT
GAACAGAGAGGACCTGCTGCGCAAGCAGCGGACCTTCGACAACGGCAGCATCCCCC
ACCAGATCCACCTGGGAGAGCTGCACGCCATTCTGCGGCGGCAGGAAGATTTTTAC
CCATTCCTGAAGGACAACCGGGAAAAGATCGAGAAGATCCTGACCTTCCGCATCCC
CTACTACGTGGGCCCTCTGGCCAGGGGAAACAGCAGATTCGCCTGGATGACCAGAA
AGAGCGAGGAAACCATCACCCCCTGGAACTTCGAGGAAGTGGTGGACAAGGGCGCT
TCCGCCCAGAGCTTCATCGAGCGGATGACCAACTTCGATAAGAACCTGCCCAACGA
GAAGGTGCTGCCCAAGCACAGCCTGCTGTACGAGTACTTCACCGTGTATAACGAGCT
GACCAAAGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTGACCGTG
AAGCAGCTGAAAGAGGACTACTTCAAGAAAATCGAGTGCTTCGACTCCGTGGAAAT
CTCCGGCGTGGAAGATCGGTTCAACGCCTCCCTGGGCACATACCACGATCTGCTGAA
AATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGCGGAG
ATACACCGGCTGGGCAGGCTGAGCCGGAAGCTGATCAACGGCATCCGGGACAAGC
AGTCCGGCAAGACAATCCTGGATTTCCTGAAGTCCGACGGCTTCGCCAACAGAAAC
TTCATGCAGCTGATCCACGACGACAGCCTGACCTTTAAAGAGGACATCCAGAAAGC
CCAGGTGTCCGGCCAGGGCGATAGCCTGCACGAGCACATTGCCAATCTGGCCGGCA
GCCCCGCCATTAAGAAGGGCATCCTGCAGACAGTGAAGGTGGTGGACGAGCTCGTG
AAAGTGATGGGCCGGCACAAGCCCGAGAACATCGTGATCGccATGGCCAGAGAGAA
CCAGACCACCCAGAAGGGACAGAAGAACAGCCGCGAGAGAATGAAGCGGATCGAA
GAGGGCATCAAAGAGCTGGGCAGCCAGATCCTGAAAGAACACCCCGTGGAAAACA
CCCAGCTGCAGAACGAGAAGCTGTACCTGTACTACCTGCAGAATGGGCGGGATATG
TACGTGGACCAGGAACTGGACATCAACCGGCTGTCCGACTACGATGTGGACCATAT
CGTGCCTCAGAGCTTTCTGAAGGACGACTCCATCGACAACAAGGTGCTGACCAGAA
GCGACAAGAACCGGGGCAAGAGCGACAACGTGCCCTCCGAAGAGGTCGTGAAGAA
GATGAAGAACTACTGGCGGCAGCTGCTGAACGCCAAGCTGATTACCCAGAGAAAGT
TCGACAATCTGACCAAGGCCGAGAGAGGCGGCCTGAGCGAACTGGATAAGGCCGGC
TTCATCAAGAGACAGCTGGTGGAAACCCGGCAGATCACAAAGCACGTGGCACAGAT
CCTGGACTCCCGGATGAACACTAAGTACGACGAGAATGACAAGCTGATCCGGGAAG
TGAAAGTGATCACCCTGAAGTCCAAGCTGGTGTCCGATTTCCGGAAGGATTTCCAGT
TTTACAAAGTGCGCGAGATCAACAACTACCACCACGCCCACGACGCCTACCTGAAC
GCCGTCGTGGGAACCGCCCTGATCAAAAAGTACCCTAAGCTGGAAAGCGAGTTCGT
GTACGGCGACTACAAGGTGTACGACGTGCGGAAGATGATCGCCAAGAGCGAGCAGG
AAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACA
```

-continued

```
AACGGCGAAACCGGGGAGATCGTGTGGGATAAGGGCCGGGATTTTGCCACCGTGCG
GAAAGTGCTGAGCATGCCCCAAGTGAATATCGTGAAAAAGACCGAGGTGCAGACAG
GCGGCTTCAGCAAAGAGTCTATCCTGCCCAAGAGGAACAGCGATAAGCTGATCGCC
AGAAAGAAGGACTGGGACCCTAAGAAGTACGGCGGCTTCGACAGCCCCACCGTGGC
CTATTCTGTGCTGGTGGTGGCCAAAGTGGAAAAGGGCAAGTCCAAGAAACTGAAGA
GTGTGAAAGAGCTGCTGGGGATCACCATCATGGAAAGAAGCAGCTTCGAGAAGAAT
CCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGG
CCTCTGCCGGCGAACTGCAGAAGGGAAACGAACTGGCCCTGCCCTCCAAATATGTG
AACTTCCTGTACCTGGCCAGCCACTATGAGAAGCTGAAGGGCTCCCCCGAGGATAA
TGAGCAGAAACAGCTGTTTGTGGAACAGCACAAGCACTACCTGGACGAGATCATCG
AGCAGATCAGCGAGTTCTCCAAGAGAGTGATCCTGGCCGACGCTAATCTGGACAAA
GTGCTGTCCGCCTACAACAAGCACCGGGATAAGCCCATCAGAGAGCAGGCCGAGAA
TATCATCCACCTGTTTACCCTGACCAATCTGGGAGCCCCTGCCGCCTTCAAGTACTTT
GACACCACCATCGACCGGAAGAGGTACACCAGCACCAAAGAGGTGCTGGACGCCAC
CCTGATCCACCAGAGCATCACCGGCCTGTACGAGACACGGATCGACCTGTCTCAGCT
GGGAGGCGACAAAAGGCCGGCGGCCACGAAAAAGGCCGGCCAGGCAAAAAAGAA
AAAGtaa (SEQ ID NO: 72)
```

>NLS-H982A-NLS

```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGAACCCCGACAACAGCGACGTGGACAAGCTGTTCATCCAG
CTGGTGCAGACCTACAACCAGCTGTTCGAGGAAAACCCCATCAACGCCAGCGGCGT
GGACGCCAAGGCCATCCTGTCTGCCGACATGAGCAAGAGCAGACGGCTGGAAAATC
TGATCGCCCAGCTGCCCGGCGAGAAGAAGAATGGCCTGTTCGGAAACCTGATTGCC
CTGAGCCTGGGCCTGACCCCCAACTTCAAGAGCAACTTCGACCTGGCCGAGGATGC
CAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCC
ATCCTGCTGAGCGACATCCTGAGAGTGAACACCGAGATCACCAAGGCCCCCCTGAG
CGCCTCTATGATCAAGAGATACGACGAGCACCACCAGGACCTGACCCTGCTGAAAG
CTCTCGTGCGGCAGCAGCTGCCTGAGAAGTACAAAGAGATTTTCTTCGACCAGAGCA
AGAACGGCTACGCCGGCTACATTGACGGCGGAGCCAGCCAGGAAGAGTTCTACAAG
TTCATCAAGCCCATCCTGGAAAAGATGGACGGCACCGAGGAACTGCTCGTGAAGCT
GAACAGAGAGGACCTGCTGCGGAAGCAGCGGACCTTCGACAACGGCAGCATCCCCC
ACCAGATCCACCTGGGAGAGCTGCACGCCATTCTGCGGCGGCAGGAAGATTTTTAC
CCATTCCTGAAGGACAACCGGGAAAAGATCGAGAAGATCCTGACCTTCCGCATCCC
CTACTACGTGGGCCCTCTGGCCAGGGGAAACAGCAGATTCGCCTGGATGACCAGAA
AGAGCGAGGAAACCATCACCCCCTGGAACTTCGAGGAAGTGGTGGACAAGGGCGCT
TCCGCCCAGAGCTTCATCGAGCGGATGACCAACTTCGATAAGAACCTGCCCAACGA
GAAGGTGCTGCCCAAGCACAGCCTGCTGTACGAGTACTTCACCGTGTATAACGAGCT
GACCAAAGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTGACCGTG
AAGCAGCTGAAAGAGGACTACTTCAAGAAAATCGAGTGCTTCGACTCCGTGGAAAT
CTCCGGCGTGGAAGATCGGTTCAACGCCTCCCTGGGCACATACCACGATCTGCTGAA
AATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGGCGGAG
ATACACCGGCTGGGGCAGGCTGAGCCGGAAGCTGATCAACGGCATCCGGGACAAGC
AGTCCGGCAAGACAATCCTGGATTTCCTGAAGTCCGACGGCTTCGCCAACAGAAAC
TTCATGCAGCTGATCCACGACGACAGCCTGACCTTTAAAGAGGACATCCAGAAAGC
CCAGGTGTCCGGCCAGGGCGATAGCCTGCACGAGCACATTGCCAATCTGGCCGGCA
GCCCCGCCATTAAGAAGGGCATCCTGCAGACAGTGAAGGTGGTGGACGAGCTCGTG
AAAGTGATGGGCCGGCACAAGCCCGAGAACATCGTGATCGAAATGGCCAGAGAGA
ACCAGACCACCCAGAAGGGACAGAAGAACAGCCGCGAGAGAATGAAGCGGATCGA
AGAGGGCATCAAAGAGCTGGGCAGCCAGATCCTGAAAGAACACCCCGTGGAAAAC
ACCCAGCTGCAGAACGAGAAGCTGTACCTGTACTACCTGCAGAATGGGCGGGATAT
GTACGTGGACCAGGAACTGGACATCAACCGGCTGTCCGACTACGATGTGGACCATA
TCGTGCCTCAGAGCTTTCTGAAGGACGACTCCATCGACAACAAGGTGCTGACCAGA
AGCGACAAGAACCGGGGCAAGAGCGACAACGTGCCCTCCGAAGAGGTCGTGAAGA
AGATGAAGAACTACTGGCGGCAGCTGCTGAACGCCAAGCTGATTACCCAGAGAAAG
TTCGACAATCTGACCAAGGCCGAGAGAGGCGGCCTGAGCGAACTGGATAAGGCCGG
CTTCATCAAGAGACAGCTGGTGGAAACCCGGCAGATCACAAAGCACGTGGCACAGA
TCCTGGACTCCCGGATGAACACTAAGTACGACGAGAATGACAAGCTGATCCGGGAA
GTGAAAGTGATCACCCTGAAGTCCAAGCTGGTGTCCGATTTCCGGAAGGATTTCCAG
TTTTACAAAGTGCGCGAGATCAACAACTACgccCACGCCCACGACGCCTACCTGAAC
GCCGTCGTGGGAACCGCCCTGATCAAAAGTACCCTAAGCTGGAAAGCGAGTTCGT
GTACGGCGACTACAAGGTGTACGACGTGCGGAAGATGATCGCCAAGAGCGAGCAGG
AAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACA
```

-continued

```
AACGGCGAAACCGGGGAGATCGTGTGGGATAAGGGCCGGGATTTTGCCACCGTGCG
GAAAGTGCTGAGCATGCCCCAAGTGAATATCGTGAAAAAGACCGAGGTGCAGACAG
GCGGCTTCAGCAAAGAGTCTATCCTGCCCAAGAGGAACAGCGATAAGCTGATCGCC
AGAAAGAAGGACTGGGACCCTAAGAAGTACGGCGGCTTCGACAGCCCCACCGTGGC
CTATTCTGTGCTGGTGGTGGCCAAAGTGGAAAAGGGCAAGTCCAAGAAACTGAAGA
GTGTGAAAGAGCTGCTGGGGATCACCATCATGGAAAGAAGCAGCTTCGAGAAGAAT
CCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGG
CCTCTGCCGGCGAACTGCAGAAGGGAAACGAACTGGCCCTGCCCTCCAAATATGTG
AACTTCCTGTACCTGGCCAGCCACTATGAGAAGCTGAAGGGCTCCCCCGAGGATAA
TGAGCAGAAACAGCTGTTTGTGGAACAGCACAAGCACTACCTGGACGAGATCATCG
AGCAGATCAGCGAGTTCTCCAAGAGAGTGATCCTGGCCGACGCTAATCTGGACAAA
GTGCTGTCCGCCTACAACAAGCACCGGGATAAGCCCATCAGAGAGCAGGCCGAGAA
TATCATCCACCTGTTTACCCTGACCAATCTGGGAGCCCCTGCCGCCTTCAAGTACTTT
GACACCACCATCGACCGGAAGAGGTACACCAGCACCAAAGAGGTGCTGGACGCCAC
CCTGATCCACCAGAGCATCACCGGCCTGTACGAGACACGGATCGACCTGTCTCAGCT
GGGAGGCGACAAAAGGCCGGCGGCCACGAAAAAGGCCGGCCAGGCAAAAAAGAA
AAAGtaa (SEQ ID NO: 73)
```

>NLS-H983A-NLS

```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGAACCCCGACAACAGCGACGTGGACAAGCTGTTCATCCAG
CTGGTGCAGACCTACAACCAGCTGTTCGAGGAAAACCCCATCAACGCCAGCGGCGT
GGACGCCAAGGCCATCCTGTCTGCCGACATGAGCAAGAGCAGACGGCTGGAAAATC
TGATCGCCCAGCTGCCCGGCGAGAAGAAGAATGGCCTGTTCGGAAACCTGATTGCC
CTGAGCCTGGGCCTGACCCCCAACTTCAAGAGCAACTTCGACCTGGCCGAGGATGC
CAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCC
ATCCTGCTGAGCGACATCCTGAGAGTGAACACCGAGATCACCAAGGCCCCCCTGAG
CGCCTCTATGATCAAGAGATACGACGAGCACCACCAGGACCTGACCCTGCTGAAAG
CTCTCGTGCGGCAGCAGCTGCCTGAGAAGTACAAAGAGATTTTCTTCGACCAGAGCA
AGAACGGCTACGCCGGCTACATTGACGGCGGAGCCAGCCAGGAAGAGTTCTACAAG
TTCATCAAGCCCATCCTGGAAAAGATGGACGGCACCGAGGAACTGCTCGTGAAGCT
GAACAGAGAGGACCTGCTGCGGAAGCAGCGGACCTTCGACAACGGCAGCATCCCCC
ACCAGATCCACCTGGGAGAGCTGCACGCCATTCTGCGGCGGCAGGAAGATTTTTAC
CCATTCCTGAAGGACAACCGGGAAAAGATCGAGAAGATCCTGACCTTCCGCATCCC
CTACTACGTGGGCCCTCTGGCCAGGGGAAACAGCAGATTCGCCTGGATGACCAGAA
AGAGCGAGGAAACCATCACCCCCTGGAACTTCGAGGAAGTGGTGGACAAGGGCGCT
TCCGCCCAGAGCTTCATCGAGCGGATGACCAACTTCGATAAGAACCTGCCCAACGA
GAAGGTGCTGCCCAAGCACAGCCTGCTGTACGAGTACTTCACCGTGTATAACGAGCT
GACCAAAGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTGACCGTG
AAGCAGCTGAAAGAGGACTACTTCAAGAAAATCGAGTGCTTCGACTCCGTGGAAAT
CTCCGGCGTGGAAGATCGGTTCAACGCCTCCCTGGGCACATACCACGATCTGCTGAA
AATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGGCGGAG
ATACACCGGCTGGGGCAGGCTGAGCCGGAAGCTGATCAACGGCATCCGGGACAAGC
AGTCCGGCAAGACAATCCTGGATTTCCTGAAGTCCGACGGCTTCGCCAACAGAAAC
TTCATGCAGCTGATCCACGACGACAGCCTGACCTTTAAAGAGGACATCCAGAAAGC
CCAGGTGTCCGGCCAGGGCGATAGCCTGCACGAGCACATTGCCAATCTGGCCGGCA
GCCCCGCCATTAAGAAGGGCATCCTGCAGACAGTGAAGGTGGTGGACGAGCTCGTG
AAAGTGATGGGCCGGCACAAGCCCGAGAACATCGTGATCGAAATGGCCAGAGAGA
ACCAGACCACCCAGAAGGGACAGAAGAACAGCCGCGAGAGAATGAAGCGGATCGA
AGAGGGCATCAAAGAGCTGGGCAGCCAGATCCTGAAAGAACACCCCGTGGAAAAC
ACCCAGCTGCAGAACGAGAAGCTGTACCTGTACTACCTGCAGAATGGGCGGGATAT
GTACGTGGACCAGGAACTGGACATCAACCGGCTGTCCGACTACGATGTGGACCATA
TCGTGCCTCAGAGCTTTCTGAAGGACGACTCCATCGACAACAAGGTGCTGACCAGA
AGCGACAAGAACCGGGGCAAGAGCGACAACGTGCCCTCCGAAGAGGTCGTGAAGA
AGATGAAGAACTACTGGCGGCAGCTGCTGAACGCCAAGCTGATTACCCAGAGAAAG
TTCGACAATCTGACCAAGGCCGAGAGAGGCGGCCTGAGCGAACTGGATAAGGCCGG
CTTCATCAAGAGACAGCTGGTGGAAACCCGGCAGATCACAAAGCACGTGGCACAGA
TCCTGGACTCCCGGATGAACACTAAGTACGACGAGAATGACAAGCTGATCCGGGAA
GTGAAAGTGATCACCCTGAAGTCCAAGCTGGTGTCCGATTTCCGGAAGGATTTCCAG
TTTTACAAAGTGCGCGAGATCAACAACTACCACgccGCCCACGACGCCTACCTGAAC
GCCGTCGTGGGAACCGCCCTGATCAAAAAGTACCCTAAGCTGGAAAGCGAGTTCGT
GTACGGCGACTACAAGGTGTACGACGTGCGGAAGATGATCGCCAAGAGCGAGCAGG
AAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACA
```

-continued

```
AACGGCGAAACCGGGGAGATCGTGTGGGATAAGGGCCGGGATTTTGCCACCGTGCG
GAAAGTGCTGAGCATGCCCCAAGTGAATATCGTGAAAAAGACCGAGGTGCAGACAG
GCGGCTTCAGCAAAGAGTCTATCCTGCCCAAGAGGAACAGCGATAAGCTGATCGCC
AGAAAGAAGGACTGGGACCCTAAGAAGTACGGCGGCTTCGACAGCCCCACCGTGGC
CTATTCTGTGCTGGTGGTGGCCAAAGTGGAAAAGGGCAAGTCCAAGAAACTGAAGA
GTGTGAAAGAGCTGCTGGGGATCACCATCATGGAAAGAAGCAGCTTCGAGAAGAAT
CCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGG
CCTCTGCCGGCGAACTGCAGAAGGGAAACGAACTGGCCCTGCCCTCCAAATATGTG
AACTTCCTGTACCTGGCCAGCCACTATGAGAAGCTGAAGGGCTCCCCCGAGGATAA
TGAGCAGAAACAGCTGTTTGTGGAACAGCACAAGCACTACCTGGACGAGATCATCG
AGCAGATCAGCGAGTTCTCCAAGAGAGTGATCCTGGCCGACGCTAATCTGGACAAA
GTGCTGTCCGCCTACAACAAGCACCGGGATAAGCCCATCAGAGAGCAGGCCGAGAA
TATCATCCACCTGTTTACCCTGACCAATCTGGGAGCCCCTGCCGCCTTCAAGTACTTT
GACACCACCATCGACCGGAAGAGGTACACCAGCACCAAAGAGGTGCTGGACGCCAC
CCTGATCCACCAGAGCATCACCGGCCTGTACGAGACACGGATCGACCTGTCTCAGCT
GGGAGGCGACAAAAGGCCGGCGGCCACGAAAAAGGCCGGCCAGGCAAAAAAGAA
AAAGtaa (SEQ ID NO: 74)
```

>NLS-D986A-NLS

```
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGCTGGGCC
GTGATCACCGACGAGTACAAGGTGCCCAGCAAGAAATTCAAGGTGCTGGGCAACAC
CGACCGGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCAGACG
GAAGAACCGGATCTGCTATCTGCAAGAGATCTTCAGCAACGAGATGGCCAAGGTGG
ACGACAGCTTCTTCCACAGACTGGAAGAGTCCTTCCTGGTGGAAGAGGATAAGAAG
CACGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGCCG
ACCTGCGGCTGATCTATCTGGCCCTGGCCCACATGATCAAGTTCCGGGGCCACTTCC
TGATCGAGGGCGACCTGAACCCCGACAACAGCGACGTGGACAAGCTGTTCATCCAG
CTGGTGCAGACCTACAACCAGCTGTTCGAGGAAAACCCCATCAACGCCAGCGGCGT
GGACGCCAAGGCCATCCTGTCTGCCGACTGAGCAAGAGCAGACGGCTGGAAAATC
TGATCGCCCAGCTGCCCGGCGAGAAGAAGAATGGCCTGTTCGGAAACCTGATTGCC
CTGAGCCTGGGCCTGACCCCCAACTTCAAGAGCAACTTCGACCTGGCCGAGGATGC
CAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCC
ATCCTGCTGAGCGACATCCTGAGAGTGAACACCGAGATCACCAAGGCCCCCCTGAG
CGCCTCTATGATCAAGAGATACGACGAGCACCACCAGGACCTGACCCTGCTGAAAG
CTCTCGTGCGGCAGCAGCTGCCTGAGAAGTACAAAGAGATTTTCTTCGACCAGAGCA
AGAACGGCTACGCCGGCTACATTGACGGCGGAGCCAGCCAGGAAGAGTTCTACAAG
TTCATCAAGCCCATCCTGGAAAAGATGGACGGCACCGAGGAACTGCTCGTGAAGCT
GAACAGAGAGGACCTGCTGCGGAAGCAGCGGACCTTCGACAACGGCAGCATCCCCC
ACCAGATCCACCTGGGAGAGCTGCACGCCATTCTGCGGCGGCAGGAAGATTTTTAC
CCATTCCTGAAGGACAACCGGGAAAAGATCGAGAAGATCCTGACCTTCCGCATCCC
CTACTACGTGGGCCCTCTGGCCAGGGGAAACAGCAGATTCGCCTGGATGACCAGAA
AGAGCGAGGAAACCATCACCCCCTGGAACTTCGAGGAAGTGGTGGACAAGGGCGCT
TCCGCCCAGAGCTTCATCGAGCGGATGACCAACTTCGATAAGAACCTGCCCAACGA
GAAGGTGCTGCCCAAGCACAGCCTGCTGTACGAGTACTTCACCGTGTATAACGAGCT
GACCAAAGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTGACCGTG
AAGCAGCTGAAAGAGGACTACTTCAAGAAAATCGAGTGCTTCGACTCCGTGGAAAT
CTCCGGCGTGGAAGATCGGTTCAACGCCTCCCTGGGCACATACCACGATCTGCTGAA
AATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGGCGGAG
ATACACCGGCTGGGGCAGGCTGAGCCGGAAGCTGATCAACGGCATCCGGGACAAGC
AGTCCGGCAAGACAATCCTGGATTTCCTGAAGTCCGACGGCTTCGCCAACAGAAAC
TTCATGCAGCTGATCCACGACGACAGCCTGACCTTTAAGGAGGACATCCAGAAAGC
CCAGGTGTCCGGCCAGGGCGATAGCCTGCACGAGCACATTGCCAATCTGGCCGGCA
GCCCCGCCATTAAGAAGGGCATCCTGCAGACAGTGAAGGTGGTGGACGAGCTCGTG
AAAGTGATGGGCCGGCACAAGCCCGAGAACATCGTGATCGAAATGGCCAGAGAGA
ACCAGACCACCCAGAAGGGACAGAAGAACAGCCGCGAGAGAATGAAGCGGATCGA
AGAGGGCATCAAAGAGCTGGGCAGCCAGATCCTGAAAGAACACCCCGTGGAAAAC
ACCCAGCTGCAGAACGAGAAGCTGTACCTGTACTACCTGCAGAATGGGCGGGATAT
GTACGTGGACCAGGAACTGGACATCAACCGGCTGTCCGACTACGATGTGGACCATA
TCGTGCCTCAGAGCTTTCTGAAGGACGACTCCATCGACAACAAGGTGCTGACCAGA
AGCGACAAGAACCGGGGCAAGAGCGACAACGTGCCCTCCGAAGAGGTCGTGAAGA
AGATGAAGAACTACTGGCGGCAGCTGCTGAACGCCAAGCTGATTACCCAGAGAAAG
TTCGACAATCTGACCAAGGCCGAGAGAGGCGGCCTGAGCGAACTGGATAAGGCCGG
CTTCATCAAGAGACAGCTGGTGGAAACCCGGCAGATCACAAAGCACGTGGCACAGA
TCCTGGACTCCCGGATGAACACTAAGTACGACGAGAATGACAAGCTGATCCGGGAA
GTGAAAGTGATCACCCTGAAGTCCAAGCTGGTGTCCGATTTCCGGAAGGATTTCCAG
TTTTACAAAGTGCGCGAGATCAACAACTACCACCACGCCCACGcCGCCTACCTGAAC
GCCGTCGTGGGAACCGCCCTGATCAAAAAGTACCCTAAGCTGGAAAGCGAGTTCGT
GTACGGCGACTACAAGGTGTACGACGTGCGGAAGATGATCGCCAAGAGCGAGCAGG
AAATCGGCAAGGCTACCGCCAAGTACTTCTTCTACAGCAACATCATGAACTTTTTCA
AGACCGAGATTACCCTGGCCAACGGCGAGATCCGGAAGCGGCCTCTGATCGAGACA
```

-continued

```
AACGGCGAAACCGGGGAGATCGTGTGGGATAAGGGCCGGGATTTTGCCACCGTGCG
GAAAGTGCTGAGCATGCCCCAAGTGAATATCGTGAAAAAGACCGAGGTGCAGACAG
GCGGCTTCAGCAAAGAGTCTATCCTGCCCAAGAGGAACAGCGATAAGCTGATCGCC
AGAAAGAAGGACTGGGACCCTAAGAAGTACGGCGGCTTCGACAGCCCCACCGTGGC
CTATTCTGTGCTGGTGGTGGCCAAAGTGGAAAAGGGCAAGTCCAAGAAACTGAAGA
GTGTGAAAGAGCTGCTGGGGATCACCATCATGGAAAGAAGCAGCTTCGAGAAGAAT
CCCATCGACTTTCTGGAAGCCAAGGGCTACAAAGAAGTGAAAAAGGACCTGATCAT
CAAGCTGCCTAAGTACTCCCTGTTCGAGCTGGAAAACGGCCGGAAGAGAATGCTGG
CCTCTGCCGGCGAACTGCAGAAGGGAAACGAACTGGCCCTGCCCTCCAAATATGTG
AACTTCCTGTACCTGGCCAGCCACTATGAGAAGCTGAAGGGCTCCCCCGAGGATAA
TGAGCAGAAACAGCTGTTTGTGGAACAGCACAAGCACTACCTGGACGAGATCATCG
AGCAGATCAGCGAGTTCTCCAAGAGAGTGATCCTGGCCGACGCTAATCTGGACAAA
GTGCTGTCCGCCTACAACAAGCACCGGGATAAGCCCATCAGAGAGCAGGCCGAGAA
TATCATCCACCTGTTTACCCTGACCAATCTGGGAGCCCCTGCCGCCTTCAAGTACTTT
GACACCACCATCGACCGGAAGAGGTACACCAGCACCAAAGAGGTGCTGGACGCCAC
CCTGATCCACCAGAGCATCACCGGCCTGTACGAGACACGGATCGACCTGTCTCAGCT
GGGAGGCGACAAAAGGCCGGCGGCCACGAAAAAGGCCGGCCAGGCAAAAAGAA
AAAG (SEQ ID NO: 75)
```

Example 4

Truncating and Creating Chimeric Cas9s Based on S. pyogenes Cas9 Crystal Structure Herein FIGS. 5A-C pertain to truncating and creating chimeric Cas9s based on the herein crystal structure. These figures provide schematics illustrating A. SpCas9 mutants designed for mapping out essential functional domains of Cas9 for truncation of protein. B. chimeric Cas9s that contain sequences (regions in pink) from Cas9 from S. thermophilus CRISPR 1, S. thermophilus CRISPR 3, Staphylococcus aureus, Neisseria meningiditis, or other Cas9 orthologs. C. Designs for creating chemically inducible dimerization of SpCas9. The chemically inducible SpCas9 functions.

DNA sequences for chimeric Cas9s are optimized for human expression by GenScript and synthesized de novo. Chimeric Cas9 proteins can be constructed by cloning and ligating individual functional domains from Cas9 orthologs (i.e. by PCR-amplifying individual functional domains from a desired Cas9 ortholog, then assembling the pieces together by either Gibson or Golden Gate-cloning). Additionally, a set of chemically-inducible Cas9s were constructed as two-component systems, where one portion of the Cas9 protein is fused to FKBP, and the remainder fused to FRB (e.g. FKBP-Cas9(amino acids 1-1098), FRB-Cas(1099-1368)). In absence of chemical induction, co-transfection of the two inducible Cas9 components have no catalytic activity, but the functional assembly of the components may be induced using Rapamycin [5 nM to 10 µM].

Example 5

Crystal Structure of Cas9 in Complex with Guide RNA and Target DNA

Cas9 is an RNA-guided nuclease from the microbial CRISPR-Cas system that can be targeted to specific genomic loci by single guide RNAs (sgRNAs). Applicants report the crystal structure of Streptococcus pyogenes Cas9 in complex with sgRNA and its target DNA at 2.4 Å resolution. The structure revealed a bilobed architecture composed of target recognition and nuclease lobes, accommodating a sgRNA: DNA duplex in a positively-charged groove at their interface. Whereas the recognition lobe is essential for sgRNA and DNA binding, the nuclease lobe contains the HNH and RuvC nuclease domains, which are properly positioned for the cleavage of complementary and non-complementary strands of the target DNA, respectively. This high-resolution structure and accompanying functional analyses elucidate the molecular mechanism of RNA-guided DNA targeting by Cas9, paving the way for rational design of new and versatile genome-editing technologies.

The CRISPR (clustered regularly interspaced palindromic repeat)-Cas system is a naturally occurring microbial adaptive immune system for defense against invading phages and other mobile genetic elements (Deveau et al., 2010; Horvath and Barrangou, 2010; Marraffini and Sontheimer, 2010; Terns and Terns, 2011). Three types (I-III) of CRISPR-Cas systems have been functionally identified across a wide range of microbial species (Barrangou et al., 2007; Brouns et al., 2008; Marraffini and Sontheimer, 2008), each containing a cluster of CRISPR-associated (Cas) genes and its corresponding CRISPR array. These characteristic CRISPR arrays consist of repetitive sequences (direct repeats, referred to as repeats) interspaced by short stretches of non-repetitive sequences (spacers) derived from short segments of foreign genetic material (protospacers). The CRISPR array is transcribed and processed into short CRISPR RNAs (crRNAs), which direct Cas proteins to the target nucleic acids, DNA or RNA, via Watson-Crick base pairing to facilitate the nucleic acid destruction.

Type I and III CRISPR systems utilize ensembles of Cas proteins in complex with crRNA to mediate recognition and subsequent degradation of target nucleic acids (Spilman et al., 2013; Wiedenheft et al., 2011). In contrast, the Type II CRISPR system achieves recognition and cleavage of the target DNA (Garneau et al., 2010) via a single enzyme called Cas9 (Sapranauskas et al., 2011) along with two non-coding RNAs, the crRNA and a trans-activating crRNA (tracrRNA) (Deltcheva et al., 2011). The crRNA hybridizes with the tracrRNA to form a crRNA:tracrRNA duplex, which is then loaded onto Cas9 to direct cleavage of cognate DNA sequences bearing appropriate protospacer adjacent motifs (PAM) (Mojica et al., 2009).

The Type II CRISPR system was the first to be adapted for facilitating genome editing in eukaryotic cells (Cong et al., 2013; Mali et al., 2013b). The Cas9 protein from Streptococcus pyogenes, along with a single guide RNA (sgRNA), a synthetic fusion of crRNA and minimal tracrRNA (Jinek et al., 2012), could be programmed to instruct cleavage of virtually any sequence preceding a 5'-NGG PAM sequence in mammalian cells (Cong et al., 2013; Mali et al., 2013b). This unprecedented flexibility has enabled a broad range of applications including rapid generation of genetically modified cells and animal models (Gratz et al., 2013; Hwang et al., 2013; Wang et al., 2013; Yang et al., 2013), and genome-scale genetic screening (Qi et al., 2013; Shalem et al., 2014; Wang et al., 2014).

However, despite brisk progress in the development of the Cas9 technology, the mechanism of how the Cas9-sgRNA complex recognizes and cleaves its target DNA remains to be elucidated. Up to date, biochemical analyses at the domain levels have enabled site-specific engineering to convert the native Cas9 into a DNA nicking enzyme (Gasiunas et al., 2012; Jinek et al., 2012; Sapranauskas et al., 2011) that facilitates homology-directed repair in eukaryotic cells (Cong et al., 2013; Mali et al., 2013b) and further cleaves DNA with improved specificity given appropriately paired sgRNAs (Mali et al., 2013a; Ran et al., 2013). Moreover, a catalytically inactive Cas9 can serve as a RNA-guided DNA-binding platform to target effector domains and modulate endogenous transcription (Gilbert et al., 2013; Konermann et al., 2013; Maeder et al., 2013; Perez-Pinera et al., 2013; Qi et al., 2013). These Cas9 engineering advances represent just the first steps of what is possible in fully realizing the potential of this flexible RNA-guided genome positioning system. A precise structural information on Cas9 will thus not only enhance the understanding of how this elegant RNA-guided microbial adaptive immune system functions, but also inform further improvements of Cas9 targeting specificity, simplification of in vitro and in vivo delivery, and engineering of Cas9 for novel functions and optimized features.

In this example, Applicants report the crystal structure of S. pyogenes Cas9 in complex with sgRNA and its target DNA at 2.4 Å resolution. This high-resolution structure along with functional analysis reveals the key functional interactions that integrate the guide RNA, target DNA, and Cas9 protein, paving the way towards enhancing Cas9 function as well as engineering novel applications.

Figure 15:
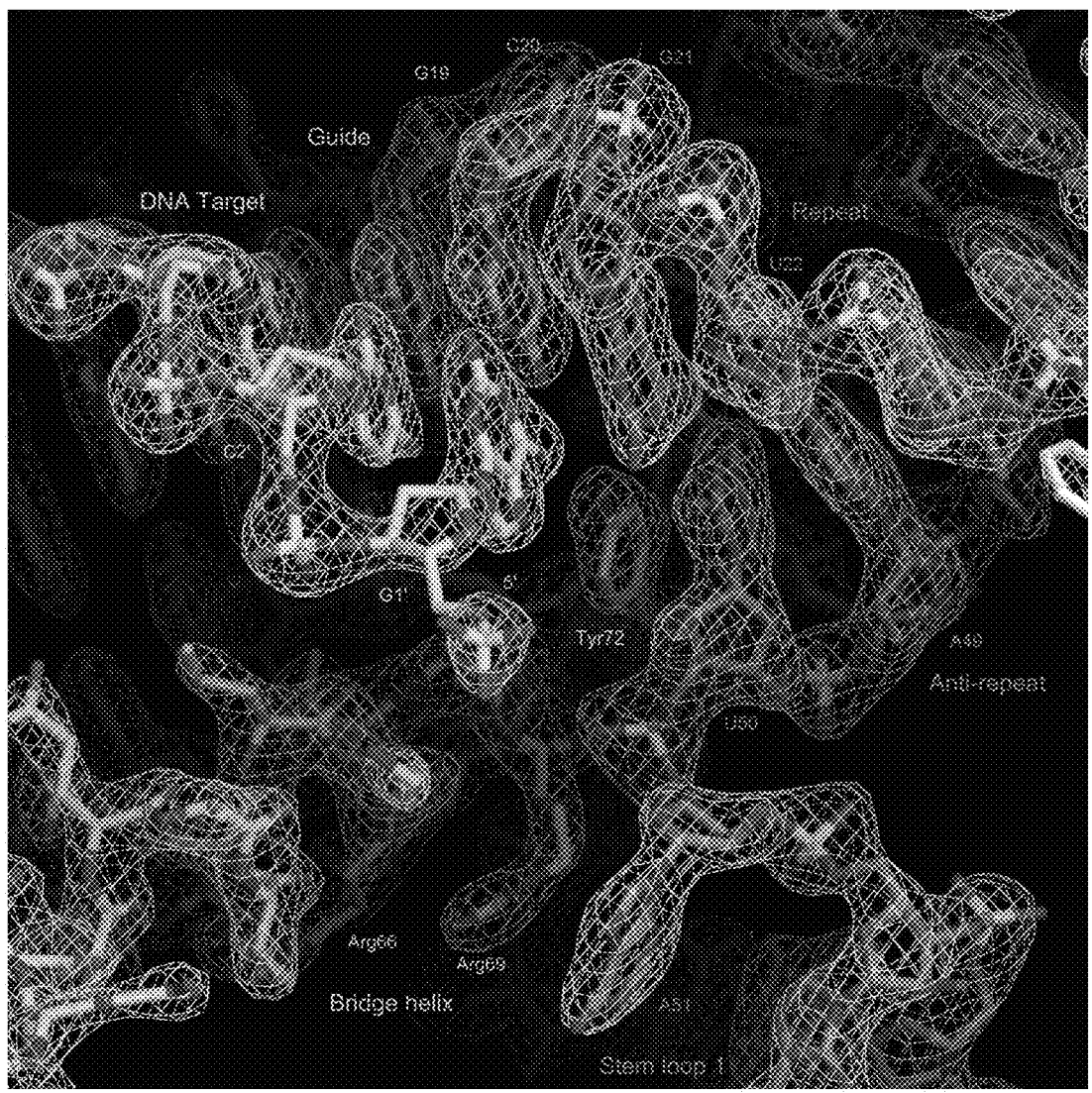
FIG. 15 shows Electron density map. The $2mF_O$-$DF_C$ electron density map around the three-way junction is shown as a gray mesh (contoured at 2.5σ).

Overall structure of the Cas9-sgRNA-DNA ternary complex: Applicants solved the crystal structure of full-length S. pyogenes Cas9 (residues 1-1368; D10A/C80L/C574E/H840A) in complex with a 98-nucleotide (nt) sgRNA and a 23-nt target DNA, at 2.4 Å resolution, by the SAD (single-wavelength anomalous dispersion) method using a SeMet-labeled protein (FIG. 15 and Table 1). To improve the solution behavior of Cas9, Applicants replaced two less conserved cysteine residues (Cys80 and Cys574) with leucine and glutamic acid, respectively. This C80L/C574E mutant retained the ability to efficiently cleave genomic DNA in human embryonic kidney 293FT (HEK293FT) cells, confirming that these mutations have no effects on Cas9 nuclease function (FIG. 16). Additionally, to prevent cleavage of the target DNA during crystallization, Applicants replaced the two catalytic residues, Asp10 from the RuvC domain and His840 from the HNH domain, with alanine.

TABLE 1

Data collection and refinement statistics

|  | Native Cas9 | SeMet Cas9 |
|---|---|---|
| Data collection |  |  |
| Beamline | SPring-8 BL32XU | SPring-8 BL41XU |
| Wavelength (Å) | 1.000 | 0.9791 |
| Space group | P1 | P1 |
| Cell dimensions |  |  |
| a, b, c (Å) | 76.7, 105.7, 126.8 | 76.2, 104.5, 125.5 |
| α, β, γ (°) | 97.7, 98.4, 100.3 | 97.0, 98.2, 101.1 |
| Resolution (Å) | 50-2.4 (2.54-2.4) | 50-2.6 (2.67-2.6) |
| $R_{sym}$ | 0.07 (1.53) | 0.167 (1.96) |

TABLE 1-continued

Data collection and refinement statistics

|  | Native Cas9 | SeMet Cas9 |
|---|---|---|
| I/σI | 22.53 (1.45) | 12.62 (1.44) |
| Completeness (%) | 98.2 (96.3) | 99.9 (99.9) |
| Redundancy | 7.93 (7.88) | 19.1 (15.9) |
| CC(1/2) | 0.999 (0.671) | 0.999 (0.736) |
| Refinement |  |  |
| Resolution (Å) | 50-2.4 |  |
| No. reflections | 146,862 |  |
| $R_{work}/R_{free}$ | 0.241/0.276 |  |
| No. atoms |  |  |
| Protein | 19,021 |  |
| Nucleic acid | 5,013 |  |
| Solvent | 200 |  |
| B-factors |  |  |
| Protein | 72.6 |  |
| Nucleic acid | 72.6 |  |
| Solvent | 53.3 |  |
| R.m.s deviations |  |  |
| Bond lengths (Å) | 0.002 |  |
| Bond angles (°) | 0.454 |  |
| Ramachandran plot |  |  |
| Favored region | 96.8% |  |
| Allowed region | 3.2% |  |
| Outlier region | 0.0% |  |

*Highest resolution shell is shown in parenthesis.

The crystallographic asymmetric unit contained two Cas9-sgRNA-DNA ternary complexes (Mol A and Mol B). Although there are conformational differences between the two complexes, sgRNA and DNA are recognized by Cas9 in a similar manner. Most notably, while the HNH domain in Mol A is connected with the RuvC domain by a disordered linker, the HNH domain in Mol B is not visible in the electron density map, indicating the flexible nature of the HNH domain. Thus, Applicants first describe the structural features of Mol A unless otherwise stated, and then discuss the structural differences between the two complexes, which suggest the conformational flexibility of Cas9.

Figures 8A, 8B:
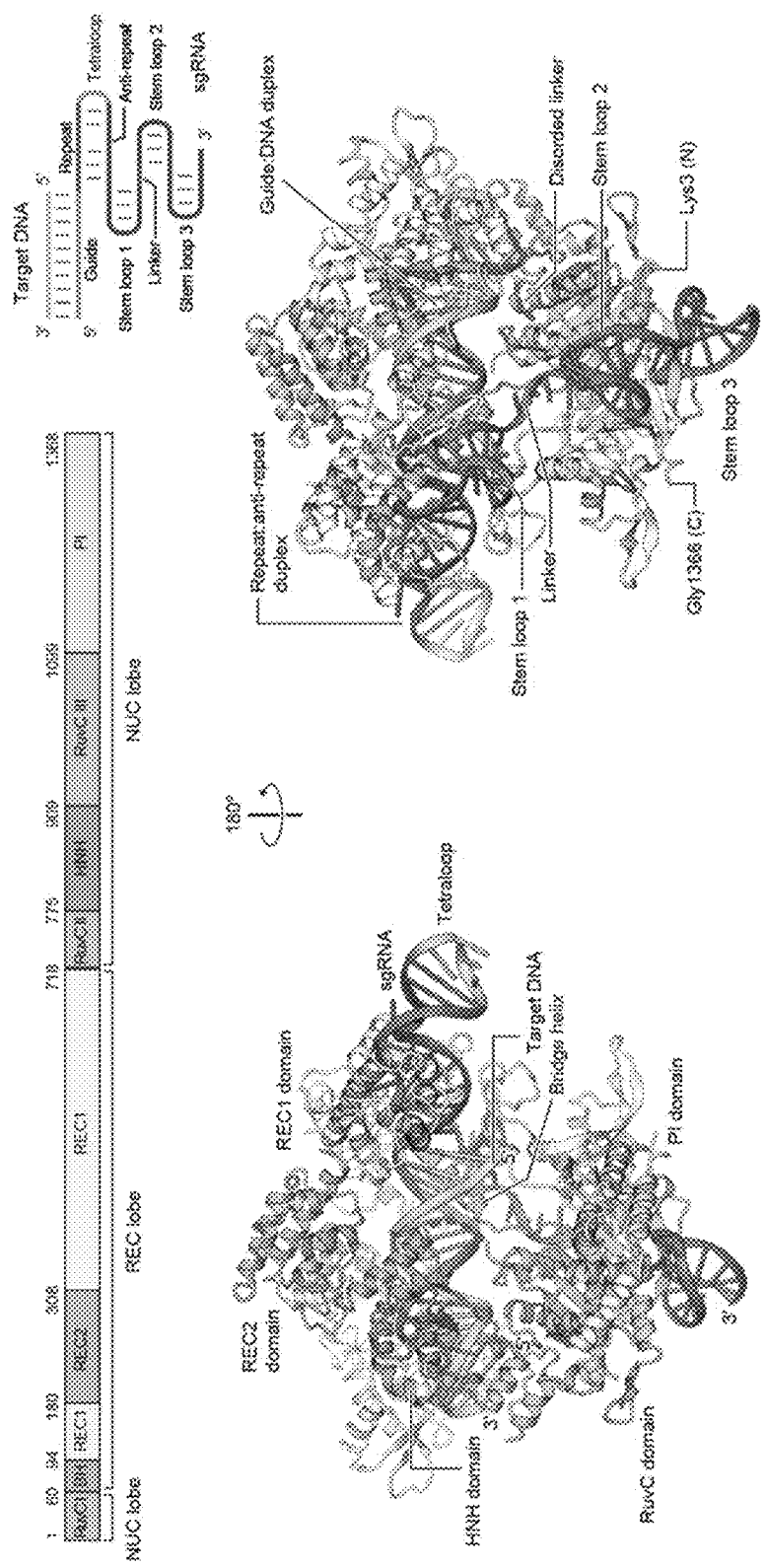
FIG. 8A-D shows the overall structure. (A) Domain organization of S. pyogenes Cas9, and schematic of the sgRNA:target DNA complex. (B) Ribbon representation of the Cas9-sgRNA-DNA complex. Disordered linkers are shown as red dotted lines. (C) Surface representation of the Cas9-sgRNA-DNA complex. The active sites of the RuvC (D10A) and HNH (H840A) domains are indicated by dashed yellow circles. (D) Electrostatic surface potential of the Cas9-sgRNA-DNA complex. The HNH domain is omitted for clarity. Molecular graphic images were prepared using CueMol (see website at cuemol.org). Also refer to FIGS. 37 and 38.
Figure 8C:
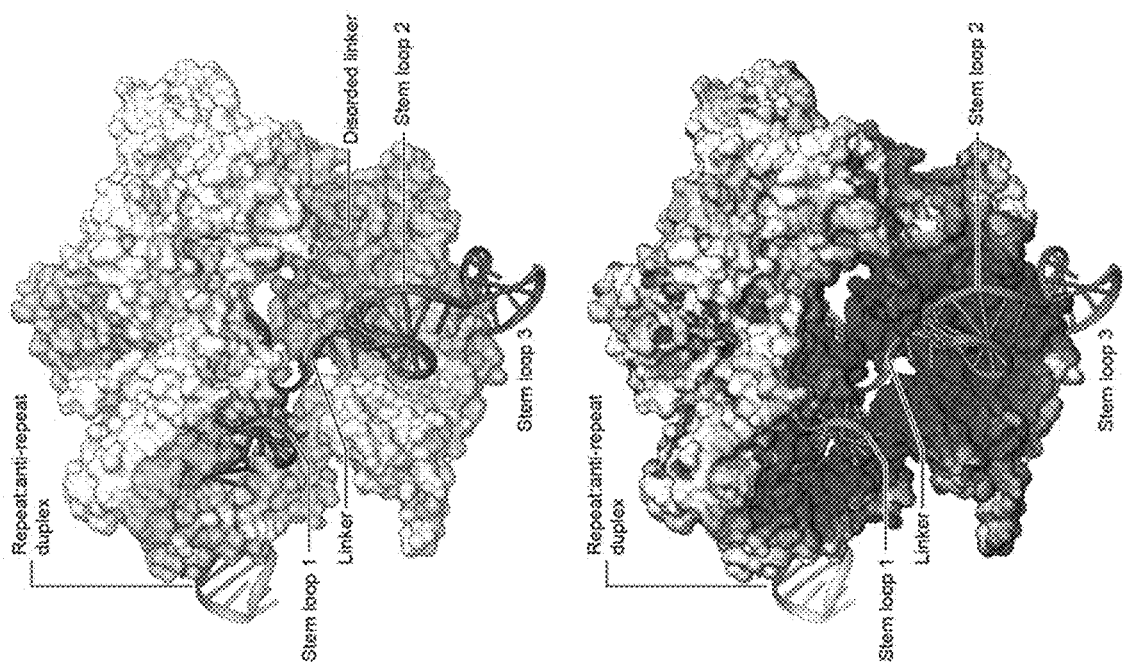
Figure 8D:
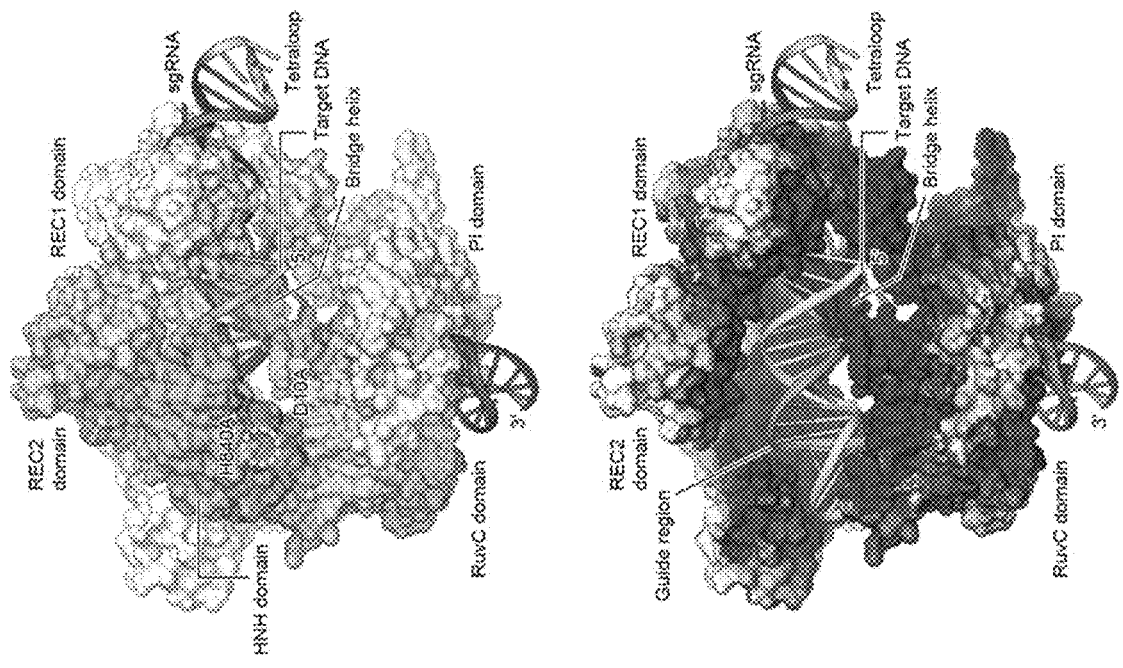

The crystal structure revealed that Cas9 consists of two lobes, a recognition (REC) lobe and a nuclease (NUC) lobe (FIG. 8A-C). The REC lobe can be divided into three regions, a long α-helix referred to as Bridge helix (BH) (residues 60-93), the REC1 (residues 94-179 and 308-713), and REC2 (residues 180-307) domains (FIG. 8A-C). The NUC lobe consists of the RuvC (residues 1-59, 718-769, and 909-1098), HNH (residues 775-908), and PAM-interacting (PI) (residues 1099-1368) domains (FIG. 8A-C). The negatively-charged sgRNA:DNA hybrid duplex is accommodated in a positively-charged groove at the interface between the REC and NUC lobes (FIG. 8D). In the NUC lobe, the RuvC domain is assembled from the three split RuvC motifs (RuvC which interfaces with the PI domain to form a positively-charged surface that interacts with the 3' tail of the sgRNA (FIG. 8D). The HNH domain lies in between the RuvC motifs and forms only a few contacts with the rest of the protein.

Figures 9A, 9B, 9C, 9D:
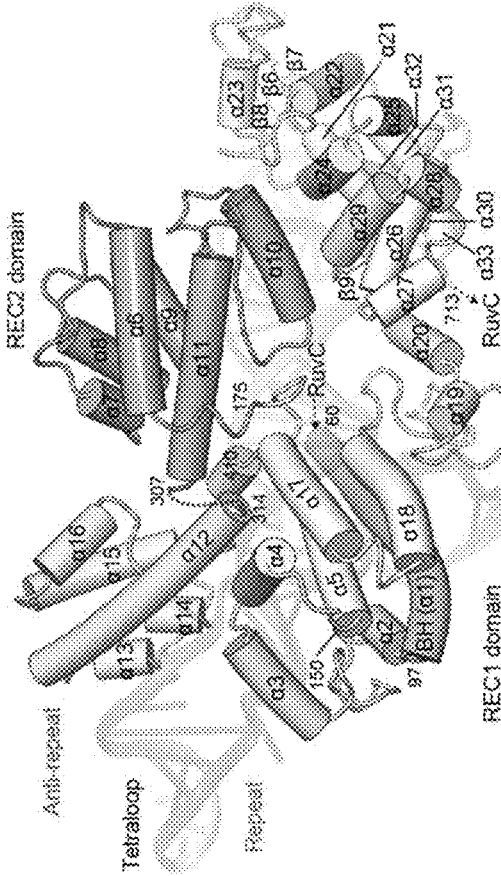
FIG. 9A-E shows the REC lobe and PI domain. (A) Structure of the REC lobe. The REC2 domain and Bridge helix are colored dark gray and green, respectively. The REC1 domain is colored gray, with the repeat-interacting and anti-repeat-interacting regions colored pale blue and pink, respectively. The bound sgRNA:DNA is shown as semi-transparent ribbon representation. (B) Schematics indicating positions of SpCas9 truncations in the REC1 and REC2 domains. Bars on the right show indel mutations generated by the truncation mutants, measured by SURVEYOR assay (n=3, error bars show mean±S.E.M., N.D., not detectable). (C) Western blot showing expression of truncation mutants in HEK 293FT cells. (D) Structure of the PI domain. The bound sgRNA is shown as semi-transparent ribbon representation. (E) Schematics showing wild-type SpCas9 and St3Cas9, chimeric Cas9, as well as SpCas9 PI domain truncation constructs. Cas9s are assayed for indel generation at target sites upstream of either NGG (left bar graph) or NGGNG (right bar graph) PAMs (n=3, error bars show mean±S.E.M., N.D., not detectable). See also FIGS. 39-41.
Figure 17:
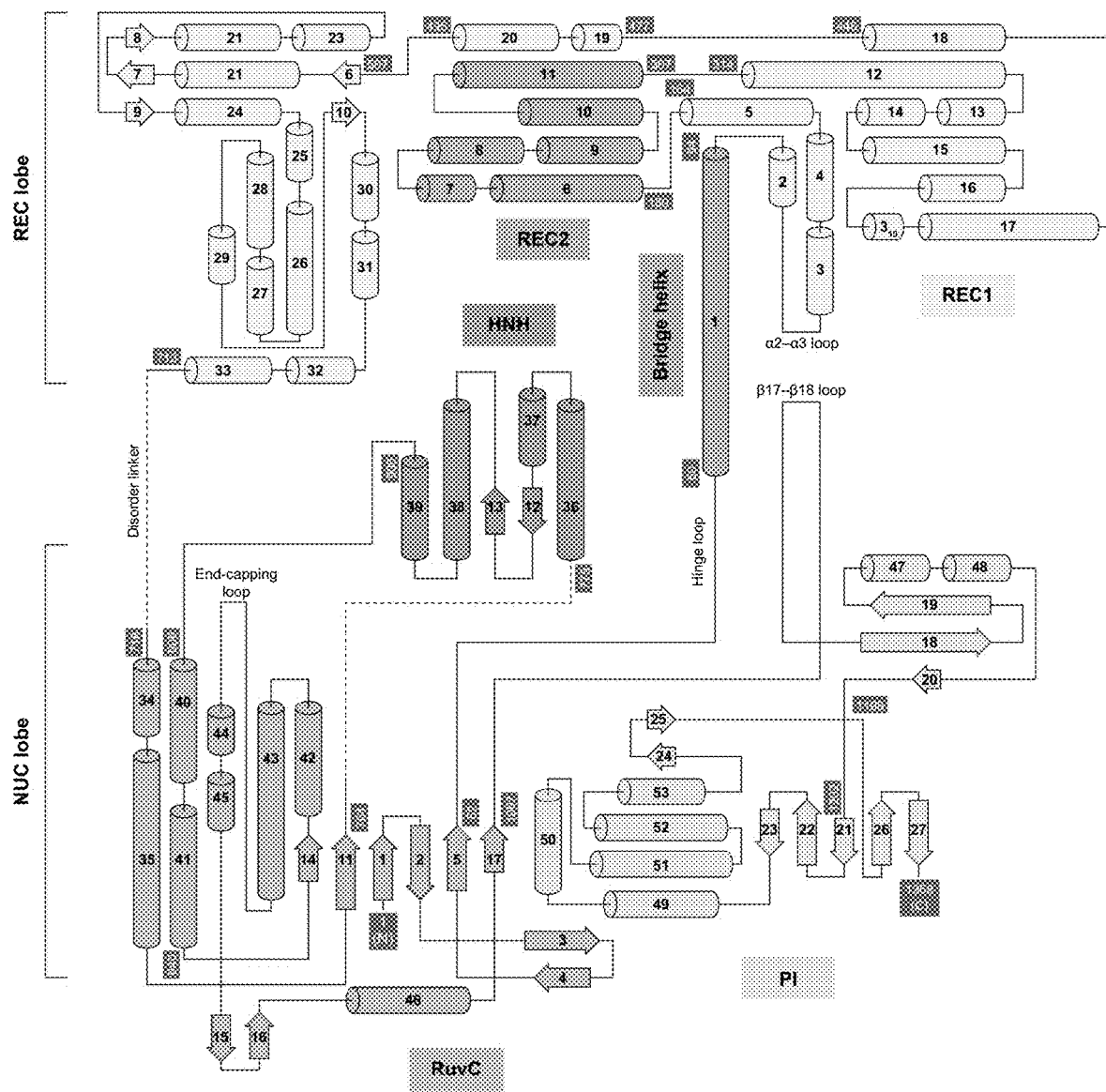
FIG. 17 shows a schematic drawing of the secondary structural elements of Cas9.

The REC lobe of Cas9 interacted with the repeat:anti-repeat duplex: The REC lobe comprises the REC1 and REC2 domains. REC1 adopted an elongated, α-helical structure comprising 26 α-helices (α2-α5 and α12-α33) and two β-sheets (β6/β10 and β7-β9), whereas REC2 adopted a six-helix bundle structure (α6-α11) (FIGS. 9A and 17). A Dali search (Holm and Rosenstrom, 2010) revealed that the REC lobe did not share structural similarity with other known proteins, indicating that it is a Cas9-specific functional domain.

Figure 18A:
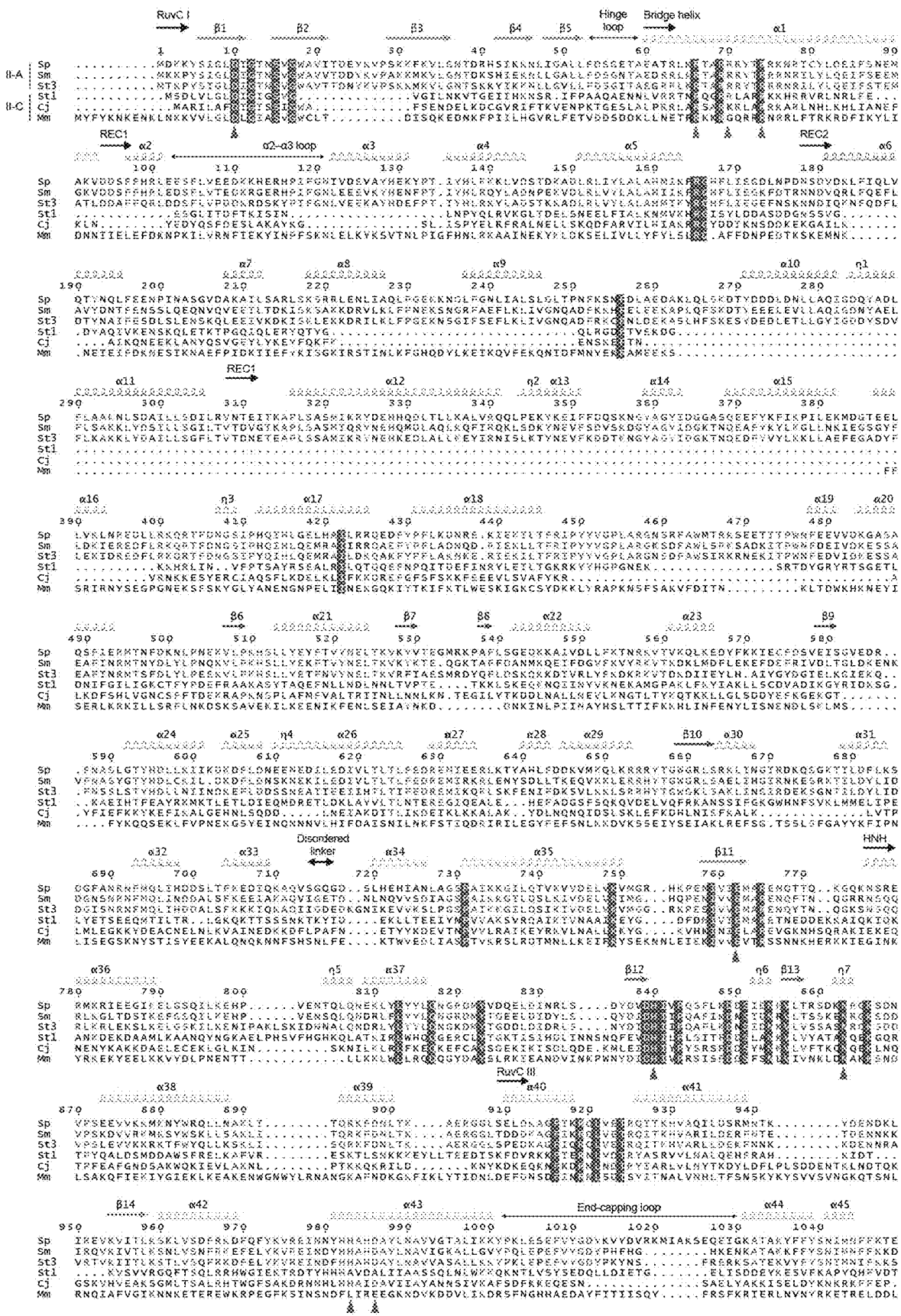
Figure 19:
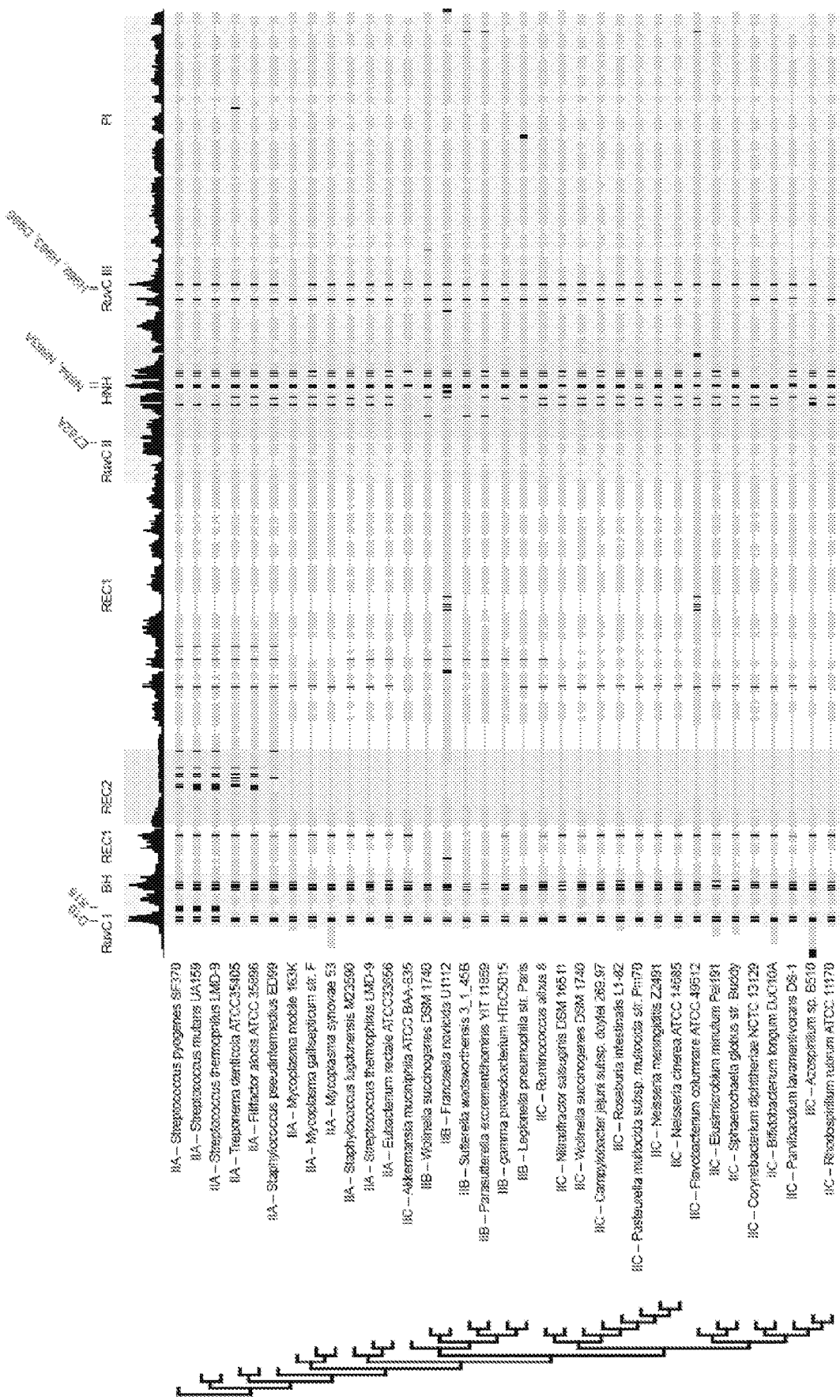
FIG. 19 shows the sequence alignment of Cas9 orthologs in families II-A, II-B and II-C. 35 Cas9 orthologs from families IIA, IIB and IIC are aligned (BLOSUM62) and clustered (Jukes-Cantor model Neighbor-Joining method, with *S. pyogenes* Cas9 as outgroup). Bars on top show conservation by amino acid. In each line, black bars show residues with at least 75% consensus, and gray bars non-conserved residues.

The REC lobe is one of the least conserved regions across the three families of Cas9 within the Type II CRISPR system (IIA, IIB and IIC) and many Cas9s contain significantly shorter REC lobes (FIGS. 18, 19). Applicants hypothesized that truncations in the REC lobe could be tolerated. As expected, and consistent with the observation that the REC2 domain does not contact the bound sgRNA:DNA hybrid duplex, a Cas9 mutant lacking the REC2 domain (Δ175-307) showed ~50% of the wild-type Cas9 activity (FIG. 9B), indicating that the REC2 domain is not critical for DNA cleavage. The lower cleavage efficiency may be attributed in part to the reduced levels of Cas9 (Δ175-307) expression relative to that of the wild-type protein (FIG. 9C). In striking contrast, deletion of the crRNA repeat-interacting region (Δ97-150) or tracrRNA anti-repeat-interacting region (Δ312-409) of the REC1 domain abolished DNA cleavage activity (FIG. 9B), indicating that the recognition of the repeat:anti-repeat duplex by the REC1 domain is critical for Cas9 function.

The PAM-interacting (PI) domain confers PAM specificity: The NUC lobe contains the PI domain, which adopts an elongated structure comprising seven α-helices (α47-α53), a three-stranded antiparallel β-sheet (β18-β20), a five-stranded antiparallel β-sheet (β21-β23, β26 and β27), and two-stranded antiparallel β-sheet (β24 and β25) (FIGS. 9D and 17). Similar to the REC lobe, the PI domain also represents a novel protein fold unique to the Cas9 family.

The locations of the bound complementary strand DNA and the active site of the RuvC domain in the present structure suggest that the PI domain is positioned to recognize the PAM sequence on the non-complementary strand of the target DNA. Applicants tested whether replacement of the *S. pyogenes* Cas9 (SpCas9; Cas9 in this study) PI domain with that of an orthologous Cas9 protein recognizing a different PAM would be sufficient to alter SpCas9 PAM specificity. The *Streptococcus thermophilus* CRISPR-3 Cas9 (St3Cas9) shares ~60% sequence identity with SpCas9; furthermore, their crRNA repeats and tracrRNAs are interchangeable (Fonfara et al., 2013). However, SpCas9 and St3Cas9 require different PAM sequences (5'-NGG for Cas9 and 5'-NGGNG for St3Cas9) for target DNA cleavage (Fonfara et al., 2013).

Figure 9E:
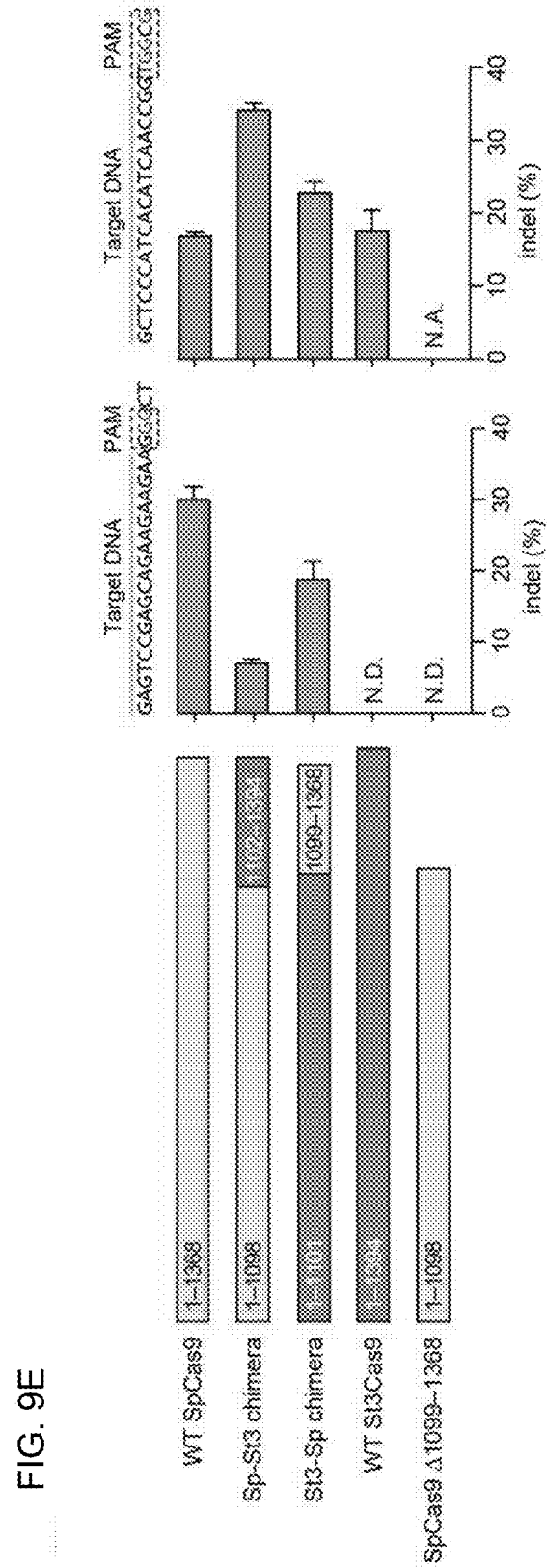

Applicants swapped the two PI domains to generate two chimeras, Sp-St3Cas9 (SpCas9 with the PI domain of St3Cas9) and St3-SpCas9 (St3Cas9 with the PI domain of SpCas9), and examined their cleavage activities for target DNA sequences bearing 5'-NGG PAM (5'-GGGCT) or 5'-NGGNG PAM (5'-GGGCG) (FIG. 9E). SpCas9 and St3-SpCas9, but not St3Cas9, cleaved the target DNA with 5'-NGG PAM (FIG. 9E), indicating that the PI domain of SpCas9 is required for the recognition of 5'-NGG PAM and is sufficient to alter the PAM recognition of St3Cas9. Sp-St3Cas9 retained cleavage activity for the target DNA with 5'-NGG PAM, albeit at a lower level than that of SpCas9 (FIG. 9E). Additionally, deletion of the PI domain (Δ1099-1368) abolished the cleavage activity (FIG. 9E), indicating that the PI domain is critical for Cas9 function. These results reveal that the PI domain is a major determinant of PAM specificity.

Figure 10B:
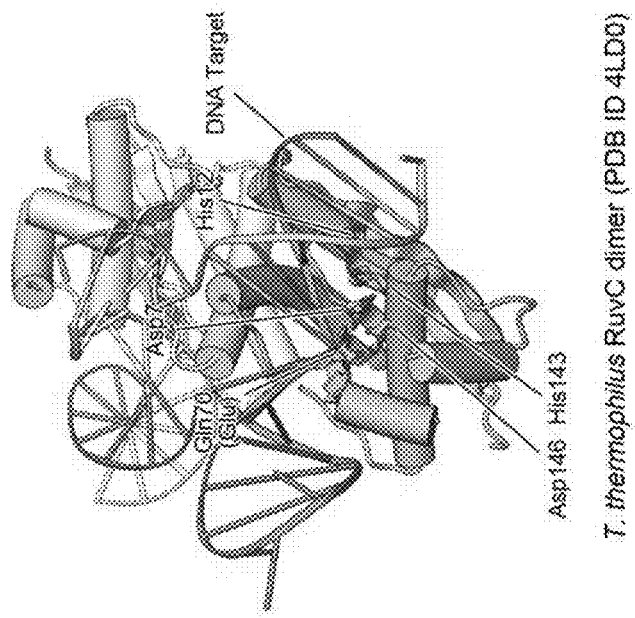
FIG. 10A-F shows the NUC lobe. (A) Structure of the RuvC domain. The core structure of the RNase H fold core is highlighted in cyan. The active-site residues are shown as stick models. (B) Structure of the *T. thermophilus* RuvC dimer in complex with a Holliday junction (PDB ID 4LD0). The two protomers are colored cyan and gray, respectively. (C) Sequence (top) (SEQ ID NO: 154) illustrates Cas9 nicking targets on opposite strands of DNA. Targets 1 and 2 are offset by a distance of 4-bp in between. Heatmap (bottom) shows the ability of each catalytic mutant to induce double-(with either sgRNA 1 or 2) or single-stranded breaks (only with both sgRNA together). Gray boxes: not assayed. (D) Indel formation by Cas9 nickases depends on off-set distance between sgRNA pairs (right panel). Off-set distance is defined as the number of base pairs between the PAM-distal (5') ends of the guide sequence of a given sgRNA pair (n=3, error bars show mean±S.E.M., N.D., not detectable). (E) Structure of the HNH domain. The core structure of the ββα-metal fold is highlighted in magenta. The active-site residues are shown as stick models. (F) Structure of the T4 Endo VII dimer in complex with a Holliday junction (PDB ID 2QNC). The two protomers are colored pink and gray, respectively, with the ββα-metal fold core highlighted in magenta. The bound $Mg^{2+}$ ion is shown as an orange sphere.
Figure 10A:
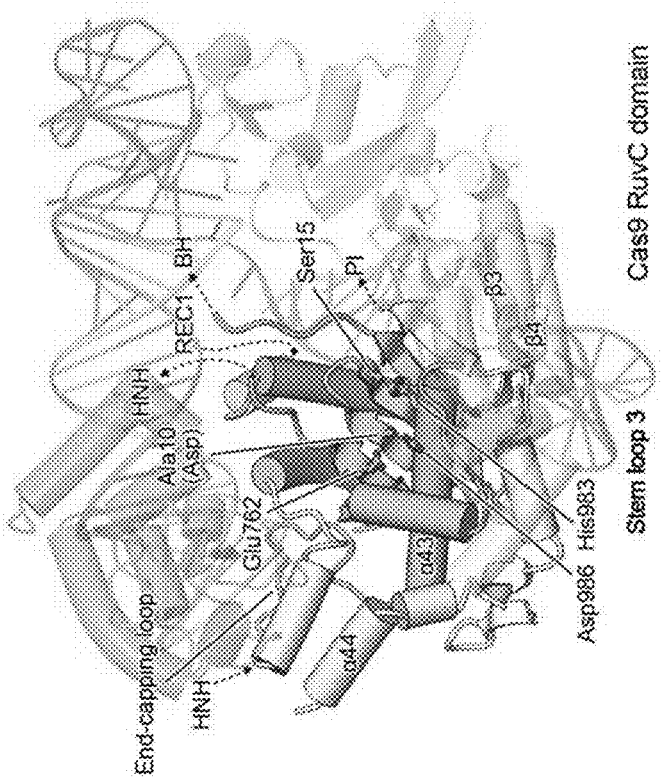
Figure 10C:
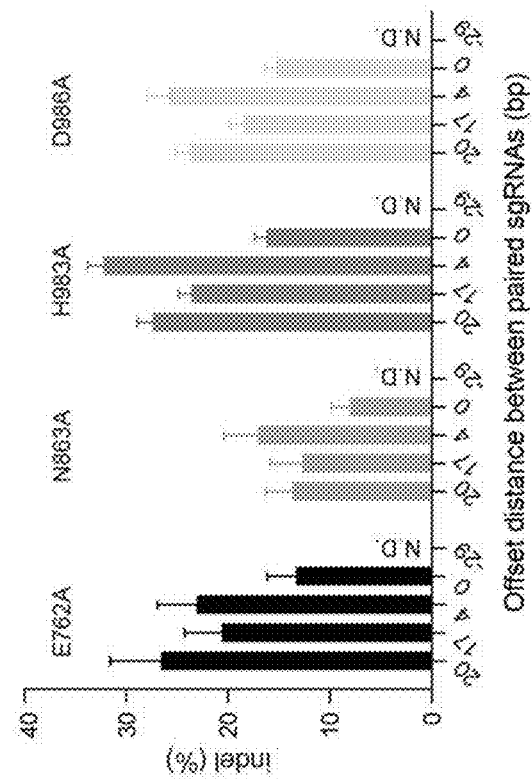
Figure 10D:
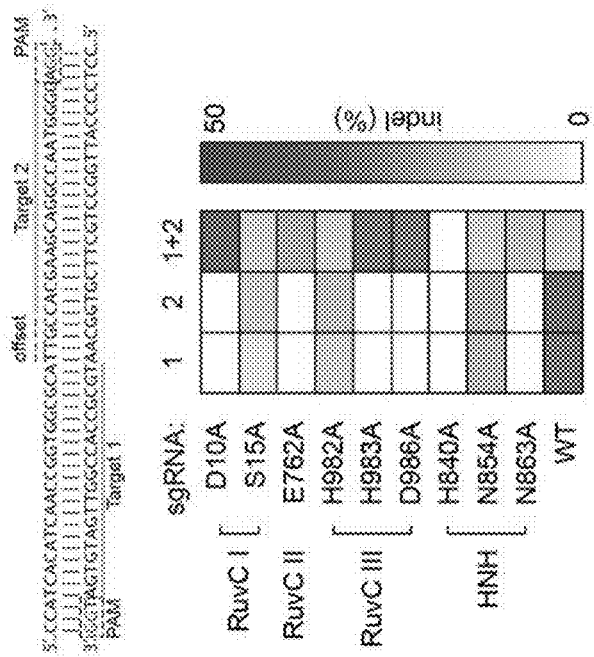

The RuvC domain targets the non-complementary strand DNA: The RuvC domain consists of a six-stranded mixed β-sheet (β1, β2, β5, β11, β14 and β17) flanked by α-helices (α34, α35 and α40-α46) and two additional two-stranded antiparallel β-sheets (β3/β4 and β15/β16) (FIGS. 10A and 17). It shares structural similarity with retroviral integrase superfamily members characterized by an RNase H fold, such as *Escherichia coli* RuvC (PDB code 1HJR, 13% identity, root-mean-square deviation (rmsd) of 3.4 Å for 123 equivalent Cα atoms) (Ariyoshi et al., 1994) and *Thermus thermophilus* RuvC (PDB code 4LD0, 17% identity, rmsd of 3.4 Å for 129 equivalent Cα atoms) (Ariyoshi et al., 1994) and *Thermus thermophilus* RuvC (PDB code 4LD0, 17% identity, rmsd of 3.4 Å for 129 equivalent Cα atoms) (Gorecka et al., 2013) (FIG. 10B). RuvC nucleases have four catalytic residues (e.g., Asp7, Glu70, His143 and Asp146 in *T. thermophilus* RuvC), and cleave Holliday junctions through a two-metal mechanism (Ariyoshi et al., 1994; Chen et al., 2013; Gorecka et al., 2013). Asp10 (Ala), Glu762, His983 and Asp986 of the Cas9 RuvC domain are located at positions similar to those of the catalytic residues of *T. thermophilus* RuvC (FIG. 10A, B), consistent with the previous results that the D10A mutation abolished cleavage of the non-complementary DNA strand and that Cas9 requires Mg2+ ions for cleavage activity (Gasiunas et al., 2012; Jinek et al., 2012). Moreover, alanine substitution of Glu762, His983 or Asp986 also converted Cas9 into nickases (FIG. 10C, D). Each nickase mutant was able to facilitate targeted double strand breaks using pairs of juxtaposed sgRNAs (FIG. 10C, D), as demonstrated with the D10A nickase previously (Ran et al., 2013). This combination of structural observations and mutational analysis suggest that the Cas9 RuvC domain cleaves the non-complementary strand of the target DNA through the two-metal mechanism previously observed for other retroviral integrase superfamily nucleases.

It is important to note that there are key structural dissimilarities between the Cas9 RuvC domain and RuvC nucleases, explaining their functional differences. Unlike the Cas9 RuvC domain, RuvC nucleases forms a dimer and recognize a Holliday junction (Gorecka et al., 2013) (FIG. 10B). In addition to the conserved RNase H fold, the RuvC domain of Cas9 has additional structural elements involved in the interactions with the guide:DNA duplex (an end-capping loop between α43 and α44), and the PI domain/stem loop 3 (β-hairpin formed by β3 and β4) (FIG. 10A).

Figure 10E:
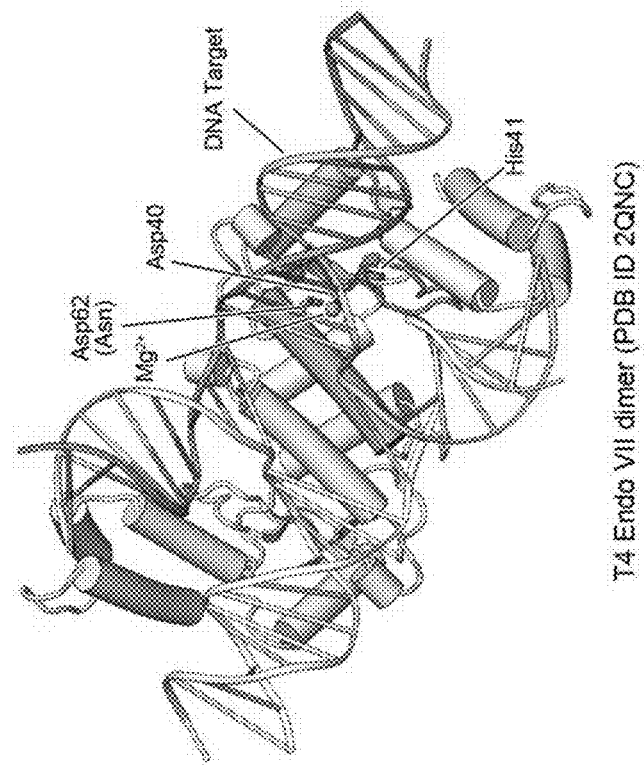
Figure 10F:
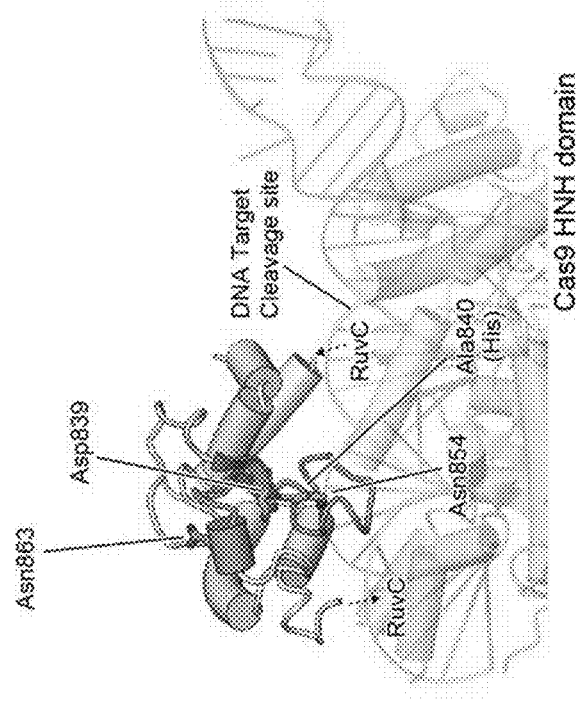

The HNH domain targets the complementary strand DNA: The HNH domain comprises a two-stranded antiparallel β-sheet (β12 and β13) flanked by four α-helices (α36-α42) (FIG. 10E). Likewise, it shares structural similarity with HNH endonucleases characterized by a ββα-metal fold, such as the phage T4 endonuclease VII (Endo VII) (Biertumpfel et al., 2007) (PDB code 2QNC, 8% identity, rmsd of 2.6 Å for 60 equivalent Cα atoms) (FIG. 10F) and *Vibrio vulnificus* nuclease (Li et al., 2003) (PDB code 1OUP, 8% identity, rmsd of 2.9 Å for 78 equivalent Cα atoms). HNH nucleases have three catalytic residues (e.g., Asp40, His41, and Asn62 in Endo VII), and cleave nucleic acid substrates through a single-metal mechanism (Biertumpfel et al., 2007; Li et al., 2003). In the structure of the Endo VII N62D mutant in complex with a Holliday junction, a Mg2+ ion is coordinated by Asp40, Asp62, and oxygen atoms of the scissile phosphate group of the substrate, while His41 acts as a general base to activate a water molecule for catalysis (FIG. 10F). Asp839, His840, and Asn863 of the Cas9 HNH domain correspond to Asp40, His41, and Asn62 of Endo VII, respectively (FIG. 10E), consistent with the observation that His840 is critical for the cleavage of the complementary DNA strand (Gasiunas et al., 2012; Jinek et al., 2012). The N863A mutant functions as a nickase (FIG. 10C, D), indicating that Asn863 participates in catalysis. These observations suggest that the Cas9 HNH domain may cleave the complementary strand of the target DNA through a single-metal mechanism as observed for other HNH superfamily nucleases. However, in the present structure, Asn863 of Cas9 is located at a position different from that of Asn62 in Endo VII (Biertumpfel et al., 2007), whereas Asp839 and His840 (Ala) of Cas9 are located at positions similar to those of Asp40 and His41 of Endo VII, respectively (FIG. 10E, F). This might be due to the absence of divalent ions, such as Mg2+, in Applicants' crystallization solution, suggesting that Asn863 can point towards the active site and participate in catalysis. Whereas the HNH domain shares a ββα-metal fold with other HNN endonuclease, their overall structures are different (FIG. 10E, F), consistent with the differences in their substrate specificities.

sgRNA recognizes target DNA via Watson-Crick base pairing: The sgRNA consists of crRNA- and tracrRNA-derived sequences connected by an artificial tetraloop (FIG. 11A). The crRNA sequence can be subdivided into guide (20-nt) and repeat (12-nt) regions, and the tracrRNA sequence likewise into anti-repeat (14-nt) and three tracrRNA stem loops (FIG. 11A). The crystal structure reveals that the sgRNA binds the target DNA to form a T-shaped architecture comprising a guide:DNA duplex, repeat:anti-repeat duplex and stem loops 1-3 (FIG. 11A, B). The repeat:anti-repeat duplex and stem loop 1 are connected by a single nucleotide (A51), and stem loops 1 and 2 are connected by a 5-nt single-stranded linker (nucleotides 63-67).

Figure 11C:
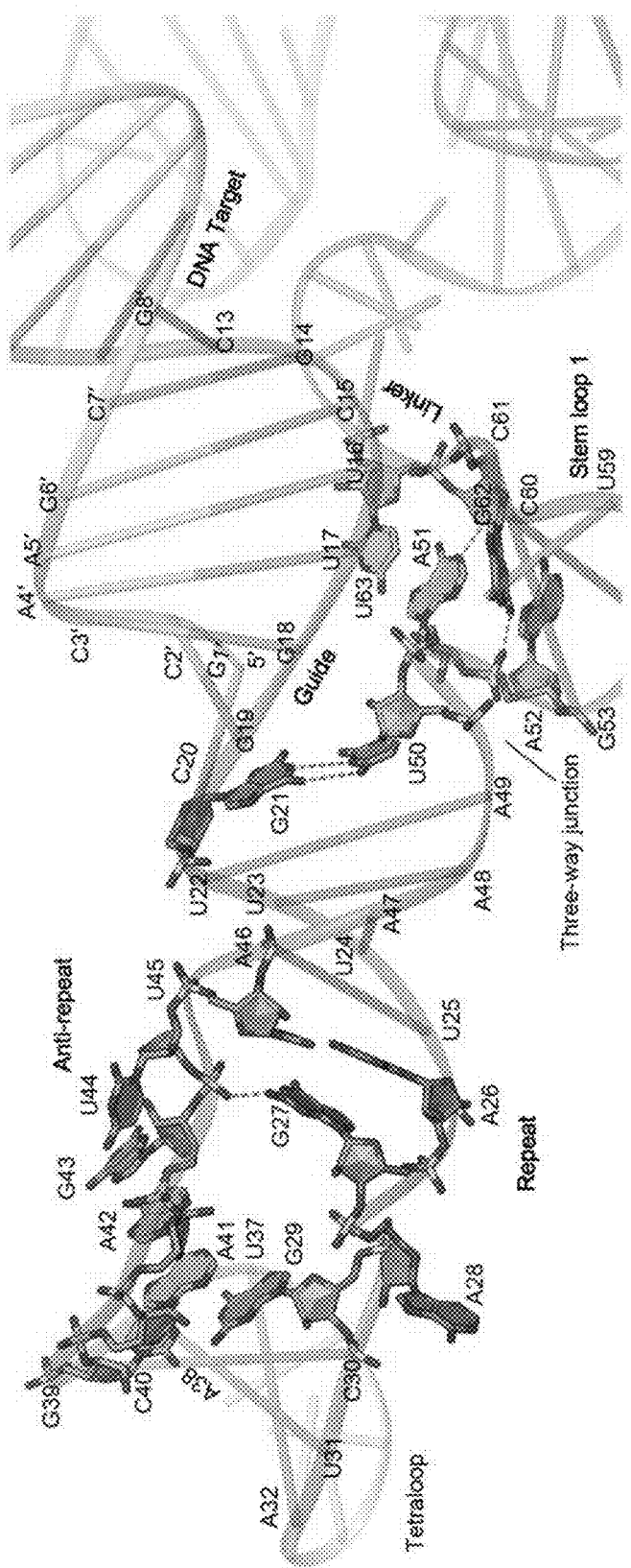
Figure 20:
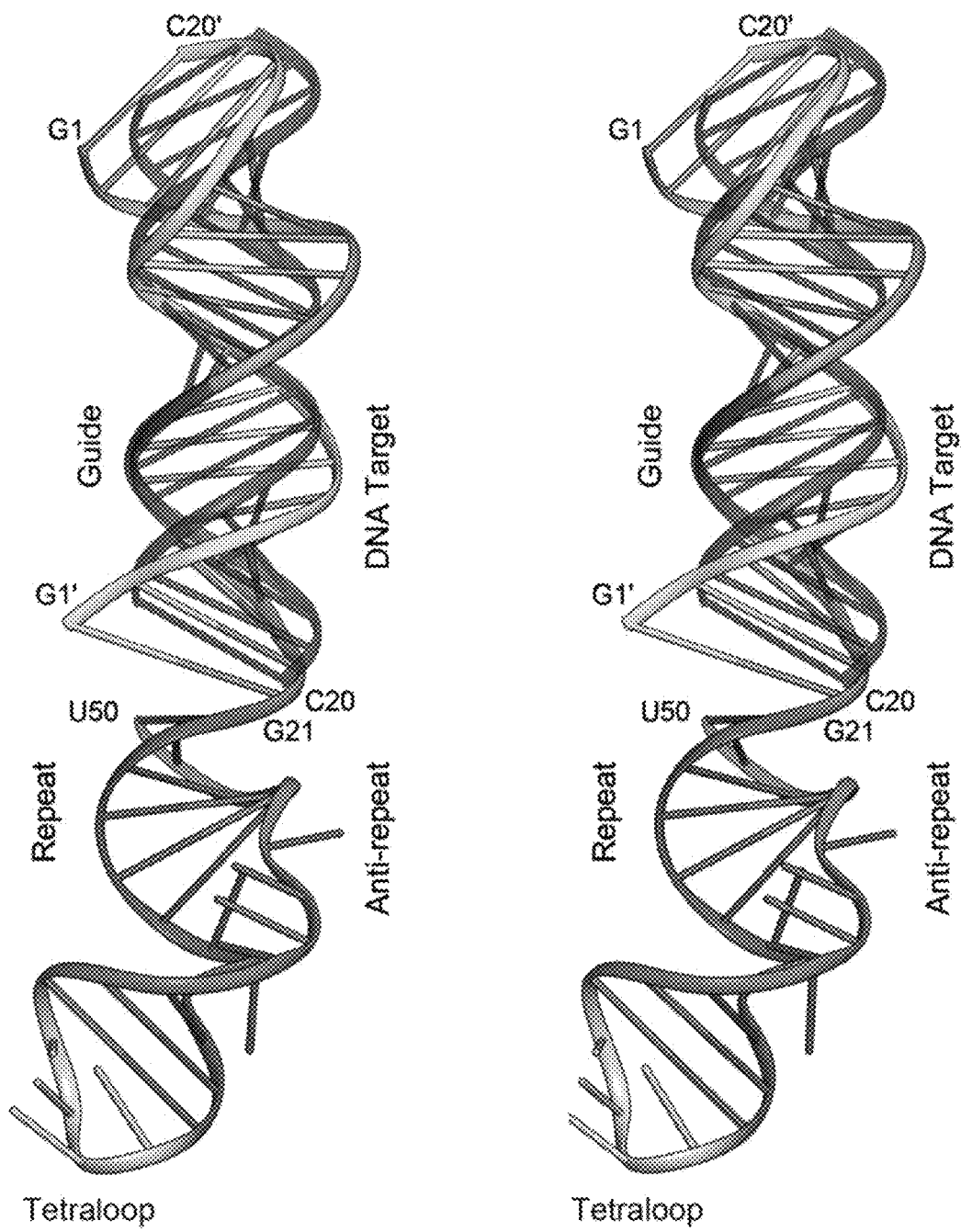
FIG. 20 shows the comparison of the sgRNA:DNA heteroduplex with a canonical A-form RNA duplex. The sgRNA:DNA heteroduplex are superimposed on an A-form RNA duplex based on their phosphorus atoms. The A-form RNA duplex is colored dark gray. Nucleotides 51-97 of the sgRNA are omitted for clarity.

The guide (nucleotides 1-20) and target DNA (nucleotides 3'-23') form the guide:DNA hybrid duplex via 20 Watson-Crick base pairs, with the conformation of the duplex distorted from a canonical A-form RNA duplex (FIGS. 11B and 20). The crRNA repeat (nucleotides 21-32) and tracrRNA anti-repeat (nucleotides 37-50) form the repeat:anti-repeat duplex via nine Watson-Crick base pairs (U22:A49-A26:U45 and G29:C40-A32:U37) (FIG. 11A, B). Within this region, G27, A28, A41, A42, G43, and U44 are unpaired, with A28 and U44 flipped out from the duplex (FIG. 11C). The nucleobases of G27 and A41 stack with the A26:U45 and G29:C40 pairs, respectively, and the 2-amino group of G27 interacts with the backbone phosphate group between G43 and U44, stabilizing the duplex structure (FIG. 11C). G21 and U50 form a wobble base pair at the three-way junction between the guide:DNA/repeat:anti-repeat duplexes and stem loop 1, stabilizing the T-shaped architecture (FIG. 11C).

As expected from the RNA-fold predictions of the nucleotide sequence, the tracrRNA 3' tail (nucleotides 68-81 and 82-96) form stem loops 2 and 3 via four and six Watson-Crick base pairs (A69:U80-U72:A77 and G82:C96-G87:C91), respectively (FIG. 11A, B). Previously unappreciated, nucleotides 52-62 also form a stem loop (stem loop 1) via three Watson-Crick base pairs (G53:C61, G54:C60 and C55:G58), with U59 flipped out from the stem (FIG. 11A, B). Stem loop 1 is stabilized by the G62-G53:C61 stacking interaction and the G62-A51/A52 polar interactions (FIG. 11C).

The guide:DNA and repeat:anti-repeat duplexes are accommodated and deeply buried in a positively-charged groove at the interface of the two lobes, while the rest of the sgRNA extensively interacts with the positively-charged surface on the back side of the protein (FIG. 8D). In Mol A, the 3'-terminal bases of the target DNA (3'-ACC complementary to the PAM) are not visible in the electron density map. In contrast, the two adjacent bases (3'-AC) in Mol B are not recognized by Cas9, although they are structurally ordered due to the crystal packing interactions and are visible in the electron density map. These observations suggest that the 3'-ACC sequence complementary to the PAM (5'-TGG) is not recognized by Cas9, consistent with the previous biochemical data demonstrating that Cas9-catalyzed DNA cleavage requires the 5'-NGG PAM on the non-complementary strand, but not the 3'-NCC sequence on the complementary strand (Jinek et al., 2012).

Previous studies showed that although sgRNA with a 48-nt tracrRNA tail (referred to as sgRNA(+48)) is a minimal region for the Cas9-catalyzed DNA cleavage in vitro (Jinek et al., 2012), sgRNAs with extended tracrRNA tails, sgRNA(+67) and sgRNA(+85), dramatically improved Cas9 cleavage activity in vivo (Hsu et al., 2013). The present structure revealed that sgRNA(+48), sgRNA(+67) and sgRNA(+85) contain stem loop 1, stem loops 1-2 and stem loops 1-3, respectively (FIG. 11A, B). These observations indicated that, whereas stem loop 1 is essential for the formation of the functional Cas9-sgRNA complex, stem loops 2 and 3 further support the stable complex formation as well as enhance sgRNA stability, thus improving the in vivo activity.

Figure 11D:
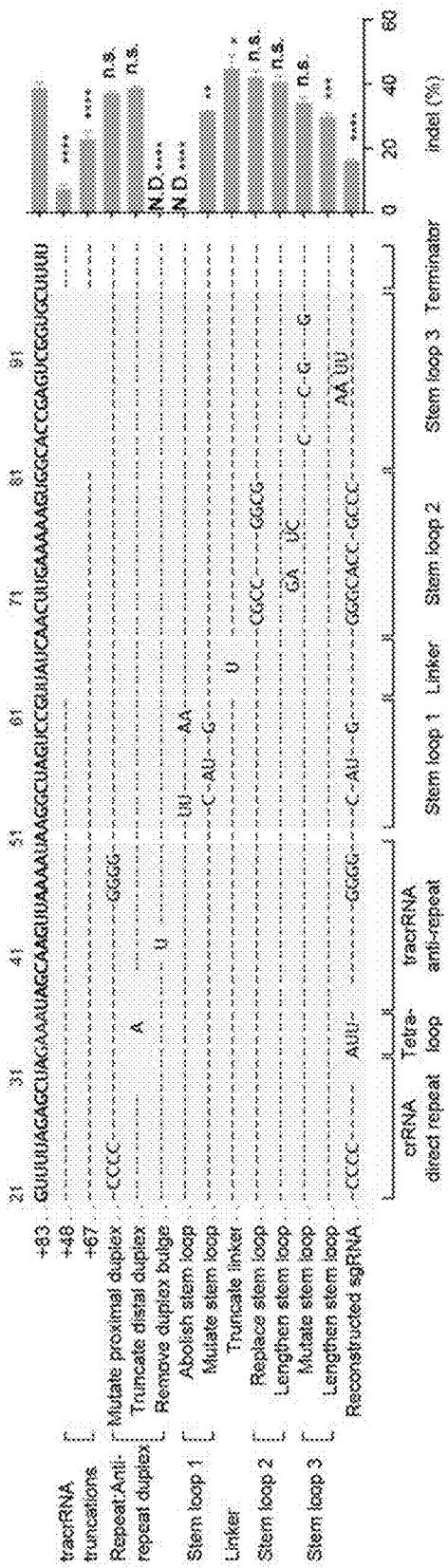

To confirm the significance of each sgRNA structural component on Cas9 function, Applicants tested a number of sgRNAs with mutations in the repeat:anti-repeat duplex, stem loops 1-3, and the linker between stem loops 1 and 2. Applicants' results revealed that, whereas stem loops 2 and 3 as well as the linker region can tolerate a large number of mutations, the repeat:anti-repeat duplex and stem loop 1 are critical for Cas9 function (FIG. 11D). Moreover, the sgRNA sequence can tolerate a large number of mutations (FIG. 11D, reconstructed sgRNA). These results highlight the functional significance of the structure-dependent recognition of the repeat:anti-repeat duplex by Cas9.

Figure 12A:
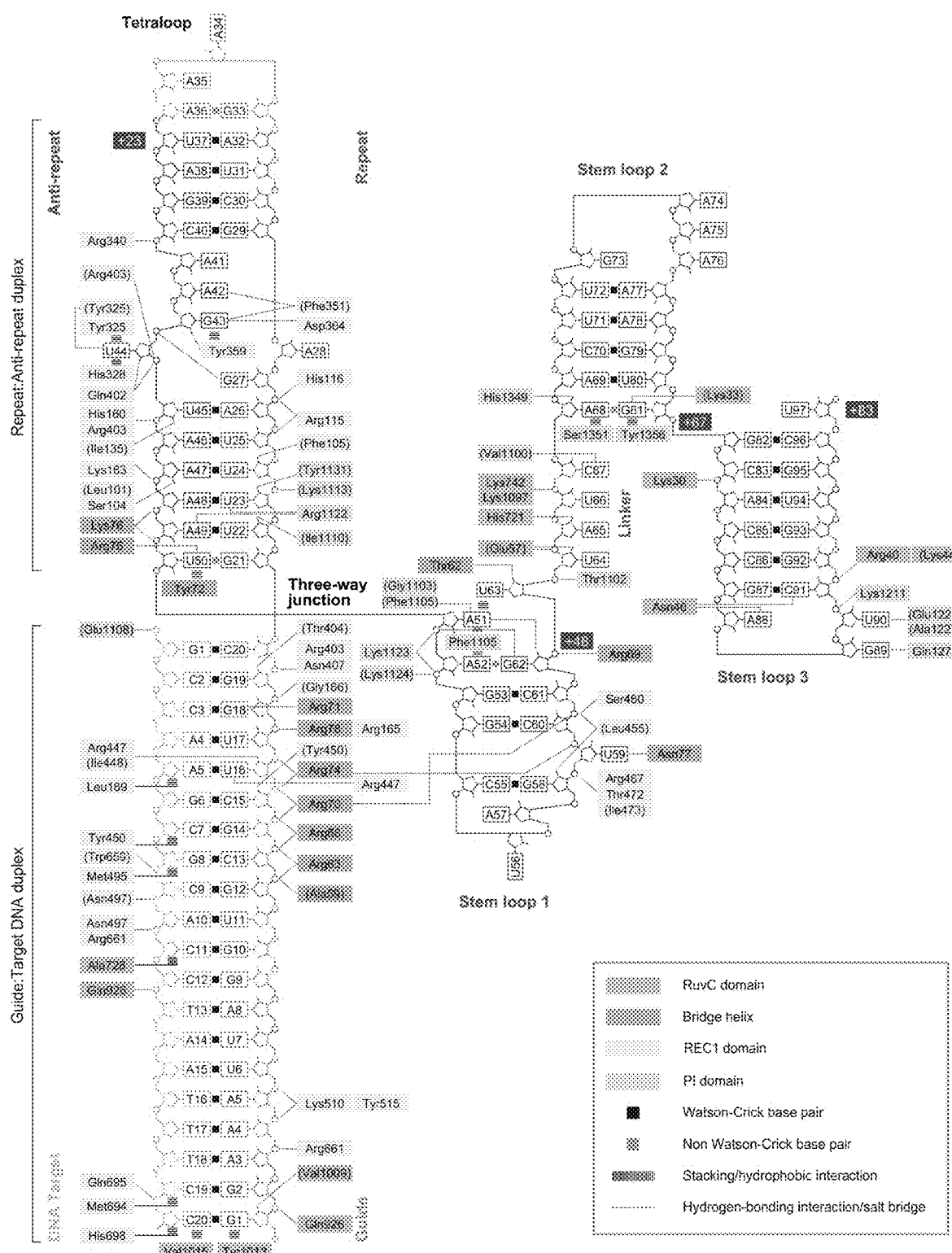

Conserved arginine cluster on Bridge helix play a critical role in sgRNA:DNA interaction: The crRNA guide region is primarily recognized by the REC lobe (FIG. 12A). The backbone phosphate groups of the crRNA guide region (nucleotides 4-6 and 13-20) interact with the REC1 domain (Arg165, Gly166, Arg403, Asn407, Lys510, Tyr515 and Arg661) and Bridge helix (Ala59, Arg63, Arg66, Arg70, Arg71, Arg74 and Arg78) (FIG. 12B), and the 2'-hydroxyl groups of C15, U16 and G19 hydrogen bond with Tyr450, Arg447/Ile448 and Thr404 in the REC1 domain (FIG. 12B), respectively. These observations suggested that the Watson-Crick faces of eight PAM-proximal nucleotides of the Cas9-bound sgRNA are exposed to the solvent, thus serving as a nucleation site for pairing with the target complementary strand. This is consistent with previous reports that the 10-12 bp PAM-proximal "seed" region is critical for Cas9-catalyzed DNA cleavage (Cong et al., 2013; Fu et al., 2013; Hsu et al., 2013; Jinek et al., 2012; Mali et al., 2013a; Pattanayak et al., 2013).

Mutational analysis demonstrated that the R66A, R70A and R74A mutations on Bridge helix markedly reduced DNA cleavage activities (FIG. 12C), highlighting the functional significance of the recognition of the sgRNA "seed" region by the Bridge helix. Although Arg78 and Arg165 also interact with the "seed" region, the R78A and R165A mutants showed only moderately decreased activities (FIG. 12C). These results may reflect that, whereas Arg66, Arg70 and Arg74 form bifurcated salt bridges with the sgRNA backbone, Arg78 and Arg165 form a single salt bridge with the sgRNA backbone. A cluster of arginine residues on the Bridge helix are highly conserved among Cas9 proteins in the Type II-A-C systems (FIGS. 18, 19), suggesting that the Bridge helix is a universal structural feature of Cas9 proteins involved in recognition of the sgRNA and target DNA. This notion is supported by a previous observation that a strictly conserved arginine residue, equivalent to Arg70 of *S. pyogenes* Cas9, is essential for the function of *Francisella novicida* Cas9 in the Type II-B system (Sampson et al., 2013). Moreover, the alanine mutation of the repeat:anti-repeat duplex-interacting residues (Arg75 and Lys163) and stem loop 1-interacting residue (Arg69) resulted in decreased DNA cleavage activity (FIG. 12C), confirming the functional importance of the recognition of the repeat:anti-repeat duplex and stem loop 1 by Cas9.

The crRNA guide region is recognized by Cas9 in a sequence-independent manner except for the U16-Arg447 and G18-Arg71 interactions (FIG. 12A, B). This base-specific G18-Arg71 interaction may partly explain the observed preference of Cas9 for sgRNAs having guanines in the four PAM-proximal guide sequences (Wang et al., 2014). The REC1 and RuvC domains facilitate RNA-guided DNA targeting: Cas9 recognizes the 20-bp DNA target site in a sequence-independent manner (FIG. 12A). The backbone phosphate groups of the target DNA (nucleotides 1', 9'-11', 13', and 20') interact with the REC1 (Asn497, Trp659, Arg661 and Gln695), RuvC (Gln926), and PI (Glu1108) domains. The C2' atoms of the target DNA (nucleotides 5', 7', 8', 11', 19', and 20') form van der Waals interactions with the REC1 domain (Leu169, Tyr450, Met495, Met694 and His698) and RuvC domain (Ala728) (FIG. 12D). These interactions are likely to contribute towards discriminating between DNA vs. RNA targets by Cas9. The terminal base pair of the guide:DNA duplex (G1:C20') is recognized by the RuvC domain via end-capping interactions (FIG. 12D); the nucleobases of sgRNA G1 and target DNA C20' interact with the side chains of Tyr1013 and Val1015, respectively, whereas the 2'-hydroxyl and phosphate groups of sgRNA G1 interact with Val1009 and Gln926, respectively. These end-capping interactions are consistent with the previous observation that Cas9 recognizes a 17-20-bp guide:DNA duplex, and that extended guide sequences are degraded in cells and do not contribute to improving sequence specificity (Mali et al., 2013a; Ran et al., 2013). Taken together, these structural findings explain the RNA-guided DNA targeting mechanism of Cas9.

The repeat:anti-repeat duplex is recognized by the REC and NUC lobes in a sequence-dependent manner: The repeat:anti-repeat duplex is extensively recognized by the REC and NUC lobes (FIG. 12A). The backbone phosphate groups of the crRNA repeat (nucleotides 24, 26, and 27) and anti-repeat (nucleotides 41, 45, 46, and 48-50) interact with the REC1 domain (Arg115, His116, His160, Lys163, Arg340, and Arg403), PI domain (Lys1113), and Bridge helix (Lys76) (FIG. 12E, F). The 2'-hydroxyl groups of the crRNA repeat (nucleotides 22-24) and anti-repeat (nucleotides 43-45 and 47) hydrogen bond with the REC1 domain (Leu101, Ser104, Phe105, Ile135, Tyr359, and Gln402) and the PI domain (Ile1110 and Tyr1131).

In contrast to the sequence-independent recognition of the guide region, there are sequence-dependent interactions between Cas9 and the repeat:anti-repeat duplex. The nucleobase of the flipped U44 is sandwiched between the side chains of Tyr325 and His328, with its N3 atom hydrogen bonded with the carbonyl group of Tyr325, while that of unpaired G43 stacks with the side chain of Tyr359 and hydrogen bonds with the side chain of Asp364 (FIG. 12A, F). Finally, the nucleobases of U23/A49 and A42/G43 hydrogen bond with the side chain of Arg1122 and the main-chain carbonyl group of Phe351, respectively.

In the present structure, the repeat:anti-repeat duplex is recognized primarily by the REC lobe, which is divergent in sequence and length among Cas9 orthologs within the Type II-A-C systems (FIGS. 18, 19), consistent with the previous observation that Cas9 and sgRNA are interchangeable only between closely related Type II systems (Fonfara et al., 2013). The three PAM-distal base pairs (C30:G39-A32:U37) are not recognized by Cas9 and protrude from the complex (FIG. 12A), consistent with a proposed model in which a Cas9-bound repeat:anti-repeat duplex is processed by the host RNase III enzyme (Deltcheva et al., 2011).

The nucleobases of G21 and U50 in the G21:U50 wobble pair stack with the terminal C20:G1' pair in the guide:DNA duplex and the side chain of Tyr72 on Bridge helix, respectively, with the U50 O4 atom hydrogen bonded with the side chain of Arg75 (FIG. 12E). Notably, A51 adopts the syn-conformation, and is oriented in the direction opposite to U50 (FIGS. 11C and 12G). The nucleobase of A51 is sandwiched between the Phe1105 side chain in the PI domain and the U63 nucleobase in the linker, with its N7 and N1 atoms hydrogen bonded with the main-chain amide group of Phe1105 and the G62 2'-hydroxyl group in stem loop 1, respectively (FIG. 12G). Whereas a repeat:anti-repeat duplex is diverse in sequence and length among the Type II-A-C systems, the G21:U50 base pair is highly conserved among Cas9s (Fonfara et al., 2013), suggesting that this wobble pairing is a universal structural feature involved in the three-way junction formation.

To verify the sequence-dependent recognition of the repeat:anti-repeat duplex, Applicants evaluated the effect of repeat:anti-repeat mutations on Cas9-meditated DNA cleavage, and found multiple mutations that significantly reduce Cas9 activity (FIG. 12C). Notably, replacement of G43, which forms a base-specific hydrogen bond with Asp364, with adenine reduced Cas9 activity by over 3-fold. In addition, replacement of the flipped U44 in the repeat:anti-repeat duplex with adenine resulted in over a 5-fold drop in cleavage activity, whereas replacement of U44 with another pyrimidine base (cytosine) did not significantly affect cleavage activity (FIG. 12C). These results suggest that base-specific recognition of G43 and U44 could play an important role in sgRNA recognition by Cas9.

sgRNA stem loops 1-3 interact with Cas9: Stem loop 1 is primarily recognized by the REC lobe together with the PI domain (FIG. 12A). The backbone phosphate groups of stem loop 1 (nucleotides 52, 53, and 59-61) interact with the REC1 domain (Leu455, Ser460, Arg467, Thr472, and Ile473), PI domain (Lys1123 and Lys1124), and Bridge helix (Arg70 and Arg74), with the 2'-hydroxyl group of G58 hydrogen bonded with Leu455 in the REC1 domain. A52 interacts with Phe1105 through a face-to-edge π-π stacking interaction (FIG. 12G), and the flipped U59 nucleobase hydrogen bonds with the side chain of Asn77 (FIG. 12H).

Stem loops 2 and 3, and the single-stranded linker are primarily recognized by the NUC lobe (FIG. 12A); this contrasts with stem loop 1 and the guide:DNA/repeat:anti-repeat duplexes, which are recognized by both of the NUC and REC lobes. The backbone phosphate groups of the linker (nucleotides 63-65 and 67) interact with the RuvC domain (Glu57, Lys742, and Lys1097), PI domain (Thr1102), and Bridge helix (Arg69), with the 2'-hydroxyl groups of U64 and A65 hydrogen bonded with Glu57 and His721, respectively (FIG. 12I). The nucleobase of C67 hydrogen bonds with the main-chain amide group of Val1100 (FIG. 12I).

Stem loop 2 is recognized by Cas9 via the interactions between the NUC lobe and the non-Watson-Crick A68:G81 pair, which is formed by direct (between the A68 N6 and G81 O6 atoms) and water-mediated (between the A68 N1 and G81 N1 atoms) hydrogen-bonding interactions (FIG. 12J). The nucleobases of A68 and G81 contact the side chains of Ser1351 and Tyr1356, respectively, with the A68:G81 pair recognized by Thr1358 via a water-mediated hydrogen bond (FIG. 12J). The 2'-hydroxyl group of A68 hydrogen bonds with the side chain of His1349, and the 2-amino group of G81 hydrogen bonds with the main-chain carbonyl group of Lys33 (FIG. 12J).

Stem loop 3 interacts with the NUC lobe more extensively relative to stem loop 2 (FIG. 12K). The backbone phosphate groups of C91 and G92 interact with the RuvC domain (Arg40 and Lys44) (FIG. 12K), while the nucleobases of G89 and U90 hydrogen bond with Gln1272 and Glu1225/Ala1227, respectively (FIG. 12K). The nucleobases of A88 and C91 are recognized by the side chain of Asn46 via multiple hydrogen-bonding interactions (FIG. 12K).

Figure 13A:
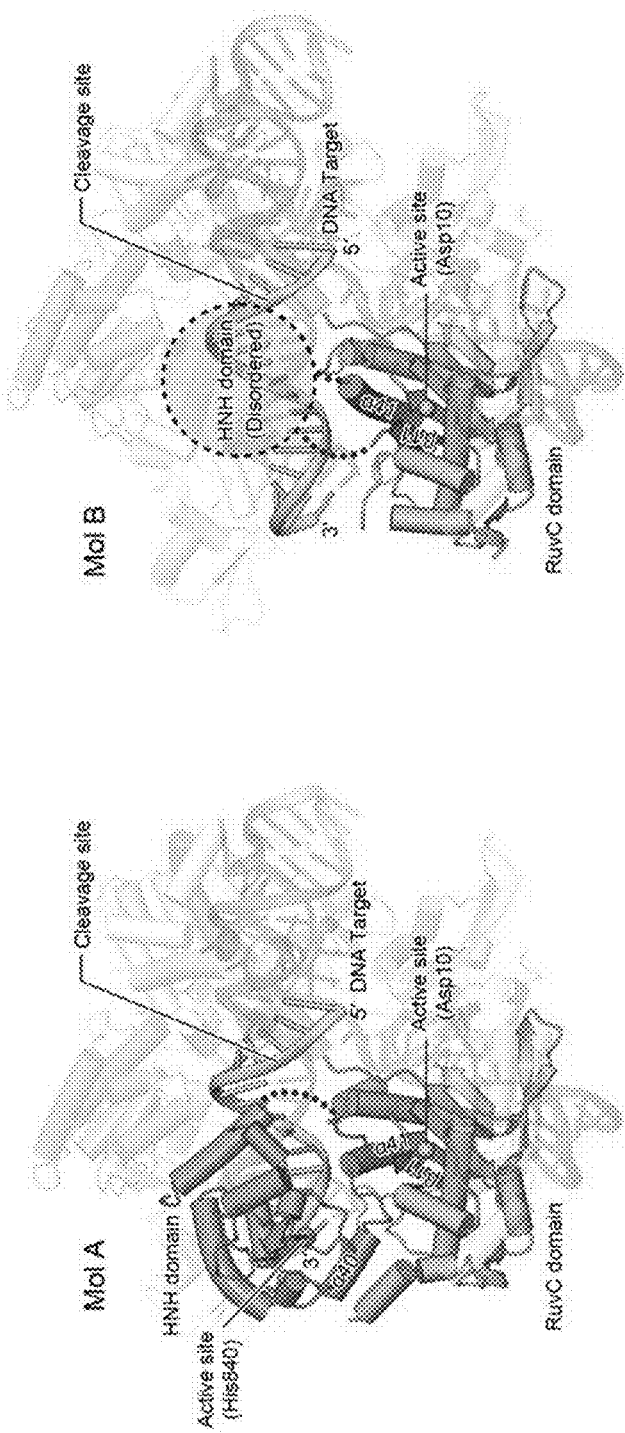
FIG. 13A-D shows Structural flexibility of the complex. (A) Structural comparison of Mol A and Mol B. In Mol A (left), disordered linker between the RuvC and HNH domain is indicated by a dotted line. In Mol B (right), the disordered HNH domain is shown as a dashed circle. The flexible connecting segment (α40 and α41) in the RuvC domain is highlighted in orange. (B) Superimposition of the Cas9 proteins in Mol A and Mol B. The two complexes are superimposed based on the core β-sheet of their RuvC domains. The HNH domain and bound sgRNA:DNA are omitted for clarity. (C) Superimposition of the bound sgRNA:DNA in Mol A and Mol B. After superimposition of the two complexes as in (B), the Cas9 proteins are omitted to show the sgRNA:DNA. (D) Molecular surface of Cas9. The HNH domain and bound sgRNA:DNA complex are omitted for clarity. Note that there is no direct contact between the REC and NUC lobes, expect for the interactions between the a2-α3 loop and 1317-1318 loop.

Structural flexibility of Cas9 and sgRNA: Although the HNH domain cleaves the complementary strand of the target DNA at a position three nucleotides upstream of the PAM sequence (Gasiunas et al., 2012; Jinek et al., 2012), in the present structure the HNH domain is positioned away from the scissile phosphate group of the bound complementary strand (FIG. 13A). A structural comparison of Mol A and Mol B provided mechanistic insights into the complementary strand cleavage by the HNH domain. In Mol A, the HNH domain is followed by the α40 helix of the RuvC domain, which is connected with the α41 helix by an α40-α41 linker (residues 919-925) (FIG. 13A). Whereas in Mol A residues 913-925 form the C-terminal portion of the α43 helix and α43-α44 linker, in Mol B these residues form an extended α-helix, which is directed toward the cleavage site of the complementary strand (FIG. 13A). These observations suggest that the HNH domain can approach and cleave the target DNA through conformational changes in the segment connecting the HNH and RuvC domains.

Figure 13B:
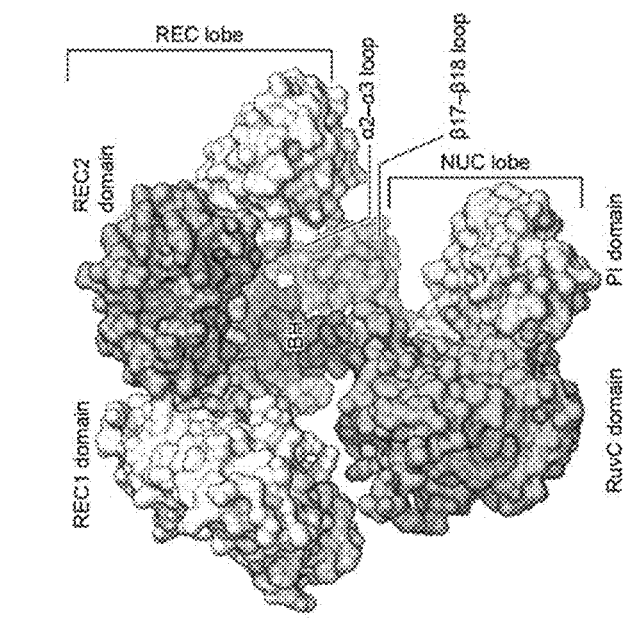
Figure 13C:
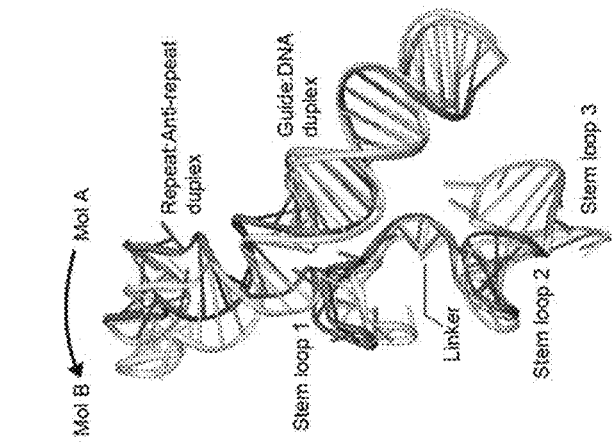
Figure 13D:
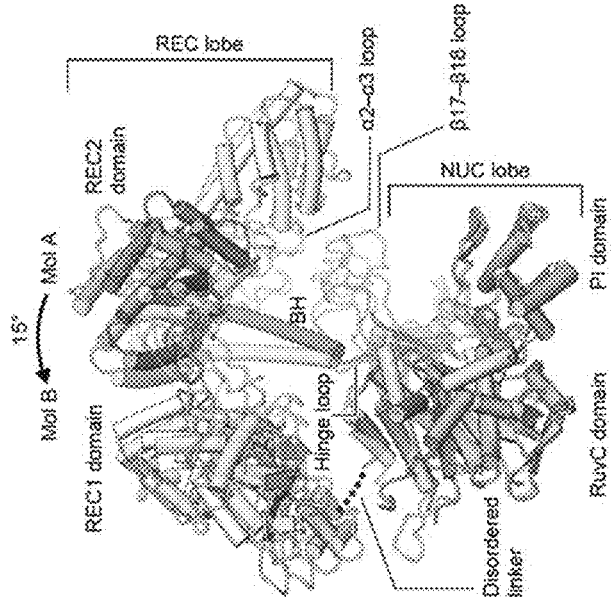

Moreover, the structural comparison revealed a conformational flexibility between the REC and NUC lobes (FIG. 13B). Compared to Mol A, Mol B adopts a more open conformation, in which the two lobes are rotated by 15° at a hinge loop between Bridge helix and the strand β5 in the RuvC domain (FIG. 13B). The bound sgRNA also undergoes an accompanying conformational change at the single-stranded linker, which interacts with the hinge loop (FIG. 13C). Applicants also observed an accompanying displacement of the β17-β18 loop of the PI domain, which interacts with the repeat:anti-repeat duplex and the α2-α3 loop of the REC1 domain (FIG. 13B). Notably, there is no direct contact between the two lobes in the present structure, except for the interactions between the α2-α3 and β17-β18 loops (FIG. 13D), suggesting that Cas9 is highly flexible in the absence of the sgRNA. The flexible nature of Cas9 is likely to play a role in the assembly of the Cas9-sgRNA-DNA ternary complex.

The crystal structure of Cas9 in complex with guide RNA and target DNA reveals that the 20-bp heteroduplex formed by the crRNA guide region and the complementary strand of the target DNA is accommodated in the positively-charged groove at the interface between the REC and NUC lobes of Cas9, with the scissile phosphate group of the target properly positioned for cleavage by the HNH domain. Although the present structure does not contain the non-complementary DNA strand, the position of the bound complementary strand suggests that the scissile phosphate of the non-complementary strand is located in the vicinity of the active site of the RuvC domain, consistent with previous biochemical data (Gasiunas et al., 2012; Jinek et al., 2012). Furthermore, Applicants' structural and functional analyses indicate that the PI domain participates in the recognition of the PAM sequence of the non-complementary strand.

Figure 14:
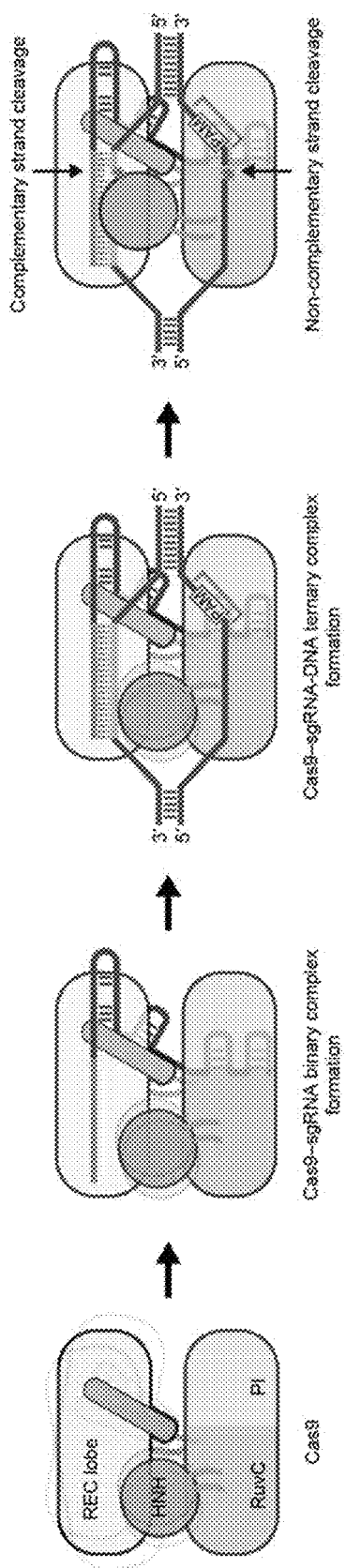
FIG. 14 shows a Model of RNA-guided DNA cleavage by Cas9.

Based on these observations, Applicants propose a model for the Cas9-catalyzed RNA-guided DNA cleavage (FIG. 14). Cas9 recognizes the PAM-proximal guide region and repeat:anti-repeat duplex of sgRNA to form a Cas9-sgRNA binary complex. The binary complex subsequently recognizes the DNA sequence complementary to the 20-nt guide region of the bound sgRNA, forming the final Cas9-sgRNA-target DNA ternary complex. During the ternary complex formation, the PI domain recognizes the PAM sequence of the non-complementary strand, facilitating the R-loop formation. Upon assembly of the ternary complex, the mobile HNH domain approaches and cleaves the complementary strand in the guide:DNA duplex, whereas the RuvC domain cleaves the single-stranded, non-complementary strand.

Applicants' crystal structure provides a critical step towards understanding the molecular mechanism of RNA-guided DNA targeting by Cas9. Further structural and functional studies with *S. pyogenes* Cas9 or related orthologs, including the structural determination of the Cas9-sgRNA-DNA ternary complex containing the non-complementary strand, may be important for illuminating details such as Cas9-mediated recognition of PAM sequences on the target DNA or mismatch tolerance between the sgRNA:DNA duplex. However, the present structural and functional analyses already provide a useful scaffold for rational engineering of Cas9-based genome modulating technologies. Applicants reported, for example, an *S. pyogenes* Cas9 truncation mutant (FIG. 9B) that will facilitate packaging of Cas9 into size-constrained viral vectors for in vivo and therapeutic applications. Similarly, future engineering of the PI domain allows for programming of PAM specificity, improving target site recognition fidelity, and increasing the versatility of the Cas9 genome engineering platform.

Experimental Procedures

Protein preparation: The gene encoding full-length *S. pyogenes* Cas9 (residues 1-1368) was cloned between the NdeI and XhoI sites of the modified pCold-GST vector (TaKaRa). The protein was expressed at 20° C. in *Escherichia coli* Rosetta 2 (DE3) (Novagen), and was purified by Ni-NTA Superflow resin (QIAGEN). The eluted protein was incubated overnight at 4° C. with TEV protease to remove the GST-tag, and further purified by chromatography on Ni-NTA, Mono S (GE Healthcare) and HiLoad Superdex 200 16/60 (GE Healthcare) columns. The SeMet-labeled protein was prepared using a similar protocol for the native protein. The sgRNA was in vitro transcribed by T7 polymerase using a PCR-amplified template, and was purified on 10% denaturing polyacrylamide gel electrophoresis. The target DNA was purchased from Sigma-Aldrich. The purified Cas9 protein was mixed with sgRNA and DNA (molar ratio 1:1.5:2), and then the complex was purified using a Superdex 200 Increase column (GE Healthcare) in a buffer containing 10 mM Tris-HCl, pH 8.0, 150 mM NaCl and 1 mM DTT.

Crystallography: The purified Cas9-sgRNA-DNA complex was crystallized at 20° C. by the hanging-drop vapor diffusion method. Crystals were obtained by mixing 1 μl of complex solution ($A_{260\ nm}$=15) and 1 μl of reservoir solution (12% PEG 3,350, 100 mM Tris-HCl, pH 8.0, 200 mM ammonium acetate, 150 mM NaCl and 100 mM NDSB-256). The SeMet-labeled protein was crystallized under conditions similar to those for the native protein. X-ray diffraction data were collected at 100 K on the beamlines BL32XU and BL41XU at SPring-8 (Hyogo, Japan). The crystals were cryoprotected in reservoir solution supplemented with 25% ethylene glycol. X-ray diffraction data were processed using XDS (Kabsch, 2010). The structure was determined by the SAD method, using the 2.8 Å resolution data from the SeMet-labeled crystal. Forty of the potential 44 Se atoms were located using SHELXD (Sheldrick, 2008) and autoSHARP (delaFortelle and Bricogne, 1997). The initial phases were calculated using autoSHARP, and further improved by 2-fold NCS averaging using DM (Winn et al., 2011). The model was automatically built using PHENIX AutoSol (Adams et al., 2002), followed by manual model building using COOT (Emsley and Cowtan, 2004) and refinement using PHENIX (Adams et al., 2002). The resulting model was further refined using for native 2.4 Å resolution data.

Cell culture and transfection: Human embryonic kidney (HEK) cell line 293FT (Life Technologies) or mouse Neuro 2a (Sigma-Aldrich) cell line was maintained in Dulbecco's modified Eagle's Medium (DMEM) supplemented with 10% fetal bovine serum (HyClone), 2 mM GlutaMAX (Life Technologies), 100 U/ml penicillin, and 100 µg/ml streptomycin at 37° C. with 5% $CO_2$ incubation. Cells were seeded onto 24-well plates (Corning) at a density of 120,000 cells/well, 24 h prior to transfection. Cells were transfected using Lipofectamine 2000 (Life Technologies) at 70-80% confluency following the manufacturer's recommended protocol. A total of 400 ng Cas9 plasmid and 100 ng of U6:sgRNA PCR product was transfected.

SURVEYOR nuclease assay for genome modification: 293FT cells were transfected with DNA as described above. Cells were incubated at 37° C. for 72 h post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 min, 68° C. for 15 min, and 98° C. for 10 min.

The genomic region flanking the CRISPR target site for each gene was PCR amplified, and products were purified using QiaQuick Spin Column (Qiagen) following the manufacturer's protocol. 400 ng total of the purified PCR products were mixed with 2 µl 10× Taq DNA Polymerase PCR buffer (Enzymatics) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 min and imaged with a Gel Doc gel imaging system (Bio-rad). Quantification was based on relative band intensities. Indel percentage was determined by the formula, $100\times(1-(1-(b+c)/(a+b+c))^{1/2})$, where a is the integrated intensity of the undigested PCR product, and b and c are the integrated intensities of each cleavage product.

Western blot: HEK 293FT cells were transfected and lysed in 1×RIPA buffer (Sigma-Aldrich) supplemented with Protease Inhibitor (Roche). Lysates were loaded onto Bolt 4-12% Bis-Tris Plus Gel (Invitrogen) and transferred to nitrocellulose membranes. Membranes were blocked in Tris-buffered saline containing 0.1% Tween-20 and 5% blocking agent (G-Biosciences). Membrane was probed with rabbit anti-FLAG (1:5000, Abcam), HRP-conjugated anti-GAPDH (1:5,000 Cell Signaling Technology), and HRP-conjugated anti-rabbit (1:1000). Blots were visualized on Gel Doc XR+ System (Bio-rad).

Sequence Information:

```
Italic: 3XFLAG sequence
Underlined: NLS sequences
```

Wildtype SpCas9

```
ATGGACTATAAGGACCACGACGGAGACTACAAGGATCATGATATTGATTACAAAGACGATGACGATAAGATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATCGCCCAGCTGCCCGGCGAGAAGAAGAATGGCCTGTTCGGCAAC
CTGATTGCCCTGAGCCTGGGCCTGACCCCCAACTTCAAGAGCAACTTCGACCTGGCCGAGGATGCCAAACTGCAGCTGAGCAAGGACACCTAC
GACGACGACCTGGACAACCTGCTGGCCCAGATCGGCGACCAGTACGCCGACCTGTTTCTGGCCGCCAAGAACCTGTCCGACGCCATCCTGCTG
AGCGACATCCTGAGAGTGAACACCGAGATCACCAAGGCCCCCCTGAGCGCCTCTATGATCAAGAGATACGACGAGCACCACCAGGACCTGACC
CTGCTGAAAGCTCTCGTGCGGCAGCAGCTGCCTGAGAAGTACAAAGAGATTTTCTTCGACCAGAGCAAGAACGGCTACGCCGGCTACATTGAC
GGCGGAGCCAGCCAGGAAGAGTTCTACAAGTTCATCAAGCCCATCCTGGAAAAGATGGACGGCACCGAGGAACTGCTCGTGAAGCTGAACAGA
GAGGACCTGCTGCGGAAGCAGCGGACCTTCGACAACGGCAGCATCCCCCACCAGATCCACCTGGGAGAGCTGCACGCCATTCTGCGGCGGCAG
GAAGATTTTTACCCATTCCTGAAGGACAACCGGGAAAAGATCGAGAAGATCCTGACCTTCCGCATCCCCTACTACGTGGGCCCTCTGGCCAGG
GGAAACAGCAGATTCGCCTGGATGACCAGAAAGAGCGAGGAAACCATCACCCCCTGGAACTTCGAGGAAGTGGTGGACAAGGGCGCTTCCGCC
CAGAGCTTCATCGAGCGGATGACCAACTTCGATAAGAACCTGCCCAACGAGAAGGTGCTGCCCAAGCACAGCCTGCTGTACGAGTACTTCACC
GTGTATAACGAGCTGACCAAAGTGAAATACGTGACCGAGGGAATGAGAAAGCCCGCCTTCCTGAGCGGCGAGCAGAAAAAGGCCATCGTGGAC
CTGCTGTTCAAGACCAACCGGAAAGTGACCGTGAAGCAGCTGAAAGAGGACTACTTCAAGAAAATCGAGTGCTTCGACTCCGTGGAAATCTCC
GGCGTGGAAGATCGGTTCAACGCCTCCCTGGGCACATACCACGATCTGCTGAAAATTATCAAGGACAAGGACTTCCTGGACAATGAGGAAAAC
GAGGACATTCTGGAAGATATCGTGCTGACCCTGACACTGTTTGAGGACAGAGAGATGATCGAGGAACGGCTGAAAACCTATGCCCACCTGTTC
GACGACAAAGTGATGAAGCAGCTGAAGCGGCGGAGATACACCGGCTGGGGCAGGCTGAGCCGGAAGCTGATCAACGGCATCCGGGACAAGCAG
TCCGGCAAGACAATCCTGGATTTCCTGAAGTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGGCACAAGCCCGAGAACATCGTGATCGAAATGGCCAGAGAGAAC
CAGACCACCCAGAAGGGACAGAAGAACAGCCGCGAGAGAATGAAGCGGATCGAAGAGGGCATCAAAGAGCTGGGCAGCCAGATCCTGAAAGAA
CACCCCGTGGAAAACACCCAGCTGCAGAACGAGAAGCTGTACCTGTACTACCTGCAGAATGGGCGGGATATGTACGTGGACCAGGAACTGGAC
ATCAACCGGCTGTCCGACTACGATGTGGACCATATCGTGCCTCAGAGCTTTCTGAAGGACGACTCCATCGACAACAAGGTGCTGACCAGAAGC
```

-continued

```
GACAAGAACCGGGGCAAGAGCGACAACGTGCCCTCCGAAGAGGTCGTGAAGAAGATGAAGAACTACTGGCGGCAGCTGCTGAACGCCAAGCTG
ATTACCCAGAGAAAGTTCGACAATCTGACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACTAAGTACGACGAGAATGACAAGCTGATCCGGGAAGTG
AAAGTGATCACCCTGAAGTCCAAGCTGGTGTCCGATTTCCGGAAGGATTTCCAGTTTTACAAAGTGCGCGAGATCAACAACTACCACCACGCC
CACGACGCCTACCTGAACGCCGTCGTGGGAACCGCCCTGATCAAAAAGTACCCTAAGCTGGAAAGCGAGTTCGTGTACGGCGACTACAAGGTG
TACGACGTGCGGAAGATGATCGCCAAGAGCGAGCAGGAAATCGGCAAGGCTACCGCCAAGTACTTCTTCTACAGCAACATCATGAACTTTTTC
AAGACCGAGATTACCCTGGCCAACGGCGAGATCCGGAAGCGGCCTCTGATCGAGACAAACGGCGAAACCGGGGAGATCGTGTGGGATAAGGGC
CGGGATTTTGCCACCGTGCGGAAAGTGCTGAGCATGCCCCAAGTGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGACTGGGACCCTAAGAAGTACGGCGGCTTCGACAGCCCCACCGTG
GCCTATTCTGTGCTGGTGGTGGCCAAAGTGGAAAAGGGCAAGTCCAAGAAACTGAAGAGTGTGAAAGAGCTGCTGGGGATCACCATCATGGAA
AGAAGCAGCTTCGAGAAGAATCCCATCGACTTTCTGGAAGCCAAGGGCTACAAAGAAGTGAAAAAGGACCTGATCATCAAGCTGCCTAAGTAC
TCCCTGTTCGAGCTGGAAAACGGCCGGAAGAGAATGCTGGCCTCTGCCGGCGAACTGCAGAAGGGAAACGAACTGGCCCTGCCCTCCAAATAT
GTGAACTTCCTGTACCTGGCCAGCCACTATGAGAAGCTGAAGGGCTCCCCCGAGGATAATGAGCAGAAACAGCTGTTTGTGGAACAGCACAAG
CACTACCTGGACGAGATCATCGAGCAGATCAGCGAGTTCTCCAAGAGAGTGATCCTGGCCGACGCTAATCTGGACAAAGTGCTGTCCGCCTAC
AACAAGCACCGGGATAAGCCCATCAGAGAGCAGGCCGAGAATATCATCCACCTGTTTACCCTGACCAATCTGGGAGCCCCTGCCGCCTTCAAG
TACTTTGACACCACCATCGACCGGAAGAGGTACACCAGCACCAAAGAGGTGCTGGACGCCACCCTGATCCACCAGAGCATCACCGGCCTGTAC
GAGACACGGATCGACCTGTCTCAGCTGGGAGGCGACAAAAAGGCCGGCGGCCACGAAAAGGCCGGCCAGGCAAAAAAGAAAAAG
(SEQ ID NO: 76)
```

Sp_del(97-150)

```
ATGGACTATAAGGACCACGACGGAGACTACAAGGATCATGATATTGATTACAAAGACGATGACGATAAGATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCCTGCGGCTGCTATCTGCCCTGGCCCACATGATCAAGTTCCGGGGCCACTTCCTGATC
GAGGGCGACCTGAACCCCGACAACAGCGACGTGGACAAGCTGTTCATCCAGCTGGTGCAGACATACAACCAGCTGTTCGAGGAAAACCCCATC
AACGCCAGCGGCGTGGACGCCAAGGCCATCCTGTCTGCCAGACTGAGCAAGAGCAGACGGCTGGAAAATCTGATCGCCCAGCTGCCCGGCGAG
AAGAAGAATGGCCTGTTCGGAAACCTGATTGCCCTGAGCCTGGGCCTGACCCCCAACTTCAAGAGCAACTTCGACCTGGCCGAGGATGCCAAA
CTGCAGCTGAGCAAGGACACCTACGACGACGATCTGGACAACCTGCTGGCCCAGATCGGCGACCAGTACGCCGACCTGTTTCTGGCCGCCAAG
AACCTGTCCGACGCCATCCTGCTGAGCGACATCCTGAGAGTGAACACCGAGATCACCAAGGCCCCCCTGAGCGCCTCTATGATCAAGAGATAC
GACGAGCACCACCAGGACCTGACCCTGCTGAAAGCTCTCGTGCGGCAGCAGCTGCCTGAGAAGTACAAAGAGATTTTCTTCGACCAGAGCAAG
AACGGCTACGCCGGCTACATTGACGGCGGAGCCAGCCAGGAAGAGTTCTACAAGTTCATCAAGCCCATCCTGGAAAAGATGGACGGCACCGAG
GAACTGCTCGTGAAGCTGAACAGAGAGGACCTGCTGCGGAAGCAGCGGACCTTCGACAACGGCAGCATCCCCCACCAGATCCACCTGGGAGAG
CTGCACGCCATTCTGCGGCGGCAGGAAGATTTTTACCCATTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGAAAGAGCGAGGAAACCATCACCCCCTGGAACTTCGAGGAA
GTGGTGGACAAGGGCGCTTCCGCCCAGAGCTTCATCGAGCGGATGACCAACTTCGATAAGAACCTGCCCAACGAGAAGGTGCTGCCCAAGCAC
AGCCTGCTCTACGAGTACTTCACCGTGTATAACGAGCTGACCAAAGTGAAATACGTGACCGAGGGAATGAGAAAGCCCGCCTTCCTGAGCGGC
GAGCAGAAAAAGGCCATCGTGGACCTGCTGTTCAAGACCAACCGGAAAGTGACCGTGAAGCAGCTGAAAGAGGACTACTTCAAGAAAATCGAG
TGCTTCGACTCCGTGGAAATCTCCGGCGTGGAAGATCGGTTCAACGCCTCCCTGGGCACATACCACGATCTGCTGAAAATTATCAAGGACAAG
GACTTCCTGGACAATGAGGAAAACGAGGACATTCTGGAAGATATCGTGCTGACCCTGACACTGTTTGAGGACAGAGAGATGATCGAGGAACGG
CTGAAAACCTATGCCCACCTGTTCGACGACAAAGTGATGAAGCAGCTGAAGCGGCGGAGATACACCGGCTGGGGCAGGCTGAGCCGGAAGCTG
ATCAACGGCATCCGGGACAAGCAGTCCGGCAAGACAATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCAGGGCGATAGCCTGCACGAGCACATTGCCAATCTGGCC
GGCAGCCCCGCCATTAAGAAGGGCATCCTGCAGACAGTGAAGGTGGTGGACGAGCTCGTGAAAGTGATGGGCCGGCACAAGCCCGAGAACATC
GTGATCGAAATGGCCAGAGAGAACCAGACCACCCAGAAGGGACAGAAGAACAGCCGCGAGAGAATGAAGCGGATCGAAGAGGGCATCAAAGAG
CTGGGCAGCCAGATCCTGAAAGAACACCCCGTGGAAAACACCCAGCTGCAGAACGAGAAGCTGTACCTGTACTACCTGCAGAATGGGCGGGAT
ATGTACGTGGACCAGGAACTGGACATCAACCGGCTGTCCGACTACGATGTGGACCATATCGTGCCTCAGAGCTTTCTGAAGGACGACTCCATC
GACAACAAGGTGCTGACCAGAAGCGACAAGAACCGGGGCAAGAGCGACAACGTGCCCTCCGAAGAGGTCGTGAAGAAGATGAAGAACTACTGG
CGGCAGCTGCTGAACGCCAAGCTGATTACCCAGAGAAAGTTCGACAATCTGACCAAGGCCGAGAGAGGCGGCCTGAGCGAACTGGATAAGGCC
GGCTTCATCAAGAGACAGCTGGTGGAAACCCGGCAGATCACAAAGCACGTGGCACAGATCCTGGACTCCCGGATGAACACTAAGTACGACGAG
AATGACAAGCTGATCCGGGAAGTGAAAGTGATCACCCTGAAGTCCAAGCTGGTGTCCGATTTCCGGAAGGATTTCCAGTTTTACAAAGTGCGC
GAGATCAACAACTACCACCACGCCCACGACGCCTACCTGAACGCCGTCGTGGGAACCGCCCTGATCAAAAAGTACCCTAAGCTGGAAAGCGAG
TTCGTGTACGGCGACTACAAGGTGTACGACGTGCGGAAGATGATCGCCAAGAGCGAGCAGGAAATCGGCAAGGCTACCGCCAAGTACTTCTTC
TACAGCAACATCATGAACTTTTTCAAGACCGAGATTACCCTGGCCAACGGCGAGATCCGGAAGCGGCCTCTGATCGAGACAAACGGCGAAACC
GGGGAGATCGTGTGGGATAAGGGCCGGGATTTTGCCACCGTGCGGAAAGTGCTGAGCATGCCCCAAGTGAATATCGTGAAAAAGACCGAGGTG
CAGACAGGCGGCTTCAGCAAAGAGTCTATCCTGCCCAAGAGGAACAGCGATAAGCTGATCGCCAGAAAGAAGGACTGGGACCCTAAGAAGTAC
GGCGGCTTCGACAGCCCCACCGTGGCCTATTCTGTGCTGGTGGTGGCCAAAGTGGAAAAGGGCAAGTCCAAGAAACTGAAGAGTGTGAAAGAG
CTGCTGGGGATCACCATCATGGAAAGAAGCAGCTTCGAGAAGAATCCCATCGACTTTCTGGAAGCCAAGGGCTACAAAGAAGTGAAAAAGGAC
CTGATCATCAAGCTGCCTAAGTACTCCCTGTTCGAGCTGGAAAACGGCCGGAAGAGAATGCTGGCCTCTGCCGGCGAACTGCAGAAGGGAAAC
GAACTGGCCCTGCCCTCCAAATATGTGAACTTCCTGTACCTGGCCAGCCACTATGAGAAGCTGAAGGGCTCCCCCGAGGATAATGAGCAGAAA
CAGCTGTTTGTGGAACAGCACAAGCACTACCTGGACGAGATCATCGAGCAGATCAGCGAGTTCTCCAAGAGAGTGATCCTGGCCGACGCTAAT
CTGGACAAAGTGCTGTCCGCCTACAACAAGCACCGGGATAAGCCCATCAGAGAGCAGGCCGAGAATATCATCCACCTGTTTACCCTGACCAAT
CTGGGAGCCCCTGCCGCCTTCAAGTACTTTGACACCACCATCGACCGGAAGAGGTACACCAGCACCAAAGAGGTGCTGGACGCCACCCTGATC
CACCAGAGCATCACCGGCCTGTACGAGACACGGATCGACCTGTCTCAGCTGGGAGGCGACAAAAAGGCCGGCGGCCACGAAAAGGCCGGCCAG
GCAAAAAAGAAAAAG (SEQ ID NO: 77)
```

Sp_del (175-307)

```
ATGGACTATAAGGACCACGACGGAGACTACAAGGATCATGATATTGATTACAAAGACGATGACGATAAGATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGGTGAACACCGAG
ATCACCAAGGCCCCCCTGAGCGCCTCTATGATCAAGAGATACGACGAGCACCACCAGGACCTGACCCTGCTGAAAGCTCTCGTGCGGCAGCAG
CTGCCTGAGAAGTACAAAGAGATTTTCTTCGACCAGAGCAAGAACGGCTACGCCGGCTACATTGACGGCGGAGCCAGCCAGGAAGAGTTCTAC
AAGTTCATCAAGCCCATCCTGGAAAAGATGGACGGCACCGAGGAACTGCTCGTGAAGCTGAACAGAGAGGACCTGCTGCGGAAGCAGCGGACC
```

```
TTCGACAACGGCAGCATCCCCCACCAGATCCACCTGGGAGAGCTGCACGCCATTCTGCGGCGGCAGGAAGATTTTTACCCATTCCTGAAGGAC
AACCGGGAAAAGATCGAGAAGATCCTGACCTTCCGCATCCCCTACTACGTGGGCCCTCTGGCCAGGGGAAACAGCAGATTCGCCTGGATGACC
AGAAAGAGCGAGGAAACCATCACCCCCTGGAACTTCGAGGAAGTGGTGGACAAGGGCGCTTCCGCCCAGAGCTTCATCGAGCGGATGACCAAC
TTCGATAAGAACCTGCCCAACGAGAAGGTGCTGCCCAAGCACAGCCTGCTGTACGAGTACTTCACCGTGTATAACGAGCTGACCAAAGTGAAA
TACGTGACCGAGGGAATGAGAAAGCCCGCCTTCCTGAGCGGCGAGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGACTCCGTGGAAATCTCCGGCGTGGAAGATCGGTTCAACGCCTCC
CTGGGCACATACCACGATCTGCTGAAAATTATCAAGGACAAGGACTTCCTGGACAATGAGGAAAACGAGGACATTCTGGAAGATATCGTGCTG
ACCCTGACACTGTTTGAGGACAGAGAGATGATCGAGGAACGGCTGAAAACCTATGCCCACCTGTTCGACGACAAAGTGATGAAGCAGCTGAAG
CGGCGGAGATACACCGGCTGGGGCAGGCTGAGCCGGAAGCTGATCAACGGCATCCGGGACAAGCAGTCCGGCAAGACAATCCTGGATTTCCTG
AAGTCCGACGGCTTCGCCAACAGAAACTTCATGCAGCTGATCCACGACGACAGCCTGACCTTTAAAGAGGACATCCAGAAAGCCCAGGTGTCC
GGCCAGGGCGATAGCCTGCACGAGCACATTGCCAATCTGGCCGGCAGCCCCGCCATTAAGAAGGGCATCCTGCAGACAGTGAAGGTGGTGGAC
GAGCTCGTGAAAGTGATGGGCCGGCACAAGCCCGAGAACATCGTGATCGAAATGGCCAGAGAGAACCAGACCACCCAGAAGGGACAGAAGAAC
AGCCGCGAGAGAATGAAGCGGATCGAAGAGGGCATCAAAGAGCTGGGCAGCCAGATCCTGAAAGAACACCCCGTGGAAAACACCCAGCTGCAG
AACGAGAAGCTGTACCTGTACTACCTGCAGAATGGGCGGGATATGTACGTGGACCAGGAACTGGACATCAACCGGCTGTCCGACTACGATGTG
GACCATATCGTGCCTCAGAGCTTTCTGAAGGACGACTCCATCGACAACAAGGTGCTGACCAGAAGCGACAAGAACCGGGGCAAGAGCGACAAC
GTGCCCTCCGAAGAGGTCGTGAAGAAGATGAAGAACTACTGGCGGCAGCTGCTGAACGCCAAGCTGATTACCCAGAGAAAGTTCGACAATCTG
ACCAAGGCCGAGAGAGGCGGCCTGAGCGAACTGGATAAGGCCGGCTTCATCAAGAGACAGCTGGTGGAAACCCGGCAGATCACAAAGCACGTG
GCACAGATCCTGGACTCCCGGATGAACACTAAGTACGACGAGAATGACAAGCTGATCCGGGAAGTGAAAGTGATCACCCTGAAGTCCAAGCTG
GTGTCCGATTTCCGGAAGGATTTCCAGTTTTACAAAGTGCGCGAGATCAACAACTACCACCACGCCCACGACGCCTACCTGAACGCCGTCGTG
GGAACCGCCCTGATCAAAAAGTACCCTAAGCTGGAAAGCGAGTTCGTGTACGGCGACTACAAGGTGTACGACGTGCGGAAGATGATCGCCAAG
AGCGAGCAGGAAATCGGCAAGGCTACCGCCAAGTACTTCTTCTACAGCAACATCATGAACTTTTTCAAGACCGAGATTACCCTGGCCAACGGC
GAGATCCGGAAGCGGCCTCTGATCGAGACAAACGGCGAAACCGGGGAGATCGTGTGGGATAAGGGCCGGGATTTTGCCACCGTGCGGAAAGTG
CTGAGCATGCCCCAAGTGAATATCGTGAAAAAGACCGAGGTGCAGACAGGCGGCTTCAGCAAAGAGTCTATCCTGCCCAAGAGGAACAGCGAT
AAGCTGATCGCCAGAAAGAAGGACTGGGACCCTAAGAAGTACGGCGGCTTCGACAGCCCCACCGTGGCCTATTCTGTGCTGGTGGTGGCCAAA
GTGGAAAAGGGCAAGTCCAAGAAACTGAAGAGTGTGAAAGAGCTGCTGGGGATCACCATCATGGAAAGAAGCAGCTTCGAGAAGAATCCCATC
GACTTTCTGGAAGCCAAGGGCTACAAAGAAGTGAAAAAGGACCTGATCATCAAGCTGCCTAAGTACTCCCTGTTCGAGCTGGAAAACGGCCGG
AAGAGAATGCTGGCCTCTGCCGGCGAACTGCAGAAGGGAAACGAACTGGCCCTGCCCTCCAAATATGTGAACTTCCTGTACCTGGCCAGCCAC
TATGAGAAGCTGAAGGGCTCCCCCGAGGATAATGAGCAGAAACAGCTGTTTGTGGAACAGCACAAGCACTACCTGGACGAGATCATCGAGCAG
ATCAGCGAGTTCTCCAAGAGAGTGATCCTGGCCGACGCTAATCTGGACAAAGTGCTGTCCGCCTACAACAAGCACCGGGATAAGCCCATCAGA
GAGCAGGCCGAGAATATCATCCACCTGTTTACCCTGACCAATCTGGGAGCCCCTGCCGCCTTCAAGTACTTTGACACCACCATCGACCGGAAG
AGGTACACCAGCACCAAAGAGGTGCTGGACGCCACCCTGATCCACCAGAGCATCACCGGCCTGTACGAGACACGGATCGACCTGTCTCAGCTG
GGGAGGCGACAAAAGGCCGGCGGCCACGAAAAAGGCCGGCCAGGCAAAAAAGAAAAAG (SEQ ID NO: 78)
```

Sp_del(312-409)

```
ATGGACTATAAGGACCACGACGGAGACTACAAGGATCATGATATTGATTACAAAGACGATGACGATAAGATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGA
AGCGGCGAAACAGCCGAGGCCACCCGGCTGAAGAGAACCGCCAGAAGAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATCGCCCAGCTGCCCGGCGAGAAGAAGAATGGCCTGTTCGGAAAC
CTGATTGCCCTGAGCCTGGGCCTGACCCCCAACTTCAAGAGCAACTTCGACCTGGCCGAGGATGCCAAACTGCAGCTGAGCAAGGACACCTAC
GACGACGACCTGGACAACCTGCTGGCCCAGATCGGCGACCAGTACGCCGACCTGTTTCTGGCCGCCAAGAACCTGTCCGACGCCATCCTGCTG
AGCGACATCCTGAGAGTGAACACCGAGATCCCCCACCAGATCCACCTGGGAGAGCTGCACGCCATTCTGCGGCGGCAGGAAGATTTTTACCCA
TTCCTGAAGGACAACCGGGAAAAGATCGAGAAGATCCTGACCTTCCGCATCCCCTACTACGTGGGCCCTCTGGCCAGGGGAAACAGCAGATTC
GCCTGGATGACCAGAAAGAGCGAGGAAACCATCACCCCCTGGAACTTCGAGGAAGTGGTGGACAAGGGCGCTTCCGCCCAGAGCTTCATCGAG
CGGATGACCAACTTCGATAAGAACCTGCCCAACGAGAAGGTGCTGCCCAAGCACAGCCTGCTGTACGAGTACTTCACCGTGTATAACGAGCTG
ACCAAAGTGAAATACGTGACCGAGGGAATGAGAAAGCCCGCCTTCCTGAGCGGCGAGCAGAAAAAAGCCATCGTGGACCTGCTGTTCAAGACC
AACCGGAAAGTGACCGTGAAGCAGCTGAAAGAGGACTACTTCAAGAAAATCGAGTGCTTCGACTCCGTGGAAATCTCCGGCGTGGAAGATCGG
TTCAACGCCTCCCTGGGCACATACCACGATCTGCTGAAAATTATCAAGGACAAGGACTTCCTGGACAATGAGGAAAACGAGGACATTCTGGAA
GATATCGTGCTGACCCTGACACTGTTTGAGGACAGAGAGATGATCGAGGAACGGCTGAAAACCTATGCCCACCTGTTCGACGACAAAGTGATG
AAGCAGCTGAAGCGGCGGAGATACACCGGCTGGGGCAGGCTGAGCCGGAAGCTGATCAACGGCATCCGGGACAAGCAGTCCGGCAAGACAATC
CTGGATTTCCTGAAGTCCGACGGCTTCGCCAACAGAAACTTCATGCAGCTGATCCACGACGACAGCCTGACCTTTAAAGAGGACATCCAGAAA
GCCCAGGTGTCCGGCCAGGGCGATAGCCTGCACGAGCACATTGCCAATCTGGCCGGCAGCCCCGCCATTAAGAAGGGCATCCTGCAGACAGTG
AAGGTGGTGGACGAGCTCGTGAAAGTGATGGGCCGGCACAAGCCCGAGAACATCGTGATCGAAATGGCCAGAGAGAACCAGACCACCCAGAAG
GGACAGAAGAACAGCCGCGAGAGAATGAAGCGGATCGAAGAGGGCATCAAAGAGCTGGGCAGCCAGATCCTGAAAGAACACCCCGTGGAAAAC
ACCCAGCTGCAGAACGAGAAGCTGTACCTGTACTACCTGCAGAATGGGCGGGATATGTACGTGGACCAGGAACTGGACATCAACCGGCTGTCC
GACTACGATGTGGACCATATCGTGCCTCAGAGCTTTCTGAAGGACGACTCCATCGACAACAAGGTGCTGACCAGAAGCGACAAGAACCGGGGC
AAGAGCGACAACGTGCCCTCCGAAGAGGTCGTGAAGAAGATGAAGAACTACTGGCGGCAGCTGCTGAACGCCAAGCTGATTACCCAGAGAAAG
TTCGACAATCTGACCAAGGCCGAGAGAGGCGGCCTGAGCGAACTGGATAAGGCCGGCTTCATCAAGAGACAGCTGGTGGAAACCCGGCAGATC
ACAAAGCACGTGGCACAGATCCTGGACTCCCGGATGAACACTAAGTACGACGAGAATGACAAGCTGATCCGGGAAGTGAAAGTGATCACCCTG
AAGTCCAAGCTGGTGTCCGATTTCCGGAAGGATTTCCAGTTTTACAAAGTGCGCGAGATCAACAACTACCACCACGCCCACGACGCCTACCTG
AACGCCGTCGTGGGAACCGCCCTGATCAAAAAGTACCCTAAGCTGGAAAGCGAGTTCGTGTACGGCGACTACAAGGTGTACGACGTGCGGAAG
ATGATCGCCAAGAGCGAGCAGGAAATCGGCAAGGCTACCGCCAAGTACTTCTTCTACAGCAACATCATGAACTTTTTCAAGACCGAGATTACC
CTGGCCAACGGCGAGATCCGGAAGCGGCCTCTGATCGAGACAAACGGCGAAACCGGGGAGATCGTGTGGGATAAGGGCCGGGATTTTGCCACC
GTGCGGAAAGTGCTGAGCATGCCCCAAGTGAATATCGTGAAAAAGACCGAGGTGCAGACAGGCGGCTTCAGCAAAGAGTCTATCCTGCCCAAG
AGGAACAGCGATAAGCTGATCGCCAGAAAGAAGGACTGGGACCCTAAGAAGTACGGCGGCTTCGACAGCCCCACCGTGGCCTATTCTGTGCTG
GTGGTGGCCAAAGTGGAAAAGGGCAAGTCCAAGAAACTGAAGAGTGTGAAAGAGCTGCTGGGGATCACCATCATGGAAAGAAGCAGCTTCGAG
AAGAATCCCATCGACTTTCTGGAAGCCAAGGGCTACAAAGAAGTGAAAAAGGACCTGATCATCAAGCTGCCTAAGTACTCCCTGTTCGAGCTG
GAAAACGGCCGGAAGAGAATGCTGGCCTCTGCCGGCGAACTGCAGAAGGGAAACGAACTGGCCCTGCCCTCCAAATATGTGAACTTCCTGTAC
CTGGCCAGCCACTATGAGAAGCTGAAGGGCTCCCCCGAGGATAATGAGCAGAAACAGCTGTTTGTGGAACAGCACAAGCACTACCTGGACGAG
ATCATCGAGCAGATCAGCGAGTTCTCCAAGAGAGTGATCCTGGCCGACGCTAATCTGGACAAAGTGCTGTCCGCCTACAACAAGCACCGGGAT
AAGCCCATCAGAGAGCAGGCCGAGAATATCATCCACCTGTTTACCCTGACCAATCTGGGAGCCCCTGCCGCCTTCAAGTACTTTGACACCACC
ATCGACCGGAAGAGGTACACCAGCACCAAAGAGGTGCTGGACGCCACCCTGATCCACCAGAGCATCACCGGCCTGTACGAGACACGGATCGAC
CTGTCTCAGCTGGGGAGGCGACAAAAGGCCGGCGGCCACGAAAAAGGCCGGCCAGGCAAAAAAGAAAAAG (SEQ ID NO: 79)
```

Sp_del (1098-end)

*ATGGACTATAAGGACCACGACGGAGACTACAAGGATCATGATATTGATTACAAAGACGATGACGATAAGATGGCCCCAAAGAAGAAGCGGAAG*
*GTCGGTATCCACGGAGTCCCAGCAGCC*GACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATCGCCCAGCTGCCCGGCGAGAAGAAGAATGGCCTGTTCGGAAAC
CTGATTGCCCTGAGCCTGGGCCTGACCCCCAACTTCAAGAGCAACTTCGACCTGGCCGAGGATGCCAAACTGCAGCTGAGCAAGGACACCTAC
GACGACGACCTGGACAACCTGCTGGCCCAGATCGGCGACCAGTACGCCGACCTGTTTCTGGCCGCCAAGAACCTGTCCGACGCCATCCTGCTG
AGCGACATCCTGAGAGTGAACACCGAGATCACCAAGGCCCCCCTGAGCGCCTCTATGATCAAGAGATACGACGAGCACCACCAGGACCTGACC
CTGCTGAAAGCTCTCGTGCGGCAGCAGCTGCCTGAGAAGTACAAAGAGATTTTCTTCGACCAGAGCAAGAACGGCTACGCCGGCTACATTGAC
GGCGGAGCCAGCCAGGAAGAGTTCTACAAGTTCATCAAGCCCATCCTGGAAAAGATGGACGGCACCGAGGAACTGCTCGTGAAGCTGAACAGA
GAGGACCTGCTGCGGAAGCAGCGGACCTTCGACAACGGCAGCATCCCCCACCAGATCCACCTGGGAGAGCTGCACGCCATTCTGCGGCGGCAG
GAAGATTTTTACCCATTCCTGAAGGACAACCGGGAAAAGATCGAGAAGATCCTGACCTTCCGCATCCCCTACTACGTGGGCCCTCTGGCCAGG
GGAAACAGCAGATTCGCCTGGATGACCAGAAAGAGCGAGGAAACCATCACCCCCTGGAACTTCGAGGAAGTGGTGGACAAGGGCGCTTCCGCC
CAGAGCTTCATCGAGCGGATGACCAACTTCGATAAGAACCTGCCCAACGAGAAGGTGCTGCCCAAGCACAGCCTGCTGTACGAGTACTTCACC
GTGTATAACGAGCTGACCAAAGTGAAATACGTGACCGAGGGAATGAGAAAGCCCGCCTTCCTGAGCGGCGAGCAGAAAAAGGCCATCGTGGAC
CTGCTGTTCAAGACCAACCGGAAAGTGACCGTGAAGCAGCTGAAAGAGGACTACTTCAAGAAAATCGAGTGCTTCGACTCCGTGGAAATCTCC
GGCGTGGAAGATCGGTTCAACGCCTCCCTGGGCACATACCACGATCTGCTGAAAATTATCAAGGACAAGGACTTCCTGGACAATGAGGAAAAC
GAGGACATTCTGGAAGATATCGTGCTGACCCTGACACTGTTTGAGGACAGAGAGATGATCGAGGAACGGCTGAAAACCTATGCCCACCTGTTC
GACGACAAAGTGATGAAGCAGCTGAAGCGGCGGAGATACACCGGCTGGGGCAGGCTGAGCCGGAAGCTGATCAACGGCATCCGGGACAAGCAG
TCCGGCAAGACAATCCTGGATTTCCTGAAGTCCGACGGCTTCGCCAACAGAAACTTCATGCAGCTGATCCACGACGACAGCCTGACCTTTAAA
GAGGACATCCAGAAAGCCCAGGTGTCCGGACAGGGCGATAGCCTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGGCACAAGCCCGAGAACATCGTGATCGAAATGGCCAGAGAGAAC
CAGACCACCCAGAAGGGACAGAAGAACAGCCGCGAGAGAATGAAGCGGATCGAAGAGGGCATCAAAGAGCTGGGCAGCCAGATCCTGAAAGAA
CACCCCGTGGAAAACACCCAGCTGCAGAACGAGAAGCTGTACCTGTACTACCTGCAGAATGGGCGGGATATGTACGTGGACCAGGAACTGGAC
ATCAACCGGCTGTCCGACTACGATGTGGACCATATCGTGCCTCAGAGCTTTCTGAAGGACGACTCCATCGACAACAAGGTGCTGACCAGAAGC
GACAAGAACCGGGGCAAGAGCGACAACGTGCCCTCCGAAGAGGTCGTGAAGAAGATGAAGAACTACTGGCGGCAGCTGCTGAACGCCAAGCTG
ATTACCCAGAGAAAGTTCGACAATCTGACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACCAAGTACGACGAGAATGACAAGCTGATCCGGGAAGTG
AAAGTGATCACCCTGAAGTCCAAGCTGGTGTCCGATTTCCGGAAGGATTTCCAGTTTTACAAAGTGCGCGAGATCAACAACTACCACCACGCC
CACGACGCCTACCTGAACGCCGTCGTGGGAACCGCCCTGATCAAAAAGTACCCTAAGCTGGAAAGCGAGTTCGTGTACGGCGACTACAAGGTG
TACGACGTGCGGAAGATGATCGCCAAGAGCGAGCAGGAAATCGGCAAGGCTACCGCCAAGTACTTCTTCTACAGCAACATCATGAACTTTTTC
AAGACCGAGATTACCCTGGCCAACGGCGAGATCCGGAAGCGGCCTCTGATCGAGACAAACGGCGAAACCGGGGAGATCGTGTGGGATAAGGGC
CGGGATTTTGCCACCGTGCGGAAAGTGCTGAGCATGCCCCAAGTGAATATCGTGAAAAAGACC*AAAAGGCCGGCGGCCACGAAAAAGCCGGC*
*CAGGCAAAAAAGAAAAAG* (SEQ ID NO: 80)

St3Cas9

*ATGGACTATAAGGACCACGACGGAGACTACAAGGATCATGATATTGATTACAAAGACGATGACGATAAGATGGCCCCCAAAGAAGAAGCGGAAG*
*GTCGGTATCCACGGAGTCCCAGCAGCC*ACCAAGCCCTACAGCATCGGCCTGGACATCGGCACCAATAGCGTGGGCTGGGCCGTGACCACCGAC
AACTACAAGGTGCCCAGCAAGAAAATGAAGGTGCTGGGCAACACCTCCAAGAAGTACATCAAGAAAAACCTGCTGGGCGTGCTGCTGTTCGAC
AGCGGCATTACAGCCGAGGGCAGACGGCTGAAGAGAACCGCCAGACGGCGGTACACCCGGCGGAAGAACAGAATCCTGTATCTGCAAGAGATC
TTCAGCACCGAGATGGCTACCCTGGACGACGCCTTCTTCCAGCGGCTGGACGACAGCTTCCTGGTGCCCGACGACAAGCGGGACAGCAAGTAC
CCCATCTTCGGCAACCTGGTGGAAGAGAAGGCCTACCACGACGAGTTCCCCACCATCTACCACCTGAGAAAGTACCTGGCCGACAGCACCAAG
AAGGCCGACCTGAGACTGGTGTATCTGGCCCTGGCCCACATGATCAAGTACCGGGGCCACTTCCTGATCGAGGGCGAGTTCAACAGCAAGAAC
AACGACATCCAGAAGAACTTCCAGGACTTCCTGGACACCTACAACGCCATCTTCGAGAGCGACCTGTCCCTGGAAAACAGCAAGCAGCTGGAA
GAGATCGTGAAGGACAAGATCAGCAAGCTGGAAAAGAAGGACCGCATCCTGAAGCTGTTCCCCGGCGAGAAGAACAGCGGAATCTTCAGCGAG
TTTCTGAAGCTGATCGTGGGCAACCAGGCCGACTTCAGAAAGTGCTTCAACCTGGACGAGAAGGCCAGCCTGCACTTCAGCAAAGAGAGCTAC
GACGAGGACCTGGAAACCCTGCTGGGATATATCGGCGACGACTACAGCGACGTGTTCCTGAAGGCCAAGAAGCTGTACGACGCTATCCTGCTG
AGCGGCTTCCTGACCGTGACCGACAACGAGACAGAGGCCCCACTGAGCAGCGCCATGATTAAGCGGTACAACGAGCACAAAGAGGATCTGGCT
CTGCTGAAAGAGTACATCCGGAACATCAGCCTGAAAACCTACAATGAGGTGTTCAAGGACGACACCAAGAACGGCTACGCCGGCTACATCGAC
GGCAAGACCAACCAGGAAGAGGAAGATTTCTATGTGTACCTGAAGAAGCTGCTGGCCGAGTTCGAGGGGGCCGACTACTTTCTGGAAAAAATC
GACCGCGAGGATTTCCTGCGGAAGCAGCGGACCTTCGACAACGGCAGCATCCCCTACCAGATCCATCTGCAGGAAATGCGGGCCATCCTGGAC
AAGCAGGCCAAGTTCTACCCATTCCTGGCCAAGAACAAAGAGCGGATCGAGAAGATCCTGACCTTCCGCATCCCTTACTACGTGGGCCCCCTG
GCCAGAGGCAACAGCGATTTTGCCTGGTCCATCCGGAAGCGCAATGAGAAGATCACCCCCTGGAACTTCGAGGACGTGATCGACAAAGAGTCC
AGCGCCGAGGCCTTCATCAACCGGATGACCAGCTTCGACCTGTACCTGCCCGAGGAAAAGGTGCTGCCCAAGCACAGCCTGCTGTACGAGACA
TTCAATGTGTATAACGAGCTGACCAAAGTGCGGTTTATCGCCGAGTCTATGCGGGACTACCAGTTCCTGGACTCCAAGCAGAAAAAGGACATC
GTGCGCCTGTACTTCAAGGACAAGCGGAAAGTGACCGATAAGGACATCATCGAATACCTGCACGCCATCTACGGCTACGATGGCATCGAGCTG
AAGGGCATCGAGAAGCAGTTCAACTCCAGCCTGAGCACATACCACGACCTGCTGAACATTATCAACGACAAAGAATTCTTGGACGACTCCAGC
AACGAGGCCATCATCGAAGAGATCATCCACACCCTGACCATCTTTGAGGACCGCGAGATGATCAAGCAGCGGCTGAGCAAGTTCGAGAACATC
TTCGACAAGAGCGTGCTGAAAAAGCTGAGCAGACGGCACTACACCGGCTGGGGCAAGCTGAGCGCCAAGCTGATCAACGGCATCCGGGACGAG
AAGTCCGGCAACACAATCCTGGACTACCTGATCGACGACGGCATCAGCAACCGGAACTTCATGCAGCTGATCCACGACGACGCCCTGAGCTTC
AAGAAGAAGATCCAGAAGGCCCAGATCATCGGGGACGAGGACAAAGGCAACATCAAAGAAGTCGTGAAGTCCCTGCCCGGCAGCCCCGCCATC
AAGAAGGGAATCCTGCAGAGCATCAAGATCGTGGACGAGCTCGTGAAAGTGATGGGCGGCAGAAAGCCCGAGAGCATCGTGGTGGAAATGGCTAGAGAGAACCAGTACACCAATCAGGGCAAGAGCAACAGCCAGCAGAGACTGAAGAGACTGGAAAAGTCCCTGAAAGAGCTGGGCAGC
AAGATTCTGAAAGAGAATATCCCTGCCAAGCTGTCCAAGATCGACAACAACGCCCTGCAGAACGACCGGCTGTACCTGTACTACCTGCAGAAT
GGCAAGGACATGTATACAGGCGACGACCTGGATATCGACCGCCTGAGCAACTACGACATCGACCATATTATCCCCCAGGCCTTCCTGAAAGAC
AACAGCATTGACAACAAAGTGCTGGTGTCCTCCGCCAGCAACCGCGGCAAGTCCGATGATGTGCCCAGCCTGGAAGTGGTGAAAAGAGAAAG
ACCTTCTGGTATCAGCTGCTGAAAAGCAAGCTGATTAGCCAGAGGAAGTTCGACAACCTGACCAAGGCCGAGAGAGGCGGCCTGAGCCCTGAA
GATAAGGCCGGCTTCATCCAGAGACAGCTGGTGGAAACCCGGCAGATCACCAAGCACGTGGCCAGACTGCTGGATGAGAAGTTTAACAACAAG
AAGGACGAGAACAACCGGGCCGTGCGGACCGTGAAGATCATCACCCTGAAGTCCACCCTGGTGTCCCAGTTCCGGAAGGACTTCGAGCTGTAT
AAAGTGCGCGAGATCAATGACTTTCACCACGCCCACGACGCCTACCTGAATGCCGTGGTGGCTTCCGCCCTGCTGAAGAAGTACCCTAAGCTG
GAACCCGAGTTCGTGTACGGCGACTACCCCAAGTACAACTCCTTCAGAGAGCGGAAGTCCGCCACCGAGAAGGTGTACTTCTACTCCAACATC
ATGAATATCTTTAAGAAGTCCATCTCCCTGGCCGATGGCAGAGTGATCGAGCGGCCCCTGATCGAAGTGAACGAAGAGACAGGCGAGAGCGTG

-continued

TGGAACAAAGAAAGCGACCTGGCCACCGTGCGGGGGTGCTGAGTTATCCTCAAGTGAATGTCGTGAAGAAGGTGGAAGAACAGAACCACGGC
CTGGATCGGGGCAAGCCCAAGGGCCTGTTCAACGCCAACCTGTCCAGCAAGCCTAAGCCCAACTCCAACGAGAATCTCGTGGGGGCCAAAGAG
TACCTGGACCCTAAGAAGTACGGGTACGGCGGATACGCCCGGCATCTCCAATAGCTTCACCGTGCTCGTGAAGGGCACAATCGAGAAGGGCGCT
AAGAAAAAGATCACAAACGTGCTGGAATTTCAGGGGATCTCTATCCTGGACCGGATCAACTACCGGAAGGATAAGCTGAACTTTCTGCTGGAA
AAAGGCTACAAGGACATTGAGCTGATTATCGAGCTGCCTAAGTACTCCCTGTTCGAACTGAGCGACGGCTCCAGACGGATGCTGGCCTCCATC
CTGTCCACCAACAACAAGCGGGGCGAGATCCACAAGGGAAACCAGATCTTCCTGAGCCAGAAATTTGTGAAACTGCTGTACCACGCCAAGCGG
ATCTCCAACACCATCAATGAGAACCACCGGAAATACGTGGAAAACCACAAGAAAGAGTTTGAGGAACTGTTCTACTACATCCTGGAGTTCAAC
GAGAACTATGTGGGAGCCAAGAAGAACGGCAAACTGCTGAACTCCGCCTTCCAGAGCTGGCAGAACCACAGCATCGACGAGCTGTGCAGCTCC
TTCATCGGCCCTACCGGCAGCGAGCGGAAGGGACTGTTTGAGCTGACCTCCAGAGGCTCTGCCGCCGACTTTGAGTTCCTGGGAGTGAAGATC
CCCCGGTACAGAGACTACACCCCCTCTAGTCTGCTGAAGGACGCCACCCTGATCCACCAGAGCGTGACCGGCCTGTACGAAACCCGGATCGAC
CTGGCTAAGCTGGGCGAGGGA<u>AAAAGGCCGGCGGCCACGAAAAAGGCCGGCCAGGCAAAAAAGAAAAAG</u> (SEQ ID NO: 81)

SpCas9(C80L, C574A)

ATGGACAAGAAGTACAGCATCGGCCTGGACATCGGCACCAACTCTGTGGGCTGGGCCGTGATCACCGACGAGTACAAGGTGCCCAGCAAGAAA
TTCAAGGTGCTGGGCAACACCGACCGGCACAGCATCAAGAAGAACCTGATCGGAGCCCTGCTGTTCGACAGCGGCGAAACAGCCGAGGCCACC
CGGCTGAAGAGAACCGCCAGAAGAAGATACACCAGACGGAAGAACCGGATCctgTATCTGCAAGAGATCTTCAGCAACGACGATGGCCAAGGTG
GACGACAGCTTCTTCCACAGACTGGAAGAGTCCTTCCTGGTGGAAGAGGATAAGAAGCACGAGCGGCACCCCATCTTCGGCAACATCGTGGAC
GAGGTGGCCTACCACGAGAAGTACCCCACCATCTACCACCTGAGAAAGAAACTGGTGGACAGCACCGACAAGGCCGACCTGCGGCTGATCTAT
CTGGCCCTGGCCCACATGATCAAGTTCCGGGGCCACTTCCTGATCGAGGGCGACCTGAACCCCGACAACAGCGACGTGGACAAGCTGTTCATC
CAGCTGGTGCAGACCTACAACCAGCTGTTCGAGGAAAACCCCATCAACGCCAGCGGCGTGGACGCCAAGGCCATCCTGTCTGCCAGACTGAGC
AAGAGCAGACGGCTGGAAAATCTGATCGCCCAGCTGCCCGGCGAGAAGAAGAATGGCCTGTTCGGAAACCTGATTGCCCTGAGCCTGGGCCTG
ACCCCCAACTTCAAGAGCAACTTCGACCTGGCCGAGGATGCCAAACTGCAGCTGAGCAAGGACACCTACGATGACGACCTGGACAACCTGCTG
GCCCAGATCGGCGACCAGTACGCCGACCTGTTTCTGGCCGCCAAGAACCTGTCCGACGCCATCCTGCTGAGCGACATCCTGAGAGTGAACACC
GAGATCACCAAGGCCCCCCTGAGCGCCTCTATGATCAAGAGATACGACGAGCACCACCAGGACCTGACCCTGCTGAAAGCTCTCGTGCGGCAG
CAGCTGCCTGAGAAGTACAAAGAGATTTTCTTCGACCAGAGCAAGAACGGCTACGCCGGCTACATTGACGGCGGAGCCAGCCAGGAAGAGTTC
TACAAGTTCATCAAGCCCATCCTGGAAAAGATGGACGGCACCGAGGAACTGCTCGTGAAGCTGAACAGAGAGGACCTGCTGCGGAAGCAGCGG
ACCTTCGACAACGGCAGCATCCCCCACCAGATCCACCTGGGAGAGCTGCACGCCATTCTGCGGCGGCAGGAAGATTTTTACCCATTCCTGAAG
GACAACCGGGAAAAGATCGAGAAGATCCTGACCTTCCGCATCCCCTACTACGTGGGCCCTCTGGCCAGGGGAAACAGCAGATTCGCCTGGATG
ACCAGAAAGAGCGAGGAAACCATCACCCCCTGGAACTTCGAGGAAGTGGTGGACAAGGGTGTACGACGTGCGGAAGATGATCGCCAAGAGCGAG
CAGGAAATCGGCAAGGCTACCGCCAAGTACTTCTTCTACAGCAACATCATGAACTTTTTCAAGACCGAGATTACCCTGGCCAACGGCGAGATCCGGAAGCGGCCTCTGATCGAGACAAACGGCGAAACCGGGGAGATCGTGTGGGATAAGGGCCGGGATTTTGCCACCGTGCGGAAAGTGCTGAGCATGCCCCAAGTGAATATCGTGAAAAAGACCGAGGTGCAGACAGGCGGCTTCAGCAAAGAGTCTATCCTGCCCAAGAGGAACAGCGATAAGCTGATCGCCAGAAAGAAGGACTGGGACCCTAAGAAGTACGGCGGCTTCGACAGCCCCACCGTGGCCTATTCTGTGCTGGTGGTGGCCAAAGTGGAAAAGGGCAAGTCCAAGAAACTGAAGAGTGTGAAAGAGCTGCTGGGGATCACCATCATGGAAAAGGAAGCAGCTTCGAGAAGAATCCCATCGACTTTCTGGAAGCCAAGGGCTACAAAGAAGTGAAAAAGGACCTGATCATCAAGCTGCCTAAGTACTCCCTGTTCGAGCTGGAAAACGGCCGGAAGAGAATGCTGGCCTCTGCCGGCGAACTGCAGAAGGGAAACGAACTGGCCCTGCCCTCCAAATATGTGAACTTCCTGTACCTGGCCAGCCACTATGAGAAGCTGAAGGGCTCCCCCGAGGATAATGAGCAGAAACAGCTGTTTGTGGAACAGCACAAGCACTACCTGGACGAGATCATCGAGCAGATCAGCGAGTTCTCCAAGAGAGTGATCCTGGCCGACGCTAATCTGGACAAAGTGCTGTCCGCCTACAACAAGCACCGGGATAAGCCCATCAGAGAGCAGGCCGAGAATATCATCCACCTGTTTACCCTGACCAATCTGGGAGCCCCTGCCGCCTTCAAGTACTTTGACACCACCATCGACCGGAAGAGGTACACCAGCACCAAAGAGGTGCTGGACGCCACCCTGATCCACCAGAGCATCACCGGCCTGTACGAGACACGGATCGACCTGTCTCAGCTGGGAGGCGAC (SEQ ID NO: 82)

Sp_St3 Cas9 chimera(St3 in bold)

*ATGGACTATAAGGACCACGACGGAGACTACAAGGATCATGATATTGATTACAAAGACGATGACGATAAG*ATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATCGCCCAGCTGCCCGGCGAGAAGAAGAATGGCCTGTTCGGAAAC
CTGATTGCCCTGAGCCTGGGCCTGACCCCCAACTTCAAGAGCAACTTCGACCTGGCCGAGGATGCCAAACTGCAGCTGAGCAAGGACACCTAC
GACGACGACCTGGACAACCTGCTGGCCCAGATCGGCGACCAGTACGCCGACCTGTTTCTGGCCGCCAAGAACCTGTCCGACGCCATCCTGCTG
AGCGACATCCTGAGAGTGAACACCGAGATCACCAAGGCCCCCCTGAGCGCCTCTATGATCAAGAGATACGACGAGCACCACCAGGACCTGACC
CTGCTGAAAGCTCTCGTGCGGCAGCAGCTGCCTGAGAAGTACAAAGAGATTTTCTTCGACCAGAGCAAGAACGGCTACGCCGGCTACATTGAC
GGCGGAGCCAGCCAGGAAGAGTTCTACAAGTTCATCAAGCCCATCCTGGAAAAGATGGACGGCACCGAGGAACTGCTCGTGAAGCTGAACAGA
GAGGACCTGCTGCGGAAGCAGCGGACCTTCGACAACGGCAGCATCCCCCACCAGATCCACCTGGGAGAGCTGCACGCCATTCTGCGGCGGCAG
GAAGATTTTTACCCATTCCTGAAGGACAACCGGGAAAAGATCGAGAAGATCCTGACCTTCCGCATCCCCTACTACGTGGGCCCTCTGGCCAGG
GGAAACAGCAGATTCGCCTGGATGACCAGAAAGAGCGAGGAAACCATCACCCCCTGGAACTTCGAGGAAGTGGTGGACAAGGGCGCTTCCGCC

-continued

```
CAGAGCTTCATCGAGCGGATGACCAACTTCGATAAGAACCTGCCCAACGAGAAGGTGCTGCCCAAGCACAGCCTGCTGTACGAGTACTTCACC
GTGTATAACGAGCTGACCAAAGTGAAATACGTGACCGAGGGAATGAGAAAGCCCGCCTTCCTGAGCGGCGAGCAGAAAAAGGCCATCGTGGAC
CTGCTGTTCAAGACCAACCGGAAAGTGACCGTGAAGCAGCTGAAAGAGGACTACTTCAAGAAAATCGAGTGCTTCGACTCCGTGGAAATCTCC
GGCGTGGAAGATCGGTTCAACGCCTCCCTGGGCACATACCACGATCTGCTGAAAATTATCAAGGACAAGGACTTCCTGGACAATGAGGAAAAC
GAGGACATTCTGGAAGATATCGTGCTGACCCTGACACTGTTTGAGGACAGAGAGATGATCGAGGAACGGCTGAAAACCTATGCCCACCTGTTC
GACGACAAAGTGATGAAGCAGCTGAAGCGGCGGAGATACACCGGCTGGGGCAGGCTGAGCCGGAAGCTGATCAACGGCATCCGGGACAAGCAG
TCCGGCAAGACAATCCTGGATTTCCTGAAGTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATCTGGCCGGCAGCCCCGCCATTAAGAAGGGC
ATCCTGCAGACAGTGAAGGTGGTGGACGAGCTCGTGAAGTGATGGGCCGGCACAAGCCCGAGAACATCGTGATCGAAATGGCCAGAGAGAAC
CAGACCACCCAGAAGGGACAGAAGAACAGCCGCGAGAGAATGAAGCGGATCGAAGAGGGCATCAAAGAGCTGGGCAGCCAGATCCTGAAAGAA
CACCCCGTGGAAAACACCCAGCTGCAGAACGAGAAGCTGTACCTGTACTACCTGCAGAATGGGCGGGATATGTACGTGGACCAGGAACTGGAC
ATCAACCGGCTGTCCGACTACGATGTGGACCATATCGTGCCTCAGAGCTTTCTGAAGGACGACTCCATCGACAACAAGGTGCTGACCAGAAGC
GACAAGAACCGGGGCAAGAGCGACAACGTGCCCTCCGAAGAGGTCGTGAAGAAGATGAAGAACTACTGGCGGCAGCTGCTGAACGCCAAGCTG
ATTACCCAGAGAAAGTTCGACAATCTGACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACTAAGTACGACGAGAATGACAAGCTGATCCGGGAAGTG
AAAGTGATCACCCTGAAGTCCAAGCTGGTGTCCGATTTCCGGAAGGATTTCCAGTTTTACAAAGTGCGCGAGATCAACAACTACCACCACGCC
CACGACGCCTACCTGAACGCCGTCGTGGGAACCGCCCTGATCAAAAAGTACCCTAAGCTGGAAAGCGAGTTCGTGTACGGCGACTACAAGGTG
TACGACGTGCGGAAGATGATCGCCAAGAGCGAGCAGGAAATCGGCAAGGCTACCGCCAAGTACTTCTTCTACAGCAACATCATGAACTTTTTC
AAGACCGAGATTACCCTGGCCAACGGCGAGATCCGGAAGCGGCCTCTGATCGAGACAAACGGCGAAACCGGGGAGATCGTGTGGGATAAGGGC
CGGGATTTTGCCACCGTGCGGAAAGTGCTGAGCATGCCCCAAGTGAATATCGTGAAAAAGACCGTGGAAGAACAGAACCACGGCCTGGATCGG
GGCAAGCCCAAGGGCCTGTTCAACGCCAACCTGTCCAGCAAGCCTAAGCCCAACTCCAACGAGAATCTCGTGGGGCCAAAGAGTACCTGGA
CCCTAAGAAGTACGGGTACGGCGGATACGCCGGCATCTCCAATAGCTTCACCGTGCTCGTGAAGGGCACAATCGAGAAGGGCGCTAAGAAAA
AGATCACAAACGTGCTGGAATTTCAGGGGATCTCTATCCTGGACCGGATCAACTACCGGAAGGATAAGCTGAACTTTCTGCTGGAAAAAGGC
TACAAGGACATTGAGCTGATTATCGAGCTGCCTAAGTACTCCCTGTTCGAACTGAGCGACGGCTCCAGACGGATGCTGGCCTCCATCCTGTC
CACCAACAACAAGCGGGGCGAGATCCACAAGGGAAACCAGATCTTCCTGAGCCAGAAATTTGTGAAACTGCTGTACCACGCCAAGCGGATCT
CCAACACCATCAATGAGAACCACCGGAAATACGTGGAAAACCACAAGAAAGAGTTTGAGGAACTGTTTCTACTACATCCTGGAGTTCAACGAG
AACTATGTGGGAGCCAAGAAGAACGGCAAACTGCTGAACTCCGCCTTCCAGAGCTGGCAGAACCACAGCATCGACGAGCTGTGCAGCTCCTT
CATCGGCCCTACCGGCAGCGAGCGGAAGGGACTGTTTGAGCTGACCTCCAGAGGCTCTGCCGCCGACTTTGAGTTCCTGGGAGTGAAGATCC
CCCGGTACGAGAGACTACACCCCCTCTAGTCTGCTGAAGGACGCCACCCTGATCCACCAGAGCGTGACCGGCCTGTACGAAACCCGGATCGAC
CTGGCTAAGCTGGGCGAGGGAAAAAGGCCGGCGGCCACGAAAAAGGCCGGCCAGGCAAAAAAGAAAAAG (SEQ ID NO: 83)
```

St3_Sp Cas9 chimera(St3 in bold)

```
ATGGCCCCAAAGAAGAAGCGGAAGGTCGGTATCCACGGAGTCCCAGCAGCCatgACCAAGCCCTACAGCATCGGCCTGGACATCGGCACCAAT
AGCGTGGGCTGGGCCGTGACCACCGACAACTACAAGGTGCCCAGCAAGAAAATGAAGGTGCTGGGCAACACCTCCAAGAAGTACATCAAGAA
AAACCTGCTGGGCGTGCTGCTGTTCGACAGCGGCATTACAGCCGAGGGCAGACGGCTGAAGAGAACCGCCAGACGGCGGTACACCCGGCGGA
GAAACAGAATCCTGTATCTGCAAGAGATCTTCAGCACCGAGATGGCTACCCTGGACGACGCCTTCTTCCAGCGGCTGGACGACAGCTTCCTG
GTGCCCGACGACAAGCGGGACAGCAAGTACCCCATCTTCGGCAACCTGGTGGAAGAGAAGGCCTACCACGACGAGTTCCCCACCATCTACCA
CCTGAGAAAGTACCTGGCCGACAGCACCAAGAAGGCCGACCTGAGACTGGTGTATCTGGCCCTGGCCCACATGATCAAGTACCGGGGCCACT
TCCTGATCGAGGGCGAGTTCAACAGCAAGAACAACGACATCCAGAAGAACTTCCAGGACTTCCTGGACACCTACAACGCCATCTTCGAGAGC
GACCTGTCCCTGGAAAACAGCAAGCAGCTGGAAGAGATCGTGAAGGACAAGATCAGCAAGCTGGAAAAGAAGGACCGCATCCTGAAGCTGTT
CCCCGGCGAGAAGAACAGCGGAATCTTCAGCGAGTTTCTGAAGCTGATCGTGGGCAACCAGGCCGACTTCAGAAAGTGCTTCAACCTGGACG
AGAAAGCCAGCCTGCACTTCAGCAAAGAGAGCTACGACGAGGACCTGGAAACCCTGCTGGGATATATCGGCGACGACTACAGCGACGTGTTC
CTGAAGGCCAAGAAGCTGTACGACGCTATCCTGCTGAGCGGCTTCCTGACCGTGACCGACAACGAGACAGAGGCCCCACTGAGCGCGCCAT
GATTAAGCGGTACAACGAGCACAAAGAGGATCTGGCTCTGCTGAAAGAGTACATCCGGAACATCAGCCTGAAAACCTACAATGAGGTTCA
AGGACGACACCAAGAACGGCTACGCCGGCTACATCGACGGCAAGACCAACCAGGAAGAGGAAGATTTCTATGTGTACCTGAAGAAGCTGCTG
GCCGAGTTCGAGGGGGCCGACTACTTTCTGGAAAAAATCGACCGCGAGGATTTCCTGCGCAAGCAGCGGACCTTCGACAACGGCAGCATCCC
CTACCAGATCCATCTGCAGGAAATGCGGGCCATCCTGGACAAGCAGGCCAAGTTCTACCCATTCCTGGCCAAGAACAAAGAGCGGATCGAGA
AGATCCTGACCTTCCGCATCCCTTACTACGTGGGCCCCCTGGCCAGAGGCAACAGCGATTTTGCCTGGTCCATCCGGAAGCGCAATGAGAAG
ATCACCCCCTGGAACTTCGAGGACGTGATCGACAAAGAGTCCAGCGCCGAGGCCTTCATCAACCGGATGACCAGCTTCGACCTGTACCTGCC
CGAGGAAAAGGTGCTGCCCAAGCACAGCCTGCTGTACGAGCATTCAAATGTGCTATAACGAGCTGACCAAAGTGCGGTTTATCGCGAGTGTA
TGCGGGACTACCAGTTCCTGGACTCCAAGCAGAAAAAGGACATCGTGCGGCTGTACTTCAAGGACAAGCGGAAAGTGACCGATAAGGACATC
ATCGAGTACCTGCACGCCATCTACGGCTACGATGGCATCGAGCTGAAGGGCATCGAGAAGCAGTTCAACTCCAGCCTGAGCACATACCACGA
CCTGCTGAACATTATCAACGACAAAGAATTTCTGGACGACTCCAGCAACGAGGCCATCATCGAAGAGATCATCCACACCCTGACCATCTTTG
AGGACCGCGAGATGATCAAGCAGCGGCTGAGCCAGTTCGAGAACATCTTCGACAAGAGCGTGCTGAAAAAGCTGAGCAGACGGCACTACACC
GGCTGGGGCAAGCTGAGCGCCAAGCTGATCAACGGCATCCGGGACGAAGTCCGGCAACAATCCTGGACTACCTGATCGACAACGGCAT
CAGCAACCGGAACTTCATGCAGCTGATCCACGACGACGCCCTGAGCTTCAAGAAGAAGATCCAGAAGGCCCAGATCATCGGGACGAGGACA
AGGGCAACATCAAAGAAGTCGTGAAGTCCCTGCCCGGCAGCCCCGCCATCAAGAAGGGAATCCTGCAGAGCATCAAGATCGTGGACGAGCTC
GTGAAAGTGATGGGCGGCAGAAAGCCCGAGAGCATCGTGGTGGTGATGGCTAGAGAACAGTACACCAATCAGGGCAAGAGCCAA
CAGCCACAGAGACTGAAGAGACTGGAAAAGTCCCTGAAAGAGCTGGGCAGCAAGATTCTGAAAGAGAATATCCCTGCCAAGCTGTCCAAGA
TCGACAACAACGCCCTGCAGAACGACCGGCTGTACCTGTACTACCTGCAGAATGGCAAGGACATGTATACAGGCGACGACCTGGATATCGAC
CGCCTGAGCAACTACGACATCGACCATATTATCCCCCAGGCCTTCCTGAAAGACAACAGCATTGACAACAAAGTGCTGGTGTCCTCCGCCAG
CAACCGCGGCAAGTCCGATGATGTGCCCAGCCTGGAAGTCGTGAAAAAGAGAAAGACCTTCTGGTATCAGCTGCTGAAAAGCAAGCTGATTA
GCCAGAGGAAGTTCGACAACCTGACCAAGGCCGAGAGAGGCGGCCTGAGCCCTGAAGATAAGGCCGGCTTCATCCAGAGACAGCTGGTGGAA
ACCCGGCAGATCACCAAGCACGTGGCCAGACTGCTGGATGAGAAGTTTAACAACAAGGACGAGAACAACCGGGCCGTGCGGACCGTGAAA
GATCATCACCCTGAAGTCCACCCTGGTGTCCCAGTTCCGGAAGGACTTCGAGCTGTATAAAGTGCGCGAGATCAATGACTTTCACCACGCCC
ACGACGCCTACCTGAATGCCGTGGTGGCTTCCGCCCTGCTGAAGAAGTACCCTAAGCTGGAACCCGAGTTCGTGTACGGCGACTACCCAAG
TACAACTCCTTCAGAGCGGAAGTCCGCCACCAAGGAAGTGCTTCTACCACAATATTAAGGAAGTCATCTCCCTGGC
CGATGGCAGAGTGATCGAGCGGCCCCTGATCGAAGTGAACGAAGACAGGCGAGAGCGTGTGGAACAAAGAAAGCGACCTGGCCACCGTGC
GGCGGGTGCTGAGTTACCTCAAGTGAATGTCGTGAAGAAGACCGAGGTGCAGACAGGCGGCTTCAGCAAAGAGTCTATCCTGCCCAAGAGGA
ACAGCGATAAGCTGATCGCCAGAAAGAAGGACTGGGACCCTAAGAAGTACGGCGGCTTCGACAGCCCCACCGTGGCCTATTCTGTGCTGGTGG
TGGCCAAAGTGGAAAAGGGCAAGTCCAAGAAACTGAAGAGTGTGAAAGAGCTGCTGGGGATCACCATCATGGAAAGAAGCAGCTTCGAGAAGA
ATCCCATCGACTTTCTGGAAGCCAAGGGCTACAAAGAAGTGAAAAAGGACCTCATCATCAAGCTGCCTAAGTACTCCCTGTTCGAGCTGGAAA
ACGGCCGGAAGAGAATGCTGGCCTCTGCCGGCGAACTGCAGAAGGGAAACGAACTGGCCCTGCCCTCCAAATATGTGAACTTCCTGTACCTGG
CCAGCCACTATGAGAAGCTGAAGGGCTCCCCCGAGGATAATGAGCAGAAACAGCTGTTTGTGGAACAGCACAAGCACTACCTGGACGAGATCA
TCGAGCAGATCAGCGAGTTCTCCAAGAGAGTGATCCTGGCCGACGCTAATCTGGACAAAGTGCTGTCCGCCTACAACAAGCACCGGGATAAGC
CCATCAGAGAGCAGGCCGAGAATATCATCCACCTGTTTACCCTGACCAATCTGGGAGCCCCTGCCGCCTTCAAGTACTTTGACACCACCATCG
ACCGGAAGAGGTACACCAGCACCAAAGAGGTGCTGGACGCGACCCTGATCCACCAGAGCATCACCGGCCTGTACGAGACACGGATCGACCTGT
CTCAGCTGGGAGGCGACAAAAGGCCGGCGGCCACGAAAAAGGCCGGCCAGGCAAAAAAGAAAAAG (SEQ ID NO: 84)
```

SpCas9 nickases
Mutated residues (changed to GCC) bolded in order: D10, E762, N863, H983, D986

ATGGACTATAAGGACCACGACGGAGACTACAAGGATCATGATATTGATTACAAAGACGATGACGATAAGATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATCGCCCAGCTGCCCGGCGAGAAGAAGAATGGCCTGTTCGGCAAC
CTGATTGCCCTGAGCCTGGGCCTGACCCCCAACTTCAAGAGCAACTTCGACCTGGCCGAGGATGCCAAACTGCAGCTGAGCAAGGACACCTAC
GACGACGACCTGGACAACCTGCTGGCCCAGATCGGCGACCAGTACGCCGACCTGTTTCTGGCCGCCAAGAACCTGTCCGACGCCATCCTGCTG
AGCGACATCCTGAGAGTGAACACCGAGATCACCAAGGCCCCCCTGAGCGCCTCTATGATCAAGAGATACGACGAGCACCACCAGGACCTGACC
CTGCTGAAAGCTCTCGTGCGGCAGCAGCTGCCTGAGAAGTACAAAGAGATTTTCTTCGACCAGAGCAAGAACGGCTACGCCGGCTACATTGAC
GGCGGAGCCAGCCAGGAAGAGTTCTACAAGTTCATCAAGCCCATCCTGGAAAAGATGGACGGCACCGAGGAACTGCTCGTGAAGCTGAACAGA
GAGGACCTGCTGCGGAAGCAGCGGACCTTCGACAACGGCAGCATCCCCCACCAGATCCACCTGGGAGAGCTGCACGCCATTCTGCGGCGGCAG
GAAGATTTTTACCCATTCCTGAAGGACAACCGGGAAAAGATCGAGAAGATCCTGACCTTCCGCATCCCCTACTACGTGGGCCCTCTGGCCAGG
GGAAACAGCAGATTCGCCTGGATGACCAGAAAGAGCGAGGAAACCATCACCCCCTGGAACTTCGAGGAAGTGGTGGACAAGGGCGCTTCCGCC
CAGAGCTTCATCGAGCGGATGACCAACTTCGATAAGAACCTGCCCAACGAGAAGGTGCTGCCCAAGCACAGCCTGCTGTACGAGTACTTCACC
GTGTATAACGAGCTGACCAAAGTGAAATACGTGACCGAGGGAATGAGAAAGCCCGCCTTCCTGAGCGGCGAGCAGAAAAAGGCCATCGTGGAC
CTGCTGTTCAAGACCAACCGGAAAGTGACCGTGAAGCAGCTGAAAGAGGACTACTTCAAGAAATCGAGTGCTTCGACTCCGTGGAAATCTCC
GGCGTGGAAGATCGGTTCAACGCCTCCCTGGGCACATACCACGATCTGCTGAAAATTATCAAGGACAAGGACTTCCTGGACAATGAGGAAAAC
GAGGACATTCTGGAAGATATCGTGCTGACCCTGACACTGTTTGAGGACAGAGAGATGATCGAGGAACGGCTGAAAACCTATGCCCACCTGTTC
GACGACAAAGTGATGAAGCAGCTGAAGCGGCGGAGATACACCGGCTGGGGCAGGCTGAGCCGGAAGCTGATCAACGGCATCCGGGACAAGCAG
TCCGGCAAGACAATCCTGGATTTCCTGAAGTCCGACGGCTTCGCCAACAGAAACTTCATGCAGCTGATCCACGACGACAGCCTGACCTTTAAA
GAGGACATCCAGAAAGCCCAGGTGTCCGGCCAGGGCGATAGCCTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGGCACAAGCCCGAGAACATCGTGATCGAAATGGCCAGAGAGAAC
CAGACCACCCAGAAGGGACAGAAGAACAGCCGCGAGAGAATGAAGCGGATCGAAGAGGGCATCAAAGAGCTGGGCGCCAGATCCTGAAAGAA
CACCCCGTGGAAAACACCCAGCTGCAGAACGAGAAGCTGTACCTGTACTACCTGCAGAATGGGCGGGATATGTACGTGGACCAGGAACTGGAC
ATCAACCGGCTGTCCGACTACGATGTGGACCATATCGTGCCTCAGAGCTTTCTGAAGGACGACTCCATCGACAACAAGGTGCTGACCAGAAGC
GACAAGAACCGGGACAAGAGCGACAACGTGCCCTCCGAAGAGGTCGTGAAGAAGATGAAGAACTACTGGCGGCAGCTGCTGAACGCCAAGCTG
ATTACCCAGAGAAAGTTCGACAATCTGACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACTAAGTACGACGAGAATGACAAGCTGATCCGGGAAGTG
AAAGTGATCACCCTGAAGTCCAAGCTGGTGTCCGATTTCCGGAAGGATTTCCAGTTTTACAAAGTGCGCGAGATCAACAACTACCACCACGCC
CACGACGCCTACCTGAACGCCGTGGTCGGCACCGCCCTGATCAAAAAGTACCCTAAGCTGGAAAGCGAGTTCGTGTACGGCGACTACAAGGTG
TACGACGTGCGGAAGATGATCGCCAAGAGCGAGCAGGAAATCGGCAAGGCTACCGCCAAGTACTTCTTCTACAGCAACATCATGAACTTTTTC
AAGACCGAGATTACCCTGGCCAACGGCGAGATCCGGAAGCGGCCTCTGATCGAGACAAACGGCGAAACCGGGGAGATCGTGTGGGATAAGGGC
CGGGATTTTGCCACCGTGCGGAAAGTGCTGAGCATGCCCCAAGTGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGACTGGGACCCTAAGAAGTACGGCGGCTTCGACAGCCCCACCGTG
GCCTATTCTGTGCTGGTGGTGGCCAAAGTGGAAAAGGGCAAGTCCAAGAAACTGAAGAGTGTGAAAGAGCTGCTGGGGATCACCATCATGGAA
AGAAGCAGCTTCGAGAAGAATCCCATCGACTTTCTGGAAGCCAAGGGCTACAAAGAAGTGAAAAAGGACCTGATCATCAAGCTGCCTAAGTAC
TCCCTGTTCGAGCTGGAAAACGGCCGGAAGAGAATGCTGGCCTCTGCCGGCGAACTGCAGAAGGGAAACGAACTGGCCCTGCCCTCCAAATAT
GTGAACTTCCTGTACCTGGCCAGCCACTATGAGAAGCTGAAGGGCTCCCCCGAGGATAATGAGCAGAAACAGCTGTTTGTGGAACAGCACAAG
CACTACCTGGACGAGATCATCGAGCAGATCAGCGAGTTCTCCAAGAGAGTGATCCTGGCCGACGCTAATCTGGACAAAGTGCTGTCCGCCTAC
AACAAGCACCGGGATAAGCCCATCAGAGAGCAGGCCGAGAATATCATCCACCTGTTTACCCTGACCAATCTGGGAGCCCCTGCCGCCTTCAAG
TACTTTGACACCACCATCGACCGGAAGAGGTACACCAGCACCAAAGAGGTGCTGGACGCCACCCTGATCCACCAGAGCATCACCGGCCTGTAC
GAGACACGGATCGACCTGTCTCAGCTGGGAGGCGACAAAAGGCCGGCGGCCACGAAAAAGGCCGGCCAGGCAAAAAAGAAAAAG
(SEQ ID NO: 85)

SpCas9 point mutants
Mutated residues (changed to (GCC bolded in order: R63A, R66A, R69A, R70A, R74A,
R75A, R78A, K163A, R165A, K510A
ATGGACTATAAGGACCACGACGGAGACTACAAGGATCATGATATTGATTACAAAGACGATGACGATAAGATGGCCCCAAAGAAGAAGCGGAAG
GTCGGTATCCACGGAGTCCCAGCAGCCGACAAGAAGTACAGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACACCAGACGGAAGAACCGGATCTGCTATCTGCAAGAGATC
TTCAGCAACGAGATGGCCAAGGTGGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATCGCCCAGCTGCCCGGCGAGAAGAAGAATGGCCTGTTCGGCAAC
CTGATTGCCCTGAGCCTGGGCCTGACCCCCAACTTCAAGAGCAACTTCGACCTGGCCGAGGATGCCAAACTGCAGCTGAGCAAGGACACCTAC
GACGACGACCTGGACAACCTGCTGGCCCAGATCGGCGACCAGTACGCCGACCTGTTTCTGGCCGCCAAGAACCTGTCCGACGCCATCCTGCTG
AGCGACATCCTGAGAGTGAACACCGAGATCACCAAGGCCCCCCTGAGCGCCTCTATGATCAAGAGATACGACGAGCACCACCAGGACCTGACC
CTGCTGAAAGCTCTCGTGCGGCAGCAGCTGCCTGAGAAGTACAAAGAGATTTTCTTCGACCAGAGCAAGAACGGCTACGCCGGCTACATTGAC
GGCGGAGCCAGCCAGGAAGAGTTCTACAAGTTCATCAAGCCCATCCTGGAAAAGATGGACGGCACCGAGGAACTGCTCGTGAAGCTGAACAGA
GAGGACCTGCTGCGGAAGCAGCGGACCTTCGACAACGGCAGCATCCCCCACCAGATCCACCTGGGAGAGCTGCACGCCATTCTGCGGCGGCAG
GAAGATTTTTACCCATTCCTGAAGGACAACCGGGAAAAGATCGAGAAGATCCTGACCTTCCGCATCCCCTACTACGTGGGCCCTCTGGCCAGG
GGAAACAGCAGATTCGCCTGGATGACCAGAAAGAGCGAGGAAACCATCACCCCCTGGAACTTCGAGGAAGTGGTGGACAAGGGCGCTTCCGCC
CAGAGCTTCATCGAGCGGATGACCAACTTCGATAAGAACCTGCCCAACGAGAAGGTGCTGCCCAAGCACAGCCTGCTGTACGAGTACTTCACC
GTGTATAACGAGCTGACCAAAGTGAAATACGTGACCGAGGGAATGAGAAAGCCCGCCTTCCTGAGCGGCGAGCAGAAAAAGGCCATCGTGGAC
CTGCTGTTCAAGACCAACCGGAAAGTGACCGTGAAGCAGCTGAAAGAGGACTACTTCAAGAAATCGAGTGCTTCGACTCCGTGGAAATCTCC
GGCGTGGAAGATCGGTTCAACGCCTCCCTGGGCACATACCACGATCTGCTGAAAATTATCAAGGACAAGGACTTCCTGGACAATGAGGAAAAC
GAGGACATTCTGGAAGATATCGTGCTGACCCTGACACTGTTTGAGGACAGAGAGATGATCGAGGAACGGCTGAAAACCTATGCCCACCTGTTC
GACGACAAAGTGATGAAGCAGCTGAAGCGGCGGAGATACACCGGCTGGGGCAGGCTGAGCCGGAAGCTGATCAACGGCATCCGGGACAAGCAG
TCCGGCAAGACAATCCTGGATTTCCTGAAGTCCGACGGCTTCGCCAACAGAAACTTCATGCAGCTGATCCACGACGACAGCCTGACCTTTAAA

```
GAGGACATCCAGAAAGCCCAGGTGTCCGGCCAGGGCGATAGCCTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGGCACAAGCCCGAGAACATCGTGATCGAAATGGCCAGAGAGAAC
CAGACCACCCAGAAGGGACAGAAGAACAGCCGCGAGAGAATGAAGCGGATCGAAGAGGGCATCAAAGAGCTGGGCAGCCAGATCCTGAAAGAA
CACCCCGTGGAAAACACCCAGCTGCAGAACGAGAAGCTGTACCTGTACTACCTGCAGAATGGGCGGGATATGTACGTGGACCAGGAACTGGAC
ATCAACCGGCTGTCCGACTACGATGTGGACCATATCGTGCCTCAGAGCTTTCTGAAGGACGACTCCATCGACAACAAGGTGCTGACCAGAAGC
GACAAGAACCGGGCAAGAGCGACAACGTGCCCTCCGAAGAGGTCGTGAAGAAGATGAAGAACTACTGGCGGCAGCTGCTGAACGCCAAGCTG
ATTACCCAGAGAAAGTTCGACAATCTGACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACTAAGTACGACGAGAATGACAAGCTGATCCGGGAAGTG
AAAGTGATCACCCTGAAGTCCAAGCTGGTGTCCGATTTCCGGAAGGATTTCCAGTTTTACAAAGTGCGCGAGATCAACAACTACCACCACGCC
CACGACGCCTACCTGAACGCCGTCGTGGGAACCGCCCTGATCAAAAAGTACCCTAAGCTGGAAAGCGAGTTCGTGTACGGCGACTACAAGGTG
TACGACGTGCGGAAGATGATCGCCAAGAGCGAGCAGGAAATCGGCAAGGCTACCGCCAAGTACTTCTTCTACAGCAACATCATGAACTTTTTC
AAGACCGAGATTACCCTGGCCAACGGCGAGATCCGGAAGCGGCCTCTGATCGAGACAAACGGCGAAACCGGGGAGATCGTGTGGGATAAGGGC
CGGGATTTTGCCACCGTGCGGAAAGTGCTGAGCATGCCCCAAGTGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGACTGGGACCCTAAGAAGTACGGCGGCTTCGACAGCCCCACCGTG
GCCTATTCTGTGCTGGTGGTGGCCAAAGTGGAAAAGGGCAAGTCCAAGAAACTGAAGAGTGTGAAAGAGCTGCTGGGGATCACCATCATGGAA
AGAAGCAGCTTCGAGAAGAATCCCATCGACTTTCTGGAAGCCAAGGGCTACAAAGAAGTGAAAAAGGACCTGATCATCAAGCTGCCTAAGTAC
TCCCTGTTCGAGCTGGAAAACGGCCGGAAGAGAATGCTGGCCTCTGCCGGCGAACTGCAGAAGGGAAACGAACTGGCCCTGCCCTCCAAATAT
GTGAACTTCCTGTACCTGGCCAGCCACTATGAAGAGCTGAAGGGCTCCCCCGAGGATAATGAGCAGAAACAGCTGTTTGTGGAACAGCACAAG
CACTACCTGGACGAGATCATCGAGCAGATCAGCGAGTTCTCCAAGAGAGTGATCCTGGCCGACGCTAATCTGGACAAAGTGCTGTCCGCCTAC
AACAAGCACCGGGATAAGCCCATCAGAGAGCAGGCCGAGAATATCATCCACCTGTTTACCCTGACCAATCTGGGAGCCCCTGCCGCCTTCAAG
TACTTTGACACCACCATCGACCGGAAGAGGTACACCAGCACCAAAGAGGTGCTGGACGCCACCCTGATCCACCAGAGCATCACCGGCCTGTAC
GAGACACGGATCGACCTGTCTCAGCTGGGAGGCGACAAAAGGCCGGCGGCCACGAAAAGGCCGGCCAGGCAAAAAGAAAAAG
(SEQ ID NO: 86)
``` sgRNA sequences:
guide sequence underlined
+83

```
GAGUCCGAGCAGAAGAAGAAGCCCCAGAGCUAGAAAUAGCAAGUUGGGGUAAGGCUAGUCCGUUAUCAACUUGAAAAAGUGGCACCGAGUCGG
UGCUUUU (SEQ ID NO: 87)
```

+47

```
GAGUCCGAGCAGAAGAAGAAGUUUUAGAGCUAGAAAUAGCAAGUUAAAAUAAGGCUAGUCCGUUUU (SEQ ID NO: 88)
```

+67

```
GAGUCCGAGCAGAAGAAGAAGUUUUAGAGCUAGAAAUAGCAAGUUAAAAUAAGGCUAGUCCGUUAUCAACUUGAAAAAGUGUUUU
(SEQ ID NO: 89)
``` mutate proximal crRNA:tracrRNA duplex

```
GAGUCCGAGCAGAAGAAGAAGCCCCAGAGCUAGAAAUAGCAAGUUGGGGUAAGGCUAGUCCGUUAUCAACUUGAAAAAGUGGCACCGAGUCGG
UGCUUUU (SEQ ID NO: 90)
``` truncate distal crRNA:tracrRNA duplex

```
GAGUCCGAGCAGAAGAAGAAGUUUUAGAGACAAGUUAAAAUAAGGCUAGUCCGUUAUCAACUUGAAAAAGUGGCACCGAGUCGGUGCUUUU
(SEQ ID NO: 91)
``` remove crRNA:tracrRNA duplex bulge

```
GAGUCCGAGCAGAAGAAGAAGUUUUAGAGCUAGAAAUAGCUUUAAAUAAGGCUAGUCCGUUAUCAACUUGAAAAAGUGGCACCGAGUCGGUG
CUUUU (SEQ ID NO: 92)
``` abolish stemloop 1

```
GAGUCCGAGCAGAAGAAGAAGUUUUAGAGCUAGAAAUAGCAAGUUAAAAUAAUUCUAGUAAGUUAUCAACUUGAAAAAGUGGCACCGAGUCGG
UGCUUUU (SEQ ID NO: 93)
``` mutate stemloop 1

```
GAGUCCGAGCAGAAGAAGAAGUUUUAGAGCUAGAAAUAGCAAGUUAAAAUAAGCCAUGUGCGUUAUCAACUUGAAAAAGUGGCACCGAGUCGG
UGCUUUU (SEQ ID NO: 94)
``` truncate linker

```
GAGUCCGAGCAGAAGAAGAAGUUUUAGAGCUAGAAAUAGCAAGUUAAAAUAAGGCUAGUCCGUAACUUGAAAAAGUGGCACCGAGUCGGUGCU
UUU (SEQ ID NO: 95)
``` replace stemloop 2

```
GAGUCCGAGCAGAAGAAGAAGUUUUAGAGCUAGAAAUAGCAAGUUAAAAUAAGGCUAGUCCGUUAUCACGCCGAAAGGCGGGCACCGAGUCGG
UGCUUUU (SEQ ID NO: 96)
``` lengthen stemloop 2

```
GAGUCCGAGCAGAAGAAGAAGUUUUAGAGCUAGAAAUAGCAAGUUAAAAUAAGGCUAGUCCGUUAUCAACUUGAGAAAUCAAGUGGCACCGAG
UCGGUGCUUUU (SEQ ID NO: 97)
``` mutate stemloop 3

GAGUCCGAGCAGAAGAAGAAGUUUUAGAGCUAGAAAUAGCAAGUUAAAAUAAGGCUAGUCCGUUAUCAACUUGAAAAAGUGGCCCCGCGGCGG
GGCUUUU (SEQ ID NO: 98)

lengthen stemloop 3

GAGUCCGAGCAGAAGAAGAAGUUUUAGAGCUAGAAAUAGCAAGUUAAAAUAAGGCUAGUCCGUUAUCAACUUGAAAAAGUGGCACCGAAAGUU
UCGGUGCUUUU (SEQ ID NO: 99)

reconstructed sgRNA

GAGUCCGAGCAGAAGAAGAAGCCCCAGAGCAUUAGCAAGUUGGGGUAAGCCAUGUGCGUUAUCAGGGCACCAGCCCGGCACCGAGUCGGUGCU
UUU (SEQ ID NO: 100)

G43A

GAGUCCGAGCAGAAGAAGAAGUUUUAGAGCUAGAAAUAGCAACUUAAAAUAAGGCUAGUCCGUUAUCAACUUGAAAAAGUGGCACCGAGUCGG
UGCUUUU (SEQ ID NO: 101)

U44G

GAGUCCGAGCAGAAGAAGAAGUUUUAGAGCUAGAAAUAGCAAGGUAAAAUAAGGCUAGUCCGUUAUCAACUUGAAAAAGUGGCACCGAGUCGG
UGCUUUU (SEQ ID NO: 102)

U44C

GAGUCCGAGCAGAAGAAGAAGUUUUAGAGCUAGAAAUAGCAAGCUAAAAUAAGGCUAGUCCGUUAUCAACUUGAAAAAGUGGCACCGAGUCGG
UGCUUUU (SEQ ID NO: 103)

Primers (SEQ ID NOS 104-107, respectively, in order of appearance)

| Cas9 | Target | PAM | SURVEYOR primer F | SURVEYOR PRIMER R |
|---|---|---|---|---|
| Sp | GAGTCCGAGCAGAAGAAGAA | GGG | CCATCCCCTTCTGTGAATGT | GGAGATTGGAGACACGGAGA |
| St3 | GCTCCCATCACATCAACCGG | TGGCG | same | same |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

1. Urnov, F. D., Rebar, E. J., Holmes, M. C., Zhang, H. S. & Gregory, P. D. Genome editing with engineered zinc finger nucleases. Nat. Rev. Genet. 11, 636-646 (2010).
2. Bogdanove, A. J. & Voytas, D. F. TAL effectors: customizable proteins for DNA targeting. Science 333, 1843-1846 (2011).
3. Stoddard, B. L. Homing endonuclease structure and function. Q. Rev. Biophys. 38, 49-95 (2005).
4. Bae, T. & Schneewind, O. Allelic replacement in Staphylococcus aureus with inducible counter-selection. Plasmid 55, 58-63 (2006).
5. Sung, C. K., Li, H., Claverys, J. P. & Morrison, D. A. An rpsL cassette, janus, for gene replacement through negative selection in Streptococcus pneumoniae. Appl. Environ. Microbiol. 67, 5190-5196 (2001).
6. Sharan, S. K., Thomason, L. C., Kuznetsov, S. G. & Court, D. L. Recombineering: a homologous recombination-based method of genetic engineering. Nat. Protoc. 4, 206-223 (2009).
7. Jinek, M. et al. A programmable dual-RNA-guided DNA endonuclease in adaptive bacterial immunity. Science 337, 816-821 (2012).
8. Deveau, H., Garneau, J. E. & Moineau, S. CRISPR/Cas system and its role in phage-bacteria interactions. Annu. Rev. Microbiol. 64, 475-493 (2010).
9. Horvath, P. & Barrangou, R. CRISPR/Cas, the immune system of bacteria and archaea. Science 327, 167-170 (2010).
10. Terns, M. P. & Terns, R. M. CRISPR-based adaptive immune systems. Curr. Opin. Microbiol. 14, 321-327 (2011).
11. van der Oost, J., Jore, M. M., Westra, E. R., Lundgren, M. & Brouns, S. J. CRISPR-based adaptive and heritable immunity in prokaryotes. Trends. Biochem. Sci. 34, 401-407 (2009).
12. Brouns, S. J. et al. Small CRISPR RNAs guide antiviral defense in prokaryotes. Science 321, 960-964 (2008).
13. Carte, J., Wang, R., Li, H., Terns, R. M. & Terns, M. P. Cas6 is an endoribonuclease that generates guide RNAs for invader defense in prokaryotes. Genes Dev. 22, 3489-3496 (2008).
14. Deltcheva, E. et al. CRISPR RNA maturation by trans-encoded small RNA and host factor RNase III. Nature 471, 602-607 (2011).
15. Hatoum-Aslan, A., Maniv, I. & Marraffini, L. A. Mature clustered, regularly interspaced, short palindromic repeats RNA (crRNA) length is measured by a ruler mechanism anchored at the precursor processing site. *Proc. Natl. Acad. Sci. U.S.A.* 108, 21218-21222 (2011).
16. Haurwitz, R. E., Jinek, M., Wiedenheft, B., Zhou, K. & Doudna, J. A. Sequence- and structure-specific RNA processing by a CRISPR endonuclease. *Science* 329, 1355-1358 (2010).
17. Deveau, H. et al. Phage response to CRISPR-encoded resistance in *Streptococcus thermophilus*. *J. Bacteriol.* 190, 1390-1400 (2008).
18. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* (2012).
19. Makarova, K. S., Aravind, L., Wolf, Y. I. & Koonin, E. V. Unification of Cas protein families and a simple scenario for the origin and evolution of CRISPR-Cas systems. *Biol. Direct.* 6, 38 (2011).
20. Barrangou, R. RNA-mediated programmable DNA cleavage. *Nat. Biotechnol.* 30, 836-838 (2012).
21. Brouns, S. J. Molecular biology. A Swiss army knife of immunity. *Science* 337, 808-809 (2012).
22. Carroll, D. A CRISPR Approach to Gene Targeting. *Mol. Ther.* 20, 1658-1660 (2012).
23. Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
24. Sapranauskas, R. et al. The *Streptococcus thermophilus* CRISPR/Cas system provides immunity in *Escherichia coli*. *Nucleic Acids Res.* (2011).
25. Semenova, E. et al. Interference by clustered regularly interspaced short palindromic repeat (CRISPR) RNA is governed by a seed sequence. *Proc. Natl. Acad. Sci. U.S.A.* (2011).
26. Wiedenheft, B. et al. RNA-guided complex from a bacterial immune system enhances target recognition through seed sequence interactions. *Proc. Natl. Acad. Sci. U.S.A.* (2011).
27. Zahner, D. & Hakenbeck, R. The *Streptococcus pneumoniae* beta-galactosidase is a surface protein. *J. Bacteriol.* 182, 5919-5921 (2000).
28. Marraffini, L. A., Dedent, A. C. & Schneewind, O. Sortases and the art of anchoring proteins to the envelopes of gram-positive bacteria. *Microbiol. Mol. Biol. Rev.* 70, 192-221 (2006).
29. Motamedi, M. R., Szigety, S. K. & Rosenberg, S. M. Double-strand-break repair recombination in *Escherichia coli*: physical evidence for a DNA replication mechanism in vivo. *Genes Dev.* 13, 2889-2903 (1999).
30. Hosaka, T. et al. The novel mutation K87E in ribosomal protein S12 enhances protein synthesis activity during the late growth phase in *Escherichia coli*. *Mol. Genet. Genomics* 271, 317-324 (2004).
31. Costantino, N. & Court, D. L. Enhanced levels of lambda Red-mediated recombinants in mismatch repair mutants. *Proc. Natl. Acad. Sci. U.S.A.* 100, 15748-15753 (2003).
32. Edgar, R. & Qimron, U. The *Escherichia coli* CRISPR system protects from lambda lysogenization, lysogens, and prophage induction. *J. Bacteriol.* 192, 6291-6294 (2010).
33. Marraffini, L. A. & Sontheimer, E. J. Self versus non-self discrimination during CRISPR RNA-directed immunity. *Nature* 463, 568-571 (2010).
34. Fischer, S. et al. An archaeal immune system can detect multiple Protospacer Adjacent Motifs (PAMs) to target invader DNA. *J. Biol. Chem.* 287, 33351-33363 (2012).
35. Gudbergsdottir, S. et al. Dynamic properties of the *Sulfolobus* CRISPR/Cas and CRISPR/Cmr systems when challenged with vector-borne viral and plasmid genes and protospacers. *Mol. Microbiol.* 79, 35-49 (2011).
36. Wang, H. H. et al. Genome-scale promoter engineering by coselection MAGE. *Nat Methods* 9, 591-593 (2012).
37. Cong L, Ran F A, Cox D, Lin S, Barretto R, Habib N, Hsu P D, Wu X, Jiang W, Marraffini L A, Zhang F. Multiplex Genome Engineering Using CRISPR/Cas Systems. *Science*. 2013 Feb. 15; 339(6121):819-23.
38. Mali, P., Yang, L., Esvelt, K. M., Aach, J., Guell, M., DiCarlo, J. E., Norville, J. E., and Church, G M. (2013b). RNA-guided human genome engineering via Cas9. *Science* 339, 823-826.
39. Hoskins, J. et al. Genome of the bacterium *Streptococcus pneumoniae* strain R6. *J. Bacteriol.* 183, 5709-5717 (2001).
40. Havarstein, L. S., Coomaraswamy, G. & Morrison, D. A. An unmodified heptadecapeptide pheromone induces competence for genetic transformation in *Streptococcus pneumoniae*. *Proc. Natl. Acad. Sci. U.S.A.* 92, 11140-11144 (1995).
41. Horinouchi, S. & Weisblum, B. Nucleotide sequence and functional map of pC194, a plasmid that specifies inducible chloramphenicol resistance. *J. Bacteriol.* 150, 815-825 (1982).
42. Horton, R. M. In Vitro Recombination and Mutagenesis of DNA: SOEing Together Tailor-Made Genes. *Methods Mol. Biol.* 15, 251-261 (1993).
43. Podbielski, A., Spellerberg, B., Woischnik, M., Pohl, B. & Lutticken, R. Novel series of plasmid vectors for gene inactivation and expression analysis in group A streptococci (GAS). *Gene* 177, 137-147 (1996).
44. Husmann, L. K., Scott, J. R., Lindahl, G. & Stenberg, L. Expression of the Arp protein, a member of the M protein family, is not sufficient to inhibit phagocytosis of *Streptococcus pyogenes*. *Infection and immunity* 63, 345-348 (1995).
45. Gibson, D. G. et al. Enzymatic assembly of DNA molecules up to several hundred kilobases. *Nat Methods* 6, 343-345 (2009).
46. Garneau J. E. et al. The CRISPR/Cas bacterial immune system cleaves bacteriophage and plasmid DNA. *Nature* 468, 67-71(4 Nov. 2010)
47. Barrangou R. et al. CRISPR provides acquired resistance against viruses in prokaryotes. *Science*. 2007 Mar. 23; 315(5819):1709-12.
48. Ishino Y. et al. Nucleotide sequence of the iap gene, responsible for alkaline phosphatase isozyme conversion in *Escherichia coli*, and identification of the gene product. J Bacteriol. 1987 December; 169(12):5429-33.
49. Mojica F. J. M et al. Biological significance of a family of regularly spaced repeats in the genomes of Archaea, Bacteria and mitochondria. Molecular Microbiology (2000) 36(1), 244-246.
50. Jansen R. et al. Identification of genes that are associated with DNA repeats in prokaryotes. Molecular Microbiology (2002) 43(6), 1565-1575.
51. Gouet, P., Courcelle, E., Stuart, D. I., and Metoz, F. (1999). ESPript: analysis of multiple sequence alignments in PostScript. Bioinformatics 15, 305-308.
52. Notredame, C., Higgins, D. G., and Heringa, J. (2000). T-Coffee: A novel method for fast and accurate multiple sequence alignment. J Mol Biol 302, 205-217.
53. Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C.

(2002). PHENIX: building new software for automated crystallographic structure determination. Acta Crystallogr D Biol Crystallogr 58, 1948-1954.

54. Ariyoshi, M., Vassylyev, D. G., Iwasaki, H., Nakamura, H., Shinagawa, H., and Morikawa, K. (1994). Atomic structure of the RuvC resolvase: a holliday junction-specific endonuclease from *E. coli*. Cell 78, 1063-1072.

55. Biertumpfel, C., Yang, W., and Suck, D. (2007). Crystal structure of T4 endonuclease VII resolving a Holliday junction. Nature 449, 616-620.

56. Chen, L., Shi, K., Yin, Z., and Aihara, H. (2013). Structural asymmetry in the *Thermus thermophilus* RuvC dimer suggests a basis for sequential strand cleavages during Holliday junction resolution. Nucleic acids research 41, 648-656.

57. delaFortelle, E., and Bricogne, G. (1997). Maximum-likelihood heavy-atom parameter refinement for multiple isomorphous replacement and multiwavelength anomalous diffraction methods. Methods Enzymol 276, 472-494.

58. Emsley, P., and Cowtan, K. (2004). Coot: model-building tools for molecular graphics. Acta Crystallogr D Biol Crystallogr 60, 2126-2132.

59. Fonfara, I., Le Rhun, A., Chylinski, K., Makarova, K. S., Lecrivain, A. L., Bzdrenga, J., Koonin, E. V., and Charpentier, E. (2013). Phylogeny of Cas9 determines functional exchangeability of dual-RNA and Cas9 among orthologous type II CRISPR-Cas systems. Nucleic acids research.

60. Fu, Y., Foden, J. A., Khayter, C., Maeder, M. L., Reyon, D., Joung, J. K., and Sander, J. D. (2013). High-frequency off-target mutagenesis induced by CRISPR-Cas nucleases in human cells. Nature biotechnology 31, 822-826.

61. Gilbert, L. A., Larson, M. H., Morsut, L., Liu, Z., Brar, G. A., Tones, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.

62. Gorecka, K. M., Komorowska, W., and Nowotny, M. (2013). Crystal structure of RuvC resolvase in complex with Holliday junction substrate. Nucleic Acids Res 41, 9945-9955.

63. Gratz, S. J., Cummings, A. M., Nguyen, J. N., Hamm, D. C., Donohue, L. K., Harrison, M. M., Wildonger, J., and O'Connor-Giles, K. M. (2013). Genome engineering of *Drosophila* with the CRISPR RNA-guided Cas9 nuclease. Genetics 194, 1029-1035.

64. Holm, L., and Rosenstrom, P. (2010). Dali server: conservation mapping in 3D. Nucleic acids research 38, W545-549.

65. Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832.

66. Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using a CRISPR-Cas system. Nature biotechnology 31, 227-229.

67. Kabsch, W. (2010). Xds. Acta crystallographica Section D, Biological crystallography 66, 125-132.

68. Konermann, S., Brigham, M. D., Trevino, A. E., Hsu, P. D., Heidenreich, M., Cong, L., Platt, R. J., Scott, D. A., Church, G. M., and Zhang, F. (2013). Optical control of mammalian endogenous transcription and epigenetic states. Nature 500, 472-476.

69. Li, C. L., Hor, L. I., Chang, Z. F., Tsai, L. C., Yang, W. Z., and Yuan, H. S. (2003). DNA binding and cleavage by the periplasmic nuclease Vvn: a novel structure with a known active site. The EMBO journal 22, 4014-4025.

70. Maeder, M. L., Linder, S. J., Cascio, V. M., Fu, Y., Ho, Q. H., and Joung, J. K. (2013). CRISPR RNA-guided activation of endogenous human genes. Nature methods 10, 977-979.

71. Mali, P., Aach, J., Stranges, P. B., Esvelt, K. M., Moosburner, M., Kosuri, S., Yang, L., and Church, G. M. (2013a). CAS9 transcriptional activators for target specificity screening and paired nickases for cooperative genome engineering. Nature biotechnology 31, 833-838.

72. Marraffini, L. A., and Sontheimer, E. J. (2008). CRISPR interference limits horizontal gene transfer in staphylococci by targeting DNA. Science 322, 1843-1845.

73. Marraffini, L. A., and Sontheimer, E. J. (2010). CRISPR interference: RNA-directed adaptive immunity in bacteria and archaea. Nat Rev Genet 11, 181-190.

74. Mojica, F. J., Diez-Villasenor, C., Garcia-Martinez, J., and Almendros, C. (2009). Short motif sequences determine the targets of the prokaryotic CRISPR defence system. Microbiology 155, 733-740.

75. Pattanayak, V., Lin, S., Guilinger, J. P., Ma, E., Doudna, J. A., and Liu, D. R. (2013). High-throughput profiling of off-target DNA cleavage reveals RNA-programmed Cas9 nuclease specificity. Nature biotechnology 31, 839-843.

76. Perez-Pinera, P., Kocak, D. D., Vockley, C. M., Adler, A. F., Kabadi, A. M., Polstein, L. R., Thakore, P. I., Glass, K. A., Ousterout, D. G., Leong, K. W., et al. (2013). RNA-guided gene activation by CRISPR-Cas9-based transcription factors. Nature methods 10, 973-976.

77. Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell 152, 1173-1183.

78. Ran, F. A., Hsu, P. D., Lin, C. Y., Gootenberg, J. S., Konermann, S., Trevino, A. E., Scott, D. A., Inoue, A., Matoba, S., Zhang, Y., et al. (2013). Double nicking by RNA-guided CRISPR Cas9 for enhanced genome editing specificity. Cell 154, 1380-1389.

79. Sampson, T. R., Saroj, S. D., Llewellyn, A. C., Tzeng, Y. L., and Weiss, D. S. (2013). A CRISPR/Cas system mediates bacterial innate immune evasion and virulence. Nature 497, 254-257.

80. Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

81. Sheldrick, G. M. (2008). A short history of SHELX Acta crystallographica Section A, Foundations of crystallography 64, 112-122.

82. Spilman, M., Cocozaki, A., Hale, C., Shao, Y., Ramia, N., Terns, R., Terns, M., Li, H., and Stagg, S. (2013). Structure of an RNA silencing complex of the CRISPR-Cas immune system. Molecular cell 52, 146-152.

83. Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

84. Wang, T., Wei, J. J., Sabatini, D. M., and Lander, E. S. (2014). Genetic screens in human cells using the CRISPR-Cas9 system. Science 343, 80-84.

85. Wiedenheft, B., Lander, G. C., Zhou, K., Jore, M. M., Brouns, S. J., van der Oost, J., Doudna, J. A., and Nogales, E. (2011). Structures of the RNA-guided surveillance complex from a bacterial immune system. Nature 477, 486-489.
86. Winn, M. D., Ballard, C. C., Cowtan, K. D., Dodson, E. J., Emsley, P., Evans, P. R., Keegan, R. M., Krissinel, E. B., Leslie, A. G., McCoy, A., et al. (2011). Overview of the CCP4 suite and current developments. Acta crystallographica Section D, Biological crystallography 67, 235-242.
87. Yang, H., Wang, H., Shivalila, C. S., Cheng, A. W., Shi, L., and Jaenisch, R. (2013). One-step generation of mice carrying reporter and conditional alleles by CRISPR/Cas-mediated genome engineering. Cell 154, 1370-1379.

LENGTHY TABLES

The patent contains a lengthy table section. A copy of the table is available in electronic form from the USPTO web site (https://seqdata.uspto.gov/?pageRequest=docDetail&DocID=US11155795B2). An electronic copy of the table will also be available from the USPTO upon request and payment of the fee set forth in 37 CFR 1.19(b)(3).

What is claimed is:

1. A method for synthesizing compounds to fit within or bind to a CRISPR-cas9 system or a functional portion thereof comprising:

(a) inputting into a programmed computer comprising a processor through an input device, data comprising a three-dimensional (3D) co-ordinates of a subset of amino acid residues from a CRISPR-cas9 crystal structure according to Table A, wherein the amino acid residues are located in a Cas9 domain of the CRISPR-cas9 system, thereby generating a 3D structure data set of the Cas9;

(b) comparing, using said processor, said data set to a computer database of structures of compounds that bind or putatively bind or that are desired to bind to one or more residues within the 3D structure of the Cas9 domain;

(c) selecting from said database, using computer methods, compounds with desired structures that bind to one or more residues within the Cas9 domain, based on the CRISPR-cas9 crystal structure according to Table A;

(d) constructing, using computer methods, a model of the selected compounds;

(e) outputting to an output device the selected compounds;

(f) synthesizing one or more of the selected compounds that bind to one or more residues within the Cas9 domain; and (g) testing binding of said synthesized selected compounds to the CRISPR-cas9 system.

2. A method for synthesizing compounds to fit within or bind to a CRISPR-cas9 system or a Cas9 ortholog comprising:

providing co-ordinates of amino acid residues from a Cas9 domain of the CRISPR-cas9 crystal structure according to Table A on a computer, providing the structure of a candidate compound, fitting the structure of the candidate compound to the selected co-ordinates, to thereby obtain product data comprising desired compounds that bind to one or more residues within the Cas9 domain, with output thereof; synthesizing compound(s) from said product data that bind to one or more residues within the Cas9 domain; and testing binding of said synthesized compound(s) to a CRISPR-cas9 system.

3. The method of claim 1 or claim 2, further comprising analyzing the binding or a desired function of a CRISPR-cas9 system resulting from said synthesized selected compound(s) or structure(s).

4. The method of claim 1 or claim 2, wherein the Cas9 domain is a REC1 domain, a REC2 domain, a RuvC domain, a HNH domain, or a PI domain.

5. The method of claim 1 or claim 2, wherein the amino acid residues located in the Cas9 domain are selected from R63, R65, R66, R69, R70, R74, R78, S104, F105, R115, H116, I135, H160, K163, R165, Y325, H328, R340, F351, D364, Q402, R403, T404, N407, L455, S460, T472, R487, N497, K510, W659, R661, Q695, H721, K742, R895, Q926, V1009, W1010, Y1013, V1100, E1108, I1110, R1122, Y1131, H1349, or a combination thereof.

6. The method of claim 1 or claim 2, wherein the amino acid residues located in the Cas9 domain are selected from R63, R65, R66, R69, R70, R74, R78, K163, R165, N407, N497, K510, W659, R661, Q695, R895, Q926, V1009, W1010, Y1013, E1108, or a combination thereof.

* * * * *

```
                            SEQUENCE LISTING

<160> NUMBER OF SEQ ID NOS: 202

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Gly Ser
1

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Glu Ala Ala Ala Lys
1               5

<210> SEQ ID NO 3
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 3
nnnnnnnnnn nnnnnnnnnn gttttgtac tctcaagatt tagaaataaa tcttgcagaa        60
gctacaaaga taaggcttca tgccgaaatc aacaccctgt cattttatgg cagggtgttt      120
tcgttattta attttt                                                     137
```

```
<210> SEQ ID NO 4
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 4
nnnnnnnnnn nnnnnnnnnn gtttttgtac tctcagaaat gcagaagcta caaagataag      60
gcttcatgcc gaaatcaaca ccctgtcatt ttatggcagg gtgttttcgt tatttaattt     120
ttt                                                                   123

<210> SEQ ID NO 5
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gtttttgtac tctcagaaat gcagaagcta caaagataag      60
gcttcatgcc gaaatcaaca ccctgtcatt ttatggcagg gtgttttttt                 110

<210> SEQ ID NO 6
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gttttagagc tagaaatagc aagttaaaat aaggctagtc      60
cgttatcaac ttgaaaaagt ggcaccgagt cggtgctttt tt                        102

<210> SEQ ID NO 7
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 7
nnnnnnnnnn nnnnnnnnnn gttttagagc tagaaatagc aagttaaaat aaggctagtc      60
```

```
cgttatcaac ttgaaaaagt gtttttttt                                              88
```

<210> SEQ ID NO 8
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 8

```
nnnnnnnnnn nnnnnnnnnn gttttagagc tagaaatagc aagttaaaat aaggctagtc           60
cgttatcatt tttttt                                                           76
```

<210> SEQ ID NO 9
<211> LENGTH: 20
<212> TYPE: DNA
<213> ORGANISM: Homo sapiens

<400> SEQUENCE: 9

```
gagtccgagc agaagaagaa                                                       20
```

<210> SEQ ID NO 10
<211> LENGTH: 20
<212> TYPE: DNA
<213> ORGANISM: Homo sapiens

<400> SEQUENCE: 10

```
gagtcctagc aggagaagaa                                                       20
```

<210> SEQ ID NO 11
<211> LENGTH: 20
<212> TYPE: DNA
<213> ORGANISM: Homo sapiens

<400> SEQUENCE: 11

```
gagtctaagc agaagaagaa                                                       20
```

<210> SEQ ID NO 12
<211> LENGTH: 7
<212> TYPE: PRT
<213> ORGANISM: Simian virus 40

<400> SEQUENCE: 12

```
Pro Lys Lys Lys Arg Lys Val
1               5
```

<210> SEQ ID NO 13
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 13

```
Lys Arg Pro Ala Ala Thr Lys Lys Ala Gly Gln Ala Lys Lys Lys Lys
1               5                   10                  15
```

```
<210> SEQ ID NO 14
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 14

Pro Ala Ala Lys Arg Val Lys Leu Asp
1               5

<210> SEQ ID NO 15
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 15

Arg Gln Arg Arg Asn Glu Leu Lys Arg Ser Pro
1               5                   10

<210> SEQ ID NO 16
<211> LENGTH: 38
<212> TYPE: PRT
<213> ORGANISM: Homo sapiens

<400> SEQUENCE: 16

Asn Gln Ser Ser Asn Phe Gly Pro Met Lys Gly Asn Phe Gly Gly
1               5                   10                  15

Arg Ser Ser Gly Pro Tyr Gly Gly Gly Gln Tyr Phe Ala Lys Pro
                20                  25                  30

Arg Asn Gln Gly Gly Tyr
            35

<210> SEQ ID NO 17
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 17

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 18
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T Protein sequence"

<400> SEQUENCE: 18
```

Val Ser Arg Lys Arg Pro Arg Pro
1               5

<210> SEQ ID NO 19
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T Protein sequence"

<400> SEQUENCE: 19

Pro Pro Lys Lys Ala Arg Glu Asp
1               5

<210> SEQ ID NO 20
<211> LENGTH: 8
<212> TYPE: PRT
<213> ORGANISM: Homo sapiens

<400> SEQUENCE: 20

Pro Gln Pro Lys Lys Lys Pro Leu
1               5

<210> SEQ ID NO 21
<211> LENGTH: 12
<212> TYPE: PRT
<213> ORGANISM: Mus musculus

<400> SEQUENCE: 21

Ser Ala Leu Ile Lys Lys Lys Lys Lys Met Ala Pro
1               5                   10

<210> SEQ ID NO 22
<211> LENGTH: 5
<212> TYPE: PRT
<213> ORGANISM: Influenza virus

<400> SEQUENCE: 22

Asp Arg Leu Arg Arg
1               5

<210> SEQ ID NO 23
<211> LENGTH: 7
<212> TYPE: PRT
<213> ORGANISM: Influenza virus

<400> SEQUENCE: 23

Pro Lys Gln Lys Lys Arg Lys
1               5

<210> SEQ ID NO 24
<211> LENGTH: 10
<212> TYPE: PRT
<213> ORGANISM: Hepatitis delta virus

<400> SEQUENCE: 24

Arg Lys Leu Lys Lys Lys Ile Lys Lys Leu
1               5                   10

<210> SEQ ID NO 25
<211> LENGTH: 10
<212> TYPE: PRT
<213> ORGANISM: Mus musculus

```
<400> SEQUENCE: 25

Arg Glu Lys Lys Lys Phe Leu Lys Arg Arg
1               5                   10

<210> SEQ ID NO 26
<211> LENGTH: 20
<212> TYPE: PRT
<213> ORGANISM: Homo sapiens

<400> SEQUENCE: 26

Lys Arg Lys Gly Asp Glu Val Asp Gly Val Asp Glu Val Ala Lys Lys
1               5                   10                  15

Lys Ser Lys Lys
            20

<210> SEQ ID NO 27
<211> LENGTH: 17
<212> TYPE: PRT
<213> ORGANISM: Homo sapiens

<400> SEQUENCE: 27

Arg Lys Cys Leu Gln Ala Gly Met Asn Leu Glu Ala Arg Lys Thr Lys
1               5                   10                  15

Lys

<210> SEQ ID NO 28
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Gly Ser Gly Gly Gly Ser Gly Gly Gly Ser
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Glu Ala Ala Ala Lys Ala
1               5

<210> SEQ ID NO 30
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
guuuuagagc ua                                                          12

<210> SEQ ID NO 31
<211> LENGTH: 4203
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
atggccccaa agaagaagcg aaggtcggt atccacggag tcccagcagc cgacaagaag      60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct ccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tgcccacat gatcaagttc    540
cggggccact tcctgatcga gggcgacctg aaccccgaca cagcgacgt ggacaagctg    600
ttcatccagc tggtgcagac ctacaaccag ctgttcgagg aaaacccat caacgccagc    660
ggcgtggacg ccaaggccat cctgtctgcc agactgagca agagcagacg gctggaaaat    720
ctgatcgccc agctgcccgg cgagaagaag aatggcctgt cggaaacct gattgccctg    780
agcctgggcc tgaccccaa cttcaagagc aacttcgacc tggccgagga tgccaaactg    840
cagctgagca aggacaccta cgacgacgac ctggacaacc tgctggccca gatcggcgac    900
cagtacgccg acctgttct ggccgccaag aacctgtccg acgccatcct gctgagcgac    960
atcctgagag tgaacaccga gatcaccaag gcccccctga gcgcctctat gatcaagaga   1020
tacgacgagc accaccagga cctgaccctg ctgaaagctc tcgtgcggca gcagctgcct   1080
gagaagtaca agagattttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga agatcctg    1380
accttccgca tcccctacta cgtgggccct ctggccaggg aaacagcag attcgcctgg   1440
atgaccagaa agagcgagga aaccatcacc ccctggaact cgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact caccgtgta taacgagctg   1620
accaaagtga aatacgtgac cgagggaatg agaaagcccg ccttcctgag cggcgagcag   1680
aaaaaggcca tcgtggacct gctgttcaag accaaccgga agtgaccgt gaagcagctg   1740
aaagaggact acttcaagaa aatcgagtgc ttcgactccg tggaaatctc cggcgtggaa   1800
gatcggttca acgcctccct gggcacatac acgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcg agatacaccg ctggggcag gctgagccgg   2040
aagctgatca acggcatccg ggacaagcag tccggcaaga caatcctgga tttcctgaag   2100
```

-continued

```
tccgacggct tcgccaacag aaacttcatg cagctgatcc acgacgacag cctgaccttt    2160
aaagaggaca tccagaaagc ccaggtgtcc ggccagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga acatcgtgat cgaaatggcc    2340
agagagaacc agaccaccca aagggacag aagaacagcc gcgagagaat gaagcggatc     2400
gaagagggca tcaaagagct gggcagccag atcctgaaag aacacccgt ggaaaacacc     2460
cagctgcaga cgagaagct gtacctgtac tacctgcaga atgggcggga tatgtacgtg     2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca agagacagct ggtggaaacc    2820
cggcagatca caaagcacgt ggcacagatc ctggactccc ggatgaacac taagtacgac    2880
gagaatgaca gctgatccg ggaagtgaaa gtgatcaccc tgaagtccaa gctggtgtcc     2940
gatttccgga aggatttcca gttttacaaa gtgcgcgaga tcaacaacta ccaccacgcc    3000
cacgacgcct acctgaacgc cgtcgtggga accgccctga tcaaaagta ccctaagctg     3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180
ttttcaaga ccgagattac cctggccaac ggcgagatcc ggaagcggcc tctgatcgag     3240
acaaacggcg aaaccgggga gatcgtgtgg gataagggcc gggattttgc caccgtgcgg    3300
aaagtgctga gcatgcccca agtgaatatc gtgaaaaaga ccgaggtgca gacaggcggc    3360
ttcagcaaag agtctatcct gcccaagagg aacagcgata agctgatcgc cagaaagaag    3420
gactgggacc ctaagaagta cggcggcttc gacagcccca ccgtggccta ttctgtgctg    3480
gtggtggcca agtggaaaaa gggcaagtcc aagaaactga agagtgtgaa agagctgctg    3540
gggatcacca tcatggaaag aagcagcttc gagaagaatc ccatcgactt tctggaagcc    3600
aagggctaca aagaagtgaa aaaggacctg atcatcaagc tgcctaagta ctccctgttc    3660
gagctggaaa acgccggaa gagaatgctg gcctctgccg cgaactgca gaagggaaac     3720
gaactggccc tgccctccaa atatgtgaac ttcctgtacc tggccagcca ctatgagaag    3780
ctgaagggct cccccgagga taatgagcag aaacagctgt ttgtggaaca gcacaagcac    3840
tacctggacg agatcatcga gcagatcagc gagttctcca agagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140
ctgggaggcg acaaaaggcc ggcggccacg aaaaaggccg ccaggcaaa aagaaaaag      4200
taa                                                                 4203
```

<210> SEQ ID NO 32
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
atggccccaa agaagaagcg aaggtcggt atccacggag tcccagcagc c         51

<210> SEQ ID NO 33
<211> LENGTH: 171
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
gacaagaagt acagcatcgg cctggacatc ggcaccaact ctgtgggctg ggccgtgatc    60
accgacgagt acaaggtgcc cagcaagaaa ttcaaggtgc tgggcaacac cgaccggcac   120
agcatcaaga agaacctgat cggagccctg ctgttcgaca gcggcgaaac a            171

<210> SEQ ID NO 34
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gccgaggcca cccggctgaa gagaaccgcc agaagaagat acaccagacg gaagaaccgg    60
atctgctatc tgcaagagat cttc                                          84

<210> SEQ ID NO 35
<211> LENGTH: 261
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
agcaacgaga tggccaaggt ggacgacagc ttcttccaca gactggaaga gtccttcctg    60
gtggaagagg ataagaagca cgagcggcac cccatcttcg gcaacatcgt ggacgaggtg   120
gcctaccacg agaagtaccc caccatctac cacctgagaa agaaactggt ggacagcacc   180
gacaaggccg acctgcggct gatctatctg gccctggccc acatgatcaa gttccggggc   240
cacttcctga tcgagggcga c                                             261

<210> SEQ ID NO 36
<211> LENGTH: 414
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
ctgaaccccg acaacagcga cgtggacaag ctgttcatcc agctggtgca gacctacaac    60
cagctgttcg aggaaaaccc catcaacgcc agcggcgtgg acgccaaggc catcctgtct   120

```
gccagactga gcaagagcag acggctggaa aatctgatcg cccagctgcc cggcgagaag      180
aagaatggcc tgttcggaaa cctgattgcc ctgagcctgg gcctgacccc caacttcaag      240
agcaacttcg acctggccga ggatgccaaa ctgcagctga gcaaggacac ctacgacgac      300
gacctggaca acctgctggc ccagatcggc gaccagtacg ccgacctgtt tctggccgcc      360
aagaacctgt ccgacgccat cctgctgagc gacatcctga gagtgaacac cgag            414
```

<210> SEQ ID NO 37
<211> LENGTH: 1200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
atcaccaagg cccccctgag cgcctctatg atcaagagat acgacgagca ccaccaggac      60
ctgaccctgc tgaaagctct cgtgcggcag cagctgcctg agaagtacaa agagattttc      120
ttcgaccaga gcaagaacgg ctacgccggc tacattgacg gcggagccag ccaggaagag      180
ttctacaagt tcatcaagcc catcctggaa agatggacg gcaccgagga actgctcgtg      240
aagctgaaca gagaggacct gctgcggaag cagcggacct tcgacaacgg cagcatcccc      300
caccagatcc acctgggaga gctgcacgcc attctgcggc ggcaggaaga tttttaccca      360
ttcctgaagg acaaccggga aaagatcgag aagatcctga ccttccgcat ccctactac      420 gtgggccctc tggccagggg aaacagcaga ttcgcctgga tgaccagaaa gagcgaggaa      480
accatcaccc cctggaactt cgaggaagtg gtggacaagg gcgcttccgc ccagagcttc      540
atcgagcgga tgaccaactt cgataagaac ctgcccaacg agaaggtgct gcccaagcac      600
agcctgctgt acgagtactt caccgtgtat aacgagctga ccaaagtgaa atacgtgacc      660
gagggaatga gaaagcccgc cttcctgagc ggcgagcaga aaaaggccat cgtggacctg      720
ctgttcaaga ccaaccggaa agtgaccgtg aagcagctga aagaggacta cttcaagaaa      780
atcgagtgct tcgactccgt ggaaatctcc ggcgtggaag atcggttcaa cgcctccctg      840
ggcacatacc acgatctgct gaaaattatc aaggacaagg acttcctgga caatgaggaa      900
aacgaggaca ttctggaaga tatcgtgctg accctgacac tgtttgagga cagagagatg      960
atcgaggaac ggctgaaaac ctatgcccac ctgttcgacg acaaagtgat gaagcagctg      1020
aagcggcgga gatacaccgg ctggggcagg ctgagccgga agctgatcaa cggcatccgg      1080
gacaagcagt ccggcaagac aatcctggat ttcctgaagt ccgacggctt cgccaacaga      1140
aacttcatgc agctgatcca cgacgacagc ctgacctta aagaggacat ccagaaagcc      1200
```

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38

```
caggtgtccg gccagggcga t                                                21
```

<210> SEQ ID NO 39
<211> LENGTH: 24

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
atcgtgatcg aaatggccag agag                                          24

<210> SEQ ID NO 40
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gactacgatg tggaccatat cgtgcctcag agctttctga aggacgactc catcgacaac    60
aaggtgctga ccagaagcga caagaac                                       87

<210> SEQ ID NO 41
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
caccacgccc acgacgccta cctg                                          24

<210> SEQ ID NO 42
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
accgaggtgc agacaggcgg cttcagcaaa gagtctatcc tgcccaagag gaacagcgat    60
aagctgatcg ccagaaagaa ggactgggac cctaagaagt acggcggctt cgacagcccc   120
accgtggcct attctgtgct ggtggtggcc aaagtggaaa agggcaagtc caagaaactg   180
aagagtgtga agagctgct ggggatcacc atcatggaaa gaagcagctt cgagaagaat   240
cccatcgact ttctggaagc caagggctac aagaagtga aaaggacct gatcatcaag   300 ctgcctaagt actccctgtt cgagctggaa acggccggaa gagaatgct ggcctctgcc   360 ggcgaactgc agaagggaaa cgaactggcc ctgccctcca aatatgtgaa cttcctgtac   420
ctggccagcc actatgagaa gctgaagggc tcccccgagg ataatgagca gaaacagctg   480
tttgtggaac agcacaagca ctacctggac gagatcatcg agcagatcag cgagttctcc   540
aagagagtga tcctggccga cgctaatctg gacaaagtgc tgtccgccta caacaagcac   600
cgggataagc ccatcagaga gcaggccgag aatatcatcc acctgtttac cctgaccaat   660
ctggagcccc tgccgccctt caagtacttt gacaccacca tcgaccggaa gaggtacacc   720
agcaccaaag aggtgctgga cgccaccctg atccaccaga gcatcaccgg cctgtacgag   780
```

-continued acacggatcg acctgtctca gctgggaggc gac                          813

<210> SEQ ID NO 43
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
aaaaggccgg cggccacgaa aaaggccggc caggcaaaaa agaaaaag        48

<210> SEQ ID NO 44
<211> LENGTH: 3789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
atggccccaa agaagaagcg gaaggtcggt atccacggag tcccagcagc cgacaagaag        60
tacagcatcg gcctggacat cggcaccaac tctgtgggct gggccgtgat caccgacgag       120
tacaaggtgc ccagcaagaa attcaaggtg ctgggcaaca ccgaccggca cagcatcaag       180
aagaacctga tcggagccct gctgttcgac agcggcgaaa cagccgaggc cacccggctg       240
aagagaaccg ccagaagaag atacaccaga cggaagaacc ggatctgcta tctgcaagag       300
atcttcagca acgagatggc caaggtggac gacagcttct tccacagact ggaagagtcc       360
ttcctggtgg aagaggataa gaagcacgag cggcacccca tcttcggcaa catcgtggac       420
gaggtggcct accacgagaa gtaccccacc atctaccacc tgagaaagaa actggtggac       480
agcaccgaca aggccgacct gcggctgatc tatctggccc tggcccacat gatcaagttc       540
cggggccact tcctgatcga gggcgacatc accaaggcac cactgagcgc tctctatgatc      600 aagagatacg acgagcacca ccaggacctg accctgctga agctctcgt gcggcagcag        660 ctgcctgaga agtacaaaga dattttcttc gaccagagca agaacggcta cgccggctac        720
attgacggcg gagccagcca ggaagagttc tacaagttca tcaagcccat cctgaaaaag       780
atggacggca ccgaggaact gctcgtgaag ctgaacagag gacctgct gcggaagcag         840 cggaccttcg acaacggcag catccccac cagatccacc tgggagagct gcacgccatt        900
ctgcggcggc aggaagattt ttacccattc ctgaaggaca ccgggaaaa gatcgagaag       960 atcctgacct tccgcatccc ctactacgtg ggccctctgg ccaggggaaa cagcagattc      1020
gcctggatga ccagaaagag cgaggaaacc atcaccccct ggaacttcga ggaagtggtg     1080
gacaagggcg cttccgccca gagcttcatc gagcggatga ccaacttcga taagaacctg     1140
cccaacgaga aggtgctgcc caagcacagc ctgctgtacg agtacttcac cgtgtataac     1200
gagctgacca aagtgaaata cgtgaccgag ggaatgagaa agcccgcctt cctgagcggc     1260
gagcagaaaa aggccatcgt ggacctgctg ttcaagacca ccggaaagt gaccgtgaag      1320 cagctgaaag aggactactt caagaaaatc gagtgcttcg actccgtgga aatctccggc     1380
gtggaagatc ggttcaacgc ctccctgggc acataccacg atctgctgaa aattatcaag     1440
gacaaggact cctggacaa tgaggaaaac gaggacattc tggaagatat cgtgctgacc     1500
ctgacactgt ttgaggacag agagatgatc gaggaacggc tgaaaaccta tgcccacctg     1560

```
ttcgacgaca aagtgatgaa gcagctgaag cggcggagat acaccggctg gggcaggctg    1620
agccggaagc tgatcaacgg catccgggac aagcagtccg gcaagacaat cctggatttc    1680
ctgaagtccg acggcttcgc caacagaaac ttcatgcagc tgatccacga cgacagcctg    1740
acctttaaag aggacatcca gaaagcccag gtgtccggcc agggcgatag cctgcacgag    1800
cacattgcca atctggccgg cagccccgcc attaagaagg gcatcctgca gacagtgaag    1860
gtggtggacg agctcgtgaa agtgatgggc cggcacaagc ccgagaacat cgtgatcgaa    1920
atggccagag agaaccagac cacccagaag ggacagaaga cagccgcga gagaatgaag    1980 cggatcgaag agggcatcaa agagctgggc agccagatcc tgaaagaaca ccccgtggaa    2040
aacacccagc tgcagaacga gaagctgtac ctgtactacc tgcagaatgg cgcggatatg    2100
tacgtggacc aggaactgga catcaaccgg ctgtccgact acgatgtgga ccatatcgtg    2160
cctcagagct ttctgaagga cgactccatc gacaacaagg tgctgaccag aagcgacaag    2220
aaccggggca gagcgacaa cgtgcccctcc gaagaggtcg tgaagaagat gaagaactac    2280
tggcggcagc tgctgaacgc caagctgatt acccagagaa agttcgacaa tctgaccaag    2340
gccgagagag cggcctgag cgaactggat aaggccggct tcatcaagag acagctggtg    2400
gaaacccggc agatcacaaa gcacgtggca cagatcctgg actcccggat gaacactaag    2460
tacgacgaga atgacaagct gatccgggaa gtgaaagtga tcaccctgaa gtccaagctg    2520
gtgtccgatt ccggaaggaa tttccagttt tacaaagtgc gcgagatcaa caactaccac    2580
cacgcccacg acgcctacct gaacgccgtc gtgggaaccg ccctgatcaa aaagtaccct    2640
aagctggaaa gcgagttcgt gtacggcgac tacaaggtgt acgacgtgcg gaagatgatc    2700
gccaagagcg agcaggaaat cggcaaggct accgccaagt acttcttcta cagcaacatc    2760
atgaactttt tcaagaccga gattacccctg gccaacggcg agatccggaa gcggcctctg    2820
atcgagacaa acggcgaaac cggggagatc gtgtgggata agggccggga ttttgccacc    2880
gtgcggaaag tgctgagcat gccccaagtg aatatcgtga aaagaccga ggtgcagaca    2940 ggcggcttca gcaaagagtc tatcctgccc aagaggaaca gcgataagct gatcgccaga    3000
aagaaggact gggaccctaa gaagtacggc ggcttcgaca gccccaccgt ggcctattct    3060
gtgctggtgg tggccaaagt ggaaaagggc aagtccaaga aactgaagag tgtgaaagag    3120
ctgctgggga tcaccatcat ggaaagaagc agcttcgaga gaatcccat cgactttctg    3180 gaagccaagg gctacaaaga agtgaaaaag gacctgatca tcaagctgcc taagtactcc    3240
ctgttcgagc tggaaaacgg ccggaagaga atgctggcct ctgccggcga actgcagaag    3300
ggaaacgaac tggccctgcc ctccaaatat gtgaacttcc tgtacctggc cagccactat    3360
gagaagctga agggctcccc cgaggataat gagcagaaac agctgtttgt ggaacagcac    3420
aagcactacc tggacgagat catcgagcag atcagcgagt tctccaagag agtgatcctg    3480
gccgacgcta atctggacaa agtgctgtcc gcctacaaca gcaccggga taagcccatc    3540 agagagcagg ccgagaatat catccacctg tttaccctga ccaatctggg agcccctgcc    3600
gccttcaagt actttgacac caccatcgac cggaagaggt acaccagcac caaagaggtg    3660
ctggacgcca ccctgatcca ccagagcatc accggcctgt acgagacacg gatcgacctg    3720
tctcagctgg gaggcgacaa aaggccggcg gccacgaaaa aggccggcca ggcaaaaaag    3780
aaaaagtaa                                                           3789
```

<210> SEQ ID NO 45

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 3834
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46 atggcccaa agaagaagcg aaggtcggt atccacggag tcccagcagc cgacaagaag      60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcgagcccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac acagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact cctgatcga gggcgacggt ggcggtggct cgggtggcgg tggctcgggt    600
ggcggtggct cgatcaccaa ggcccccctg agcgcctcta tgatcaagag atacgacgag    660
caccaccagg acctgaccct gctgaaagct ctcgtgcggc agcagctgcc tgagaagtac    720
aaagagattt tcttcgacca gagcaagaac ggctacgccg gctacattga cggcggagcc    780
agccaggaag agttctacaa gttcatcaag cccatcctgg aaaagatgga cggcaccgag    840
gaactgctcg tgaagctgaa cagagaggac ctgctgcgga gcagcggac cttcgacaac    900 ggcagcatcc ccaccagat ccacctggga gagctgcacg ccattctgcg gcggcaggaa    960
gatttttacc cattcctgaa ggacaaccgg gaaaagatcg agaagatcct gaccttccgc   1020
atcccctact acgtgggccc tctggccagg ggaaacagca gattcgcctg gatgaccaga   1080
aagagcgagg aaaccatcac ccctggaac ttcgaggaag tggtggacaa gggcgcttcc    1140
gcccagagct tcatcgagcg gatgaccaac ttcgataaga acctgcccaa cgagaaggtg   1200
ctgcccaagc acagcctgct gtacgagtac ttcaccgtgt ataacgagct gaccaaagtg   1260
aaatacgtga ccgagggaat gagaaagccc gccttcctga gcggcgagca gaaaaaggcc   1320
atcgtggacc tgctgttcaa gaccaaccgg aaagtgaccg tgaagcagct gaaagaggac   1380
tacttcaaga aaatcgagtg cttcgactcc gtggaaatct ccggcgtgga agatcggttc   1440
aacgcctccc tgggcacata ccacgatctg ctgaaaatta tcaaggacaa ggacttcctg   1500
gacaatgagg aaaacgagga cattctggaa gatatcgtgc tgaccctgac actgtttgag   1560
gacagagaga tgatcgagga acggctgaaa acctatgccc acctgttcga cgacaaagtg   1620
```

```
atgaagcagc tgaagcggcg gagatacacc ggctggggca ggctgagccg gaagctgatc   1680
aacggcatcc gggacaagca gtccggcaag acaatcctgg atttcctgaa gtccgacggc   1740
ttcgccaaca gaaacttcat gcagctgatc cacgacgaca gcctgacctt taaagaggac   1800
atccagaaag cccaggtgtc cggccagggc gatagcctgc acgagcacat tgccaatctg   1860
gccggcagcc ccgccattaa gaagggcatc ctgcagacag tgaaggtggt ggacgagctc   1920
gtgaaagtga tgggccggca caagcccgag aacatcgtga tcgaaatggc cagagagaac   1980
cagaccaccc agaagggaca agaacagc cgcgagagaa tgaagcggat cgaagagggc   2040
atcaaagagc tgggcagcca gatcctgaaa gaacacccg tggaaaacac ccagctgcag   2100
aacgagaagc tgtacctgta ctacctgcag aatgggcggg atatgtacgt ggaccaggaa   2160
ctggacatca accggctgtc cgactacgat gtggaccata tcgtgcctca gagctttctg   2220
aaggacgact ccatcgacaa caaggtgctg accagaagcg acaagaaccg gggcaagagc   2280
gacaacgtgc cctccgaaga ggtcgtgaag aagatgaaga actactggcg gcagctgctg   2340
aacgccaagc tgattaccca gagaaagttc gacaatctga ccaaggccga gagaggcggc   2400
ctgagcgaac tggataaggc cggcttcatc aagagacagc tggtggaaac ccggcagatc   2460
acaaagcacg tggcacagat cctggactcc cggatgaaca ctaagtacga cgagaatgac   2520
aagctgatcc gggaagtgaa agtgatcacc ctgaagtcca gctggtgtc cgatttccgg   2580 aaggatttcc agttttacaa agtgcgcgag atcaacaact accaccacgc ccacgacgcc   2640
tacctgaacg ccgtcgtggg aaccgccctg atcaaaaagt accctaagct ggaaagcgag   2700
ttcgtgtacg gcgactacaa ggtgtacgac gtgcggaaga tgatcgccaa gagcgagcag   2760
gaaatcggca aggctaccgc caagtacttc ttctacagca acatcatgaa cttttttcaag   2820 accgagatta ccctggccaa cggcgagatc cggaagcggc ctctgatcga gacaaacggc   2880
gaaaccgggg agatcgtgtg ggataagggc cgggattttg ccaccgtgcg gaaagtgctg   2940
agcatgcccc aagtgaatat cgtgaaaaag accgaggtgc agacaggcgg cttcagcaaa   3000
gagtctatcc tgcccaagag gaacagcgat aagctgatcg ccagaaagaa ggactgggac   3060
cctaagaagt acggcggctt cgacagcccc accgtggcct attctgtgct ggtggtggcc   3120
aaagtggaaa agggcaagtc caagaaactg aagagtgtga agagctgct ggggatcacc   3180 atcatggaaa gagcagctt cgagaagaat cccatcgact ttctggaagc caagggctac   3240
aaagaagtga aaaaggacct gatcatcaag ctgcctaagt actccctgtt cgagctggaa   3300
aacggccgga agaatgct ggcctctgcc ggcgaactgc agaagggaaa cgaactggcc   3360
ctgccctcca aatatgtgaa cttcctgtac ctggccagcc actatgagaa gctgaagggc   3420
tcccccgagg ataatgagca gaaacagctg tttgtggaac agcacaagca ctacctggac   3480
gagatcatcg agcagatcag cgagttctcc aagagagtga tcctggccga cgctaatctg   3540
gacaaagtgc tgtccgccta caacaagcac cgggataagc ccatcagaga gcaggccgag   3600
aatatcatcc acctgtttac cctgaccaat ctggagcccc tgccgccttt caagtacttt   3660
gacaccacca tcgaccggaa gaggtacacc agcaccaaag aggtgctgga cgccaccctg   3720
atccaccaga gcatcaccgg cctgtacgag acacggatcg acctgtctca gctgggaggc   3780
gacaaaaggc cggcggccac gaaaaaggcc ggccaggcaa aaagaaaaa gtaa         3834
```

<210> SEQ ID NO 47
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30

<210> SEQ ID NO 48
<211> LENGTH: 3879
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

| | |
|---|---|
| atggcccaa agaagaagcg aaggtcggt atccacggag tcccagcagc cgacaagaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgaccggca cagcatcaag | 180 |
| aagaacctga tcgagcccct gctgttcgac agcggcgaaa cagccgaggc cacccggctg | 240 |
| aagagaaccg ccagaagaag atacaccaga cggaagaacc ggatctgcta tctgcaagag | 300 |
| atcttcagca acgagatggc caaggtggac gacagcttct ccacagact ggaagagtcc | 360 |
| ttcctggtgg aagaggataa gaagcacgag cggcacccca tcttcggcaa catcgtggac | 420 |
| gaggtggcct accacgagaa gtaccccacc atctaccacc tgagaaagaa actggtggac | 480 |
| agcaccgaca aggccgacct gcggctgatc tatctggccc tggcccacat gatcaagttc | 540 |
| cggggccact tcctgatcga gggcgacggt ggcggtggct cgggtggcgg tggctcgggt | 600 |
| ggcggtggct cgggtggcgg tggctcgggt ggcggtggct cgggtggcgg tggctcgatc | 660 |
| accaaggccc ccctgagcgc ctctatgatc aagagatacg acgagcacca ccaggacctg | 720 |
| accctgctga agctctcgt gcggcagcag ctgcctgaga agtacaaaga gattttcttc | 780 |
| gaccagagca gaacggcta cgccggctac attgacggcg gagccagcca ggaagagttc | 840 |
| tacaagttca tcaagcccat cctggaaaag atggacggca ccgaggaact gctcgtgaag | 900 |
| ctgaacagag aggacctgct gcggaagcag cggaccttcg acaacggcag catcccccac | 960 |
| cagatccacc tggagagct gcacgccatt ctgcggcggc aggaagattt ttacccattc | 1020 |
| ctgaaggaca accgggaaaa gatcgagaag atcctgacct tccgcatccc ctactacgtg | 1080 |
| ggccctctgg ccagggggaaa cagcagattc gcctggatga ccagaaagag cgaggaaacc | 1140 |
| atcacccct ggaacttcga ggaagtggtg acaagggcg cttccgccca gagcttcatc | 1200 |
| gagcggatga ccaacttcga taagaacctg cccaacgaga ggtgctgcc caagcacagc | 1260 |
| ctgctgtacg agtacttcac cgtgtataac gagctgacca aagtgaaata cgtgaccgag | 1320 |
| ggaatgagaa agcccgcctt cctgagcggc gagcagaaaa aggccatcgt ggacctgctg | 1380 |
| ttcaagacca accggaaagt gaccgtgaag cagctgaaag gactactt caagaaaatc | 1440 |
| gagtgcttcg actccgtgga aatctccggc gtggaagatc ggttcaacgc ctccctgggc | 1500 |
| acataccacg atctgctgaa aattatcaag gacaaggact cctggacaa tgaggaaaac | 1560 |
| gaggacattc tggaagatat cgtgctgacc ctgacactgt ttgaggacag agatgatc | 1620 |

-continued

```
gaggaacggc tgaaaaccta tgcccacctg ttcgacgaca agtgatgaa gcagctgaag      1680
cggcggagat acaccggctg gggcaggctg agccggaagc tgatcaacgg catccgggac      1740
aagcagtccg gcaagacaat cctggatttc ctgaagtccg acggcttcgc caacagaaac      1800
ttcatgcagc tgatccacga cgacagcctg acctttaaag aggacatcca gaaagcccag      1860
gtgtccggcc agggcgatag cctgcacgag cacattgcca atctggccgg cagccccgcc      1920
attaagaagg gcatcctgca gacagtgaag gtggtggacg agctcgtgaa agtgatgggc      1980
cggcacaagc ccgagaacat cgtgatcgaa atggccagag agaaccagac cacccagaag      2040
ggacagaaga acagccgcga gagaatgaag cggatcgaag agggcatcaa agagctgggc      2100
agccagatcc tgaaagaaca ccccgtggaa acacccagc tgcagaacga aagctgtac      2160
ctgtactacc tgcagaatgg gcgggatatg tacgtggacc aggaactgga catcaaccgg      2220
ctgtccgact acgatgtgga ccatatcgtg cctcagagct ttctgaagga cgactccatc      2280
gacaacaagg tgctgaccag aagcgacaag aaccggggca agagcgacaa cgtgcccctcc     2340
gaagaggtcg tgaagaagat gaagaactac tggcggcagc tgctgaacgc caagctgatt      2400
acccagagaa agttcgacaa tctgaccaag gccgagagag cggcctgag cgaactggat       2460
aaggccggct tcatcaagag acagctggtg gaaacccggc agatcacaaa gcacgtggca      2520
cagatcctgg actcccggat gaacactaag tacgacgaga atgacaagct gatccgggaa      2580
gtgaaagtga tcaccctgaa gtccaagctg gtgtccgatt ccggaagga tttccagttt       2640
tacaaagtgc gcgagatcaa caactaccac cacgcccacg acgcctacct gaacgccgtc      2700
gtgggaaccg ccctgatcaa aaagtaccct aagctggaaa gcgagttcgt gtacggcgac      2760
tacaaggtgt acgacgtgcg gaagatgatc gccaagagcg agcaggaaat cggcaaggct      2820
accgccaagt acttcttcta cagcaacatc atgaacttttt tcaagaccga gattaccctg      2880
gccaacggcg agatccggaa gcggcctctg atcgagacaa acggcgaaac cggggagatc      2940
gtgtgggata agggccggga ttttgccacc gtgcggaaag tgctgagcat gccccaagtg      3000
aatatcgtga aaaagaccga ggtgcagaca ggcggcttca gcaaagagtc tatcctgccc      3060
aagaggaaca gcgataagct gatcgccaga aagaaggact gggaccctaa gaagtacggc      3120
ggcttcgaca gccccaccgt ggcctattct gtgctggtgg tggccaaagt ggaaaagggc      3180
aagtccaaga aactgaagag tgtgaaagag ctgctgggga tcaccatcat ggaaagaagc      3240
agcttcgaga agaatcccat cgactttctg gaagccaagg gctacaaaga agtgaaaaag      3300
gacctgatca tcaagctgcc taagtactcc ctgttcgagc tggaaaacgg ccggaagaga      3360
atgctggcct ctgccggcga actgcagaag ggaaacgaac tggccctgcc ctccaaatat      3420
gtgaacttcc tgtacctggc cagccactat gagaagctga agcctcccc gaggataat        3480
gagcagaaac agctgtttgt ggaacagcac aagcactacc tggacgagat catcgagcag      3540
atcagcgagt ctccaagag agtgatcctg gccgacgcta atctggacaa agtgctgtcc      3600
gcctacaaca gcaccggga taagcccatc agagagcagg ccgagaatat catccacctg      3660
tttaccctga ccaatctggg agcccctgcc gccttcaagt actttgacac caccatcgac      3720
cggaagaggt acaccagcac caaagaggtg ctggacgcca ccctgatcca ccagagcatc      3780
accggcctgt acgagacacg gatcgacctg tctcagctgg aggcgacaa aaggccggcg      3840
gccacgaaaa aggccggcca ggcaaaaaag aaaaagtaa                            3879
```

<210> SEQ ID NO 49
<211> LENGTH: 45

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser Gly Gly Gly Ser
            35                  40                  45

<210> SEQ ID NO 50
<211> LENGTH: 3924
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
atggccccaa agaagaagcg gaaggtcggt atccacggag tcccagcagc cgacaagaag     60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacggg ggcggtggct cgggtggcgg tggctcgggt    600
ggcggtggct cgggtggcgg tggctcgggt ggcggtggct cgggtggcgg tggctcgggt    660
ggcggtggct cgggtggcgg tggctcgggt ggcggtggct cgatcaccaa ggccccctg    720 agcgcctcta tgatcaagag atacgacgag caccaccagg acctgaccct gctgaaagct    780
ctcgtgcggc agcagctgcc tgagaagtac aaagagattt cttcgacca gagcaagaac    840 ggctacgccg gctacattga cggcggagcc agccaggaag agttctacaa gttcatcaag    900
cccatcctgg aaaagatgga cggcaccgag gaactgctcg tgaagctgaa cagagaggac    960
ctgctgcgga agcagcggac cttcgacaac ggcagcatcc ccaccagat ccacctggga   1020 gagctgcacg ccattctgcg gcggcaggaa gattttttacc cattcctgaa ggacaaccgg   1080
gaaaagatcg agaagatcct gaccttccgc atccctact acgtgggccc tctggccagg   1140
ggaaacagca gattcgcctg gatgaccaga aagagcgagg aaaccatcac ccctggaac   1200 ttcgaggaag tggtggacaa gggcgcttcc gcccagagct tcatcgagcg gatgaccaac   1260
ttcgataaga acctgcccaa cgagaaggtg ctgcccaagc acagcctgct gtacgagtac   1320
ttcaccgtgt ataacgagct gaccaaagtg aaatacgtga ccgagggaat gagaagccc   1380 gccttcctga cgcggagca gaaaaaggcc atcgtggacc tgctgttcaa gaccaaccgg   1440
aaagtgaccg tgaagcagct gaaagaggac tacttcaaga aaatcgagtg cttcgactcc   1500
```

-continued

```
gtggaaatct ccggcgtgga agatcggttc aacgcctccc tgggcacata ccacgatctg    1560
ctgaaaatta tcaaggacaa ggacttcctg gacaatgagg aaaacgagga cattctggaa    1620
gatatcgtgc tgaccctgac actgtttgag gacagagaga tgatcgagga acggctgaaa    1680
acctatgccc acctgttcga cgacaaagtg atgaagcagc tgaagcggcg agatacacc     1740 ggctggggca ggctgagccg gaagctgatc aacggcatcc gggacaagca gtccggcaag    1800
acaatcctgg atttcctgaa gtccgacggc ttcgccaaca gaaacttcat gcagctgatc    1860
cacgacgaca gcctgacctt taaagaggac atccagaaag cccaggtgtc cggccagggc    1920
gatagcctgc acgagcacat tgccaatctg gccggcagcc ccgccattaa gaagggcatc    1980
ctgcagacag tgaaggtggt ggacgagctc gtgaaagtga tgggccggca agcccgag     2040 aacatcgtga tcgaaatggc cagagagaac cagaccaccc agaagggaca gaagaacagc    2100
cgcgagagaa tgaagcggat cgaagagggc atcaaagagc tgggcagcca gatcctgaaa    2160
gaacaccccg tggaaaacac ccagctgcag aacgagaagc tgtacctgta ctacctgcag    2220
aatgggcggg atatgtacgt ggaccaggaa ctggacatca accggctgtc cgactacgat    2280
gtggaccata tcgtgcctca gagctttctg aaggacgact ccatcgacaa caaggtgctg    2340
accagaagcg acaagaaccg gggcaagagc gacaacgtgc cctccgaaga ggtcgtgaag    2400
aagatgaaga actactggcg gcagctgctg aacgccaagc tgattaccca gagaaagttc    2460
gacaatctga ccaaggccga gagaggcggc ctgagcgaac tggataaggc cggcttcatc    2520
aagagacagc tggtggaaac ccggcagatc acaaagcacg tggcacagat cctggactcc    2580
cggatgaaca ctaagtacga cgagaatgac aagctgatcc gggaagtgaa agtgatcacc    2640
ctgaagtcca gctggtgtc cgatttccgg aaggatttcc agttttacaa agtgcgcgag    2700
atcaacaact accaccacgc ccacgacgcc tacctgaacg ccgtcgtggg aaccgccctg    2760
atcaaaaagt accctaagct ggaaagcgag ttcgtgtacg gcgactacaa ggtgtacgac    2820
gtgcggaaga tgatcgccaa gagcgagcag gaaatcggca aggctaccgc caagtacttc    2880
ttctacagca acatcatgaa cttttttcaag accgagatta ccctggccaa cggcgagatc    2940
cggaagcggc ctctgatcga gacaaacggc gaaaccgggg agatcgtgtg gataagggc    3000 cgggattttg ccaccgtgcg gaaagtgctg agcatgcccc aagtgaatat cgtgaaaaag    3060
accgaggtgc agacaggcgg cttcagcaaa gagtctatcc tgcccaagag gaacagcgat    3120
aagctgatcg ccagaaagaa ggactgggac cctaagaagt acggcggctt cgacagcccc    3180
accgtggcct attctgtgct ggtggtggcc aaagtggaaa agggcaagtc caagaaactg    3240
aagagtgtga aagagctgct ggggatcacc atcatggaaa agcagcttt cgagaagaat    3300 cccatcgact ttctggaagc caagggctac aagaagtga aaaaggacct gatcatcaag    3360
ctgcctaagt actccctgtt cgagctggaa aacggccgga gagaatgct ggcctctgcc    3420 ggcgaactgc agaagggaaa cgaactgccc ctgcccctcca aatatgtgaa cttcctgtac    3480
ctggccagcc actatgagaa gctgaagggc tcccccgagg ataatgagca gaaacagctg    3540
tttgtggaac agcacaagca ctacctggac gagatcatcg agcagatcag cgagttctcc    3600
aagagagtga tcctggccga cgctaatctg gacaaagtgc tgtccgccta caacaagcac    3660
cgggataagc ccatcagaga gcaggccgag aatatcatcc acctgtttac cctgaccaat    3720
ctgggagccc ctgccgcctt caagtacttt gacaccacca tcgaccggaa gaggtacacc    3780
agcaccaaag aggtgctgga cgccaccctg atccaccaga gcatcaccgg cctgtacgag    3840
```

```
acacggatcg acctgtctca gctgggaggc gacaaaaggc cggcggccac gaaaaaggcc    3900
ggccaggcaa aaagaaaaa gtaa                                            3924
```

<210> SEQ ID NO 51
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60
```

<210> SEQ ID NO 52
<211> LENGTH: 3969
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcggagccct gctgttcgac agcggcgaaa cagccgaggc cacccggctg     240
aagagaaccg ccagaagaag atacaccaga cggaagaacc ggatctgcta tctgcaagag     300
atcttcagca acgagatggc caaggtggac gacagcttct ccacagact ggaagagtcc     360 ttcctggtgg aagaggataa gaagcacgag cggcacccca tcttcggcaa catcgtggac     420
gaggtggcct accacgagaa gtaccccacc atctaccacc tgagaaagaa actggtggac     480
agcaccgaca ggccgacct gcggctgatc tatctggccc tggcccacat gatcaagttc     540
cggggccact tcctgatcga gggcgacggt ggcggtggct cgggtggcgg tggctcgggt     600
ggcggtggct cgggtggcgg tggctcgggt ggcggtggct cgggtggcgg tggctcgggt     660
ggcggtggct cgggtggcgg tggctcgggt ggcggtggct cgggtggcgg tggctcgggt     720
ggcggtggct cgggtggcgg tggctcgatc accaaggccc ccctgagcgc ctctatgatc     780
aagagatacg acgagcacca ccaggacctg accctgctga aagctctcgt gcggcagcag     840
ctgcctgaga agtacaaaga gattttcttc gaccagagca gaacggcta cgccggctac     900 attgacggcg gagccagcca ggaagagttc tacaagttca tcaagcccat cctggaaaag     960
atggacggca ccgaggaact gctcgtgaag ctgaacagag aggacctgct gcggaagcag    1020
cggaccttcg acaacggcag catcccccac cagatccacc tgggagagct gcacgccatt    1080
ctgcggcggc aggaagattt ttacccattc ctgaaggaca ccggggaaaa gatcgagaag    1140
atcctgacct tccgcatccc ctactacgtg ggccctctgg ccaggggaaa cagcagattc    1200
```

```
gcctggatga ccagaaagag cgaggaaacc atcacccct ggaacttcga ggaagtggtg      1260
gacaagggcg cttccgccca gagcttcatc gagcggatga ccaacttcga taagaacctg      1320
cccaacgaga aggtgctgcc caagcacagc ctgctgtacg agtacttcac cgtgtataac      1380
gagctgacca aagtgaaata cgtgaccgag gaatgagaa agcccgcctt cctgagcggc       1440
gagcagaaaa aggccatcgt ggacctgctg ttcaagacca accggaaagt gaccgtgaag      1500
cagctgaaag aggactactt caagaaaatc gagtgcttcg actccgtgga aatctccggc      1560
gtggaagatc ggttcaacgc ctccctgggc acataccacg atctgctgaa aattatcaag      1620
gacaaggact tcctggacaa tgaggaaaac gaggacattc tggaagatat cgtgctgacc      1680
ctgacactgt ttgaggacag agagatgatc gaggaacggc tgaaaaccta tgcccacctg      1740
ttcgacgaca aagtgatgaa gcagctgaag cggcggagat acaccggctg ggcaggctg       1800 agccggaagc tgatcaacgg catccgggac aagcagtccg gcaagacaat cctggatttc      1860
ctgaagtccg acggcttcgc caacagaaac ttcatgcagc tgatccacga cgacagcctg      1920
acctttaaag aggacatcca gaaagcccag gtgtccggcc agggcgatag cctgcacgag      1980
cacattgcca atctggccgg cagccccgcc attaagaagg gcatcctgca gacagtgaag      2040
gtggtggacg agctcgtgaa agtgatgggc cggcacaagc ccgagaacat cgtgatcgaa      2100
atggccagag agaaccagac cacccagaag ggacagaaga acagccgcga gagaatgaag      2160
cggatcgaag agggcatcaa agagctgggc agccagatcc tgaaagaaca ccccgtggaa      2220
aacacccagc tgcagaacga gaagctgtac ctgtactacc tgcagaatgg gcgggatatg      2280
tacgtggacc aggaactgga catcaaccgg ctgtccgact acgatgtgga ccatatcgtg      2340
cctcagagct ttctgaagga cgactccatc gacaacaagg tgctgaccag aagcgacaag      2400
aaccggggca agagcgacaa cgtgcccctcc gaagaggtcg tgaagaagat gaagaactac      2460
tggcggcagc tgctgaacgc caagctgatt acccagagaa agttcgacaa tctgaccaag      2520
gccgagagag gcggcctgag cgaactggat aaggccggct tcatcaagag acagctggtg      2580
gaaacccggc agatcacaaa gcacgtggca cagatcctgg actccgggat gaacactaag      2640
tacgacgaga atgacaagct gatccggaa gtgaaagtga tcaccctgaa gtccaagctg      2700
gtgtccgatt tccggaagga ttttccagttt tacaaagtgc gcgagatcaa caactaccac      2760
cacgcccacg acgcctacct gaacgccgtc gtgggaaccg ccctgatcaa aaagtaccct      2820
aagctggaaa gcgagttcgt gtacggcgac tacaaggtgt acgacgtgcg gaagatgatc      2880
gccaagagcg agcaggaaat cggcaaggct accgccaagt acttcttcta cagcaacatc      2940
atgaactttt tcaagaccga gattaccctg gccaacggcg agatccggaa gcggcctctg      3000
atcgagacaa cggcgaaac cggggagatc gtgtgggata agggccggga ttttgccacc      3060
gtgcggaaag tgctgagcat gccccaagtg aatatcgtga aaaagaccga ggtgcagaca      3120
ggcggcttca gcaaagagtc tatcctgccc aagaggaaca gcgataagct gatcgccaga      3180
aagaaggact gggaccctaa gaagtacggc ggcttcgaca gccccaccgt ggcctattct      3240
gtgctggtgg tggccaaagt ggaaaagggc aagtccaaga aactgaagag tgtgaaagag      3300
ctgctgggga tcaccatcat ggaaagaagc agcttcgaga agaatccat cgactttctg      3360 gaagccaagg gctacaaaga agtgaaaaag gacctgatca tcaagctgcc taagtactcc      3420
ctgttcgagc tggaaaacgg ccggaagaga atgctggcct ctgccggcga actgcagaag      3480
ggaaacgaac tggccctgcc ctccaaatat gtgaacttcc tgtacctggc cagccactat      3540
```

| | |
|---|---|
| gagaagctga agggctcccc cgaggataat gagcagaaac agctgtttgt ggaacagcac | 3600 |
| aagcactacc tggacgagat catcgagcag atcagcgagt tctccaagag agtgatcctg | 3660 |
| gccgacgcta atctggacaa agtgctgtcc gcctacaaca agcaccggga taagcccatc | 3720 |
| agagagcagg ccgagaatat catccacctg tttaccctga ccaatctggg agcccctgcc | 3780 |
| gccttcaagt actttgacac caccatcgac cggaagaggt acaccagcac caaagaggtg | 3840 |
| ctggacgcca ccctgatcca ccagagcatc accggcctgt acgagacacg gatcgacctg | 3900 |
| tctcagctgg gaggcgacaa aaggccggcg gccacgaaaa aggccggcca ggcaaaaaag | 3960 |
| aaaaagtaa | 3969 |

<210> SEQ ID NO 53
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 53

Ala Glu Ala Ala Ala Lys Glu Ala Ala Ala Lys Glu Ala Ala Ala Lys
1               5                   10                  15

Ala

<210> SEQ ID NO 54
<211> LENGTH: 3840
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

| | |
|---|---|
| atggccccaa agaagaagcg gaaggtcggt atccacggag tcccagcagc cgacaagaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgaccggca cagcatcaag | 180 |
| aagaacctga tcggagccct gctgttcgac agcggcgaaa cagccgaggc caccggctg | 240 |
| aagagaaccg ccagaagaag atacaccaga cggaagaacc ggatctgcta tctgcaagag | 300 |
| atcttcagca acgagatggc caaggtggac gacagcttct tccacagact ggaagagtcc | 360 |
| ttcctggtgg aagaggataa gaagcacgag cggcacccca tcttcggcaa catcgtggac | 420 |
| gaggtggcct accacgagaa gtaccccacc atctaccacc tgagaaagaa actggtggac | 480 |
| agcaccgaca aggccgacct gcggctgatc tatctggccc tggcccacat gatcaagttc | 540 |
| cggggccact tcctgatcga gggcgacgct gaagctgctg ctaaagaagc tgctgctaaa | 600 |
| gaagctgctg ctaaagctat caccaaggcc cccctgagcg cctctatgat caagagatac | 660 |
| gacgagcacc accaggacct gaccctgctg aaagctctcg tgcggcagca gctgcctgag | 720 |
| aagtacaaag atttttcttc gaccagagc aagaacggct acgccggcta cattgacggc | 780 |
| ggagccagcc aggaagagtt ctacaagttc atcaagccca tcctggaaaa gatggacggc | 840 |
| accgaggaac tgctcgtgaa gctgaacaga gaggacctgc tgcggaagca gcggaccttc | 900 |
| gacaacggca gcatccccca ccagatccac ctgggagagc tgcacgccat tctgcggcgg | 960 |
| caggaagatt tttacccatt cctgaaggac aaccgggaaa agatcgagaa gatcctgacc | 1020 |

```
ttccgcatcc cctactacgt gggccctctg gccagggcaa acagcagatt cgcctggatg    1080
accagaaaga gcgaggaaac catcaccccc tggaacttcg aggaagtggt ggacaagggc    1140
gcttccgccc agagcttcat cgagcggatg accaacttcg ataagaacct gcccaacgag    1200
aaggtgctgc ccaagcacag cctgctgtac gagtacttca ccgtgtataa cgagctgacc    1260
aaagtgaaat acgtgaccga gggaatgaga aagcccgcct tcctgagcgg cgagcagaaa    1320
aaggccatcg tggacctgct gttcaagacc aaccggaaag tgaccgtgaa gcagctgaaa    1380
gaggactact tcaagaaaat cgagtgcttc gactccgtgg aaatctccgg cgtggaagat    1440
cggttcaacg cctccctggg cacataccac gatctgctga aaattatcaa ggacaaggac    1500
ttcctggaca atgaggaaaa cgaggacatt ctggaagata tcgtgctgac cctgacactg    1560
tttgaggaca gagagatgat cgaggaacgg ctgaaaacct atgcccacct gttcgacgac    1620
aaagtgatga agcagctgaa gcggcggaga tacaccggct ggggcaggct gagccggaag    1680
ctgatcaacg gcatccggga caagcagtcc ggcaagacaa tcctggattt cctgaagtcc    1740
gacggcttcg ccaacagaaa cttcatgcag ctgatccacg acgacagcct gacctttaaa    1800
gaggacatcc agaaagccca ggtgtccggc cagggcgata gcctgcacga gcacattgcc    1860
aatctggccg gcagccccgc cattaagaag ggcatcctgc agacagtgaa ggtggtggac    1920
gagctcgtga aagtgatggg ccggcacaag cccgagaaca tcgtgatcga aatggccaga    1980
gagaaccaga ccacccagaa gggacagaag aacagccgcg agagaatgaa gcggatcgaa    2040
gagggcatca agagctggg cagccagatc ctgaaagaac accccgtgga aaacacccag    2100
ctgcagaacg agaagctgta cctgtactac ctgcagaatg gcggggatat gtacgtggac    2160
caggaactgg acatcaaccg gctgtccgac tacgatgtgg accatatcgt gcctcagagc    2220
tttctgaagg acgactccat cgacaacaag gtgctgacca aagcgacaa gaaccggggc    2280 aagagcgaca acgtgccctc cgaagaggtc gtgaagaaga tgaagaacta ctggcggcag    2340
ctgctgaacg ccaagctgat tacccagaga aagttcgaca atctgaccaa ggccgagaga    2400
ggcggcctga gcgaactgga taaggccggc ttcatcaaga gacagctggt ggaaacccgg    2460
cagatcacaa agcacgtggc acagatcctg gactcccgga tgaacactaa gtacgacgag    2520
aatgacaagc tgatccggga agtgaaagtg atcacctga gtccaagct ggtgtccgat    2580 ttccggaagg atttccagtt ttacaaagtg cgcgagatca caactacca ccacgcccac    2640 gacgcctacc tgaacgccgt cgtgggaacc gccctgatca aaagtaccc taagctggaa    2700 agcgagttcg tgtacggcga ctacaaggtg tacgacgtgc ggaagatgat cgccaagagc    2760
gagcaggaaa tcggcaaggc taccgccaag tacttcttct acagcaacat catgaacttt    2820
ttcaagaccg agattaccct ggccaacggc gagatccgga agcggcctct gatcgagaca    2880
aacggcgaaa ccggggagat cgtgtgggat aagggccggg attttgccac cgtgcggaaa    2940
gtgctgagca tgccccaagt gaatatcgtg aaaaagaccg aggtgcagac aggcggcttc    3000
agcaaagagt ctatcctgcc caagaggaac agcgataagc tgatcgccag aaagaaggac    3060
tgggacccta agaagtacgg cggcttcgac agccccaccg tggcctattc tgtgctggtg    3120
gtggccaaag tggaaaaggg caagtccaag aaactgaaga gtgtgaaaga gctgctgggg    3180
atcaccatca tggaaagaag cagcttcgag aagaatccca tcgactttct ggaagccaag    3240
ggctacaaag aagtgaaaaa ggacctgatc atcaagctgc ctaagtactc cctgttcgag    3300
ctggaaaacg gccggaagag aatgctggcc tctgccggcg aactgcagaa gggaaacgaa    3360
ctggccctgc cctccaaata tgtgaacttc ctgtacctgg ccagccacta tgagaagctg    3420
```

```
aagggctccc ccgaggataa tgagcagaaa cagctgtttg tggaacagca caagcactac    3480
ctggacgaga tcatcgagca gatcagcgag ttctccaaga gagtgatcct ggccgacgct    3540
aatctggaca aagtgctgtc cgcctacaac aagcaccggg ataagcccat cagagagcag    3600
gccgagaata tcatccacct gtttaccctg accaatctgg agcccctgc cgccttcaag     3660 tactttgaca ccaccatcga ccggaagagg tacaccagca ccaaagaggt gctggacgcc    3720
accctgatcc accagagcat caccggcctg tacgagacac ggatcgacct gtctcagctg    3780
ggaggcgaca aaaggccggc ggccacgaaa aaggccggcc aggcaaaaaa gaaaaagtaa    3840
```

<210> SEQ ID NO 55
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Ala Glu Ala Ala Ala Lys Glu Ala Ala Ala Lys Glu Ala Ala Ala Lys
1               5                   10                  15

Ala Leu Glu Ala Glu Ala Ala Ala Lys Glu Ala Ala Ala Lys Glu Ala
            20                  25                  30

Ala Ala Lys Ala
        35
```

<210> SEQ ID NO 56
<211> LENGTH: 3897
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56

```
atggccccaa agaagaagcg gaaggtcggt atccacggag tcccagcagc cgacaagaag     60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacgct gaagccgctg ctaaagaagc cgctgctaaa    600
gaagccgctg ctaaagccct ggaggctgaa gccgctgcta agaagccgc tgctaaagaa     660 gccgctgcta agctatcac caaggccccc ctgagcgcct ctatgatcaa agatacgac      720 gagcaccacc aggacctgac cctgctgaaa gctctcgtgc ggcagcagct gcctgagaag    780
tacaaagaga ttttcttcga ccagagcaag aacggctacg ccggctacat tgacggcgga    840
gccagccagg aagagttcta caagttcatc aagcccatcc tggaaaagat ggacggcacc    900
gaggaactgc tcgtgaagct gaacagagag gacctgctgc ggaagcagcg gaccttcgac    960
```

```
aacggcagca tcccccacca gatccacctg ggagagctgc acgccattct gcggcggcag    1020
gaagattttt acccattcct gaaggacaac cgggaaaaga tcgagaagat cctgaccttc    1080
cgcatcccct actacgtggg ccctctggcc aggggaaaca gcagattcgc ctggatgacc    1140
agaaagagcg aggaaaccat caccccctgg aacttcgagg aagtggtgga caagggcgct    1200
tccgcccaga gcttcatcga gcggatgacc aacttcgata agaacctgcc caacgagaag    1260
gtgctgccca gcacagcct gctgtacgag tacttcaccg tgtataacga gctgaccaaa    1320
gtgaaatacg tgaccgaggg aatgagaaag cccgccttcc tgagcggcga gcagaaaaag    1380
gccatcgtgg acctgctgtt caagaccaac cggaaagtga ccgtgaagca gctgaaagag    1440
gactacttca agaaaatcga gtgcttcgac tccgtggaaa tctccggcgt ggaagatcgg    1500
ttcaacgcct ccctgggcac ataccacgat ctgctgaaaa ttatcaagga caaggacttc    1560
ctggacaatg aggaaaacga ggacattctg gaagatatcg tgctgaccct gacactgttt    1620
gaggacagag agatgatcga ggaacggctg aaaacctatg cccacctgtt cgacgacaaa    1680
gtgatgaagc agctgaagcg gcggagatac accggctggg gcaggctgag ccggaagctg    1740
atcaacggca tccgggacaa gcagtccggc aagacaatcc tggatttcct gaagtccgac    1800
ggcttcgcca acagaaactt catgcagctg atccacgacg acagcctgac ctttaaagag    1860
gacatccaga aagcccaggt gtccggccag ggcgatagcc tgcacgagca cattgccaat    1920
ctggccggca gccccgccat taagaagggc atcctgcaga cagtgaaggt ggtggacgag    1980
ctcgtgaaag tgatgggccg gcacaagccc gagaacatcg tgatcgaaat ggccagagag    2040
aaccagacca cccagaaggg acagaagaac agccgcgaga gaatgaagcg gatcgaagag    2100
ggcatcaaag agctgggcag ccagatcctg aaagaacacc ccgtggaaaa cacccagctg    2160
cagaacgaga agctgtacct gtactacctg cagaatgggc gggatatgta cgtggaccag    2220
gaactggaca tcaaccggct gtccgactac gatgtggacc atatcgtgcc tcagagcttt    2280
ctgaaggacg actccatcga caacaaggtg ctgaccagag cgacaagaa ccggggcaag    2340 agcgacaacg tgccctccga agaggtcgtg aagaagatga aaaactactg gcggcagctg    2400
ctgaacgcca agctgattac ccagagaaag ttcgacaatc tgaccaaggc cgagagaggc    2460
ggcctgagcg aactggataa ggccggcttc atcaagagac agctggtgga aacccggcag    2520
atcacaaagc acgtggcaca gatcctggac tcccggatga acactaagta cgacgagaat    2580
gacaagctga tccgggaagt gaaagtgatc accctgaagt ccaagctggt gtccgatttc    2640
cggaaggatt tccagtttta caaagtgcgc gagatcaaca actaccacca cgcccacgac    2700
gcctacctga acgccgtcgt gggaaccgcc ctgatcaaaa agtaccctaa gctggaaagc    2760
gagttcgtgt acggcgacta caaggtgtac gacgtgcgga agatgatcgc caagagcgag    2820
caggaaatcg gcaaggctac cgccaagtac ttcttctaca gcaacatcat gaacttttc    2880 aagaccgaga ttaccctggc caacggcgag atccggaagc ggcctctgat cgagacaaac    2940
ggcgaaaccg gggagatcgt gtgggataag gccgggatt ttgccaccgt gcggaaagtg    3000
ctgagcatgc cccaagtgaa tatcgtgaaa aagaccgagg tgcagacagg cggcttcagc    3060
aaagagtcta tcctgcccaa gaggaacagc gataagctga tcgccagaaa gaaggactgg    3120
gaccctaaga gtacggcgg cttcgacagc cccaccgtgg cctattctgt gctggtggtg    3180
gccaaagtgg aaaagggcaa gtccaagaaa ctgaagagtg tgaaagagct gctgggatc    3240 accatcatgg aaagaagcag cttcgagaag aatcccatcg actttctgga agccaagggc    3300
```

-continued

```
tacaaagaag tgaaaaagga cctgatcatc aagctgccta agtactccct gttcgagctg      3360
gaaaacggcc ggaagagaat gctggcctct gccggcgaac tgcagaaggg aaacgaactg      3420
gccctgccct ccaaatatgt gaacttcctg tacctggcca ccactatga aagctgaag        3480 ggctcccccg aggataatga gcagaaacag ctgtttgtgg aacagcacaa gcactacctg      3540
gacgagatca tcgagcagat cagcgagttc tccaagagag tgatcctggc cgacgctaat      3600
ctggacaaag tgctgtccgc ctacaacaag accgggata agcccatcag agagcaggcc       3660
gagaatatca tccacctgtt taccctgacc aatctgggag ccccctgccgc cttcaagtac     3720 tttgacacca ccatcgaccg gaagaggtac accagcacca agaggtgct ggacgccacc       3780 ctgatccacc agagcatcac cggcctgtac gagacacgga tcgacctgtc tcagctggga     3840
ggcgacaaaa ggccggcggc cacgaaaaag gccggccagg caaaaaagaa aaagtaa        3897
```

```
<210> SEQ ID NO 57
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ala Glu Ala Ala Ala Lys Glu Ala Ala Ala Lys Glu Ala Ala Ala Lys
1               5                   10                  15

Ala Leu Glu Ala Glu Ala Ala Ala Lys Glu Ala Ala Ala Lys Glu Ala
            20                  25                  30

Ala Ala Lys Ala Leu Glu Ala Glu Ala Ala Lys Glu Ala Ala Ala
        35                  40                  45

Lys Glu Ala Ala Ala Lys Ala
    50                  55
```

```
<210> SEQ ID NO 58
<211> LENGTH: 3954
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
atggccccaa agaagaagcg gaaggtcggt atccacggag tcccagcagc cgacaagaag        60
tacagcatcg gcctggacat cggcaccaac tctgtgggct gggccgtgat caccgacgag      120
tacaaggtgc ccagcaagaa attcaaggtg ctgggcaaca ccgaccggca cagcatcaag      180
aagaacctga tcggagccct gctgttcgac agcggcgaaa cagccgaggc cacccggctg      240
aagagaaccg ccagaagaag atacaccaga cggaagaacc ggatctgcta tctgcaagag      300
atcttcagca acgagatggc caaggtggac gacagcttct ccacagact ggaagagtcc       360 ttcctggtgg aagaggataa gaagcacgag cggcacccca tcttcggcaa catcgtggac      420
gaggtggcct accacgagaa gtaccccacc atctaccacc tgagaaagaa actggtggac      480
agcaccgaca aggccgacct gcggctgatc tatctggccc tggcccacat gatcaagttc      540
cggggccact ccctgatcga gggcgacgct gaagctgctg ctaaagaagc tgctgctaaa      600
gaagctgctg ctaaagccct ggaggctgaa gctgctgcta agaagctgc tgctaaagaa       660 gctgctgcta agcccctgga ggctgaagct gctgctaaag aagctgctgc taaagaagct      720
```

```
gctgctaaag ctatcaccaa ggccccctg agcgcctcta tgatcaagag atacgacgag      780
caccaccagg acctgaccct gctgaaagct ctcgtgcggc agcagctgcc tgagaagtac      840
aaagagattt tcttcgacca gagcaagaac ggctacgccg gctacattga cggcggagcc      900
agccaggaag agttctacaa gttcatcaag cccatcctgg aaaagatgga cggcaccgag      960
gaactgctcg tgaagctgaa cagagaggac ctgctgcgga agcagcggac cttcgacaac     1020
ggcagcatcc cccaccagat ccacctggga gagctgcacg ccattctgcg gcggcaggaa     1080 gattttacc cattcctgaa ggacaaccgg gaaaagatcg agaagatcct gaccttccgc     1140
atcccctact acgtgggccc tctggccagg ggaaacagca gattcgcctg gatgaccaga     1200
aagagcgagg aaaccatcac ccctggaac ttcgaggaag tggtggacaa gggcgcttcc      1260
gcccagagct tcatcgagcg gatgaccaac ttcgataaga acctgcccaa cgagaaggtg     1320
ctgcccaagc acagcctgct gtacgagtac ttcaccgtgt ataacgagct gaccaaagtg     1380
aaatacgtga ccgagggaat gagaaagccc gccttcctga cggcgagca gaaaaaggcc      1440 atcgtggacc tgctgttcaa gaccaaccgg aaagtgaccg tgaagcagct gaaagaggac     1500
tacttcaaga aaatcgagtg cttcgactcc gtggaaatct ccggcgtgga agatcggttc     1560
aacgcctccc tgggcacata ccacgatctg ctgaaaatta tcaaggacaa ggacttcctg     1620
gacaatgagg aaaacgagga cattctggaa gatatcgtgc tgaccctgac actgtttgag     1680
gacagagaga tgatcgagga acggctgaaa acctatgccc acctgttcga cgacaaagtg     1740
atgaagcagc tgaagcggcg gagatacacc ggctggggca ggctgagccg gaagctgatc     1800
aacggcatcc gggacaagca gtccggcaag acaatcctgg atttcctgaa gtccgacggc     1860
ttcgccaaca gaaacttcat gcagctgatc cacgacgaca gcctgacctt taaagaggac     1920
atccagaaag cccaggtgtc cggccagggc gatagcctgc acgagcacat tgccaatctg     1980
gccggcagcc ccgccattaa gaagggcatc ctgcagacag tgaaggtggt ggacgagctc     2040
gtgaaagtga tgggccggca aagcccgag aacatcgtga tcgaaatggc cagagagaac     2100
cagaccaccc agaagggaca aagaacagc cgcgagagaa tgaagcggat cgaagagggc     2160
atcaaagagc tgggcagcca gatcctgaaa gaacaccccg tggaaaacac ccagctgcag     2220
aacgagaagc tgtacctgta ctacctgcag aatgggcggg atatgtacgt ggaccaggaa     2280
ctggacatca accggctgtc cgactacgat gtggaccata tcgtgcctca gagctttctg     2340
aaggacgact ccatcgacaa caaggtgctg accagaagcg acaagaaccg gggcaagagc     2400
gacaacgtgc cctccgaaga ggtcgtgaag aagatgaaga actactggcg gcagctgctg     2460
aacgccaagc tgattaccca gagaaagttc gacaatctga ccaaggccga gagaggcggc     2520
ctgagcgaac tggataaggc cggcttcatc aagagacagc tggtggaaac ccggcagatc     2580
acaaagcacg tggcacagat cctggactcc cggatgaaca ctaagtacga cgagaatgac     2640
aagctgatcc gggaagtgaa agtgatcacc ctgaagtcca gctggtgtc cgatttccgg     2700 aaggatttcc agttttacaa agtgcgcgag atcaacaact accaccacgc ccacgacgcc     2760
tacctgaacg ccgtcgtggg aaccgccctg atcaaaaagt accctaagct ggaaagcgag     2820
ttcgtgtacg gcgactacaa ggtgtacgac gtgcggaaga tgatcgccaa gagcgagcag     2880
gaaatcggca aggctaccgc caagtacttc ttctacagca acatcatgaa cttttttcaag     2940 accgagatta ccctggccaa cggcgagatc cggaagcggc ctctgatcga gacaaacggc     3000
gaaaccgggg agatcgtgtg ggataagggc cgggattttg ccaccgtgcg gaaagtgctg     3060
```

```
agcatgcccc aagtgaatat cgtgaaaaag accgaggtgc agacaggcgg cttcagcaaa      3120
gagtctatcc tgcccaagag gaacagcgat aagctgatcg ccagaaagaa ggactgggac      3180
cctaagaagt acggcggctt cgacagcccc accgtggcct attctgtgct ggtggtggcc      3240
aaagtggaaa agggcaagtc caagaaactg aagagtgtga agagctgctg ggggatcacc      3300
atcatggaaa gaagcagctt cgagaagaat cccatcgact ttctggaagc caagggctac      3360
aaagaagtga aaaaggacct gatcatcaag ctgcctaagt actccctgtt cgagctggaa      3420
aacggccgga gagaatgctg ggcctctgcc ggcgaactgc agaagggaaa cgaactggcc      3480
ctgccctcca aatatgtgaa cttcctgtac ctggccagcc actatgagaa gctgaagggc      3540
tcccccgagg ataatgagca gaaacagctg tttgtggaac agcacaagca ctacctggac      3600
gagatcatcg agcagatcag cgagttctcc aagagagtga tcctggccga cgctaatctg      3660
gacaaagtgc tgtccgccta caacaagcac cgggataagc ccatcagaga gcaggccgag      3720
aatatcatcc acctgtttac cctgaccaat ctgggagccc tgccgccttc aagtactttt      3780
gacaccacca tcgaccggaa gaggtacacc agcaccaaaa aggtgctgga cgccaccctg      3840
atccaccaga gcatcaccgg cctgtacgag acacggatcg acctgtctca gctgggaggc      3900
gacaaaaggc cggcggccac gaaaaaggcc ggccaggcaa aaagaaaaa gtaa            3954
```

<210> SEQ ID NO 59
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Ala Glu Ala Ala Ala Lys Glu Ala Ala Ala Lys Glu Ala Ala Ala Lys
1               5                   10                  15

Leu Glu Glu Ala Ala Ala Lys Glu Ala Ala Ala Lys Glu Ala Ala Ala
            20                  25                  30

Lys Leu Glu Glu Ala Ala Ala Lys Glu Ala Ala Ala Lys Glu Ala Ala
        35                  40                  45

Ala Lys Leu Glu Glu Ala Ala Ala Lys Glu Ala Ala Ala Lys Glu Ala
    50                  55                  60

Ala Ala Lys Ala
65
```

<210> SEQ ID NO 60
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60

```
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcggagccct gctgttcgac agcggcgaaa cagccgaggc cacccggctg     240
aagagaaccg ccagaagaag atacaccaga cggaagaacc ggatctgcta tctgcaagag     300
```

```
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtacccacc atctaccacc tgagaaagaa actggtggac     480
agcaccgaca aggccgacct gcggctgatc tatctggccc tggcccacat gatcaagttc    540
cggggccact tcctgatcga gggcgacgct gaagctgctg ctaaagaagc tgctgctaaa    600
gaagctgctg ctaaagccct ggaggctgaa gctgctgcta agaagctgc tgctaaagaa     660 gctgctgcta aagccctgga ggctgaagct gctgctaaag aagctgctgc taaagaagct    720
gctgctaaag ccctggaggc tgaagctgct gctaaagaag ctgctgctaa gaagctgct     780 gctaaagcta tcaccaaggc cccctgagc gcctctatga tcaagagata cgacgagcac     840
caccaggacc tgaccctgct gaaagctctc gtgcggcagc agctgcctga agtacaaa      900 gagattttct tcgaccagag caagaacggc tacgccggct acattgacgg cggagccagc    960
caggaagagt tctacaagtt catcaagccc atcctggaaa agatggacgg caccgaggaa   1020
ctgctcgtga agctgaacag agaggacctg ctgcggaagc agcggacctt cgacaacggc   1080
agcatccccc accagatcca cctgggagag ctgcacgcca ttctgcggcg gcaggaagat   1140 tttacccat tcctgaagga caaccgggaa aagatcgaga gatcctgac cttccgcatc      1200 ccctactacg tgggccctct ggccagggga acagcagat cgcctggat gaccagaaag      1260 agcgaggaaa ccatcacccc ctggaacttc gaggaagtgg tggacaaggg cgcttccgcc   1320
cagagcttca tcgagcggat gaccaacttc gataagaacc tgcccaacga aggtgctg      1380 cccaagcaca gcctgctgta cgagtacttc accgtgtata cgagctgac caaagtgaaa    1440 tacgtgaccg agggaatgag aaagcccgcc ttcctgagcg gcgagcagaa aaaggccatc   1500
gtggacctgc tgttcaagac caaccggaaa gtgaccgtga agcagctgaa agaggactac   1560
ttcaagaaaa tcgagtgctt cgactccgtg gaaatctccg gcgtggaaga tcggttcaac   1620
gcctccctgg gcacatacca cgatctgctg aaaattatca aggacaagga cttcctggac   1680
aatgaggaaa acgaggacat tctggaagat atcgtgctga ccctgacact gtttgaggac   1740
agagagatga tcgaggaacg gctgaaaacc tatgcccacc tgttcgacga caaagtgatg   1800
aagcagctga agcggcggag ataccggc tggggcaggc tgagccggaa gctgatcaac    1860
ggcatccggg acaagcagtc cggcaagaca atcctggatt tcctgaagtc cgacggcttc   1920
gccaacagaa acttcatgca gctgatccac gacgacagcc tgacctttaa agaggacatc   1980
cagaaagccc aggtgtccgg ccagggcgat agcctgcacg agcacattgc caatctggcc   2040
ggcagccccg ccattaagaa gggcatcctg cagacagtga aggtggtgga cgagctcgtg   2100
aaagtgatgg gccggcacaa gcccgagaac atcgtgatcg aaatggccag agagaaccag   2160
accacccaga agggacagaa gaacagccgc gagagaatga gcggatcga agagggcatc    2220 aaagagctgg gcagccagat cctgaaagaa caccccgtgg aaaacaccca gctgcagaac   2280
gagaagctgt acctgtacta cctgcagaat gggcgggata tgtacgtgga ccaggaactg   2340
gacatcaacc ggctgtccga ctacgatgtg gaccatatcg tgcctcagag ctttctgaag   2400
gacgactcca tcgacaacaa ggtgctgacc agaagcgaca gaaccgggg caagagcgac   2460 aacgtgccct ccgaagaggt cgtgaagaag atgaagaact actggcggca gctgctgaac   2520
gccaagctga ttacccagag aaagttcgac aatctgacca aggccgagag aggcggcctg   2580
agcgaactga taaggccgg cttcatcaag agacagctgg tggaaacccg gcagatcaca   2640
aagcacgtgg cacagatcct ggactcccgg atgaacacta agtacgacga gaatgacaag   2700
```

| | |
|---|---|
| ctgatccggg aagtgaaagt gatcaccctg aagtccaagc tggtgtccga tttccggaag | 2760 |
| gatttccagt tttacaaagt gcgcgagatc aacaactacc accacgccca cgacgcctac | 2820 |
| ctgaacgccg tcgtgggaac cgccctgatc aaaaagtacc ctaagctgga aagcgagttc | 2880 |
| gtgtacggcg actacaaggt gtacgacgtg cggaagatga tcgccaagag cgagcaggaa | 2940 |
| atcggcaagg ctaccgccaa gtacttcttc tacagcaaca tcatgaactt tttcaagacc | 3000 |
| gagattaccc tggccaacgg cgagatccgg aagcggcctc tgatcgagac aaacggcgaa | 3060 |
| accggggaga tcgtgtggga taagggccgg gattttgcca ccgtgcggaa agtgctgagc | 3120 |
| atgccccaag tgaatatcgt gaaaaagacc gaggtgcaga caggcggctt cagcaaagag | 3180 |
| tctatcctgc caagaggaa cagcgataag ctgatcgcca gaaagaagga ctgggaccct | 3240 |
| aagaagtacg gcggcttcga cagccccacc gtggcctatt ctgtgctggt ggtgccaaa | 3300 |
| gtggaaaagg gcaagtccaa gaaactgaag agtgtgaaag agctgctggg gatcaccatc | 3360 |
| atggaaagaa gcagcttcga gaagaatccc atcgactttc tggaagccaa gggctacaaa | 3420 |
| gaagtgaaaa aggacctgat catcaagctg cctaagtact ccctgttcga gctggaaaac | 3480 |
| ggccggaaga gaatgctggc ctctgccggc gaactgcaga agggaaacga actggccctg | 3540 |
| ccctccaaat atgtgaactt cctgtacctg gccagccact atgagaagct gaagggctcc | 3600 |
| cccgaggata tgagcagaa acagctgttt gtggaacagc acaagcacta cctggacgag | 3660 |
| atcatcgagc agatcagcga gttctccaag agagtgatcc tggccgacgc taatctggac | 3720 |
| aaagtgctgt ccgcctacaa caagcaccgg gataagccca tcagagagca ggccgagaat | 3780 |
| atcatccacc tgtttaccct gaccaatctg ggagccctg ccgccttcaa gtactttgac | 3840 |
| accaccatcg accggaagag gtacaccagc accaaagagg tgctggacgc cacccctgatc | 3900 |
| caccagagca tcaccggcct gtacgagaca cggatcgacc tgtctcagct gggaggcgac | 3960 |
| aaaaggccgg cggccacgaa aaaggccggc caggcaaaaa agaaaaagta a | 4011 |

<210> SEQ ID NO 61
<211> LENGTH: 3804
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

| | |
|---|---|
| atggccccaa agaagaagcg gaaggtcggt atccacggag tcccagcagc cgacaagaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgaccggca cagcatcaag | 180 |
| aagaacctga tcggagccct gctgttcgac agcggcgaaa cagccgaggc cacccggctg | 240 |
| aagagaaccg ccagaagaag atacaccaga cggaagaacc ggatctgcta tctgcaagag | 300 |
| atcttcagca acgagatggc caaggtggac gacagcttct tccacagact ggaagagtcc | 360 |
| ttcctggtgg aagaggataa gaagcacgag cggcacccca tcttcggcaa catcgtggac | 420 |
| gaggtggcct accacgagaa gtaccccacc atctaccacc tgagaaagaa actggtggac | 480 |
| agcaccgaca aggccgacct gcggctgatc tatctggccc tggcccacat gatcaagttc | 540 |
| cggggccact tcctgatcga gggcgacctg gtgaacccg agatcaccaa ggccccctg | 600 |
| agcgcctcta tgatcaagag atacgacgag caccaccagg acctgaccct gctgaaagct | 660 |

```
ctcgtgcggc agcagctgcc tgagaagtac aaagagattt tcttcgacca gagcaagaac    720
ggctacgccg gctacattga cggcggagcc agccaggaag agttctacaa gttcatcaag    780
cccatcctgg aaaagatgga cggcaccgag gaactgctcg tgaagctgaa cagagaggac    840
ctgctgcgga agcagcggac cttcgacaac ggcagcatcc cccaccagat ccacctggga    900
gagctgcacg ccattctgcg gcggcaggaa gatttttacc cattcctgaa ggacaaccgg    960
gaaaagatcg agaagatcct gaccttccgc atccccctact acgtgggccc tctggccagg   1020
ggaaacagca gattcgcctg gatgaccaga agagcgagg aaaccatcac ccctggaac    1080
ttcgaggaag tggtggacaa gggcgcttcc gcccagagct tcatcgagcg gatgaccaac   1140
ttcgataaga acctgcccaa cgagaaggtg ctgcccaagc acagcctgct gtacgagtac   1200
ttcaccgtgt ataacgagct gaccaaagtg aaatacgtga ccgagggaat gagaaagccc   1260
gccttcctga gcggcgagca gaaaaaggcc atcgtggacc tgctgttcaa gaccaaccgg   1320
aaagtgaccg tgaagcagct gaaagaggac tacttcaaga aaatcgagtg cttcgactcc   1380
gtggaaatct ccggcgtgga agatcggttc aacgcctccc tgggcacata ccacgatctg   1440
ctgaaaatta tcaaggacaa ggacttcctg gacaatgagg aaaacgagga cattctggaa   1500
gatatcgtgc tgacccctgac actgtttgag acagagaga tgatcgagga acggctgaaa   1560
acctatgccc acctgttcga cgacaaagtg atgaagcagc tgaagcggcg gagatacacc   1620
ggctggggca ggctgagccg gaagctgatc aacggcatcc gggacaagca gtccggcaag   1680
acaatcctgg atttcctgaa gtccgacggc ttcgccaaca gaaacttcat gcagctgatc   1740
cacgacgaca gcctgacctt taaagaggac atccagaaag cccaggtgtc cggccagggc   1800
gatagcctgc acgagcacat tgccaatctg gccggcagcc ccgccattaa gaagggcatc   1860
ctgcagacag tgaaggtggt ggacgagctc gtgaaagtga gggccggca aagcccgag   1920
aacatcgtga tcgaaatggc cagagagaac cagaccaccc agaagggaca gaagaacagc   1980
cgcgagagaa tgaagcggat cgaagagggc atcaaagagc tgggcagcca gatcctgaaa   2040
gaacaccccg tggaaaacac ccagctgcag aacgagaagc tgtacctgta ctacctgcag   2100
aatgggcggg atatgtacgt ggaccaggaa ctggacatca accggctgtc cgactacgat   2160
gtggaccata tcgtgcctca gagctttctg aaggacgact ccatcgacaa caaggtgctg   2220
accagaagcg acaagaaccg gggcaagagc gacaacgtgc cctccgaaga ggtcgtgaag   2280
aagatgaaga actactggcg gcagctgctg aacgccaagc tgattaccca gagaaagttc   2340
gacaatctga ccaaggccga gagaggcggc ctgagcgaac tggataaggc cggcttcatc   2400
aagagacagc tggtggaaac ccggcagatc acaaagcacg tggcacagat cctggactcc   2460
cggatgaaca ctaagtacga cgagaatgac aagctgatcc gggaagtgaa agtgatcacc   2520
ctgaagtcca agctggtgtc cgatttccgg aaggatttcc agttttacaa agtgcgcgag   2580
atcaacaact accaccacgc ccacgacgcc tacctgaacg ccgtcgtggg aaccgccctg   2640
atcaaaaagt accctaagct ggaaagcgag ttcgtgtacg gcgactacaa ggtgtacgac   2700
gtgcggaaga tgatcgccaa gagcgagcag gaaatcggca aggctaccgc caagtacttc   2760
ttctacagca acatcatgaa ctttttcaag accgagatta ccctggccaa cggcgagatc   2820
cggaagcggc ctctgatcga gacaaacggc gaaaccgggg agatcgtgtg ggataagggc   2880
cgggattttg ccaccgtgcg gaaagtgctg agcatgcccc aagtgaatat cgtgaaaaag   2940
accgaggtg agacaggcgg cttcagcaaa gagtctatcc tgcccaagag gaacagcgat   3000
aagctgatcg ccagaaagaa ggactgggac cctaagaagt acggcggctt cgacagcccc   3060
```

```
accgtggcct attctgtgct ggtggtggcc aaagtggaaa agggcaagtc caagaaactg    3120
aagagtgtga aagagctgct ggggatcacc atcatgaaaa gaagcagctt cgagaagaat    3180
cccatcgact ttctggaagc caagggctac aaagaagtga aaaggacct gatcatcaag     3240 ctgcctaagt actccctgtt cgagctggaa acggccgga agagaatgct ggcctctgcc    3300
ggcgaactgc agaagggaaa cgaactggcc ctgccctcca atatgtgaa cttcctgtac    3360 ctggccagcc actatgagaa gctgaagggc tcccccgagg ataatgagca gaaacagctg    3420
tttgtggaac agcacaagca ctacctggac gagatcatcg agcagatcag cgagttctcc    3480
aagagagtga tcctggccga cgctaatctg gacaaagtgc tgtccgccta caacaagcac    3540
cgggataagc ccatcagaga gcaggccgag aatatcatcc acctgtttac cctgaccaat    3600
ctgggagccc ctgccgcctt caagtacttt gacaccacca tcgaccggaa gaggtacacc    3660
agcaccaaag aggtgctgga cgccaccctg atccaccaga gcatcaccgg cctgtacgag    3720
acacggatcg acctgtctca gctgggaggc gacaaaaggc cggcggccac gaaaaaggcc    3780
ggccaggcaa aaagaaaaa gtaa                                             3804
```

<210> SEQ ID NO 62
<211> LENGTH: 3393
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62

```
atggccccaa agaagaagcg gaaggtcggt atccacggag tcccagcagc cgacaagaag      60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc caccccggctg    240 aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact cctgatcga gggcgacctg aaccccgaca cagcgacgt ggacaagctg    600 ttcatccagc tggtgcagac ctacaaccag ctgttcgagg aaaaccccat caacgccagc    660
ggcgtggacg ccaaggccat cctgtctgcc agactgagca gagcagacg gctggaaaat    720 ctgatcgccc agctgcccgg cgagaagaag aatggcctgt cggaaaccct gattgccctg    780
agcctgggcc tgacccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gcccccctga gcgcctctat gatcaagaga    1020
tacgacgagc accaccagga cctgaccctg ctgaaagctc tcgtgcggca gcagctgcct    1080
gagaagtaca aagagatttt cttcgaccag agcaagaacg gctacgccgg ctacattgac    1140
ggcggagcca gccaggaaga gttctacaag ttcatcaagc ccatcctgga aaagatggac    1200
```

-continued

```
ggcaccgagg aactgctcgt gaagctgaac agagaggacc tgctgcggaa gcagcggacc    1260
ttcgacaacg gcagcatccc ccaccagatc cacctgggag agctgcacgc cattctgcgg    1320
cggcaggaag attttacccc attcctgaag gacaaccggg aaaagatcga agatcctg     1380 accttccgca tccctacta cgtgggccct ctggccaggg aaacagcag attcgcctgg     1440 atgaccagaa agagcgagga aaccatcacc ccctggaact tcgaggaagt ggtggacaag    1500
ggcgcttccg cccagagctt catcgagcgg atgaccaact tcgataagaa cctgcccaac    1560
gagaaggtgc tgcccaagca cagcctgctg tacgagtact tcaccgtgta taacgagctg    1620
accaaagtga atacgtgac cgagggaatg agaaagcccg ccttcctgag cggcgagcag    1680
aaaaaggcca tcgtggacct gctgttcaag accaaccgga agtgaccgt gaagcagctg    1740 aaagaggact acttcaagaa atcgagtgc ttcgactccg tggaaatctc cggcgtggaa    1800
gatcggttca acgcctccct gggcacatac cacgatctgc tgaaaattat caaggacaag    1860
gacttcctgg acaatgagga aaacgaggac attctggaag atatcgtgct gaccctgaca    1920
ctgtttgagg acagagagat gatcgaggaa cggctgaaaa cctatgccca cctgttcgac    1980
gacaaagtga tgaagcagct gaagcggcgg agatacaccg ctggggcag gctgagccgg    2040 aagctgatca acggcatccg ggacaagcag tccggcaaga caatcctgga tttcctgaag    2100
tccgacggct tcgccaacag aaacttcatg cagctgatcc acgacgacag cctgaccttt    2160
aaagaggaca tccagaaagc ccaggtgtcc ggcagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga catcgtgat cgaaatggcc    2340 agagagaacc agaccaccca aagggacag aagaacagcc gcgagagaat gaagcggatc    2400
gaagagggca tcaaagagct gggcagccag atcctgaaag aacacccgt ggaaaacacc    2460 cagctgcaga acgagaagct gtacctgtac tacctgcaga atgggcggga tatgtacgtg    2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca agagacagct ggtggaaacc    2820
cggcagatca caaagcacgt ggcacagatc ctggactccc ggatgaacac taagtacgac    2880
gagaatgaca agctgatccg ggaagtgaaa gtgatcaccc tgaagtccaa gctggtgtcc    2940
gatttccgga aggatttcca gttttacaaa gtgcgcgaga tcaacaacta ccaccacgcc    3000
cacgacgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180 ttttcaaga ccgagattac cctggccaac ggcgagatcc ggaagcggcc tctgatcgag    3240
acaaacggcg aaaccgggga atcgtgtgg gataagggcc gggattttgc caccgtgcgg    3300
aaagtgctga gcatgcccca agtgaatatc gtgaaaaaga ccaaaaggcc ggcggccacg    3360
aaaaaggccg gccaggcaaa aaagaaaaag taa                                 3393
```

<210> SEQ ID NO 63
<211> LENGTH: 3849
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

| | |
|---|---|
| atggccccaa agaagaagcg gaaggtcggt atccacggag tcccagcagc cgacaagaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgaccggca cagcatcaag | 180 |
| aagaacctga tcggagccct gctgttcgac agcggcgaaa cagccgaggc cacccggctg | 240 |
| aagagaaccg ccagaagaag atacaccaga cggaagaacc ggatctgcta tctgcaagag | 300 |
| atcttcagca acgagatggc caaggtggac gacagcttct tccacagact ggaagagtcc | 360 |
| ttcctggtgg aagaggataa gaagcacgag cggcacccca tcttcggcaa catcgtggac | 420 |
| gaggtggcct accacgagaa gtaccccacc atctaccacc tgagaaagaa actggtggac | 480 |
| agcaccgaca aggccgacct gcggctgatc tatctggccc tggcccacat gatcaagttc | 540 |
| cggggccact tcctgatcga gggcgacctg gtggaggtg gctcgggtgg aggtggctcg | 600 |
| ggtggaggtg gctcggtgaa caccgagatc accaaggccc ccctgagcgc ctctatgatc | 660 |
| aagagatacg acgagcacca ccaggacctg accctgctga agctctcgt gcggcagcag | 720 |
| ctgcctgaga gtacaaaga gattttcttc gaccagagca gaacggcta cgccggctac | 780 |
| attgacggcg gagccagcca ggaagagttc tacaagttca tcaagcccat cctggaaaag | 840 |
| atggacggca ccgaggaact gctcgtgaag ctgaacagag aggacctgct gcggaagcag | 900 |
| cggaccttcg acaacggcag catcccccac cagatccacc tgggagagct gcacgccatt | 960 |
| ctgcggcggc aggaagattt ttacccattc ctgaaggaca ccggaaaa gatcgagaag | 1020 |
| atcctgacct tccgcatccc ctactacgtg ggccctctgg ccaggggaaa cagcagattc | 1080 |
| gcctggatga ccagaaagag cgaggaaacc atcacccct ggaacttcga ggaagtggtg | 1140 |
| gacaagggcg cttccgccca gagcttcatc gagcggatga ccaacttcga taagaacctg | 1200 |
| cccaacgaga aggtgctgcc caagcacagc ctgctgtacg agtacttcac cgtgtataac | 1260 |
| gagctgacca aagtgaaata cgtgaccgag ggaatgagaa agcccgcctt cctgagcggc | 1320 |
| gagcagaaaa aggccatcgt ggacctgctg ttcaagacca accggaaagt gaccgtgaag | 1380 |
| cagctgaaag gactactt caagaaaatc gagtgcttcg actccgtgga aatctccggc | 1440 |
| gtggaagatc ggttcaacgc ctccctgggc acataccacg atctgctgaa aattatcaag | 1500 |
| gacaaggact cctggacaa tgaggaaaac gaggacattc tggaagatat cgtgctgacc | 1560 |
| ctgacactgt ttgaggacag agagatgatc gaggaacggc tgaaaaccta tgcccacctg | 1620 |
| ttcgacgaca aagtgatgaa gcagctgaag cggcggagat acaccggctg gggcaggctg | 1680 |
| agccggaagc tgatcaacgg catccgggac aagcagtccg gcaagacaat cctggatttc | 1740 |
| ctgaagtccg acggcttcgc caacagaaac ttcatgcagc tgatccacga cgacagcctg | 1800 |
| acctttaaag aggacatcca gaaagcccag gtgtccggcc agggcgatag cctgcacgag | 1860 |
| cacattgcca atctggccgg cagccccgcc attaagaagg gcatcctgca cagagtgaag | 1920 |
| gtggtggaca gctcgtgaa agtgatgggc cggcacaagc ccgagaacat cgtgatcgaa | 1980 |
| atggccagag agaaccagac cacccagaag ggacagaaga acagccgcga gagaatgaag | 2040 |
| cggatcgaag agggcatcaa agagctgggc agccagatcc tgaaagaaca ccccgtggaa | 2100 |
| aacacccagc tgcagaacga gaagctgtac ctgtactacc tgcagaatgg gcgggatatg | 2160 |

| | |
|---|---|
| tacgtggacc aggaactgga catcaaccgg ctgtccgact acgatgtgga ccatatcgtg | 2220 |
| cctcagagct ttctgaagga cgactccatc gacaacaagg tgctgaccag aagcgacaag | 2280 |
| aaccggggca agagcgacaa cgtgccctcc aagaggtcg tgaagaagat gaagaactac | 2340 |
| tggcggcagc tgctgaacgc caagctgatt acccagagaa agttcgacaa tctgaccaag | 2400 |
| gccgagagag gcggcctgag cgaactggat aaggccggct tcatcaagag acagctggtg | 2460 |
| gaaacccggc agatcacaaa gcacgtggca cagatcctgg actcccggat gaacactaag | 2520 |
| tacgacgaga atgacaagct gatccgggaa gtgaaagtga tcaccctgaa gtccaagctg | 2580 |
| gtgtccgatt tccggaagga tttccagttt tacaaagtgc gcgagatcaa caactaccac | 2640 |
| cacgcccacg acgcctacct gaacgccgtc gtgggaaccg ccctgatcaa aaagtaccct | 2700 |
| aagctggaaa gcgagttcgt gtacggcgac tacaaggtgt acgacgtgcg gaagatgatc | 2760 |
| gccaagagcg agcaggaaat cggcaaggct accgccaagt acttcttcta cagcaacatc | 2820 |
| atgaactttt tcaagaccga gattaccctg gccaacggcg agatccggaa gcggcctctg | 2880 |
| atcgagacaa acggcgaaac cggggagatc gtgtgggata agggccggga ttttgccacc | 2940 |
| gtgcggaaag tgctgagcat gccccaagtg aatatcgtga aaagaccga ggtgcagaca | 3000 |
| ggcggcttca gcaaagagtc tatcctgccc aagaggaaca gcgataagct gatcgccaga | 3060 |
| aagaaggact gggaccctaa gaagtacggc ggcttcgaca gccccaccgt ggcctattct | 3120 |
| gtgctggtgg tggccaaagt ggaaaagggc aagtccaaga aactgaagag tgtgaaagag | 3180 |
| ctgctgggga tcaccatcat ggaaagaagc agcttcgaga gaatcccat cgactttctg | 3240 |
| gaagccaagg gctacaaaga agtgaaaaag gacctgatca tcaagctgcc taagtactcc | 3300 |
| ctgttcgagc tggaaaacgg ccggaagaga atgctggcct ctgccggcga actgcagaag | 3360 |
| ggaaacgaac tggcccctgcc ctccaaatat gtgaacttcc tgtacctggc cagccactat | 3420 |
| gagaagctga agggctcccc cgaggataat gagcagaaac agctgtttgt ggaacagcac | 3480 |
| aagcactacc tggacgagat catcgagcag atcagcgagt ctccaagag agtgatcctg | 3540 |
| gccgacgcta atctggacaa agtgctgtcc gcctacaaca gcaccggga taagcccatc | 3600 |
| agagagcagg ccgagaatat catccaccctg tttaccctga ccaatctggg agcccctgcc | 3660 |
| gccttcaagt actttgacac caccatcgac cggaagaggt acaccagcac caaagaggtg | 3720 |
| ctggacgcca ccctgatcca ccagagcatc accggcctgt acgagacacg gatcgacctg | 3780 |
| tctcagctgg gaggcgacaa aaggccggcg gccacgaaaa aggccggcca ggcaaaaaag | 3840 |
| aaaaagtaa | 3849 |

<210> SEQ ID NO 64
<211> LENGTH: 3894
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 64

| | |
|---|---|
| atggccccaa agaagaagcg gaaggtcggt atccacggag tcccagcagc cgacaagaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgaccggca cagcatcaag | 180 |
| aagaacctga tcggagccct gctgttcgac agcggcgaaa cagccgaggc cacccggctg | 240 |
| aagagaaccg ccagaagaag atacaccaga cggaagaacc ggatctgcta tctgcaagag | 300 |

```
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacctg gtggaggtg gctcgggtgg aggtggctcg    600
ggtggaggtg gctcgggtgg aggtggctcg gtggaggtg gctcgggtgg aggtggctcg    660
gtgaacaccg agatcaccaa ggccccctg agcgcctcta tgatcaagag atacgacgag    720
caccaccagg acctgaccct gctgaaagct ctcgtgcggc agcagctgcc tgagaagtac    780
aaagagattt tcttcgacca gagcaagaac ggctacgccg ctacattga cggcggagcc    840
agccaggaag agttctacaa gttcatcaag cccatcctgg aaaagatgga cggcaccgag    900
gaactgctcg tgaagctgaa cagagaggac ctgctgcgga gcagcggac cttcgacaac    960
ggcagcatcc ccaccagat ccacctggga gagctgcacg ccattctgcg gcggcaggaa   1020
gattttacc cattcctgaa ggacaaccgg gaaaagatcg agaagatcct gaccttccgc   1080
atcccctact acgtgggccc tctggccagg ggaaacagca gattcgcctg gatgaccaga   1140
aagagcgagg aaaccatcac cccctggaac ttcgaggaag tggtggacaa gggcgcttcc   1200
gcccagagct tcatcgagcg gatgaccaac ttcgataaga acctgcccaa cgagaaggtg   1260
ctgcccaagc acagcctgct gtacgagtac ttcaccgtgt ataacgagct gaccaaagtg   1320
aaatacgtga ccgagggaat gagaaagccc gccttcctga cggcgagca gaaaaaggcc   1380
atcgtggacc tgctgttcaa gaccaaccgg aaagtgaccg tgaagcagct gaaagaggac   1440
tacttcaaga aaatcgagtg cttcgactcc gtggaaatct ccggcgtgga agatcggttc   1500
aacgcctccc tgggcacata ccacgatctg ctgaaaatta tcaaggacaa ggacttcctg   1560
gacaatgagg aaaacgagga cattctggaa gatatcgtgc tgaccctgac actgtttgag   1620
gacagagaga tgatcgagga acggctgaaa acctatgccc acctgttcga cgacaaagtg   1680
atgaagcagc tgaagcggcg agatacacc ggctggggca ggctgagccg gaagctgatc   1740
aacggcatcc gggacaagca gtccggcaag acaatcctgg atttcctgaa gtccgacggc   1800
ttcgccaaca gaaacttcat gcagctgatc cacgacgaca gcctgacctt taaagaggac   1860
atccagaaag cccaggtgtc cggccagggc gatagcctgc acgagcacat tgccaatctg   1920
gccggcagcc cgccattaa gaagggcatc ctgcagacag tgaaggtggt ggacgagctc   1980
gtgaaagtga tgggccggca aagcccgag aacatcgtga tcgaaatggc cagagagaac   2040
cagaccaccc agaagggaca gaagaacagc cgcgagagaa tgaagcggat cgaagagggc   2100
atcaaagagc tggcagcca gatcctgaaa gaacacccg tggaaaacac ccagctgcag   2160
aacgagaagc tgtacctgta ctacctgcag aatgggcggg atatgtacgt ggaccaggaa   2220
ctggacatca accggctgtc cgactacgat gtggaccata tcgtgcctca gagctttctg   2280
aaggacgact ccatcgacaa caaggtgctg accagaagcg acaagaaccg ggcaagagc   2340
gacaacgtgc cctccgaaga ggtcgtgaag aagatgaaga actactggcg gcagctgctg   2400
aacgccaagc tgattaccca gagaaagttc gacaatctga ccaaggccga gagagcggc   2460
ctgagcgaac tggataaggc cggcttcatc aagagacagc tggtggaaac ccggcagatc   2520
acaaagcacg tggcacagat cctggactcc cggatgaaca ctaagtacga cgagaatgac   2580
aagctgatcc gggaagtgaa agtgatcacc ctgaagtcca agctggtgtc cgatttccgg   2640
```

```
aaggatttcc agttttacaa agtgcgcgag atcaacaact accaccacgc ccacgacgcc    2700
tacctgaacg ccgtcgtggg aaccgccctg atcaaaaagt accctaagct ggaaagcgag    2760
ttcgtgtacg gcgactacaa ggtgtacgac gtgcggaaga tgatcgccaa gagcgagcag    2820
gaaatcggca aggctaccgc caagtacttc ttctacagca acatcatgaa ctttttcaag    2880
accgagatta ccctggccaa cggcgagatc cggaagcggc tctgatcga gacaaacggc    2940 gaaaccgggg agatcgtgtg ggataagggc cgggattttg ccaccgtgcg gaaagtgctg    3000
agcatgcccc aagtgaatat cgtgaaaaag accgaggtgc agacaggcgg cttcagcaaa    3060
gagtctatcc tgcccaagag gaacagcgat aagctgatcg ccagaaagaa ggactgggac    3120
cctaagaagt acggcggctt cgacagcccc accgtggcct attctgtgct ggtggtggcc    3180
aaagtggaaa agggcaagtc caagaaactg aagagtgtga agagctgct ggggatcacc    3240 atcatggaaa gaagcagctt cgagaagaat cccatcgact tctggaagc caagggctac    3300 aaagaagtga aaaaggacct gatcatcaag ctgcctaagt actccctgtt cgagctggaa    3360
aacggccgga gagaatgct ggcctctgcc ggcgaactgc agaagggaaa cgaactggcc    3420 ctgcccctcca aatatgtgaa cttcctgtac ctggccagcc actatgagaa gctgaagggc    3480
tcccccgagg ataatgagca gaaacagctg tttgtggaac agcacaagca ctacctggac    3540
gagatcatcg agcagatcag cgagttctcc aagagagtga tcctggccga cgctaatctg    3600
gacaaagtgc tgtccgccta caacaagcac cgggataagc ccatcagaga gcaggccgag    3660
aatatcatcc acctgtttac cctgaccaat ctgggagccc ctgccgcctt caagtacttt    3720
gacaccacca tcgaccggaa gaggtacacc agcaccaaag aggtgctgga cgccacccctg    3780 atccaccaga gcatcaccgg cctgtacgag acacggatcg acctgtctca gctgggaggc    3840
gacaaaaggc cggcggccac gaaaaaggcc ggccaggcaa aaaagaaaaa gtaa          3894
```

<210> SEQ ID NO 65
<211> LENGTH: 3939
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

```
atggcccaa agaagaagcg gaaggtcggt atccacggag tcccagcagc cgacaagaag     60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacctg aacccggaggtg gctcgggtgg aggtggctcg    600
ggtggaggtg gctcgggtgg aggtggctcg ggtggaggtg gctcgggtgg aggtggctcg    660
ggtggaggtg gctcgggtgg aggtggctcg ggtggaggtg gctcggtgaa caccgagatc    720
accaaggccc ccctgagcgc ctctatgatc aagagatacg acgagcacca ccaggacctg    780
```

```
accctgctga aagctctcgt gcggcagcag ctgcctgaga agtacaaaga gattttcttc      840
gaccagagca agaacggcta cgccggctac attgacggcg gagccagcca ggaagagttc      900
tacaagttca tcaagcccat cctggaaaag atggacggca ccgaggaact gctcgtgaag      960
ctgaacagag aggacctgct gcggaagcag cggaccttcg acaacggcag catccccac      1020 cagatccacc tgggagagct gcacgccatt ctgcggcggc aggaagattt tacccattc      1080 ctgaaggaca accgggaaaa gatcgagaag atcctgacct cccgcatccc ctactacgtg     1140
ggccctctgg ccaggggaaa cagcagattc gcctggatga ccagaaagag cgaggaaacc     1200
atcaccccct ggaacttcga ggaagtggtg gacaagggcg cttccgccca gagcttcatc     1260
gagcggatga ccaacttcga taagaacctg cccaacgaga aggtgctgcc caagcacagc     1320
ctgctgtacg agtacttcac cgtgtataac gagctgacca agtgaaaata cgtgaccgag     1380
ggaatgagaa agcccgcctt cctgagcggc gagcagaaaa aggccatcgt ggacctgctg     1440
ttcaagacca accggaaagt gaccgtgaag cagctgaaag aggactactt caagaaaatc     1500
gagtgcttcg actccgtgga aatctccggc gtggaagatc ggttcaacgc ctccctgggc     1560
acataccacg atctgctgaa aattatcaag gacaaggact tcctggacaa tgaggaaaac     1620
gaggacattc tggaagatat cgtgctgacc ctgacactgt ttgaggacag agagatgatc     1680
gaggaacggc tgaaaaccta tgcccacctg ttcgacgaca agtgatgaa gcagctgaag      1740 cggcggagat acaccggctg gggcaggctg agccggaagc tgatcaacgg catccgggac     1800
aagcagtccg gcaagacaat cctgattttc ctgaagtccg acggcttcgc caacagaaac     1860
ttcatgcagc tgatccacga cgacagcctg acctttaaag aggacatcca gaaagcccag     1920
gtgtccggcc agggcgatag cctgcacgag cacattgcca atctggccgg cagccccgcc     1980
attaagaagg gcatcctgca gacagtgaag gtggtggacg agctcgtgaa agtgatgggc     2040
cggcacaagc ccgagaacat cgtgatcgaa atggccagag agaaccagac cacccagaag     2100
ggacagaaga cagccgcga gagaatgaag cggatcgaag agggcatcaa agagctgggc     2160
agccagatcc tgaaagaaca ccccgtggaa aacacccagc tgcagaacga gaagctgtac     2220
ctgtactacc tgcagaatgg gcgggatatg tacgtggacc aggaactgga catcaaccgg     2280
ctgtccgact acgatgtgga ccatatcgtg cctcagagct ttctgaagga cgactccatc     2340
gacaacaagg tgctgaccag aagcgacaag aaccggggca gagcgacaa cgtgccctcc     2400 gaagaggtcg tgaagaagat gaagaactac tggcggcagc tgctgaacgc caagctgatt     2460
acccagagaa agttcgacaa tctgaccaag gccgagagag cggcctgag cgaactggat     2520 aaggccggct tcatcaagag acagctggtg gaaaacccgg cagatcacaa gcacgtggca     2580
cagatcctgg actcccggat gaacactaag tacgacgaga atgacaagct gatccgggaa     2640
gtgaaagtga tcaccctgaa gtccaagctg gtgtccgatt ccggaagga tttccagttt     2700 tacaaagtgc gcgagatcaa caactaccac cacgcccacg acgcctacct gaacgccgtc     2760
gtgggaaccg ccctgatcaa aaagtaccct aagctggaaa gcgagttcgt gtacggcgac     2820
tacaaggtgt acgacgtgcg gaagatgatc gccaagagcg agcaggaaat cggcaaggct     2880
accgccaagt acttcttcta cagcaacatc atgaactttt tcaagaccga gattaccctg     2940
gccaacggcg agatccggaa gcggcctctg atcgagacaa acggcgaaac cggggagatc     3000
gtgtgggata agccggga tttgccacc gtgcggaaag tgctgagcat gccccaagtg      3060
aatatcgtga aaagaccga ggtgcagaca ggcggcttca gcaaagagtc tatcctgccc     3120
```

```
aagaggaaca gcgataagct gatcgccaga aagaaggact gggaccctaa gaagtacggc   3180
ggcttcgaca gccccaccgt ggcctattct gtgctggtgg tggccaaagt ggaaaagggc   3240
aagtccaaga aactgaagag tgtgaaagag ctgctgggga tcaccatcat ggaaagaagc   3300
agcttcgaga agaatcccat cgactttctg gaagccaagg gctacaaaga agtgaaaaag   3360
gacctgatca tcaagctgcc taagtactcc ctgttcgagc tggaaaacgg ccggaagaga   3420
atgctggcct ctgccggcga actgcagaag gaaacgaac  tggccctgcc ctccaaatat   3480
gtgaacttcc tgtacctggc cagccactat gagaagctga agggctcccc cgaggataat   3540
gagcagaaac agctgtttgt ggaacagcac aagcactacc tggacgagat catcgagcag   3600
atcagcgagt tctccaagag agtgatcctg ccgacgcta  atctggacaa agtgctgtcc   3660
gcctacaaca gcaccggga  taagcccatc agagagcagg ccgagaatat catccacctg   3720
tttaccctga ccaatctggg agcccctgcc gccttcaagt actttgacac caccatcgac   3780
cggaagaggt acaccagcac caaagaggtg ctggacgcca ccctgatcca ccagagcatc   3840
accggcctgt acgagacacg gatcgacctg tctcagctgg gaggcgacaa aaggccggcg   3900
gccacgaaaa aggccggcca ggcaaaaaag aaaaagtaa                          3939
```

<210> SEQ ID NO 66
<211> LENGTH: 3984
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

```
atggccccaa agaagaagcg gaaggtcggt atccacggag tcccagcagc cgacaagaag    60
tacagcatcg gcctggacat cggcaccaac tctgtgggct gggccgtgat caccgacgag   120
tacaaggtgc ccagcaagaa attcaaggtg ctgggcaaca ccgaccggca cagcatcaag   180
aagaacctga tcggagccct gctgttcgac agcggcgaaa cagccgaggc cacccggctg   240
aagagaaccg ccagaagaag atacaccaga cggaagaacc ggatctgcta tctgcaagag   300
atcttcagca acgagatggc caaggtggac gacagcttct tccacagact ggaagagtcc   360
ttcctggtgg aagaggataa gaagcacgag cggcacccca tcttcggcaa catcgtggac   420
gaggtggcct accacgagaa gtaccccacc atctaccacc tgagaaagaa actggtggac   480
agcaccgaca aggccgacct gcggctgatc tatctggccc tggcccacat gatcaagttc   540
cggggccact tcctgatcga gggcgacctg ggtggaggtg gttcgggtgg cggtggctcg   600
ggtggaggtg gatcgggtgg cggtggttcg ggtggaggtg gctcgggcgg aggtggatcg   660
ggtggcggtg gctcgggtgg aggtggctcg ggtggaggtg gctcgggtgg cggtggatcg   720
ggtggaggtg gatcgggtgg aggtggttcg gtgaacaccg agatcaccaa ggcccccctg   780
agcgcctcta tgatcaagag atacgacgag caccaccagg acctgaccct gctgaaagct   840
ctcgtgcggc agcagctgcc tgagaagtac aaagagattt tcttcgacca gagcaagaac   900
ggctacgccg gctacattga cggcggagcc agccaggaag agttctacaa gttcatcaag   960
cccatcctgg aaaagatgga cggcaccgag gaactgctcg tgaagctgaa cagagaggac  1020
ctgctgcgca agcagcggac cttcgacaac ggcagcatcc cccaccagat ccacctggga  1080
gagctgcacg ccattctgcg gcggcaggaa gattttttac cattcctgaa ggacaaccgg  1140
gaaaagatcg agaagatcct gaccttccgc atccctact  acgtgggccc tctggccagg  1200
```

```
ggaaacagca gattcgcctg gatgaccaga aagagcgagg aaaccatcac cccctggaac   1260
ttcgaggaag tggtggacaa gggcgcttcc gcccagagct tcatcgagcg gatgaccaac   1320
ttcgataaga acctgcccaa cgagaaggtg ctgcccaagc acagcctgct gtacgagtac   1380
ttcaccgtgt ataacgagct gaccaaagtg aaatacgtga ccgagggaat gagaaagccc   1440
gccttcctga gcggcgagca gaaaaaggcc atcgtggacc tgctgttcaa gaccaaccgg   1500
aaagtgaccg tgaagcagct gaaagaggac tacttcaaga aaatcgagtg cttcgactcc   1560
gtggaaatct ccggcgtgga agatcggttc aacgcctccc tgggcacata ccacgatctg   1620
ctgaaaatta tcaaggacaa ggacttcctg gacaatgagg aaaacgagga cattctggaa   1680
gatatcgtgc tgaccctgac actgtttgag gacagagaga tgatcgagga acggctgaaa   1740
acctatgccc acctgttcga cgacaaagtg atgaagcagc tgaagcggcg agatacacc   1800 ggctggggca ggctgagccg gaagctgatc aacggcatcc gggacaagca gtccggcaag   1860
acaatcctgg atttcctgaa gtccgacggc ttcgccaaca gaaacttcat gcagctgatc   1920
cacgacgaca gcctgacctt taaagaggac atccagaaag cccaggtgtc cggccagggc   1980
gatagcctgc acgagcacat tgccaatctg gccggcagcc ccgccattaa gaagggcatc   2040
ctgcagacag tgaaggtggt ggacgagctc gtgaaagtga tgggccggca aagcccgag   2100 aacatcgtga tcgaaatggc cagagagaac cagaccaccc agaagggaca gaagaacagc   2160
cgcgagagaa tgaagcggat cgaagagggc atcaaagagc tgggcagcca gatcctgaaa   2220
gaacaccccg tggaaaacac ccagctgcag aacgagaagc tgtacctgta ctacctgcag   2280
aatgggcggg atatgtacgt ggaccaggaa ctggacatca accggctgtc cgactacgat   2340
gtggaccata tcgtgcctca gagctttctg aaggacgact ccatcgacaa caaggtgctg   2400
accagaagcg acaagaaccg gggcaagagc gacaacgtgc cctccgaaga ggtcgtgaag   2460
aagatgaaga actactggcg gcagctgctg aacgccaagc tgattaccca gagaaagttc   2520
gacaatctga ccaaggccga gagaggcggc ctgagcgaac tggataaggc cggcttcatc   2580
aagagacagc tggtggaaac ccggcagatc acaaagcacg tggcacagat cctggactcc   2640
cggatgaaca ctaagtacga cgagaatgac aagctgatcc gggaagtgaa agtgatcacc   2700
ctgaagtcca gctggtgtc cgatttccgg aaggatttcc agttttacaa agtgcgcgag   2760
atcaacaact accaccacgc ccacgacgcc tacctgaacg ccgtcgtggg aaccgccctg   2820
atcaaaaagt accctaagct ggaaagcgag ttcgtgtacg gcgactacaa ggtgtacgac   2880
gtgcggaaga tgatcgccaa gagcgagcag gaaatcggca aggctaccgc caagtacttc   2940
ttctacagca acatcatgaa cttttttcaag accgagatta ccctggccaa cggcgagatc   3000
cggaagcggc ctctgatcga cgaaaacggc gaaaccgggg agatcgtgtg ggataaggc   3060 cgggattttg ccaccgtgcg gaaagtgctg agcatgcccc aagtgaatat cgtgaaaaag   3120
accgaggtgc agacaggcgg cttcagcaaa gagtctatcc tgcccaagag gaacagcgat   3180
aagctgatcg ccagaaagaa ggactgggac cctaagaagt acggcggctt cgacagcccc   3240
accgtggcct attctgtgct ggtggtggcc aaagtggaaa agggcaagtc caagaaactg   3300
aagagtgtga aagagctgct ggggatcacc atcatggaaa gagcagctt cgagaagaat   3360 cccatcgact ttctggaagc caagggctac aaagaagtga aaaggacct gatcatcaag   3420 ctgcctaagt actccctgtt cgagctgaaa acggccgga agagaatgct ggcctctgcc   3480
ggcgaactgc agaagggaaa cgaactggcc ctgccctcca aatatgtgaa cttcctgtac   3540
```

| | |
|---|---:|
| ctggccagcc actatgagaa gctgaagggc tcccccgagg ataatgagca gaaacagctg | 3600 |
| tttgtggaac agcacaagca ctacctggac gagatcatcg agcagatcag cgagttctcc | 3660 |
| aagagagtga tcctggccga cgctaatctg acaaagtgc tgtccgccta caacaagcac | 3720 |
| cgggataagc ccatcagaga gcaggccgag aatatcatcc acctgtttac cctgaccaat | 3780 |
| ctgggagccc ctgccgcctt caagtacttt gacaccacca tcgaccggaa gaggtacacc | 3840 |
| agcaccaaag aggtgctgga cgccaccctg atccaccaga gcatcaccgg cctgtacgag | 3900 |
| acacggatcg acctgtctca gctgggaggc gacaaaaggc cggcggccac gaaaaaggcc | 3960 |
| ggccaggcaa aaagaaaaa gtaa | 3984 |

<210> SEQ ID NO 67
<211> LENGTH: 3855
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

| | |
|---|---:|
| atggccccaa agaagaagcg gaaggtcggt atccacggag tcccagcagc cgacaagaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgaccggca cagcatcaag | 180 |
| aagaacctga tcggagccct gctgttcgac agcggcgaaa cagccgaggc cacccggctg | 240 |
| aagagaaccg ccagaagaag atacaccaga cggaagaacc ggatctgcta tctgcaagag | 300 |
| atcttcagca acgagatggc caaggtggac gacagcttct tccacagact ggaagagtcc | 360 |
| ttcctggtgg aagaggataa gaagcacgag cggcacccca tcttcggcaa catcgtggac | 420 |
| gaggtggcct accacgagaa gtaccccacc atctaccacc tgagaaagaa actggtggac | 480 |
| agcaccgaca aggccgacct gcggctgatc tatctggccc tggcccacat gatcaagttc | 540 |
| cggggccact tcctgatcga gggcgacctg gctgaagctg ctgctaaaga agctgctgct | 600 |
| aaagaagctg ctgctaaagc tgtgaacacc gagatcacca aggccccct gagcgcctct | 660 |
| atgatcaaga gatacgacga gcaccaccag gacctgaccc tgctgaaagc tctcgtgcgg | 720 |
| cagcagctgc ctgagaagta caaagagatt ttcttcgacc agagcaagaa cggctacgcc | 780 |
| ggctacattg acggcggagc cagccaggaa gagttctaca gttcatcaa gcccatcctg | 840 |
| gaaaagatgg acggcaccga ggaactgctc gtgaagctga acagagga cctgctgcgg | 900 |
| aagcagcgga ccttcgacaa cggcagcatc ccccaccaga tccacctggg agagctgcac | 960 |
| gccattctgc ggcggcagga agattttac ccattcctga aggacaaccg ggaaaagatc | 1020 |
| gagaagatcc tgaccttccg catcccctac tacgtgggcc ctctggccag ggaaacagc | 1080 |
| agattcgcct ggatgaccag aaagagcgag gaaaccatca ccccctggaa cttcgaggaa | 1140 |
| gtggtggaca agggcgcttc cgcccagagc ttcatcgagc ggatgaccaa cttcgataag | 1200 |
| aacctgccca cgagaaggt gctgcccaag cacagcctgc tgtacgagta cttcaccgtg | 1260 |
| tataacgagc tgaccaaagt gaaatacgtg accgagggaa tgagaaagcc cgccttcctg | 1320 |
| agcggcgagc agaaaaaggc catcgtggac ctgctgttca gaccaaccg gaaagtgacc | 1380 |
| gtgaagcagc tgaaagagga ctacttcaag aaaatcgagt gcttcgactc cgtggaaatc | 1440 |
| tccggcgtgg aagatcggtt caacgcctcc ctgggcacat accacgatct gctgaaaatt | 1500 |
| atcaaggaca aggacttcct ggacaatgag gaaaacgagg acattctgga agatatcgtg | 1560 |

```
ctgaccctga cactgtttga ggacagagag atgatcgagg aacggctgaa aacctatgcc   1620
cacctgttcg acgacaaagt gatgaagcag ctgaagcggc ggagatacac cggctggggc   1680
aggctgagcc ggaagctgat caacggcatc cgggacaagc agtccggcaa gacaatcctg   1740
gatttcctga agtccgacgg cttcgccaac agaaacttca tgcagctgat ccacgacgac   1800
agcctgacct ttaaagagga catccagaaa gcccaggtgt ccggccaggg cgatagcctg   1860
cacgagcaca ttgccaatct ggccggcagc cccgccatta agaagggcat cctgcagaca   1920
gtgaaggtgg tggacgagct cgtgaaagtg atgggccggc acaagcccga acatcgtg    1980 atcgaaatgg ccagagagaa ccagaccacc cagaagggac agaagaacag ccgcgagaga   2040
atgaagcgga tcgaagaggg catcaaagag ctgggcagcc agatcctgaa agaacacccc   2100
gtggaaaaca cccagctgca gaacgagaag ctgtacctgt actacctgca gaatgggcgg   2160
gatatgtacg tggaccagga actggacatc aaccggctgt ccgactacga tgtggaccat   2220
atcgtgcctc agagctttct gaaggacgac tccatcgaca caaggtgct gaccagaagc    2280 gacaagaacc ggggcaagag cgacaacgtg ccctccgaag aggtcgtgaa gaagatgaag   2340
aactactggc ggcagctgct gaacgccaag ctgattaccc agagaaagtt cgacaatctg   2400
accaaggccg agagaggcgg cctgagcgaa ctggataagg ccggcttcat caagagacag   2460
ctggtggaaa cccggcagat cacaaagcac gtggcacaga tcctggactc ccggatgaac   2520
actaagtacg acgagaatga caagctgatc cgggaagtga aagtgatcac cctgaagtcc   2580
aagctggtgt ccgatttccg gaaggatttc cagttttaca agtgcgcga gatcaacaac    2640 taccaccacg cccacgacgc ctacctgaac gccgtcgtgg aaccgccct gatcaaaaag     2700 taccctaagc tggaaagcga gttcgtgtac ggcgactaca aggtgtacga cgtgcggaag   2760
atgatcgcca agagcgagca ggaaatcggc aaggctaccg ccaagtactt cttctacagc   2820
aacatcatga acttttttcaa gaccgagatt accctggcca acggcgagat ccggaagcgg   2880
cctctgatcg agacaaacgg cgaaaccggg gagatcgtgt gggataaggg ccgggatttt   2940
gccaccgtgc ggaaagtgct gagcatgccc caagtgaata tcgtgaaaaa gaccgaggtg   3000
cagacaggcg gcttcagcaa agagtctatc ctgcccaaga ggaacagcga taagctgatc   3060
gccagaaaga aggactggga ccctaagaag tacggcggct tcgacagccc caccgtggcc   3120
tattctgtgc tggtggtggc caaagtggaa aagggcaagt ccaagaaact gaagagtgtg   3180
aaagagctgc tggggatcac catcatggaa agaagcagct tcgagaagaa tcccatcgac   3240
tttctggaag ccaagggcta caaagaagtg aaaaaggacc tgatcatcaa gctgcctaag   3300
tactccctgt tcgagctgga aaacggccgg aagagaatgc tggcctctgc cggcgaactg   3360
cagaagggaa acgaactggc cctgccctcc aaatatgtga acttcctgta cctgccagc    3420 cactatgaga agctgaaggg ctcccccgag gataatgagc agaaacagct gtttgtggaa   3480
cagcacaagc actacctgga cgagatcatc gagcagatca gcgagttctc caagagagtg   3540
atcctggccg acgctaatct ggacaaagtg ctgtccgcct acaacaagca ccgggataag   3600
cccatcagag agcaggccga gaatatcatc cacctgttta ccctgaccaa tctgggagcc   3660
cctgccgcct tcaagtactt tgacaccacc atcgaccgga gaggtacac cagcaccaaa    3720 gaggtgctgg acgccaccct gatccaccag agcatcaccg gcctgtacga gacacggatc   3780
gacctgtctc agctgggagg cgacaaaagg ccggcggcca cgaaaaaggc cggccaggca   3840
aaaaagaaaa agtaa                                                    3855
```

<210> SEQ ID NO 68
<211> LENGTH: 3912
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

| | | | | | |
|---|---|---|---|---|---|
| atggccccaa | agaagaagcg | gaaggtcggt | atccacggag | tcccagcagc | cgacaagaag | 60 |
| tacagcatcg | gcctggacat | cggcaccaac | tctgtgggct | gggccgtgat | caccgacgag | 120 |
| tacaaggtgc | ccagcaagaa | attcaaggtg | ctgggcaaca | ccgaccggca | cagcatcaag | 180 |
| aagaacctga | tcggagccct | gctgttcgac | agcggcgaaa | cagccgaggc | cacccggctg | 240 |
| aagagaaccg | ccagaagaag | atacaccaga | cggaagaacc | ggatctgcta | tctgcaagag | 300 |
| atcttcagca | acgagatggc | caaggtggac | gacagcttct | tccacagact | ggaagagtcc | 360 |
| ttcctggtgg | aagaggataa | gaagcacgag | cggcacccca | tcttcggcaa | catcgtggac | 420 |
| gaggtggcct | accacgagaa | gtaccccacc | atctaccacc | tgagaaagaa | actggtggac | 480 |
| agcaccgaca | aggccgacct | gcggctgatc | tatctggccc | tggcccacat | gatcaagttc | 540 |
| cggggccact | tcctgatcga | gggcgacctg | aatccagacaacc | tctctatg | 600 |
| aaagaagccg | ctgctaaagc | cctggaggct | gaagccgctg | ctaaagaagc | cgctgctaaa | 660 |
| gaagccgctg | ctaaagctgt | gaacaccgag | atcaccaagg | ccccctgag | cgcctctatg | 720 |
| atcaagagat | acgacgagca | ccaccaggac | ctgaccctgc | tgaaagctct | cgtgcggcag | 780 |
| cagctgcctg | agaagtacaa | agagattttc | ttcgaccaga | gcaagaacgg | ctacgccggc | 840 |
| tacattgacg | gcggagccag | ccaggaagag | ttctacaagt | tcatcaagcc | catcctggaa | 900 |
| aagatggacg | gcaccgagga | actgctcgtg | aagctgaaca | gagaggacct | gctgcggaag | 960 |
| cagcggacct | tcgacaacgg | cagcatcccc | caccagatcc | acctgggaga | gctgcacgcc | 1020 |
| attctgcggc | ggcaggaaga | tttttaccca | ttcctgaagg | acaaccggga | aaagatcgag | 1080 |
| aagatcctga | ccttccgcat | ccctactac | gtgggccctc | tggccagggg | aaacagcaga | 1140 |
| ttcgcctgga | tgaccagaaa | gagcgaggaa | accatcaccc | cctggaactt | cgaggaagtg | 1200 |
| gtggacaagg | gcgcttccgc | ccagagcttc | atcgagcgga | tgaccaactt | cgataagaac | 1260 |
| ctgcccaacg | agaaggtgct | gcccaagcac | agcctgctgt | acgagtactt | caccgtgtat | 1320 |
| aacgagctga | ccaaagtgaa | atacgtgacc | gagggaatga | gaaagcccgc | cttcctgagc | 1380 |
| ggcgagcaga | aaaaggccat | cgtggacctg | ctgttcaaga | ccaaccggaa | agtgaccgtg | 1440 |
| aagcagctga | agaggactac | ttcaagaaa | atcgagtgct | tcgactccgt | ggaaatctcc | 1500 |
| ggcgtggaag | atcggttcaa | cgcctccctg | ggcacatacc | acgatctgct | gaaaattatc | 1560 |
| aaggacaagg | acttcctgga | caatgaggaa | aacgaggaca | ttctggaaga | tatcgtgctg | 1620 |
| accctgacac | tgtttgagga | cagagagatg | atcgaggaac | ggctgaaaac | ctatgcccac | 1680 |
| ctgttcgacg | acaaagtgat | gaagcagctg | aagcggcgga | gataccggg | ctggggcagg | 1740 |
| ctgagccgga | agctgatcaa | cggcatccgg | gacaagcagt | ccggcaagac | aatcctggat | 1800 |
| ttcctgaagt | ccgacggctt | cgccaacaga | aacttcatgc | agctgatcca | cgacgacagc | 1860 |
| ctgacctta | aagaggacat | ccagaaagcc | caggtgtccg | gccagggcga | tagcctgcac | 1920 |
| gagcacattg | ccaatctggc | cggcagcccc | gccattaaga | agggcatcct | gcagacagtg | 1980 |
| aaggtggtgg | acgagctcgt | gaaagtgatg | ggccggcaca | agcccgagaa | catcgtgatc | 2040 |

```
gaaatggcca gagagaacca gaccacccag aagggacaga agaacagccg cgagagaatg    2100
aagcggatcg aagagggcat caaagagctg ggcagccaga tcctgaaaga acaccccgtg    2160
gaaaacaccc agctgcagaa cgagaagctg tacctgtact acctgcagaa tgggcgggat    2220
atgtacgtgg accaggaact ggacatcaac cggctgtccg actacgatgt ggaccatatc    2280
gtgcctcaga gctttctgaa ggacgactcc atcgacaaca aggtgctgac cagaagcgac    2340
aagaaccggg gcaagagcga caacgtgccc tccgaagagg tcgtgaagaa gatgaagaac    2400
tactggcggc agctgctgaa cgccaagctg attacccaga gaaagttcga caatctgacc    2460
aaggccgaga gaggcggcct gagcgaactg gataaggccg gcttcatcaa gagacagctg    2520
gtggaaaccc ggcagatcac aaagcacgtg gcacagatcc tggactcccg gatgaacact    2580
aagtacgacg agaatgacaa gctgatccgg gaagtgaaag tgatcaccct gaagtccaag    2640
ctggtgtccg atttccggaa ggatttccag ttttacaaag tgcgcgagat caacaactac    2700
caccacgccc acgacgccta cctgaacgcc gtcgtgggaa ccgccctgat caaaaagtac    2760
cctaagctgg aaagcgagtt cgtgtacggc gactacaagg tgtacgacgt gcggaagatg    2820
atcgccaaga gcgagcagga aatcggcaag gctaccgcca agtacttctt ctacagcaac    2880
atcatgaact tttttcaagac cgagattacc ctggccaacg gcgagatccg gaagcggcct    2940
ctgatcgaga caaacggcga aaccggggag atcgtgtggg ataagggccg ggattttgcc    3000
accgtgcgga aagtgctgag catgccccaa gtgaatatcg tgaaaaagac cgaggtgcag    3060
acaggcggct tcagcaaaga gtctatcctg cccaagagga cagcgataa gctgatcgcc     3120 agaaagaagg actgggaccc taagaagtac ggcggcttcg acagccccac cgtggcctat    3180
tctgtgctgg tggtggccaa agtggaaaag ggcaagtcca agaaactgaa gagtgtgaaa    3240
gagctgctgg ggatcaccat catggaaaga agcagcttcg agaagaatcc catcgacttt    3300
ctggaagcca agggctacaa agaagtgaaa aaggacctga tcatcaagct gcctaagtac    3360
tccctgttcg agctggaaaa cggccggaag agaatgctgg cctctgccgg cgaactgcag    3420
aagggaaacg aactggccct gccctccaaa tatgtgaact tcctgtacct ggccagccac    3480
tatgagaagc tgaagggctc ccccgaggat aatgagcaga acagctgttt tgtgaacag    3540 cacaagcact acctggacga gatcatcgag cagatcagcg agttctccaa gagagtgatc    3600
ctggccgacg ctaatctgga caaagtgctg tccgcctaca acaagcaccg ggataagccc    3660
atcagagagc aggccgagaa tatcatccac ctgtttaccc tgaccaatct gggagcccct    3720
gccgccttca gtactttga caccaccatc gaccggaaga ggtacaccag caccaaagag    3780
gtgctggacg ccaccctgat ccaccagagc atcaccggcc tgtacgagac acggatcgac    3840
ctgtctcagc tgggaggcga caaaaggccg gcggccacga aaaaggccgg ccaggcaaaa    3900
aagaaaaagt aa                                                       3912
```

<210> SEQ ID NO 69
<211> LENGTH: 3969
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
atggccccaa agaagaagcg gaaggtcggt atccacggag tcccagcagc cgacaagaag    60
```

-continued

```
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacctg gctgaagctg ctgctaaaga agctgctgct    600
aaagaagctg ctgctaaagc cctggaggct gaagctgctg ctaaagaagc tgctgctaaa    660
gaagctgctg ctaaagccct ggaggctgaa gctgctgcta agaagctgc tgctaaagaa    720
gctgctgcta agctgtgaa caccgagatc accaaggccc ccctgagcgc ctctatgatc    780
aagagatacg acgagcacca ccaggacctg accctgctga agctctcgt gcggcagcag    840
ctgcctgaga agtacaaaga gattttcttc gaccagagca gaacggcta cgccggctac    900
attgacggcg gagccagcca ggaagagttc tacaagttca tcaagcccat cctggaaaag    960
atggacggca ccgaggaact gctcgtgaag ctgaacagag aggacctgct gcggaagcag   1020
cggaccttcg acaacggcag catccccac cagatccacc tgggagagct gcacgccatt   1080
ctgcggcggc aggaagattt ttacccattc ctgaaggaca ccgggaaaa gatcgagaag   1140
atcctgacct tccgcatccc ctactacgtg ggccctctgg ccaggggaaa cagcagattc   1200
gcctggatga ccagaaagag cgaggaaacc atcaccccct ggaacttcga ggaagtggtg   1260
gacaagggcg cttccgccca gagcttcatc gagcggatga ccaacttcga taagaacctg   1320
cccaacgaga aggtgctgcc caagcacagc ctgctgtacg agtacttcac cgtgtataac   1380
gagctgacca aagtgaaata cgtgaccgag ggaatgagaa agcccgcctt cctgagcggc   1440
gagcagaaaa aggccatcgt ggacctgctg ttcaagacca ccggaaagt gaccgtgaag   1500
cagctgaaag gactactt caagaaaatc gagtgcttcg actccgtgga atctccggc   1560
gtggaagatc ggttcaacgc ctccctgggc acataccacg atctgctgaa aattatcaag   1620
gacaaggact cctggacaa tgaggaaaac gaggacattc tggaagatat cgtgctgacc   1680
ctgacactgt ttgaggacag agagatgatc gaggaacggc tgaaaaccta tgcccacctg   1740
ttcgacgaca aagtgatgaa gcagctgaag cggcggagat acaccggctg ggcaggctg   1800
agccggaagc tgatcaacgg catccgggac aagcagtccg gcaagacaat cctggatttc   1860
ctgaagtccg acggcttcgc caacagaaac ttcatgcagc tgatccacga cgacagcctg   1920
acctttaaag aggacatcca gaaagcccag gtgtccggcc agggcgatag cctgcacgag   1980
cacattgcca atctggccgg cagccccgcc attaagaagg gcatcctgca gacagtgaag   2040
gtggtggaca gctcgtgaa agtgatgggc cggcacaagc ccgagaacat cgtgatcgaa   2100
atggccagag agaaccagac cacccagaag ggacagaaga cagccgcga gaatgaag   2160
cggatcgaag agggcatcaa agagctgggc agccagatcc tgaaagaaca ccccgtggaa   2220
aacacccagc tgcagaacga gaagctgtac ctgtactacc tgcagaatgg cgggatatg   2280
tacgtggacc aggaactgga catcaaccgg ctgtccgact acgatgtgga ccatatcgtg   2340
cctcagagct ttctgaagga cgactccatc gacaacaagg tgctgaccag aagcgacaag   2400
aaccggggca agagcgacaa cgtgccctcc gaagaggtcg tgaagaagat gaagaactac   2460
```

```
tggcggcagc tgctgaacgc caagctgatt acccagagaa agttcgacaa tctgaccaag    2520
gccgagagag gcggcctgag cgaactggat aaggccggct tcatcaagag acagctggtg    2580
gaaacccggc agatcacaaa gcacgtggca cagatcctgg actcccggat gaacactaag    2640
tacgacgaga atgacaagct gatccgggaa gtgaaagtga tcaccctgaa gtccaagctg    2700
gtgtccgatt tccggaagga tttccagttt tacaaagtgc gcgagatcaa caactaccac    2760
cacgcccacg acgcctacct gaacgccgtc gtgggaaccg ccctgatcaa aaagtaccct    2820
aagctggaaa gcgagttcgt gtacggcgac tacaaggtgt acgacgtgcg gaagatgatc    2880
gccaagagcg agcaggaaat cggcaaggct accgccaagt acttcttcta cagcaacatc    2940
atgaactttt tcaagaccga gattaccctg gccaacggcg agatccggaa gcggcctctg    3000
atcgagacaa acggcgaaac cggggagatc gtgtgggata agggccggga ttttgccacc    3060
gtgcggaaag tgctgagcat gccccaagtg aatatcgtga aaaagaccga ggtgcagaca    3120
ggcggcttca gcaaagagtc tatcctgccc aagaggaaca gcgataagct gatcgccaga    3180
aagaaggact gggaccctaa gaagtacggc ggcttcgaca gccccaccgt ggcctattct    3240
gtgctggtgg tggccaaagt ggaaaagggc aagtccaaga aactgaagag tgtgaaagag    3300
ctgctgggga tcaccatcat ggaaagaagc agcttcgaga agaatcccat cgactttctg    3360
gaagccaagg gctacaaaga agtgaaaaag gacctgatca tcaagctgcc taagtactcc    3420
ctgttcgagc tggaaaacgg ccggaagaga atgctggcct ctgccggcga actgcagaag    3480
ggaaacgaac tggcccctgc ctccaaatat gtgaacttcc tgtacctggc cagccactat    3540
gagaagctga aggctccccc cgaggataat gagcagaaac agctgtttgt ggaacagcac    3600
aagcactacc tggacgagat catcgagcag atcagcgagt tctccaagag agtgatcctg    3660
gccgacgcta atctggacaa agtgctgtcc gcctacaaca agcaccggga taagcccatc    3720
agagagcagg ccgagaatat catccacctg tttaccctga ccaatctggg agcccctgcc    3780
gccttcaagt actttgacac caccatcgac cggaagaggt acaccagcac caaagaggtg    3840
ctggacgcca ccctgatcca ccagagcatc accggcctgt acgagacacg gatcgacctg    3900
tctcagctgg gaggcgacaa aaggccggcg gccacgaaaa aggccggcca ggcaaaaaag    3960
aaaaagtaa                                                           3969
```

<210> SEQ ID NO 70
<211> LENGTH: 4026
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70

```
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcgagcccct gctgttcgac agcggcgaaa cagccgaggc cacccggctg     240
aagagaaccg ccagaagaag atacaccaga cggaagaacc ggatctgcta tctgcaagag     300
atcttcagca acgagatggc caaggtggac gacagcttct tccacagact ggaagagtcc     360
ttcctggtgg aagaggataa gaagcacgag cggcaccccg tcttcggcaa catcgtggac     420
```

```
gaggtggcct accacgagaa gtaccccacc atctaccacc tgagaaagaa actggtggac      480
agcaccgaca aggccgacct gcggctgatc tatctggccc tggcccacat gatcaagttc      540
cggggccact tcctgatcga gggcgacctg gctgaagctg ctgctaaaga agctgctgct      600
aaagaagctg ctgctaaagc cctggaggct gaagctgctg ctaaagaagc tgctgctaaa      660
gaagctgctg ctaaagccct ggaggctgaa gctgctgcta agaagctgc tgctaaagaa      720 gctgctgcta agccctgga ggctgaagct gctgctaaag aagctgctgc taaagaagct      780
gctgctaaag ctgtgaacac cgagatcacc aaggcccccc tgagcgcctc tatgatcaag      840
agatacgacg agcaccacca ggacctgacc ctgctgaaag ctctcgtgcg gcagcagctg      900
cctgagaagt acaaagagat tttcttcgac cagagcaaga acggctacgc cggctacatt      960
gacggcggag ccagccagga agagttctac aagttcatca agcccatcct ggaaaagatg     1020
gacggcaccg aggaactgct cgtgaagctg aacagagagg acctgctgcg gaagcagcgg     1080
accttcgaca acggcagcat ccccaccag atccacctgg agagctgca cgccattctg     1140 cggcggcagg aagattttta cccattcctg aaggacaacc gggaaaagat cgagaagatc     1200
ctgaccttcc gcatcccta ctacgtgggc cctctggcca ggggaaacag cagattcgcc     1260
tggatgacca gaaagagcga ggaaaccatc accccctgga acttcgagga agtggtggac     1320
aagggcgctt ccgcccagag cttcatcgag cggatgacca acttcgataa gaacctgccc     1380
aacgagaagg tgctgcccaa gcacagcctg ctgtacgagt acttcaccgt gtataacgag     1440
ctgaccaaag tgaaatacgt gaccgaggga atgagaaagc ccgccttcct gagcggcgag     1500
cagaaaaagg ccatcgtgga cctgctgttc aagaccaacc ggaaagtgac cgtgaagcag     1560
ctgaaagagg actacttcaa gaaaatcgag tgcttcgact ccgtggaaat ctccggcgtg     1620
gaagatcggt tcaacgcctc cctgggcaca taccacgatc tgctgaaaat tatcaaggac     1680
aaggacttcc tggacaatga ggaaaacgag gacattctgg aagatatcgt gctgaccctg     1740
acactgtttg aggacagaga gatgatcgag aacggctga aaacctatgc ccacctgttc     1800
gacgacaaag tgatgaagca gctgaagcgg cggagataca ccggctgggg caggctgagc     1860
cggaagctga tcaacggcat ccgggacaag cagtccggca agacaatcct ggatttcctg     1920
aagtccgacg gcttcgccaa cagaaacttc atgcagctga tccacgacga cagcctgacc     1980 tttaagagg acatccagaa agcccaggtg tccggccagg gcgatagcct gcacgagcac     2040
attgccaatc tggccggcag ccccgccatt aagaagggca tcctgcagac agtgaaggtg     2100
gtggacgagc tcgtgaaagt gatgggccgg cacaagcccg agaacatcgt gatcgaaatg     2160
gccagagaga accagaccac ccagaaggga cagaagaaca gccgcgagag aatgaagcgg     2220
atcgaagagg gcatcaaaga gctgggcagc cagatcctga aagaacaccc cgtggaaaac     2280
acccagctgc agaacgagaa gctgtacctg tactacctgc agaatgggcg ggatatgtac     2340
gtggaccagg aactggacat caaccggctg tccgactacg atgtggacca tatcgtgcct     2400
cagagctttc tgaaggacga ctccatcgac aacaaggtgc tgaccagaag cgacaagaac     2460
cggggcaaga gcgacaacgt gccctccgaa gaggtcgtga agaagatgaa gaactactgg     2520
cggcagctgc tgaacgccaa gctgattacc cagagaaagt tcgacaatct gaccaaggcc     2580
gagagaggcg gcctgagcga actggataag gccggcttca tcaagagaca gctggtggaa     2640
acccggcaga tcacaaagca cgtggcacag atcctggact cccggatgaa cactaagtac     2700
gacgagaatg acaagctgat ccgggaagtg aaagtgatca ccctgaagtc caagctggtg     2760
tccgatttcc ggaaggattt ccagttttac aaagtgcgcg agatcaacaa ctaccaccac     2820
```

-continued

```
gcccacgacg cctacctgaa cgccgtcgtg ggaaccgccc tgatcaaaaa gtaccctaag      2880
ctggaaagcg agttcgtgta cggcgactac aaggtgtacg acgtgcggaa gatgatcgcc      2940
aagagcgagc aggaaatcgg caaggctacc gccaagtact tcttctacag caacatcatg      3000 aacttttttca agaccgagat taccctggcc aacggcgaga tccggaagcg gcctctgatc      3060
gagacaaacg gcgaaccgg ggagatcgtg tgggataagg ccgggattt tgccaccgtg        3120 cggaaagtgc tgagcatgcc ccaagtgaat atcgtgaaaa agaccgaggt gcagacaggc      3180
ggcttcagca aagagtctat cctgcccaag aggaacagcg ataagctgat cgccagaaag      3240
aaggactggg accctaagaa gtacggcggc ttcgacagcc ccaccgtggc ctattctgtg      3300
ctggtggtgg ccaaagtgga aaagggcaag tccaagaaac tgaagagtgt gaaagagctg      3360
ctggggatca ccatcatgga aaagcagc ttcgagaaga tcccatcga ctttctggaa         3420 gccaagggct acaagaagt gaaaaaggac ctgatcatca agctgcctaa gtactccctg       3480
ttcgagctgg aaaacggccg gaagagaatg ctggcctctg ccggcgaact gcagaaggga      3540
aacgaactgg ccctgccctc caaatatgtg aacttcctgt acctggccag ccactatgag      3600
aagctgaagg ctccccccga ggataatgag cagaaacagc tgtttgtgga acagcacaag      3660
cactacctgg acgagatcat cgagcagatc agcgagttct ccaagagagt gatcctggcc      3720
gacgctaatc tggacaaagt gctgtccgcc tacaacaagc accgggataa gcccatcaga      3780
gagcaggccg agaatatcat ccacctgttt accctgacca atctgggagc cctgccgcc      3840 ttcaagtact ttgacaccac catcgaccgg aagaggtaca ccagcaccaa agaggtgctg      3900
gacgccaccc tgatccacca gagcatcacc ggcctgtacg agacacggat cgacctgtct     3960
cagctgggag gcgacaaaag gccggcggcc acgaaaaagg ccggccaggc aaaaaagaaa     4020
aagtaa                                                                 4026
```

<210> SEQ ID NO 71
<211> LENGTH: 4203
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 71

```
atggccccaa agaagaagcg gaaggtcggt atccacggag tcccagcagc cgacaagaag       60
tacagcatcg gcctggacat cggcaccaac gccgtgggct gggccgtgat caccgacgag      120
tacaaggtgc ccagcaagaa attcaaggtg ctgggcaaca ccgaccggca cagcatcaag      180
aagaacctga tcggagccct gctgttcgac agcggcgaaa cagccgaggc cacccggctg      240
aagagaaccg ccagaagaag atacaccaga cggaagaacc ggatctgcta tctgcaagag      300
atcttcagca acgagatggc caaggtggac gacagcttct tccacagact ggaagagtcc      360
ttcctggtgg aagaggataa gaagcacgag cggcacccca tcttcggcaa catcgtggac      420
gaggtggcct accacgagaa gtaccccacc atctaccacc tgagaaagaa actggtggac      480
agcaccgaca aggccgacct gcggctgatc tatctggccc tggcccacat gatcaagttc      540
cggggccact tcctgatcga gggcgacctg aaccccgaca cagcgacgt ggacaagctg       600 ttcatccagc tggtgcagac ctacaaccag ctgttcgagg aaaacccat caacgccagc      660 ggcgtggacg ccaaggccat cctgtctgcc agactgagca gagcagacg gctggaaaat    720
```

-continued

```
ctgatcgccc agctgcccgg cgagaagaag aatggcctgt tcggaaacct gattgccctg      780
agcctgggcc tgaccccccaa cttcaagagc aacttcgacc tggccgagga tgccaaactg     840
cagctgagca aggacaccta cgacgacgac ctggacaacc tgctggccca gatcggcgac     900
cagtacgccg acctgtttct ggccgccaag aacctgtccg acgccatcct gctgagcgac     960
atcctgagag tgaacaccga gatcaccaag gccccctga gcgcctctat gatcaagaga    1020
tacgacgagc accaccagga cctgaccctg ctgaaagctc tcgtgcggca gcagctgcct    1080
gagaagtaca aagagatttt cttcgaccag agcaagaacg gctacgccgg ctacattgac    1140
ggcggagcca gccaggaaga gttctacaag ttcatcaagc ccatcctgga aaagatggac    1200
ggcaccgagg aactgctcgt gaagctgaac agagaggacc tgctgcggaa gcagcggacc    1260
ttcgacaacg gcagcatccc caccagatc cacctgggag agctgcacgc cattctgcgg    1320
cggcaggaag attttttaccc attcctgaag gacaaccggg aaaagatcga agatcctg    1380 accttccgca tccctactaa cgtgggccct ctggccaggg aaacagcag attcgcctgg    1440 atgaccagaa agagcgagga aaccatcacc ccctggaact tcgaggaagt ggtggacaag    1500
ggcgcttccg cccagagctt catcgagcgg atgaccaact tcgataagaa cctgcccaac    1560
gagaaggtgc tgcccaagca cagcctgctg tacgagtact tcaccgtgta taacgagctg    1620
accaaagtga aatacgtgac cgagggaatg agaaagcccg ccttcctgag cggcgagcag    1680
aaaaaggcca tcgtggacct gctgttcaag accaaccgga agtgaccgt gaagcagctg    1740 aaagaggact acttcaagaa aatcgagtgc ttcgactccg tggaaatctc cggcgtggaa    1800
gatcggttca acgcctccct gggcacatac cacgatctgc tgaaaattat caaggacaag    1860
gacttcctgg acaatgagga aaacgaggac attctggaag atatcgtgct gaccctgaca    1920
ctgtttgagg acagagagat gatcgaggaa cggctgaaaa cctatgccca cctgttcgac    1980
gacaaagtga tgaagcagct gaagcggcgg agatacaccg gctggggcag gctgagccgg    2040
aagctgatca acggcatccg ggacaagcag tccggcaaga caatcctgga tttcctgaag    2100
tccgacggct tcgccaacag aaacttcatg cagctgatcc acgacgacag cctgaccttt    2160
aaagaggaca tccagaaagc ccaggtgtcc ggccagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga acatcgtgat cgaaatggcc    2340
agagagaacc agaccaccca aagggacag aagaacagcc gcgagagaat gaagcggatc    2400
gaagagggca tcaaagagct gggcagccag atcctgaaag aacaccccgt ggaaaacacc    2460
cagctgcaga acgagaagct gtacctgtac tacctgcaga atgggcggga tatgtacgtg    2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca gagacagct ggtggaaacc    2820 cggcagatca caaagcacgt ggcacagatc ctggactccc ggatgaacac taagtacgac    2880
gagaatgaca agctgatccg ggaagtgaaa gtgatcaccc tgaagtccaa gctggtgtcc    2940
gatttccgga aggatttcca gttttacaaa gtgcgcgaga tcaacaacta ccaccacgcc    3000
cacgacgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
```

| | | | | |
|---|---|---|---|---|
| agcgagcagg | aaatcggcaa | ggctaccgcc | aagtacttct | tctacagcaa catcatgaac | 3180 |
| tttttcaaga | ccgagattac | cctggccaac | ggcgagatcc | ggaagcggcc tctgatcgag | 3240 |
| acaaacggcg | aaaccgggga | gatcgtgtgg | gataagggcc | gggattttgc caccgtgcgg | 3300 |
| aaagtgctga | gcatgcccca | agtgaatatc | gtgaaaaaga | ccgaggtgca gacaggcggc | 3360 |
| ttcagcaaag | agtctatcct | gcccaagagg | aacagcgata | agctgatcgc cagaaagaag | 3420 |
| gactgggacc | ctaagaagta | cggcggcttc | gacagcccca | ccgtggccta ttctgtgctg | 3480 |
| gtggtggcca | agtggaaaaa | gggcaagtcc | aagaaactga | agagtgtgaa agagctgctg | 3540 |
| gggatcacca | tcatggaaag | aagcagcttc | gagaagaatc | ccatcgactt tctggaagcc | 3600 |
| aagggctaca | agaagtgaa | aaaggacctg | atcatcaagc | tgcctaagta ctccctgttc | 3660 |
| gagctggaaa | acggccggaa | gagaatgctg | gcctctgccg | gcgaactgca gagggaaac | 3720 |
| gaactggccc | tgccctccaa | atatgtgaac | ttcctgtacc | tggccagcca ctatgagaag | 3780 |
| ctgaagggct | cccccgagga | taatgagcag | aaacagctgt | tgtggaaca gcacaagcac | 3840 |
| tacctggacg | agatcatcga | gcagatcagc | gagttctcca | agagagtgat cctggccgac | 3900 |
| gctaatctgg | acaaagtgct | gtccgcctac | aacaagcacc | gggataagcc catcagagag | 3960 |
| caggccgaga | atatcatcca | cctgtttacc | ctgaccaatc | tgggagcccc tgccgccttc | 4020 |
| aagtactttg | acaccaccat | cgaccggaag | aggtacacca | gcaccaaaga ggtgctggac | 4080 |
| gccaccctga | tccaccagag | catcaccggc | ctgtacgaga | cacggatcga cctgtctcag | 4140 |
| ctggaggcg | acaaaaggcc | ggcggccacg | aaaaaggccg | gccaggcaaa aaagaaaaag | 4200 |
| taa | | | | | 4203 |

<210> SEQ ID NO 72
<211> LENGTH: 4203
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72

| | | | | |
|---|---|---|---|---|
| atggccccaa | agaagaagcg | gaaggtcggt | atccacggag | tcccagcagc cgacaagaag | 60 |
| tacagcatcg | gcctggacat | cggcaccaac | tctgtgggct | gggccgtgat caccgacgag | 120 |
| tacaaggtgc | ccagcaagaa | attcaaggtg | ctgggcaaca | ccgaccggca cagcatcaag | 180 |
| aagaacctga | tcggagccct | gctgttcgac | agcggcgaaa | cagccgaggc cacccggctg | 240 |
| aagagaaccg | ccagaagaag | atacaccaga | cggaagaacc | ggatctgcta tctgcaagag | 300 |
| atcttcagca | acgagatggc | caaggtggac | gacagcttct | tccacagact ggaagagtcc | 360 |
| ttcctggtgg | aagaggataa | gaagcacgag | cggcacccca | tcttcggcaa catcgtggac | 420 |
| gaggtggcct | accacgagaa | gtaccccacc | atctaccacc | tgagaaagaa actggtggac | 480 |
| agcaccgaca | aggccgacct | gcggctgatc | tatctggccc | tggcccacat gatcaagttc | 540 |
| cggggccact | tcctgatcga | gggcgacctg | aaccccgaca | acagcgacgt ggacaagctg | 600 |
| ttcatccagc | tggtgcagac | ctacaaccag | ctgttcgagg | aaaacccat caacgccagc | 660 |
| ggcgtggacg | ccaaggccat | cctgtctgcc | agactgagca | agagcagacg gctggaaaat | 720 |
| ctgatcgccc | agctgcccgg | cgagaagaag | aatggcctgt | tcggaaacct gattgccctg | 780 |
| agcctgggcc | tgacccccaa | cttcaagagc | aacttcgacc | tggccgagga tgccaaactg | 840 |

```
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gccccctga gcgcctctat gatcaagaga   1020
tacgacgagc accaccagga cctgaccctg ctgaaagctc tcgtgcggca gcagctgcct   1080
gagaagtaca agagattttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag attttttaccc attcctgaag gacaaccggg aaaagatcga agatcctg    1380 accttccgca tccctacta cgtgggccct ctggccaggg aaacagcag attcgcctgg   1440 atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga agtgaccgt gaagcagctg   1740 aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgccatggcc   2340
agagagaacc agaccaccca aagggacag aagaacagcc gcgagagaat gaagcggatc   2400
gaagagggca tcaaagagct gggcagccag atcctgaaag aacacccgt ggaaaacacc   2460 cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca gagacagct ggtgaaaacc   2820 cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180 ttttttcaaga ccgagattac cctggccaac ggcgagatcc ggaagcggcc tctgatcgag   3240
```

```
acaaacggcg aaaccgggga gatcgtgtgg gataagggcc gggattttgc caccgtgcgg    3300
aaagtgctga gcatgcccca agtgaatatc gtgaaaaaga ccgaggtgca gacaggcggc    3360
ttcagcaaag agtctatcct gcccaagagg aacagcgata agctgatcgc cagaaagaag    3420
gactgggacc ctaagaagta cggcggcttc gacagcccca ccgtggccta ttctgtgctg    3480
gtggtggcca agtggaaaa gggcaagtcc aagaaactga agagtgtgaa agagctgctg    3540
gggatcacca tcatggaaag aagcagcttc gagaagaatc ccatcgactt tctggaagcc    3600
aagggctaca agaagtgaa aaaggacctg atcatcaagc tgcctaagta ctccctgttc    3660
gagctggaaa acggccggaa gagaatgctg gcctctgccg cgaactgca aagggaaac    3720 gaactggccc tgccctccaa atatgtgaac ttcctgtacc tggccagcca ctatgagaag    3780
ctgaagggct cccccgagga taatgagcag aaacagctgt tgtggaaca gcacaagcac    3840 tacctggacg agatcatcga gcagatcagc gagttctcca agagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140 ctggaggcg acaaaggcc ggcggccacg aaaaaggccg ccaggcaaa aagaaaag    4200 taa                                                                 4203

<210> SEQ ID NO 73
<211> LENGTH: 4203
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcggagccct gctgttcgac agcggcgaaa cagccgaggc cacccggctg     240
aagagaaccg ccagaagaag atacaccaga cggaagaacc ggatctgcta tctgcaagag     300
atcttcagca cgagatggc caaggtggac gacagcttct ccacagact ggaagagtcc     360 ttcctggtgg aagaggataa gaagcacgag cggcacccca tcttcggcaa catcgtggac     420
gaggtggcct accacgagaa gtaccccacc atctaccacc tgagaaagaa actggtggac     480
agcaccgaca aggccgacct gcggctgatc tatctggccc tggcccacat gatcaagttc     540
cggggccact tcctgatcga gggcgacctg aaccccgaca cagcgacgt ggacaagctg     600 ttcatccagc tggtgcagac ctacaaccag ctgttcgagg aaaacccat caacgccagc     660 ggcgtggacg ccaaggccat cctgtctgcc agactgagca gagcagacg gctggaaaat     720 ctgatcgccc agctgcccgg cgagaagaag aatggcctgt tcggaaacct gattgccctg     780
agcctgggcc tgacccccaa cttcaagagc aacttcgacc tggccgagga tgccaaactg     840
cagctgagca aggacaccta cgacgacgac ctggacaacc tgctggccca gatcggcgac     900
cagtacgccg acctgtttct ggccgccaag aacctgtccg acgccatcct gctgagcgac     960
```

```
atcctgagag tgaacaccga gatcaccaag gcccccctga gcgcctctat gatcaagaga    1020
tacgacgagc accaccagga cctgaccctg ctgaaagctc tcgtgcggca gcagctgcct    1080
gagaagtaca aagagatttt cttcgaccag agcaagaacg gctacgccgg ctacattgac    1140
ggcggagcca gccaggaaga gttctacaag ttcatcaagc ccatcctgga aaagatggac    1200
ggcaccgagg aactgctcgt gaagctgaac agagaggacc tgctgcggaa gcagcggacc    1260
ttcgacaacg gcagcatccc ccaccagatc cacctgggag agctgcacgc cattctgcgg    1320
cggcaggaag attttacccc attcctgaag gacaaccggg aaaagatcga agatcctg     1380 accttccgca tcccctacta cgtgggccct ctggccaggg aaacagcag attcgcctgg     1440 atgaccagaa agagcgagga accatcacc ccctggaact tcgaggaagt ggtggacaag    1500
ggcgcttccg cccagagctt catcgagcgg atgaccaact tcgataagaa cctgcccaac    1560
gagaaggtgc tgcccaagca cagcctgctg tacgagtact tcaccgtgta taacgagctg    1620
accaaagtga aatacgtgac cgagggaatg agaaagcccg ccttcctgag cggcgagcag    1680
aaaaaggcca tcgtggacct gctgttcaag accaaccgga agtgaccgt gaagcagctg    1740 aaagaggact acttcaagaa aatcgagtgc ttcgactccg tggaaatctc cggcgtggaa    1800
gatcggttca cgcctccct gggcacatac cacgatctgc tgaaaattat caaggacaag    1860
gacttcctgg acaatgagga aaacgaggac attctggaag atatcgtgct gaccctgaca    1920
ctgtttgagg acagagagat gatcgaggaa cggctgaaaa cctatgccca cctgttcgac    1980
gacaaagtga tgaagcagct gaagcggcgg agatacaccg gctggggcag gctgagccgg    2040
aagctgatca cggcatccg ggacaagcag tccggcaaga caatcctgga tttcctgaag    2100
tccgacggct tcgccaacag aaacttcatg cagctgatcc acgacgacag cctgaccttt    2160
aaagaggaca tccagaaagc ccaggtgtcc ggccagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga catcgtgat cgaaatggcc    2340 agagagaacc agaccaccca aagggacag aagaacagcc gcgagagaat gaagcggatc    2400
gaagagggca tcaaagagct gggcagccag atcctgaaag aacacccgt ggaaaacacc    2460 cagctgcaga acgagaagct gtacctgtac acctgcaga atgggcggga tatgtacgtg    2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca agagacagct ggtggaaacc    2820
cggcagatca caaagcacgt ggcacagatc ctggactccc ggatgaacac taagtacgac    2880
gagaatgaca gctgatccg ggaagtgaaa gtgatcaccc tgaagtccaa gctggtgtcc    2940
gatttccgga aggatttcca gttttacaaa gtgcgcgaga tcaacaacta cgcccacgcc    3000
cacgacgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180 ttttttcaaga ccgagattac cctggccaac ggcgagatcc ggaagcggcc tctgatcgag    3240
acaaacggcg aaaccgggga gatcgtgtgg gataagggcc gggattttgc caccgtgcgg    3300
aaagtgctga gcatgcccca agtgaatatc gtgaaaaaga ccgaggtgca gacaggcggc    3360
```

```
ttcagcaaag agtctatcct gcccaagagg aacagcgata agctgatcgc cagaaagaag    3420
gactgggacc ctaagaagta cggcggcttc gacagccccg ccgtggccta ttctgtgctg    3480
gtggtggcca agtggaaaa gggcaagtcc aagaaactga agagtgtgaa agagctgctg    3540
gggatcacca tcatggaaag aagcagcttc gagaagaatc ccatcgactt tctggaagcc    3600
aagggctaca agaagtgaa aaaggacctg atcatcaagc tgcctaagta ctccctgttc    3660
gagctggaaa acggccggaa gagaatgctg gcctctgccg cgaactgca agggaaac    3720 gaactggccc tgccctccaa atatgtgaac ttcctgtacc tggccagcca ctatgagaag    3780
ctgaagggct cccccgagga taatgagcag aaacagctgt tgtgaaca gcacaagcac    3840 tacctggacg agatcatcga gcagatcagc gagttctcca agagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140
ctgggaggcg acaaaaggcc ggcggccacg aaaaaggccg ccaggcaaa aagaaaaag    4200 taa                                                                  4203
```

<210> SEQ ID NO 74
<211> LENGTH: 4203
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcggagccct gctgttcgac agcggcgaaa cagccgaggc cacccggctg     240
aagagaaccg ccagaagaag atacaccaga cggaagaacc ggatctgcta tctgcaagag     300
atcttcagca acgagatggc caaggtggac gacagcttct tccacagact ggaagagtcc     360
ttcctggtgg aagaggataa gaagcacgag cggcacccca tcttcggcaa catcgtggac     420
gaggtggcct accacgagaa gtaccccacc atctaccacc tgagaaagaa actggtggac     480
agcaccgaca aggccgacct gcggctgatc tatctggccc tggcccacat gatcaagttc     540
cggggccact tcctgatcga gggcgacctg aaccccgaca cagcgacgt ggacaagctg     600 ttcatccagc tggtgcagac ctacaaccag ctgttcgagg aaaacccat caacgccagc     660 ggcgtggacg ccaaggccat cctgtctgcc agactgagca gagcagacg gctggaaaat     720 ctgatcgccc agctgcccgg cgagaagaag aatggcctgt tcggaaacct gattgccctg     780
agcctgggcc tgaccccaa cttcaagagc aacttcgacc tggccgagga tgccaaactg     840
cagctgagca aggacaccta cgacgacgac ctggacaacc tgctggccca gatcggcgac     900
cagtacgccg acctgttct ggccgccaag aacctgtccg acgccatcct gctgagcgac     960
atcctgagag tgaacaccga gatcaccaag gcccccctga gcgcctctat gatcaagaga    1020
tacgacgagc accaccagga cctgaccctg ctgaaagctc tcgtgcggca gcagctgcct    1080
```

```
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag attttttaccc attcctgaag gacaaccggg aaaagatcga agatcctg    1380
accttccgca tccccctacta cgtgggccct ctggccaggg aaacagcag attcgcctgg    1440
atgaccagaa agagcgagga aaccatcacc ccctggaact tcgaggaagt ggtggacaag   1500
ggcgcttccg cccagagctt catcgagcgg atgaccaact cgataagaa cctgcccaac    1560
gagaaggtgc tgcccaagca cagcctgctg tacgagtact tcaccgtgta taacgagctg   1620
accaaagtga atacgtgac cgagggaatg agaaagcccg ccttcctgag cggcgagcag    1680
aaaaaggcca tcgtggacct gctgttcaag accaaccgga agtgaccgt gaagcagctg    1740
aaagaggact acttcaagaa aatcgagtgc ttcgactccg tggaaatctc cggcgtggaa   1800
gatcggttca cgcctccct gggcacatac cacgatctgc tgaaaattat caaggacaag    1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga catcgtgat cgaaatggcc   2340
agagagaacc agaccaccca aagggacag aagaacagcc gcgagagaat gaagcggatc   2400
gaagagggca tcaaagagct gggcagccag atcctgaaag aacacccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga gatgaagaa ctactggcgg   2700
cagctgctga acgccaagct gattacccag agaaagttcg acaatctgac caaggccgag   2760
agaggcggcc tgagcgaact ggataaggcc ggcttcatca gagacagct ggtggaaacc   2820
cggcagatca caaagcacgt ggcacagatc ctggactccc ggatgaacac taagtacgac   2880
gagaatgaca gctgatccg ggaagtgaaa gtgatcaccc tgaagtccaa gctggtgtcc   2940
gatttccgga aggatttcca gttttacaaa gtgcgcgaga tcaacaacta ccacgccgcc   3000
cacgacgcct accctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
ttttttcaaga ccgagattac cctggccaac ggcgagatcc ggaagcggcc tctgatcgag   3240
acaaacggcg aaaccgggga gatcgtgtgg gataagggcc gggattttgc caccgtgcgg   3300
aaagtgctga gcatgccca gtgaatatc gtgaaaaaga ccgaggtgca gacaggcggc   3360
ttcagcaaag agtctatcct gcccaagagg aacagcgata gctgatcgc cagaaagaag   3420
gactgggacc ctaagaagta cggcggcttc gacagcccca ccgtggcctat ttctgtgctg   3480
```

```
gtggtggcca aagtggaaaa gggcaagtcc aagaaactga agagtgtgaa agagctgctg    3540
gggatcacca tcatggaaag aagcagcttc gagaagaatc ccatcgactt tctggaagcc    3600
aagggctaca agaagtgaa aaaggacctg atcatcaagc tgcctaagta ctccctgttc    3660
gagctggaaa acgccggaa gagaatgctg gcctctgccg gcgaactgca aagggaaac    3720 gaactggccc tgccctccaa atatgtgaac ttcctgtacc tggccagcca ctatgagaag    3780
ctgaagggct cccccgagga taatgagcag aaacagctgt tgtggaaca gcacaagcac    3840 tacctggacg agatcatcga gcagatcagc gagttctcca agagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140
ctgggaggcg acaaaaggcc ggcggccacg aaaaaggccg gccaggcaaa aaagaaaaag    4200
taa                                                                 4203
```

<210> SEQ ID NO 75
<211> LENGTH: 4200
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcggagccct gctgttcgac agcggcgaaa cagccgaggc caccggctg      240 aagagaaccg ccagaagaag atacaccaga cggaagaacc ggatctgcta tctgcaagag     300
atcttcagca acgagatggc caaggtggac gacagcttct tccacagact ggaagagtcc     360
ttcctggtgg aagaggataa gaagcacgag cggcacccca tcttcggcaa catcgtggac     420
gaggtggcct accacgagaa gtaccccacc atctaccacc tgagaaagaa actggtggac     480
agcaccgaca aggccgacct gcggctgatc tatctggccc tggcccacat gatcaagttc     540
cggggccact cctgatcga gggcgacctg aaccccgaca cagcgacgt ggacaagctg     600 ttcatccagc tggtgcagac ctacaaccag ctgttcgagg aaaaccccat caacgccagc     660
ggcgtggacg ccaaggccat cctgtctgcc agactgagca gagcagacg gctggaaaat     720 ctgatcgccc agctgcccgg cgagaagaag aatggcctgt tcggaaacct gattgccctg     780 agcctgggc tgacccccaa cttcaagagc aacttcgacc tggccgagga tgccaaactg     840
cagctgagca aggacaccta cgacgacgac ctggacaacc tgctggccca gatcggcgac     900
cagtacgccg acctgttct ggccgccaag aacctgtccg acgccatcct gctgagcgac     960
atcctgagag tgaacaccga gatcaccaag gccccctga cgcctctat gatcaagaga    1020 tacgacgagc accaccagga cctgaccctg ctgaaagctc tcgtgcggca gcagctgcct    1080
gagaagtaca aagagatttt cttcgaccag agcaagaacg gctacgccgg ctacattgac    1140
ggcggagcca gccaggaaga gttctacaag ttcatcaagc ccatcctgga aaagatggac    1200
```

```
ggcaccgagg aactgctcgt gaagctgaac agagaggacc tgctgcggaa gcagcggacc    1260
ttcgacaacg gcagcatccc ccaccagatc cacctgggag agctgcacgc cattctgcgg    1320
cggcaggaag atttttaccc attcctgaag acaaccggg aaaagatcga agatcctg      1380
accttccgca tccctacta cgtgggccct ctggccaggg aaacagcag attcgcctgg      1440
atgaccagaa agagcgagga aaccatcacc ccctggaact tcgaggaagt ggtggacaag    1500
ggcgcttccg cccagagctt catcgagcgg atgaccaact tcgataagaa cctgcccaac    1560
gagaaggtgc tgcccaagca cagcctgctg tacgagtact tcaccgtgta taacgagctg    1620
accaaagtga atacgtgac cgagggaatg agaaagcccg ccttcctgag cggcgagcag    1680
aaaaaggcca tcgtggacct gctgttcaag accaaccgga aagtgaccgt gaagcagctg    1740
aaagaggact acttcaagaa aatcgagtgc ttcgactccg tggaaatctc cggcgtggaa    1800
gatcggttca acgcctccct gggcacatac cacgatctgc tgaaaattat caaggacaag    1860
gacttcctgg acaatgagga aaacgaggac attctggaag atatcgtgct gaccctgaca    1920
ctgtttgagg acagagagat gatcgaggaa cggctgaaaa cctatgccca cctgttcgac    1980
gacaaagtga tgaagcagct gaagcggcgg agatacaccg ctggggcag gctgagccgg    2040
aagctgatca acggcatccg ggacaagcag tccggcaaga caatcctgga tttcctgaag    2100
tccgacggct tcgccaacag aaacttcatg cagctgatcc acgacgacag cctgaccttt    2160
aaagaggaca tccagaaagc ccaggtgtcc ggccagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga catcgtgat cgaaatggcc    2340
agagagaacc agaccaccca gaagggacag aagaacagcc gcgagagaat gaagcggatc    2400
gaagagggca tcaaagagct gggcagccag atcctgaaag aacacccagt ggaaaacacc    2460
cagctgcaga acgagaagct gtacctgtac tacctgcaga atgggcggga tatgtacgtg    2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga gatgaagaa ctactggcgg    2700
cagctgctga acgccaagct gattacccag agaaagttcg acaatctgac caaggccgag    2760
agaggcggcc tgagcgaact ggataaggcc ggcttcatca gagacagct ggtggaaacc    2820
cggcagatca caaagcacgt ggcacagatc ctggactccc ggatgaacac taagtacgac    2880
gagaatgaca gctgatccg ggaagtgaaa gtgatcaccc tgaagtccaa gctggtgtcc    2940
gatttccgga aggatttcca gttttacaaa gtgcgcgaga tcaacaacta ccaccacgcc    3000
cacgccgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180
ttttttcaaga ccgagattac cctggccaac ggcgagatcc ggaagcggcc tctgatcgag    3240
acaaacggcg aaaccgggga gatcgtgtgg gataagggcc gggattttgc caccgtgcgg    3300
aaagtgctga gcatgcccca agtgaatatc gtgaaaaaga ccgaggtgca gacaggcggc    3360
ttcagcaaag agtctatcct gcccaagagg aacagcgata agctgatcgc cagaaagaag    3420
gactgggacc ctaagaagta cggcggcttc gacagcccca ccgtggccta ttctgtgctg    3480
gtggtggcca agtggaaaa gggcaagtcc aagaaactga agagtgtgaa agagctgctg    3540
gggatcacca tcatggaaag aagcagcttc gagaagaatc ccatcgactt tctggaagcc    3600
```

| | |
|---|---|
| aagggctaca aagaagtgaa aaaggacctg atcatcaagc tgcctaagta ctccctgttc | 3660 |
| gagctggaaa acggccggaa gagaatgctg gcctctgccg gcgaactgca aagggaaac | 3720 |
| gaactggccc tgccctccaa atatgtgaac ttcctgtacc tggccagcca ctatgagaag | 3780 |
| ctgaagggct cccccgagga taatgagcag aaacagctgt tgtggaaca gcacaagcac | 3840 |
| tacctggacg agatcatcga gcagatcagc gagttctcca agagagtgat cctggccgac | 3900 |
| gctaatctgg acaaagtgct gtccgcctac aacaagcacc gggataagcc catcagagag | 3960 |
| caggccgaga atatcatcca cctgtttacc ctgaccaatc tgggagcccc tgccgccttc | 4020 |
| aagtactttg acaccaccat cgaccggaag aggtacacca gcaccaaaga ggtgctggac | 4080 |
| gccaccctga tccaccagag catcaccggc ctgtacgaga cacggatcga cctgtctcag | 4140 |
| ctgggaggcg acaaaaggcc ggcggccacg aaaaaggccg gccaggcaaa aagaaaaag | 4200 |

<210> SEQ ID NO 76
<211> LENGTH: 4269
<212> TYPE: DNA
<213> ORGANISM: Streptococcus pyogenes

<400> SEQUENCE: 76

| | |
|---|---|
| atggactata aggaccacga cggagactac aaggatcatg atattgatta caaagacgat | 60 |
| gacgataaga tggcccccaa gaagaagcgg aaggtcggta tccacggagt cccagcagcc | 120 |
| gacaagaagt acagcatcgg cctggacatc ggcaccaact ctgtgggctg ggccgtgatc | 180 |
| accgacgagt acaaggtgcc cagcaagaaa ttcaaggtgc tgggcaacac cgaccggcac | 240 |
| agcatcaaga agaacctgat cggagccctg ctgttcgaca gcggcgaaac agccgaggcc | 300 |
| acccggctga agagaaccgc cagaagaaga taccaccagac ggaagaaccg gatctgctat | 360 |
| ctgcaagaga tcttcagcaa cgagatggcc aaggtggacg acagcttctt ccacagactg | 420 |
| gaagagtcct tcctggtgga agaggataag aagcacgagc ggcacccat cttcggcaac | 480 |
| atcgtggacg aggtggccta ccacgagaag taccccacca tctaccacct gagaaagaaa | 540 |
| ctggtggaca gcaccgacaa ggccgacctg cggctgatct atctggccct ggcccacatg | 600 |
| atcaagttcc ggggccactt cctgatcgag ggcgacctga accccgacaa cagcgacgtg | 660 |
| gacaagctgt tcatccagct ggtgcagacc tacaaccagc tgttcgagga aaacccatc | 720 |
| aacgccagcg gcgtggacgc caaggccatc ctgtctgcca gactgagcaa gagcagacgg | 780 |
| ctggaaaatc tgatcgccca gctgcccggc gagaagaaga tggcctgtt cggcaacctg | 840 |
| attgccctga gcctgggcct gacccccaac ttcaagagca cttcgacct ggccgaggat | 900 |
| gccaaactgc agctgagcaa ggacacctac gacgacgacc tggacaacct gctggcccag | 960 |
| atcggcgacc agtacgccga cctgtttctg gccgccaaga acctgtccga cgccatcctg | 1020 |
| ctgagcgaca tcctgagagt gaacaccgag atcaccaagg cccccctgag cgcctctatg | 1080 |
| atcaagagat acgacgagca ccaccaggac ctgaccctgc tgaaagctct cgtgcggcag | 1140 |
| cagctgcctg agaagtacaa agagattttc ttcgaccaga gcaagaacgg ctacgccggc | 1200 |
| tacattgacg gcggagccag ccaggaagag ttctacaagt tcatcaagcc catcctggaa | 1260 |
| aagatggacg gcaccgagga actgctcgtg aagctgaaca gagaggacct gctgcggaag | 1320 |
| cagcggacct tcgacaacgg cagcatcccc caccagatcc acctgggaga gctgcacgcc | 1380 |
| attctgcggc ggcaggaaga tttttaccca ttcctgaagg acaaccggga aaagatcgag | 1440 |
| aagatcctga ccttccgcat ccctactac gtgggccctc tggccagggg aaacagcaga | 1500 |

```
ttcgcctgga tgaccagaaa gagcgaggaa accatcaccc cctggaactt cgaggaagtg    1560
gtggacaagg gcgcttccgc ccagagcttc atcgagcgga tgaccaactt cgataagaac    1620
ctgcccaacg agaaggtgct gcccaagcac agcctgctgt acgagtactt caccgtgtat    1680
aacgagctga ccaaagtgaa atacgtgacc gagggaatga aaagcccgc cttcctgagc     1740
ggcgagcaga aaaaggccat cgtggacctg ctgttcaaga ccaaccggaa agtgaccgtg    1800
aagcagctga agaggactac cttcaagaaa atcgagtgct tcgactccgt ggaaatctcc    1860
ggcgtggaag atcggttcaa cgcctccctg gcacatacc acgatctgct gaaaattatc     1920
aaggacaagg acttcctgga caatgaggaa aacgaggaca ttctggaaga tatcgtgctg    1980
accctgacac tgtttgagga cagagagatg atcgaggaac ggctgaaaac ctatgcccac    2040
ctgttcgacg acaaagtgat gaagcagctg aagcggcgga gatacaccgg ctggggcagg    2100
ctgagccgga agctgatcaa cggcatccgg gacaagcagt ccggcaagac aatcctggat    2160
ttcctgaagt ccgacggctt cgccaacaga aacttcatgc agctgatcca cgacgacagc    2220
ctgacctta aagaggacat ccagaaagcc caggtgtccg ccagggcga tagcctgcac      2280
gagcacattg ccaatctggc cggcagcccc gccattaaga agggcatcct gcagacagtg    2340
aaggtggtgg acgagctcgt gaaagtgatg ggccggcaca gcccgagaa catcgtgatc     2400
gaaatggcca gagagaacca gaccacccag aagggacaga agaacagccg cgagagaatg    2460
aagcggatcg aagagggcat caaagagctg ggcagccaga tcctgaaaga cacccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttcaagac cgagattacc ctggccaacg gcgagatccg gaagcggcct     3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc     3480
agaaagaagg actgggaccc taagaagtac ggcggcttcg acagcccac cgtggcctat    3540
tctgtgctgg tggtggccaa agtggaaaag ggcaagtcca agaaactgaa gagtgtgaaa    3600
gagctgctgg gatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gcctccaaa tatgtgaact tcctgtacct ggccagccac     3840
tatgagaagc tgaagggctc ccccgaggat aatgagcaga acagctgtt tgtggaacag    3900
```

| | |
|---|---|
| cacaagcact acctggacga gatcatcgag cagatcagcg agttctccaa gagagtgatc | 3960 |
| ctggccgacg ctaatctgga caaagtgctg tccgcctaca acaagcaccg ggataagccc | 4020 |
| atcagagagc aggccgagaa tatcatccac ctgtttaccc tgaccaatct gggagcccct | 4080 |
| gccgccttca gtactttga caccaccatc gaccggaaga ggtacaccag caccaaagag | 4140 |
| gtgctggacg ccaccctgat ccaccagagc atcaccggcc tgtacgagac acggatcgac | 4200 |
| ctgtctcagc tgggaggcga caaaaggccg gcggccacga aaaaggccgg ccaggcaaaa | 4260 |
| aagaaaaag | 4269 |

<210> SEQ ID NO 77
<211> LENGTH: 4107
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

| | |
|---|---|
| atggactata aggaccacga cggagactac aaggatcatg atattgatta caaagacgat | 60 |
| gacgataaga tggccccaaa gaagaagcgg aaggtcggta tccacggagt cccagcagcc | 120 |
| gacaagaagt acagcatcgg cctggacatc ggcaccaact ctgtgggctg ggccgtgatc | 180 |
| accgacgagt acaaggtgcc cagcaagaaa ttcaaggtgc tgggcaacac cgaccggcac | 240 |
| agcatcaaga gaacctgat cggagccctg ctgttcgaca cggcgaaac agccgaggcc | 300 |
| acccggctga agagaaccgc cagaagaaga taccaccgac ggaagaaccg gatctgctat | 360 |
| ctgcaagaga tcttcagcaa cgagatggcc aaggtggacg acagcctgcg gctgatctat | 420 |
| ctggccctgg cccacatgat caagttccgg ggccacttcc tgatcgaggg cgacctgaac | 480 |
| cccgacaaca gcgacgtgga caagctgttc atccagctgg tgcagaccta caaccagctg | 540 |
| ttcgaggaaa accccatcaa cgccagcggc gtggacgcca aggccatcct gtctgccaga | 600 |
| ctgagcaaga gcagacggct ggaaaatctg atcgcccagc tgcccggcga agaagaat | 660 |
| ggcctgttcg gaaacctgat tgccctgagc ctgggcctga cccccaactt caagagcaac | 720 |
| ttcgacctgg ccgaggatgc caaactgcag ctgagcaagg acacctacga cgacgacctg | 780 |
| gacaacctgc tggcccagat cggcgaccag tacgccgacc tgtttctggc cgccaagaac | 840 |
| ctgtccgacg ccatcctgct gagcgacatc ctgagagtga acaccgagat caccaaggcc | 900 |
| cccctgagcg cctctatgat caagagatac gacgagcacc accaggacct gaccctgctg | 960 |
| aaagctctcg tgcggcagca gctgcctgag aagtacaaag atttttctt cgaccagagc | 1020 |
| aagaacggct acgccggcta cattgacggc ggagccagcc aggaagagtt ctacaagttc | 1080 |
| atcaagccca tcctggaaaa gatggacggc accgaggaac tgctcgtgaa gctgaacaga | 1140 |
| gaggacctgc tgcggaagca gcggaccttc gacaacggca gcatccccca ccagatccac | 1200 |
| ctgggagagc tgcacgccat tctgcggcgg caggaagatt tttacccatt cctgaaggac | 1260 |
| aaccgggaaa agatcgagaa gatcctgacc ttccgcatcc cctactacgt gggccctctg | 1320 |
| gccagggaa acagcagatt cgcctggatg accagaaaga gcgaggaaac catcaccccc | 1380 |
| tggaacttcg aggaagtggt ggacaagggc gcttccgccc agagcttcat cgagcggatg | 1440 |
| accaacttcg ataagaacct gcccaacgag aaggtgctgc ccaagcacag cctgctgtac | 1500 |
| gagtacttca ccgtgtataa cgagctgacc aaagtgaaat acgtgaccga gggaatgaga | 1560 |

```
aagcccgcct tcctgagcgg cgagcagaaa aaggccatcg tggacctgct gttcaagacc    1620
aaccggaaag tgaccgtgaa gcagctgaaa gaggactact tcaagaaaat cgagtgcttc    1680
gactccgtgg aaatctccgg cgtggaagat cggttcaacg cctccctggg cacataccac    1740
gatctgctga aaattatcaa ggacaaggac ttcctggaca atgaggaaaa cgaggacatt    1800
ctggaagata tcgtgctgac cctgacactg tttgaggaca gagagatgat cgaggaacgg    1860
ctgaaaacct atgcccacct gttcgacgac aaagtgatga agcagctgaa gcggcggaga    1920
tacaccggct ggggcaggct gagccggaag ctgatcaacg gcatccggga caagcagtcc    1980
ggcaagacaa tcctggattt cctgaagtcc gacggcttcg ccaacagaaa cttcatgcag    2040
ctgatccacg acgacagcct gacctttaaa gaggacatcc agaaagccca ggtgtccggc    2100
cagggcgata gcctgcacga gcacattgcc aatctggccg gcagcccgc  cattaagaag    2160
ggcatcctgc agacagtgaa ggtggtggac gagctcgtga agtgatgggg ccggcacaag    2220
cccgagaaca tcgtgatcga aatggccaga gagaaccaga ccaccagaa  gggacagaag    2280
aacagccgcg agagaatgaa gcggatcgaa gagggcatca aagagctggg cagccagatc    2340
ctgaaagaac ccccgtggaa aaacacccag ctgcagaacg agaagctgta cctgtactac    2400
ctgcagaatg ggcgggatat gtacgtggac caggaactgg acatcaaccg gctgtccgac    2460
tacgatgtgg accatatcgt gcctcagagc tttctgaagg acgactccat cgacaacaag    2520
gtgctgacca aagcgacaa  gaaccggggc aagagcgaca acgtgccctc cgaagaggtc    2580
gtgaagaaga tgaagaacta ctggcggcag ctgctgaacg ccaagctgat tacccagaga    2640
aagttcgaca atctgaccaa ggccgagaga ggcggcctga gcgaactgga taaggccggc    2700
ttcatcaaga gacagctggt ggaaacccgg cagatcacaa agcacgtggc acagatcctg    2760
gactcccgga tgaacactaa gtacgacgag aatgacaagc tgatccggga agtgaaagtg    2820
atcacccctg agtccaagct ggtgtccgat ttccggaagg attttcagtt ttacaaagtg    2880
cgcgagatca caaactacca ccacgcccac gacgcctacc tgaacgccgt cgtgggaacc    2940
gccctgatca aaaagtaccc taagctggaa agcgagttcg tgtacggcga ctacaaggtg    3000
tacgacgtgc ggaagatgat cgccaagagc gagcaggaaa tcggcaaggc taccgccaag    3060
tacttcttct acagcaacat catgaacttt ttcaagaccg agattaccct ggccaacggc    3120
gagatccgga gcggcctct  gatcgagaca acggcgaaa  ccggggagat cgtgtgggat    3180
aagggccggg attttgccac cgtgcggaaa gtgctgagca tgccccaagt gaatatcgtg    3240
aaaaagaccg aggtgcagac aggcggcttc agcaaagagt ctatcctgcc caagaggaac    3300
agcgataagc tgatcgccag aaagaaggac tgggacccta gaagtacgg  cggcttcgac    3360
agccccaccg tggcctattc tgtgctggtg gtggccaaag tggaaaaggg caagtccaag    3420
aaactgaaga gtgtgaaaga gctgctgggg atcaccatca tggaaagaag cagcttcgag    3480
aagaatccca tcgactttct ggaagccaag ggctacaaag aagtgaaaaa ggacctgatc    3540
atcaagctgc ctaagtactc cctgttcgag ctggaaaacg gccggaagag aatgctggcc    3600
tctgccggcg aactgcagaa gggaaacgaa ctggccctgc cctccaaata tgtgaacttc    3660
ctgtacctgg ccagccacta tgagaagctg aagggctccc ccgaggataa tgagcagaaa    3720
cagctgtttg tggaacagca caagcactac ctggacgaga tcatcgagca gatcagcgag    3780
ttctccaaga gagtgatcct ggccgacgct aatctggaca aagtgctgtc cgcctacaac    3840
aagcaccggg ataagcccat cagagagcag gccgagaata tcatccacct gtttaccctg    3900
accaatctgg gagcccctgc cgccttcaag tactttgaca ccaccatcga ccggaagagg    3960
```

-continued

| | |
|---|---|
| tacaccagca ccaaagaggt gctggacgcc accctgatcc accagagcat caccggcctg | 4020 |
| tacgagacac ggatcgacct gtctcagctg ggaggcgaca aaaggccggc ggccacgaaa | 4080 |
| aaggccggcc aggcaaaaaa gaaaaag | 4107 |

<210> SEQ ID NO 78
<211> LENGTH: 3870
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78

| | |
|---|---|
| atggactata aggaccacga cggagactac aaggatcatg atattgatta caaagacgat | 60 |
| gacgataaga tggccccaaa gaagaagcgg aaggtcggta tccacggagt cccagcagcc | 120 |
| gacaagaagt acagcatcgg cctggacatc ggcaccaact ctgtgggctg gccgtgatc | 180 |
| accgacgagt acaaggtgcc cagcaagaaa ttcaaggtgc tgggcaacac cgaccggcac | 240 |
| agcatcaaga gaacctgat cggagccctg ctgttcgaca cggcgaaac agccgaggcc | 300 |
| acccggctga agagaaccgc cagaagaaga tacaccagac ggaagaaccg gatctgctat | 360 |
| ctgcaagaga tcttcagcaa cgagatggcc aaggtggacg acagcttctt ccacagactg | 420 |
| gaagagtcct tcctggtgga agaggataag aagcacgagc ggcaccccat cttcggcaac | 480 |
| atcgtggacg aggtggccta ccacgagaag taccccacca tctaccacct gagaaagaaa | 540 |
| ctggtggaca gcaccgacaa ggccgacctg cggctgatct atctggccct ggcccacatg | 600 |
| atcaagttcc ggggccactt cctgatcgag ggcgacctgg tgaacaccga gatcaccaag | 660 |
| gcccccctga gcgcctctat gatcaagaga tacgacgagc accaccagga cctgaccctg | 720 |
| ctgaaagctc tcgtgcggca gcagctgcct gagaagtaca agagattttt cttcgaccag | 780 |
| agcaagaacg gctacgccgg ctacattgac ggcggagcca gccaggaaga gttctacaag | 840 |
| ttcatcaagc ccatcctgga aaagatggac ggcaccgagg aactgctcgt gaagctgaac | 900 |
| agagaggacc tgctgcggaa gcagcggacc ttcgacaacg gcagcatccc ccaccagatc | 960 |
| cacctgggag agctgcacgc cattctgcgg cggcaggaag atttttaccc attcctgaag | 1020 |
| gacaaccggg aaaagatcga aagatcctg accttccgca tccctacta cgtgggccct | 1080 |
| ctggccaggg gaaacagcag attcgcctgg atgaccagaa agagcgagga accatcacc | 1140 |
| ccctggaact tcgaggaagt ggtggacaag ggcgcttccg cccagagctt catcgagcgg | 1200 |
| atgaccaact tcgataagaa cctgcccaac gagaaggtgc tgcccaagca gcctgctg | 1260 |
| tacgagtact tcaccgtgta taacgagctg accaaagtga atacgtgac cgagggaatg | 1320 |
| agaaagcccg ccttcctgag cggcgagcag aaaaaggcca tcgtggacct gctgttcaag | 1380 |
| accaaccgga aagtgaccgt gaagcagctg aagaggact acttcaagaa atcgagtgc | 1440 |
| ttcgactccg tggaaatctc cggcgtggaa gatcggttca acgcctccct gggcacatac | 1500 |
| cacgatctgc tgaaaattat caaggacaag gacttcctgg acaatgagga aaacgaggac | 1560 |
| attctggaag atatcgtgct gaccctgaca ctgtttgagg acagagagat gatcgaggaa | 1620 |
| cggctgaaaa cctatgccca cctgttcgac gacaaagtga tgaagcagct gaagcggcgg | 1680 |
| agatacaccg gctggggcag gctgagccgg aagctgatca acggcatccg ggacaagcag | 1740 |
| tccggcaaga caatcctgga tttcctgaag tccgacggct cgccaacag aaacttcatg | 1800 |

```
cagctgatcc acgacgacag cctgaccttt aaagaggaca tccagaaagc ccaggtgtcc      1860
ggccagggcg atagcctgca cgagcacatt gccaatctgg ccggcagccc cgccattaag      1920
aagggcatcc tgcagacagt gaaggtggtg gacgagctcg tgaaagtgat gggccggcac      1980
aagcccgaga acatcgtgat cgaaatggcc agagagaacc agaccaccca gaagggacag      2040
aagaacagcc gcgagagaat gaagcggatc gaagagggca tcaaagagct gggcagccag      2100
atcctgaaag aacaccccgt ggaaaacacc cagctgcaga acgagaagct gtacctgtac      2160
tacctgcaga atgggcggga tatgtacgtg gaccaggaac tggacatcaa ccggctgtcc      2220
gactacgatg tggaccatat cgtgcctcag agctttctga aggacgactc catcgacaac      2280
aaggtgctga ccagaagcga caagaaccgg gcaagagcg acaacgtgcc ctccgaagag      2340
gtcgtgaaga agatgaagaa ctactggcgg cagctgctga acgccaagct gattacccag      2400
agaaagttcg acaatctgac caaggccgag agaggcggcc tgagcgaact ggataaggcc      2460
ggcttcatca agacagagct ggtggaaacc cggcagatca caaagcacgt ggcacagatc      2520
ctggactccc ggatgaacac taagtacgac gagaatgaca agctgatccg ggaagtgaaa      2580
gtgatcaccc tgaagtccaa gctggtgtcc gatttccgga aggatttcca gttttacaaa      2640
gtgcgcgaga tcaacaacta ccaccacgcc cacgacgcct acctgaacgc cgtcgtggga      2700
accgccctga tcaaaagta ccctaagctg gaaagcgagt tcgtgtacgg cgactacaag      2760
gtgtacgacg tgcggaagat gatcgccaag agcgagcagg aaatcggcaa ggctaccgcc      2820
aagtacttct tctacagcaa catcatgaac ttttttcaaga ccgagattac cctggccaac      2880
ggcgagatcc ggaagcggcc tctgatcgag acaaacggcg aaaccgggga gatcgtgtgg      2940
gataagggcc gggatttgc caccgtgcgg aaagtgctga gcatgcccca agtgaatatc      3000
gtgaaaaaga ccgaggtgca gacaggcggc ttcagcaaag agtctatcct gcccaagagg      3060
aacagcgata agctgatcgc cagaaagaag gactgggacc ctaagaagta cggcggcttc      3120 gacagccca ccgtggccta ttctgtgctg gtggtggcca aagtggaaaa gggcaagtcc      3180
aagaaactga gagtgtgaa agagctgctg gggatcacca tcatggaaag aagcagcttc      3240
gagaagaatc ccatcgactt tctggaagcc aagggctaca aagaagtgaa aaaggacctg      3300
atcatcaagc tgcctaagta ctccctgttc gagctggaaa acggccggaa gagaatgctg      3360
gcctctgccg cgaactgca gaagggaaac gaactggccc tgccctccaa atatgtgaac      3420
ttcctgtacc tggccagcca ctatgagaag ctgaagggct ccccccgagga taatgagcag      3480 aaacagctgt ttgtggaaca gcacaagcac tacctgacg agatcatcga gcagatcagc      3540
gagttctcca agagagtgat cctggccgac gctaatctgg acaaagtgct gtccgcctac      3600
aacaagcacc gggataagcc catcagagag caggccgaga atatcatcca cctgtttacc      3660
ctgaccaatc tgggagcccc tgccgccttc aagtactttg acaccaccat cgaccggaag      3720
aggtacacca gcaccaaaga ggtgctggac gccaccctga tccaccagag catcaccggc      3780
ctgtacgaga cacggatcga cctgtctcag ctggaggcg acaaaaggcc ggcggccacg      3840
aaaaaggccg gccaggcaaa aagaaaaag                                        3870
```

<210> SEQ ID NO 79
<211> LENGTH: 3975
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

```
atggactata aggaccacga cggagactac aaggatcatg atattgatta caaagacgat      60
gacgataaga tggccccaaa gaagaagcgg aaggtcggta tccacggagt cccagcagcc     120
gacaagaagt acagcatcgg cctggacatc ggcaccaact ctgtgggctg gccgtgatc      180
accgacgagt acaaggtgcc cagcaagaaa ttcaaggtgc tgggcaacac cgaccggcac     240
agcatcaaga gaacctgat cggagccctg ctgttcgaca cggcgaaac agccgaggcc       300
acccggctga agagaaccgc cagaagaaga taccagac ggaagaaccg gatctgctat        360
ctgcaagaga tcttcagcaa cgagatggcc aaggtggacg acagcttctt ccacagactg     420
gaagagtcct tcctggtgga agaggataag aagcacgagc ggcaccccat cttcggcaac     480
atcgtggacg aggtggccta ccacgagaag tacccccacca tctaccacct gagaaagaaa    540
ctggtggaca gcaccgacaa ggccgacctg cggctgatct atctggccct ggcccacatg     600
atcaagttcc ggggccactt cctgatcgag ggcgacctga cccccgacaa cagcgacgtg     660
gacaagctgt tcatccagct ggtgcagacc tacaaccagc tgttcgagga aaaccccatc     720
aacgccagcg gcgtggacgc caaggccatc ctgtctgcca gactgagcaa gagcagacgg     780
ctggaaaatc tgatcgccca gctgcccggc gagaagaaga atggcctgtt cggaaacctg     840
attgccctga gcctgggcct gacccccaac ttcaagagca cttcgacct ggccgaggat      900
gccaaactgc agctgagcaa ggacacctac gacgacgacc tggacaacct gctggcccag     960
atcggcgacc agtacgccga cctgtttctg gccgccaaga acctgtccga cgccatcctg    1020
ctgagcgaca tcctgagagt gaacaccgag atcccccacc agatccacct gggagagctg    1080
cacgccattc tgcggcggca ggaagatttt tacccattcc tgaaggacaa ccgggaaaag    1140
atcgagaaga tcctgacctt ccgcatcccc tactacgtgg ccctctggc caggggaaac    1200
agcagattcg cctggatgac cagaaagagc gaggaaacca tcaccccctg gaacttcgag    1260
gaagtggtgg acaagggcgc ttccgcccag agcttcatcg agcggatgac caacttcgat    1320
aagaacctgc ccaacgagaa ggtgctgccc aagcacagcc tgctgtacga gtacttcacc    1380
gtgtataacg agctgaccaa agtgaaatac gtgaccgagg aatgagaaa gcccgccttc    1440
ctgagcggcg agcagaaaaa ggccatcgtg gacctgctgt tcaagaccaa ccggaaagtg    1500
accgtgaagc agctgaaaga ggactacttc aagaaaatcg agtgcttcga ctccgtggaa    1560
atctccggcg tggaagatcg gttcaacgcc tccctgggca cataccacga tctgctgaaa    1620
attatcaagg acaaggactt cctggacaat gaggaaaacg aggacattct ggaagatatc    1680
gtgctgaccc tgacactgtt tgaggacaga gagatgatcg aggaacggct gaaaacctat    1740
gcccacctgt tcgacgacaa agtgatgaag cagctgaagc ggcggagata caccggctgg    1800
ggcaggctga gccggaagct gatcaacggc atccgggaca gcagtccgg caagacaatc    1860
ctggattttc tgaagtccga cggcttcgcc aacagaaact tcatgcagct gatccacgac    1920
gacagcctga cctttaaaga ggacatccag aaagcccagg tgtccggcca gggcgatagc    1980
ctgcacgagc acattgccaa tctggccggc agccccgcca ttaagaaggg catcctgcag    2040
acagtgaagg tggtggacga gctcgtgaaa gtgatgggcc ggcacaagcc cgagaacatc    2100
gtgatcgaaa tggccagaga gaaccagacc acccagaagg gacagaagaa cagccgcgag    2160
agaatgaagc ggatcgaaga gggcatcaaa gagctgggca gccagatcct gaaagaacac    2220
cccgtggaaa acacccagct gcagaacgag aagctgtacc tgtactacct gcagaatggg    2280
```

| | |
|---|---|
| cgggatatgt acgtggacca ggaactggac atcaaccggc tgtccgacta cgatgtggac | 2340 |
| catatcgtgc ctcagagctt tctgaaggac gactccatcg acaacaaggt gctgaccaga | 2400 |
| agcgacaaga accggggcaa gagcgacaac gtgccctccg aagaggtcgt gaagaagatg | 2460 |
| aagaactact ggcggcagct gctgaacgcc aagctgatta cccagagaaa gttcgacaat | 2520 |
| ctgaccaagg ccgagagagg cggcctgagc gaactggata aggccggctt catcaagaga | 2580 |
| cagctggtgg aaacccggca gatcacaaag cacgtggcac agatcctgga ctcccggatg | 2640 |
| aacactaagt acgacgagaa tgacaagctg atccgggaag tgaaagtgat caccctgaag | 2700 |
| tccaagctgg tgtccgattt ccggaaggat ttccagtttt acaaagtgcg cgagatcaac | 2760 |
| aactaccacc acgcccacga cgcctacctg aacgccgtcg tgggaaccgc cctgatcaaa | 2820 |
| aagtaccct a gctggaaag cgagttcgtg tacggcgact acaaggtgta cgacgtgcgg | 2880 |
| aagatgatcg ccaagagcga gcaggaaatc ggcaaggcta ccgccaagta cttcttctac | 2940 |
| agcaacatca tgaactttt caagaccgag attaccctgg ccaacggcga gatccggaag | 3000 |
| cggcctctga tcgagacaaa cggcgaaacc ggggagatcg tgtgggataa gggccgggat | 3060 |
| tttgccaccg tgcggaaagt gctgagcatg ccccaagtga atatcgtgaa aaagaccgag | 3120 |
| gtgcagacag gcggcttcag caaagagtct atcctgccca gaggaacag cgataagctg | 3180 |
| atcgccagaa agaaggactg ggaccctaag aagtacggcg gcttcgacag ccccaccgtg | 3240 |
| gcctattctg tgctggtggt ggccaaagtg gaaaagggca gtccaagaa actgaagagt | 3300 |
| gtgaaagagc tgctggggat caccatcatg gaaagaagca gcttcgagaa gaatcccatc | 3360 |
| gactttctgg aagccaaggg ctacaaagaa gtgaaaaagg acctgatcat caagctgcct | 3420 |
| aagtactccc tgttcgagct ggaaaacggc cggaagagaa tgctggcctc tgccggcgaa | 3480 |
| ctgcagaagg gaaacgaact ggccctgccc tccaaatatg tgaacttcct gtacctggcc | 3540 |
| agccactatg agaagctgaa gggctccccc gaggataatg agcagaaaca gctgtttgtg | 3600 |
| gaacagcaca gcactacct ggacgagatc atcgagcaga tcagcgagtt ctccaagaga | 3660 |
| gtgatcctgg ccgacgctaa tctggacaaa gtgctgtccg cctacaacaa gcaccgggat | 3720 |
| aagcccatca gagagcaggc cgagaatatc atccacctgt ttaccctgac caatctggga | 3780 |
| gcccctgccg ccttcaagta cttggacacc accatcgacc ggaagaggta caccagcacc | 3840 |
| aaagaggtgc tggacgccac cctgatccac cagagcatca ccggcctgta cgagacacgg | 3900 |
| atcgacctgt ctcagctggg aggcgacaaa aggccggcgg ccacgaaaaa ggccggccag | 3960 |
| gcaaaaaaga aaaag | 3975 |

<210> SEQ ID NO 80
<211> LENGTH: 3459
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 80

| | |
|---|---|
| atggactata aggaccacga cggagactac aaggatcatg atattgatta caaagacgat | 60 |
| gacgataaga tggcccccaa gaagaagcgg aaggtcggta tccacggagt cccagcagcc | 120 |
| gacaagaagt acagcatcgg cctggacatc ggcaccaact ctgtgggctg gccgtgatc | 180 |
| accgacgagt acaaggtgcc cagcaagaaa ttcaaggtgc tgggcaacac cgaccggcac | 240 |
| agcatcaaga agaacctgat cggagccctg ctgttcgaca cggcgaaac agccgaggcc | 300 |

-continued

```
acccggctga agagaaccgc cagaagaaga tacaccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag taccccacca tctaccacct gagaaagaaa    540
ctggtggaca gcaccgacaa ggccgacctg cggctgatct atctggccct ggcccacatg    600
atcaagttcc ggggccactt cctgatcgag gcgacctga cccccgacaa cagcgacgtg     660
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga atggcctgtt cggaaacctg    840
attgccctga gctgggcct gaccccgaac ttcaagagca cttcgacct ggccgaggat      900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg    1080
atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga ttttaccca ttcctgaagg acaaccggga aaagatcgag    1440
aagatcctga ccttccgcat cccctactac gtgggccctc tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400
gaaatggcca gagagaacca gaccacccag aaggacagag aacagccg cgagagaatg   2460
aagcggatcg aagagggcat caaagagctg ggcagccaga tcctgaaaga caccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
```

| | |
|---|---|
| gtgcctcaga gctttctgaa ggacgactcc atcgacaaca aggtgctgac cagaagcgac | 2700 |
| aagaaccggg gcaagagcga caacgtgccc tccgaagagg tcgtgaagaa gatgaagaac | 2760 |
| tactggcggc agctgctgaa cgccaagctg attacccaga gaaagttcga caatctgacc | 2820 |
| aaggccgaga gaggcggcct gagcgaactg gataaggccg gcttcatcaa gagacagctg | 2880 |
| gtggaaaccc ggcagatcac aaagcacgtg gcacagatcc tggactcccg gatgaacact | 2940 |
| aagtacgacg agaatgacaa gctgatccgg gaagtgaaag tgatcaccct gaagtccaag | 3000 |
| ctggtgtccg atttccggaa ggatttccag ttttacaaag tgcgcgagat caacaactac | 3060 |
| caccacgccc acgacgccta cctgaacgcc gtcgtgggaa ccgccctgat caaaaagtac | 3120 |
| cctaagctgg aaagcgagtt cgtgtacggc gactacaagg tgtacgacgt gcggaagatg | 3180 |
| atcgccaaga gcgagcagga aatcggcaag gctaccgcca agtacttctt ctacagcaac | 3240 |
| atcatgaact tttcaagac cgagattacc ctggccaacg gcgagatccg gaagcggcct | 3300 |
| ctgatcgaga caaacggcga aaccggggag atcgtgtggg ataagggccg ggattttgcc | 3360 |
| accgtgcgga aagtgctgag catgcccaa gtgaatatcg tgaaaaagac caaaaggccg | 3420 |
| gcggccacga aaaaggccgg ccaggcaaaa aagaaaaag | 3459 |

<210> SEQ ID NO 81
<211> LENGTH: 4347
<212> TYPE: DNA
<213> ORGANISM: Streptococcus thermophilus

<400> SEQUENCE: 81

| | |
|---|---|
| atggactata aggaccacga cggagactac aaggatcatg atattgatta caaagacgat | 60 |
| gacgataaga tggcccccaaa gaagaagcgg aaggtcggta tccacggagt cccagcagcc | 120 |
| accaagccct acagcatcgg cctggacatc ggcaccaata gcgtgggctg ggccgtgacc | 180 |
| accgacaact acaaggtgcc cagcaagaaa atgaaggtgc tgggcaacac ctccaagaag | 240 |
| tacatcaaga aaaacctgct gggcgtgctg ctgttcgaca gcggcattac agccgagggc | 300 |
| agacggctga agagaaccgc cagacggcgg tacacccggc ggagaaacag aatcctgtat | 360 |
| ctgcaagaga tcttcagcac cgagatggct accctggacg acgccttctt ccagcggctg | 420 |
| gacgacagct cctggtgcc cgacgacaag cgggacagca gtacccccat cttcggcaac | 480 |
| ctggtggaag agaaggccta ccacgacgag ttccccacca tctaccacct gagaaagtac | 540 |
| ctggccgaca gcaccaagaa ggcgacctg agactggtgt atctggccct ggcccacatg | 600 |
| atcaagtacc ggggccactt cctgatcgag ggcgagttca cagcaagaa caacgacatc | 660 |
| cagaagaact tccaggactt cctggacacc tacaacgcca tcttcgagag cgacctgtcc | 720 |
| ctggaaaaca gcaagcagct ggaagagatc gtgaaggaca gatcagcaa gctggaaaag | 780 |
| aaggaccgca tcctgaagct gttccccggc gagaagaaca cggaatcttc agcgagttt | 840 |
| ctgaagctga tcgtgggcaa ccaggccgac ttcagaaagt gcttcaacct ggacgagaaa | 900 |
| gccagcctgc acttcagcaa agagagctac gacgaggacc tggaaaccct gctgggatat | 960 |
| atcggcgacg actacagcga cgtgttcctg aaggccaaga gctgtacga cgctatcctg | 1020 |
| ctgagcggct tcctgaccgt gaccgacaac gagacagagg ccccactgag cagcgccatg | 1080 |
| attaagcggt acaacgagca caaagaggat ctggctctgc tgaaagagta catccggaac | 1140 |
| atcagcctga aacctacaa tgaggtgttc aaggacgaca ccaagaacgg ctacgccggc | 1200 |
| tacatcgacg gcaagaccaa ccaggaagag gaagatttct atgtgtacct gaagaagctg | 1260 |
| ctggccgagt cgaggggc cgactacttt ctggaaaaaa tcgaccgcga ggatttcctg | 1320 |

```
cggaagcagc ggaccttcga caacggcagc atcccctacc agatccatct gcaggaaatg   1380
cgggccatcc tggacaagca ggccaagttc tacccattcc tggccaagaa caaagagcgg   1440
atcgagaaga tcctgacctt ccgcatccct tactacgtgg ccccctggc cagaggcaac   1500
agcgattttg cctggtccat ccggaagcgc aatgagaaga tcaccccctg gaacttcgag   1560
gacgtgatcg acaaagagtc cagcgccgag gccttcatca accggatgac cagcttcgac   1620
ctgtacctgc ccgaggaaaa ggtgctgccc aagcacagcc tgctgtacga cattcaat   1680
gtgtataacg agctgaccaa agtgcggttt atcgccgagt ctatgcggga ctaccagttc   1740
ctggactcca gcagaaaaa ggacatcgtg cggctgtact tcaaggacaa gcggaaagtg   1800
accgataagg acatcatcga gtacctgcac gccatctacg ctacgatgg catcgagctg   1860
aagggcatcg agaagcagtt caactccagc ctgagcacat accacgacct gctgaacatt   1920
atcaacgaca agaatttct ggacgactcc agcaacgagg ccatcatcga agagatcatc   1980
cacaccctga ccatctttga ggaccgcgag atgatcaagc agcggctgag caagttcgag   2040
aacatcttcg acaagagcgt gctgaaaaag ctgagcagac ggcactacac cggctggggc   2100
aagctgagcg ccaagctgat caacggcatc cgggacgaga gtccggcaa cacaatcctg   2160
gactacctga tcgacgacgg catcagcaac cggaacttca tgcagctgat ccacgacgac   2220
gccctgagct tcaagaagaa gatccagaag gcccagatca tcggggacga ggacaagggc   2280
aacatcaaag aagtcgtgaa gtccctgccc ggcagccccg ccatcaagaa gggaatcctg   2340
cagagcatca gatcgtgga cgagctcgtg aaagtgatgg gcggcagaaa gcccgagagc   2400
atcgtggtgg tggtggaaat ggctagagag aaccagtaca ccaatcaggg caagagcaac   2460
agccagcaga gactgaagag actggaaaag tccctgaaag agctgggcag caagattctg   2520
aaagagaata tccctgccaa gctgtccaag atcgacaaca acgccctgca gaacgaccgg   2580
ctgtacctgt actacctgca gaatggcaag gacatgtata caggcgacga cctggatatc   2640
gaccgcctga gcaactacga catcgaccat attatccccc aggccttcct gaaagacaac   2700
agcattgaca acaaagtgct ggtgtcctcc gccagcaacc gcggcaagtc cgatgatgtg   2760
cccagcctgg aagtcgtgaa aaagagaaag accttctggt atcagctgct gaaaagcaag   2820
ctgattagcc agaggaagtt cgacaacctg accaaggccg agagaggcgg cctgagccct   2880
gaagataagg ccggcttcat ccagagacag ctggtgaaaa cccggcagat caccaagcac   2940
gtggccagac tgctggatga aagtttaac aacaagaagg acgagaacaa ccgggccgtg   3000
cggaccgtga gatcatcac cctgaagtcc accctggtgt cccagttccg gaaggacttc   3060
gagctgtata agtgcgcga gatcaatgac tttcaccacg cccacgacgc ctacctgaat   3120
gccgtggtgc cttccgccct gctgaagaag taccctaagc tggaacccga gttcgtgtac   3180
ggcgactacc ccaagtacaa ctccttcaga gagcggaagt ccgccaccga aggtgtac   3240
ttctactcca acatcatgaa tatctttaag aagtccatct ccctggccga tggcagagtg   3300
atcgagcggc ccctgatcga agtgaacgaa gagacaggcg agagcgtgtg gaacaaagaa   3360
agcgacctgg ccaccgtgcg gcgggtgctg agttatcctc aagtgaatgt cgtgaagaag   3420
gtggaagaac agaaccacgg cctggatcgg gcaagccca agggcctgtt caacgccaac   3480
ctgtccagca gcctaagcc caactccaac gagaatctcg tggggccaa agagtacctg   3540
gaccctaaga gtacgggta cggcggatac gccggcatct ccaatagctt caccgtgctc   3600
gtgaagggca aatcgagaa gggcgctaag aaaaagatca caaacgtgct ggaatttcag   3660
```

```
gggatctcta tcctggaccg atcaactac cggaaggata agctgaactt tctgctggaa    3720
aaaggctaca aggacattga gctgattatc gagctgccta agtactccct gttcgaactg    3780
agcgacggct ccagacggat gctggcctcc atcctgtcca ccaacaacaa gcggggcgag    3840
atccacaagg gaaaccagat cttcctgagc cagaaatttg tgaaactgct gtaccacgcc    3900
aagcggatct ccaacaccat caatgagaac caccggaaat acgtggaaaa ccacaagaaa    3960
gagtttgagg aactgttcta ctacatcctg gagttcaacg agaactatgt gggagccaag    4020
aagaacggca aactgctgaa ctccgccttc cagagctggc agaaccacag catcgacgag    4080
ctgtgcagct ccttcatcgg ccctaccggc agcgagcgga agggactgtt tgagctgacc    4140
tccagaggct ctgccgccga ctttgagttc ctgggagtga agatccccg gtacagagac    4200 tacacccccct ctagtctgct gaaggacgcc accctgatcc accagagcgt gaccggcctg    4260
tacgaaaccc ggatcgacct ggctaagctg ggcgagggaa aaaggccggc ggccacgaaa    4320
aaggccggcc aggcaaaaaa gaaaaag                                          4347
```

<210> SEQ ID NO 82
<211> LENGTH: 4104
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

```
atggacaaga agtacagcat cggcctggac atcggcacca actctgtggg ctgggccgtg      60
atcaccgacg agtacaaggt gcccagcaag aaattcaagg tgctgggcaa caccgaccgg     120
cacagcatca gaagaacct gatcggagcc ctgctgttcg acagcggcga aacagccgag     180
gccacccggc tgaagagaac cgccagaaga agatacacca cgcggaagaa ccggatcctg     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg acagcaccga caaggccgac ctgcggctga tctatctggc cctggcccac     480
atgatcaagt tccggggcca cttcctgatc gagggcgacc tgaaccccga caacagcgac     540
gtggacaagc tgttcatcca gctggtgcag acctacaacc agctgttcga ggaaaaccccc     600 atcaacgcca gcgcgtgga cgccaaggcc atcctgtctg ccagactgag caagagcaga     660
cggctggaaa atctgatcgc ccagctgccc ggcgagaaga gaatggcct gttcggaaac     720 ctgattgccc tgagcctggg cctgacccca aacttcaaga gcaacttcga cctggccgag     780
gatgccaaac tgcagctgag caaggacacc tacgacgacg acctggacaa cctgctggcc     840
cagatcggcg accagtacgc cgacctgttt ctggccgcca gaaacctgtc cgacgccatc     900
ctgctgagcg acatcctgag agtgaacacc gagatcacca aggcccccct gagcgcctct     960
atgatcaaga gatacgacga gcaccaccag gacctgaccc tgctgaaagc tctcgtgcgg    1020
cagcagctgc ctgagaagta caaagagatt ttcttcgacc agagcaagaa cggctacgcc    1080
ggctacattg acggcggagc cagccaggaa gagttctaca agttcatcaa gcccatcctg    1140
gaaaagatgg acggcaccga ggaactgctc gtgaagctga acagagagga cctgctgcgg    1200
aagcagcgga ccttcgacaa cggcagcatc ccccaccaga tccacctggg agagctgcac    1260
gccattctgc ggcggcagga agatttttac ccattcctga aggacaaccg ggaaaagatc    1320
```

```
gagaagatcc tgaccttccg catccctac tacgtgggcc ctctggccag gggaaacagc    1380
agattcgcct ggatgaccag aaagagcgag gaaaccatca ccccctggaa cttcgaggaa    1440
gtggtggaca agggcgcttc cgcccagagc ttcatcgagc ggatgaccaa cttcgataag    1500
aacctgccca cgagaaggt gctgcccaag cacagcctgc tgtacgagta cttcaccgtg    1560
tataacgagc tgaccaaagt gaaatacgtg accgagggaa tgagaaagcc cgccttcctg    1620
agcggcgagc agaaaaaggc catcgtggac ctgctgttca agaccaaccg gaaagtgacc    1680
gtgaagcagc tgaaagagga ctacttcaag aaaatcgagg agttcgactc cgtggaaatc    1740
tccggcgtgg aagatcggtt caacgcctcc ctgggcacat accacgatct gctgaaaatt    1800
atcaaggaca aggacttcct ggacaatgag gaaaacgagg acattctgga agatatcgtg    1860
ctgaccctga cactgtttga ggacagagag atgatcgaga acggctgaa aacctatgcc    1920
cacctgttcg acgacaaagt gatgaagcag ctgaagcggc ggagatacac cggctggggc    1980
aggctgagcc ggaagctgat caacggcatc cgggacaagc agtccggcaa gacaatcctg    2040
gatttcctga gtccgacgg cttcgccaac agaaacttca tgcagctgat ccacgacgac    2100
agcctgacct ttaaagagga catccagaaa gcccaggtgt ccggccaggg cgatagcctg    2160
cacgagcaca ttgccaatct ggccggcagc cccgccatta gaagggcat cctgcagaca    2220
gtgaaggtgg tggacgagct cgtgaaagtg atgggccggc acaagcccga gaacatcgtg    2280
atcgaaatgg ccagagagaa ccagaccacc cagaagggac agaagaacag ccgcgagaga    2340
atgaagcgga tcgaagaggg catcaaagag ctgggcagcc agatcctgaa agaacacccc    2400
gtggaaaaca cccagctgca gaacgagaag ctgtacctgt actacctgca gaatgggcgg    2460
gatatgtacg tggaccagga actggacatc aaccggctgt ccgactacga tgtggaccat    2520
atcgtgcctc agagctttct gaaggacgac tccatcgaca caaggtgct gaccagaagc    2580
gacaagaacc gggcaagag cgacaacgtg ccctccgaag aggtcgtgaa aaagatgaag    2640
aactactggc ggcagctgct gaacgccaag ctgattaccc agagaaagtt cgacaatctg    2700
accaaggccg agagaggcgg cctgagcgaa ctggataagg ccggcttcat caagagacag    2760
ctggtggaaa cccggcagat cacaaagcac gtggcacaga tcctggactc ccggatgaac    2820
actaagtacg acgagaatga caagctgatc cgggaagtga aagtgatcac cctgaagtcc    2880
aagctggtgt ccgatttccg gaaggatttc cagtttaca aagtgcgcga gatcaacaac    2940
taccaccacg cccacgacgc ctacctgaac gccgtcgtgg gaaccgccct gatcaaaaag    3000
taccctaagc tggaaagcga gttcgtgtac ggcgactaca aggtgtacga cgtgcggaag    3060
atgatcgcca agagcgagca ggaaatcggc aaggctaccg ccaagtactt cttctacagc    3120
aacatcatga actttttcaa gaccgagatt accctggcca cggcgagat ccggaagcgg    3180
cctctgatcg agacaaacgg cgaaaccggg gagatcgtgt gggataaggg ccgggatttt    3240
gccaccgtgc ggaaagtgct gagcatgccc caagtgaata tcgtgaaaaa gaccgaggtg    3300
cagacaggcg gcttcagcaa agagtctatc ctgcccaaga ggaacagcga taagctgatc    3360
gccagaaaga aggactggga ccctaagaag tacggcggct tcgacagccc caccgtggcc    3420
tattctgtgc tggtggtggc caagtgaa aaggcaagt ccaagaaact gaagagtgtg    3480
aaagagctgc tggggatcac catcatggaa agaagcagct tcgagaagaa tcccatcgac    3540
tttctggaag ccaagggcta caaagaagtg aaaaaggacc tgatcatcaa gctgcctaag    3600
tactccctgt tcgagctgga aaacggccgg aagagaatgc tggcctctgc cggcgaactg    3660
```

| | |
|---|---:|
| cagaagggaa acgaactggc cctgccctcc aaatatgtga acttcctgta cctggccagc | 3720 |
| cactatgaga agctgaaggg ctcccccgag gataatgagc agaaacagct gtttgtggaa | 3780 |
| cagcacaagc actacctgga cgagatcatc gagcagatca gcgagttctc caagagagtg | 3840 |
| atcctggccg acgctaatct ggacaaagtg ctgtccgcct acaacaagca ccgggataag | 3900 |
| cccatcagag agcaggccga gaatatcatc cacctgttta ccctgaccaa tctgggagcc | 3960 |
| cctgccgcct tcaagtactt tgacaccacc atcgaccgga gaggtacac cagcaccaaa | 4020 |
| gaggtgctgg acgccaccct gatccaccag agcatcaccg cctgtacga gacacggatc | 4080 |
| gacctgtctc agctgggagg cgac | 4104 |

<210> SEQ ID NO 83
<211> LENGTH: 4338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

| | |
|---|---:|
| atggactata aggaccacga cggagactac aaggatcatg atattgatta caaagacgat | 60 |
| gacgataaga tggcccccaa gaagaagcgg aaggtcggta tccacggagt cccagcagcc | 120 |
| gacaagaagt acagcatcgg cctggacatc ggcaccaact ctgtgggctg gccgtgatc | 180 |
| accgacgagt acaaggtgcc cagcaagaaa ttcaaggtgc tgggcaacac cgaccggcac | 240 |
| agcatcaaga gaacctgat cggagccctg ctgttcgaca cggcgaaac agccgaggcc | 300 |
| acccggctga agagaaccgc cagaagaaga taccagac ggaagaaccg gatctgctat | 360 |
| ctgcaagaga tcttcagcaa cgagatggcc aaggtggacg acagcttctt ccacagactg | 420 |
| gaagagtcct tcctggtgga agaggataag aagcacgagc ggcacccccat cttcggcaac | 480 |
| atcgtggacg aggtggccta ccacgagaag tacccaccac tctaccacct gagaaagaaa | 540 |
| ctggtggaca gcaccgacaa ggcgacctg cggctgatct atctggccct ggcccacatg | 600 |
| atcaagttcc ggggccactt cctgatcgag ggcgacctga accccgacaa cagcgacgtg | 660 |
| gacaagctgt tcatccagct ggtgcagacc tacaaccagc tgttcgagga aaaccccatc | 720 |
| aacgccagcg gcgtggacgc caaggccatc ctgtctgcca gactgagcaa gagcagacgg | 780 |
| ctggaaaatc tgatcgccca gctgcccggc gagaagaaga tggcctgtt cggaaacctg | 840 |
| attgccctga gctgggcct gaccccaac ttcaagagca cttcgacct ggccgaggat | 900 |
| gccaaactgc agctgagcaa ggacacctac gacgacgacc tggacaacct gctggcccag | 960 |
| atcggcgacc agtacgccga cctgtttctg gccgccaaga acctgtccga cgccatcctg | 1020 |
| ctgagcgaca tcctgagagt gaacaccgag atcaccaagg ccccctgag cgcctctatg | 1080 |
| atcaagagat acgacgagca ccaccaggac ctgaccctgc tgaaagctct cgtgcggcag | 1140 |
| cagctgcctg agaagtacaa agagattttc ttcgaccaga gcaagaacgg ctacgccggc | 1200 |
| tacattgacg gcggagccag ccaggaagag ttctacaagt tcatcaagcc catcctggaa | 1260 |
| aagatggacg gcaccgagga actgctcgtg aagctgaaca gagaggacct gctgcggaag | 1320 |
| cagcggacct tcgacaacgg cagcatcccc caccagatcc acctgggaga gctgcacgcc | 1380 |
| attctgcggc ggcaggaaga tttttaccca ttcctgaagg acaaccggga aaagatcgag | 1440 |
| aagatcctga ccttccgcat cccctactac gtgggccctc tggccagggg aaacagcaga | 1500 |
| ttcgcctgga tgaccagaaa gagcgaggaa accatcaccc cctggaactt cgaggaagtg | 1560 |

```
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga aaagcccgc cttcctgagc    1740 ggcgagcaga aaaaggccat cgtggacctg ctgttcaaga ccaaccggaa agtgaccgtg   1800
aagcagctga agaggacta cttcaagaaa atcgagtgct cgactccgt ggaaatctcc     1860 ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220 ctgacctttta agaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400 gaaatggcca gagagaacca gaccacccag aagggacaga agaacagccg cgagagaatg   2460
aagcggatcg aagagggcat caaagagctg ggcagccaga tcctgaaaga cacccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga gaggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca agtacttctt ctacagcaac   3240
atcatgaact ttttcaagac cgagattacc ctggccaacg gcgagatccg gaagcggcct   3300
ctgatcgaga caaacggcga aaccggggag atcgtgtggg ataagggccg ggattttgcc   3360
accgtgcgga aagtgctgag catgccccaa gtgaatatcg tgaaaaagac cgtggaagaa   3420
cagaaccacg gcctggatcg gggcaagccc aagggcctgt tcaacgccaa cctgtccagc   3480
aagcctaagc ccaactccaa cgagaatctc gtggggccca agagtacct ggaccctaag   3540 aagtacgggt acggcggata cgccggcatc tccaatagct tcaccgtgct cgtgaagggc   3600
acaatcgaga agggcgctaa gaaaaagatc acaaacgtgc tggaatttca ggggatctct   3660
atcctggacc ggatcaacta ccggaaggat aagctgaact ttctgctgga aaaaggctac   3720
aaggacattg agctgattat cgagctgcct aagtactccc tgttcgaact gagcgacggc   3780
tccagacgga tgctggcctc catcctgtcc accaacaaca gcggggcga gatccacaag   3840 ggaaaccaga tcttcctgag ccagaaattt gtgaaactgc tgtaccacgc caagcggatc   3900
```

| | |
|---|---|
| tccaacacca tcaatgagaa ccaccggaaa tacgtggaaa accacaagaa agagtttgag | 3960 |
| gaactgttct actacatcct ggagttcaac gagaactatg tgggagccaa gaagaacggc | 4020 |
| aaactgctga actccgcctt ccagagctgg cagaaccaca gcatcgacga gctgtgcagc | 4080 |
| tccttcatcg gccctaccgg cagcgagcgg aagggactgt ttgagctgac ctccagaggc | 4140 |
| tctgccgccg actttgagtt cctgggagtg aagatccccc ggtacagaga ctacaccccc | 4200 |
| tctagtctgc tgaaggacgc caccctgatc caccagagcg tgaccggcct gtacgaaacc | 4260 |
| cggatcgacc tggctaagct gggcgaggga aaaaggccgg cggccacgaa aaaggccggc | 4320 |
| caggcaaaaa agaaaaag | 4338 |

<210> SEQ ID NO 84
<211> LENGTH: 4215
<212> TYPE: DNA
<213> ORGANISM: Artificial Sequence
<220> FEATURE:
<221> NAME/KEY: source
<223> OTHER INFORMATION: /note="Description of Artificial Sequence:
   Synthetic polynucleotide"

<400> SEQUENCE: 84

| | |
|---|---|
| atggccccaa agaagaagcg gaaggtcggt atccacggag tcccagcagc catgaccaag | 60 |
| ccctacagca tcggcctgga catcggcacc aatagcgtgg gctgggccgt gaccaccgac | 120 |
| aactacaagg tgcccagcaa gaaaatgaag gtgctgggca cacctccaa gaagtacatc | 180 |
| aagaaaaacc tgctgggcgt gctgctgttc gacagcggca ttacagccga gggcagacgg | 240 |
| ctgaagagaa ccgccagacg gcggtacacc cggcggagaa acagaatcct gtatctgcaa | 300 |
| gagatcttca gcaccgagat ggctaccctg gacgacgcct tcttccagcg gctggacgac | 360 |
| agcttcctgg tgcccgacga caagcgggac agcaagtacc ccatcttcgg caacctggtg | 420 |
| gaagagaagg cctaccacga cgagttcccc accatctacc acctgagaaa gtacctggcc | 480 |
| gacagcacca gaaggccga cctgagactg gtgtatctgg ccctggccca catgatcaag | 540 |
| taccggggcc acttcctgat cgaggcgag ttcaacagca gaacaacga catccagaag | 600 |
| aacttccagg acttcctgga cacctacaac gccatcttcg agagcgacct gtccctggaa | 660 |
| aacagcaagc agctggaaga gatcgtgaag gacaagatca gcaagctgga aaagaaggac | 720 |
| cgcatcctga gctgttccc cggcgagaag aacagcggaa tcttcagcga gtttctgaag | 780 |
| ctgatcgtgg gcaaccaggc cgacttcaga aagtgcttca acctggacga gaaagccagc | 840 |
| ctgcacttca gcaaagagag ctacgacgag gacctgaaa ccctgctggg atatatcggc | 900 |
| gacgactaca gcgacgtgtt cctgaaggcc aagaagctgt acgacgctat cctgctgagc | 960 |
| ggcttcctga ccgtgaccga caacgagaca gaggccccac tgagcagcgc catgattaag | 1020 |
| cggtacaacg agcacaaaga ggatctggct ctgctgaaag agtacatccg gaacatcagc | 1080 |
| ctgaaaacct acaatgaggt gttcaaggac gacaccaaga acggctacgc cggctacatc | 1140 |
| gacggcaaga ccaaccagga agaggaagat ttctatgtgt acctgaagaa gctgctggcc | 1200 |
| gagttcgagg gggccgacta ctttctggaa aaaatcgacc gcgaggattt cctgcgaag | 1260 |
| cagcggacct tcgacaacgg cagcatcccc taccagatcc atctgcagga atgcgggcc | 1320 |
| atcctggaca gcaggccaa gttctaccca ttcctggcca gaacaaaga gcggatcgag | 1380 |
| aagatcctga ccttccgcat cccttactac gtgggccccc tggccagagg caacagcgat | 1440 |
| tttgcctggt ccatccggaa gcgcaatgag aagatcaccc cctggaactt cgaggacgtg | 1500 |
| atcgacaaag agtccagcgc cgaggccttc atcaaccgga tgaccagctt cgacctgtac | 1560 |

```
ctgcccgagg aaaaggtgct gcccaagcac agcctgctgt acgagacatt caatgtgtat    1620
aacgagctga ccaaagtgcg gtttatcgcc gagtctatgc gggactacca gttcctggac    1680
tccaagcaga aaaaggacat cgtgcggctg tacttcaagg acaagcggaa agtgaccgat    1740
aaggacatca tcgagtacct gcacgccatc tacggctacg atggcatcga gctgaagggc    1800
atcgagaagc agttcaactc cagcctgagc acataccacg acctgctgaa cattatcaac    1860
gacaaagaat ttctggacga ctccagcaac gaggccatca tcgaagagat catccacacc    1920
ctgaccatct ttgaggaccg cgagatgatc aagcagcggc tgagcaagtt cgagaacatc    1980
ttcgacaaga gcgtgctgaa aaagctgagc agacggcact acaccggctg gggcaagctg    2040
agcgccaagc tgatcaacgg catccgggac gagaagtccg gcaacacaat cctggactac    2100
ctgatcgacg acggcatcag caaccggaac ttcatgcagc tgatccacga cgacgccctg    2160
agcttcaaga gaagatcca aggcccag atcatcgggg acgaggacaa gggcaacatc    2220
```

| | |
|---|---|
| gtgatcctgg ccgacgctaa tctggacaaa gtgctgtccg cctacaacaa gcaccgggat | 3960 |
| aagcccatca gagagcaggc cgagaatatc atccacctgt ttaccctgac caatctggga | 4020 |
| gcccctgccg ccttcaagta ctttgacacc accatcgacc ggaagaggta caccagcacc | 4080 |
| aaagaggtgc tggacgccac cctgatccac cagagcatca ccggcctgta cgagacacgg | 4140 |
| atcgacctgt ctcagctggg aggcgacaaa aggccggcgg ccacgaaaaa ggccggccag | 4200 |
| gcaaaaaaga aaaag | 4215 |

<210> SEQ ID NO 85
<211> LENGTH: 4269
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 85

| | |
|---|---|
| atggactata aggaccacga cggagactac aaggatcatg atattgatta caaagacgat | 60 |
| gacgataaga tggccccaaa gaagaagcgg aaggtcggta tccacggagt cccagcagcc | 120 |
| gacaagaagt acagcatcgg cctggacatc ggcaccaact ctgtgggctg ggccgtgatc | 180 |
| accgacgagt acaaggtgcc cagcaagaaa ttcaaggtgc tgggcaacac cgaccggcac | 240 |
| agcatcaaga gaacctgat cggagccctg ctgttcgaca cggcgaaac agccgaggcc | 300 |
| acccggctga gagaaccgc cagaagaaga tacaccagac ggaagaaccg gatctgctat | 360 |
| ctgcaagaga tcttcagcaa cgagatggcc aaggtggacg acagcttctt ccacagactg | 420 |
| gaagagtcct tcctggtgga agaggataag aagcacgagc ggcacccat cttcggcaac | 480 |
| atcgtggacg aggtggccta ccacgagaag taccccacca tctaccacct gagaaagaaa | 540 |
| ctggtggaca gcaccgacaa ggccgacctg cggctgatct atctggccct ggcccacatg | 600 |
| atcaagttcc ggggccactt cctgatcgag ggcgacctga accccgacaa cagcgacgtg | 660 |
| gacaagctgt tcatccagct ggtgcagacc tacaaccagc tgttcgagga aaaccccatc | 720 |
| aacgccagcg gcgtggacgc caaggccatc ctgtctgcca gactgagcaa gagcagacgg | 780 |
| ctggaaaatc tgatcgccca gctgcccggc gagaagaaga tggcctgtt cggcaacctg | 840 |
| attgccctga gctgggcct gaccccaac ttcaagagca cttcgacct ggccgaggat | 900 |
| gccaaactgc agctgagcaa ggacacctac gacgacgacc tggacaacct gctggcccag | 960 |
| atcggcgacc agtacgccga cctgtttctg gccgccaaga acctgtccga cgccatcctg | 1020 |
| ctgagcgaca tcctgagagt gaacaccgag atcaccaagg ccccctgag cgcctctatg | 1080 |
| atcaagagat acgacgagca ccaccaggac ctgaccctgc tgaaagctct cgtgcggcag | 1140 |
| cagctgcctg agaagtacaa agagattttc ttcgaccaga gcaagaacgg ctacgccggc | 1200 |
| tacattgacg gcggagccag ccaggaagag ttctacaagt tcatcaagcc catcctggaa | 1260 |
| aagatggacg gcaccgagga actgctcgtg aagctgaaca gagaggacct gctgcggaag | 1320 |
| cagcggacct tcgacaacgg cagcatcccc caccagatcc acctgggaga gctgcacgcc | 1380 |
| attctgcggc ggcaggaaga ttttacccca ttcctgaagg acaaccggga aaagatcgag | 1440 |
| aagatcctga ccttccgcat cccctactac gtgggccctc tggccagggg aaacagcaga | 1500 |
| ttcgcctgga tgaccagaaa gagcgaggaa accatcaccc cctggaactt cgaggaagtg | 1560 |
| gtggacaagg gcgcttccgc ccagagcttc atcgagcgga tgaccaactt cgataagaac | 1620 |
| ctgcccaacg agaaggtgct gcccaagcac agcctgctgt acgagtactt caccgtgtat | 1680 |

```
aacgagctga ccaaagtgaa atacgtgacc gagggaatga gaaagcccgc cttcctgagc    1740
ggcgagcaga aaaaggccat cgtggacctg ctgttcaaga ccaaccggaa agtgaccgtg    1800
aagcagctga agaggacta cttcaagaaa atcgagtgct tcgactccgt ggaaatctcc     1860
ggcgtggaag atcggttcaa cgcctccctg ggcacatacc acgatctgct gaaaattatc    1920
aaggacaagg acttcctgga caatgaggaa aacgaggaca ttctggaaga tatcgtgctg    1980
accctgacac tgtttgagga cagagagatg atcgaggaac ggctgaaaac ctatgcccac    2040
ctgttcgacg acaaagtgat gaagcagctg aagcggcgga gatacaccgg ctggggcagg    2100
ctgagccgga agctgatcaa cggcatccgg gacaagcagt ccggcaagac aatcctggat    2160
ttcctgaagt ccgacggctt cgccaacaga aacttcatgc agctgatcca cgacgacagc    2220 ctgacctttta aagaggacat ccagaaagcc caggtgtccg gccagggcga tagcctgcac    2280
gagcacattg ccaatctggc cggcagcccc gccattaaga agggcatcct gcagacagtg    2340
aaggtggtgg acgagctcgt gaaagtgatg ggccggcaca gcccgagaa catcgtgatc     2400 gaaatggcca gagagaacca gaccacccag aagggacaga agaacagccg cgagagaatg    2460
aagcggatcg aagagggcat caaagagctg ggcagccaga tcctgaaaga acaccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggattccag ttttacaaag tgcgcgagat caacaactac     3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttcaagac cgagattacc ctggccaacg cgagatccg gaagcggcct      3300 ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc     3480 agaaagaagg actgggaccc taagaagtac ggcggcttcg acagcccccac cgtggcctat    3540 tctgtgctgg tggtggccaa agtggaaaag ggcaagtcca gaaaactgaa gagtgtgaaa    3600
gagctgctgg gatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggcggaag agaatgctgg cctctgccgg cgaactgcag     3780
aagggaaacg aactggccct gccctccaaa tatgtgaact tcctgtacct ggccagccac    3840
tatgagaagc tgaagggctc ccccgaggat aatgagcaga acagctgtt tgtggaacag     3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
```

| | |
|---|---|
| atcagagagc aggccgagaa tatcatccac ctgtttaccc tgaccaatct gggagcccct | 4080 |
| gccgccttca agtactttga caccaccatc gaccggaaga ggtacaccag caccaaagag | 4140 |
| gtgctggacg ccaccctgat ccaccagagc atcaccggcc tgtacgagac acggatcgac | 4200 |
| ctgtctcagc tgggaggcga caaaaggccg gcggccacga aaaaggccgg ccaggcaaaa | 4260 |
| aagaaaaag | 4269 |

<210> SEQ ID NO 86
<211> LENGTH: 4269
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

| | |
|---|---|
| atggactata aggaccacga cggagactac aaggatcatg atattgatta caaagacgat | 60 |
| gacgataaga tggcccccaaa gaagaagcgg aaggtcggta tccacggagt cccagcagcc | 120 |
| gacaagaagt acagcatcgg cctggacatc ggcaccaact ctgtgggctg ggccgtgatc | 180 |
| accgacgagt acaaggtgcc cagcaagaaa ttcaaggtgc tgggcaacac cgaccggcac | 240 |
| agcatcaaga gaacctgat cggagccctg ctgttcgaca cggcgaaac agccgaggcc | 300 |
| acccggctga agagaaccgc cagaagaaga taccacgac ggaagaaccg gatctgctat | 360 |
| ctgcaagaga tcttcagcaa cgagatggcc aaggtggacg acagcttctt ccacagactg | 420 |
| gaagagtcct tcctggtgga agaggataag aagcacgagc ggcaccccat cttcggcaac | 480 |
| atcgtggacg aggtggccta ccacgagaag taccccacca tctaccacct gagaaagaaa | 540 |
| ctggtggaca gcaccgacaa ggccgacctg cggctgatct atctggccct ggcccacatg | 600 |
| atcaagttcc ggggccactt cctgatcgag ggcgacctga accccgacaa cagcgacgtg | 660 |
| gacaagctgt tcatccagct ggtgcagacc tacaaccagc tgttcgagga aaaccccatc | 720 |
| aacgccagcg gcgtggacgc caaggccatc ctgtctgcca gactgagcaa gagcagacgg | 780 |
| ctggaaaatc tgatcgccca gctgcccggc gagaagaaga atggcctgtt cggcaacctg | 840 |
| attgccctga gcctgggcct gacccccaac ttcaagagca cttcgacct ggccgaggat | 900 |
| gccaaactgc agctgagcaa ggacacctac gacgacgacc tggacaacct gctggcccag | 960 |
| atcggcgacc agtacgccga cctgtttctg gccgccaaga acctgtccga cgccatcctg | 1020 |
| ctgagcgaca tcctgagagt gaacaccgag atcaccaagg ccccctgag cgcctctatg | 1080 |
| atcaagagat acgacgagca ccaccaggac ctgaccctgc tgaaagctct cgtgcggcag | 1140 |
| cagctgcctg agaagtacaa agagattttc ttcgaccaga gcaagaacgg ctacgccggc | 1200 |
| tacattgacg gcggagccag ccaggaagag ttctacaagt tcatcaagcc catcctggaa | 1260 |
| aagatggacg gcaccgagga actgctcgtg aagctgaaca gagaggacct gctgcggaag | 1320 |
| cagcggacct tcgacaacgg cagcatcccc caccagatcc acctgggaga gctgcacgcc | 1380 |
| attctgcggc ggcaggaaga ttttttaccca ttcctgaagg acaaccggga aaagatcgag | 1440 |
| aagatcctga ccttccgcat cccctactac gtgggccctc tggccagggg aaacagcaga | 1500 |
| ttcgcctgga tgaccagaaa gagcgaggaa accatcaccc cctggaactt cgaggaagtg | 1560 |
| gtggacaagg gcgcttccgc ccagagcttc atcgagcgga tgaccaactt cgataagaac | 1620 |
| ctgcccaacg agaaggtgct gcccaagcac agcctgctgt acgagtactt caccgtgtat | 1680 |
| aacgagctga ccaaagtgaa atacgtgacc gagggaatga gaaagccgc cttcctgagc | 1740 |

```
ggcgagcaga aaaaggccat cgtggacctg ctgttcaaga ccaaccggaa agtgaccgtg    1800
aagcagctga agaggacta cttcaagaaa atcgagtgct tcgactccgt ggaaatctcc    1860
ggcgtggaag atcggttcaa cgcctccctg gcacatacc acgatctgct gaaaattatc    1920
aaggacaagg acttcctgga caatgaggaa acgaggaca ttctggaaga tatcgtgctg    1980
accctgacac tgtttgagga cagagagatg atcgaggaac ggctgaaaac ctatgcccac    2040
ctgttcgacg acaaagtgat gaagcagctg aagcggcgga gatacaccgg ctggggcagg    2100
ctgagccgga agctgatcaa cggcatccgg acaagcagt ccggcaagac aatcctggat    2160
ttcctgaagt ccgacggctt cgccaacaga aacttcatgc agctgatcca cgacgacagc    2220 ctgacctttta agaggacat ccagaaagcc caggtgtccg gccagggcga tagcctgcac    2280
gagcacattg ccaatctggc cggcagcccc gccattaaga agggcatcct gcagacagtg    2340
aaggtggtgg acgagctcgt gaaagtgatg ggccggcaca gcccgagaa catcgtgatc    2400 gaaatggcca gagagaacca gaccacccag aagggacaga gaacagccg cgagagaatg    2460 aagcggatcg aagagggcat caaagagctg gcagccaga tcctgaaaga cacccgtg     2520 gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagccccac cgtggcctat    3540
tctgtgctgt tggtggccaa agtggaaaag ggcaagtcca gaaaactgaa gagtgtgaaa    3600
gagctgctgg ggatcaccat catggaaaga agcagcttcg agaagaatcc catcgacttt    3660
ctggaagcca gggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtgaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
```

```
gccgccttca agtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaag                                                            4269
```

<210> SEQ ID NO 87
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
gaguccgagc agaagaagaa gccccagagc uagaaauagc aaguuggggu aaggcuaguc      60
cguuaucaac uugaaaaagu ggcaccgagu cggugcuuuu                           100
```

<210> SEQ ID NO 88
<211> LENGTH: 66
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88

```
gaguccgagc agaagaagaa guuuagagc uagaaauagc aaguuaaaau aaggcuaguc       60
cguuuu                                                                66
```

<210> SEQ ID NO 89
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 89

```
gaguccgagc agaagaagaa guuuagagc uagaaauagc aaguuaaaau aaggcuaguc       60
cguuaucaac uugaaaaagu guuuu                                           85
```

<210> SEQ ID NO 90
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90

```
gaguccgagc agaagaagaa gccccagagc uagaaauagc aaguuggggu aaggcuaguc      60
cguuaucaac uugaaaaagu ggcaccgagu cggugcuuuu                           100
```

<210> SEQ ID NO 91
<211> LENGTH: 91
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 91
gaguccgagc agaagaagaa guuuuagaga caaguuaaaa uaaggcuagu ccguuaucaa    60
cuugaaaaag uggcaccgag ucggugcuuu u    91

<210> SEQ ID NO 92
<211> LENGTH: 98
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 92
gaguccgagc agaagaagaa guuuuagagc uagaaauagc uuuaaauaa ggcuaguccg    60 uuaucaacuu gaaaaagugg caccgagucg gugcuuuu    98

<210> SEQ ID NO 93
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 93
gaguccgagc agaagaagaa guuuuagagc uagaaauagc aaguuaaaau aauucuagua    60
aguuaucaac uugaaaaagu ggcaccgagu cggugcuuuu    100

<210> SEQ ID NO 94
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 94
gaguccgagc agaagaagaa guuuuagagc uagaaauagc aaguuaaaau aagccaugug    60
cguuaucaac uugaaaaagu ggcaccgagu cggugcuuuu    100

<210> SEQ ID NO 95
<211> LENGTH: 96
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 95
gaguccgagc agaagaagaa guuuuagagc uagaaauagc aaguuaaaau aaggcuaguc    60
cguaacuuga aaaguggca ccgagucggu gcuuuu    96

<210> SEQ ID NO 96
<211> LENGTH: 100
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 96
gaguccgagc agaagaagaa guuuuagagc uagaaauagc aaguuaaaau aaggcuaguc    60
cguuaucacg ccgaaaggcg ggcaccgagu cggugcuuuu                         100

<210> SEQ ID NO 97
<211> LENGTH: 104
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gaguccgagc agaagaagaa guuuuagagc uagaaauagc aaguuaaaau aaggcuaguc    60
cguuaucaac uugagaaauc aaguggcacc gagucggugc uuuu                    104

<210> SEQ ID NO 98
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
gaguccgagc agaagaagaa guuuuagagc uagaaauagc aaguuaaaau aaggcuaguc    60
cguuaucaac uugaaaaagu ggccccgcgg cggggcuuuu                         100

<210> SEQ ID NO 99
<211> LENGTH: 104
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
gaguccgagc agaagaagaa guuuuagagc uagaaauagc aaguuaaaau aaggcuaguc    60
cguuaucaac uugaaaaagu ggcaccgaaa guuucggugc uuuu                    104

<210> SEQ ID NO 100
<211> LENGTH: 96
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gaguccgagc agaagaagaa gccccagagc auuagcaagu ugggguaagc caugugcguu    60
aucagggcac cagcccggca ccgagucggu gcuuuu                             96

<210> SEQ ID NO 101
<211> LENGTH: 100
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 101
gaguccgagc agaagaagaa guuuuagagc uagaaauagc aacuuaaaau aaggcuaguc    60
cguuaucaac uugaaaaagu ggcaccgagu cggugcuuuu                         100

<210> SEQ ID NO 102
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102
gaguccgagc agaagaagaa guuuuagagc uagaaauagc aagguaaaau aaggcuaguc    60
cguuaucaac uugaaaaagu ggcaccgagu cggugcuuuu                         100

<210> SEQ ID NO 103
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
gaguccgagc agaagaagaa guuuuagagc uagaaauagc aagcuaaaau aaggcuaguc    60
cguuaucaac uugaaaaagu ggcaccgagu cggugcuuuu                         100

<210> SEQ ID NO 104
<211> LENGTH: 23
<212> TYPE: DNA
<213> ORGANISM: Streptococcus pyogenes

<400> SEQUENCE: 104
gagtccgagc agaagaagaa ggg                                            23

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
ccatcccctt ctgtgaatgt                                                20

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
```

```
ggagattgga gacacggaga                                               20

<210> SEQ ID NO 107
<211> LENGTH: 25
<212> TYPE: DNA
<213> ORGANISM: Streptococcus thermophilus

<400> SEQUENCE: 107
gctcccatca catcaaccgg tggcg                                         25

<210> SEQ ID NO 108
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 108
nnnnnnnnnn nnnnnnnnnn guuuuagagc uagaaauagc aaguuaaaau aaggcuaguc   60
cguuaucaac uugaaaaagu ggcaccgagu cggugcuuu                          99

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gccaagcgca cctaatttcc                                               20

<210> SEQ ID NO 110
<211> LENGTH: 97
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
ggaaauuagg ugcgcuuggc guuuuagagc uagaaauagc aaguuaaaau aaggcuaguc   60
cguuaucaac uugagaaagu ggcaccgagu cggugcu                            97

<210> SEQ ID NO 111
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Glu Ala Ala Ala Lys Ala
            20                  25                  30
```

<210> SEQ ID NO 112
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 112

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Glu Ala Ala Ala Lys Glu
            20                  25                  30

Ala Ala Ala Lys Glu Ala Ala Ala Lys Glu Ala Ala Ala Lys Ala
        35                  40                  45

<210> SEQ ID NO 113
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Glu Ala Ala Ala Lys Glu
            20                  25                  30

Ala Ala Ala Lys Glu Ala Ala Ala Lys Glu Ala Ala Ala Lys Glu Ala
        35                  40                  45

Ala Ala Lys Glu Ala Ala Ala Lys Glu Ala Ala Ala Lys Ala
    50                  55                  60

<210> SEQ ID NO 114
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 114
gccccagagc tagaaatagc aagttggggt aaggctagtc cgttatcaac ttgaaaaagt    60
ggcaccgagt cggtgctttt t                                              81

<210> SEQ ID NO 115
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 115
gttttagagc ccgaaagggc aagttaaaat aaggctagtc cgttatcaac ttgaaaaagt    60
ggcaccgagt cggtgctttt t                                              81

```
<210> SEQ ID NO 116
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
gttttagagc gaaagcaagt taaaataagg ctagtccgtt atcaacttga aaaagtggca      60
ccgagtcggt gctttt                                                     77

<210> SEQ ID NO 117
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
gttttagagg aaacaagtta aaataaggct agtccgttat caacttgaaa agtggcacc      60 gagtcggtgc ttttt                                                     75

<210> SEQ ID NO 118
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
gttttagaga caagttaaaa taaggctagt ccgttatcaa cttgaaaaag tggcaccgag     60
tcggtgcttt tt                                                        72

<210> SEQ ID NO 119
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
gttttagagc tagaaatagc tttaaaataa ggctagtccg ttatcaactt gaaaagtgg     60 caccgagtcg gtgcttttt                                                 79

<210> SEQ ID NO 120
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gttttagcgc tagaaatagc gttaaaataa ggctagtccg ttatcaactt gaaaagtgg     60 caccgagtcg gtgcttttt                                                 79
```

<210> SEQ ID NO 121
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
gttttagcgc tagaaatagc aagttaaaat aaggctagtc cgttatcaac ttgaaaaagt      60
ggcaccgagt cggtgctttt t                                                81

<210> SEQ ID NO 122
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gttttagtgc tagaaatagc aagttaaaat aaggctagtc cgttatcaac ttgaaaaagt      60
ggcaccgagt cggtgctttt t                                                81

<210> SEQ ID NO 123
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gttttagggc tagaaatagc aagttaaaat aaggctagtc cgttatcaac ttgaaaaagt      60
ggcaccgagt cggtgctttt t                                                81

<210> SEQ ID NO 124
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
gttttagagc tagaaatagc ttgttaaaat aaggctagtc cgttatcaac ttgaaaaagt      60
ggcaccgagt cggtgctttt t                                                81

<210> SEQ ID NO 125
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
gttttagagc tagaaatagc aacttaaaat aaggctagtc cgttatcaac ttgaaaaagt      60
ggcaccgagt cggtgctttt t                                                81

```
<210> SEQ ID NO 126
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gttttagagc tagaaatagc aaattaaaat aaggctagtc cgttatcaac ttgaaaaagt    60
ggcaccgagt cggtgctttt t                                              81

<210> SEQ ID NO 127
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gttttagagc tagaaatagc aatttaaaat aaggctagtc cgttatcaac ttgaaaaagt    60
ggcaccgagt cggtgctttt t                                              81

<210> SEQ ID NO 128
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
gttttagagc tagaaatagc aagttaaaat aaggctagtc cgtaacttga aaagtggca    60 ccgagtcggt gctttt                                                   77

<210> SEQ ID NO 129
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gttttagagc tagaaatagc aagttaaaat aaggctagtc cgtatagaac ttgaaaaagt    60
ggcaccgagt cggtgctttt t                                              81

<210> SEQ ID NO 130
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gttttagagc tagaaatagc aagttaaaat aaggctagtc cgttatcacg ccgaaaggcg    60
```

```
ggcaccgagt cggtgctttt t                                        81
```

<210> SEQ ID NO 131
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131

```
gttttagagc tagaaatagc aagttaaaat aaggctagtc cgttatcacg ccggccgaaa    60
ggccggcggg caccgagtcg gtgcttttt                                      89
```

<210> SEQ ID NO 132
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132

```
gttttagagc tagaaatagc aagttaaaat aaggctagtc cgttatcaac ttaaagaagt    60
ggcaccgagt cggtgctttt t                                              81
```

<210> SEQ ID NO 133
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133

```
gttttagagc tagaaatagc aagttaaaat aaggctagtc cgttatcaac ttgaaaaagt    60
ggccccgcgg cggggctttt t                                              81
```

<210> SEQ ID NO 134
<211> LENGTH: 83
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134

```
gttttagagc tagaaatagc aagttaaaat aaggctagtc cgttatcaac ttgaaaaagt    60
ggcaccgaag ttcggtgctt ttt                                            83
```

<210> SEQ ID NO 135
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135

```
gttttagagc tagaaatagc aagttaaaat aaggctagtc cgttatcaac ttgaaaaagt    60
```

```
ggcaccgaaa gtttcggtgc ttttt                                          85
```

<210> SEQ ID NO 136
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136

```
gttttagagc tagaaatagc aagctaaaat aaggctagtc cgttatcaac ttgaaaaagt    60
ggcaccgagt cggtgctttt t                                              81
```

<210> SEQ ID NO 137
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137

```
gttttagatc tagaaatagc aaggtaaaat aaggctagtc cgttatcaac ttgaaaaagt    60
ggcaccgagt cggtgctttt t                                              81
```

<210> SEQ ID NO 138
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138

```
gttttagagc tagaaatagc aagataaaat aaggctagtc cgttatcaac ttgaaaaagt    60
ggcaccgagt cggtgctttt t                                              81
```

<210> SEQ ID NO 139
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139

```
gttttagagc tagaaatagc aagttaaaac aaggctagtc cgttatcaac ttgaaaaagt    60
ggcaccgagt cggtgctttt t                                              81
```

<210> SEQ ID NO 140
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140

```
tttttagagc tagaaatagc aagttaaaag aaggctagtc cgttatcaac ttgaaaaagt    60
ggcaccgagt cggtgctttt t                                              81
```

<210> SEQ ID NO 141
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141

```
gttttagagc tagaaatagc aagttaaaaa aaggctagtc cgttatcaac ttgaaaaagt    60
ggcaccgagt cggtgctttt t                                              81
```

<210> SEQ ID NO 142
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142

```
gttttagagc tagaaatagc aagttaaaat aaggctagac cgttatcaac ttgaaaaagt    60
ggcaccgagt cggtgctttt t                                              81
```

<210> SEQ ID NO 143
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143

```
gttttagagc tagaaatagc aagttaaaat aaggctagcc cgttatcaac ttgaaaaagt    60
ggcaccgagt cggtgctttt t                                              81
```

<210> SEQ ID NO 144
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144

```
gttttagagc tagaaatagc aagttaaaat aaggctagtc cgttatcaac ttgaaaaagt    60
ggcaccgaat cggtgctttt t                                              81
```

<210> SEQ ID NO 145
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
gttttagagc tagaaatagc aagttaaaat aaggctagtc cgttatcaac ttgaaaaagt    60
ggcaccgact cggtgctttt t                                              81

<210> SEQ ID NO 146
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
gttttagagc tagaaatagc aagttaaaat aaggctagtc cgttatcaac ttgaaaaagt    60
ggcaccgatt cggtgctttt t                                              81

<210> SEQ ID NO 147
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
gttttagagc tagaaatagc aagttaaaat aaggctagtc cgttatcaac ttgaaaaagt    60
ggcaccgaga cggtgctttt t                                              81

<210> SEQ ID NO 148
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gttttagagc tagaaatagc aagttaaaat aaggctagtc cgttatcaac ttgaaaaagt    60
ggcaccgagc cggtgctttt t                                              81

<210> SEQ ID NO 149
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
gttttagagc tagaaatagc aagttaaaat aaggctagtc cgttatcaac ttgaaaaagt    60
ggcaccgagt cggtgctttt t                                              81

<210> SEQ ID NO 150
<211> LENGTH: 111
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150
gttttagagc taggccaaca tgaggatcac ccatgtctgc agggcctagc aagttaaaat    60
aaggctagtc cgttatcacg ccgaaaggcg ggcaccgagt cggtgctttt t            111

<210> SEQ ID NO 151
<211> LENGTH: 111
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 151
gttttagagc tagaaatagc aagttaaaat aaggctagtc cgttatcaac ttggccaaca    60
tgaggatcac ccatgtctgc agggccaagt ggcaccgagt cggtgctttt t            111

<210> SEQ ID NO 152
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 152
gttttagagc taggccaaca tgaggatcac ccatgtctgc agggcctagc aagttaaaat    60
aaggctagtc cgttatcaac ttggccaaca tgaggatcac ccatgtctgc agggccaagt   120
ggcaccgagt cggtgctttt t                                             141

<210> SEQ ID NO 153
<211> LENGTH: 25
<212> TYPE: DNA
<213> ORGANISM: Homo sapiens

<400> SEQUENCE: 153
gagtccgagc agaagaagaa gggct                                          25

<210> SEQ ID NO 154
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ccatcacatc aaccggtggc gcattgccac gaagcaggcc aatggggagg                50

<210> SEQ ID NO 155
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
ccagccaagc gcacctaatt tcc                                            23

```
<210> SEQ ID NO 156
<211> LENGTH: 98
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
ggaaauuagg ugcgcuuggc guuuuagagc uagaaauagc aaguuaaaau aaggcuaguc    60
cguuaucaac uugaaaaagu ggcaccgagu cggugcuuu                          98

<210> SEQ ID NO 157
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
guuuuagagc uagaaauagc aaguuaaaau aaggcuaguc cguuaucaac uugaaaaagu    60
ggcaccgagu cggugcuuuu                                                80

<210> SEQ ID NO 158
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
guuuuagagc uagaaauagc aaguuaaaau aaggcuaguc cguuu                    46

<210> SEQ ID NO 159
<211> LENGTH: 65
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
guuuuagagc uagaaauagc aaguuaaaau aaggcuaguc cguuaucaac uugaaaaagu    60
guuuu                                                                65

<210> SEQ ID NO 160
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gccccagagc uagaaauagc aaguuggggu aaggcuaguc cguuaucaac uugaaaaagu    60
ggcaccgagu cggugcuuuu                                                80

<210> SEQ ID NO 161
```

```
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
guuuuagaga caaguuaaaa uaaggcuagu ccguuaucaa cuugaaaaag uggcaccgag     60
ucggugcuuu u                                                         71

<210> SEQ ID NO 162
<211> LENGTH: 78
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
guuuuagagc uagaaauagc uuuaaaauaa ggcuaguccg uuaucaacuu gaaaagugg     60 caccgagucg gugcuuuu                                                  78

<210> SEQ ID NO 163
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
guuuuagagc uagaaauagc aaguuaaaau aauucuagua aguuaucaac uugaaaaagu     60
ggcaccgagu cggugcuuuu                                                80

<210> SEQ ID NO 164
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
guuuuagagc uagaaauagc aaguuaaaau aagccaugug cguuaucaac uugaaaaagu     60
ggcaccgagu cggugcuuuu                                                80

<210> SEQ ID NO 165
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
guuuuagagc uagaaauagc aaguuaaaau aaggcuaguc cguaacuuga aaaguggca     60 ccgagucggu gcuuuu                                                    76
```

```
<210> SEQ ID NO 166
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
guuuuagagc uagaaauagc aaguuaaaau aaggcuaguc cguuaucacg ccgaaaggcg      60
ggcaccgagu cggugcuuuu                                                 80

<210> SEQ ID NO 167
<211> LENGTH: 84
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
guuuuagagc uagaaauagc aaguuaaaau aaggcuaguc cguuaucaac uugagaaauc      60
aaguggcacc gagucggugc uuuu                                            84

<210> SEQ ID NO 168
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
guuuuagagc uagaaauagc aaguuaaaau aaggcuaguc cguuaucaac uugaaaaagu      60
ggccccgcgg cggggcuuuu                                                 80

<210> SEQ ID NO 169
<211> LENGTH: 84
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
guuuuagagc uagaaauagc aaguuaaaau aaggcuaguc cguuaucaac uugaaaaagu      60
ggcaccgaaa guuucggugc uuuu                                            84

<210> SEQ ID NO 170
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
gccccagagc auuagcaagu ugggguaagc caugugcguu aucagggcac cagcccggca      60
ccgagucggu gcuuuu                                                     76
```

```
<210> SEQ ID NO 171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
gccaagcgca cctaatttcc                                                      20

<210> SEQ ID NO 172
<211> LENGTH: 97
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
ggaaauuagg ugcgcuuggc guuuuagagc uagaaauagc aaguuaaaau aaggcuaguc          60
cguuaucaac uugaaaaagu ggcaccgagu cggugcu                                   97

<210> SEQ ID NO 173
<211> LENGTH: 56
<212> TYPE: DNA
<213> ORGANISM: Homo sapiens

<400> SEQUENCE: 173
aagctggagg aggagggcct gagtccgagc agaagaagaa gggctcccat cacatc             56

<210> SEQ ID NO 174
<211> LENGTH: 1368
<212> TYPE: PRT
<213> ORGANISM: Streptococcus pyogenes

<400> SEQUENCE: 174
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro

```
            165                 170                 175
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
                    260                 265                 270

Asp Asp Leu Asp Asn Leu Leu Ala Gln Ile Gly Asp Gln Tyr Ala Asp
                    275                 280                 285

Leu Phe Leu Ala Ala Lys Asn Leu Ser Asp Ala Ile Leu Leu Ser Asp
                    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
                    340                 345                 350

Asp Gln Ser Lys Asn Gly Tyr Ala Gly Tyr Ile Asp Gly Gly Ala Ser
                    355                 360                 365

Gln Glu Glu Phe Tyr Lys Phe Ile Lys Pro Ile Leu Glu Lys Met Asp
                    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
                    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                    580                 585                 590
```

```
Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005
```

| | | | | | | | | | |
|---|---|---|---|---|---|---|---|---|---|
| Val | Tyr | Gly | Asp | Tyr | Lys | Val | Tyr | Asp | Val | Arg | Lys | Met | Ile | Ala |
| 1010 | | | | | 1015 | | | | | 1020 | | | | |
| Lys | Ser | Glu | Gln | Glu | Ile | Gly | Lys | Ala | Thr | Ala | Lys | Tyr | Phe | Phe |
| 1025 | | | | | 1030 | | | | | 1035 | | | | |
| Tyr | Ser | Asn | Ile | Met | Asn | Phe | Phe | Lys | Thr | Glu | Ile | Thr | Leu | Ala |
| 1040 | | | | | 1045 | | | | | 1050 | | | | |
| Asn | Gly | Glu | Ile | Arg | Lys | Arg | Pro | Leu | Ile | Glu | Thr | Asn | Gly | Glu |
| 1055 | | | | | 1060 | | | | | 1065 | | | | |
| Thr | Gly | Glu | Ile | Val | Trp | Asp | Lys | Gly | Arg | Asp | Phe | Ala | Thr | Val |
| 1070 | | | | | 1075 | | | | | 1080 | | | | |
| Arg | Lys | Val | Leu | Ser | Met | Pro | Gln | Val | Asn | Ile | Val | Lys | Lys | Thr |
| 1085 | | | | | 1090 | | | | | 1095 | | | | |
| Glu | Val | Gln | Thr | Gly | Gly | Phe | Ser | Lys | Glu | Ser | Ile | Leu | Pro | Lys |
| 1100 | | | | | 1105 | | | | | 1110 | | | | |
| Arg | Asn | Ser | Asp | Lys | Leu | Ile | Ala | Arg | Lys | Lys | Asp | Trp | Asp | Pro |
| 1115 | | | | | 1120 | | | | | 1125 | | | | |
| Lys | Lys | Tyr | Gly | Gly | Phe | Asp | Ser | Pro | Thr | Val | Ala | Tyr | Ser | Val |
| 1130 | | | | | 1135 | | | | | 1140 | | | | |
| Leu | Val | Val | Ala | Lys | Val | Glu | Lys | Gly | Lys | Ser | Lys | Lys | Leu | Lys |
| 1145 | | | | | 1150 | | | | | 1155 | | | | |
| Ser | Val | Lys | Glu | Leu | Leu | Gly | Ile | Thr | Ile | Met | Glu | Arg | Ser | Ser |
| 1160 | | | | | 1165 | | | | | 1170 | | | | |
| Phe | Glu | Lys | Asn | Pro | Ile | Asp | Phe | Leu | Glu | Ala | Lys | Gly | Tyr | Lys |
| 1175 | | | | | 1180 | | | | | 1185 | | | | |
| Glu | Val | Lys | Lys | Asp | Leu | Ile | Ile | Lys | Leu | Pro | Lys | Tyr | Ser | Leu |
| 1190 | | | | | 1195 | | | | | 1200 | | | | |
| Phe | Glu | Leu | Glu | Asn | Gly | Arg | Lys | Arg | Met | Leu | Ala | Ser | Ala | Gly |
| 1205 | | | | | 1210 | | | | | 1215 | | | | |
| Glu | Leu | Gln | Lys | Gly | Asn | Glu | Leu | Ala | Leu | Pro | Ser | Lys | Tyr | Val |
| 1220 | | | | | 1225 | | | | | 1230 | | | | |
| Asn | Phe | Leu | Tyr | Leu | Ala | Ser | His | Tyr | Glu | Lys | Leu | Lys | Gly | Ser |
| 1235 | | | | | 1240 | | | | | 1245 | | | | |
| Pro | Glu | Asp | Asn | Glu | Gln | Lys | Gln | Leu | Phe | Val | Glu | Gln | His | Lys |
| 1250 | | | | | 1255 | | | | | 1260 | | | | |
| His | Tyr | Leu | Asp | Glu | Ile | Ile | Glu | Gln | Ile | Ser | Glu | Phe | Ser | Lys |
| 1265 | | | | | 1270 | | | | | 1275 | | | | |
| Arg | Val | Ile | Leu | Ala | Asp | Ala | Asn | Leu | Asp | Lys | Val | Leu | Ser | Ala |
| 1280 | | | | | 1285 | | | | | 1290 | | | | |
| Tyr | Asn | Lys | His | Arg | Asp | Lys | Pro | Ile | Arg | Glu | Gln | Ala | Glu | Asn |
| 1295 | | | | | 1300 | | | | | 1305 | | | | |
| Ile | Ile | His | Leu | Phe | Thr | Leu | Thr | Asn | Leu | Gly | Ala | Pro | Ala | Ala |
| 1310 | | | | | 1315 | | | | | 1320 | | | | |
| Phe | Lys | Tyr | Phe | Asp | Thr | Thr | Ile | Asp | Arg | Lys | Arg | Tyr | Thr | Ser |
| 1325 | | | | | 1330 | | | | | 1335 | | | | |
| Thr | Lys | Glu | Val | Leu | Asp | Ala | Thr | Leu | Ile | His | Gln | Ser | Ile | Thr |
| 1340 | | | | | 1345 | | | | | 1350 | | | | |
| Gly | Leu | Tyr | Glu | Thr | Arg | Ile | Asp | Leu | Ser | Gln | Leu | Gly | Gly | Asp |
| 1355 | | | | | 1360 | | | | | 1365 | | | | |

<210> SEQ ID NO 175
<211> LENGTH: 1345
<212> TYPE: PRT
<213> ORGANISM: Streptococcus mutans

<400> SEQUENCE: 175

-continued

```
Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
                35                  40                  45

Gly Ala Leu Leu Phe Asp Ser Gly Asn Thr Ala Glu Asp Arg Arg Leu
50                      55                  60

Lys Arg Thr Ala Arg Arg Tyr Thr Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
                100                 105                 110

Gly Glu Arg His Pro Ile Phe Gly Asn Leu Glu Glu Val Lys Tyr
            115                 120                 125

His Glu Asn Phe Pro Thr Ile Tyr His Leu Arg Gln Tyr Leu Ala Asp
        130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
        275                 280                 285

Leu Phe Leu Ser Ala Lys Lys Leu Tyr Asp Ser Ile Leu Leu Ser Gly
290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
        355                 360                 365

Gln Glu Ala Phe Tyr Lys Tyr Leu Lys Gly Leu Leu Asn Lys Ile Glu
370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415
```

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
            435                 440                 445

Pro Tyr Tyr Val Gly Pro Leu Ala Arg Gly Lys Ser Asp Phe Ala Trp
            450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
            485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
            515                 520                 525

Tyr Lys Thr Glu Gln Gly Lys Thr Ala Phe Phe Asp Ala Asn Met Lys
            530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
            565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
            595                 600                 605

Asp Asn Ser Lys Asn Glu Lys Ile Leu Glu Asp Ile Val Leu Thr Leu
            610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
            645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
            675                 680                 685

Asn Ser Asn Arg Asn Phe Met Gln Leu Ile Asn Asp Asp Ala Leu Ser
            690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
            725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
            755                 760                 765

Phe Thr Asn Gln Gly Arg Arg Asn Ser Gln Gln Arg Leu Lys Gly Leu
            770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
            805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys

-continued

Asp Asn Ser Ile Asp Asn Arg Val Leu Thr Ser Ser Lys Glu Asn Arg
835             840             845
                                                850

Gly Lys Ser Asp Asp Val Pro Ser Lys Asp Val Val Arg Lys Met Lys
865             870             875             880

Ser Tyr Trp Ser Lys Leu Leu Ser Ala Lys Leu Ile Thr Gln Arg Lys
                885             890             895

Phe Asp Asn Leu Thr Lys Ala Glu Arg Gly Gly Leu Thr Asp Asp Asp
            900             905             910

Lys Ala Gly Phe Ile Lys Arg Gln Leu Val Glu Thr Arg Gln Ile Thr
            915             920             925

Lys His Val Ala Arg Ile Leu Asp Glu Arg Phe Asn Thr Glu Thr Asp
930             935             940

Glu Asn Asn Lys Lys Ile Arg Gln Val Lys Ile Val Thr Leu Lys Ser
945             950             955             960

Asn Leu Val Ser Asn Phe Arg Lys Glu Phe Glu Leu Tyr Lys Val Arg
                965             970             975

Glu Ile Asn Asp Tyr His His Ala His Asp Ala Tyr Leu Asn Ala Val
                980             985             990

Ile Gly Lys Ala Leu Leu Gly Val Tyr Pro Gln Leu Glu Pro Glu Phe
            995             1000            1005

Val Tyr Gly Asp Tyr Pro His Phe His Gly His Lys Glu Asn Lys
1010            1015            1020

Ala Thr Ala Lys Lys Phe Phe Tyr Ser Asn Ile Met Asn Phe Phe
1025            1030            1035

Lys Lys Asp Asp Val Arg Thr Asp Lys Asn Gly Glu Ile Ile Trp
1040            1045            1050

Lys Lys Asp Glu His Ile Ser Asn Ile Lys Lys Val Leu Ser Tyr
1055            1060            1065

Pro Gln Val Asn Ile Val Lys Lys Val Glu Glu Gln Thr Gly Gly
1070            1075            1080

Phe Ser Lys Glu Ser Ile Leu Pro Lys Gly Asn Ser Asp Lys Leu
1085            1090            1095

Ile Pro Arg Lys Thr Lys Lys Phe Tyr Trp Asp Thr Lys Lys Tyr
1100            1105            1110

Gly Gly Phe Asp Ser Pro Ile Val Ala Tyr Ser Ile Leu Val Ile
1115            1120            1125

Ala Asp Ile Glu Lys Gly Lys Ser Lys Lys Leu Lys Thr Val Lys
1130            1135            1140

Ala Leu Val Gly Val Thr Ile Met Glu Lys Met Thr Phe Glu Arg
1145            1150            1155

Asp Pro Val Ala Phe Leu Glu Arg Lys Gly Tyr Arg Asn Val Gln
1160            1165            1170

Glu Glu Asn Ile Ile Lys Leu Pro Lys Tyr Ser Leu Phe Lys Leu
1175            1180            1185

Glu Asn Gly Arg Lys Arg Leu Leu Ala Ser Ala Arg Glu Leu Gln
1190            1195            1200

Lys Gly Asn Glu Ile Val Leu Pro Asn His Leu Gly Thr Leu Leu
1205            1210            1215

Tyr His Ala Lys Asn Ile His Lys Val Asp Glu Pro Lys His Leu
1220            1225            1230

Asp Tyr Val Asp Lys His Lys Asp Glu Phe Lys Glu Leu Leu Asp
1235            1240            1245

-continued

```
Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Asn Lys Leu Gly Gly Asp
    1340                1345

<210> SEQ ID NO 176
<211> LENGTH: 1388
<212> TYPE: PRT
<213> ORGANISM: Streptococcus thermophilus

<400> SEQUENCE: 176

Met Thr Lys Pro Tyr Ser Ile Gly Leu Asp Ile Gly Thr Asn Ser
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                    85                  90                  95

Phe Phe Gln Arg Leu Asp Asp Ser Phe Leu Val Pro Asp Asp Lys Arg
                100                 105                 110

Asp Ser Lys Tyr Pro Ile Phe Gly Asn Leu Val Glu Glu Lys Ala Tyr
            115                 120                 125

His Asp Glu Phe Pro Thr Ile Tyr His Leu Arg Lys Tyr Leu Ala Asp
        130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                    165                 170                 175

Lys Asn Asn Asp Ile Gln Lys Asn Phe Gln Asp Phe Leu Asp Thr Tyr
                180                 185                 190

Asn Ala Ile Phe Glu Ser Asp Leu Ser Leu Glu Asn Ser Lys Gln Leu
            195                 200                 205

Glu Glu Ile Val Lys Asp Lys Ile Ser Lys Leu Glu Lys Lys Asp Arg
        210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                    245                 250                 255

Asn Leu Asp Glu Lys Ala Ser Leu His Phe Ser Lys Glu Ser Tyr Asp
```

```
              260                 265                 270
Glu Asp Leu Glu Thr Leu Leu Gly Tyr Ile Gly Asp Asp Tyr Ser Asp
            275                 280                 285

Val Phe Leu Lys Ala Lys Lys Leu Tyr Asp Ala Ile Leu Leu Ser Gly
            290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
                355                 360                 365

Gln Glu Asp Phe Tyr Val Tyr Leu Lys Lys Leu Leu Ala Glu Phe Glu
            370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
            450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
            595                 600                 605

Ser Ser Asn Glu Ala Ile Ile Glu Glu Ile Ile His Thr Leu Thr Ile
610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
            675                 680                 685
```

-continued

```
Asn Arg Asn Phe Met Gln Leu Ile His Asp Asp Ala Leu Ser Phe Lys
    690                 695                 700
Lys Lys Ile Gln Lys Ala Gln Ile Ile Gly Asp Glu Asp Lys Gly Asn
705                 710                 715                 720
Ile Lys Glu Val Val Lys Ser Leu Pro Gly Ser Pro Ala Ile Lys Lys
                725                 730                 735
Gly Ile Leu Gln Ser Ile Lys Ile Val Asp Glu Leu Val Lys Val Met
                740                 745                 750
Gly Gly Arg Lys Pro Glu Ser Ile Val Val Glu Met Ala Arg Glu Asn
            755                 760                 765
Gln Tyr Thr Asn Gln Gly Lys Ser Asn Ser Gln Gln Arg Leu Lys Arg
        770                 775                 780
Leu Glu Lys Ser Leu Lys Glu Leu Gly Ser Lys Ile Leu Lys Glu Asn
785                 790                 795                 800
Ile Pro Ala Lys Leu Ser Lys Ile Asp Asn Asn Ala Leu Gln Asn Asp
                805                 810                 815
Arg Leu Tyr Leu Tyr Leu Gln Asn Gly Lys Asp Met Tyr Thr Gly
                820                 825                 830
Asp Asp Leu Asp Ile Asp Arg Leu Ser Asn Tyr Asp Ile Asp His Ile
            835                 840                 845
Ile Pro Gln Ala Phe Leu Lys Asp Asn Ser Ile Asp Asn Lys Val Leu
850                 855                 860
Val Ser Ser Ala Ser Asn Arg Gly Lys Ser Asp Asp Val Pro Ser Leu
865                 870                 875                 880
Glu Val Val Lys Lys Arg Lys Thr Phe Trp Tyr Gln Leu Leu Lys Ser
                885                 890                 895
Lys Leu Ile Ser Gln Arg Lys Phe Asp Asn Leu Thr Lys Ala Glu Arg
                900                 905                 910
Gly Gly Leu Ser Pro Glu Asp Lys Ala Gly Phe Ile Gln Arg Gln Leu
            915                 920                 925
Val Glu Thr Arg Gln Ile Thr Lys His Val Ala Arg Leu Leu Asp Glu
        930                 935                 940
Lys Phe Asn Asn Lys Lys Asp Glu Asn Asn Arg Ala Val Arg Thr Val
945                 950                 955                 960
Lys Ile Ile Thr Leu Lys Ser Thr Leu Val Ser Gln Phe Arg Lys Asp
                965                 970                 975
Phe Glu Leu Tyr Lys Val Arg Glu Ile Asn Asp Phe His His Ala His
            980                 985                 990
Asp Ala Tyr Leu Asn Ala Val Val Ala Ser Ala Leu Leu Lys Lys Tyr
        995                 1000                1005
Pro Lys Leu Glu Pro Glu Phe Val Tyr Gly Asp Tyr Pro Lys Tyr
    1010                1015                1020
Asn Ser Phe Arg Glu Arg Lys Ser Ala Thr Glu Lys Val Tyr Phe
    1025                1030                1035
Tyr Ser Asn Ile Met Asn Ile Phe Lys Lys Ser Ile Ser Leu Ala
    1040                1045                1050
Asp Gly Arg Val Ile Glu Arg Pro Leu Ile Glu Val Asn Glu Glu
    1055                1060                1065
Thr Gly Glu Ser Val Trp Asn Lys Glu Ser Asp Leu Ala Thr Val
    1070                1075                1080
Arg Arg Val Leu Ser Tyr Pro Gln Val Asn Val Val Lys Lys Val
    1085                1090                1095
```

```
Glu Glu Gln Asn His Gly Leu Asp Arg Gly Lys Pro Lys Gly Leu
     1100                1105                1110

Phe Asn Ala Asn Leu Ser Ser Lys Pro Lys Pro Asn Ser Asn Glu
     1115                1120                1125

Asn Leu Val Gly Ala Lys Glu Tyr Leu Asp Pro Lys Lys Tyr Gly
     1130                1135                1140

Gly Tyr Ala Gly Ile Ser Asn Ser Phe Thr Val Leu Val Lys Gly
     1145                1150                1155

Thr Ile Glu Lys Gly Ala Lys Lys Ile Thr Asn Val Leu Glu
     1160                1165                1170

Phe Gln Gly Ile Ser Ile Leu Asp Arg Ile Asn Tyr Arg Lys Asp
     1175                1180                1185

Lys Leu Asn Phe Leu Leu Glu Lys Gly Tyr Lys Asp Ile Glu Leu
     1190                1195                1200

Ile Ile Glu Leu Pro Lys Tyr Ser Leu Phe Glu Leu Ser Asp Gly
     1205                1210                1215

Ser Arg Arg Met Leu Ala Ser Ile Leu Ser Thr Asn Asn Lys Arg
     1220                1225                1230

Gly Glu Ile His Lys Gly Asn Gln Ile Phe Leu Ser Gln Lys Phe
     1235                1240                1245

Val Lys Leu Leu Tyr His Ala Lys Arg Ile Ser Asn Thr Ile Asn
     1250                1255                1260

Glu Asn His Arg Lys Tyr Val Glu Asn His Lys Lys Glu Phe Glu
     1265                1270                1275

Glu Leu Phe Tyr Tyr Ile Leu Glu Phe Asn Glu Asn Tyr Val Gly
     1280                1285                1290

Ala Lys Lys Asn Gly Lys Leu Leu Asn Ser Ala Phe Gln Ser Trp
     1295                1300                1305

Gln Asn His Ser Ile Asp Glu Leu Cys Ser Ser Phe Ile Gly Pro
     1310                1315                1320

Thr Gly Ser Glu Arg Lys Gly Leu Phe Glu Leu Thr Ser Arg Gly
     1325                1330                1335

Ser Ala Ala Asp Phe Glu Phe Leu Gly Val Lys Ile Pro Arg Tyr
     1340                1345                1350

Arg Asp Tyr Thr Pro Ser Ser Leu Leu Lys Asp Ala Thr Leu Ile
     1355                1360                1365

His Gln Ser Val Thr Gly Leu Tyr Glu Thr Arg Ile Asp Leu Ala
     1370                1375                1380

Lys Leu Gly Glu Gly
     1385

<210> SEQ ID NO 177
<211> LENGTH: 1121
<212> TYPE: PRT
<213> ORGANISM: Streptococcus thermophilus

<400> SEQUENCE: 177

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
                20                  25                  30

Arg Ile Phe Pro Ala Ala Gln Ala Glu Asn Asn Leu Val Arg Arg Thr
            35                  40                  45

Asn Arg Gln Gly Arg Arg Leu Ala Arg Arg Lys Lys His Arg Arg Val
        50                  55                  60
```

-continued

```
Arg Leu Asn Arg Leu Phe Glu Glu Ser Gly Leu Ile Thr Asp Phe Thr
 65                  70                  75                  80

Lys Ile Ser Ile Asn Leu Asn Pro Tyr Gln Leu Arg Val Lys Gly Leu
             85                   90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480
```

```
Val Val Ala Lys Ser Val Arg Gln Ala Ile Lys Ile Val Asn Ala Ala
            485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
            515                 520                 525

Ala Asn Lys Asp Glu Lys Asp Ala Ala Met Leu Lys Ala Ala Asn Gln
            530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
                580                 585                 590

Asn Gln Phe Glu Val Asp His Ile Leu Pro Leu Ser Ile Thr Phe Asp
            595                 600                 605

Asp Ser Leu Ala Asn Lys Val Leu Val Tyr Ala Thr Ala Asn Gln Glu
            610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
                660                 665                 670

Phe Asp Val Arg Lys Lys Phe Ile Glu Arg Asn Leu Val Asp Thr Arg
            675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
            755                 760                 765

Leu Leu Asp Ile Glu Thr Gly Glu Leu Ile Ser Asp Asp Glu Tyr Lys
            770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
                820                 825                 830

Ala Lys Val Gly Lys Asp Lys Ala Asp Glu Thr Tyr Val Leu Gly Lys
            835                 840                 845

Ile Lys Asp Ile Tyr Thr Gln Asp Gly Tyr Asp Ala Phe Met Lys Ile
            850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
```

```
                  900             905             910
Tyr Lys Glu Glu His Gly Tyr Ile Arg Lys Tyr Ser Lys Lys Gly Asn
            915                 920                 925

Gly Pro Glu Ile Lys Ser Leu Lys Tyr Tyr Asp Ser Lys Leu Gly Asn
            930                 935             940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser Gln Glu Lys Tyr Asn Asp Ile Lys
            995                 1000                1005

Lys Lys Glu Gly Val Asp Ser Asp Ser Glu Phe Lys Phe Thr Leu
        1010            1015            1020

Tyr Lys Asn Asp Leu Leu Leu Val Lys Asp Thr Glu Thr Lys Glu
        1025            1030            1035

Gln Gln Leu Phe Arg Phe Leu Ser Arg Thr Met Pro Lys Gln Lys
        1040            1045            1050

His Tyr Val Glu Leu Lys Pro Tyr Asp Lys Gln Lys Phe Glu Gly
        1055            1060            1065

Gly Glu Ala Leu Ile Lys Val Leu Gly Asn Val Ala Asn Ser Gly
        1070            1075            1080

Gln Cys Lys Lys Gly Leu Gly Lys Ser Asn Ile Ser Ile Tyr Lys
        1085            1090            1095

Val Arg Thr Asp Val Leu Gly Asn Gln His Ile Ile Lys Asn Glu
        1100            1105            1110

Gly Asp Lys Pro Lys Leu Asp Phe
        1115            1120

<210> SEQ ID NO 178
<211> LENGTH: 984
<212> TYPE: PRT
<213> ORGANISM: Campylobacter jejuni

<400> SEQUENCE: 178

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140
```

```
Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
            165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
            195                 200                 205

Lys Lys Gln Arg Glu Phe Gly Phe Ser Phe Ser Lys Lys Phe Glu Glu
            210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
            245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
            275                 280                 285

Asp Asp Leu Asn Ala Leu Leu Asn Glu Val Leu Lys Asn Gly Thr Leu
            290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
            325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
            355                 360                 365

Lys Lys Ala Leu Ala Lys Tyr Asp Leu Asn Gln Asn Gln Ile Asp Ser
            370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
            405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
            435                 440                 445

Asn Pro Val Val Leu Arg Ala Ile Lys Glu Tyr Arg Lys Val Leu Asn
            450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
            485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
            530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
```

```
              565                 570                 575
Val Phe Thr Lys Gln Asn Gln Glu Lys Leu Asn Gln Thr Pro Phe Glu
            580                 585                 590
Ala Phe Gly Asn Asp Ser Ala Lys Trp Gln Lys Ile Glu Val Leu Ala
            595                 600                 605
Lys Asn Leu Pro Thr Lys Lys Gln Lys Arg Ile Leu Asp Lys Asn Tyr
            610                 615                 620
Lys Asp Lys Glu Gln Lys Asn Phe Lys Asp Arg Asn Leu Asn Asp Thr
625                 630                 635                 640
Arg Tyr Ile Ala Arg Leu Val Leu Asn Tyr Thr Lys Asp Tyr Leu Asp
                645                 650                 655
Phe Leu Pro Leu Ser Asp Asp Glu Asn Thr Lys Leu Asn Asp Thr Gln
                660                 665                 670
Lys Gly Ser Lys Val His Val Glu Ala Lys Ser Gly Met Leu Thr Ser
                675                 680                 685
Ala Leu Arg His Thr Trp Gly Phe Ser Ala Lys Asp Arg Asn Asn His
            690                 695                 700
Leu His His Ala Ile Asp Ala Val Ile Ile Ala Tyr Ala Asn Asn Ser
705                 710                 715                 720
Ile Val Lys Ala Phe Ser Asp Phe Lys Lys Glu Gln Glu Ser Asn Ser
                725                 730                 735
Ala Glu Leu Tyr Ala Lys Lys Ile Ser Glu Leu Asp Tyr Lys Asn Lys
                740                 745                 750
Arg Lys Phe Phe Glu Pro Phe Ser Gly Phe Arg Gln Lys Val Leu Asp
                755                 760                 765
Lys Ile Asp Glu Ile Phe Val Ser Lys Pro Glu Arg Lys Lys Pro Ser
                770                 775                 780
Gly Ala Leu His Glu Glu Thr Phe Arg Lys Glu Glu Phe Tyr Gln
785                 790                 795                 800
Ser Tyr Gly Gly Lys Glu Gly Val Leu Lys Ala Leu Glu Leu Gly Lys
                805                 810                 815
Ile Arg Lys Val Asn Gly Lys Ile Val Lys Asn Gly Asp Met Phe Arg
                820                 825                 830
Val Asp Ile Phe Lys His Lys Lys Thr Asn Lys Phe Tyr Ala Val Pro
                835                 840                 845
Ile Tyr Thr Met Asp Phe Ala Leu Lys Val Leu Pro Asn Lys Ala Val
                850                 855                 860
Ala Arg Ser Lys Lys Gly Glu Ile Lys Asp Trp Ile Leu Met Asp Glu
865                 870                 875                 880
Asn Tyr Glu Phe Cys Phe Ser Leu Tyr Lys Asp Ser Leu Ile Leu Ile
                885                 890                 895
Gln Thr Lys Asp Met Gln Glu Pro Glu Phe Val Tyr Tyr Asn Ala Phe
                900                 905                 910
Thr Ser Ser Thr Val Ser Leu Ile Val Ser Lys His Asp Asn Lys Phe
                915                 920                 925
Glu Thr Leu Ser Lys Asn Gln Lys Ile Leu Phe Lys Asn Ala Asn Glu
                930                 935                 940
Lys Glu Val Ile Ala Lys Ser Ile Gly Ile Gln Asn Leu Lys Val Phe
945                 950                 955                 960
Glu Lys Tyr Ile Val Ser Ala Leu Gly Glu Val Thr Lys Ala Glu Phe
                965                 970                 975
Arg Gln Arg Glu Asp Phe Lys Lys
                980
```

<210> SEQ ID NO 179
<211> LENGTH: 1236
<212> TYPE: PRT
<213> ORGANISM: Neisseria meningiditis

<400> SEQUENCE: 179

```
Met Tyr Phe Tyr Lys Asn Lys Glu Asn Lys Leu Asn Lys Lys Val Val
1               5                   10                  15

Leu Gly Leu Asp Leu Gly Ile Ala Ser Val Gly Trp Cys Leu Thr Asp
            20                  25                  30

Ile Ser Gln Lys Glu Asp Asn Lys Phe Pro Ile Ile Leu His Gly Val
        35                  40                  45

Arg Leu Phe Glu Thr Val Asp Asp Ser Asp Lys Leu Leu Asn Glu
50                  55                  60

Thr Arg Arg Lys Lys Arg Gly Gln Arg Arg Asn Arg Arg Leu Phe
65                  70                  75                  80

Thr Arg Lys Arg Asp Phe Ile Lys Tyr Leu Ile Asp Asn Asn Ile Ile
                85                  90                  95

Glu Leu Glu Phe Asp Lys Asn Pro Lys Ile Leu Val Arg Asn Phe Ile
            100                 105                 110

Glu Lys Tyr Ile Asn Pro Phe Ser Lys Asn Leu Glu Leu Lys Tyr Lys
        115                 120                 125

Ser Val Thr Asn Leu Pro Ile Gly Phe His Asn Leu Arg Lys Ala Ala
    130                 135                 140

Ile Asn Glu Lys Tyr Lys Leu Asp Lys Ser Glu Leu Ile Val Leu Leu
145                 150                 155                 160

Tyr Phe Tyr Leu Ser Leu Arg Gly Ala Phe Phe Asp Asn Pro Glu Asp
                165                 170                 175

Thr Lys Ser Lys Glu Met Asn Lys Asn Glu Ile Glu Ile Phe Asp Lys
            180                 185                 190

Asn Glu Ser Ile Lys Asn Ala Glu Phe Pro Ile Asp Lys Ile Ile Glu
        195                 200                 205

Phe Tyr Lys Ile Ser Gly Lys Ile Arg Ser Thr Ile Asn Leu Lys Phe
    210                 215                 220

Gly His Gln Asp Tyr Leu Lys Glu Ile Lys Gln Val Phe Glu Lys Gln
225                 230                 235                 240

Asn Ile Asp Phe Met Asn Tyr Glu Lys Phe Ala Met Glu Glu Lys Ser
                245                 250                 255

Phe Phe Ser Arg Ile Arg Asn Tyr Ser Glu Gly Pro Gly Asn Glu Lys
            260                 265                 270

Ser Phe Ser Lys Tyr Gly Leu Tyr Ala Asn Glu Asn Gly Asn Pro Glu
        275                 280                 285

Leu Ile Ile Asn Glu Lys Gly Gln Lys Ile Tyr Thr Lys Ile Phe Lys
    290                 295                 300

Thr Leu Trp Glu Ser Lys Ile Gly Lys Cys Ser Tyr Asp Lys Lys Leu
305                 310                 315                 320

Tyr Arg Ala Pro Lys Asn Ser Phe Ser Ala Lys Val Phe Asp Ile Thr
                325                 330                 335

Asn Lys Leu Thr Asp Trp Lys His Lys Asn Glu Tyr Ile Ser Glu Arg
            340                 345                 350

Leu Lys Arg Lys Ile Leu Leu Ser Arg Phe Leu Asn Lys Asp Ser Lys
        355                 360                 365

Ser Ala Val Glu Lys Ile Leu Lys Glu Glu Asn Ile Lys Phe Glu Asn
```

```
            370                 375                 380
Leu Ser Glu Ile Ala Tyr Asn Lys Asp Asp Asn Lys Ile Asn Leu Pro
385                 390                 395                 400

Ile Ile Asn Ala Tyr His Ser Leu Thr Thr Ile Phe Lys Lys His Leu
                    405                 410                 415

Ile Asn Phe Glu Asn Tyr Leu Ile Ser Asn Glu Asn Asp Leu Ser Lys
                420                 425                 430

Leu Met Ser Phe Tyr Lys Gln Gln Ser Glu Lys Leu Phe Val Pro Asn
            435                 440                 445

Glu Lys Gly Ser Tyr Glu Ile Asn Gln Asn Asn Asn Val Leu His Ile
        450                 455                 460

Phe Asp Ala Ile Ser Asn Ile Leu Asn Lys Phe Ser Thr Ile Gln Asp
465                 470                 475                 480

Arg Ile Arg Ile Leu Glu Gly Tyr Phe Glu Phe Ser Asn Leu Lys Lys
                485                 490                 495

Asp Val Lys Ser Ser Glu Ile Tyr Ser Glu Ile Ala Lys Leu Arg Glu
                500                 505                 510

Phe Ser Gly Thr Ser Ser Leu Ser Phe Gly Ala Tyr Tyr Lys Phe Ile
            515                 520                 525

Pro Asn Leu Ile Ser Glu Gly Ser Lys Asn Tyr Ser Thr Ile Ser Tyr
        530                 535                 540

Glu Glu Lys Ala Leu Gln Asn Gln Lys Asn Asn Phe Ser His Ser Asn
545                 550                 555                 560

Leu Phe Glu Lys Thr Trp Val Glu Asp Leu Ile Ala Ser Pro Thr Val
                565                 570                 575

Lys Arg Ser Leu Arg Gln Thr Met Asn Leu Leu Lys Glu Ile Phe Lys
                580                 585                 590

Tyr Ser Glu Lys Asn Asn Leu Glu Ile Glu Lys Ile Val Val Glu Val
            595                 600                 605

Thr Arg Ser Ser Asn Asn Lys His Glu Arg Lys Lys Ile Glu Gly Ile
        610                 615                 620

Asn Lys Tyr Arg Lys Glu Lys Tyr Glu Glu Leu Lys Lys Val Tyr Asp
625                 630                 635                 640

Leu Pro Asn Glu Asn Thr Thr Leu Leu Lys Lys Leu Trp Leu Leu Arg
                645                 650                 655

Gln Gln Gln Gly Tyr Asp Ala Tyr Ser Leu Arg Lys Ile Glu Ala Asn
                660                 665                 670

Asp Val Ile Asn Lys Pro Trp Asn Tyr Asp Ile Asp His Ile Val Pro
            675                 680                 685

Arg Ser Ile Ser Phe Asp Asp Ser Phe Ser Asn Leu Val Ile Val Asn
        690                 695                 700

Lys Leu Asp Asn Ala Lys Lys Ser Asn Asp Leu Ser Ala Lys Gln Phe
705                 710                 715                 720

Ile Glu Lys Ile Tyr Gly Ile Glu Lys Leu Lys Glu Ala Lys Glu Asn
                725                 730                 735

Trp Gly Asn Trp Tyr Leu Arg Asn Ala Asn Gly Lys Ala Phe Asn Asp
                740                 745                 750

Lys Gly Lys Phe Ile Lys Leu Tyr Thr Ile Asp Asn Leu Asp Glu Phe
            755                 760                 765

Asp Asn Ser Asp Phe Ile Asn Arg Asn Leu Ser Asp Thr Ser Tyr Ile
        770                 775                 780

Thr Asn Ala Leu Val Asn His Leu Thr Phe Ser Asn Ser Lys Tyr Lys
785                 790                 795                 800
```

-continued

Tyr Ser Val Val Ser Val Asn Gly Lys Gln Thr Ser Asn Leu Arg Asn
            805                 810                 815

Gln Ile Ala Phe Val Gly Ile Lys Asn Asn Lys Glu Thr Glu Arg Glu
            820                 825                 830

Trp Lys Arg Pro Glu Gly Phe Lys Ser Ile Asn Ser Asn Asp Phe Leu
            835                 840                 845

Ile Arg Glu Glu Gly Lys Asn Asp Val Lys Asp Val Leu Ile Lys
            850                 855                 860

Asp Arg Ser Phe Asn Gly His His Ala Glu Asp Ala Tyr Phe Ile Thr
865                 870                 875                 880

Ile Ile Ser Gln Tyr Phe Arg Ser Phe Lys Arg Ile Glu Arg Leu Asn
            885                 890                 895

Val Asn Tyr Arg Lys Glu Thr Arg Glu Leu Asp Asp Leu Glu Lys Asn
            900                 905                 910

Asn Ile Lys Phe Lys Glu Lys Ala Ser Phe Asp Asn Phe Leu Leu Ile
            915                 920                 925

Asn Ala Leu Asp Glu Leu Asn Glu Lys Leu Asn Gln Met Arg Phe Ser
930                 935                 940

Arg Met Val Ile Thr Lys Lys Asn Thr Gln Leu Phe Asn Glu Thr Leu
945                 950                 955                 960

Tyr Ser Gly Lys Tyr Asp Lys Gly Lys Asn Thr Ile Lys Lys Val Glu
            965                 970                 975

Lys Leu Asn Leu Leu Asp Asn Arg Thr Asp Lys Ile Lys Lys Ile Glu
            980                 985                 990

Glu Phe Phe Asp Glu Asp Lys Leu Lys Glu Asn Glu Leu Thr Lys Leu
            995                 1000                1005

His Ile Phe Asn His Asp Lys Asn Leu Tyr Glu Thr Leu Lys Ile
            1010                1015                1020

Ile Trp Asn Glu Val Lys Ile Glu Ile Lys Asn Lys Asn Leu Asn
            1025                1030                1035

Glu Lys Asn Tyr Phe Lys Tyr Phe Val Asn Lys Lys Leu Gln Glu
            1040                1045                1050

Gly Lys Ile Ser Phe Asn Glu Trp Val Pro Ile Leu Asp Asn Asp
            1055                1060                1065

Phe Lys Ile Ile Arg Lys Ile Arg Tyr Ile Lys Phe Ser Ser Glu
            1070                1075                1080

Glu Lys Glu Thr Asp Glu Ile Ile Phe Ser Gln Ser Asn Phe Leu
            1085                1090                1095

Lys Ile Asp Gln Arg Gln Asn Phe Ser Phe His Asn Thr Leu Tyr
            1100                1105                1110

Trp Val Gln Ile Trp Val Tyr Lys Asn Gln Lys Asp Gln Tyr Cys
            1115                1120                1125

Phe Ile Ser Ile Asp Ala Arg Asn Ser Lys Phe Glu Lys Asp Glu
            1130                1135                1140

Ile Lys Ile Asn Tyr Glu Lys Leu Lys Thr Gln Lys Glu Lys Leu
            1145                1150                1155

Gln Ile Ile Asn Glu Glu Pro Ile Leu Lys Ile Asn Lys Gly Asp
            1160                1165                1170

Leu Phe Glu Asn Glu Glu Lys Glu Leu Phe Tyr Ile Val Gly Arg
            1175                1180                1185

Asp Glu Lys Pro Gln Lys Leu Glu Ile Lys Tyr Ile Leu Gly Lys
            1190                1195                1200

```
Lys Ile Lys Asp Gln Lys Gln  Ile Gln Lys Pro Val  Lys Lys Tyr
    1205                1210                1215

Phe Pro Asn Trp Lys Lys Val  Asn Leu Thr Tyr Met  Gly Glu Ile
    1220                1225                1230

Phe Lys Lys
    1235

<210> SEQ ID NO 180
<211> LENGTH: 305
<212> TYPE: PRT
<213> ORGANISM: Streptococcus pyogenes

<400> SEQUENCE: 180

Lys Lys Tyr Ser Ile Gly Leu Ala Ile Gly Thr Asn Ser Val Gly Trp
1               5                   10                  15

Ala Val Ile Thr Asp Glu Tyr Lys Val Pro Ser Lys Lys Phe Lys Val
            20                  25                  30

Leu Gly Asn Thr Asp Arg His Ser Ile Lys Lys Asn Leu Ile Gly Ala
        35                  40                  45

Leu Leu Phe Asp Ser Gly Glu Thr Ala Glu Ala Thr Arg Leu Lys Arg
50                  55                  60

Thr Ala Arg Arg Arg Tyr Thr Arg Arg Lys Asn Arg Ile Leu Tyr Leu
65                  70                  75                  80

Gln Glu Ile Phe Ser Asn Glu Met Ala Lys Val Asp Asp Ser Phe Phe
                85                  90                  95

His Arg Leu Glu Glu Ser Phe Leu Val Glu Glu Asp Lys Lys His Glu
            100                 105                 110

Arg His Pro Ile Phe Gly Asn Ile Val Asp Glu Val Ala Tyr His Glu
        115                 120                 125

Lys Tyr Pro Thr Ile Tyr His Leu Arg Lys Lys Leu Val Asp Ser Thr
    130                 135                 140

Asp Lys Ala Asp Leu Arg Leu Ile Tyr Leu Ala Leu Ala His Met Ile
145                 150                 155                 160

Lys Phe Arg Gly His Phe Leu Ile Glu Gly Asp Leu Asn Pro Asp Asn
                165                 170                 175

Ser Asp Val Asp Lys Leu Phe Ile Gln Leu Val Gln Thr Tyr Asn Gln
            180                 185                 190

Leu Phe Glu Glu Asn Pro Ile Asn Ala Ser Gly Val Asp Ala Lys Ala
        195                 200                 205

Ile Leu Ser Ala Arg Leu Ser Lys Ser Arg Arg Leu Glu Asn Leu Ile
    210                 215                 220

Ala Gln Leu Pro Gly Glu Lys Lys Asn Gly Leu Phe Gly Asn Leu Ile
225                 230                 235                 240

Ala Leu Ser Leu Gly Leu Thr Pro Asn Phe Lys Ser Asn Phe Asp Leu
                245                 250                 255

Ala Glu Asp Ala Lys Leu Gln Leu Ser Lys Asp Thr Tyr Asp Asp Asp
            260                 265                 270

Leu Asp Asn Leu Leu Ala Gln Ile Gly Asp Gln Tyr Ala Asp Leu Phe
        275                 280                 285

Leu Ala Ala Lys Asn Leu Ser Asp Ala Ile Leu Leu Ser Asp Ile Leu
    290                 295                 300

Arg
305

<210> SEQ ID NO 181
```

<211> LENGTH: 326
<212> TYPE: PRT
<213> ORGANISM: Streptococcus pyogenes

<400> SEQUENCE: 181

```
Lys Ala Pro Leu Ser Ala Ser Met Ile Lys Arg Tyr Asp Glu His His
1               5                   10                  15

Gln Asp Leu Thr Leu Leu Lys Ala Leu Val Arg Gln Gln Leu Pro Glu
            20                  25                  30

Lys Tyr Lys Glu Ile Phe Phe Asp Gln Ser Lys Asn Gly Tyr Ala Gly
        35                  40                  45

Tyr Ile Asp Gly Gly Ala Ser Gln Glu Glu Phe Tyr Lys Phe Ile Lys
50                  55                  60

Pro Ile Leu Glu Lys Met Asp Gly Thr Glu Glu Leu Leu Val Lys Leu
65                  70                  75                  80

Asn Arg Glu Asp Leu Leu Arg Lys Gln Arg Thr Phe Asp Asn Gly Ser
                85                  90                  95

Ile Pro His Gln Ile His Leu Gly Glu Leu His Ala Ile Leu Arg Arg
            100                 105                 110

Gln Glu Asp Phe Tyr Pro Phe Leu Lys Asp Asn Arg Glu Lys Ile Glu
        115                 120                 125

Lys Ile Leu Thr Phe Arg Ile Pro Tyr Tyr Val Gly Pro Leu Ala Arg
130                 135                 140

Gly Asn Ser Arg Phe Ala Trp Met Thr Arg Lys Ser Glu Glu Thr Ile
145                 150                 155                 160

Thr Pro Trp Asn Phe Glu Glu Val Val Asp Lys Gly Ala Ser Ala Gln
                165                 170                 175

Ser Phe Ile Glu Arg Met Thr Asn Phe Asp Lys Asn Leu Pro Asn Glu
            180                 185                 190

Lys Val Leu Pro Lys His Ser Leu Leu Tyr Glu Tyr Phe Thr Val Tyr
        195                 200                 205

Asn Glu Leu Thr Lys Val Lys Tyr Val Thr Glu Gly Met Arg Lys Pro
210                 215                 220

Ala Phe Leu Ser Gly Glu Gln Lys Lys Ala Ile Val Asp Leu Leu Phe
225                 230                 235                 240

Lys Thr Asn Arg Lys Val Thr Val Lys Gln Leu Lys Glu Asp Tyr Phe
                245                 250                 255

Lys Lys Ile Glu Glu Phe Asp Ser Val Glu Ile Ser Gly Val Glu Asp
            260                 265                 270

Arg Phe Asn Ala Ser Leu Gly Thr Tyr His Asp Leu Leu Lys Ile Ile
        275                 280                 285

Lys Asp Lys Asp Phe Leu Asp Asn Glu Glu Asn Glu Asp Ile Leu Glu
290                 295                 300

Asp Ile Val Leu Thr Leu Thr Leu Phe Glu Asp Arg Glu Met Ile Glu
305                 310                 315                 320

Glu Arg Leu Lys Thr Tyr
                325
```

<210> SEQ ID NO 182
<211> LENGTH: 70
<212> TYPE: PRT
<213> ORGANISM: Streptococcus pyogenes

<400> SEQUENCE: 182

```
Asp Asp Lys Val Met Lys Gln Leu Lys Arg Arg Arg Tyr Thr Gly Trp
1               5                   10                  15
```

```
Gly Arg Leu Ser Arg Lys Leu Ile Asn Gly Ile Arg Asp Lys Gln Ser
            20                  25                  30

Gly Lys Thr Ile Leu Asp Phe Leu Lys Ser Asp Gly Phe Ala Asn Arg
        35                  40                  45

Asn Phe Met Gln Leu Ile His Asp Asp Ser Leu Thr Phe Lys Glu Asp
 50                  55                  60

Ile Gln Lys Ala Gln Val
 65                  70

<210> SEQ ID NO 183
<211> LENGTH: 50
<212> TYPE: PRT
<213> ORGANISM: Streptococcus pyogenes

<400> SEQUENCE: 183

Asp Ser Leu His Glu His Ile Ala Asn Leu Ala Gly Ser Pro Ala Ile
 1               5                  10                  15

Lys Lys Gly Ile Leu Gln Thr Val Lys Val Val Asp Glu Leu Val Lys
            20                  25                  30

Val Met Gly Arg His Lys Pro Glu Asn Ile Val Ile Glu Met Ala Arg
        35                  40                  45

Glu Asn
 50

<210> SEQ ID NO 184
<211> LENGTH: 19
<212> TYPE: PRT
<213> ORGANISM: Streptococcus pyogenes

<400> SEQUENCE: 184

Lys Asn Ser Arg Glu Arg Met Lys Arg Ile Glu Glu Gly Ile Lys Glu
 1               5                  10                  15

Leu Gly Ser

<210> SEQ ID NO 185
<211> LENGTH: 145
<212> TYPE: PRT
<213> ORGANISM: Streptococcus pyogenes

<400> SEQUENCE: 185

Lys Glu His Pro Val Glu Asn Thr Gln Leu Gln Asn Glu Lys Leu Tyr
 1               5                  10                  15

Leu Tyr Tyr Leu Gln Asn Gly Arg Asp Met Tyr Val Asp Gln Glu Leu
            20                  25                  30

Asp Ile Asn Arg Leu Ser Asp Tyr Asp Val Asp Ala Ile Val Pro Gln
        35                  40                  45

Ser Phe Leu Lys Asp Asp Ser Ile Asp Asn Lys Val Leu Thr Arg Ser
 50                  55                  60

Asp Lys Asn Arg Gly Lys Ser Asp Asn Val Pro Ser Glu Glu Val Val
 65                  70                  75                  80

Lys Lys Met Lys Asn Tyr Trp Arg Gln Leu Leu Asn Ala Lys Leu Ile
            85                  90                  95

Thr Gln Arg Lys Phe Asp Asn Leu Thr Lys Ala Glu Arg Gly Gly Leu
        100                 105                 110

Ser Glu Leu Asp Lys Ala Gly Phe Ile Lys Arg Gln Leu Val Glu Thr
        115                 120                 125

Arg Gln Ile Thr Lys His Val Ala Gln Ile Leu Asp Ser Arg Met Asn
```

Thr
145

<210> SEQ ID NO 186
<211> LENGTH: 58
<212> TYPE: PRT
<213> ORGANISM: Streptococcus pyogenes

<400> SEQUENCE: 186

Arg Glu Val Lys Val Ile Thr Leu Lys Ser Lys Leu Val Ser Asp Phe
1               5                   10                  15

Arg Lys Asp Phe Gln Phe Tyr Lys Val Arg Glu Ile Asn Asn Tyr His
                20                  25                  30

His Ala His Asp Ala Tyr Leu Asn Ala Val Val Gly Thr Ala Leu Ile
            35                  40                  45

Lys Lys Tyr Pro Lys Leu Glu Ser Glu Phe
50                  55

<210> SEQ ID NO 187
<211> LENGTH: 19
<212> TYPE: PRT
<213> ORGANISM: Streptococcus pyogenes

<400> SEQUENCE: 187

Gly Lys Ala Thr Ala Lys Tyr Phe Phe Tyr Ser Asn Ile Met Asn Phe
1               5                   10                  15

Phe Lys Thr

<210> SEQ ID NO 188
<211> LENGTH: 180
<212> TYPE: PRT
<213> ORGANISM: Streptococcus pyogenes

<400> SEQUENCE: 188

Ile Glu Thr Asn Gly Glu Thr Gly Glu Ile Val Trp Asp Lys Gly Arg
1               5                   10                  15

Asp Phe Ala Thr Val Arg Lys Val Leu Ser Met Pro Gln Val Asn Ile
                20                  25                  30

Val Lys Lys Thr Glu Val Gln Thr Gly Gly Phe Ser Lys Glu Ser Ile
            35                  40                  45

Leu Pro Lys Arg Asn Ser Asp Lys Leu Ile Ala Arg Lys Lys Asp Trp
50                  55                  60

Asp Pro Lys Lys Tyr Gly Gly Phe Asp Ser Pro Thr Val Ala Tyr Ser
65                  70                  75                  80

Val Leu Val Val Ala Lys Val Glu Lys Gly Lys Ser Lys Lys Leu Lys
                85                  90                  95

Ser Val Lys Glu Leu Leu Gly Ile Thr Ile Met Glu Arg Ser Ser Phe
            100                 105                 110

Glu Lys Asn Pro Ile Asp Phe Leu Glu Ala Lys Gly Tyr Lys Glu Val
        115                 120                 125

Lys Lys Asp Leu Ile Ile Lys Leu Pro Lys Tyr Ser Leu Phe Glu Leu
130                 135                 140

Glu Asn Gly Arg Lys Arg Met Leu Ala Ser Ala Gly Glu Leu Gln Lys
145                 150                 155                 160

Gly Asn Glu Leu Ala Leu Pro Ser Lys Tyr Val Asn Phe Leu Tyr Leu
                165                 170                 175

Ala Ser His Tyr
        180

<210> SEQ ID NO 189
<211> LENGTH: 118
<212> TYPE: PRT
<213> ORGANISM: Streptococcus pyogenes

<400> SEQUENCE: 189

Pro Glu Asp Asn Glu Gln Lys Gln Leu Phe Val Glu Gln His Lys His
1               5                   10                  15

Tyr Leu Asp Glu Ile Ile Glu Gln Ile Ser Glu Phe Ser Lys Arg Val
            20                  25                  30

Ile Leu Ala Asp Ala Asn Leu Asp Lys Val Leu Ser Ala Tyr Asn Lys
        35                  40                  45

His Arg Asp Lys Pro Ile Arg Glu Gln Ala Glu Asn Ile Ile His Leu
    50                  55                  60

Phe Thr Leu Thr Asn Leu Gly Ala Pro Ala Ala Phe Lys Tyr Phe Asp
65                  70                  75                  80

Thr Thr Ile Asp Arg Lys Arg Tyr Thr Ser Thr Lys Glu Val Leu Asp
                85                  90                  95

Ala Thr Leu Ile His Gln Ser Ile Thr Gly Leu Tyr Glu Thr Arg Ile
            100                 105                 110

Asp Leu Ser Gln Leu Gly
        115

<210> SEQ ID NO 190
<211> LENGTH: 97
<212> TYPE: RNA
<213> ORGANISM: Streptococcus pyogenes

<400> SEQUENCE: 190
ggaaauuggg ugcgcuuggc guuuagagc uagaaauagc aaguuaaaau aaggcuaguc      60
cguuaucaac uugagaaagu ggcaccgagu cggugcu                             97

<210> SEQ ID NO 191
<211> LENGTH: 20
<212> TYPE: DNA
<213> ORGANISM: Streptococcus pyogenes

<400> SEQUENCE: 191
gccaagcgca cccaatttcc                                                20

<210> SEQ ID NO 192
<211> LENGTH: 567
<212> TYPE: PRT
<213> ORGANISM: Streptococcus pyogenes

<400> SEQUENCE: 192

Lys Lys Tyr Ser Ile Gly Leu Ala Ile Gly Thr Asn Ser Val Gly Trp
1               5                   10                  15

Ala Val Ile Thr Asp Glu Tyr Lys Val Pro Ser Lys Lys Phe Lys Val
            20                  25                  30

Leu Gly Asn Thr Asp Arg His Ser Ile Lys Lys Asn Leu Ile Gly Ala
        35                  40                  45

Leu Leu Phe Asp Ser Gly Glu Thr Ala Glu Ala Thr Arg Leu Lys Arg
    50                  55                  60

Thr Ala Arg Arg Arg Tyr Thr Arg Arg Lys Asn Arg Ile Leu Tyr Leu
65                  70                  75                  80

```
Gln Glu Ile Phe Ser Asn Glu Met Ala Lys Val Asp Asp Ser Phe Phe
                    85                  90                  95

His Arg Leu Glu Glu Ser Phe Leu Val Glu Asp Lys Lys His Glu
            100                 105                 110

Arg His Pro Ile Phe Gly Asn Ile Val Asp Glu Val Ala Tyr His Glu
                115                 120                 125

Lys Tyr Pro Thr Ile Tyr His Leu Arg Lys Lys Leu Val Asp Ser Thr
            130                 135                 140

Asp Lys Ala Asp Leu Arg Leu Ile Tyr Leu Ala Leu Ala His Met Ile
145                 150                 155                 160

Lys Phe Arg Gly His Phe Leu Ile Glu Gly Asp Leu Asn Pro Asp Asn
                165                 170                 175

Ser Asp Val Asp Lys Leu Phe Ile Gln Leu Val Gln Thr Tyr Asn Gln
            180                 185                 190

Leu Phe Glu Glu Asn Pro Ile Asn Ala Ser Gly Val Asp Ala Lys Ala
            195                 200                 205

Ile Leu Ser Ala Arg Leu Ser Lys Ser Arg Arg Leu Glu Asn Leu Ile
            210                 215                 220

Ala Gln Leu Pro Gly Glu Lys Lys Asn Gly Leu Phe Gly Asn Leu Ile
225                 230                 235                 240

Ala Leu Ser Leu Gly Leu Thr Pro Asn Phe Lys Ser Asn Phe Asp Leu
                245                 250                 255

Ala Glu Asp Ala Lys Leu Gln Leu Ser Lys Asp Thr Tyr Asp Asp Asp
                260                 265                 270

Leu Asp Asn Leu Leu Ala Gln Ile Gly Asp Gln Tyr Ala Asp Leu Phe
            275                 280                 285

Leu Ala Ala Lys Asn Leu Ser Asp Ala Ile Leu Leu Ser Asp Ile Leu
290                 295                 300

Arg Val Asn Thr Glu Ile Thr Lys Ala Pro Leu Ser Ala Ser Met Ile
305                 310                 315                 320

Lys Arg Tyr Asp Glu His His Gln Asp Leu Thr Leu Leu Lys Ala Leu
                325                 330                 335

Val Arg Gln Gln Leu Pro Glu Lys Tyr Lys Glu Ile Phe Phe Asp Gln
            340                 345                 350

Ser Lys Asn Gly Tyr Ala Gly Tyr Ile Asp Gly Gly Ala Ser Gln Glu
            355                 360                 365

Glu Phe Tyr Lys Phe Ile Lys Pro Ile Leu Glu Lys Met Asp Gly Thr
            370                 375                 380

Glu Glu Leu Leu Val Lys Leu Asn Arg Glu Asp Leu Leu Arg Lys Gln
385                 390                 395                 400

Arg Thr Phe Asp Asn Gly Ser Ile Pro His Gln Ile His Leu Gly Glu
                405                 410                 415

Leu His Ala Ile Leu Arg Arg Gln Glu Asp Phe Tyr Pro Phe Leu Lys
                420                 425                 430

Asp Asn Arg Glu Lys Ile Glu Lys Ile Leu Thr Phe Arg Ile Pro Tyr
            435                 440                 445

Tyr Val Gly Pro Leu Ala Arg Gly Asn Ser Arg Phe Ala Trp Met Thr
        450                 455                 460

Arg Lys Ser Glu Glu Thr Ile Thr Pro Trp Asn Phe Glu Glu Val Val
465                 470                 475                 480

Asp Lys Gly Ala Ser Ala Gln Ser Phe Ile Glu Arg Met Thr Asn Phe
                485                 490                 495
```

```
Asp Lys Asn Leu Pro Asn Glu Lys Val Leu Pro Lys His Ser Leu Leu
            500                 505                 510

Tyr Glu Tyr Phe Thr Val Tyr Asn Gly Leu Thr Lys Val Lys Tyr Val
            515                 520                 525

Thr Glu Gly Met Arg Lys Pro Ala Phe Leu Ser Gly Glu Gln Lys Lys
            530                 535                 540

Ala Ile Val Asp Leu Leu Phe Lys Thr Asn Arg Lys Val Thr Val Lys
545                 550                 555                 560

Gln Leu Lys Glu Asp Tyr Phe
                565
```

<210> SEQ ID NO 193
<211> LENGTH: 62
<212> TYPE: PRT
<213> ORGANISM: Streptococcus pyogenes

<400> SEQUENCE: 193

```
Val Glu Ile Ser Gly Val Glu Asp Arg Phe Asn Ala Ser Leu Gly Thr
1               5                   10                  15

Tyr His Asp Leu Leu Lys Ile Ile Lys Asp Lys Asp Phe Leu Asp Asn
            20                  25                  30

Glu Glu Asn Glu Asp Ile Leu Glu Asp Ile Val Leu Thr Leu Thr Leu
        35                  40                  45

Phe Glu Asp Arg Glu Met Ile Glu Glu Arg Leu Lys Thr Tyr
    50                  55                  60
```

<210> SEQ ID NO 194
<211> LENGTH: 69
<212> TYPE: PRT
<213> ORGANISM: Streptococcus pyogenes

<400> SEQUENCE: 194

```
Asp Asp Lys Val Met Lys Gln Leu Lys Arg Arg Arg Tyr Thr Gly Trp
1               5                   10                  15

Gly Arg Leu Ser Arg Lys Leu Ile Asn Gly Ile Arg Asp Lys Gln Ser
            20                  25                  30

Gly Lys Thr Ile Leu Asp Phe Leu Lys Ser Asp Gly Phe Ala Asn Arg
        35                  40                  45

Asn Phe Met Gln Leu Ile His Asp Asp Ser Leu Thr Phe Lys Glu Asp
    50                  55                  60

Ile Gln Lys Ala Gln
65
```

<210> SEQ ID NO 195
<211> LENGTH: 46
<212> TYPE: PRT
<213> ORGANISM: Streptococcus pyogenes

<400> SEQUENCE: 195

```
Asp Ser Leu His Glu His Ile Ala Asn Leu Ala Gly Ser Pro Ala Ile
1               5                   10                  15

Lys Lys Gly Ile Leu Gln Thr Val Lys Val Val Asp Glu Leu Val Lys
            20                  25                  30

Val Met Gly Arg His Lys Pro Glu Asn Ile Val Ile Glu Met
        35                  40                  45
```

<210> SEQ ID NO 196
<211> LENGTH: 94
<212> TYPE: PRT

<213> ORGANISM: Streptococcus pyogenes

<400> SEQUENCE: 196

Arg Gln Leu Val Glu Thr Arg Gln Ile Thr Lys His Val Ala Gln Ile
1               5                   10                  15

Leu Asp Ser Arg Met Asn Thr Lys Tyr Asp Glu Asn Asp Lys Leu Ile
            20                  25                  30

Arg Glu Val Lys Val Ile Thr Leu Lys Ser Lys Leu Val Ser Asp Phe
        35                  40                  45

Arg Lys Asp Phe Gln Phe Tyr Lys Val Arg Glu Ile Asn Asn Tyr His
    50                  55                  60

His Ala His Asp Ala Tyr Leu Asn Ala Val Val Gly Thr Ala Leu Ile
65                  70                  75                  80

Lys Lys Tyr Pro Lys Leu Glu Ser Glu Phe Val Tyr Gly Asp
                85                  90

<210> SEQ ID NO 197
<211> LENGTH: 10
<212> TYPE: PRT
<213> ORGANISM: Streptococcus pyogenes

<400> SEQUENCE: 197

Tyr Ser Asn Ile Met Asn Phe Phe Lys Thr
1               5                   10

<210> SEQ ID NO 198
<211> LENGTH: 50
<212> TYPE: PRT
<213> ORGANISM: Streptococcus pyogenes

<400> SEQUENCE: 198

Thr Asn Gly Glu Thr Gly Glu Ile Val Trp Asp Lys Gly Arg Asp Phe
1               5                   10                  15

Ala Thr Val Arg Lys Val Leu Ser Met Pro Gln Val Asn Ile Val Lys
            20                  25                  30

Lys Thr Glu Val Gln Thr Gly Gly Phe Ser Lys Glu Ser Ile Leu Pro
        35                  40                  45

Lys Arg
    50

<210> SEQ ID NO 199
<211> LENGTH: 127
<212> TYPE: PRT
<213> ORGANISM: Streptococcus pyogenes

<400> SEQUENCE: 199

Asp Lys Leu Ile Ala Arg Lys Lys Asp Trp Asp Pro Lys Lys Tyr Gly
1               5                   10                  15

Gly Phe Asp Ser Pro Thr Val Ala Tyr Ser Val Leu Val Val Ala Lys
            20                  25                  30

Val Glu Lys Gly Lys Ser Lys Lys Leu Lys Ser Val Lys Glu Leu Leu
        35                  40                  45

Gly Ile Thr Ile Met Glu Arg Ser Ser Phe Glu Lys Asn Pro Ile Asp
    50                  55                  60

Phe Leu Glu Ala Lys Gly Tyr Lys Glu Val Lys Lys Asp Leu Ile Ile
65                  70                  75                  80

Lys Leu Pro Lys Tyr Ser Leu Phe Glu Leu Glu Asn Gly Arg Lys Arg
                85                  90                  95

```
Met Leu Ala Ser Ala Gly Glu Leu Gln Lys Gly Asn Glu Leu Ala Leu
            100                 105                 110

Pro Ser Lys Tyr Val Asn Phe Leu Tyr Leu Ala Ser His Tyr Glu
        115                 120                 125

<210> SEQ ID NO 200
<211> LENGTH: 117
<212> TYPE: PRT
<213> ORGANISM: Streptococcus pyogenes

<400> SEQUENCE: 200

Glu Asp Asn Glu Gln Lys Gln Leu Phe Val Glu Gln His Lys His Tyr
1               5                   10                  15

Leu Asp Glu Ile Ile Glu Gln Ile Ser Glu Phe Ser Lys Arg Val Ile
            20                  25                  30

Leu Ala Asp Ala Asn Leu Asp Lys Val Leu Ser Ala Tyr Asn Lys His
        35                  40                  45

Arg Asp Lys Pro Ile Arg Glu Gln Ala Glu Asn Ile Ile His Leu Phe
    50                  55                  60

Thr Leu Thr Asn Leu Gly Ala Pro Ala Ala Phe Lys Tyr Phe Asp Thr
65                  70                  75                  80

Thr Ile Asp Arg Lys Arg Tyr Thr Ser Thr Lys Glu Val Leu Asp Ala
                85                  90                  95

Thr Leu Ile His Gln Ser Ile Thr Gly Leu Tyr Glu Thr Arg Ile Asp
            100                 105                 110

Leu Ser Gln Leu Gly
        115

<210> SEQ ID NO 201
<211> LENGTH: 97
<212> TYPE: RNA
<213> ORGANISM: Streptococcus pyogenes

<400> SEQUENCE: 201
ggaaauuggg ugcgcuuggc guuuuagagc uagaaauagc aaguuaaaau aaggcuaguc    60
cguuaucaac uugagaaagu ggcaccgagu cggugcu                            97

<210> SEQ ID NO 202
<211> LENGTH: 20
<212> TYPE: DNA
<213> ORGANISM: Streptococcus pyogenes

<400> SEQUENCE: 202
gccaagcgca cccaatttcc                                               20
```